(12) United States Patent
Kim et al.

(10) Patent No.: US 11,530,225 B2
(45) Date of Patent: Dec. 20, 2022

(54) COMPOUND AND ORGANIC LIGHT-EMITTING DIODE COMPRISING SAME

(71) Applicant: LG CHEM, LTD., Seoul (KR)

(72) Inventors: Minjun Kim, Daejeon (KR); Kongkyeom Kim, Daejeon (KR); Hyok Joon Kwon, Daejeon (KR); Min Woo Lee, Daejeon (KR); Donghee Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 534 days.

(21) Appl. No.: 16/486,485

(22) PCT Filed: Jul. 20, 2018

(86) PCT No.: PCT/KR2018/008247
§ 371 (c)(1),
(2) Date: Aug. 15, 2019

(87) PCT Pub. No.: WO2019/017741
PCT Pub. Date: Jan. 24, 2019

(65) Prior Publication Data
US 2020/0055865 A1 Feb. 20, 2020

(30) Foreign Application Priority Data

Jul. 20, 2017 (KR) .................. 10-2017-0091898

(51) Int. Cl.
*C07D 401/14* (2006.01)
*C07D 403/04* (2006.01)
(Continued)

(52) U.S. Cl.
CPC ....... *C07D 491/048* (2013.01); *C07D 401/14* (2013.01); *C07D 403/04* (2013.01);
(Continued)

(58) Field of Classification Search
None
See application file for complete search history.

(56) References Cited

U.S. PATENT DOCUMENTS

2004/0251816 A1 12/2004 Leo et al.
2012/0217485 A1 8/2012 Lee et al.
(Continued)

FOREIGN PATENT DOCUMENTS

KR 2011-0013220 A 2/2011
KR 2011-0107681 A 10/2011
(Continued)

OTHER PUBLICATIONS

Computer-generated English-language translation of KR-20150061976-A.*
(Continued)

*Primary Examiner* — Vu A Nguyen
(74) *Attorney, Agent, or Firm* — Dentons US LLP

(57) ABSTRACT

The present specification provides a compound of Chemical Formula 1, and an organic light emitting device including
(Continued)

the same. The compound provides a low driving voltage, high light emission efficiency and a long lifetime of the organic light emitting device.

[Chemical Formula 1]

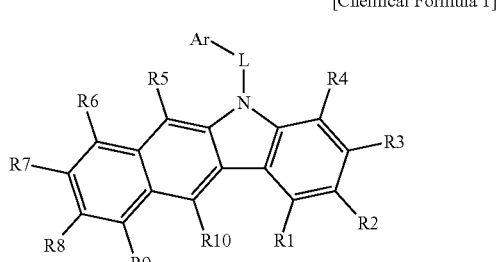

10 Claims, 8 Drawing Sheets

(51) Int. Cl.
*C07D 491/048* (2006.01)
*C07D 495/04* (2006.01)
*H01L 51/00* (2006.01)
*H01L 51/50* (2006.01)

(52) U.S. Cl.
CPC ........ *C07D 495/04* (2013.01); *H01L 51/0056* (2013.01); *H01L 51/0067* (2013.01); *H01L 51/0072* (2013.01); *H01L 51/0074* (2013.01); *H01L 51/5056* (2013.01); *H01L 51/5072* (2013.01); *H01L 51/5092* (2013.01)

(56) References Cited

U.S. PATENT DOCUMENTS

| | | |
|---|---|---|
| 2015/0144924 A1 | 5/2015 | Shin et al. |
| 2015/0243893 A1 | 8/2015 | Joseph et al. |
| 2015/0311450 A1 | 10/2015 | Park et al. |
| 2015/0349272 A1 | 12/2015 | Park et al. |
| 2016/0028020 A1* | 1/2016 | Lee ............... H01L 51/0071 257/40 |
| 2016/0233433 A1 | 8/2016 | Park et al. |
| 2016/0248024 A1 | 8/2016 | Shin et al. |
| 2016/0308142 A1 | 10/2016 | Kim et al. |
| 2016/0351826 A1 | 12/2016 | Kim et al. |
| 2017/0012216 A1 | 1/2017 | Kim et al. |
| 2017/0166581 A1 | 6/2017 | Kim et al. |
| 2017/0229659 A1 | 8/2017 | Park et al. |
| 2018/0205032 A1 | 7/2018 | Lee et al. |
| 2018/0282276 A1 | 10/2018 | Mun et al. |

FOREIGN PATENT DOCUMENTS

| | | | | |
|---|---|---|---|---|
| KR | 2012-0050557 | A | | 5/2012 |
| KR | 2014-0070425 | A | | 6/2014 |
| KR | 2015-0042387 | A | | 4/2015 |
| KR | 2015-0061976 | A | | 6/2015 |
| KR | 20150061976 | A | * | 6/2015 ......... H01L 51/0074 |
| KR | 2015-0084657 | A | | 7/2015 |
| KR | 2015-0100555 | A | | 9/2015 |
| KR | 1561566 | B1 | | 10/2015 |
| KR | 10-2015-0141179 | A | | 12/2015 |
| KR | 20150133998 | A | * | 12/2015 |
| KR | 1020160026661 | A | | 3/2016 |
| KR | 2017-0007626 | A | | 1/2017 |
| KR | 10-2017-0022505 | A | | 3/2017 |
| KR | 10-2017-0063394 | A | | 6/2017 |
| KR | 20170063394 | A | * | 6/2017 |
| KR | 10-2018-0041607 | A | | 4/2018 |
| KR | 20180041607 | A | * | 4/2018 |
| WO | 2003/012890 | A2 | | 2/2003 |
| WO | WO-2016195441 | A1 | * | 12/2016 ........... C07D 487/06 |
| WO | WO-2017030307 | A1 | * | 2/2017 ........... C07D 209/82 |
| WO | WO-2017104994 | A1 | * | 6/2017 ........... C07D 209/82 |

OTHER PUBLICATIONS

Computer-generated English-language translation of KR-20180041607-A.*

* cited by examiner

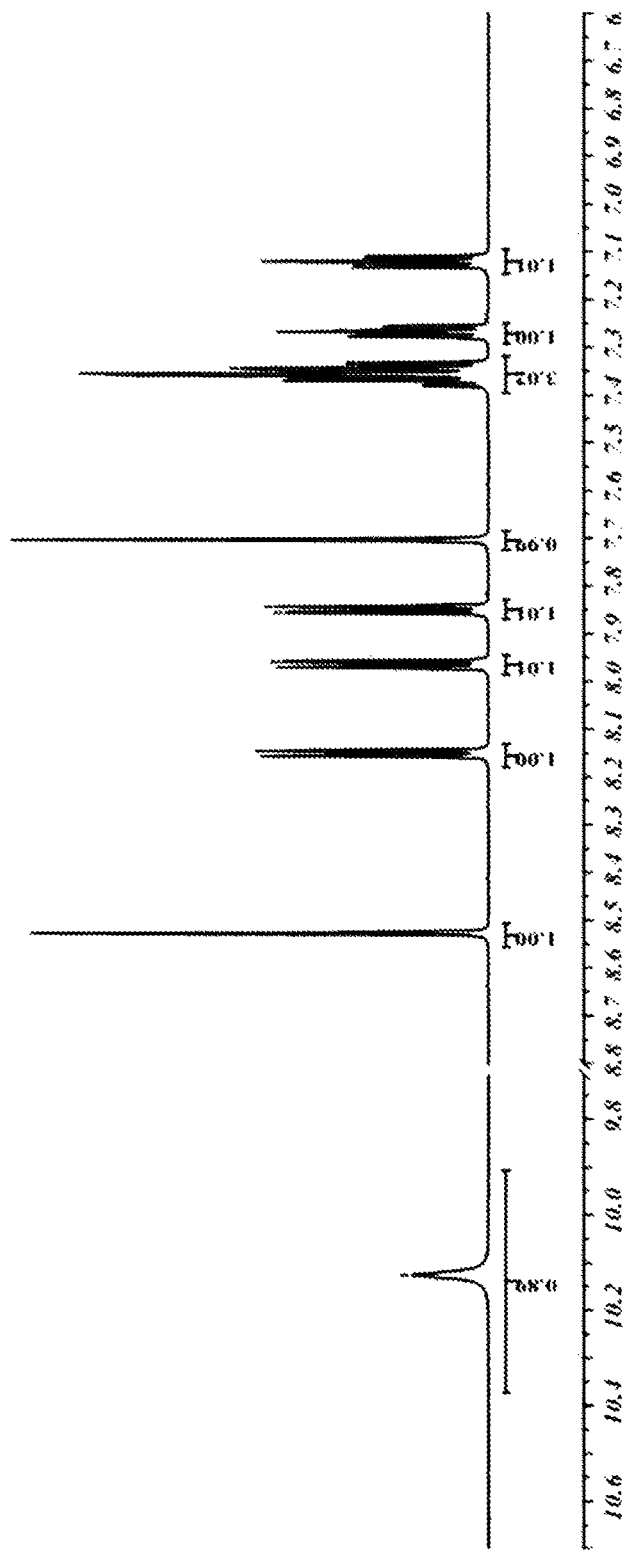
[FIG. 3]

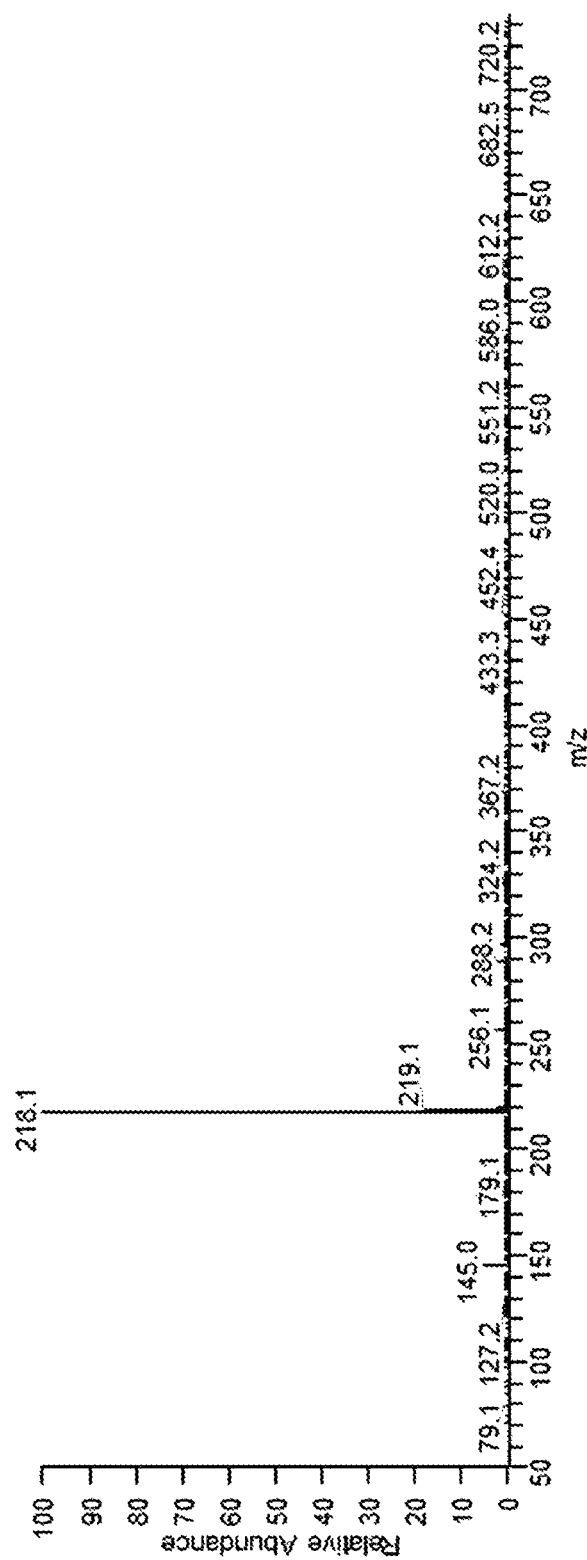
[FIG. 4]

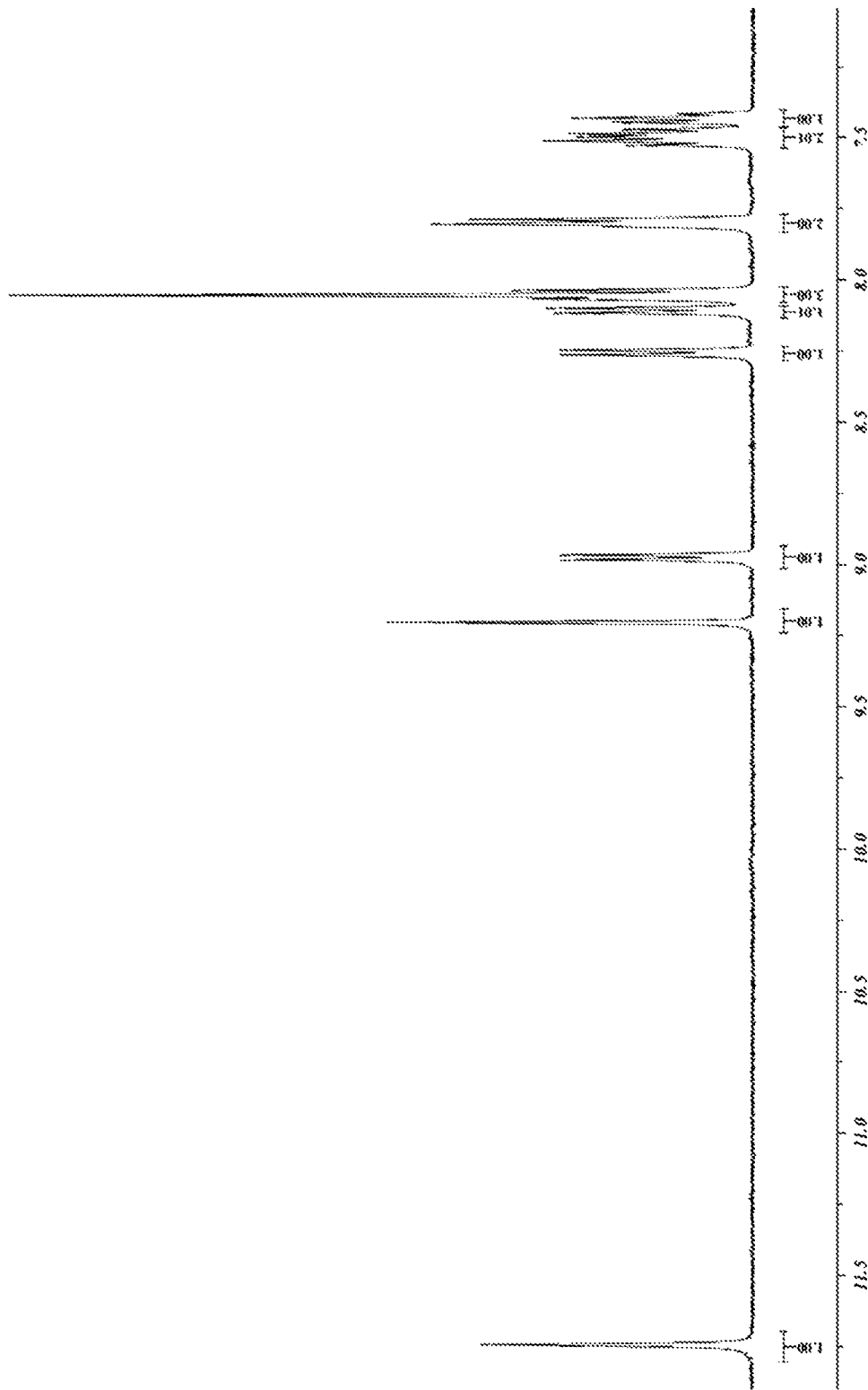
[FIG. 5]

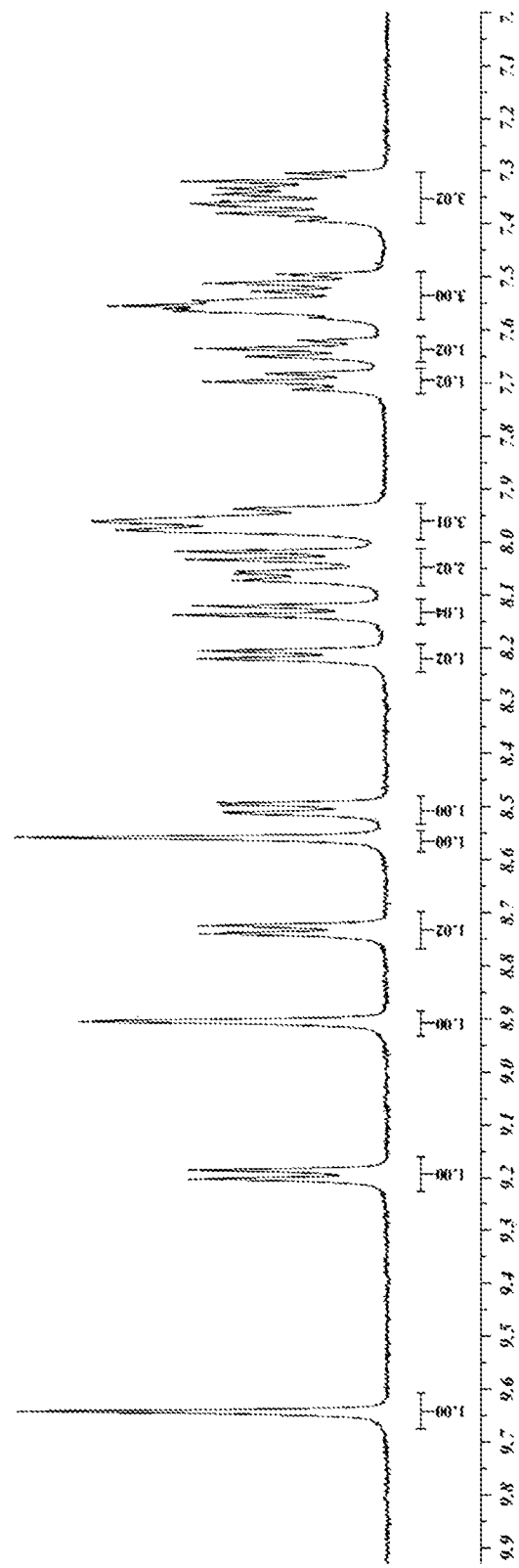
[FIG. 6]

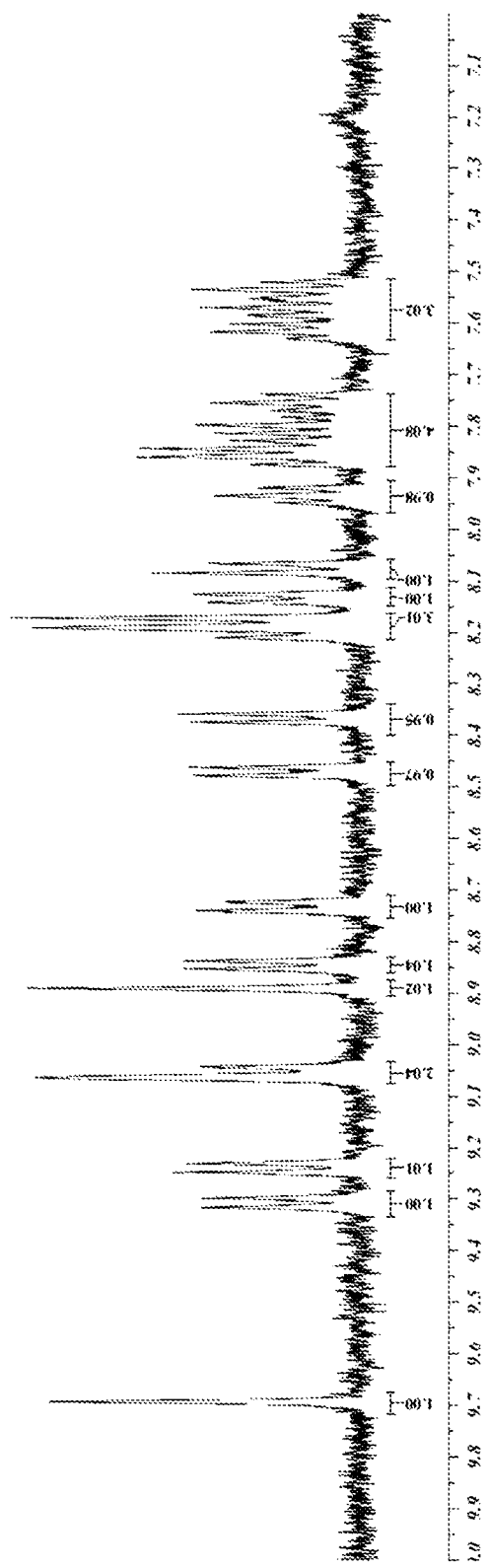
[FIG. 7]

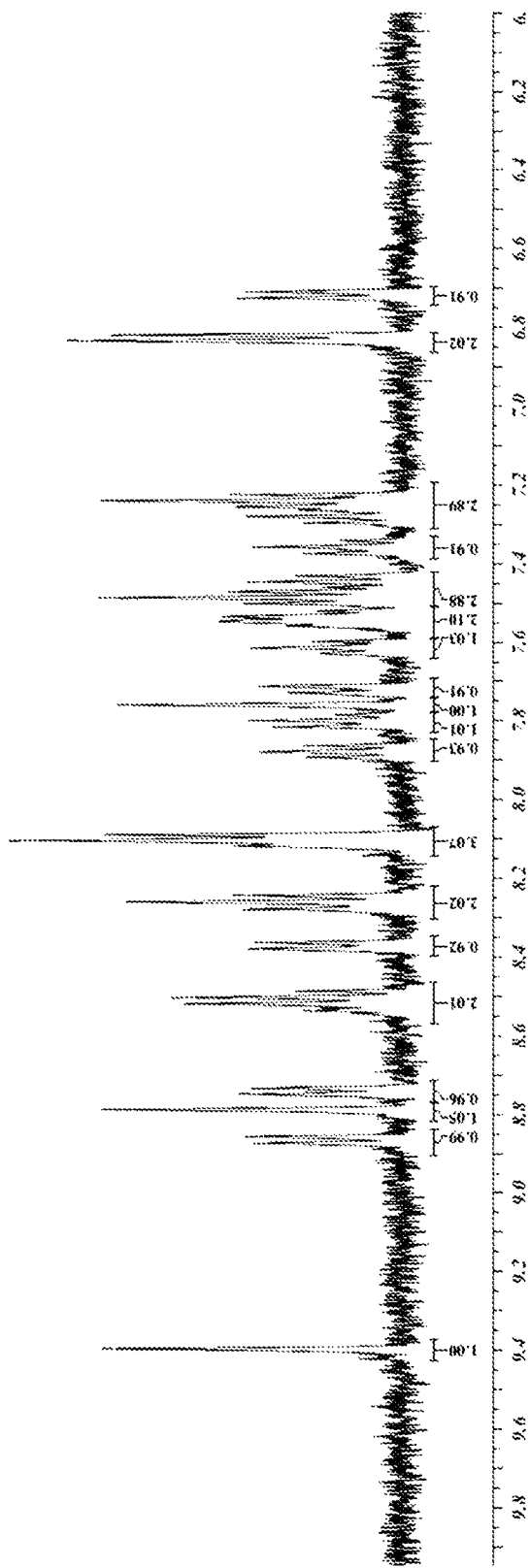
[FIG. 8]

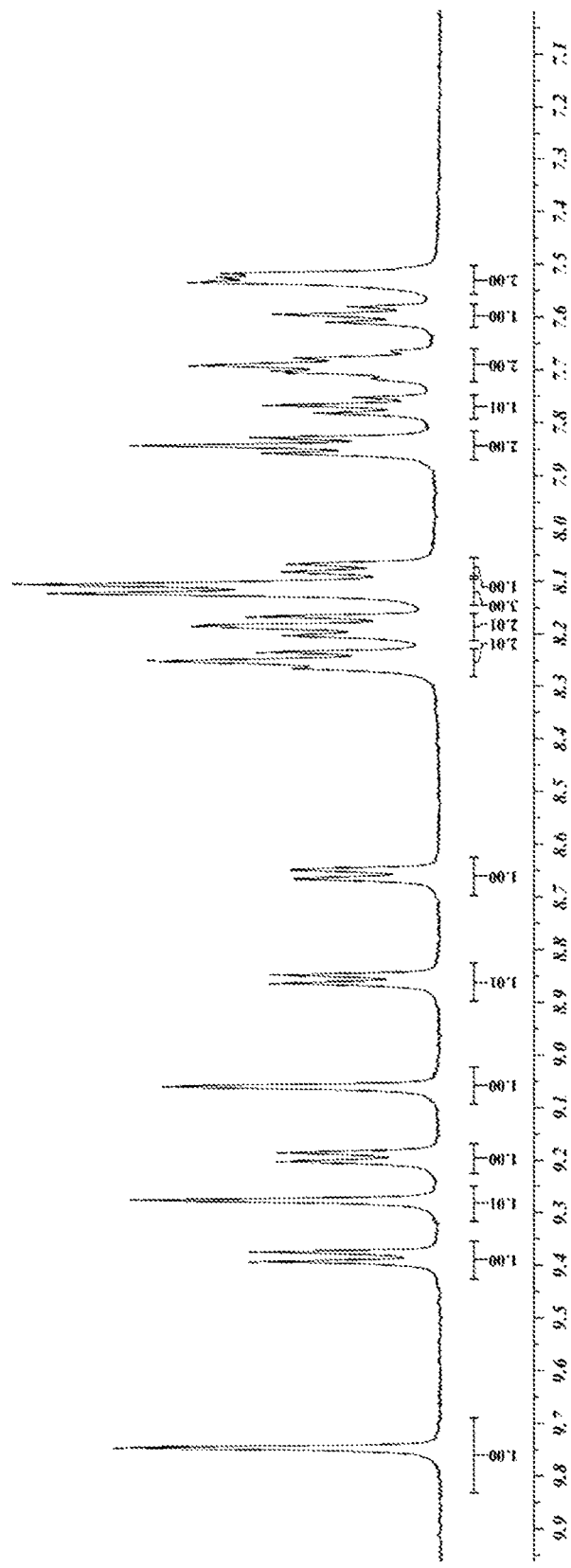
[FIG. 9]

COMPOUND AND ORGANIC LIGHT-EMITTING DIODE COMPRISING SAME

CROSS-REFERENCE APPLICATION

This is a National Stage Application of International Application No. PCT/KR2018/008247, filed Jul. 20, 2018 and claims priority to and the benefits of Korean Patent Application No. 10-2017-0091898, filed with the Korean Intellectual Property Office on Jul. 20, 2017, the entire contents of which are incorporated herein by reference.

TECHNICAL FIELD

The present application relates to a compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including a first electrode, a second electrode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the first electrode and the second electrode, respectively, and when the injected holes and electrons meet, excitons are formed, and light emits when these excitons fall back to the ground state.

Development of new materials for such an organic light emitting device has been continuously required.

DISCLOSURE

Technical Problem

The present application is directed to providing a compound, and an organic light emitting device including the same.

Technical Solution

One embodiment of the present application provides a compound represented by the following Chemical Formula 1.

[Chemical Formula 1]

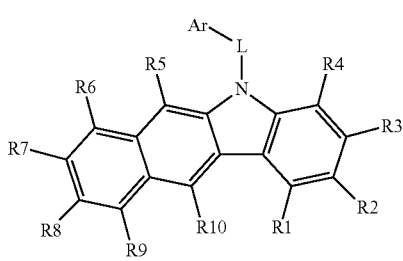

wherein in Chemical Formula 1,

R1 to R4 are each independently hydrogen or deuterium, or adjacent groups of R1 to R4 may each independently bond to each other to form a ring, R5 to R10 are each independently hydrogen; or deuterium;

L is a direct bond, a substituted or unsubstituted arylene group, or a substituted or unsubstituted heterocyclic group, and Ar is represented by the following Chemical Formula 2,

[Chemical Formula 2]

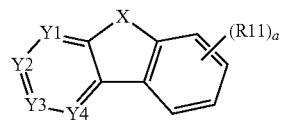

wherein in Chemical Formula 2, two of Y1 to Y4 are N, and the remaining two are C and CR, X is O, S or CR'R", R' and R" are a methyl group, R and R11 are each independently hydrogen; deuterium; a halogen group; a nitrile group; a nitro group; a hydroxyl group; an aryloxy group; an alkylthioxy group; an arylthioxy group; an alkylsulfoxy group; an arylsulfoxy group; a silyl group; a boron group; a substituted or unsubstituted alkyl group; a substituted or unsubstituted cycloalkyl group; a substituted or unsubstituted alkenyl group; a substituted or unsubstituted aryl group; a substituted or unsubstituted aralkyl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted heterocyclic group, a is an integer of 1 to 4, and when a is 2 or greater, two or more R11s are the same as or different from each other.

Another embodiment of the present application provides an organic light emitting device including a first electrode; a second electrode provided to face the first electrode; and one or more organic material layers provided between the first electrode and the second electrode, wherein one or more layers of the one or more organic material layers include the compound described above.

Advantageous Effects

An organic light emitting device using a compound according to one embodiment of the present application is capable of obtaining a low driving voltage, high light emission efficiency and/or a long lifetime.

DESCRIPTION OF DRAWINGS

FIG. 3 is a graph showing an 1H-NMR value of Chemical Formula a according to one embodiment of the present specification, and FIG. 4 is a graph showing an MS value of Chemical Formula a.

FIG. 5 is a graph showing an 1H-NMR value of Chemical Formula d according to one embodiment of the present specification.

FIG. 6 is a graph showing an 1H-NMR value of Chemical Formula 5 according to one embodiment of the present specification.

FIG. 7 is a graph showing an 1H-NMR value of Chemical Formula 40 according to one embodiment of the present specification.

FIG. 8 is a graph showing an 1H-NMR value of Chemical Formula 451 according to one embodiment of the present specification.

FIG. 9 is a graph showing an 1H-NMR value of Chemical Formula 809 according to one embodiment of the present specification.

MODE FOR DISCLOSURE

Figure 1:
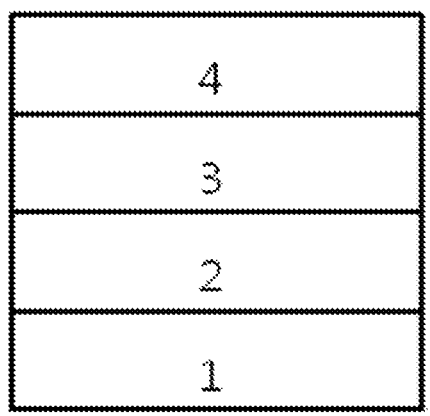
FIG. 1 illustrates an organic light emitting device in which a substrate (1), a first electrode (2), a light emitting layer (3) and a second electrode (4) are consecutively laminated.

Hereinafter, the present specification will be described in more detail.

One embodiment of the present specification provides a compound represented by Chemical Formula 1.

According to one embodiment of the present application, the compound represented by Chemical Formula 1 has, by having a core structure as above, an advantage of controlling triplet energy, and may exhibit long lifetime and high efficiency properties.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being unsubstituted or substituted with one or more substituents selected from the substituent group consisting of a halogen group; a nitrile group; a nitro group; a hydroxyl group; an alkyl group; a cycloalkyl group; an alkenyl group; an amine group; an aryl group; and a heterocyclic group, or being unsubstituted or substituted with a substituent from the above substituent group which is further substituted by one or more selected from the above substituent group.

In the present specification, examples of the halogen group may include fluorine, chlorine, bromine or iodine.

In the present specification, the number of carbon atoms of the ester group is not particularly limited, but is preferably from 1 to 50. Specifically, compounds having the following structural formulae may be included, however, the ester group is not limited thereto.

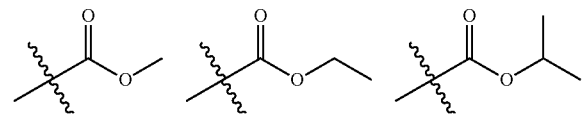

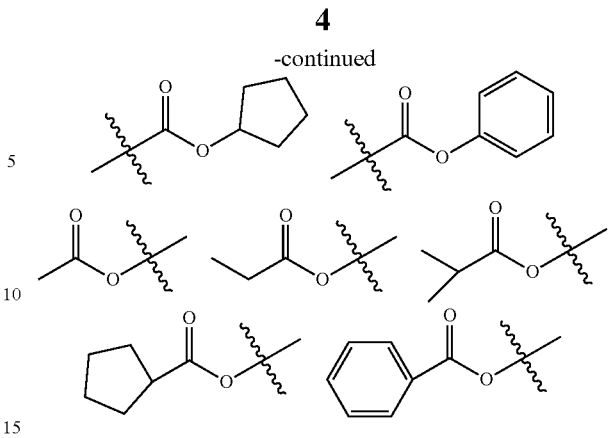

In the present specification, the number of carbon atoms of the carbonyl group is not particularly limited, but is preferably from 1 to 50. Specifically, compounds having structures as below may be included, however, the carbonyl group is not limited thereto.

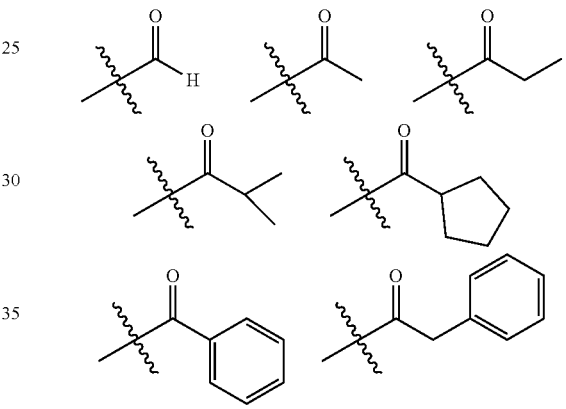

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, when the aryl group is a monocyclic aryl group, the number of carbon atoms is not particularly limited, but is preferably from 6 to 25. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 24. Specific examples of the polycyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

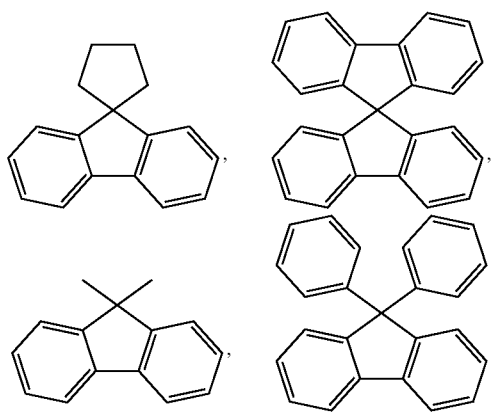

and the like may be included. However, the compound is not limited thereto.

In the present specification, the heterocyclic group is a group including one or more atoms that are not carbon, that is, heteroatoms, and specifically, the heteroatom may include one or more atoms selected from the group consisting of O, N, Se, S and the like. The number of carbon atoms of the heterocyclic group is not particularly limited, but is preferably from 2 to 60. Examples of the heterocyclic group may include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, descriptions on the aryl group provided above may be applied to the aromatic hydrocarbon ring except for those that are divalent.

In the present specification, descriptions on the heterocyclic group provided above may be applied to the heteroring except for those that are divalent.

In the present specification, descriptions on the aryl group provided above may be applied to the aryl group in the aryloxy group, the arylthioxy group, the arylsulfoxy group, the arylphosphine group, the aralkyl group, the aralkylamine group, the aralkenyl group and the arylamine group.

In the present specification, descriptions on the alkyl group provided above may be applied to the alkyl group in the alkylthioxy group, the alkylsulfoxy group, the aralkyl group, the aralkylamine group and the alkylamine group.

In the present specification, descriptions on the heterocyclic group provided above may be applied to the heteroaryl group, and the heteroaryl group in the heteroarylamine group.

In the present specification, descriptions on the alkenyl group provided above may be applied to the alkenyl group in the aralkenyl group.

In the present specification, descriptions on the aryl group provided above may be applied to the arylene except for being divalent.

In the present specification, descriptions on the heterocyclic group provided above may be applied to the heteroarylene except for being divalent.

In the present specification, adjacent groups bonding to each other to form a ring means adjacent groups bonding to each other to form a substituted or unsubstituted aliphatic hydrocarbon ring; a substituted or unsubstituted aromatic hydrocarbon ring; a substituted or unsubstituted aliphatic heteroring; or a substituted or unsubstituted aromatic heteroring.

In the present specification, the aliphatic hydrocarbon ring means, as a ring that is not aromatic, a ring formed only with carbon and hydrogen atoms.

In the present specification, examples of the aromatic hydrocarbon ring includes a phenyl group, a naphthyl group, an anthracenyl group and the like, but are not limited thereto.

In the present specification, the aliphatic heteroring means an aliphatic ring including one or more of heteroatoms.

In the present specification, the aromatic heteroring means an aromatic ring including one or more of heteroatoms.

In the present specification, the aliphatic hydrocarbon ring, the aromatic hydrocarbon ring, the aliphatic heteroring and the aromatic heteroring may be monocyclic or polycyclic.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, adjacent groups bonding to each other to form a ring means, as described above, adjacent groups bonding to each other to a 5-membered to 8-membered hydrocarbon ring or a 5-membered to 8-membered heteroring, and the ring may be monocyclic or polycyclic, aliphatic, aromatic, or a fused form thereof, but is not limited thereto.

According to one embodiment of the present application, R1 to R10 are each independently hydrogen; deuterium; a halogen group; a nitrile group; a nitro group; a hydroxyl group; an aryloxy group; an alkylthioxy group; an arylthioxy group; an alkylsulfoxy group; an arylsulfoxy group; a silyl group; a boron group; a substituted or unsubstituted alkyl group; a substituted or unsubstituted cycloalkyl group; a substituted or unsubstituted alkenyl group; a substituted or unsubstituted aryl group; a substituted or unsubstituted aralkyl group; a substituted or unsubstituted alkylamine group; a substituted or unsubstituted aralkylamine group; a substituted or unsubstituted arylamine group; or a substituted or unsubstituted arylphosphine group.

According to one embodiment of the present application, R1 to R10 are each independently hydrogen; or deuterium.

According to one embodiment of the present application, R1 to R10 are hydrogen.

According to one embodiment of the present application, adjacent groups of R1 to R4 may each independently bond to each other to form a ring.

According to one embodiment of the present application, adjacent groups of R1 to R4 may each independently bond to each other to form an aryl group having 6 to 60 carbon atoms.

According to one embodiment of the present application, adjacent groups of R1 to R4 may each independently bond to each other to form an aryl group having 6 to 30 carbon atoms.

According to one embodiment of the present application, adjacent groups of R1 to R4 may each independently bond to each other to form an aryl group having 6 to 15 carbon atoms.

According to one embodiment of the present application, adjacent groups of R1 to R4 may each independently bond to each other to form a phenyl group.

According to one embodiment of the present application, R1 and R2; R2 and R3; or R3 and R4 may bond to each other to form a phenyl group.

According to one embodiment of the present application, L is a direct bond; a substituted or unsubstituted arylene group, or a substituted or unsubstituted heterocyclic group.

According to one embodiment of the present application, L is a direct bond; a substituted or unsubstituted arylene group having 6 to 60 carbon atoms, or a substituted or unsubstituted heterocyclic group having 2 to 60 carbon atoms.

According to one embodiment of the present application, L is a direct bond; a substituted or unsubstituted arylene group having 6 to 30 carbon atoms, or a substituted or unsubstituted heterocyclic group having 2 to 30 carbon atoms.

According to one embodiment of the present application, L is a direct bond; a substituted or unsubstituted arylene group having 6 to 15 carbon atoms, or a substituted or unsubstituted heterocyclic group having 2 to 15 carbon atoms.

According to one embodiment of the present application, L is a direct bond; a substituted or unsubstituted arylene group having 6 to 15 carbon atoms, or a substituted or unsubstituted heterocyclic group having 2 to 15 carbon atoms including at least one N.

According to one embodiment of the present application, Ar is represented by the following Chemical Formula 2.

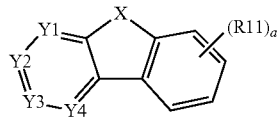

[Chemical Formula 2]

In Chemical Formula 2, two of Y1 to Y4 are N, and the remaining two are C which is a bonding site to L and CR, X is O, S or CR'R", and R and R11 are each independently hydrogen; deuterium; a halogen group; a nitrile group; a nitro group; a hydroxyl group; an aryloxy group; an alkylthioxy group; an arylthioxy group; an alkylsulfoxy group; an arylsulfoxy group; a silyl group; a boron group; a substituted or unsubstituted alkyl group; a substituted or unsubstituted cycloalkyl group; a substituted or unsubstituted alkenyl group; a substituted or unsubstituted aryl group; a substituted or unsubstituted aralkyl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted heterocyclic group, R' and R" are a methyl group, a is an integer of 1 to 4, and when a is 2 or greater, two or more R11s are the same as or different from each other.

According to one embodiment of the present application, Chemical Formula 1 is represented by any one selected from among the following Chemical Formulae 1-1 to 1-3.

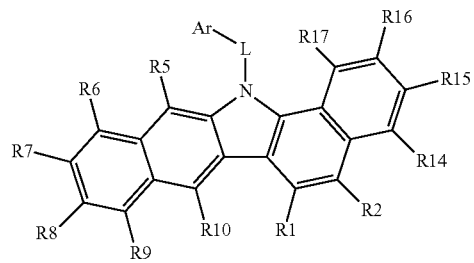

[Chemical Formula 1-1]

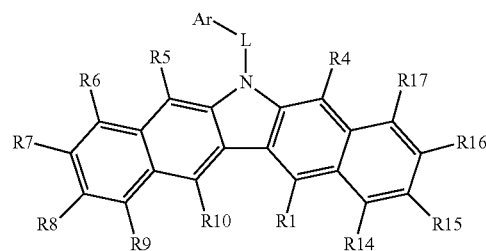

[Chemical Formula 1-2]

[Chemical Formula 1-3]

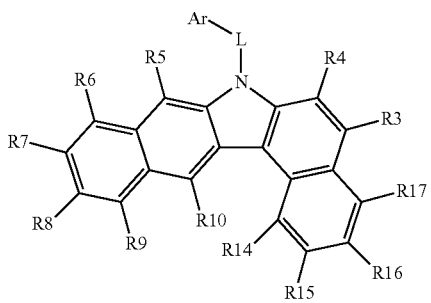

In Chemical Formulae 1-1 to 1-3,

R1 to R10, Ar and L have the same definitions as in Chemical Formulae 1, and

R14 to R17 are each independently hydrogen; or deuterium.

According to one embodiment of the present specification, Y1 and Y3 are N, Y2 is C, and Y4 is CR.

According to one embodiment of the present specification, Y1 and Y3 are N, Y4 is C, and Y2 is CR.

According to one embodiment of the present specification, Y1 and Y4 are N, Y2 is C, and Y3 is CR.

According to one embodiment of the present specification, Y1 and Y4 are N, Y3 is C, and Y2 is CR.

According to one embodiment of the present specification, Y1 and Y4 are N, Y3 is C, and Y2 is CR.

According to one embodiment of the present specification, Y2 and Y4 are N, Y1 is C, and Y3 is CR.

According to one embodiment of the present specification, R is a substituted or unsubstituted aryl group; or a substituted or unsubstituted heterocyclic group.

According to one embodiment of the present specification, R is a substituted or unsubstituted aryl group having 6 to 30 carbon atoms; or a substituted or unsubstituted heterocyclic group having 3 to 30 carbon atoms.

According to one embodiment of the present specification, Chemical Formula 2 is represented by any one selected from among the following Chemical Formulae 2-1 to 2-3.

[Chemical Formula 2-1]

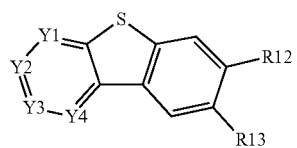

[Chemical Formula 2-2]

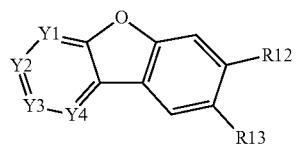

[Chemical Formula 2-3]

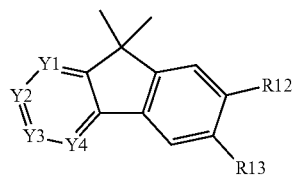

In Chemical Formulae 2-1 to 2-3,

Y1 to Y4 have the same definitions as above, and R12 and R13 each independently have the same definition as R11.

According to one embodiment of the present specification, the compound represented by Chemical Formula 1 is any one selected from among the following structural formulae.

1

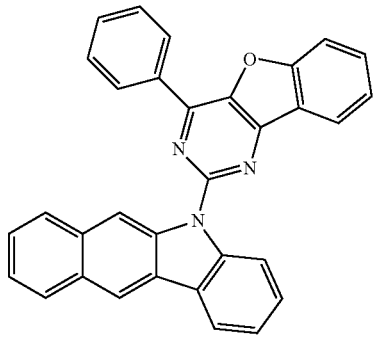

2

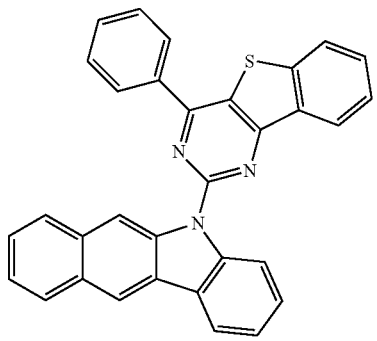

3

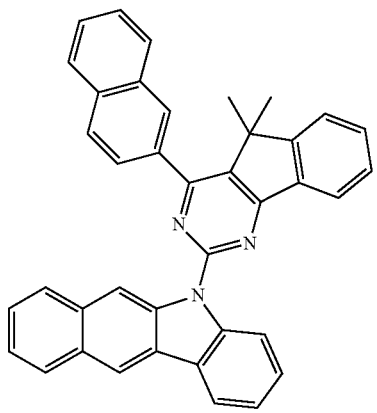

4
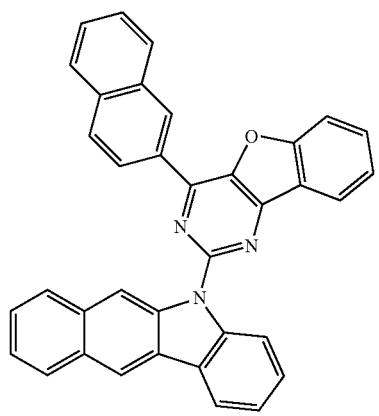
5
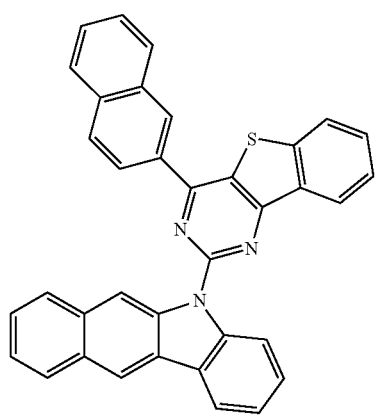
6
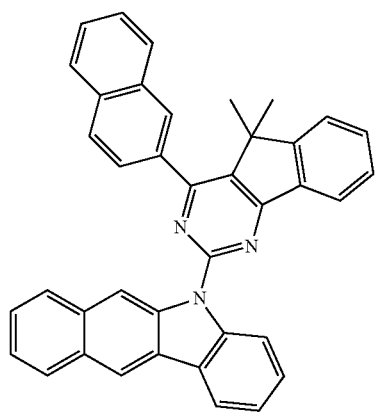
7
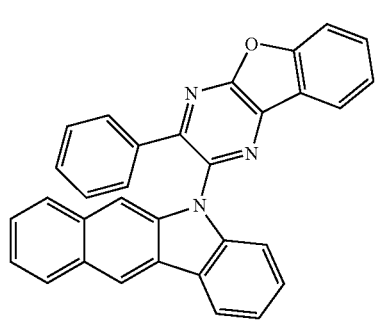
8
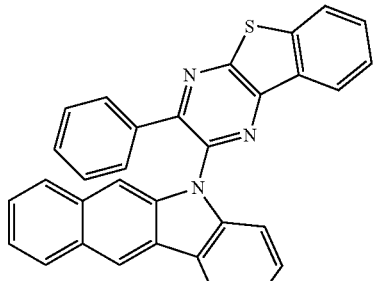
9
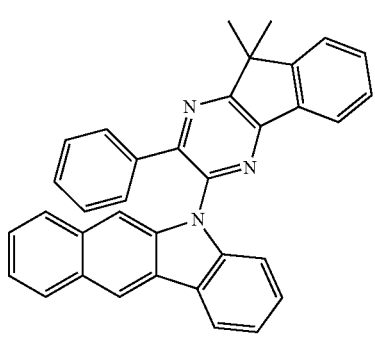
10
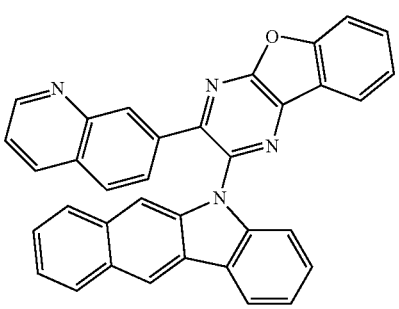
11
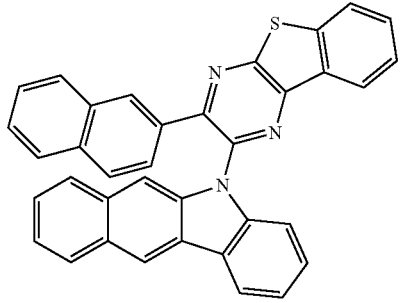
12
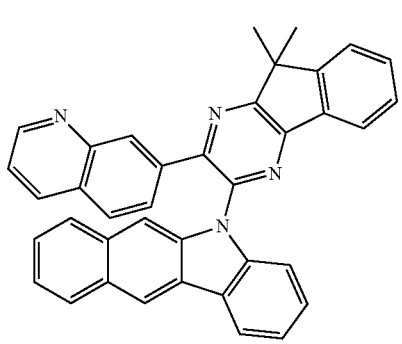

13
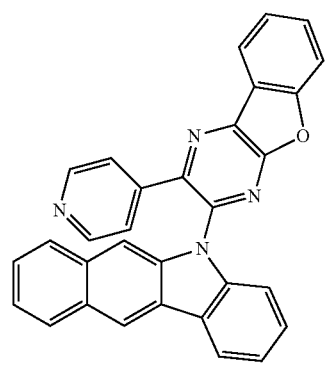
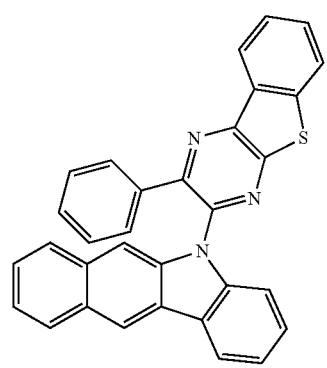
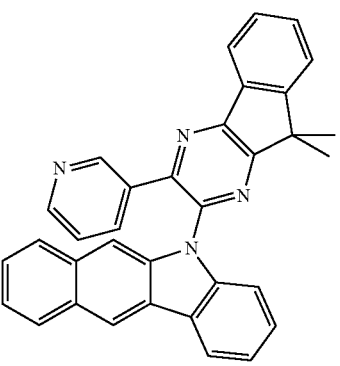
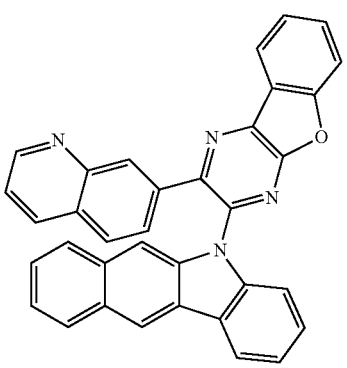
14
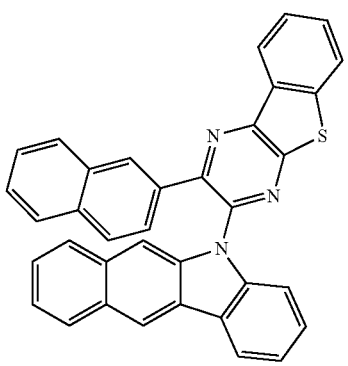
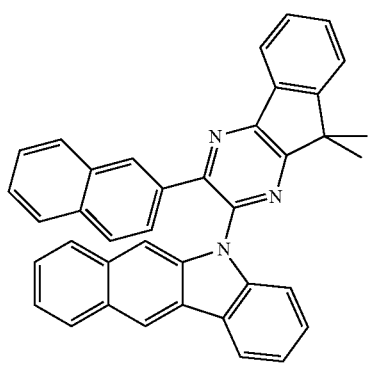
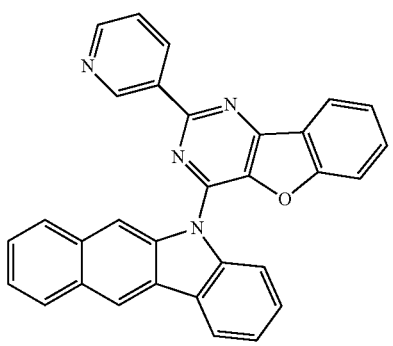
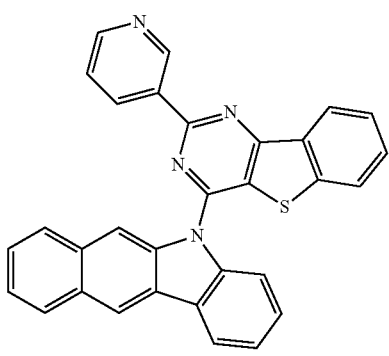

21
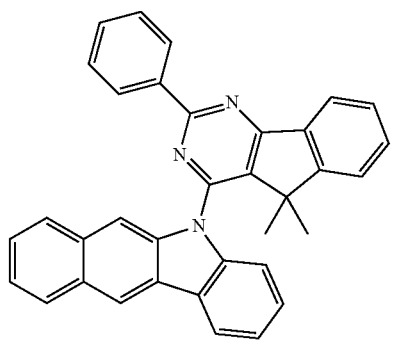
22
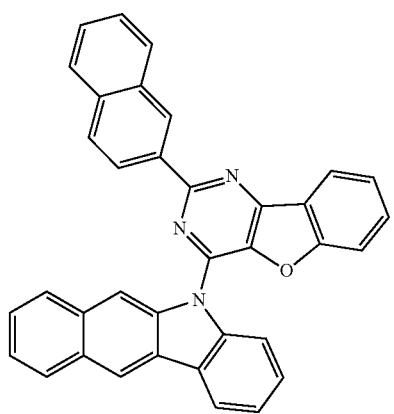
23
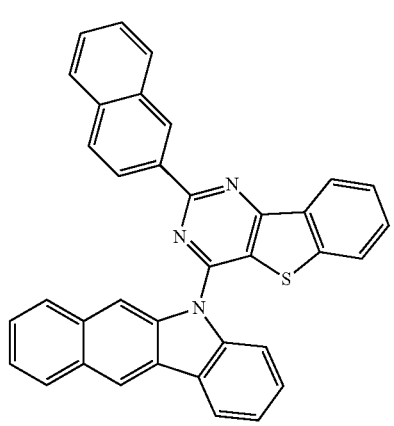
24
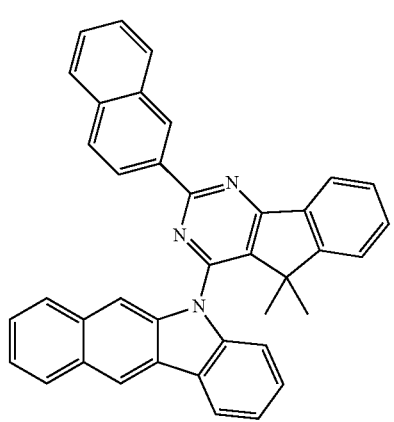
25
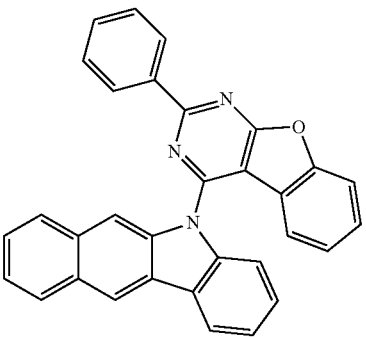
26
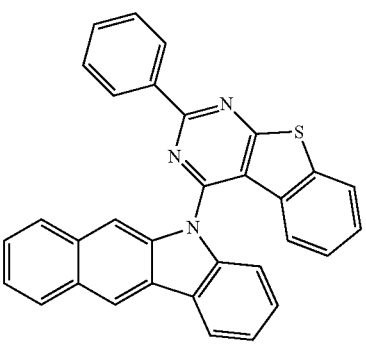
27
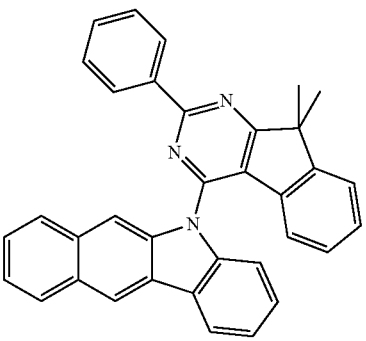
28
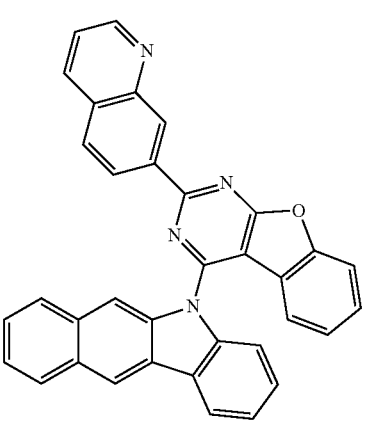

29
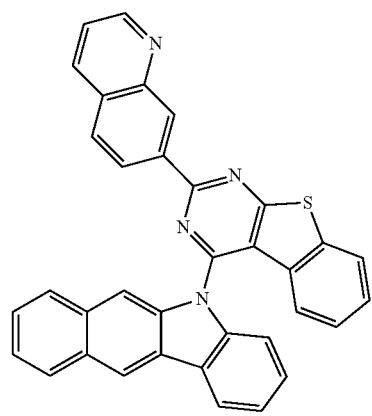
30
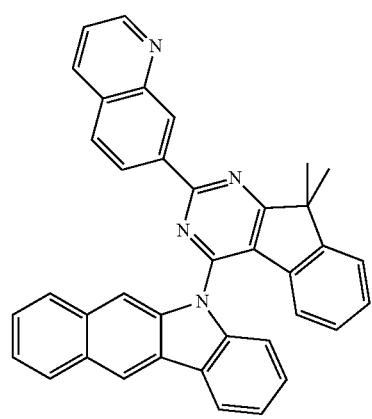
31
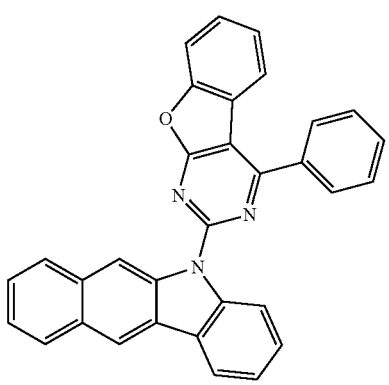
32
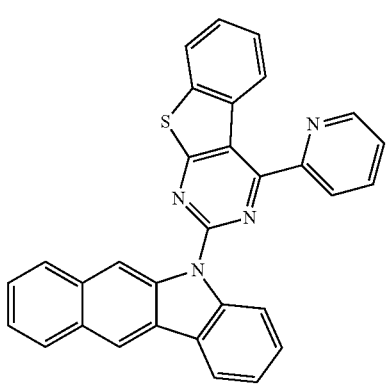
33
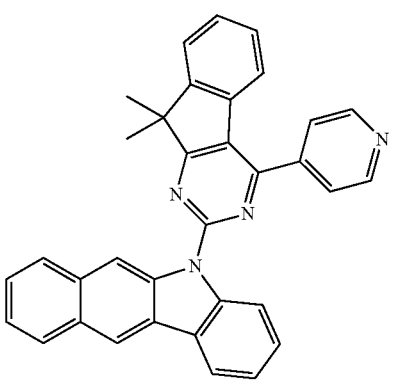
34

35
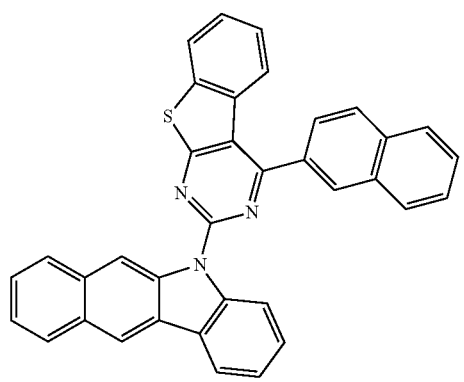
36
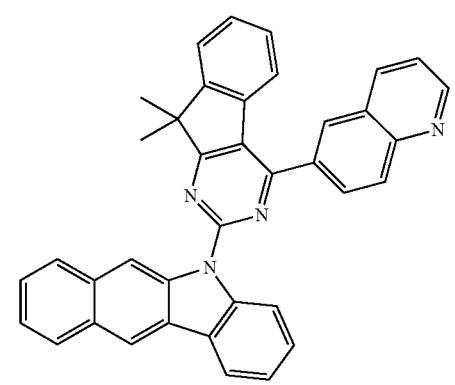

37
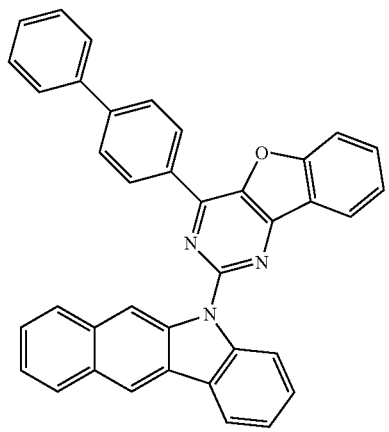
38
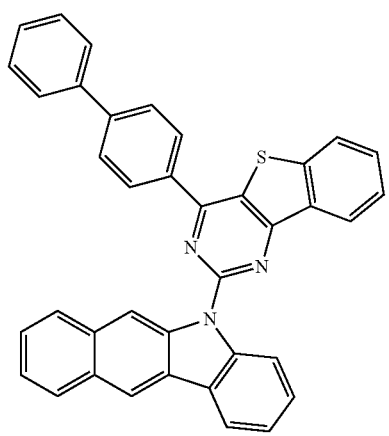
39
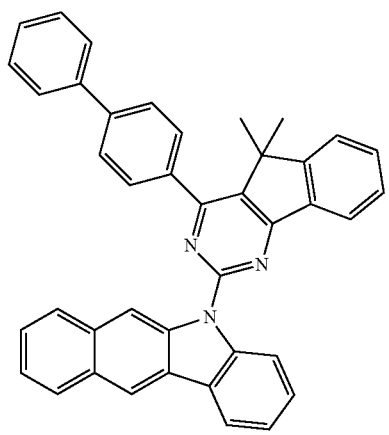
40
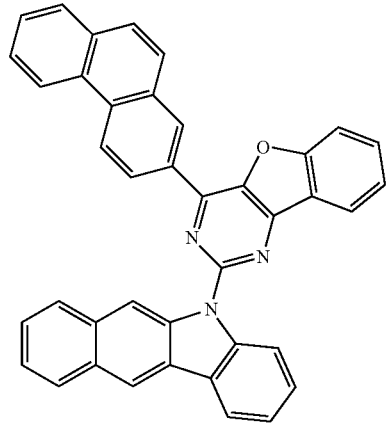
41
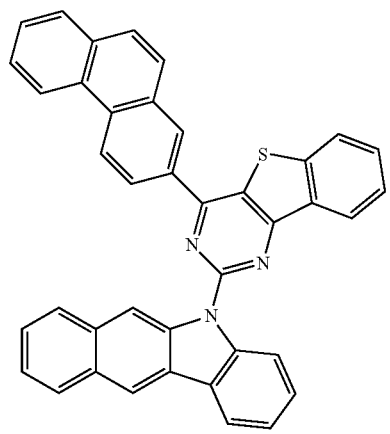
42
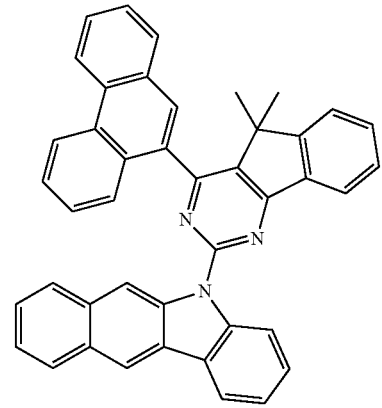
43
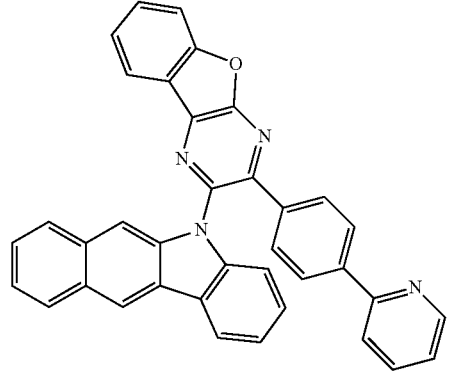

44
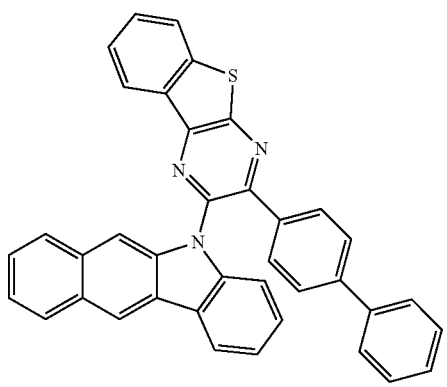
45
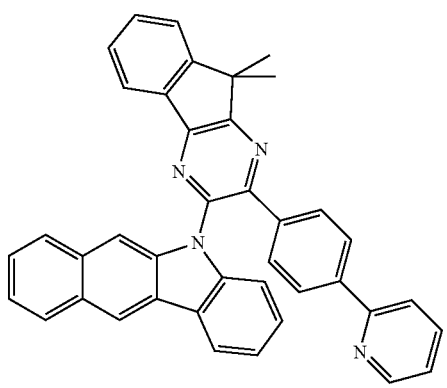
46
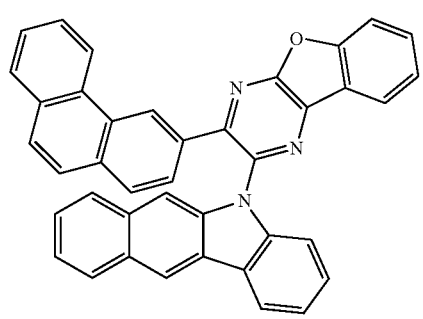
47
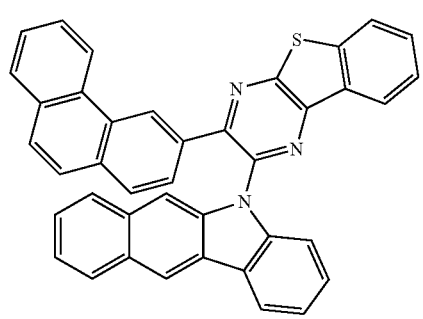
48
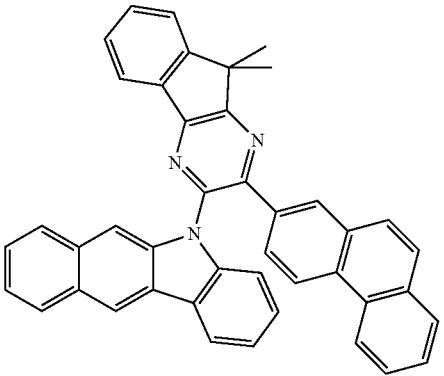
49
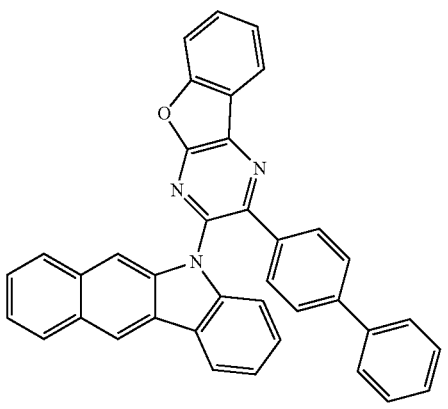
50
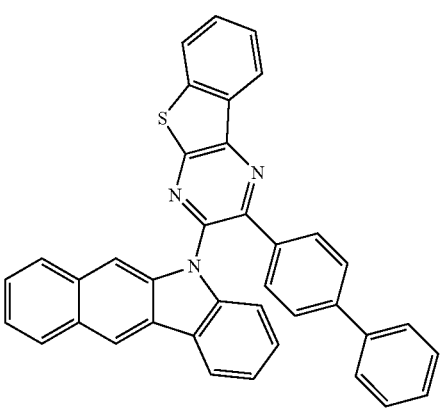
51
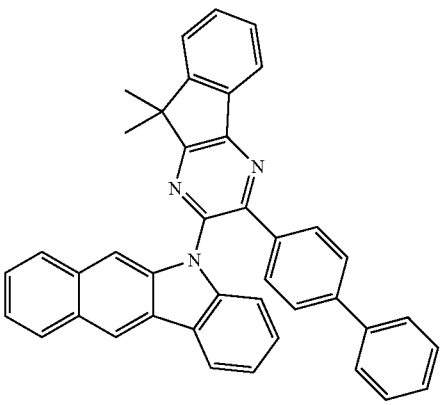

-continued
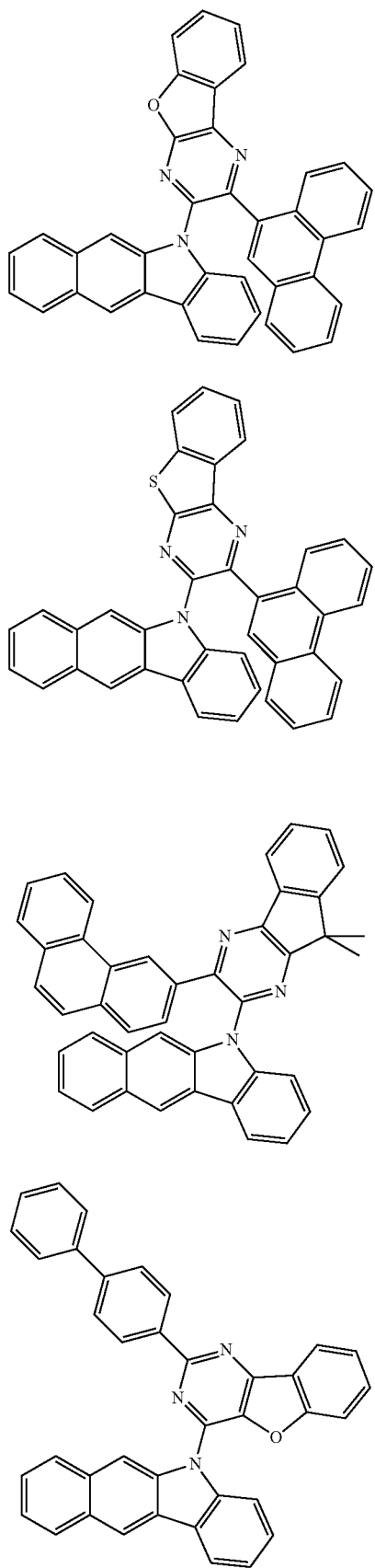
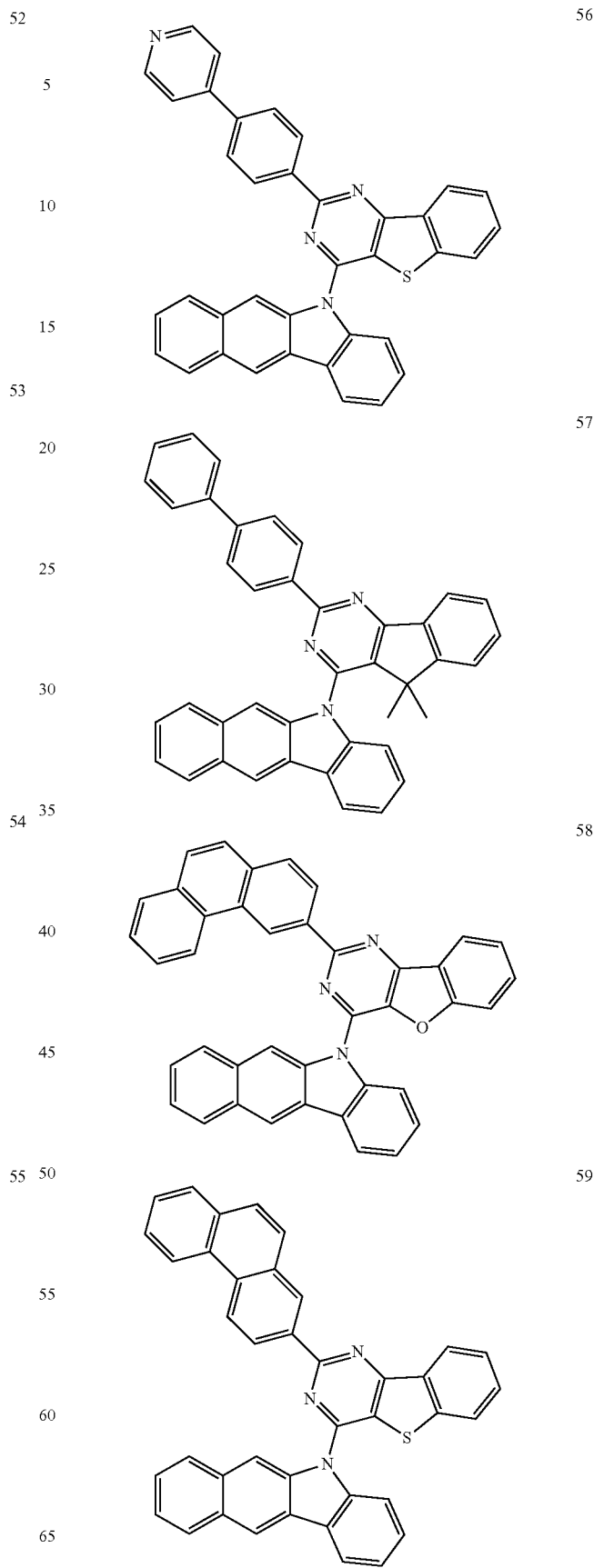

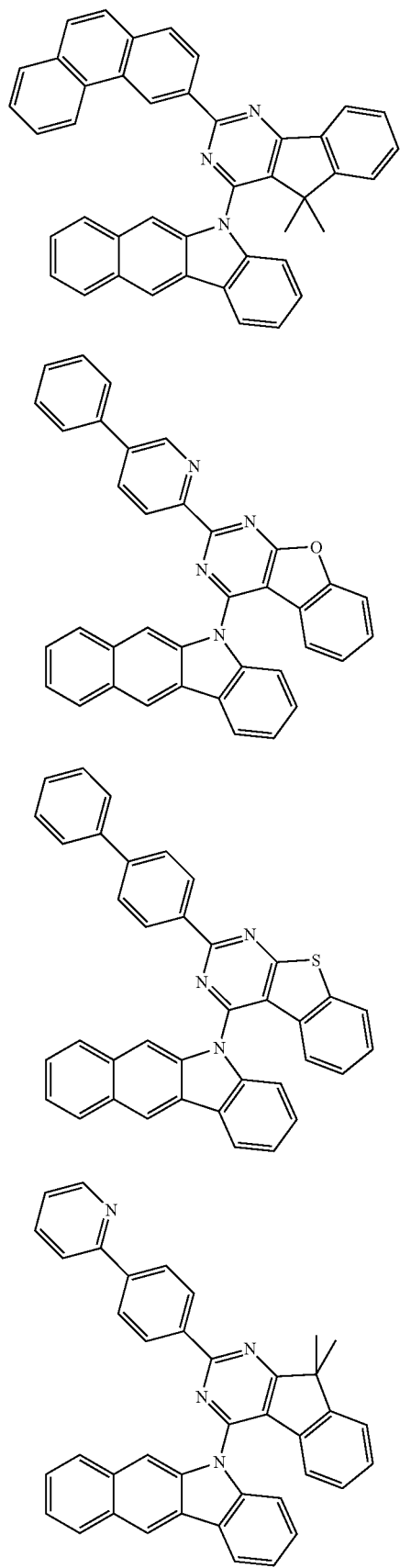

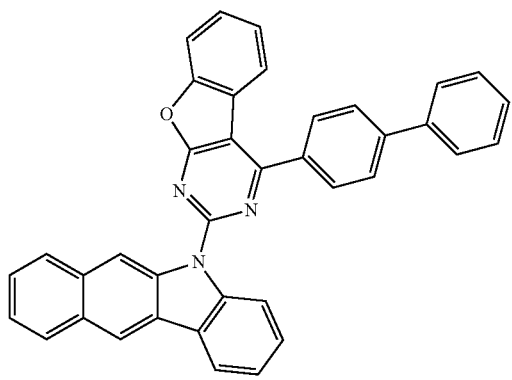 67
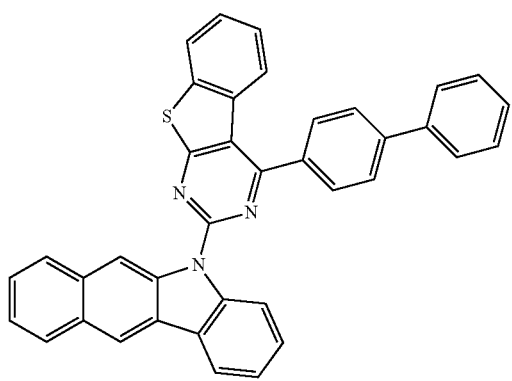 68
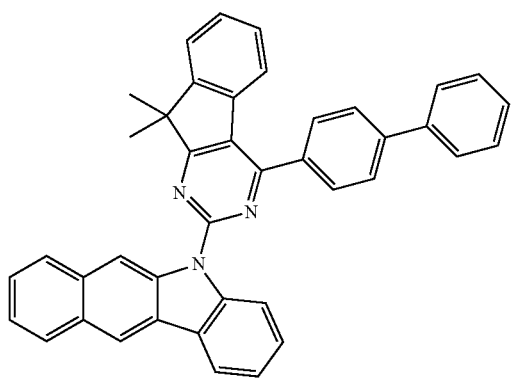 69
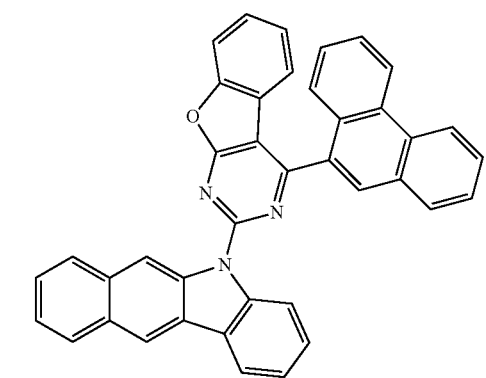 70
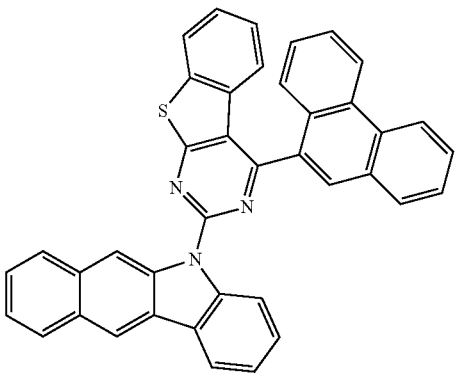 71
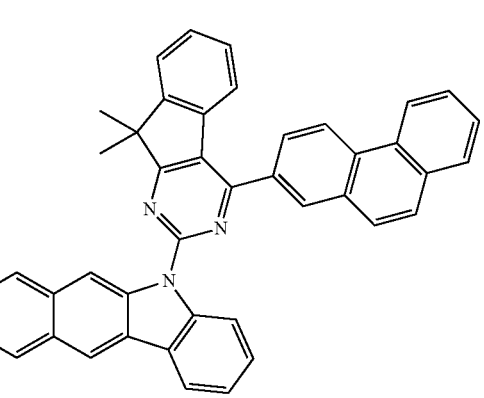 72
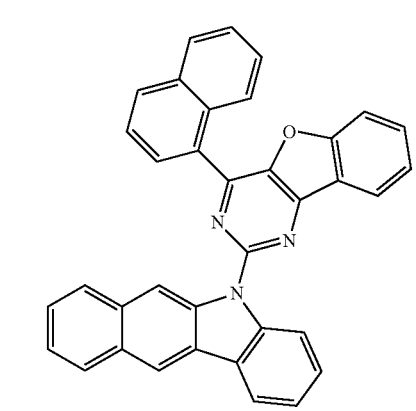 73
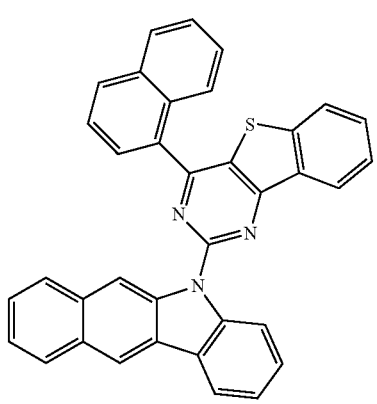 74

75
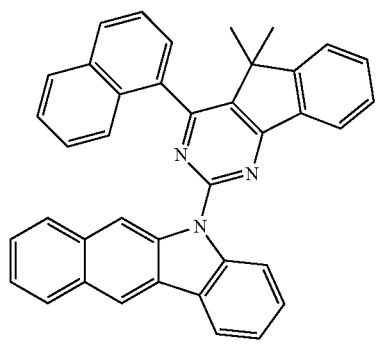
76
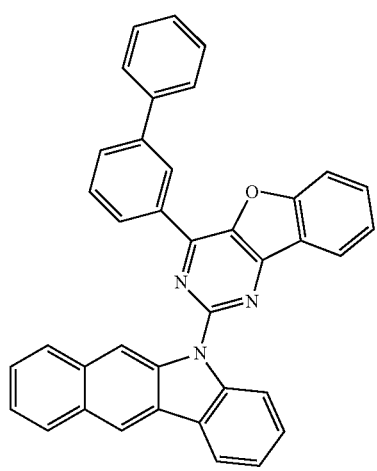
77
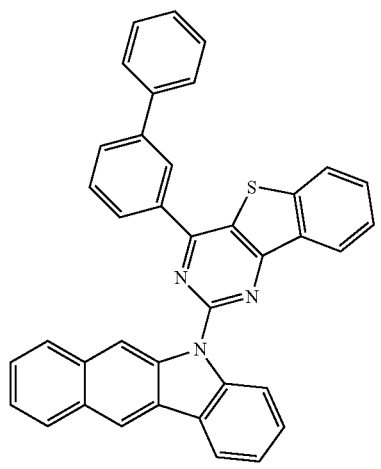
78
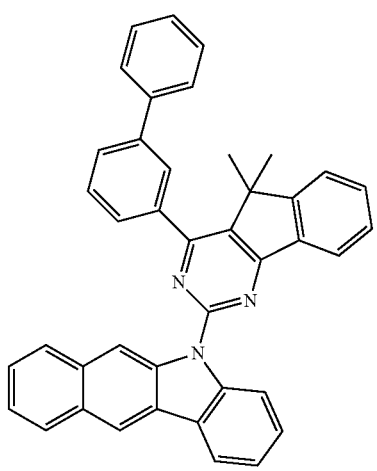
79
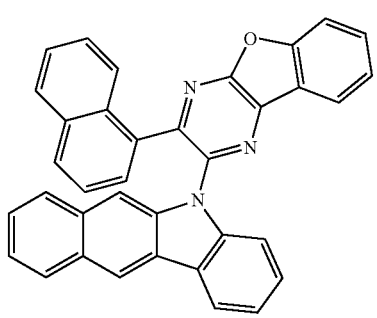
80
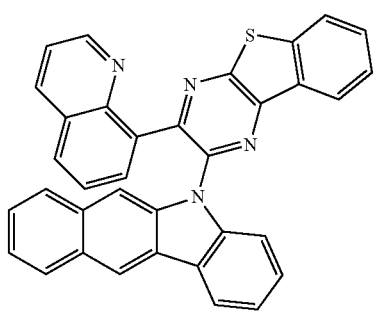
81
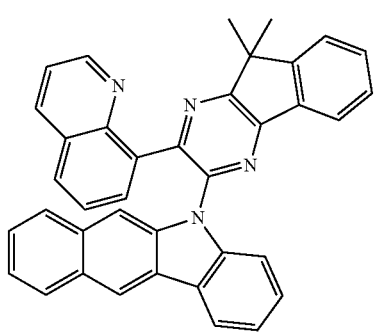

-continued
82
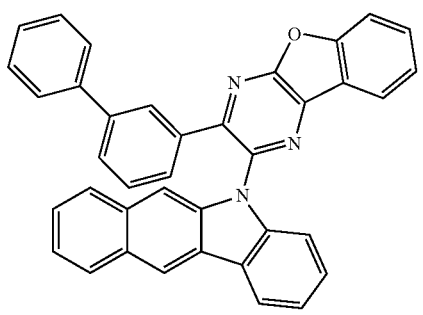
83
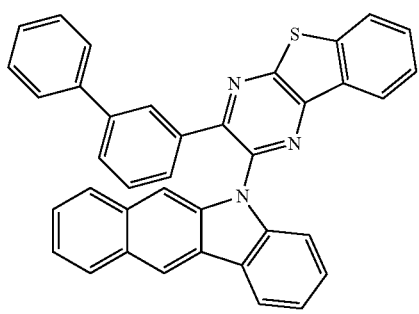
84
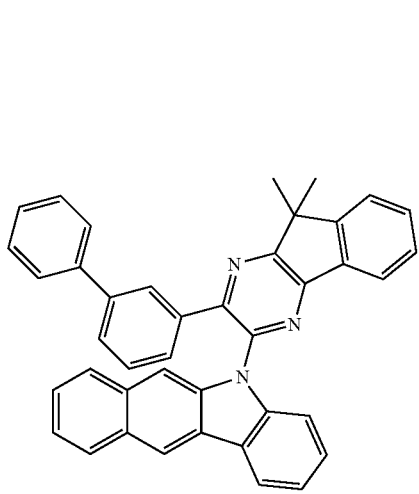
85
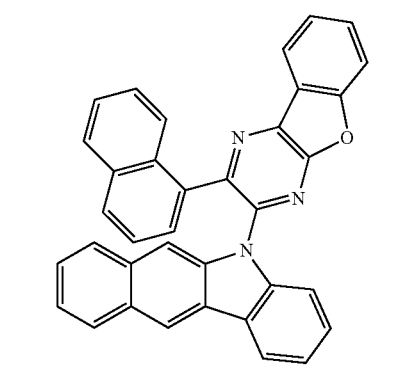
-continued
86
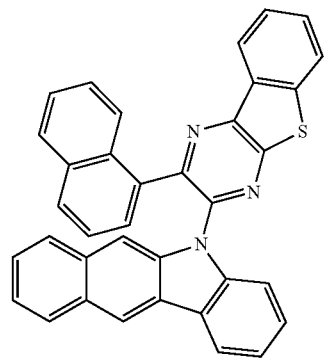
87
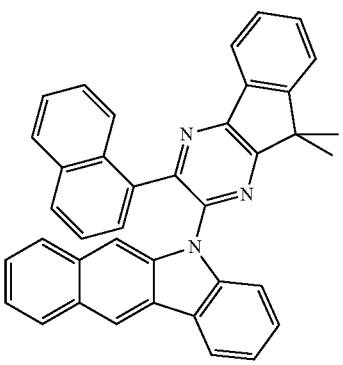
88
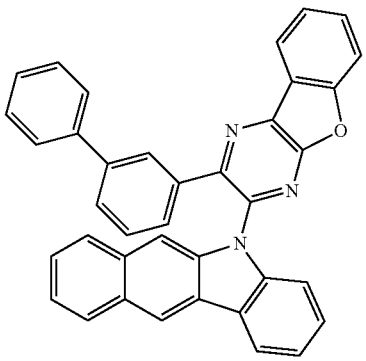
89
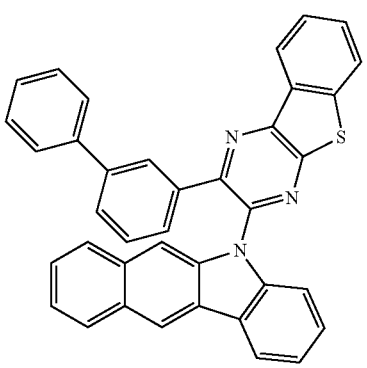

90
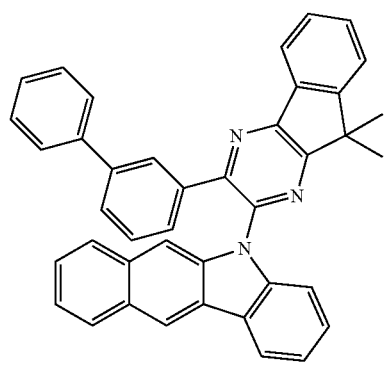
91
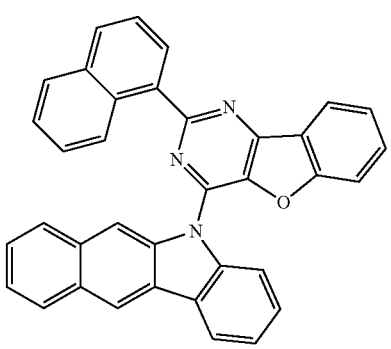
92
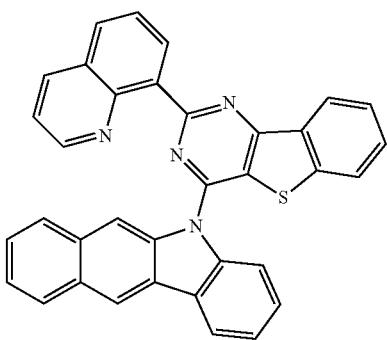
93
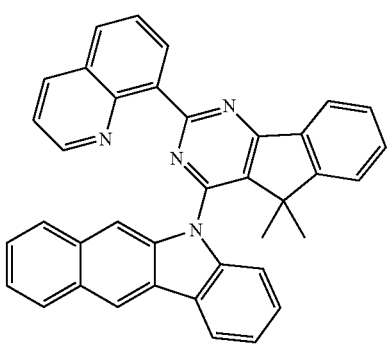
94
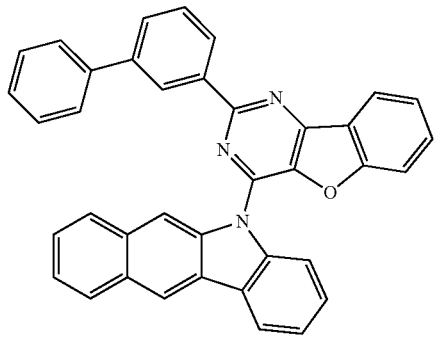
95
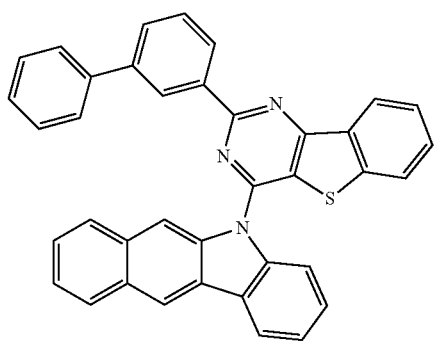
96
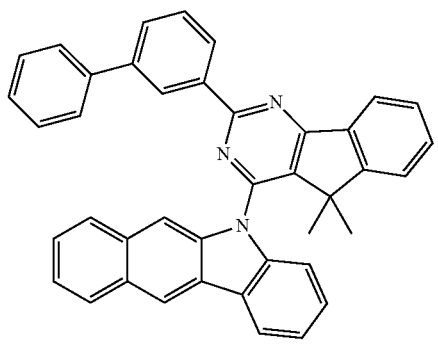
97
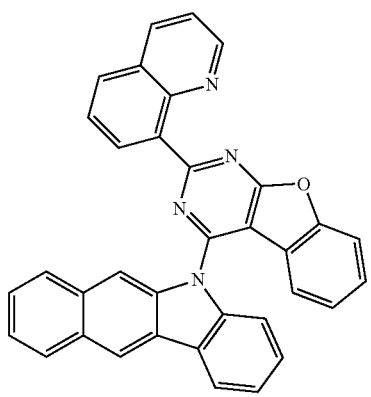

98
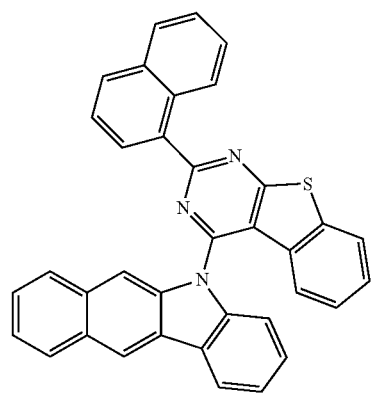
99
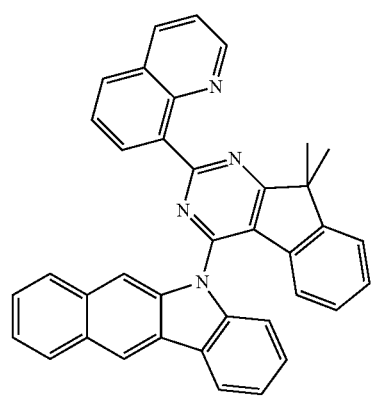
100
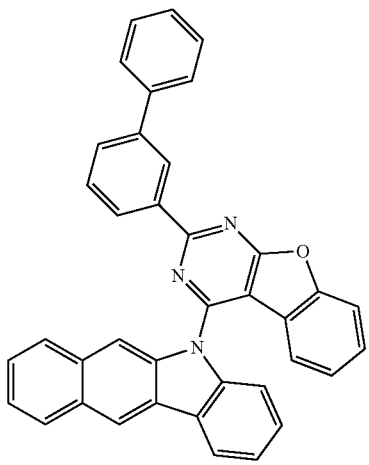
101
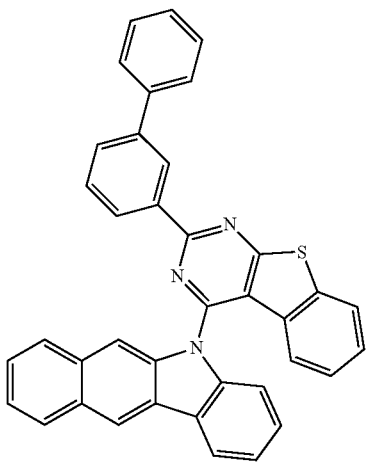
102
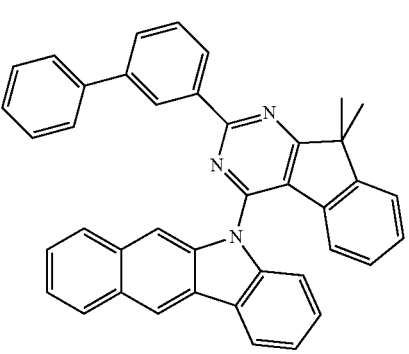
103
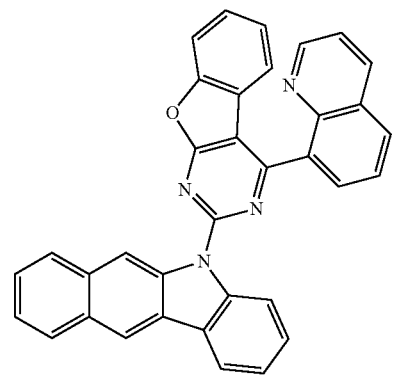
104
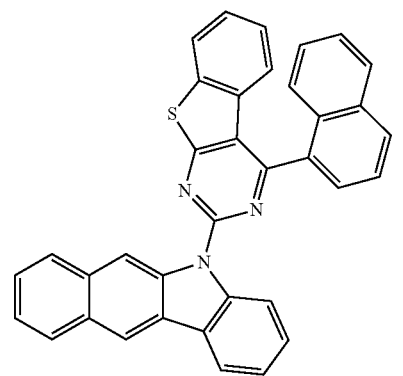

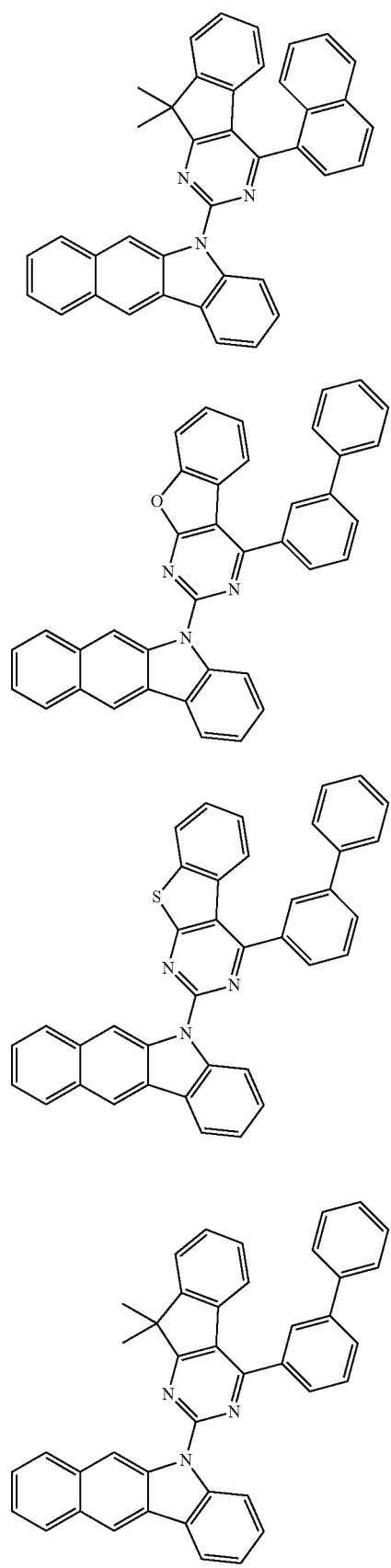
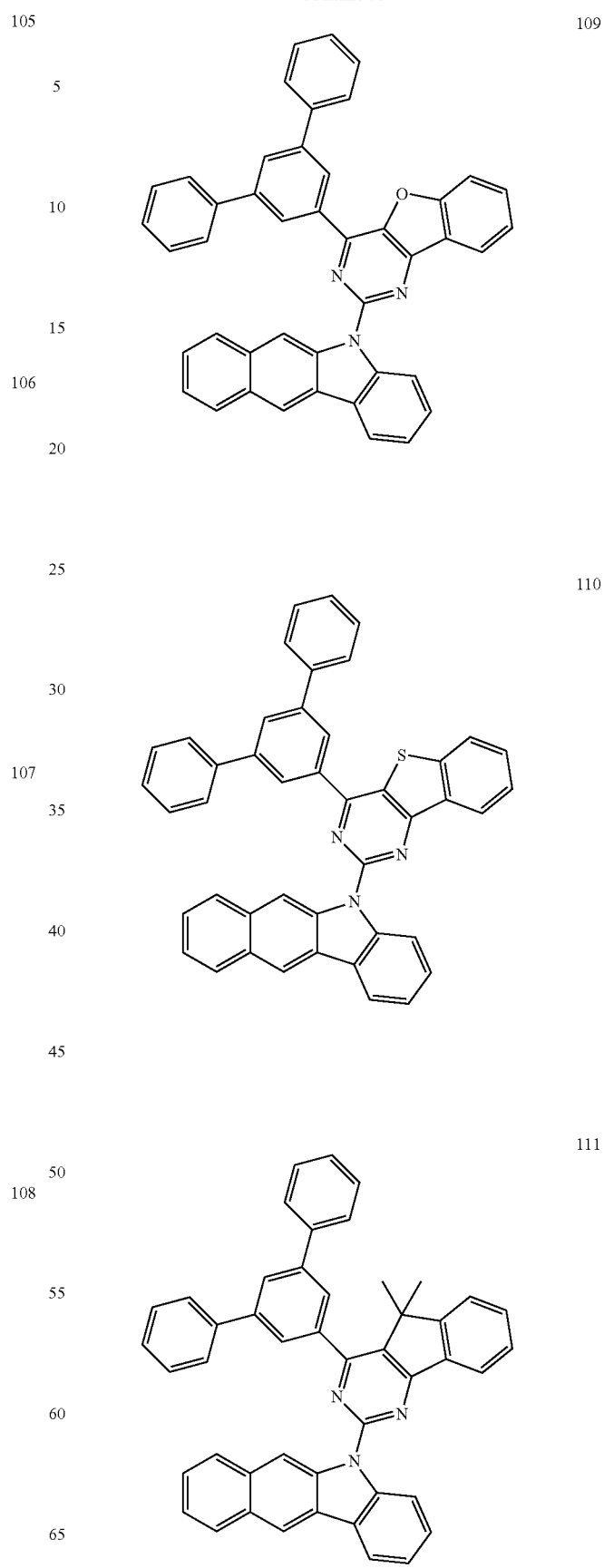

-continued
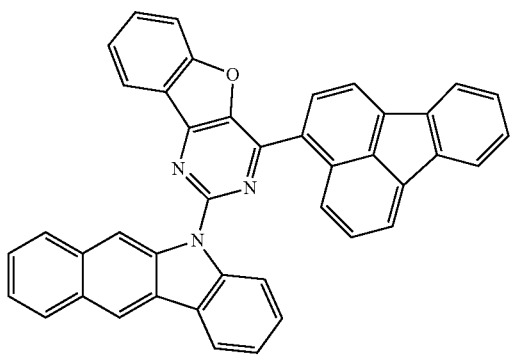
112
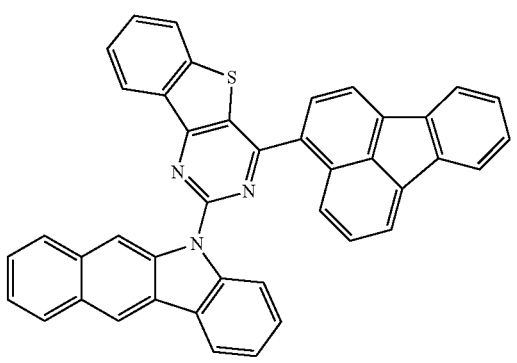
113
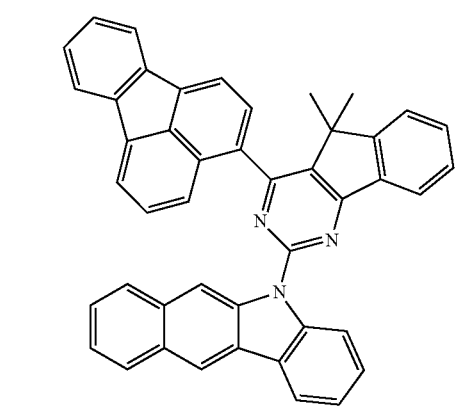
114
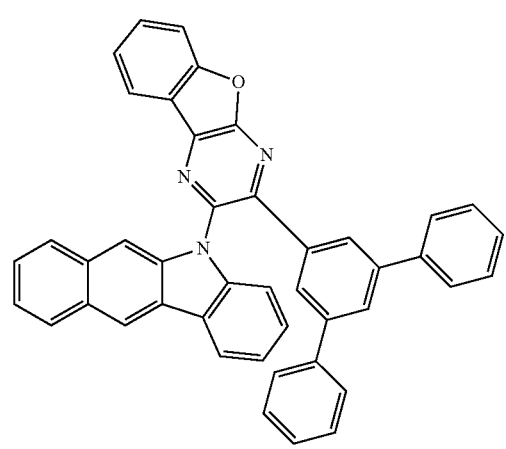
115
-continued
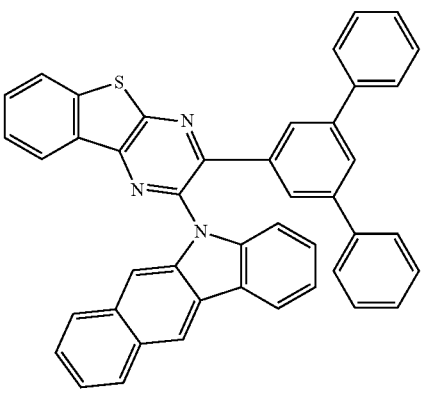
116
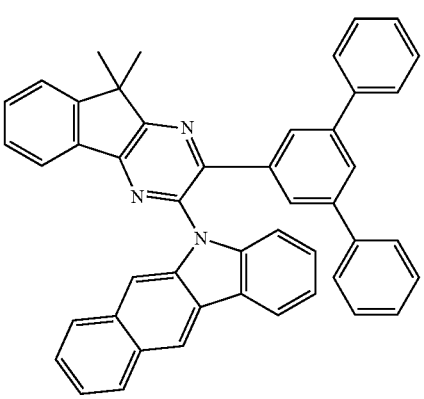
117
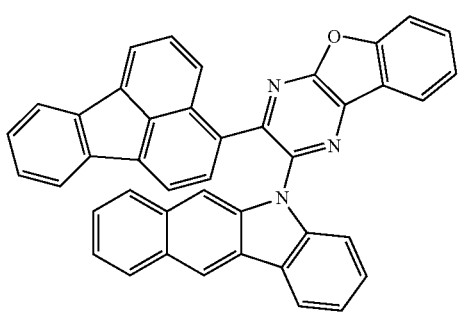
118
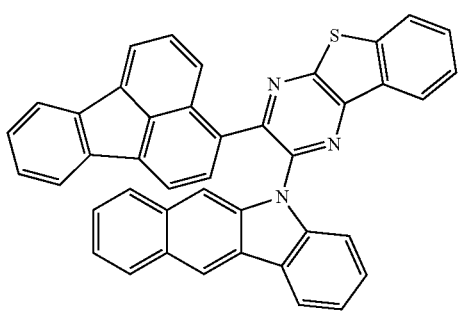
119

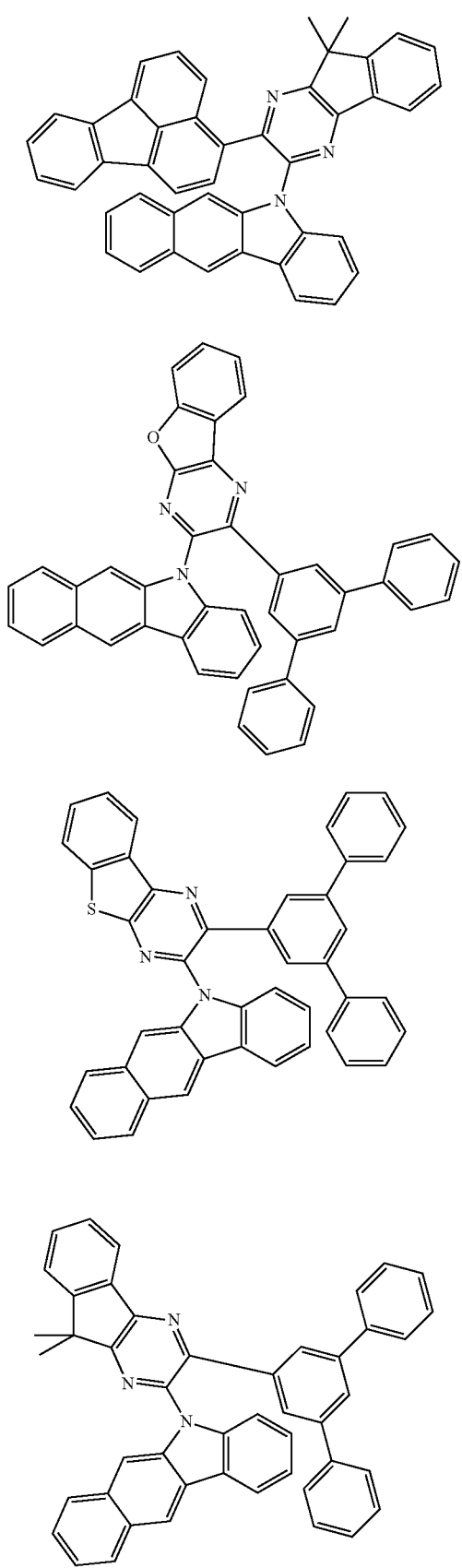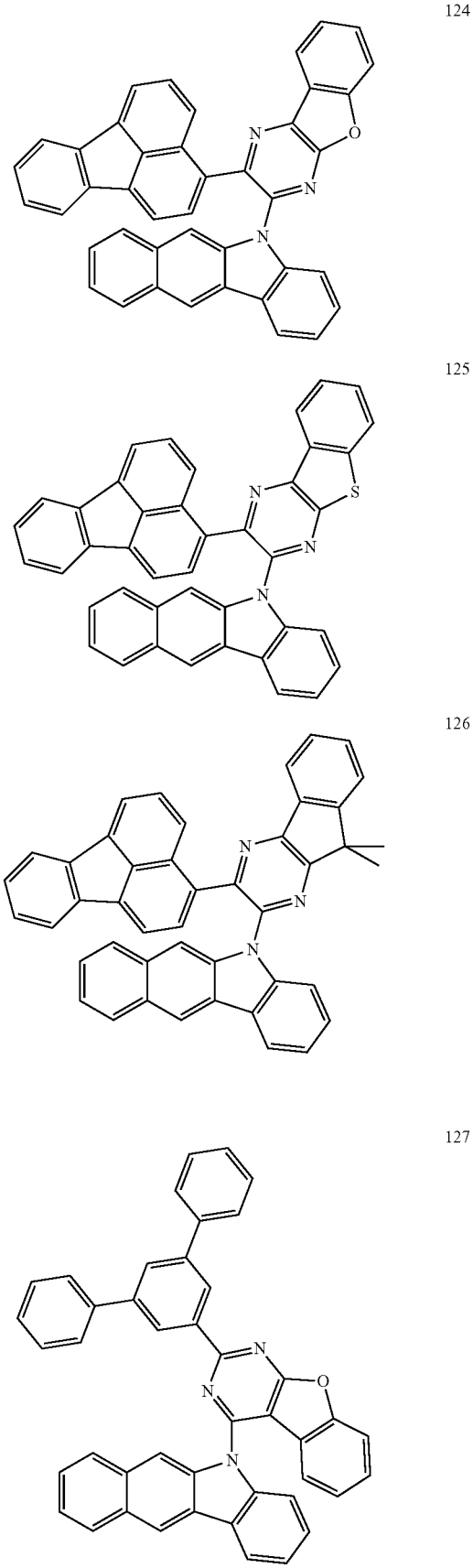

128
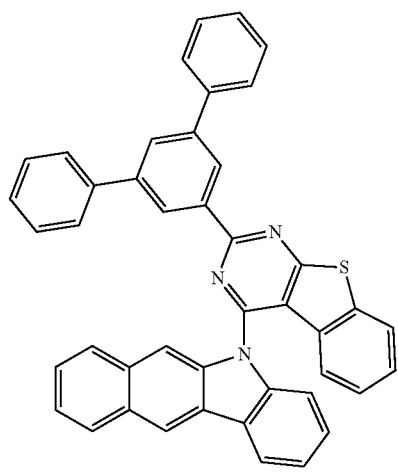
129
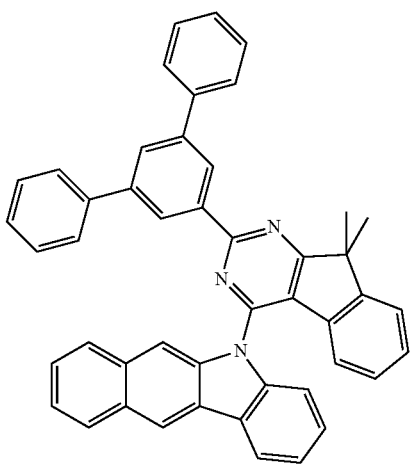
130
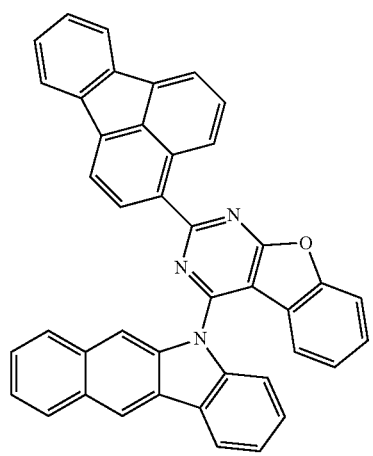
131
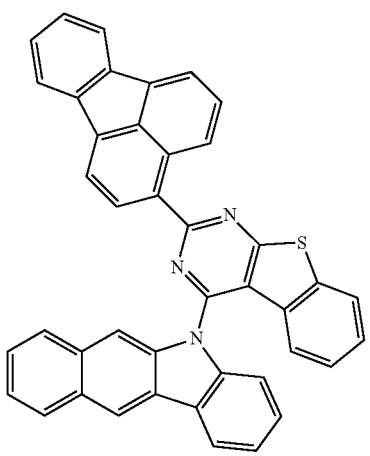
132
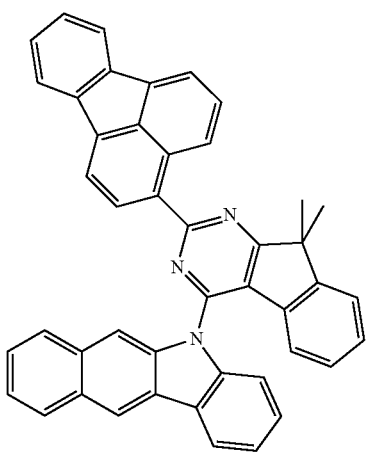
133
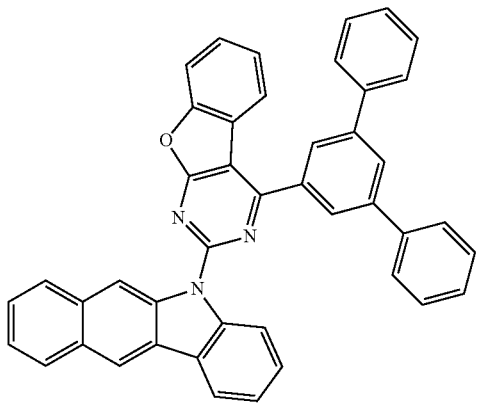

134
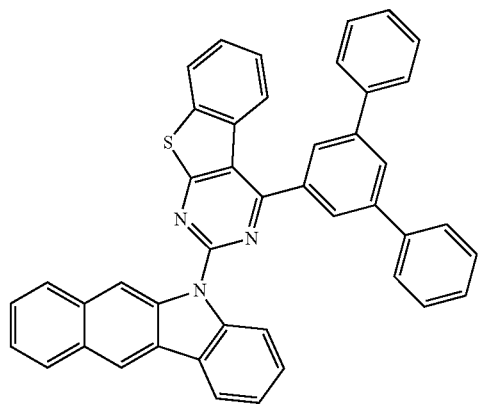
135
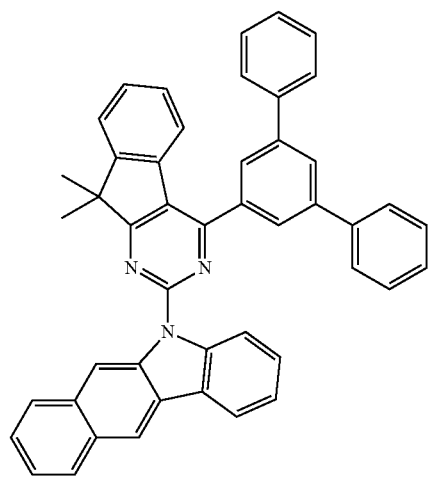
136
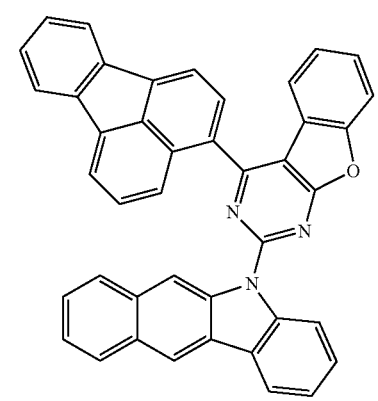
137
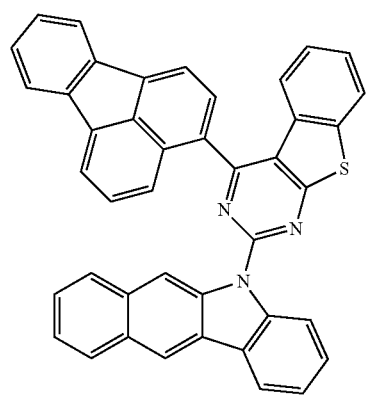
138
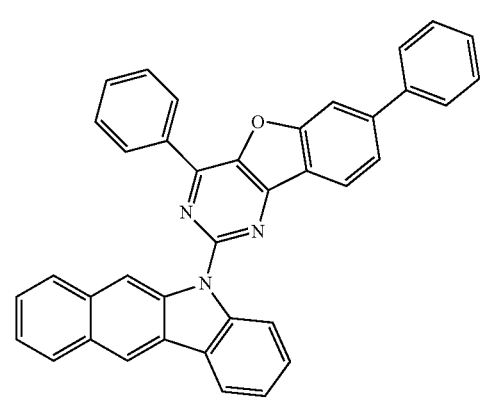
139
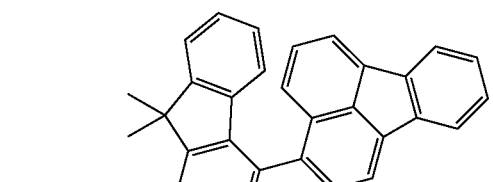
140
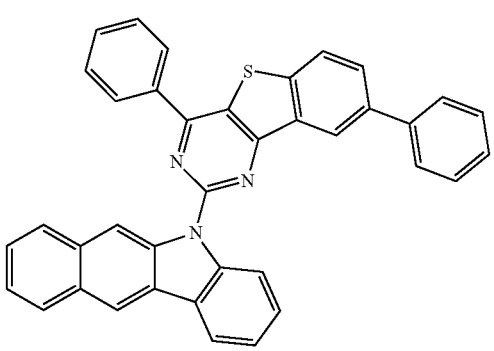

141 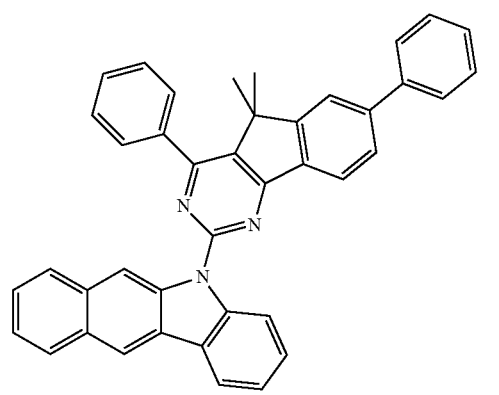
142 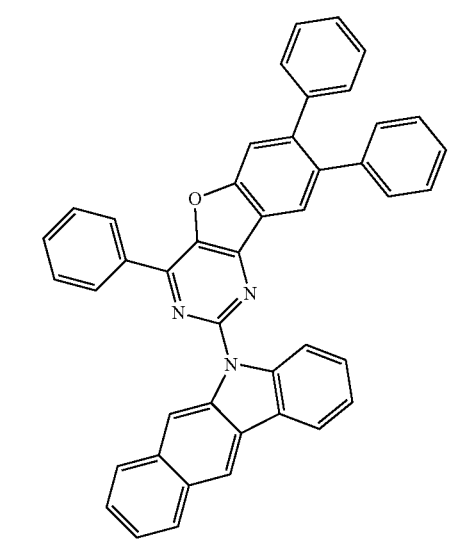
143 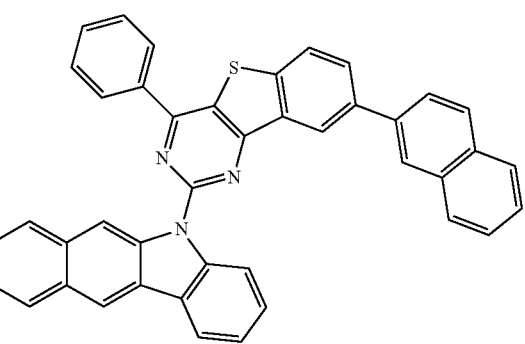
144 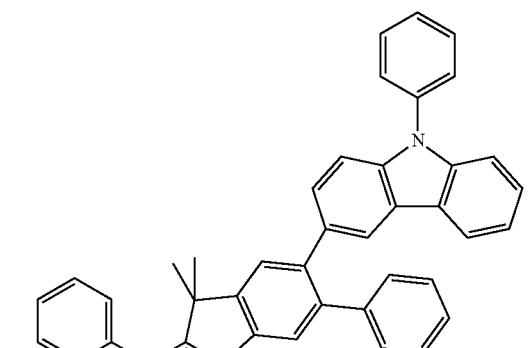
145 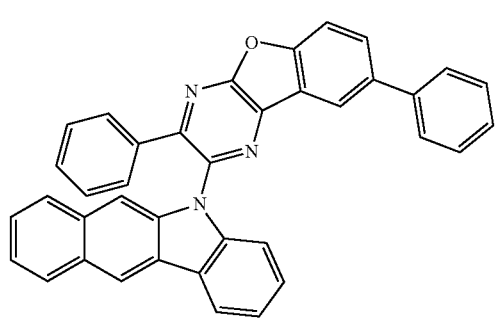
146 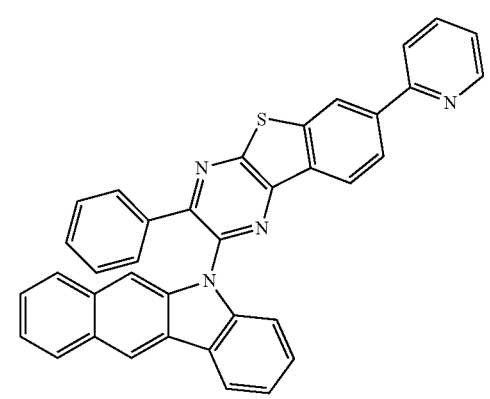
147 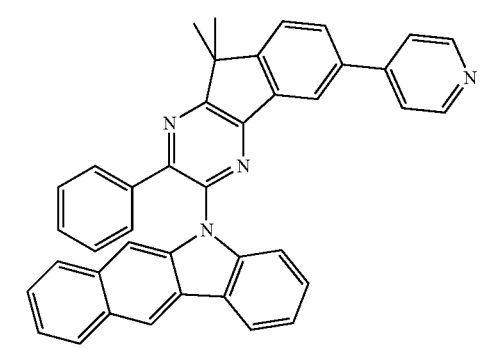

148
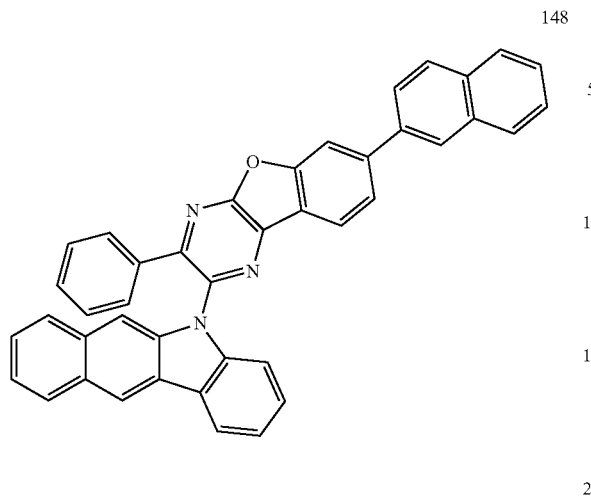
149
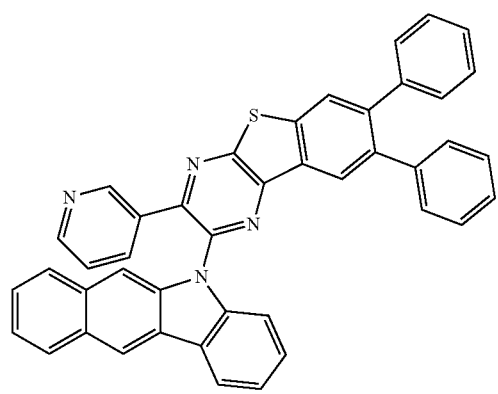
150
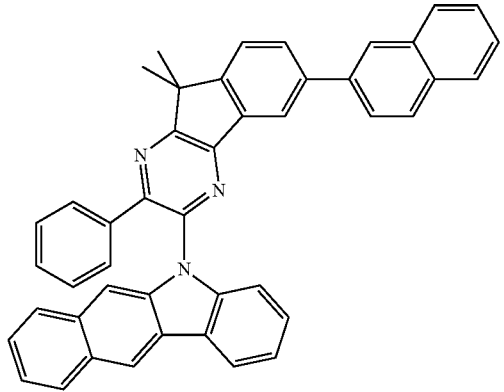
151
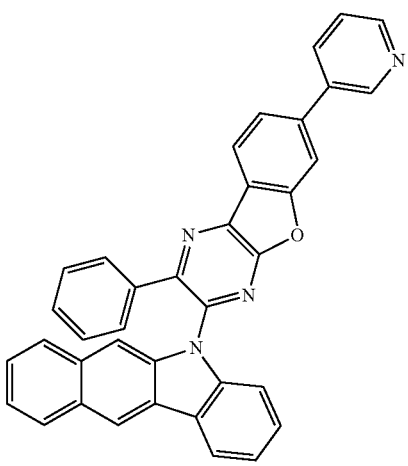
152
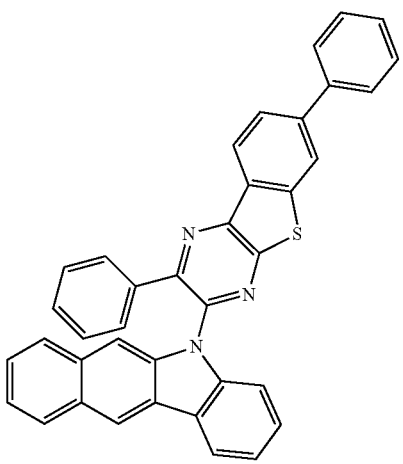
153
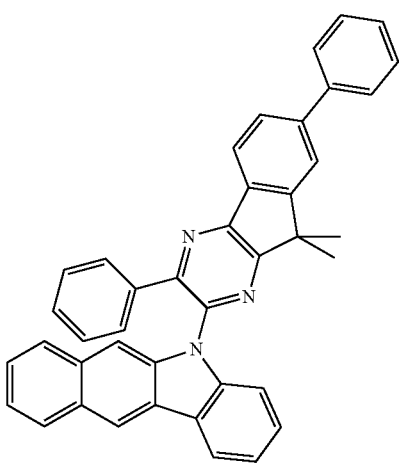

154
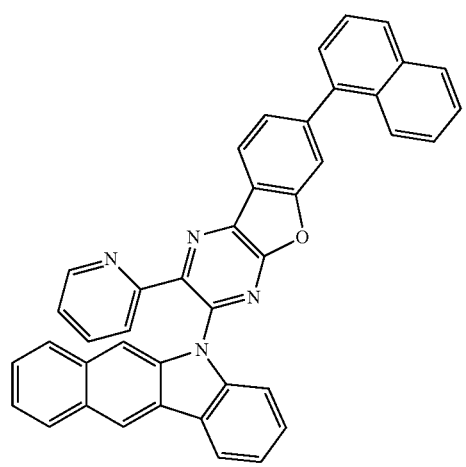
155
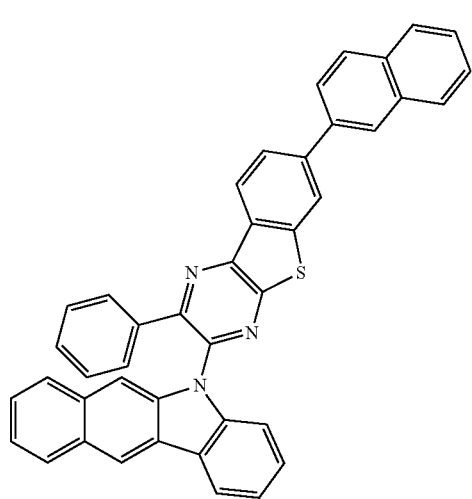
156
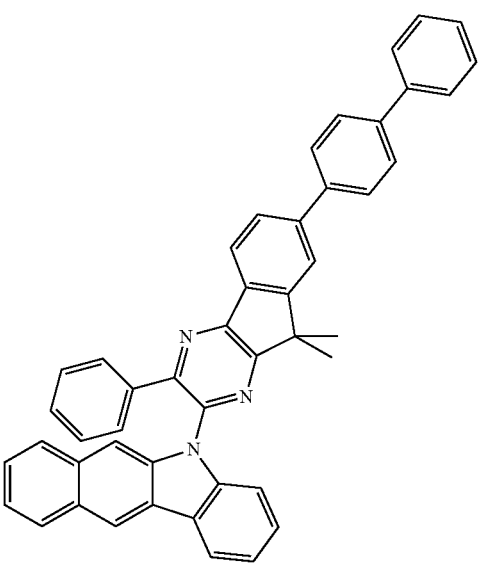
157

158
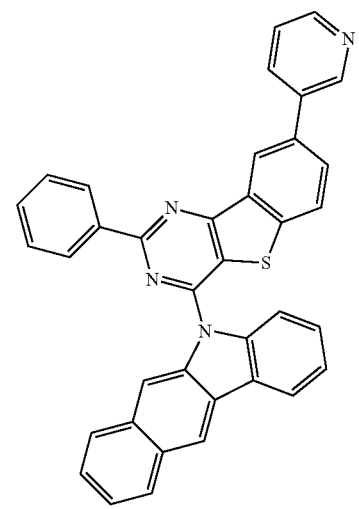
159
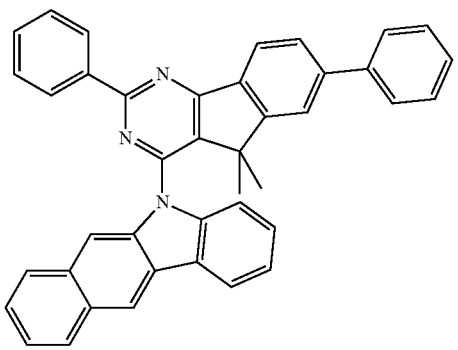

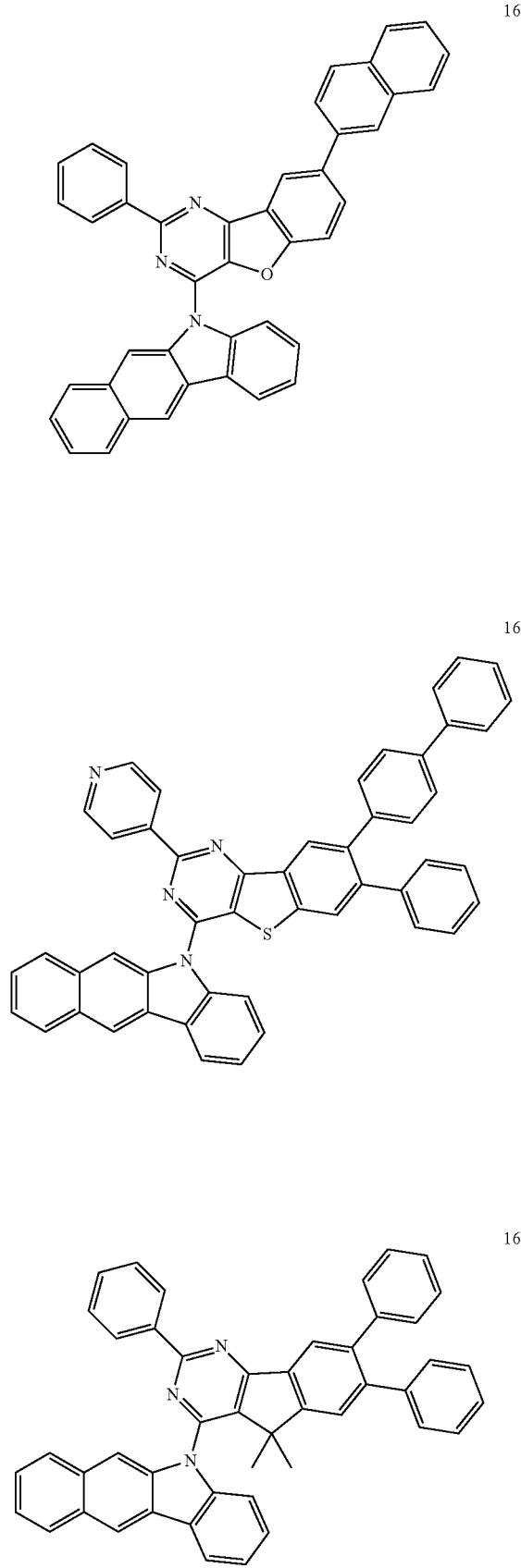
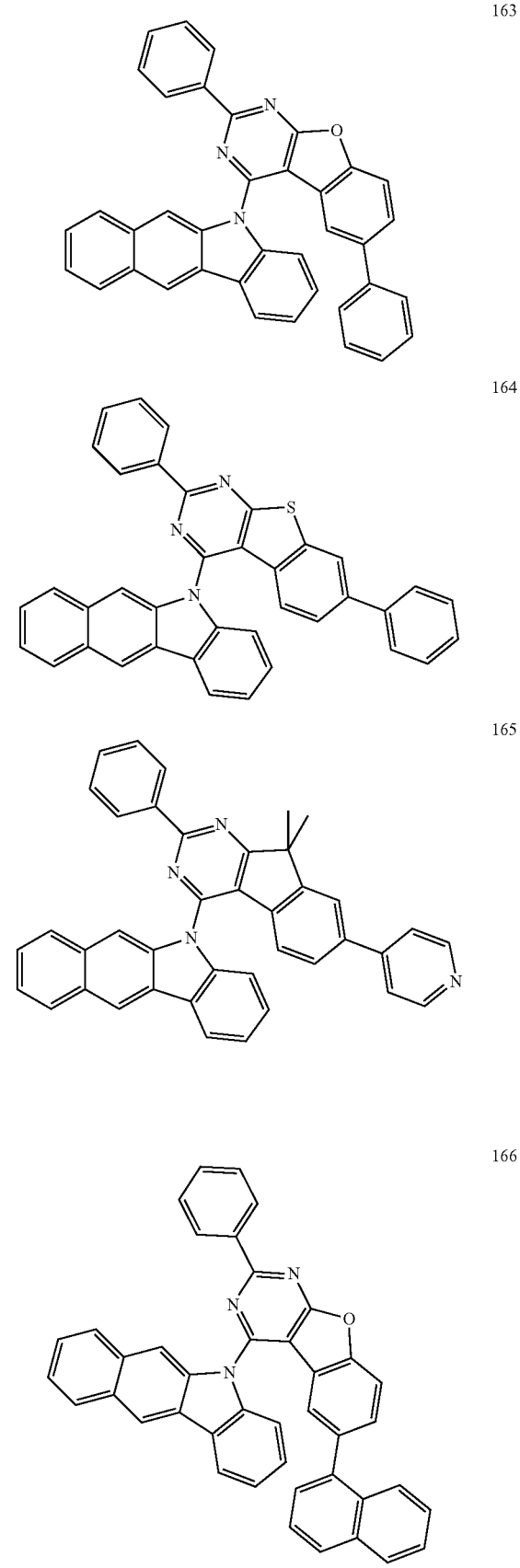

167
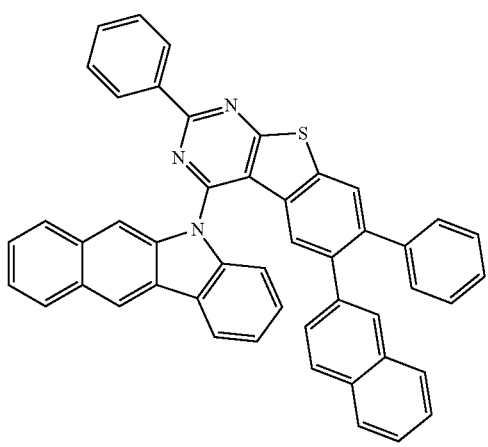
168
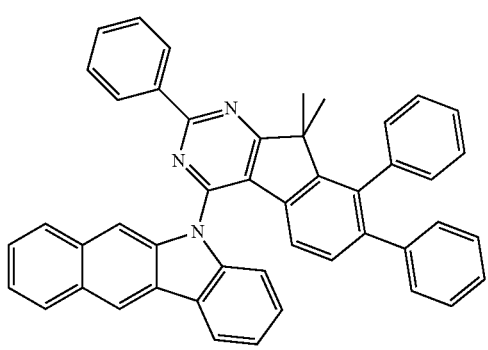
169
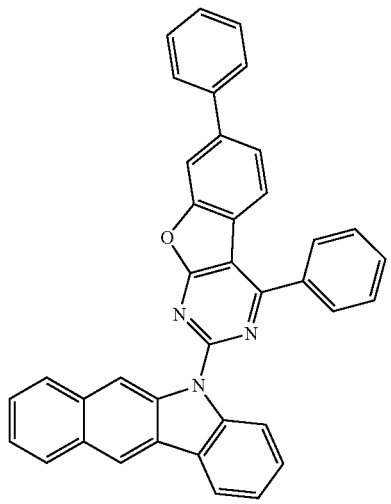
170
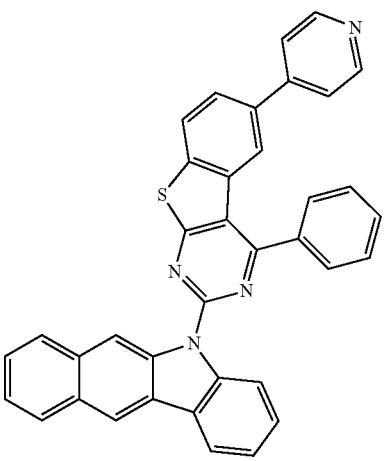
171
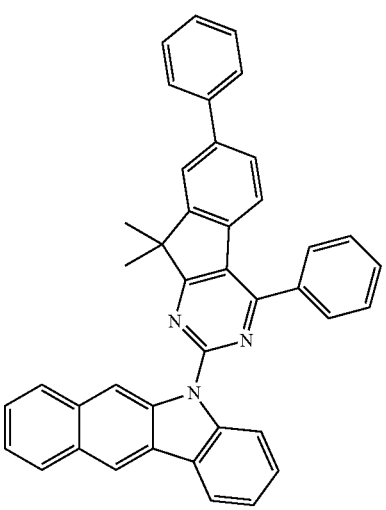
172
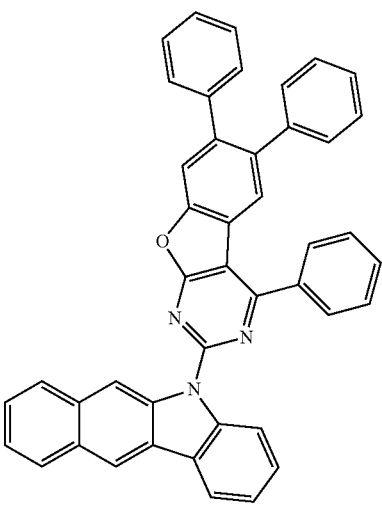

173
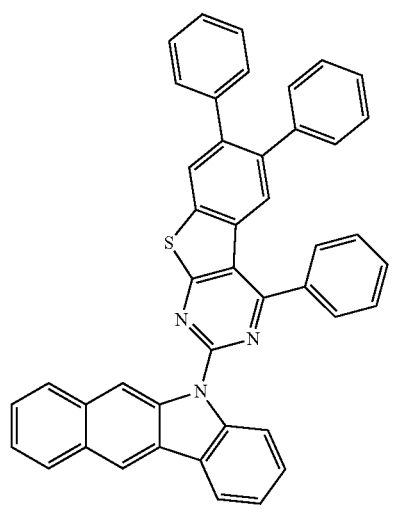
174
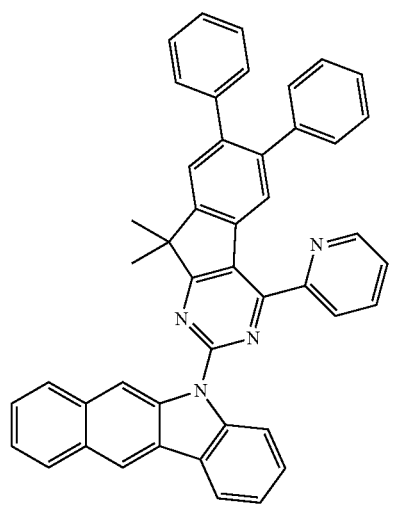
175
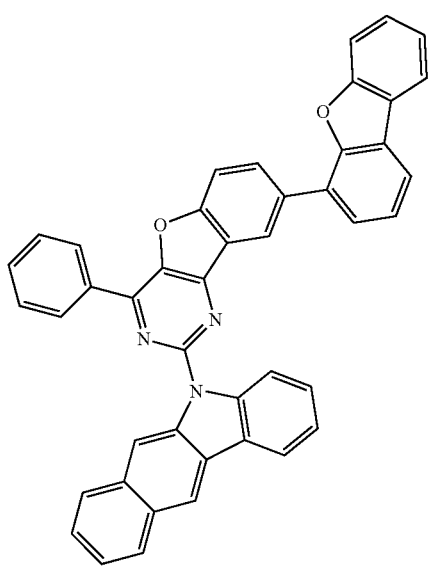
176
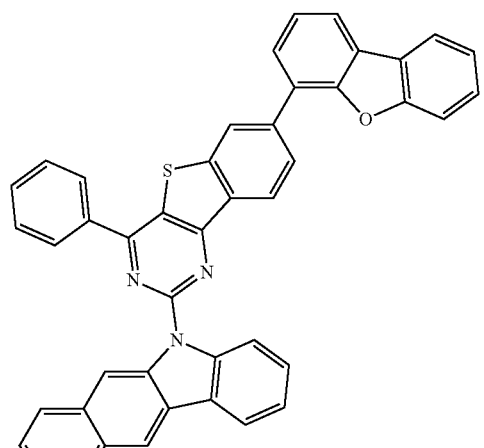
177
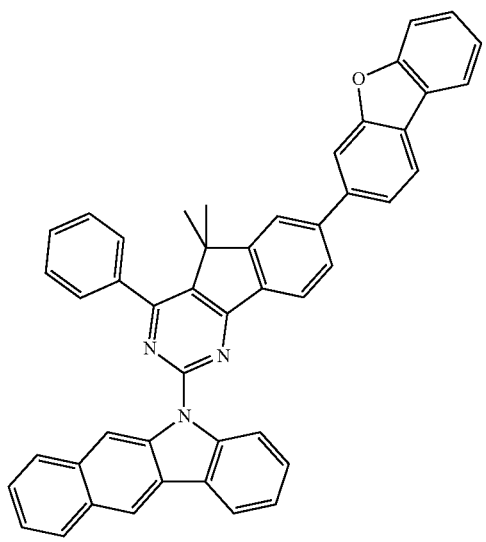
178
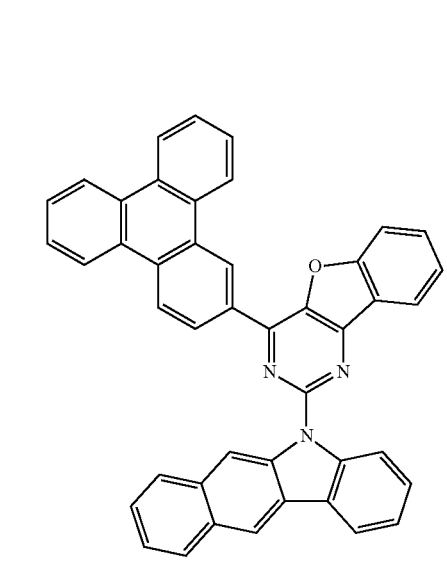

59
-continued
179
180
181
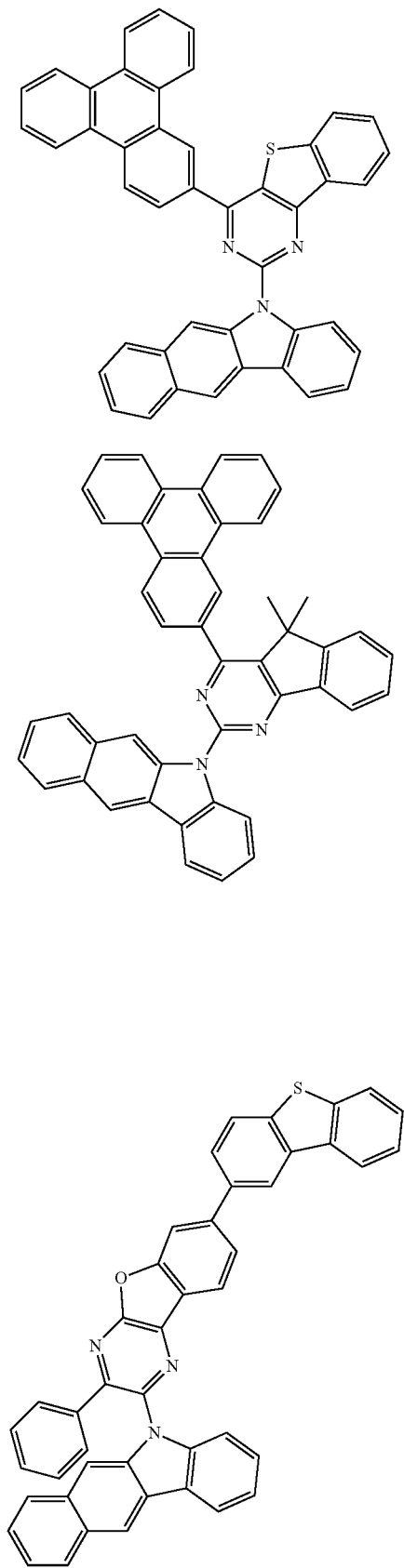
60
-continued
182
183
184
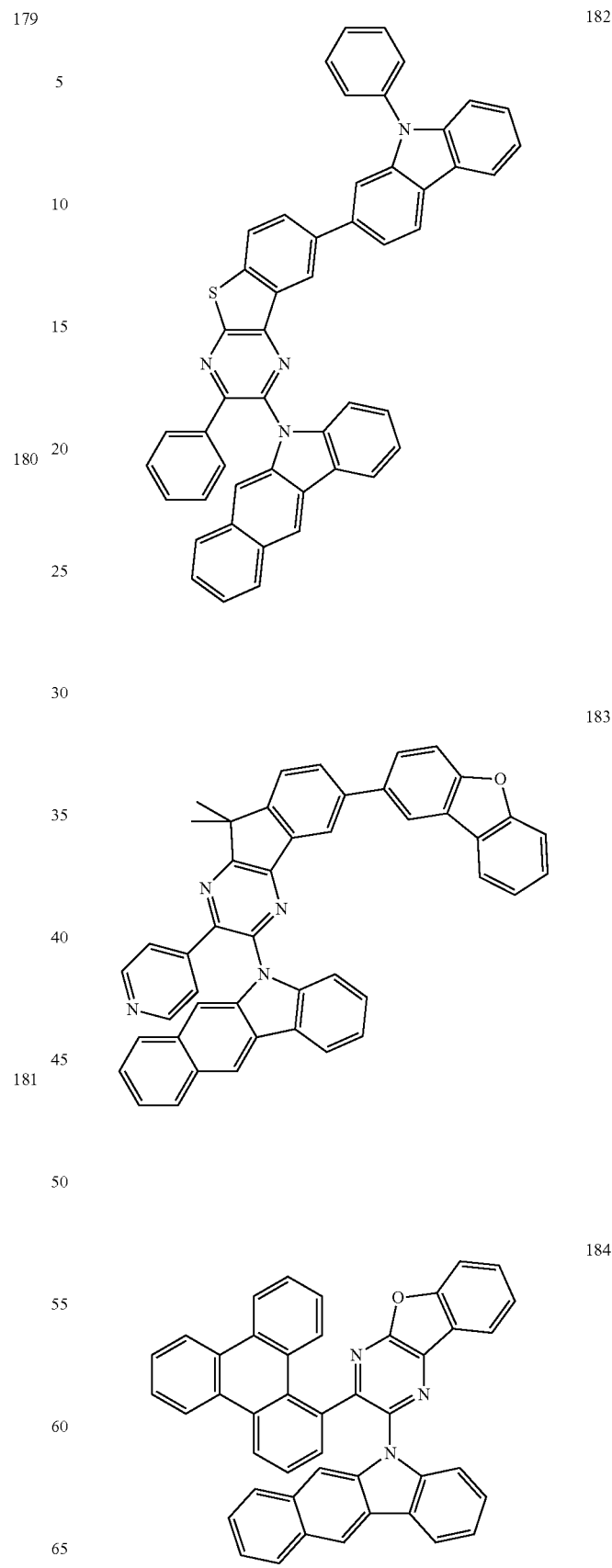

61
-continued
185
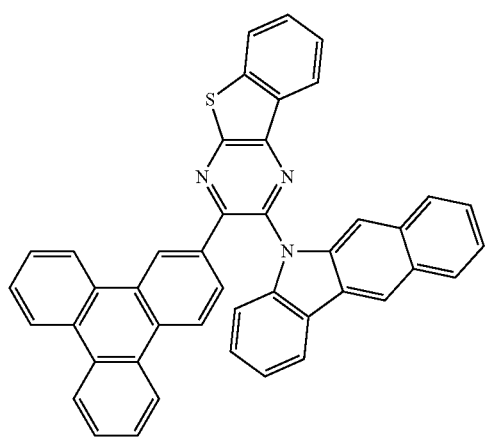
186
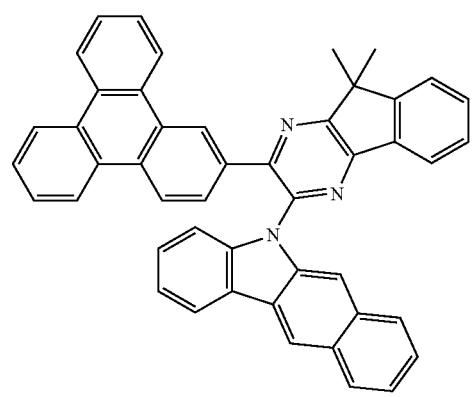
187
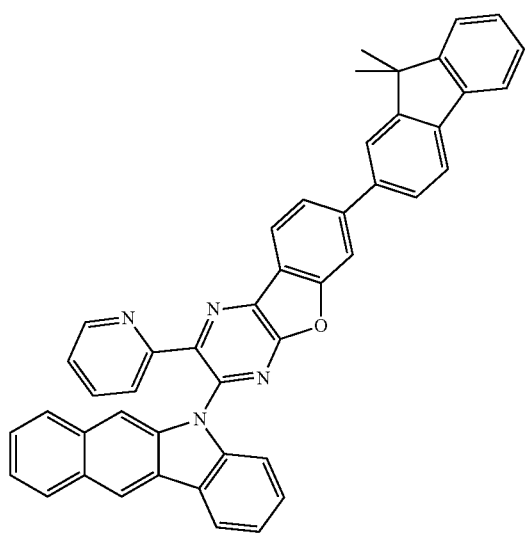
62
-continued
188
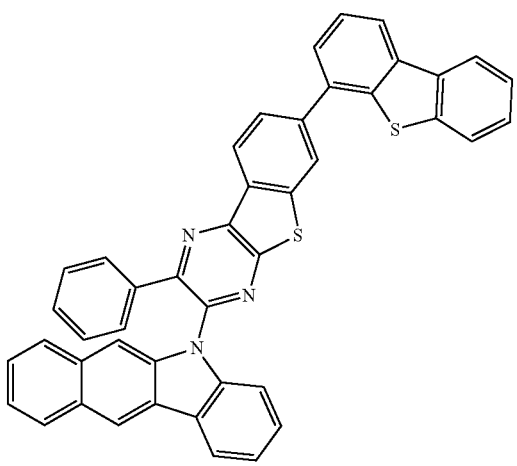
189
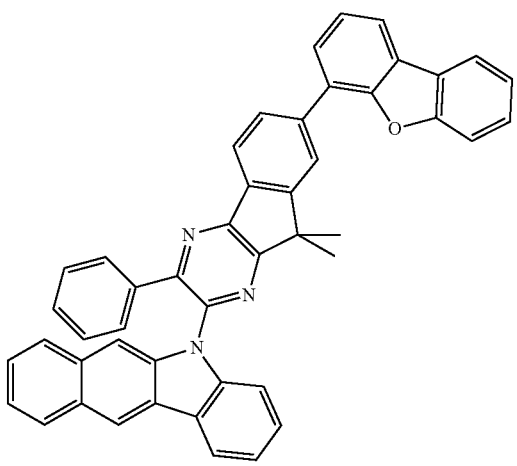
190
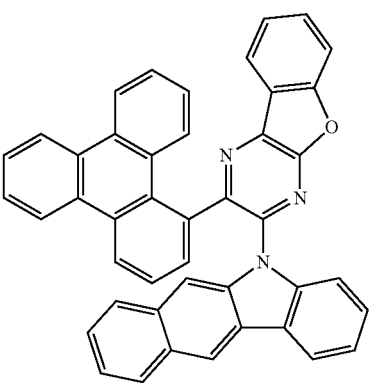

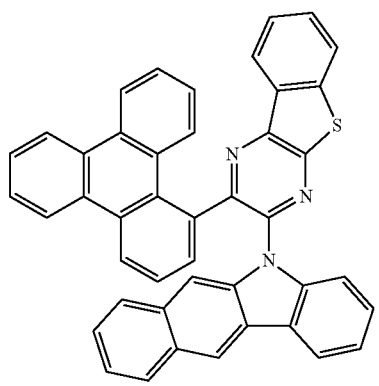
191
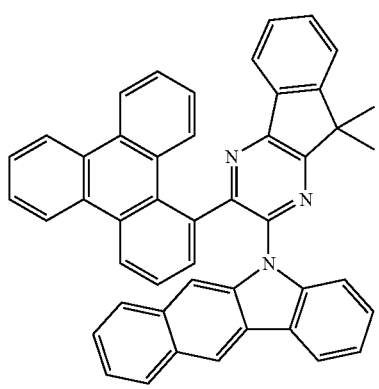
192
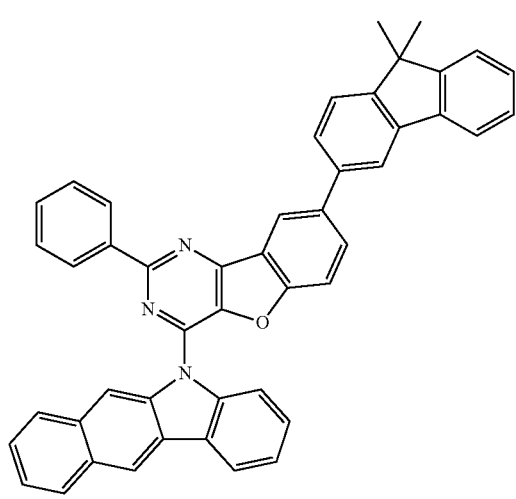
193
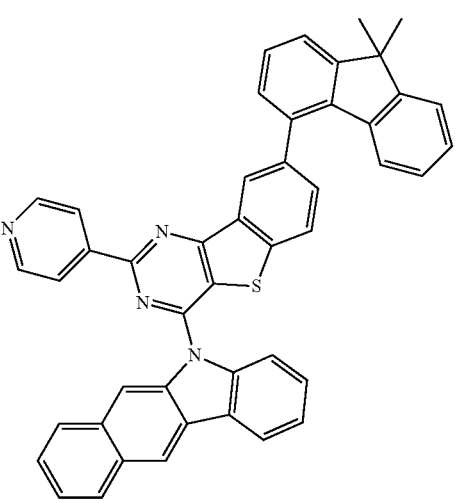
194
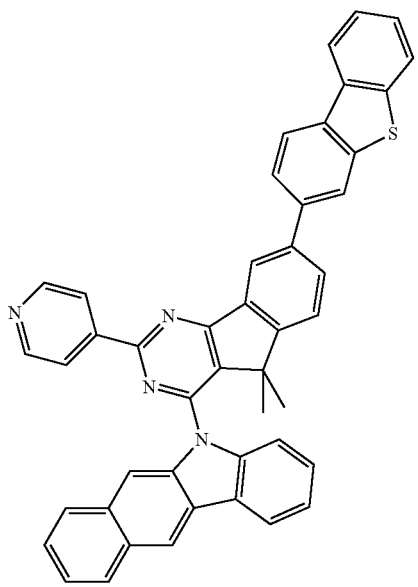
195
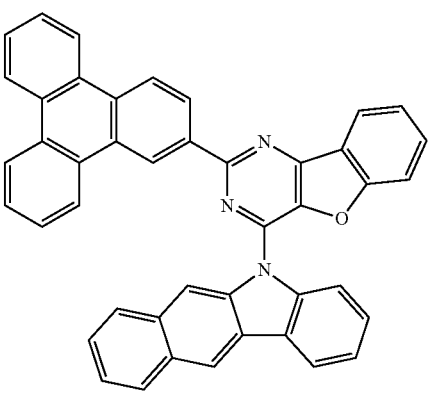
196

197
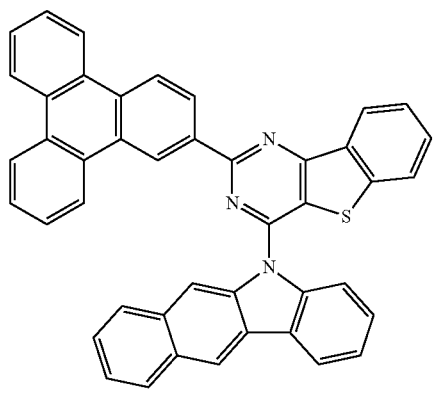
198
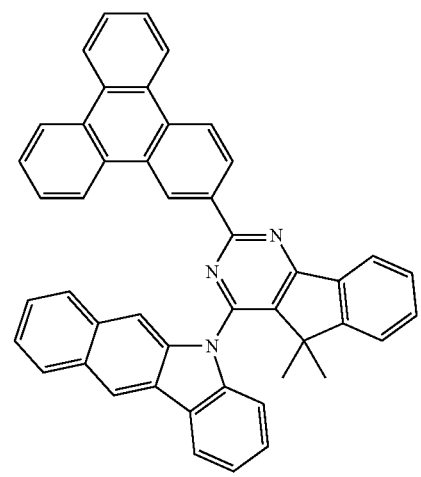
199
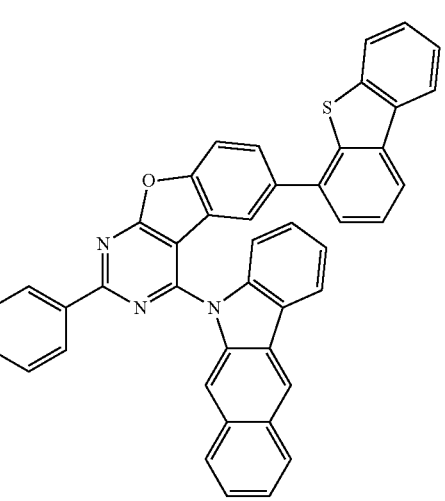
200
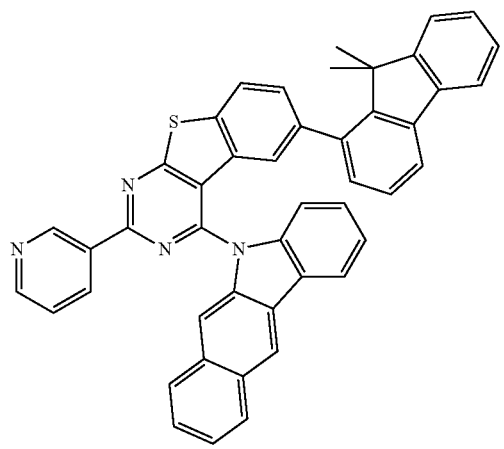
201
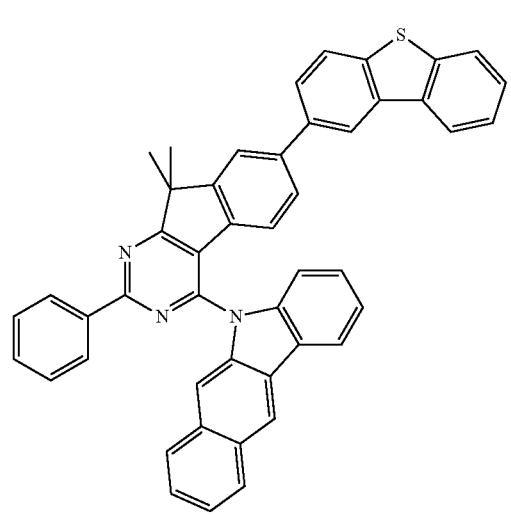
202
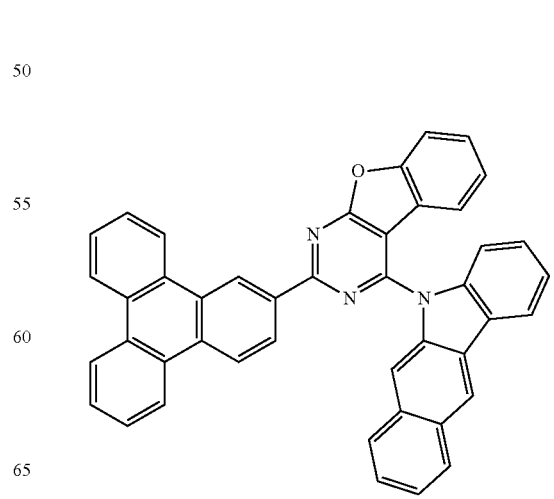

203
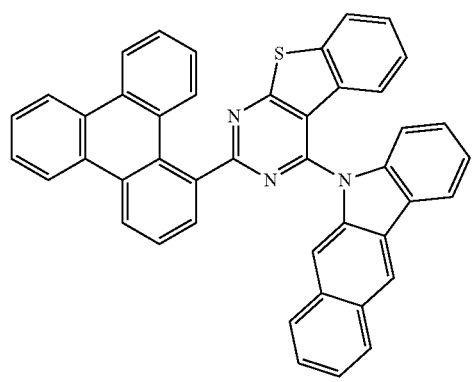
204
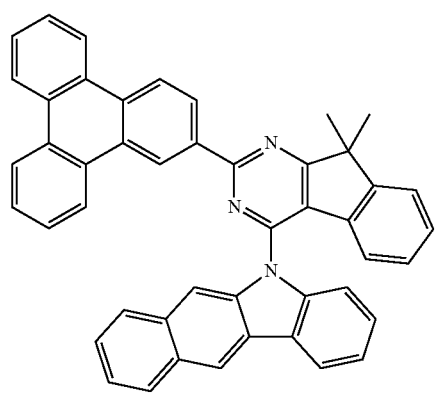
205
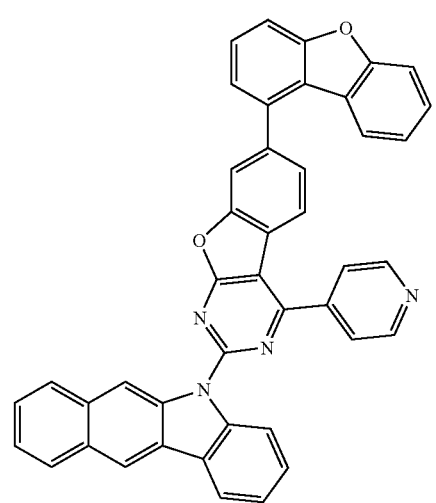
206
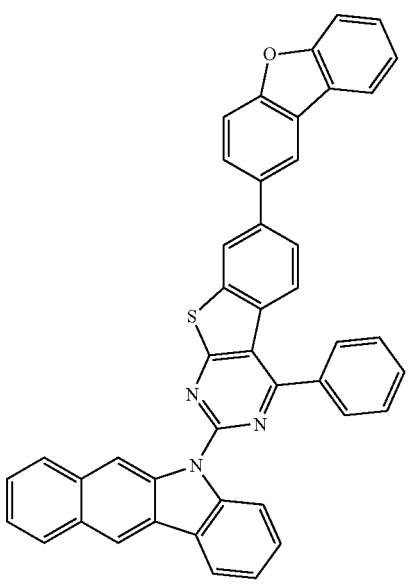
207
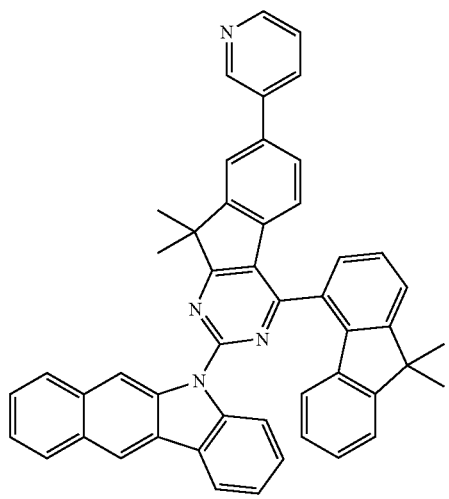
208
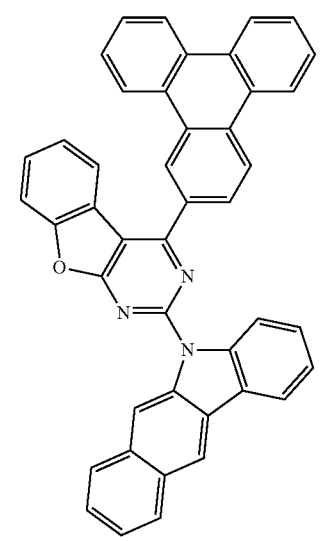

209 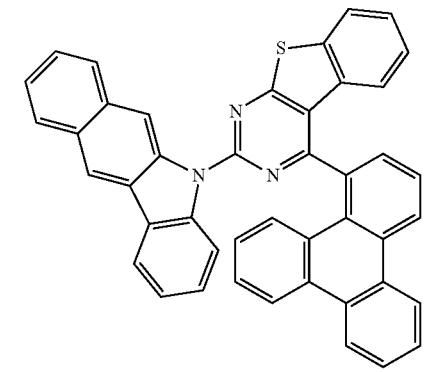
210 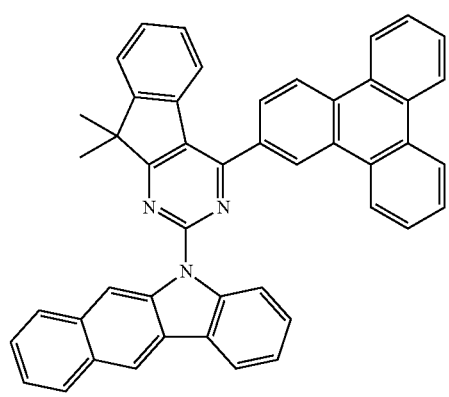
211 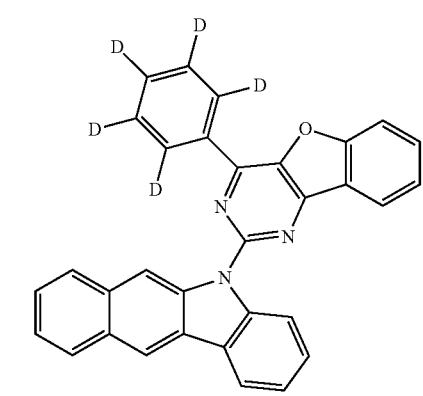
212 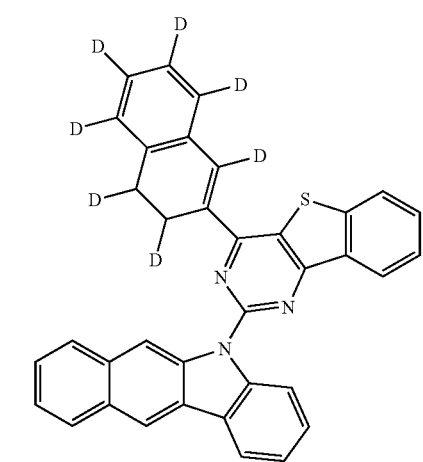
213 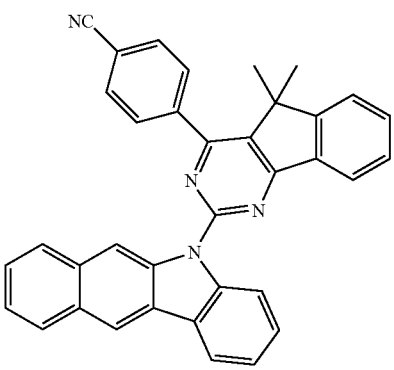
214 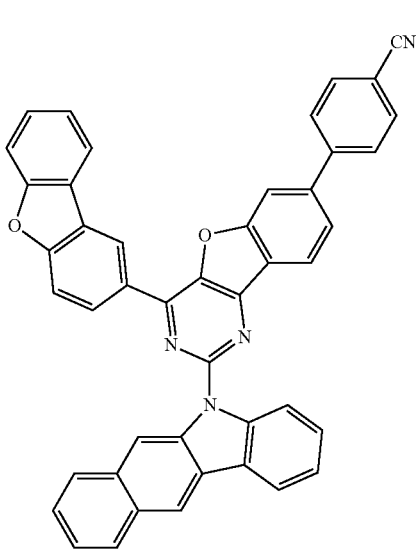
215 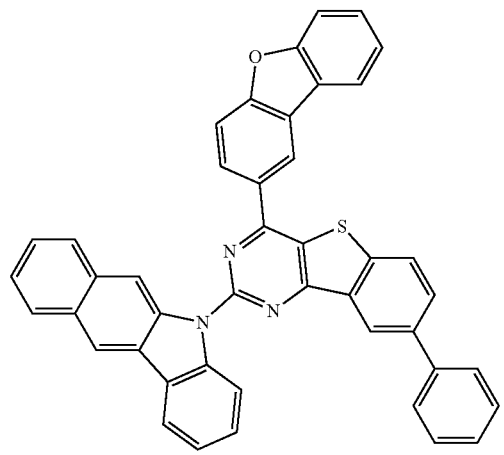

71
-continued
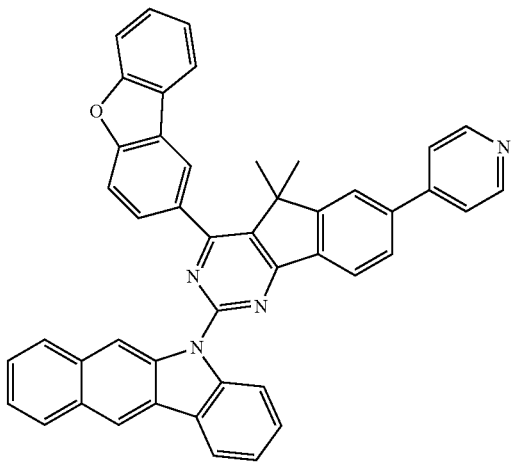
216
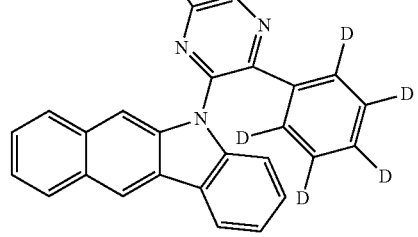
217
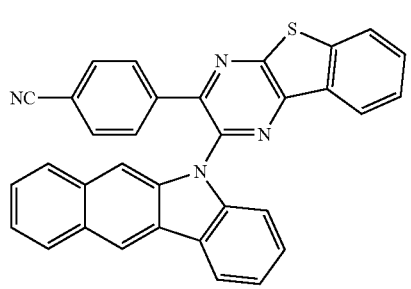
218
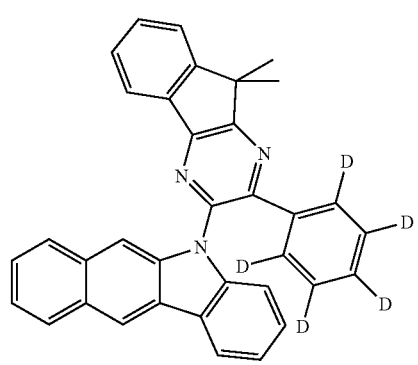
219
72
-continued
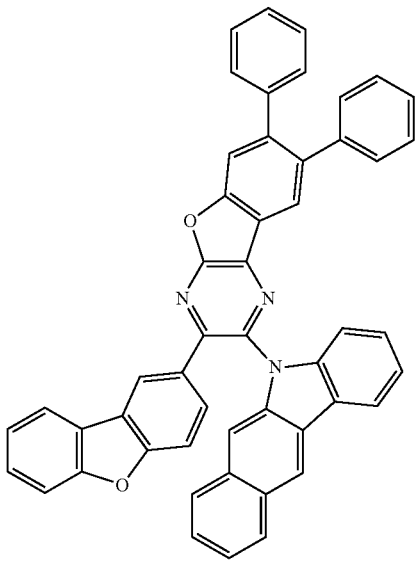
220
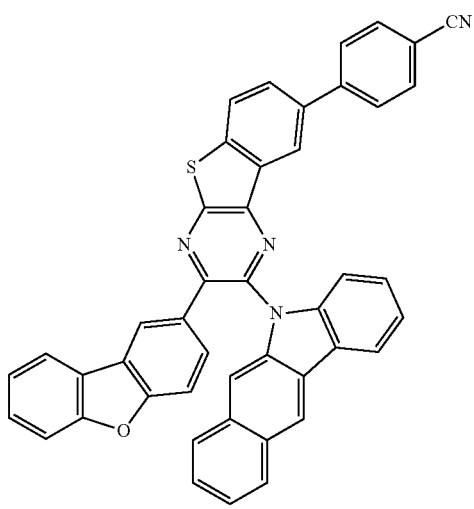
221
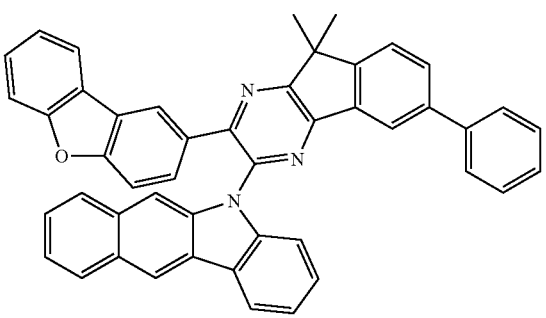
222

223 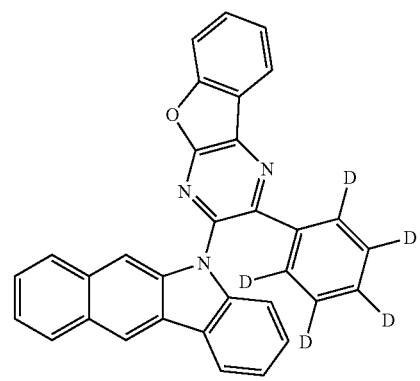
224 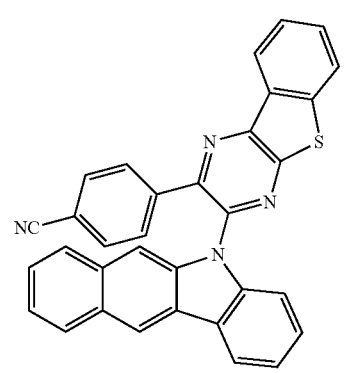
225 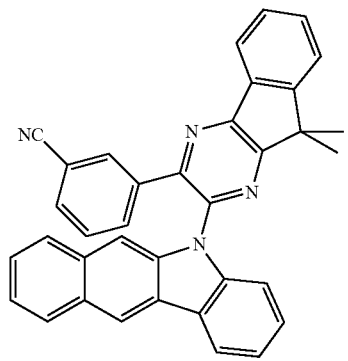
226 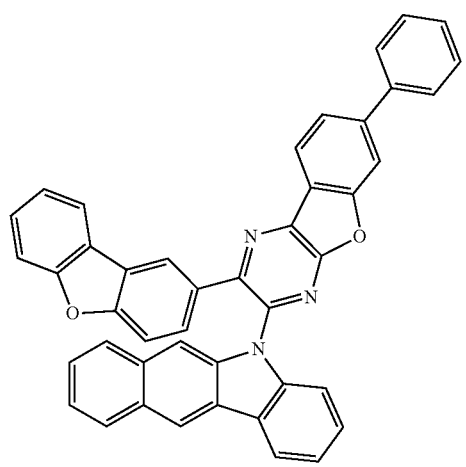
227 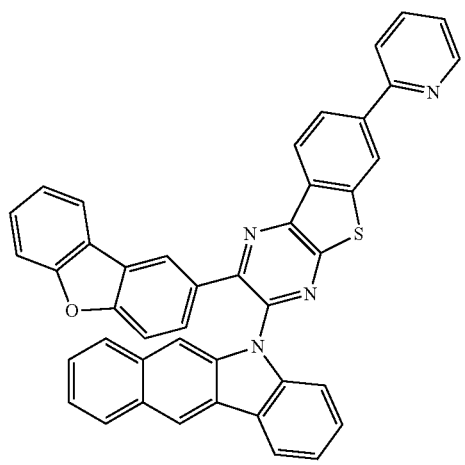
228 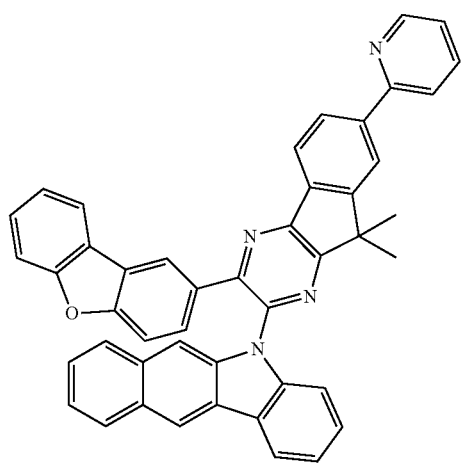
229 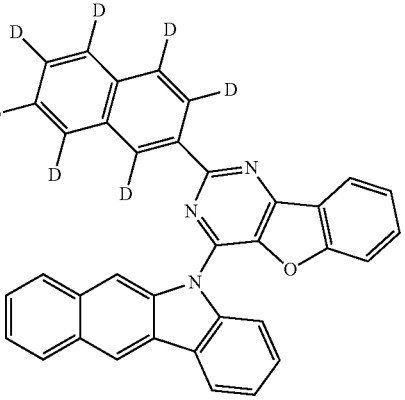

230
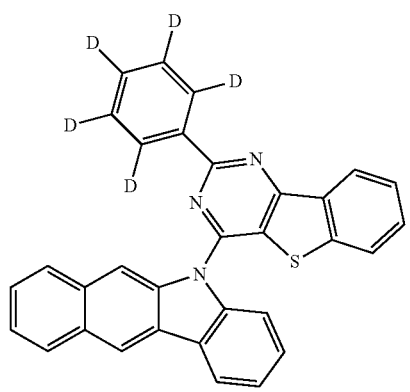
231
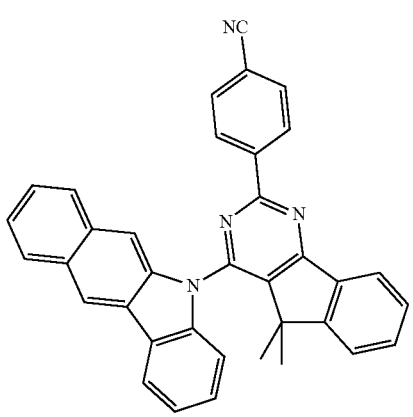
232
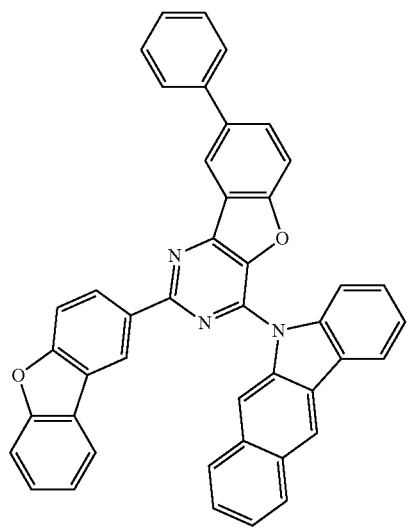
233
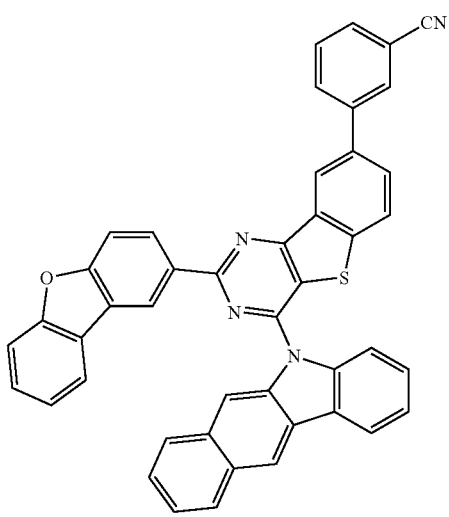
234
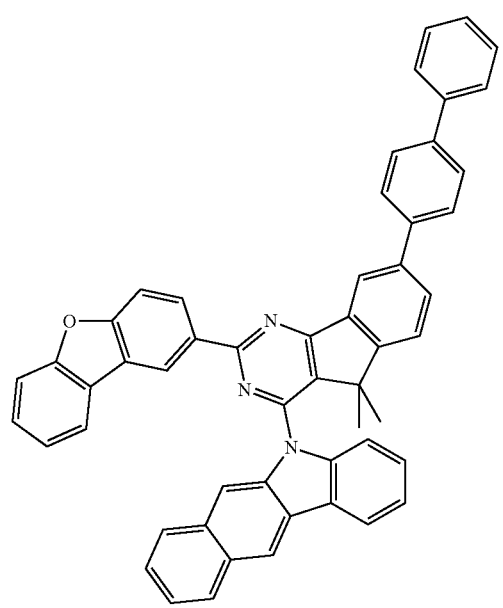
235
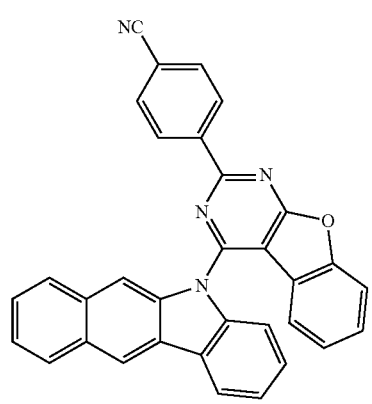

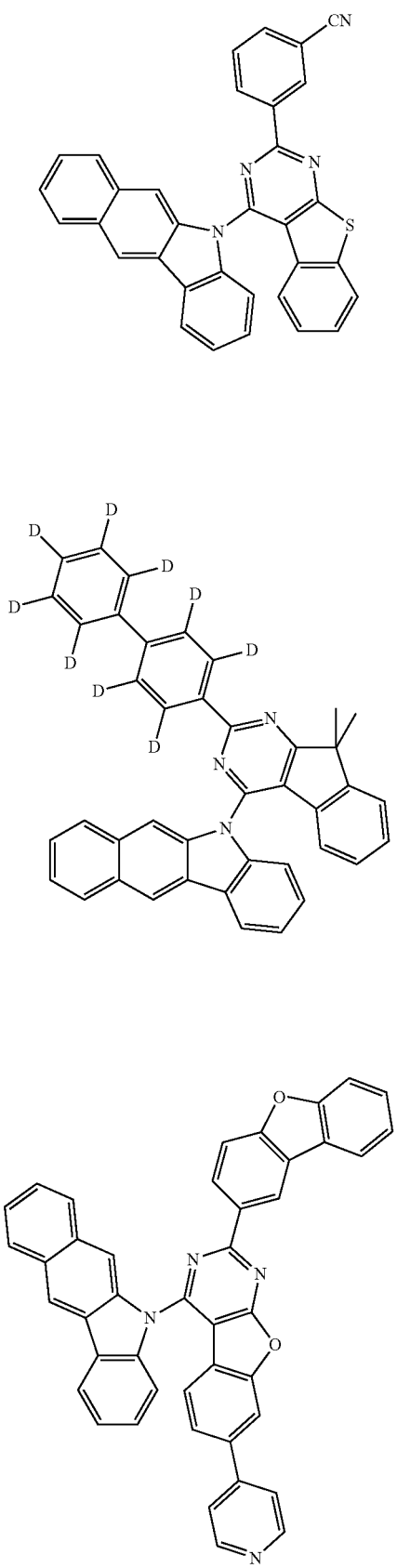
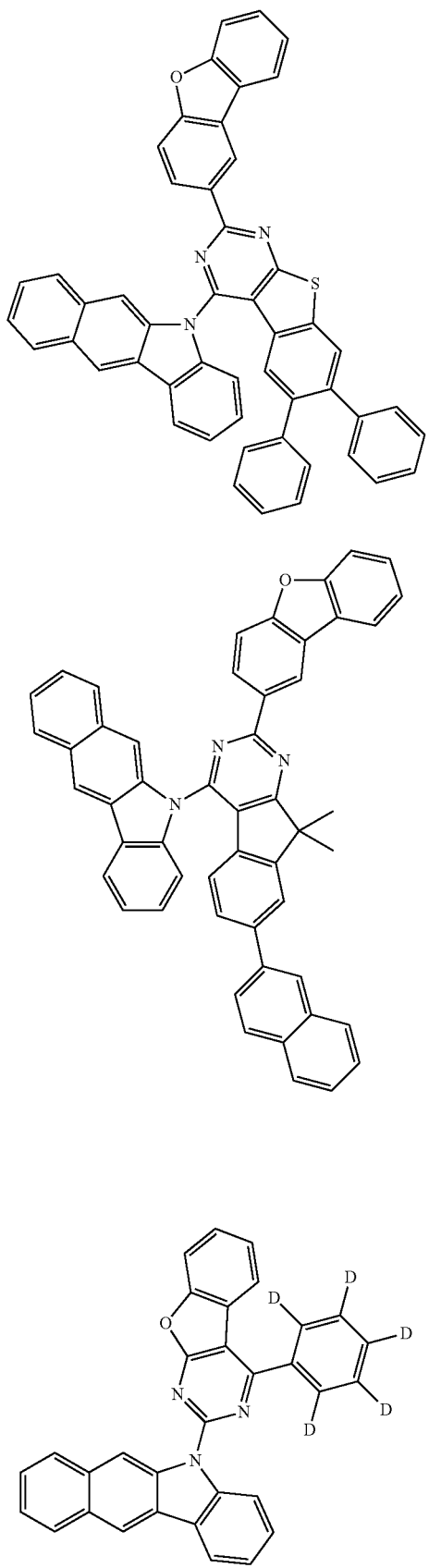

242
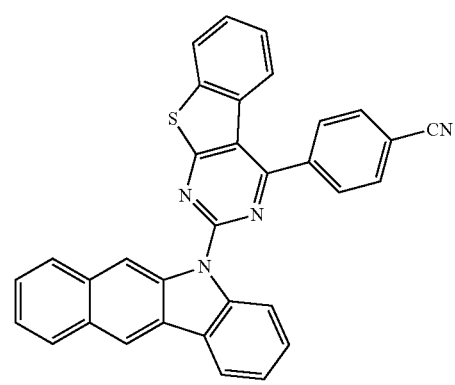
243
244
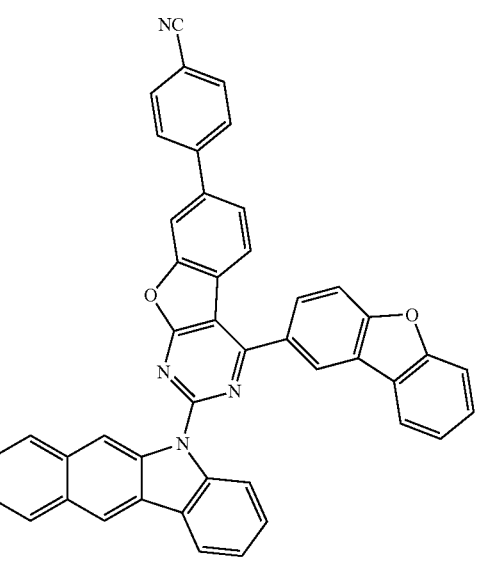
245
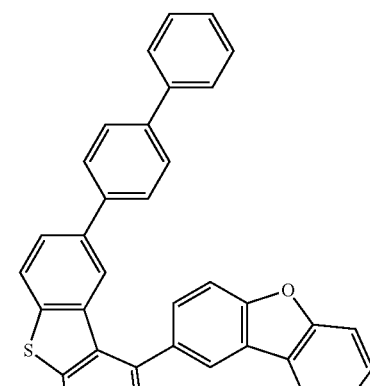
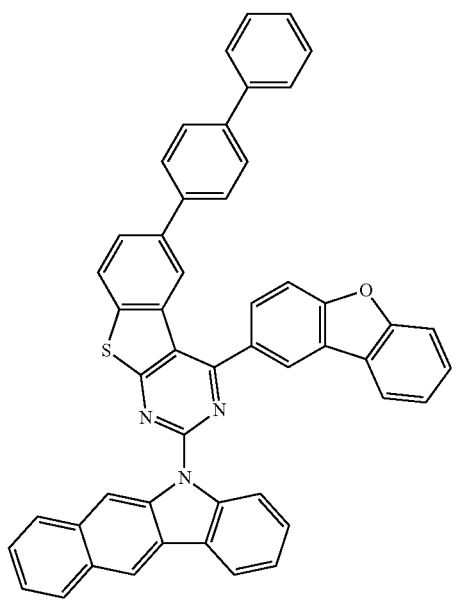
246
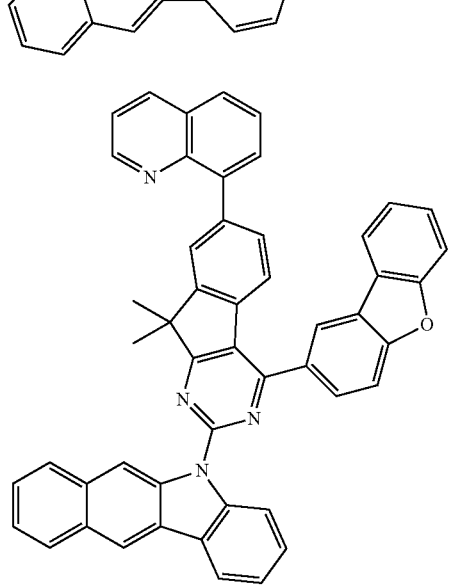
247
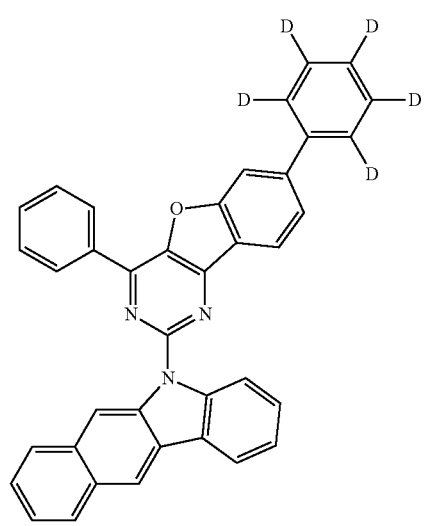

-continued
248
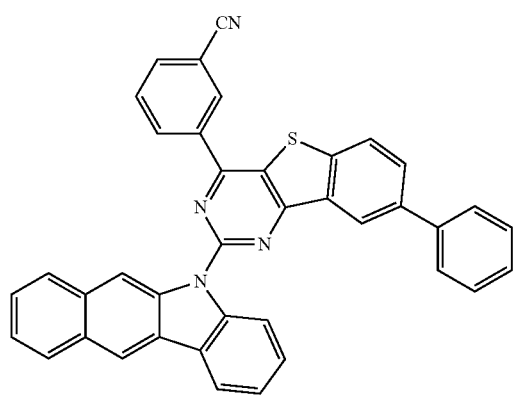
249
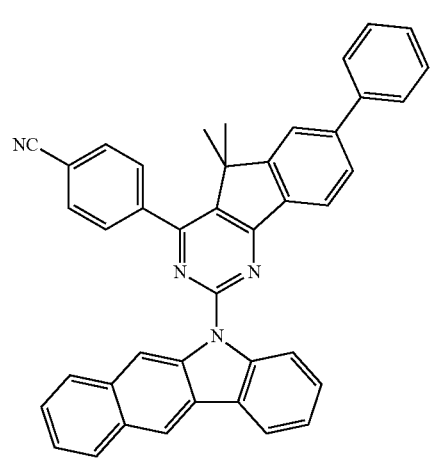
250
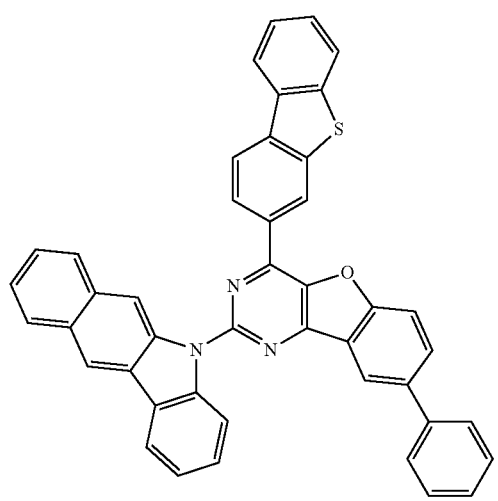
-continued
251
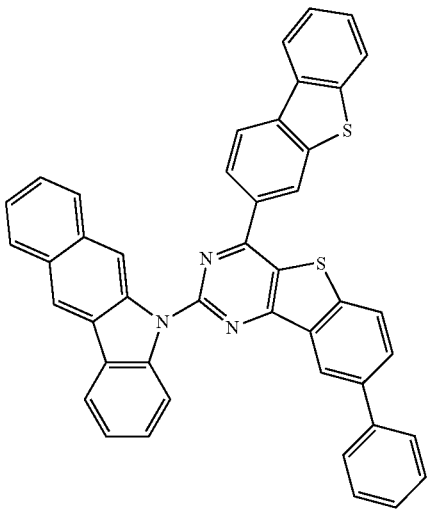
252
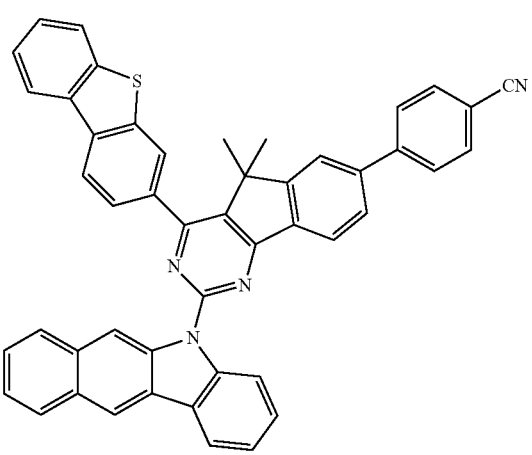
253
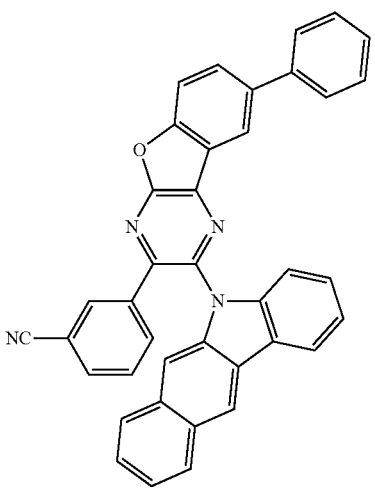

-continued
254
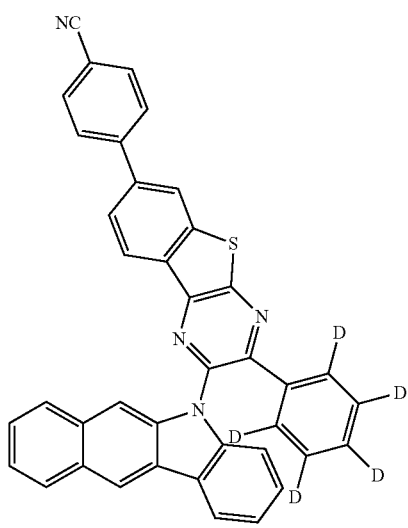
255
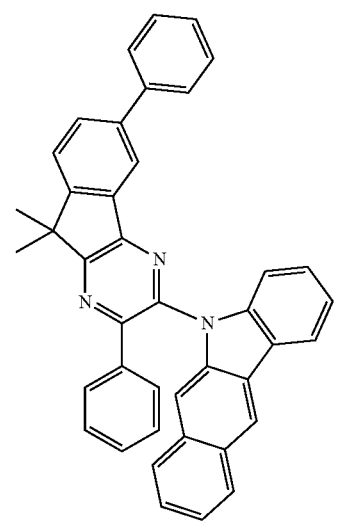
256
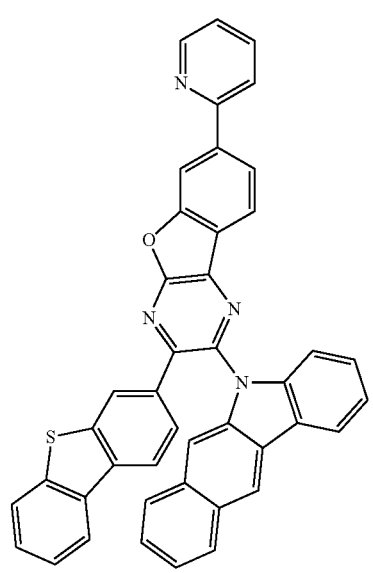
-continued
257
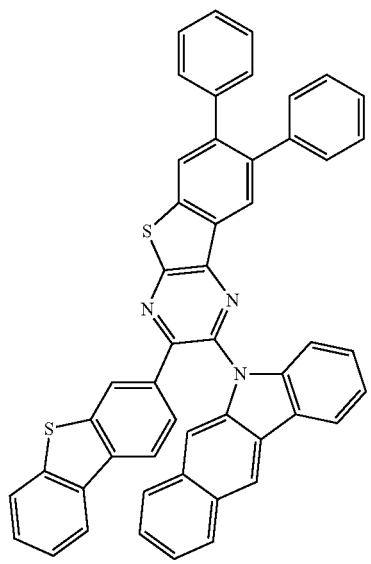
258
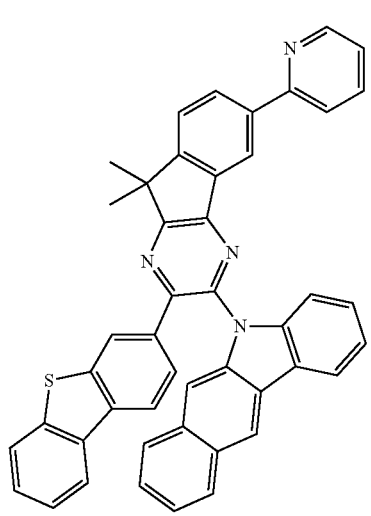
259
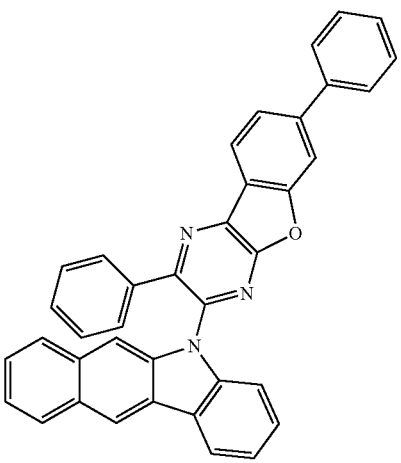

85
-continued
260
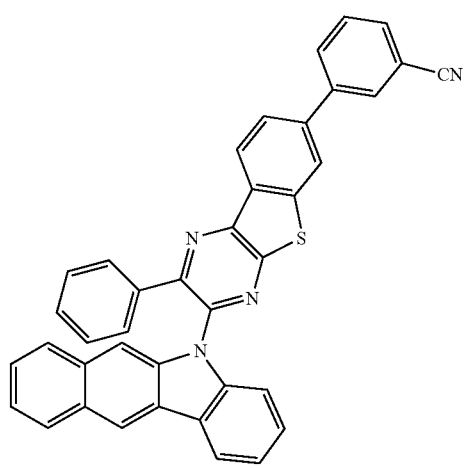
261
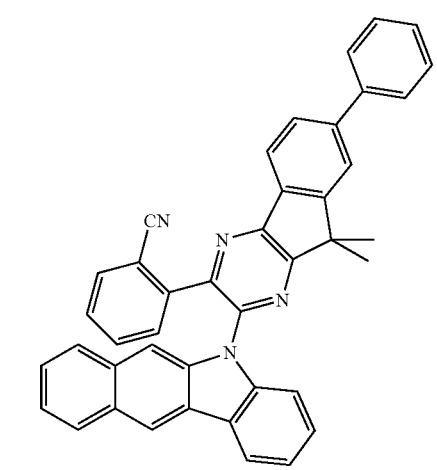
262
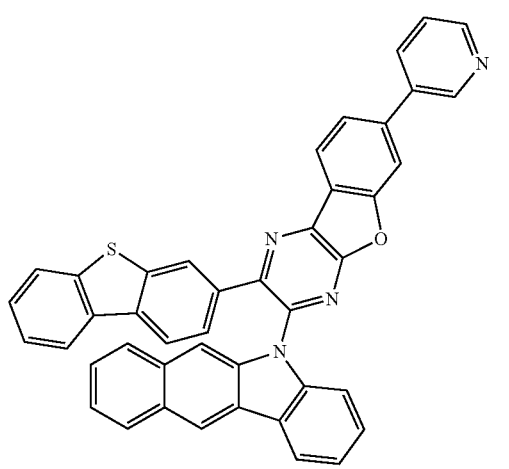
86
-continued
263
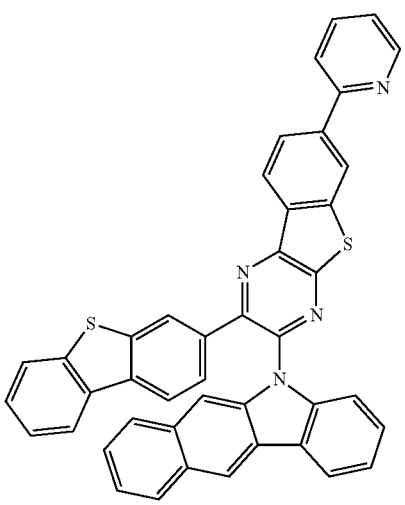
264
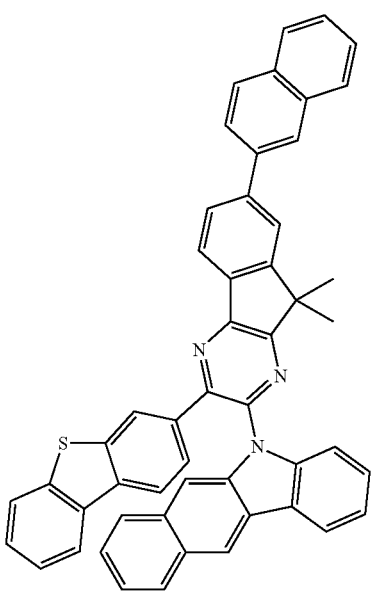
265
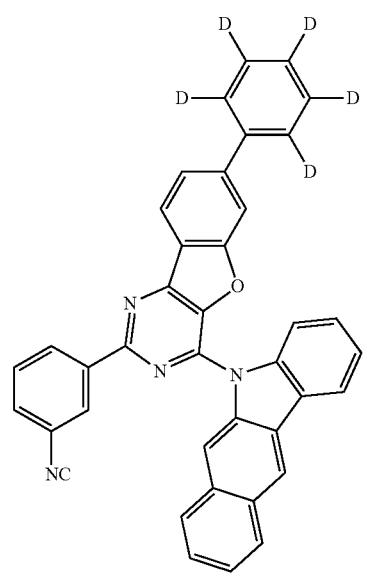

266
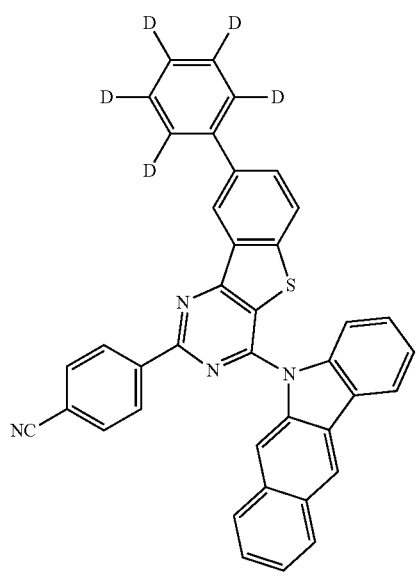
267
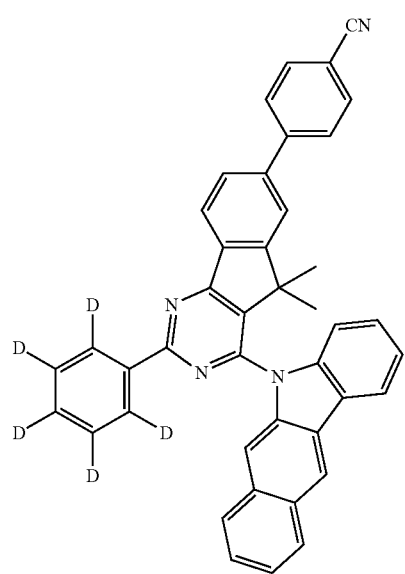
268
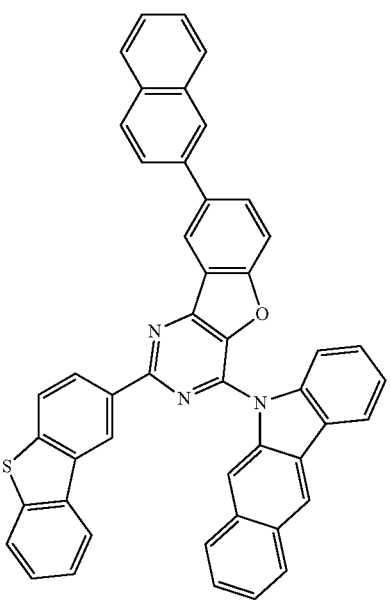
269
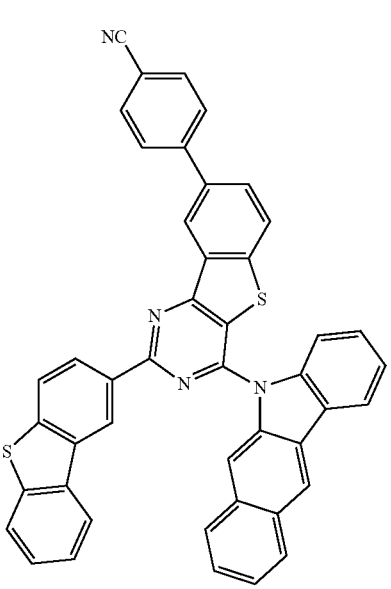

270
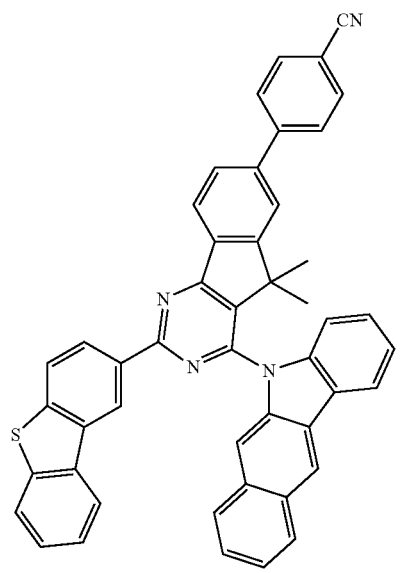
271
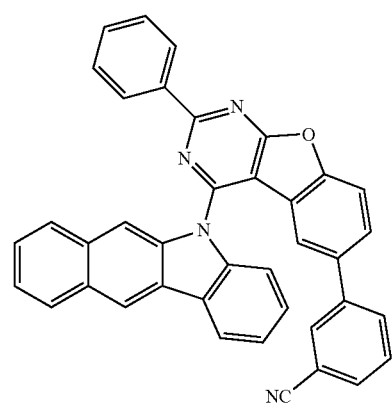
272
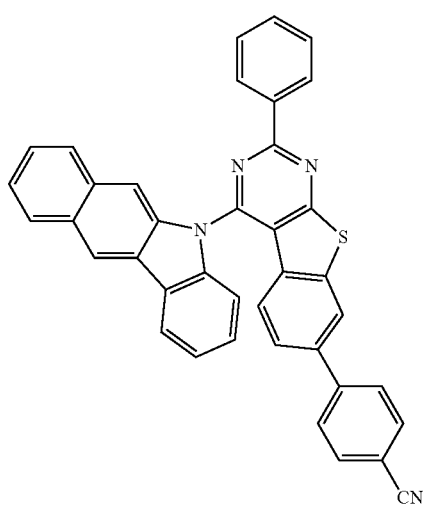
273
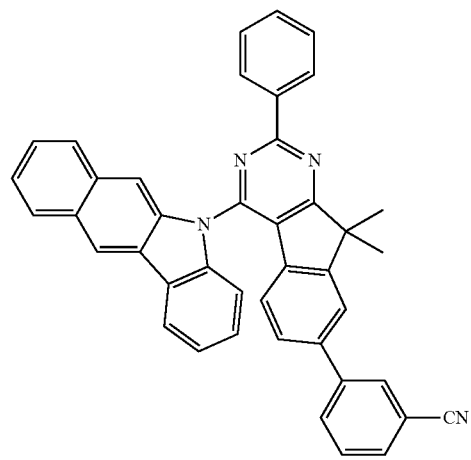
274
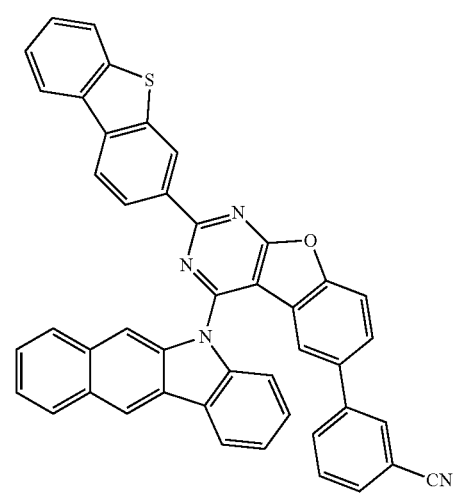
275
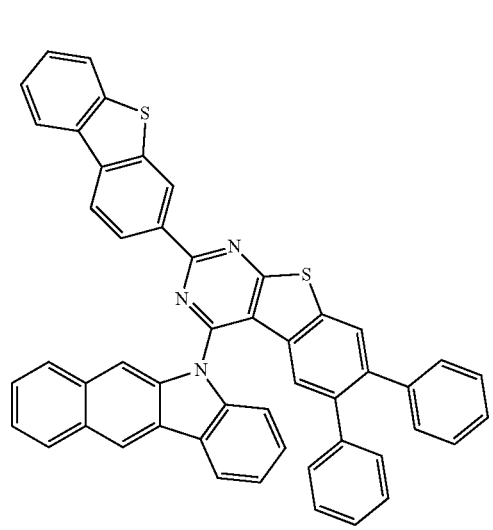

276
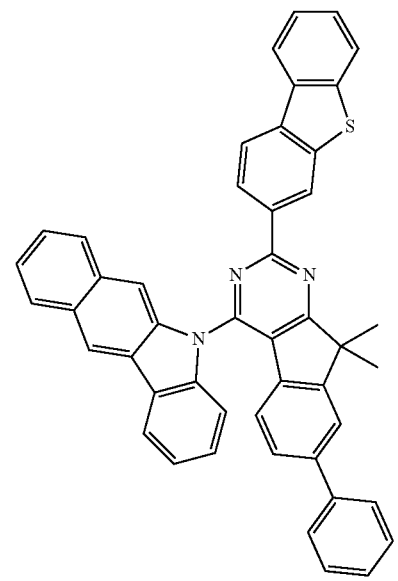
277
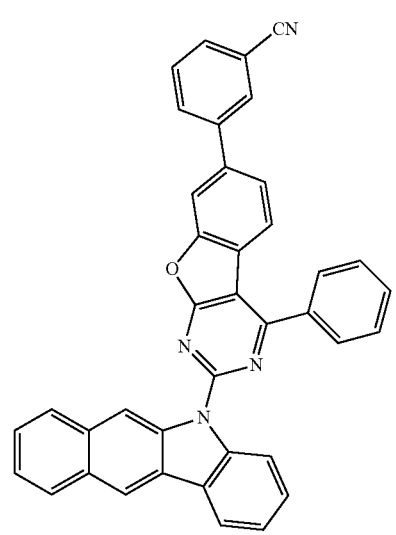
278
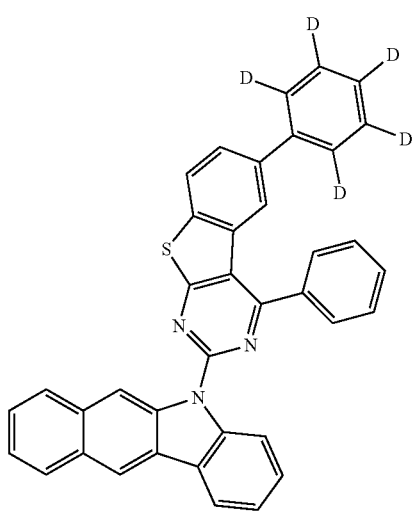
279
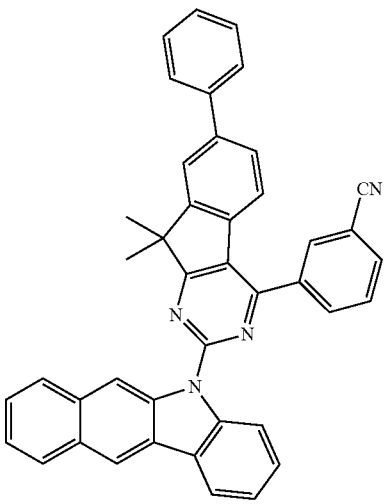
280
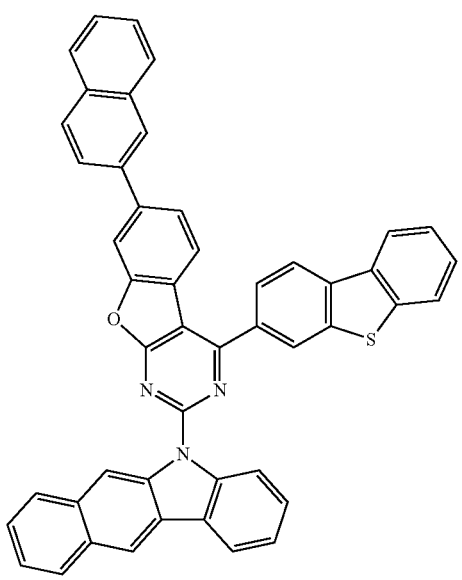
281
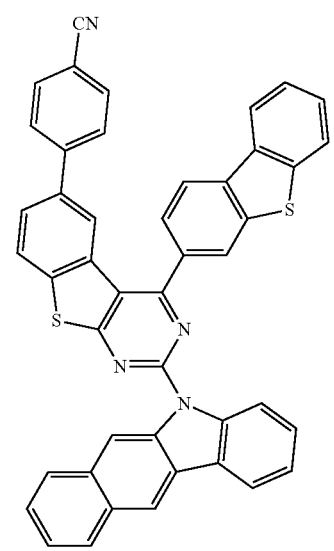

-continued
282
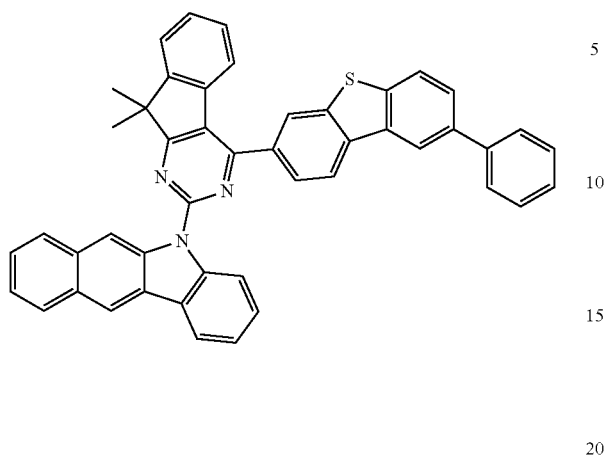
283
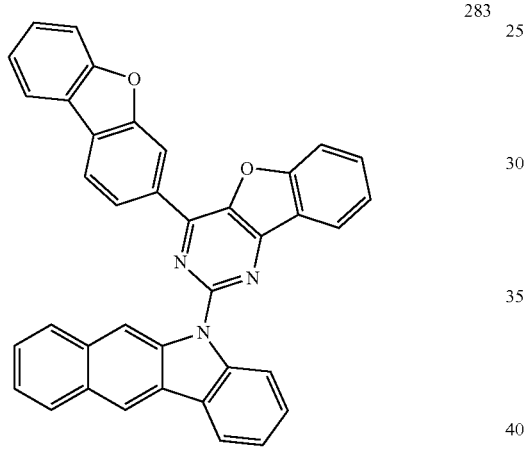
284
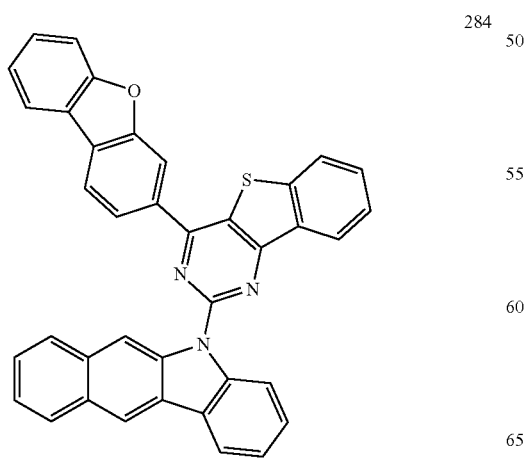
-continued
285
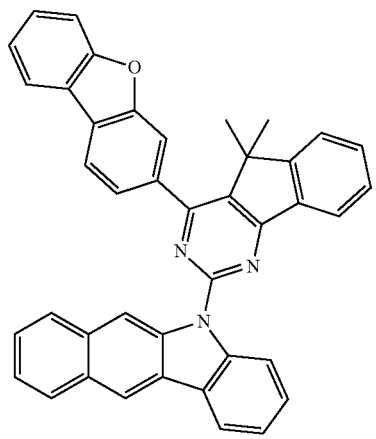
286
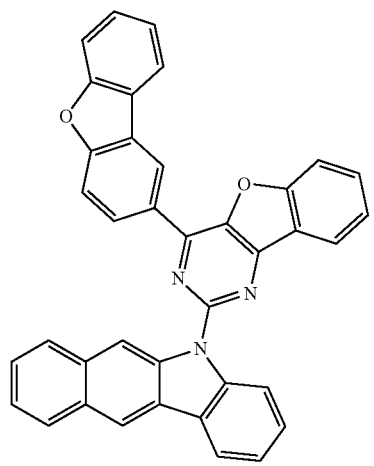
287
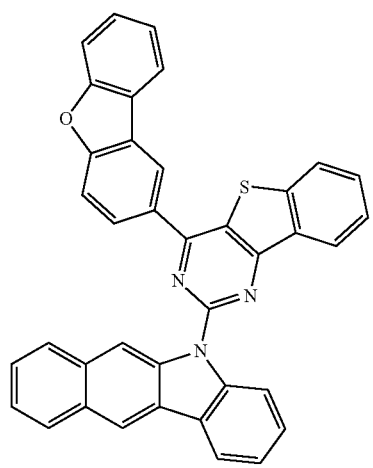

288
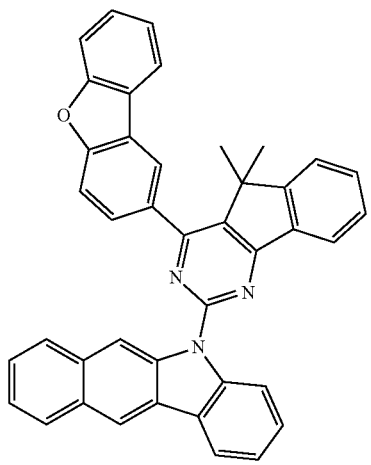
289
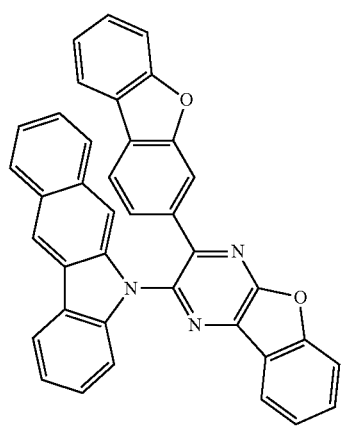
290
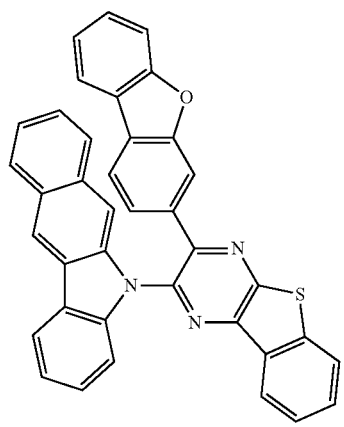
291
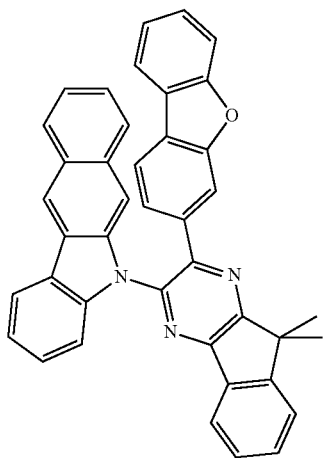
292
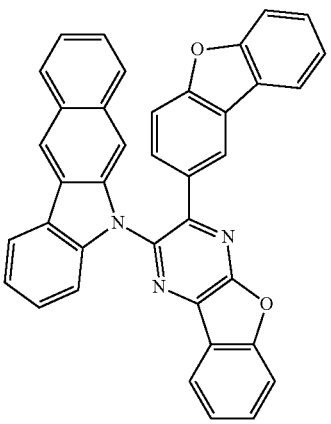
293
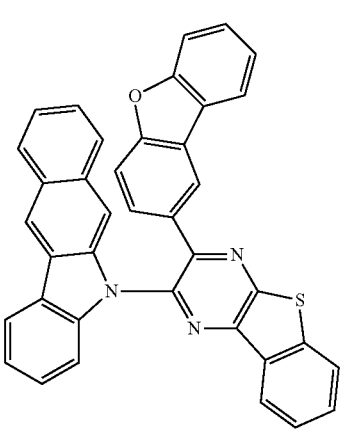

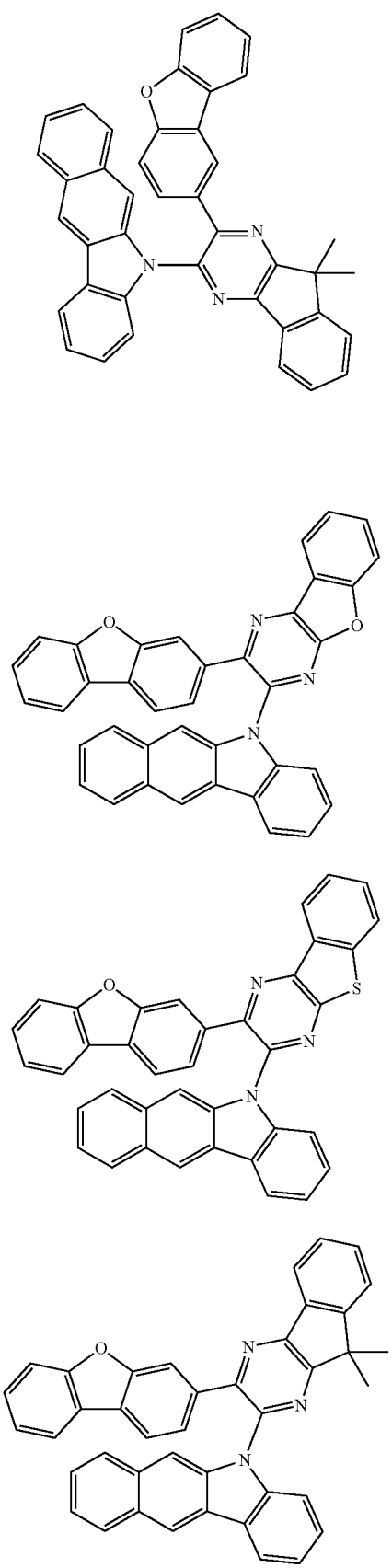
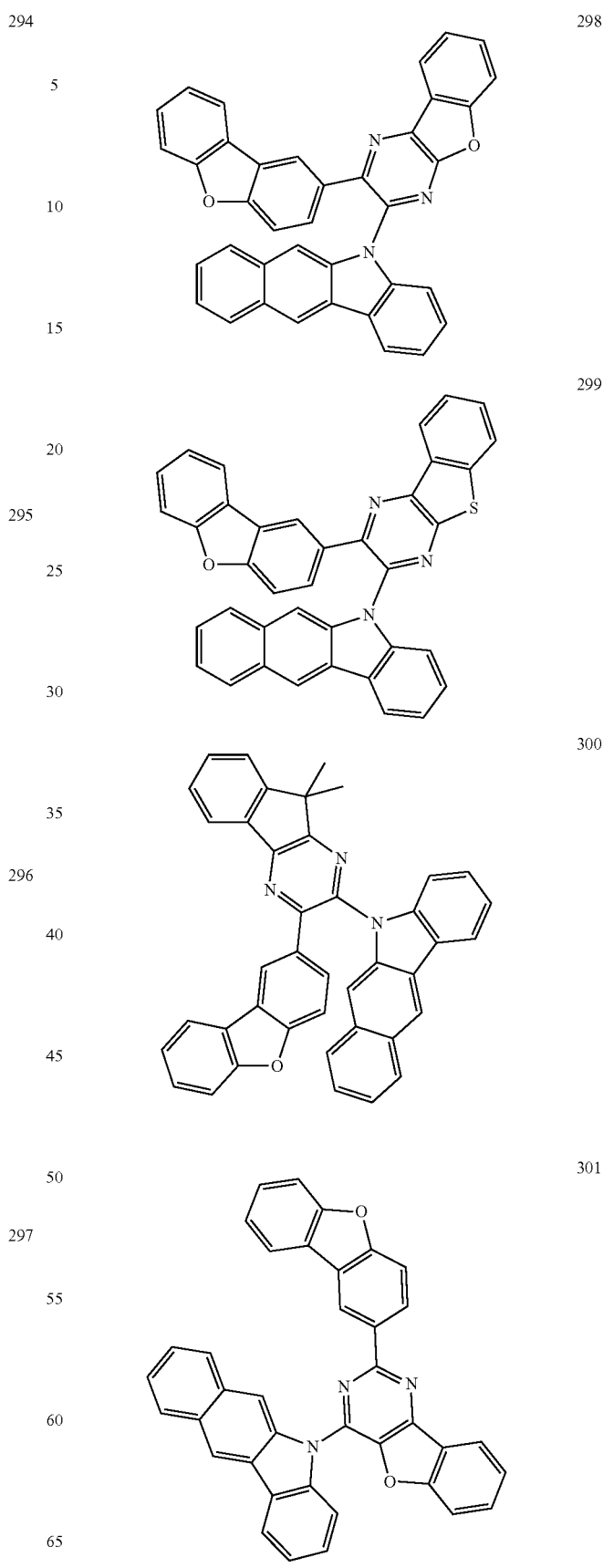

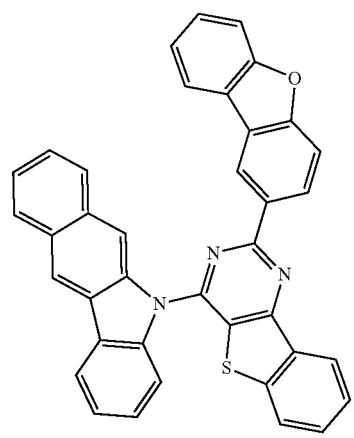
302
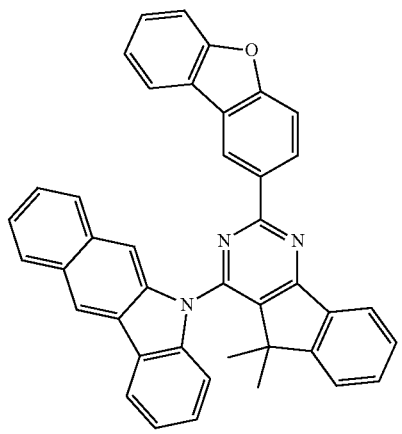
303
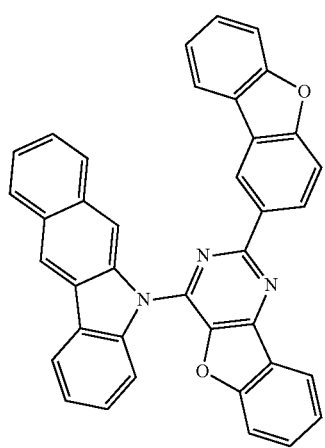
304
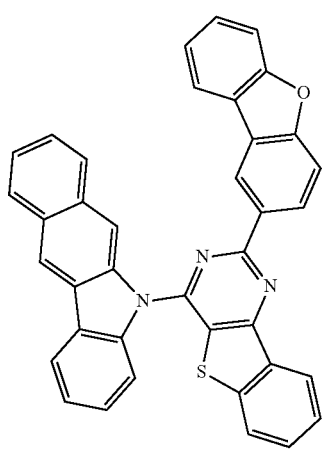
305
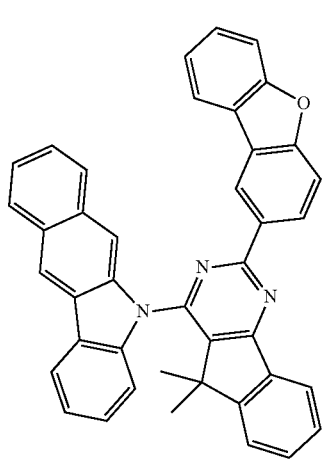
306
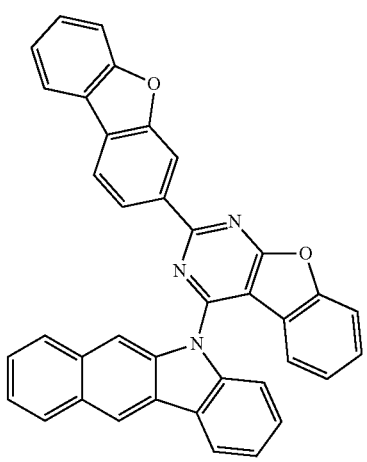
307

308
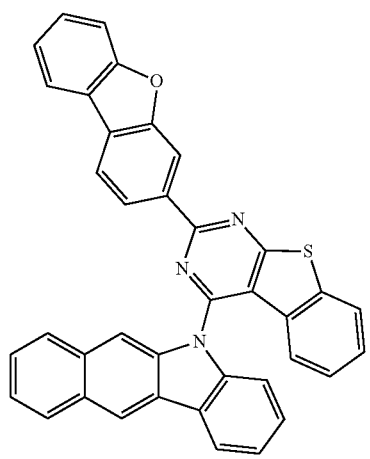
309
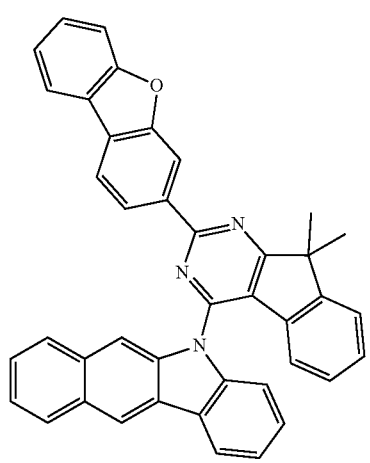
310
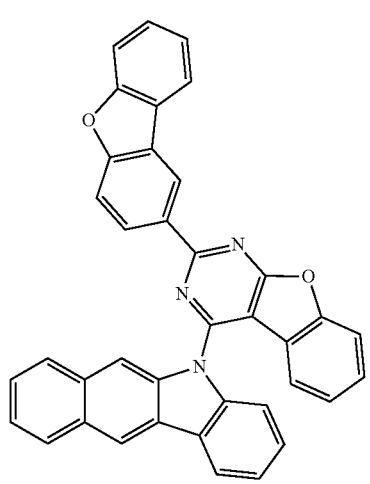
311
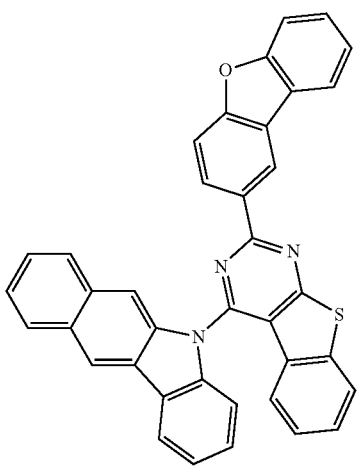
312
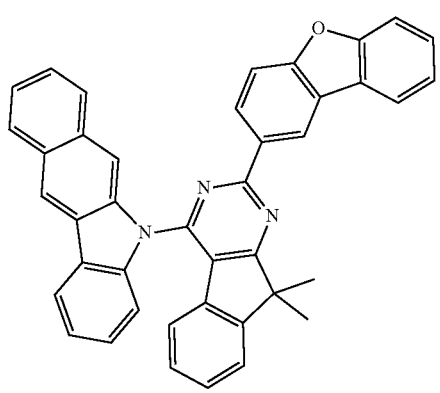
313
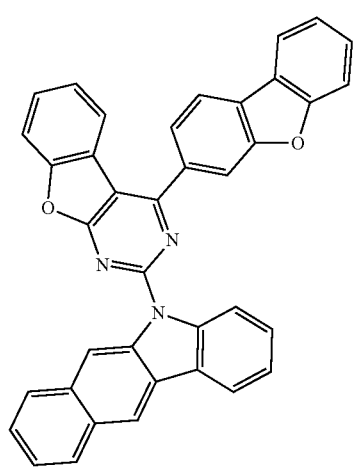

314
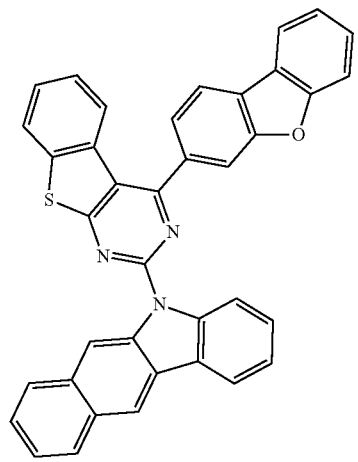
315
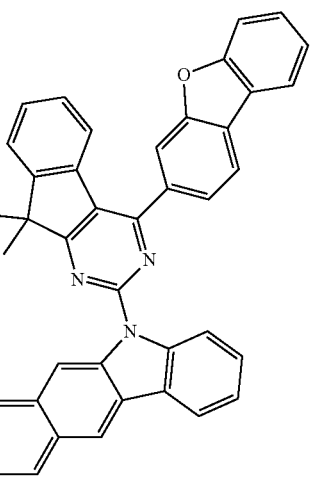
316
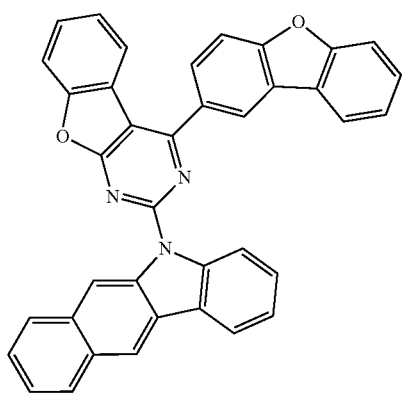
317
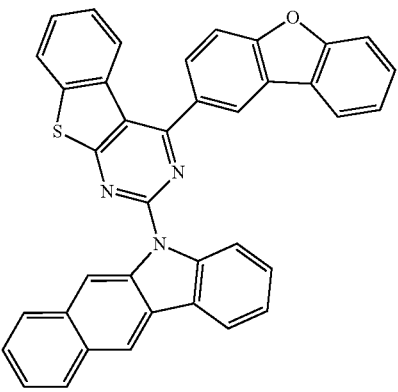
318
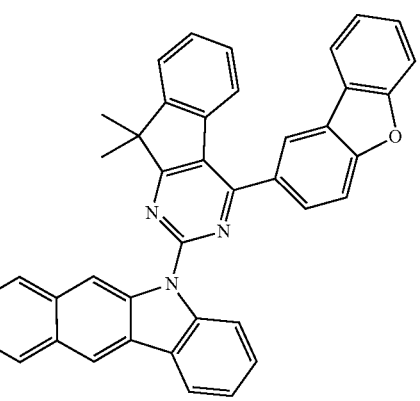
319
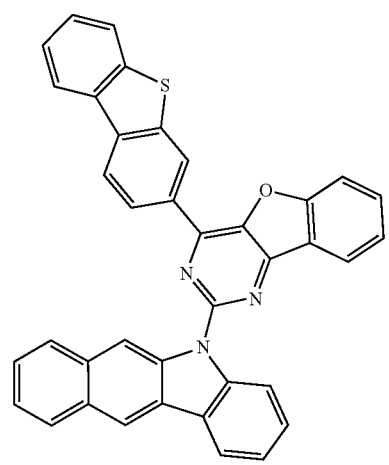

| | |
|---|---|
| 320 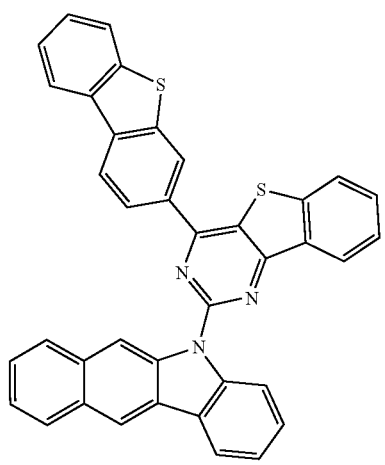 | 323 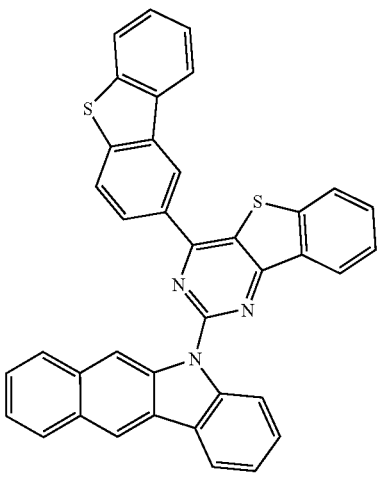 |
| 321 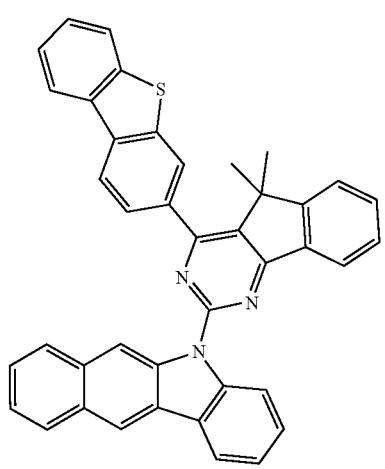 | 324 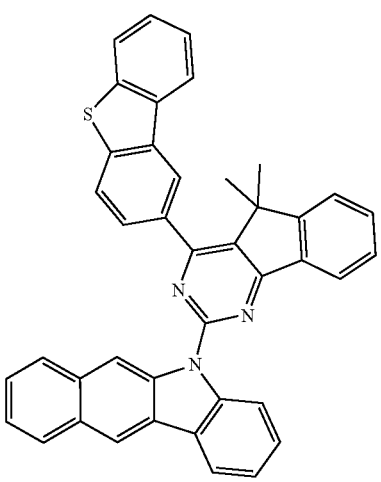 |
| 322 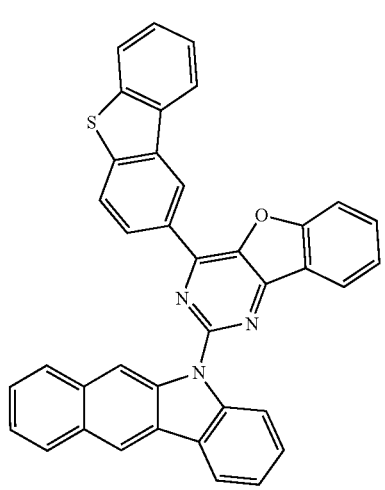 | 325 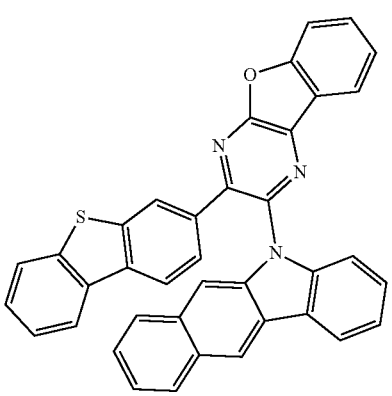 |

326
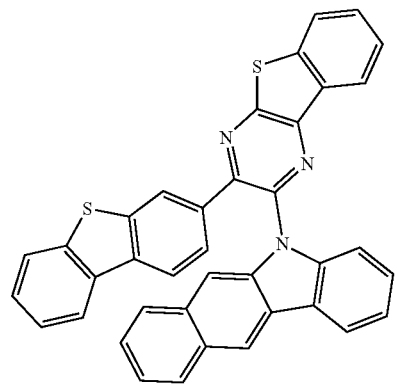
327
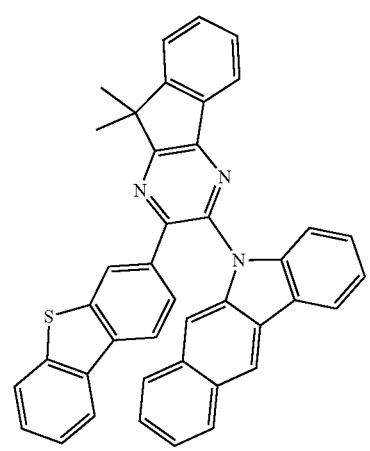
328
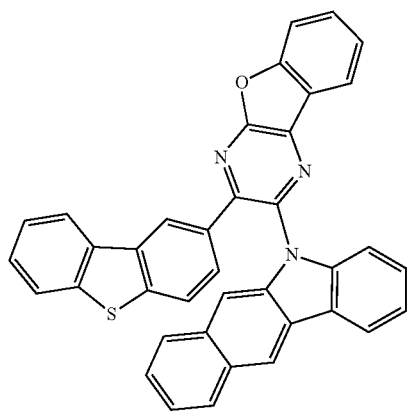
329
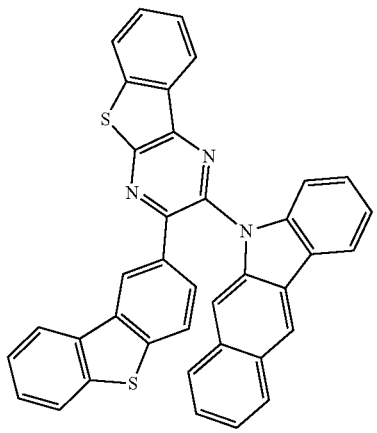
330
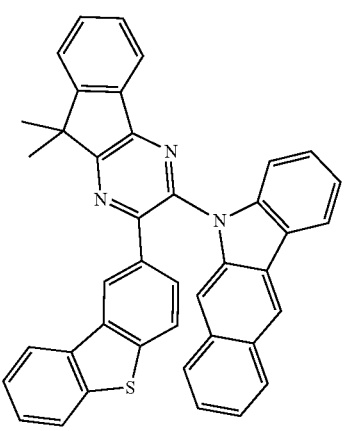
331
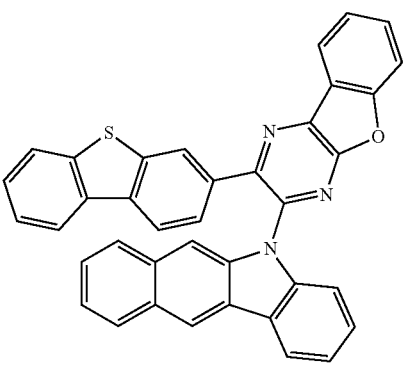
332
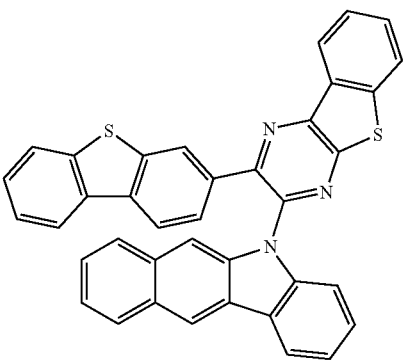

333
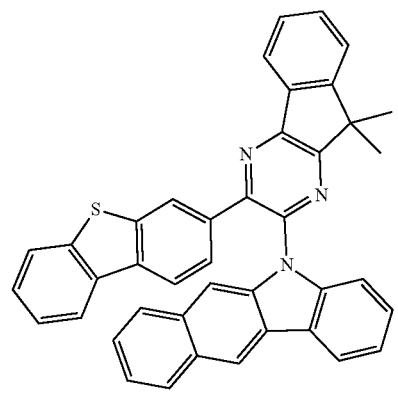
334
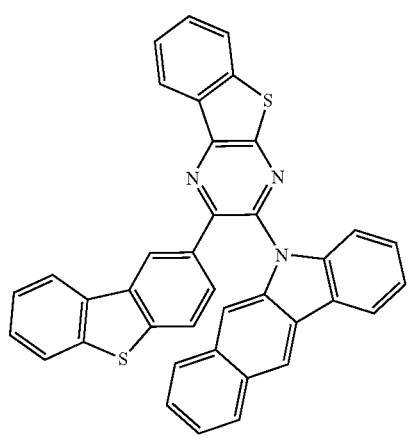
335
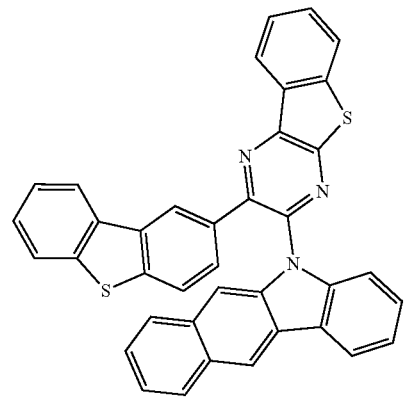
336
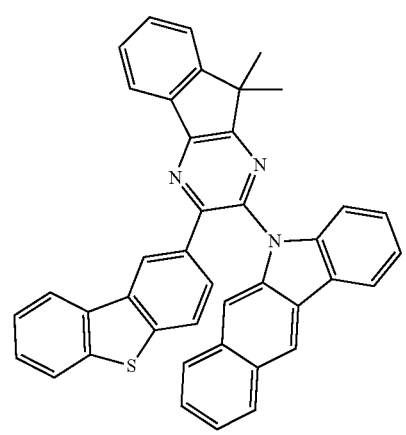
337
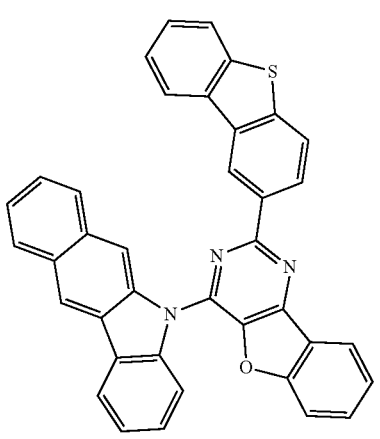
338
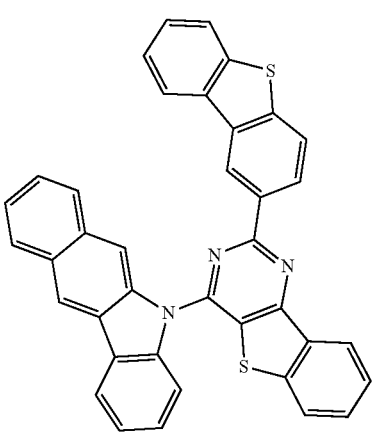
339
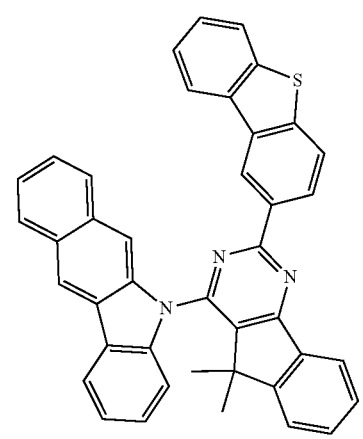

340
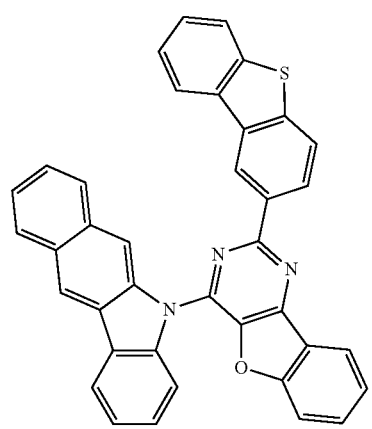
341
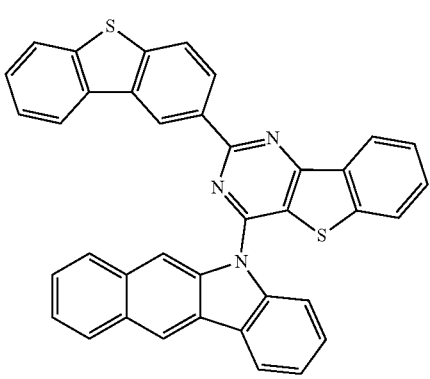
342
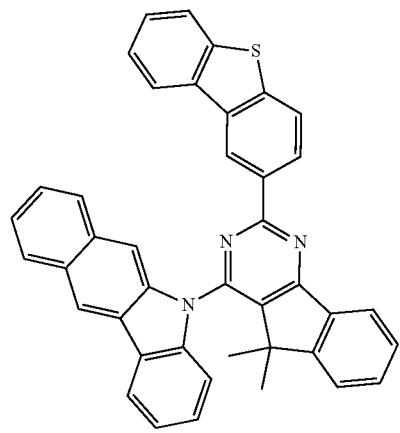
343
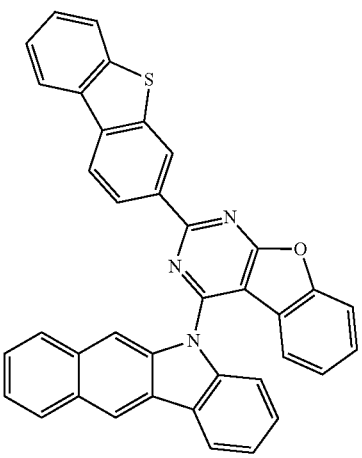
344
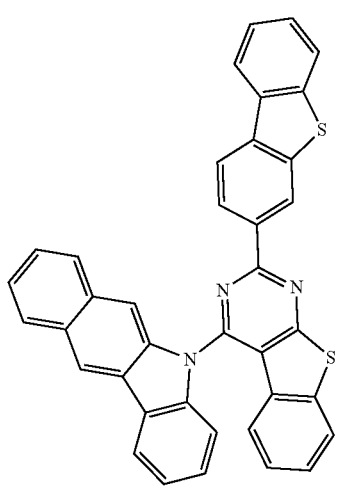
345
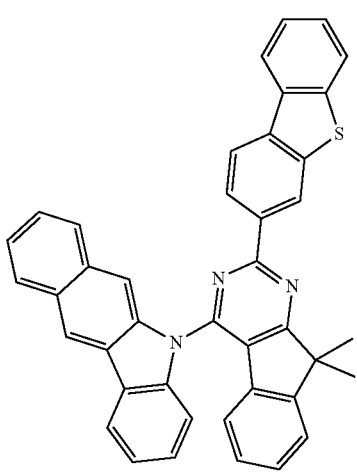

346
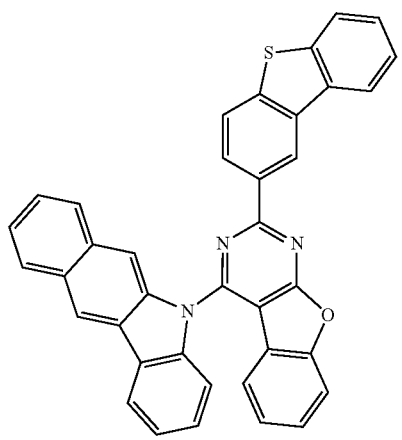
347
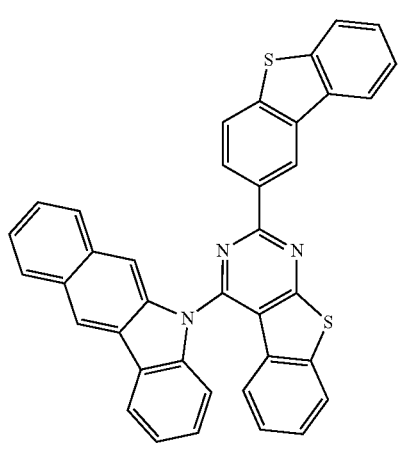
348
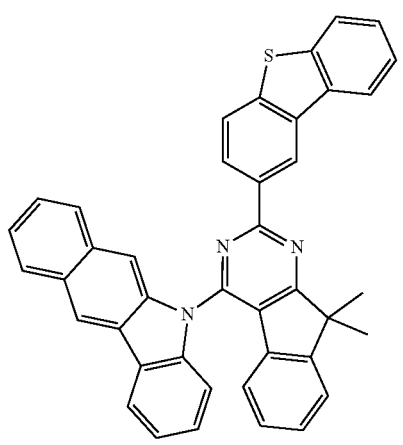
349
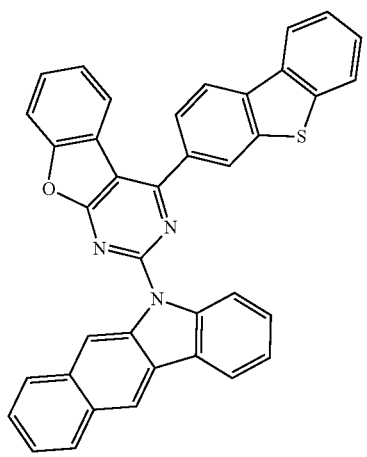
350
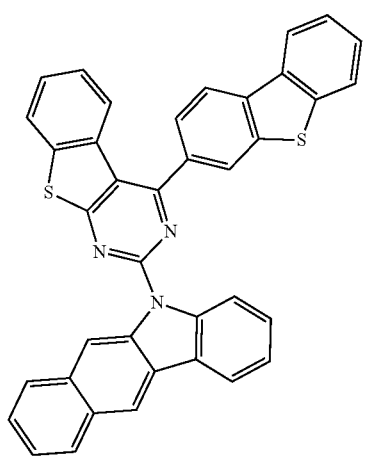
351
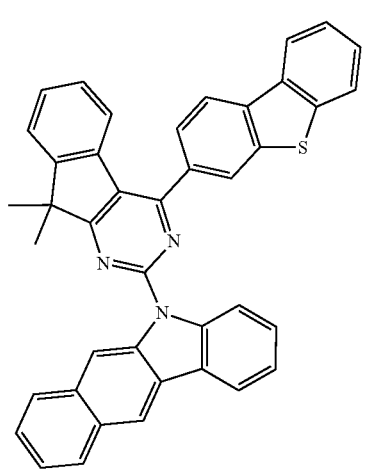

115
-continued
352
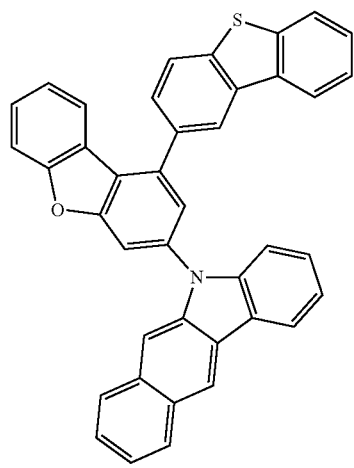
353
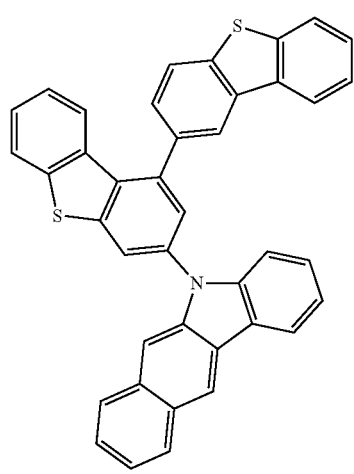
354
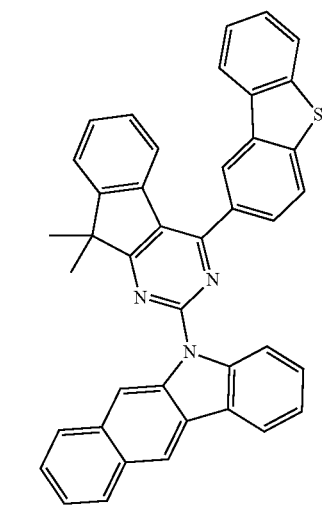
116
-continued
355
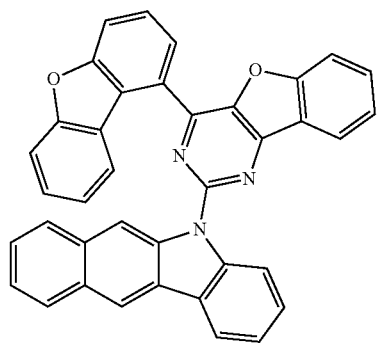
356
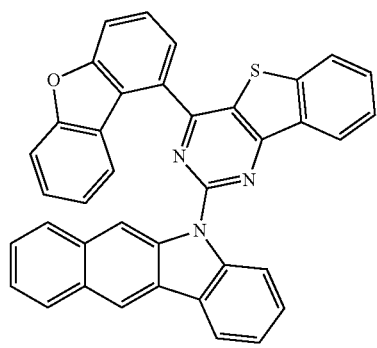
357
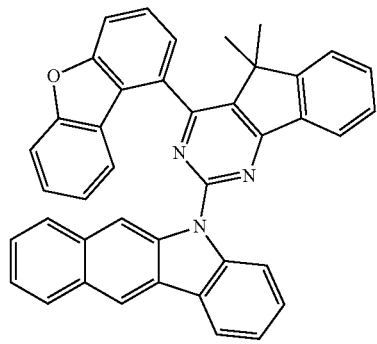
358
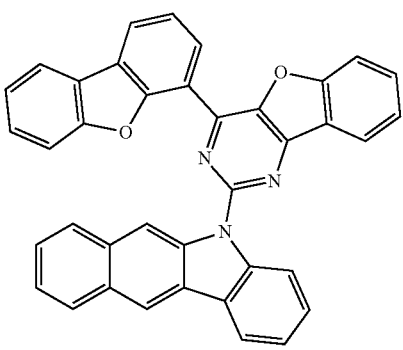

359
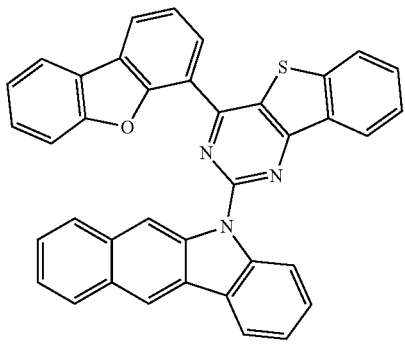
360
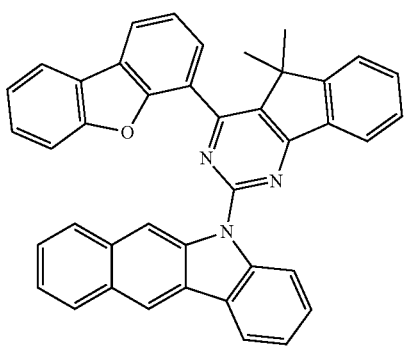
361
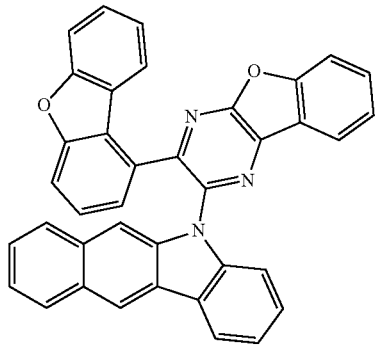
362
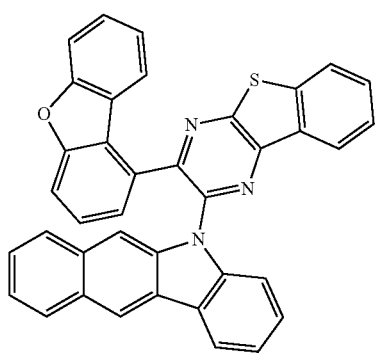
363
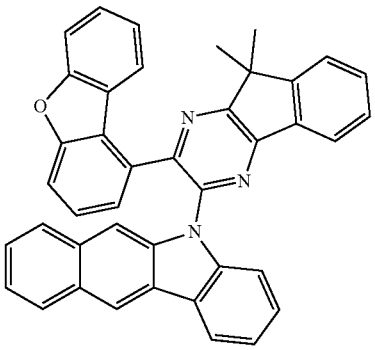
364
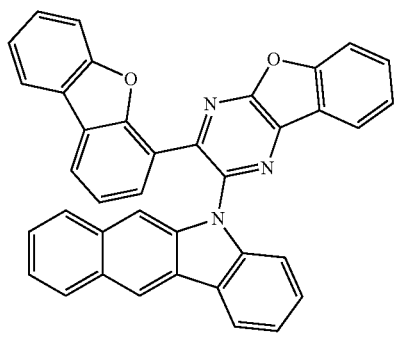
365
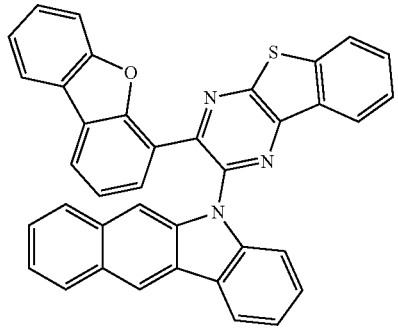
366
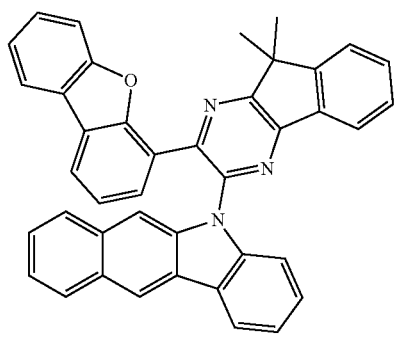

361
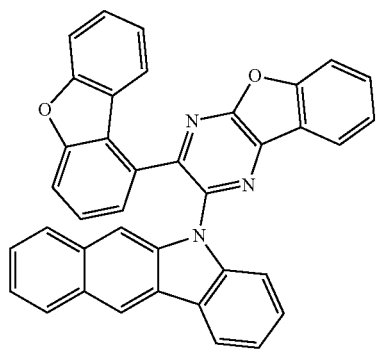
362
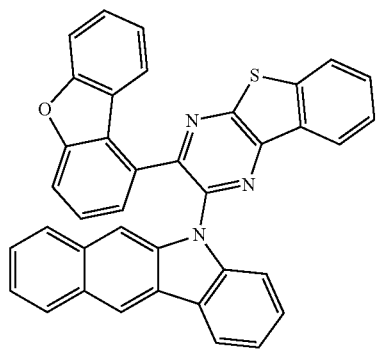
363
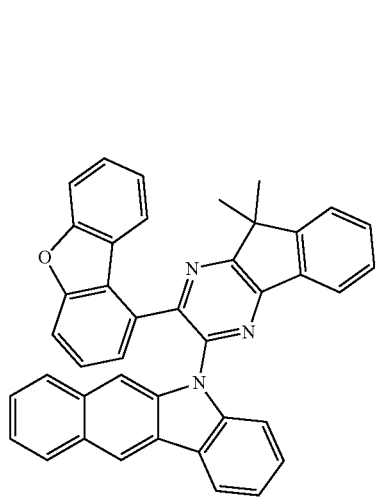
364
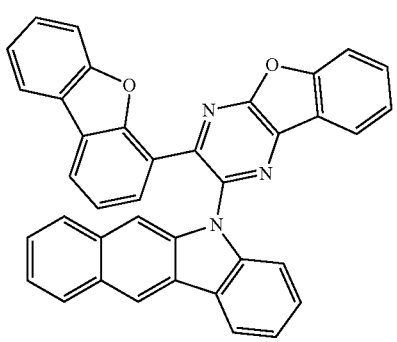
365
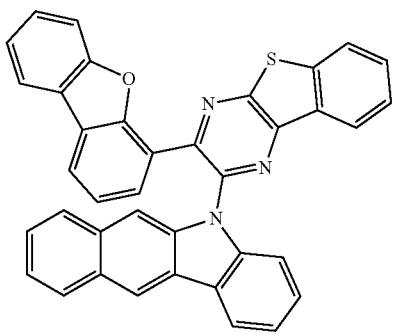
366
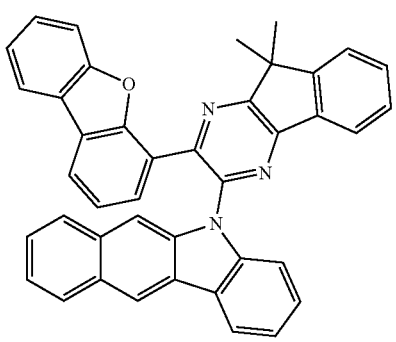
367
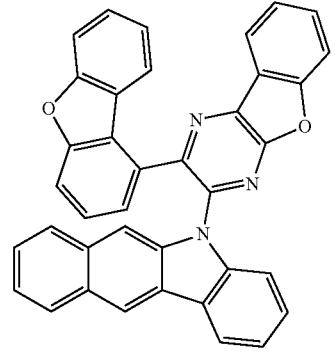
368
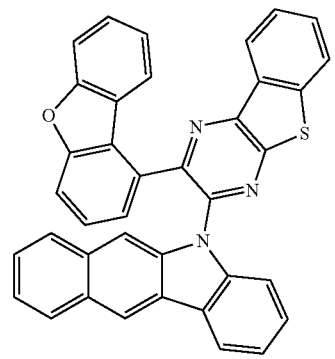

369
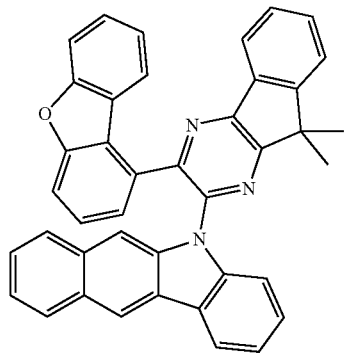
370
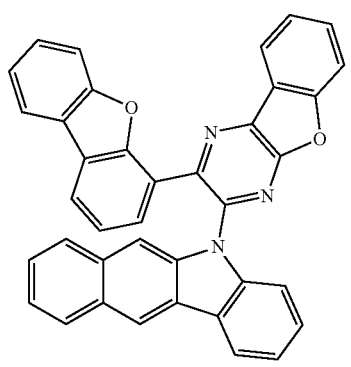
371
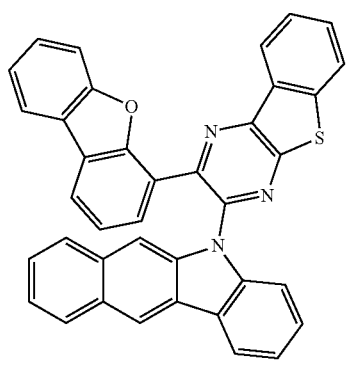
372
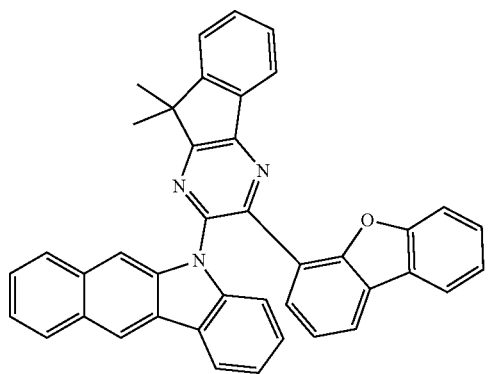
373
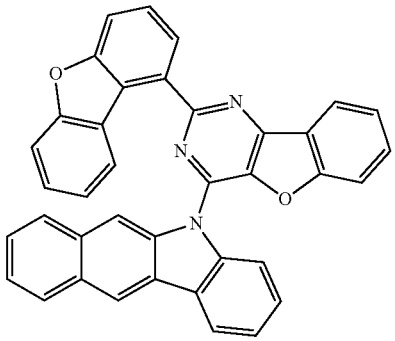
374
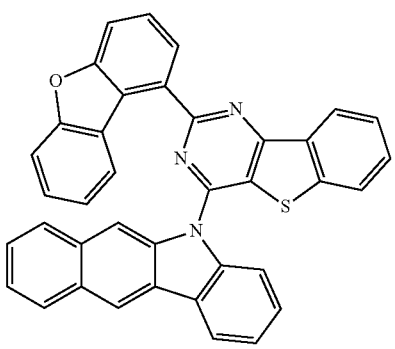
375
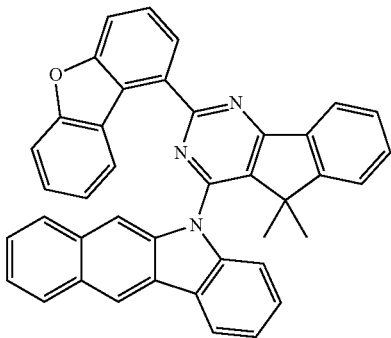
376
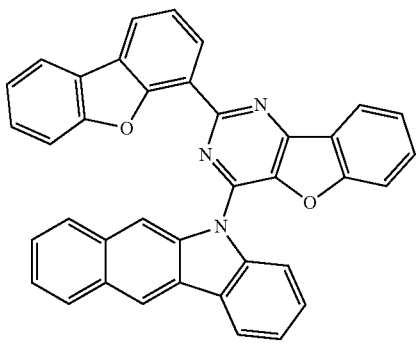

-continued
377
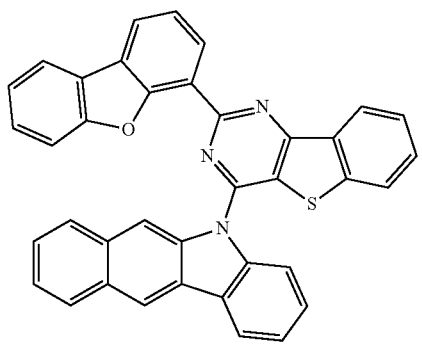
378
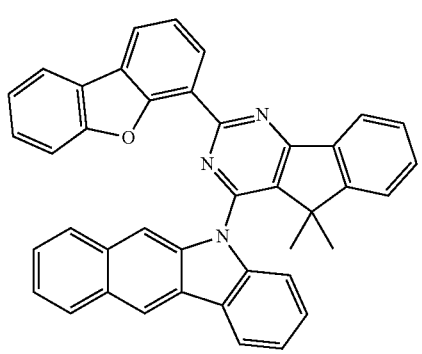
379
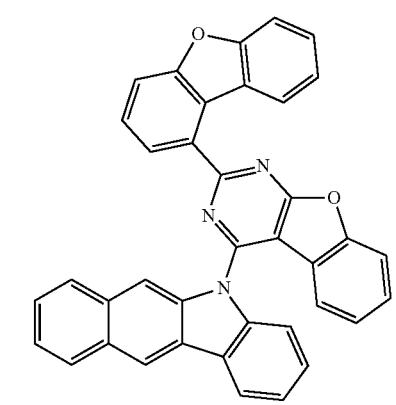
380
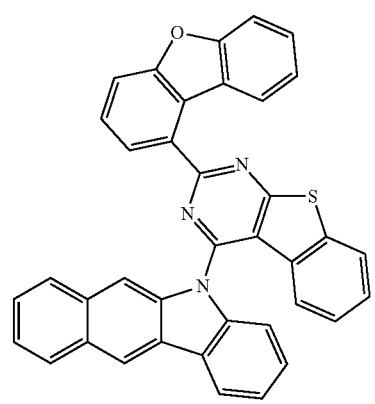
-continued
381
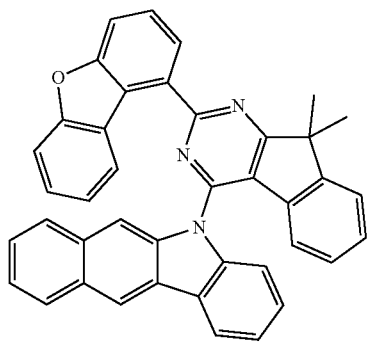
382
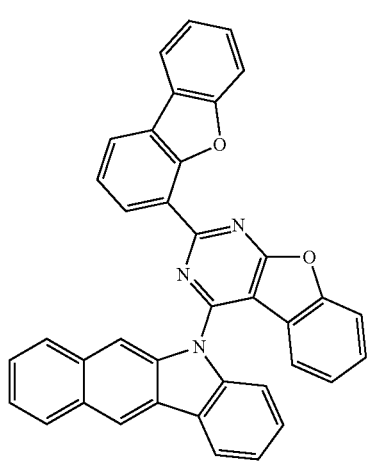
383
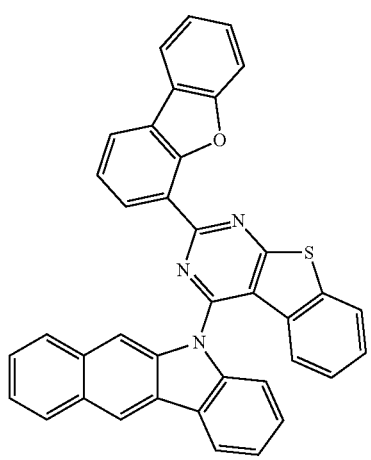
384
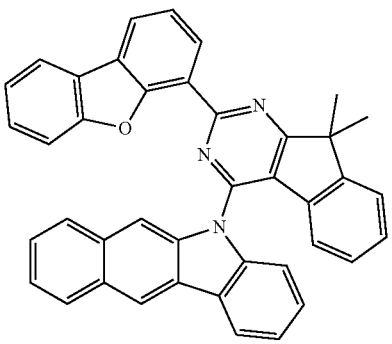

385
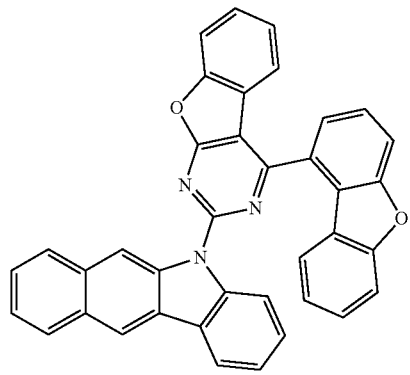
386
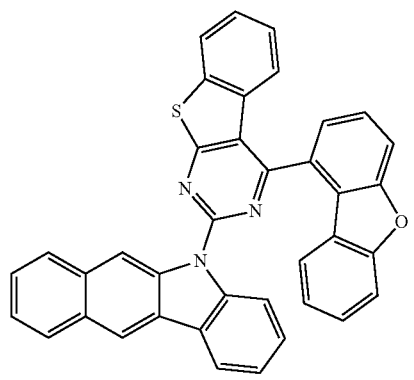
387
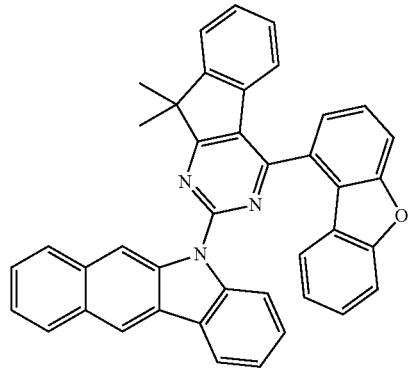
388
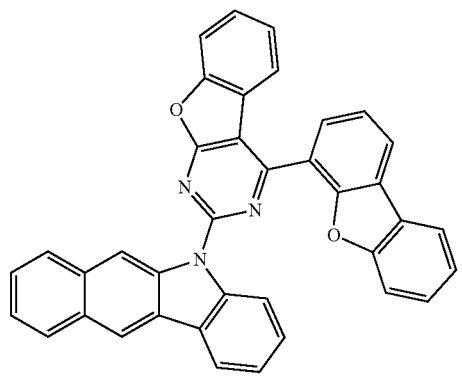
389
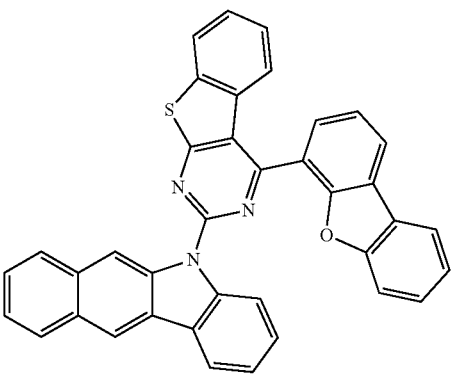
390
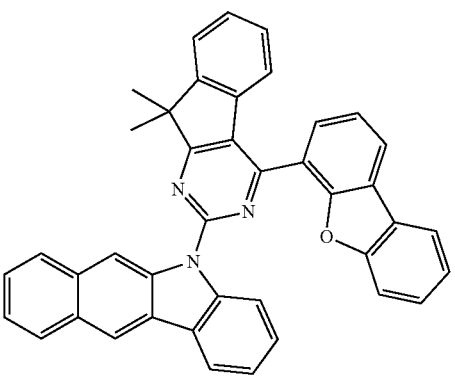
391
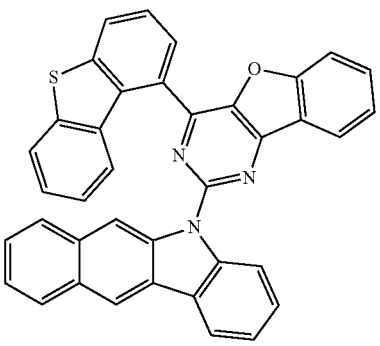
392
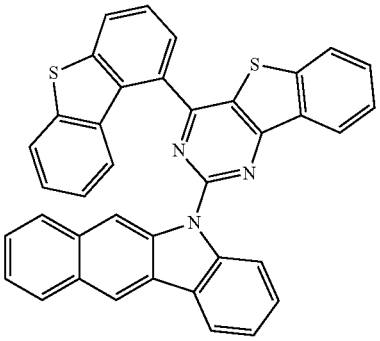

393
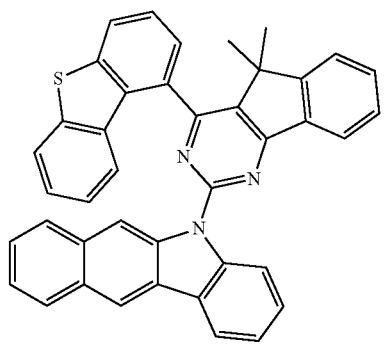
394
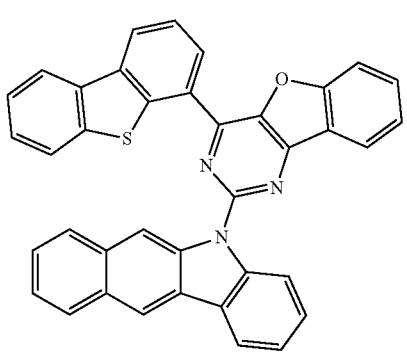
395
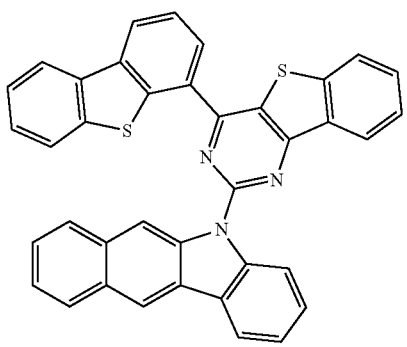
396
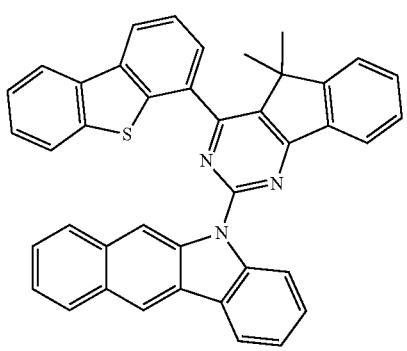
397
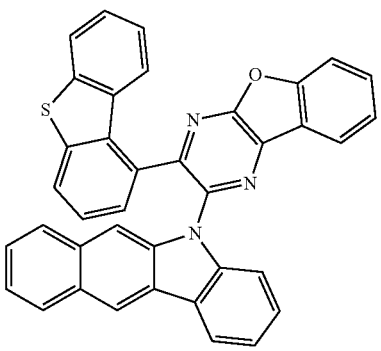
398
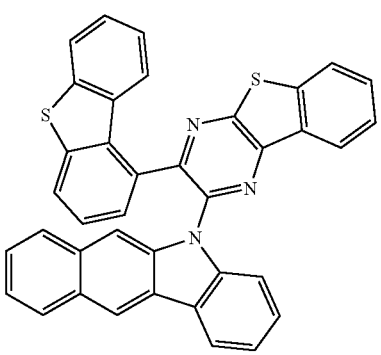
399
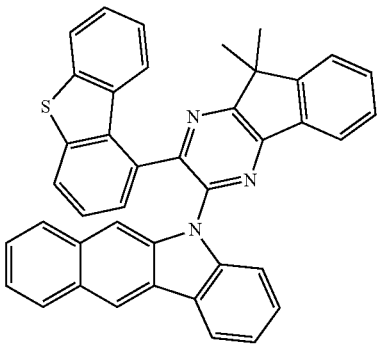
400
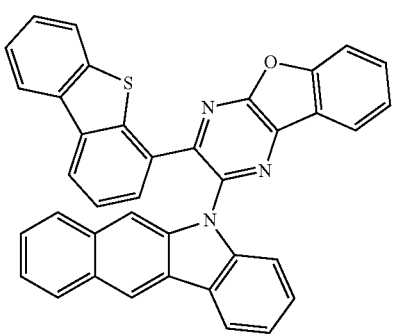

401
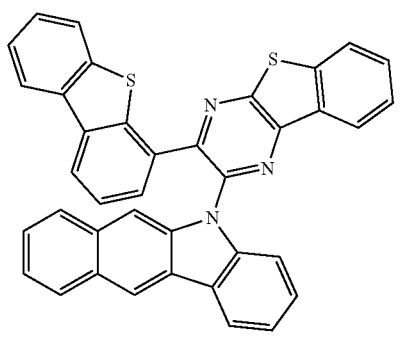
402
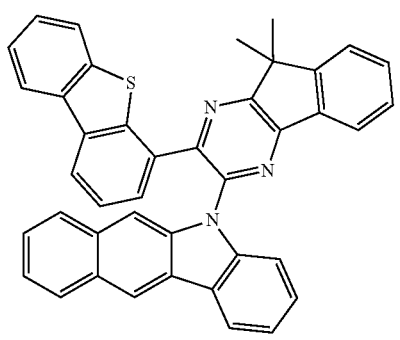
403
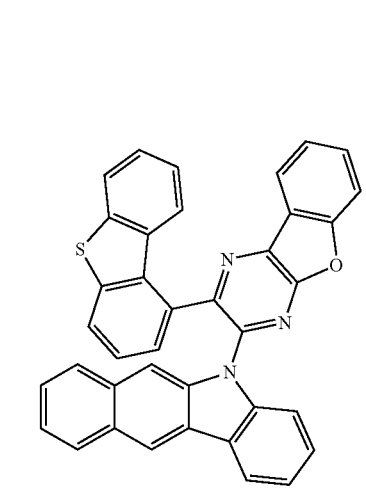
404
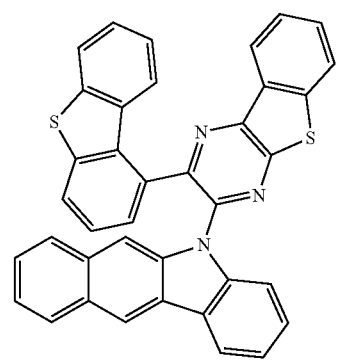
405
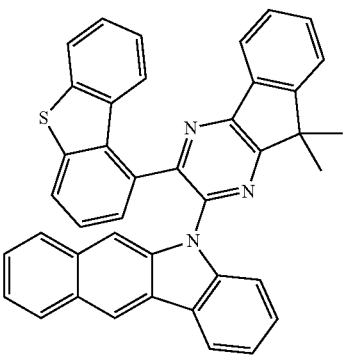
407
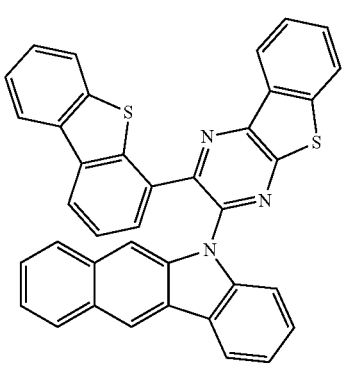
408
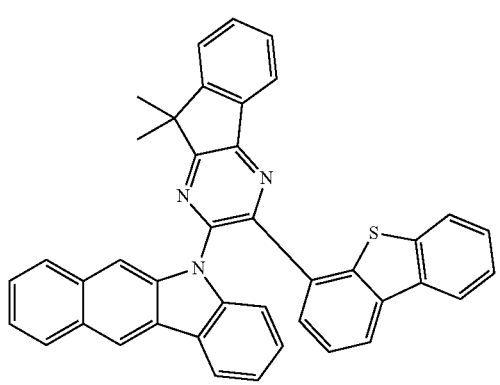
409
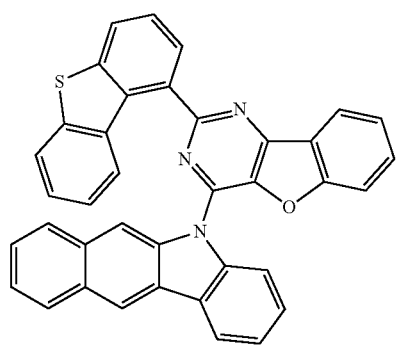

-continued
410
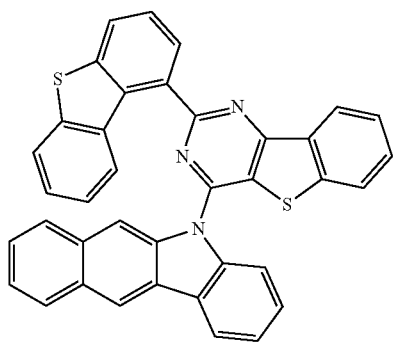
411
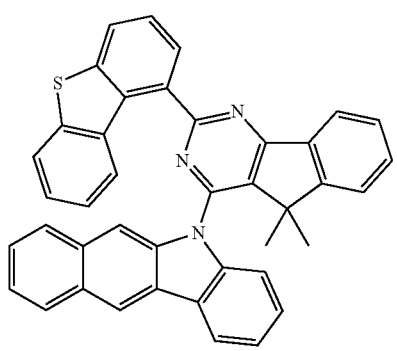
412
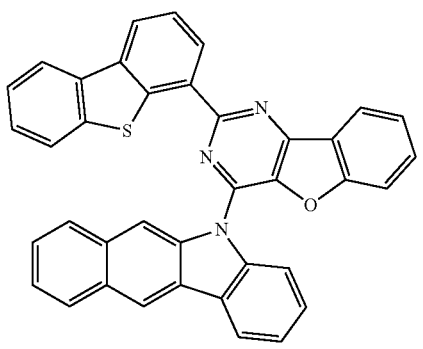
413
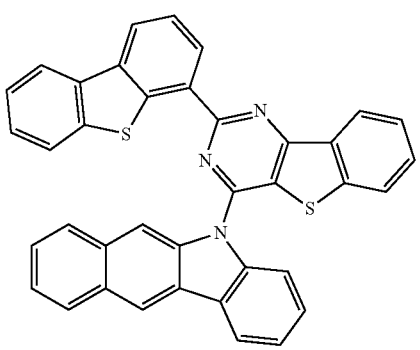
-continued
414
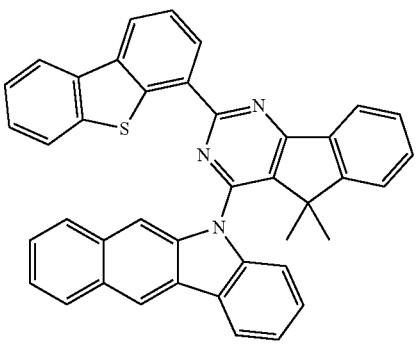
415
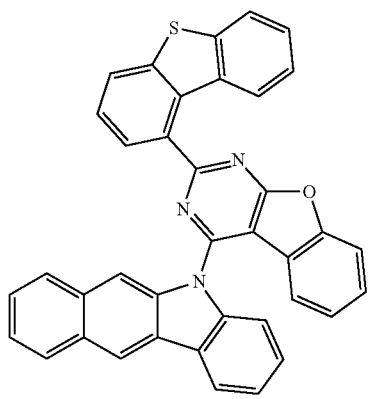
416
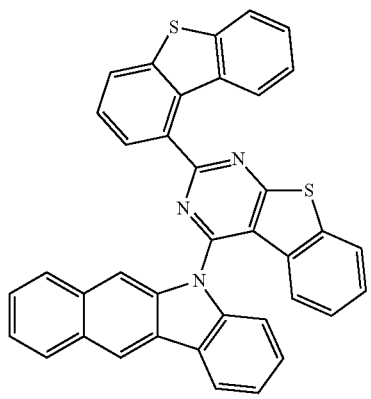
417
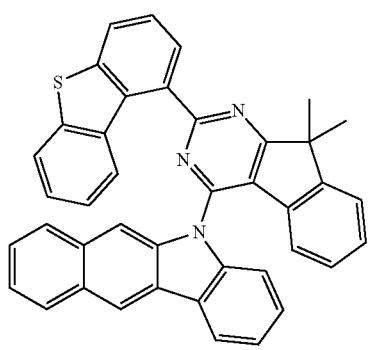

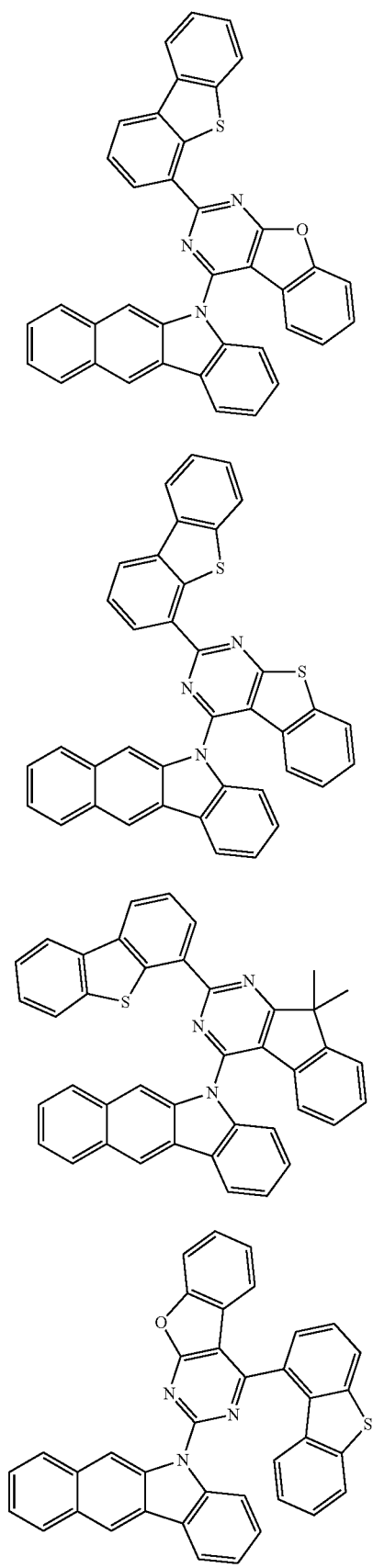

426
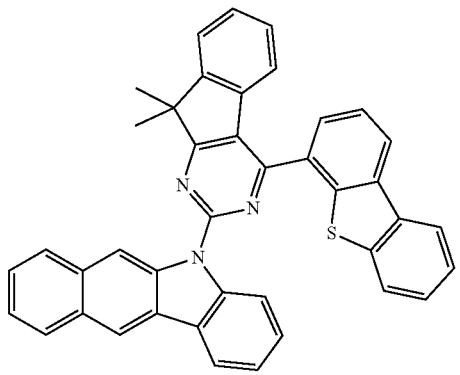
427
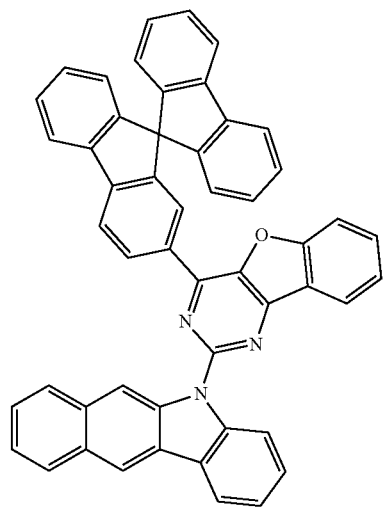
428
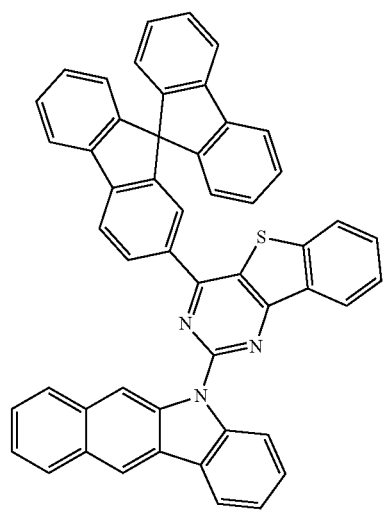
429
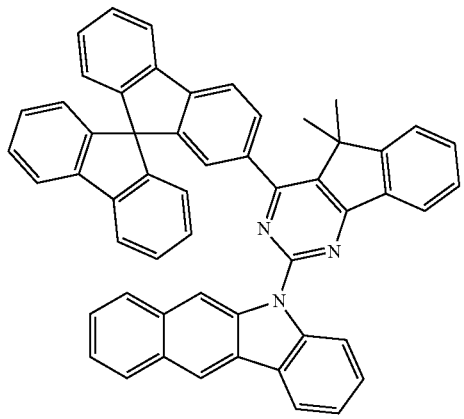
430
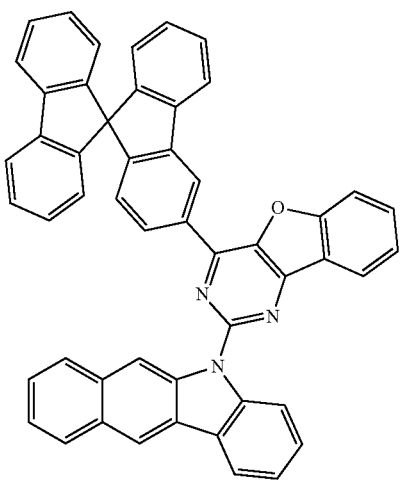
431
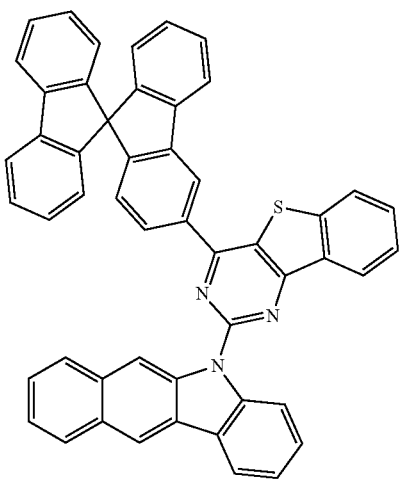

432
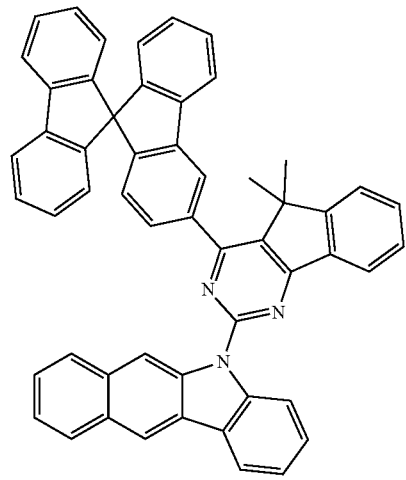
433
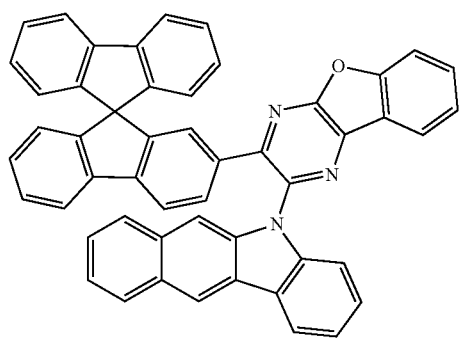
434
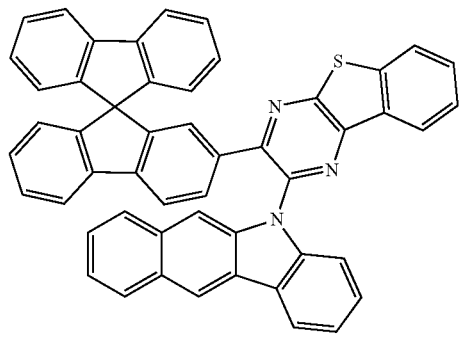
435
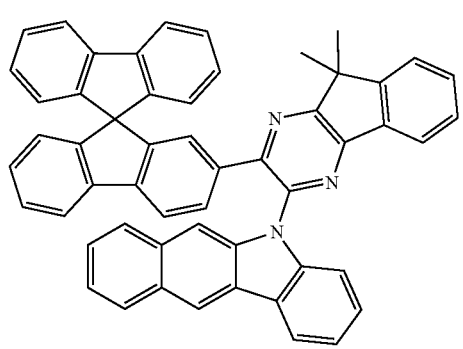
436
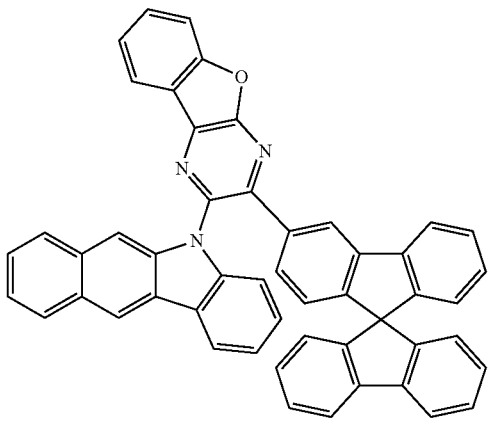
437
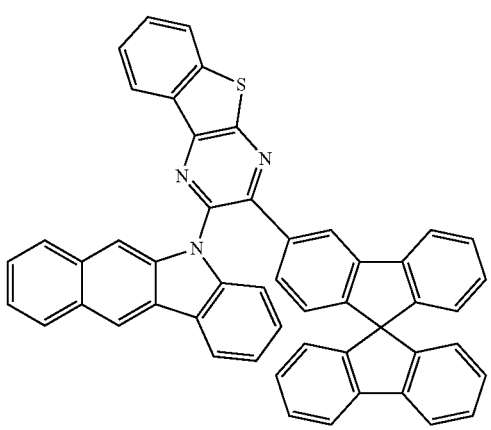
438
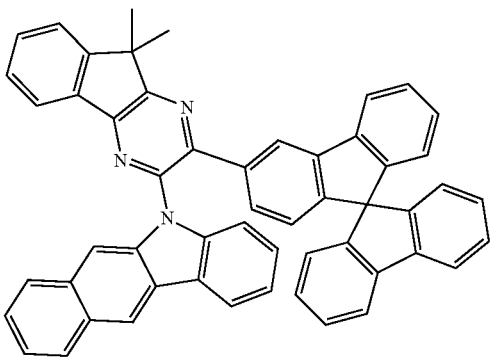
439
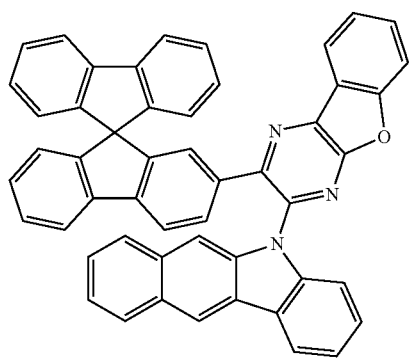

440
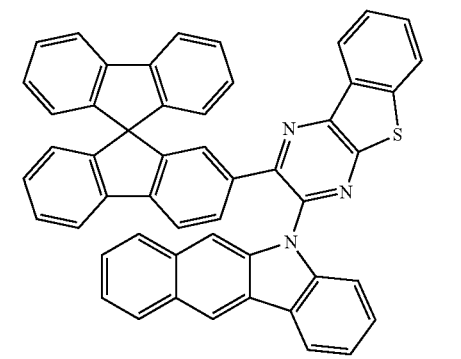
441
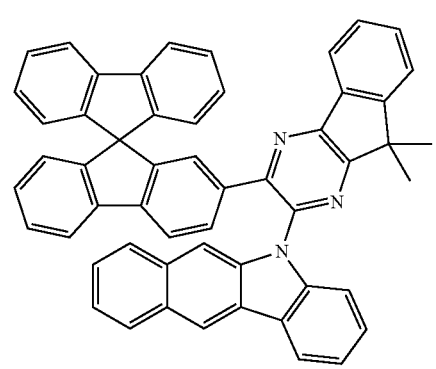
442
444
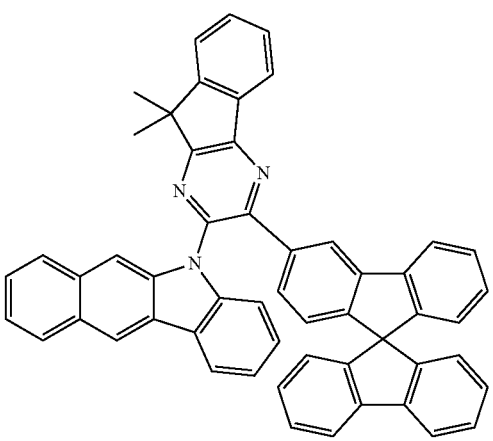
445
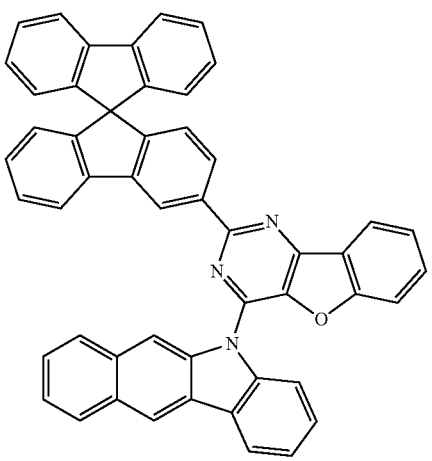
443
446
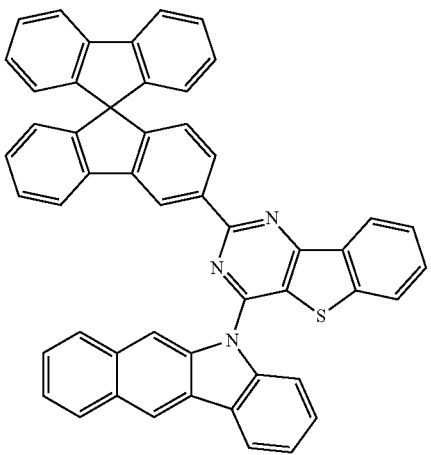

447
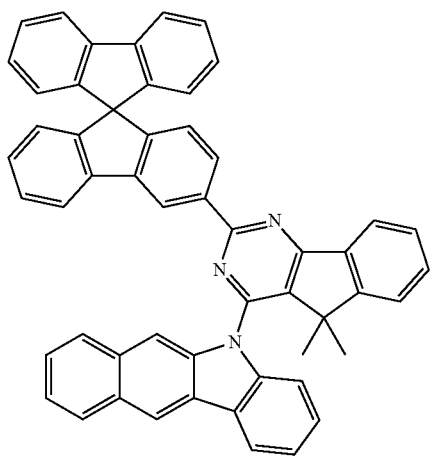
450
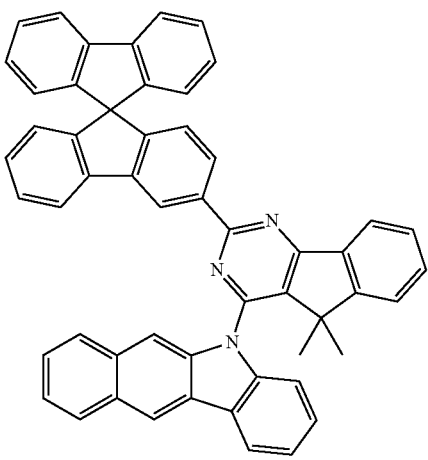
448
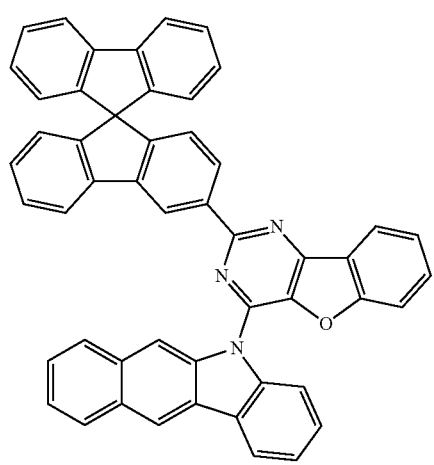
451
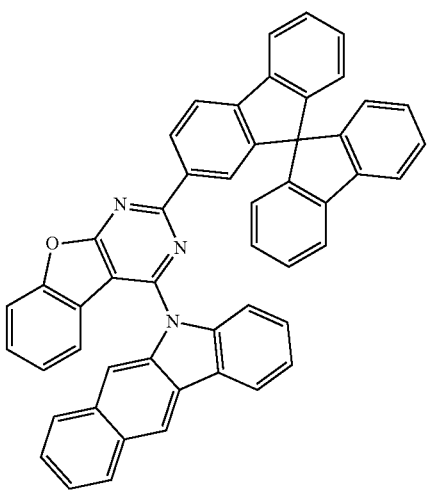
449
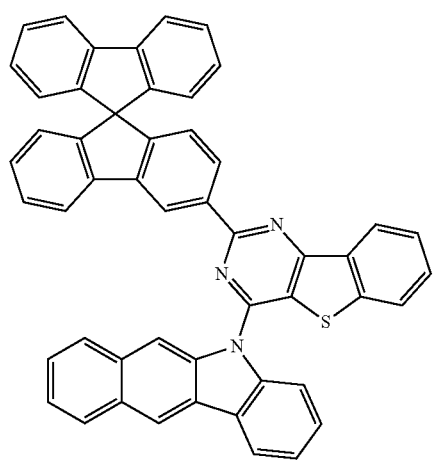
452
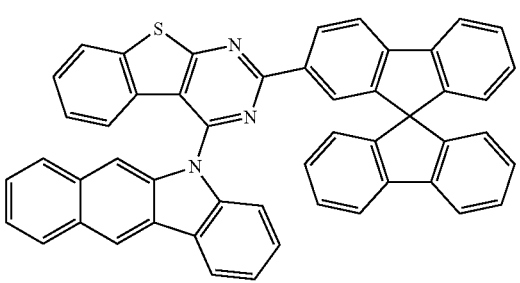

453
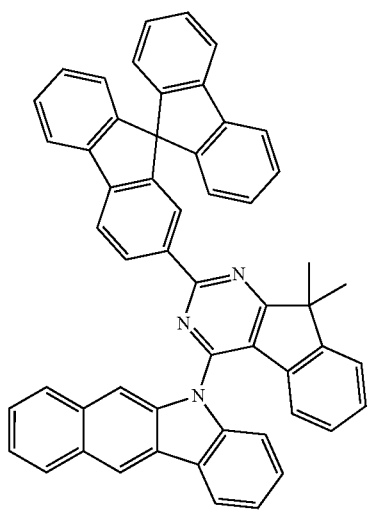
454
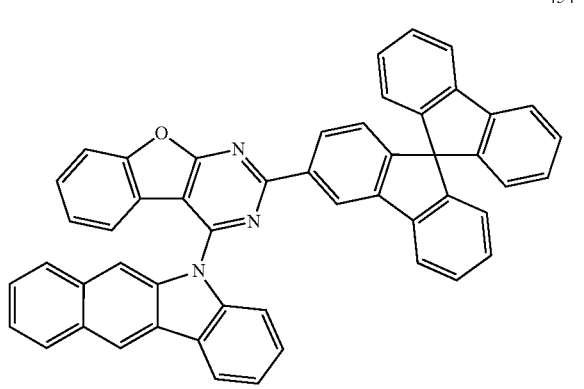
455
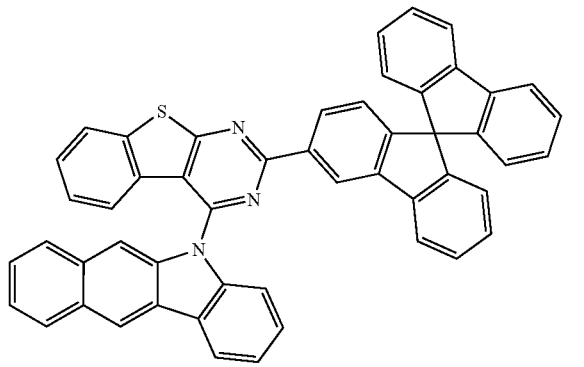
456
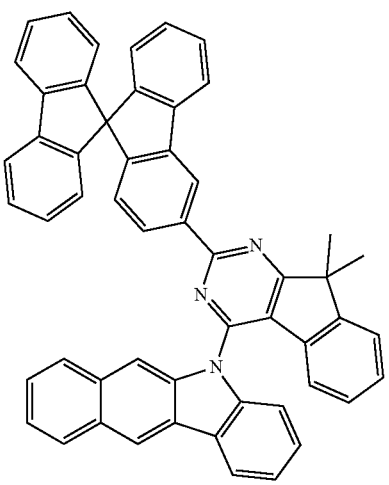
457
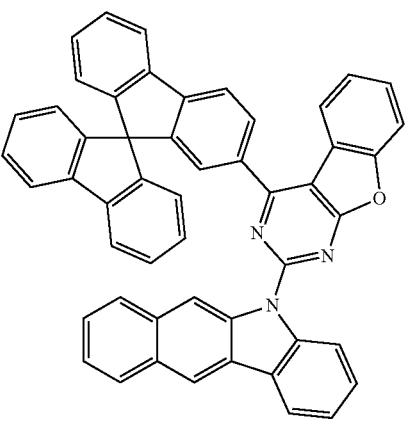
458
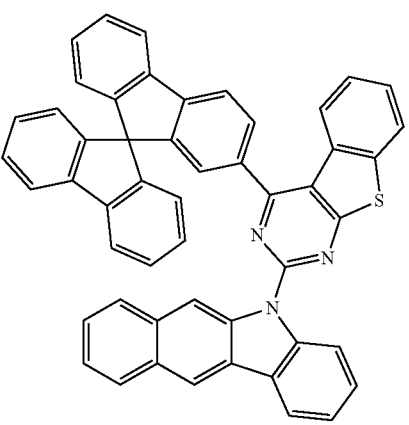

459
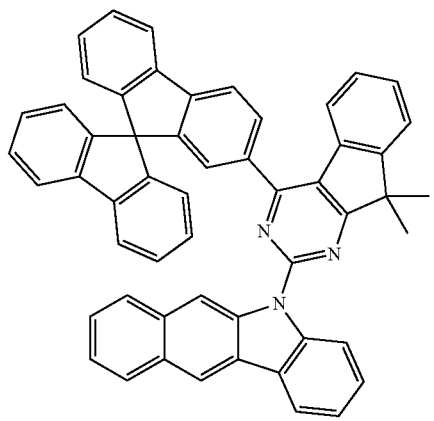
460
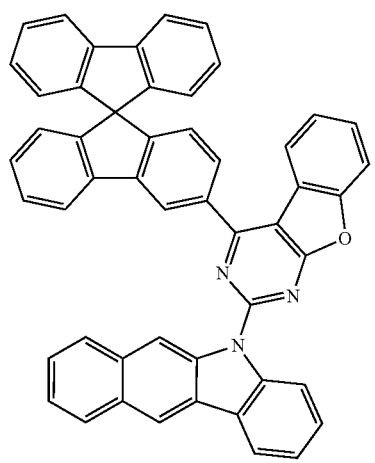
461
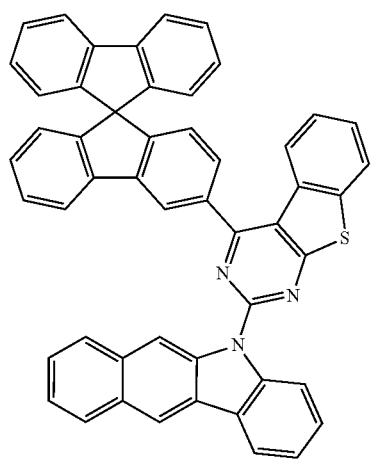
462
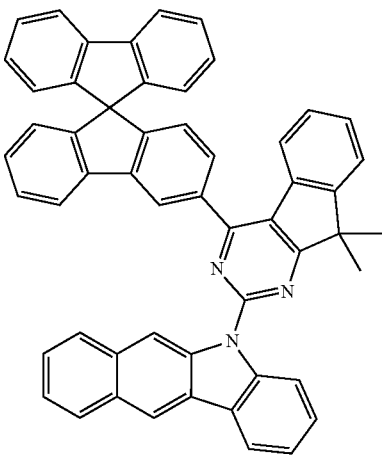
463
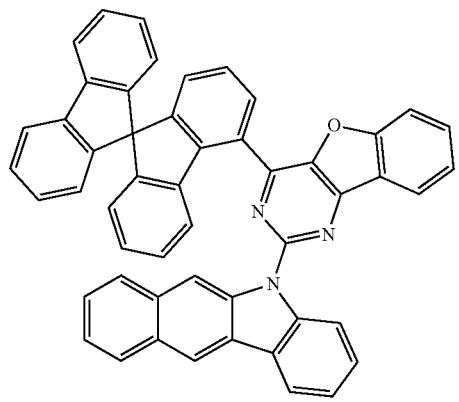
464
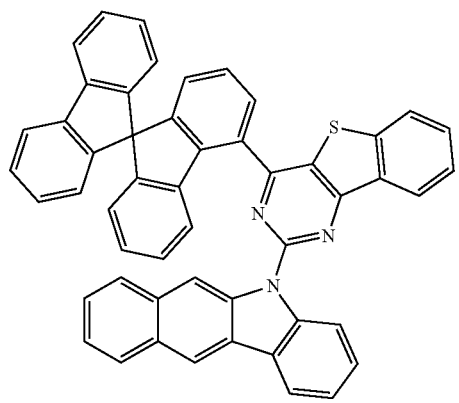
465
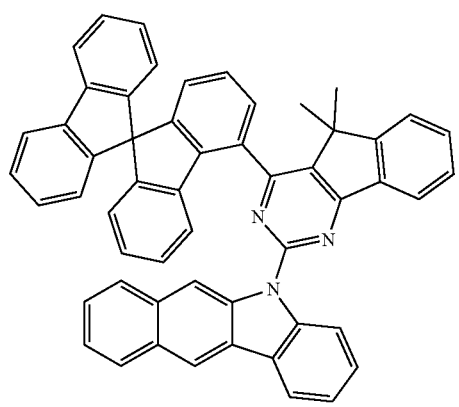

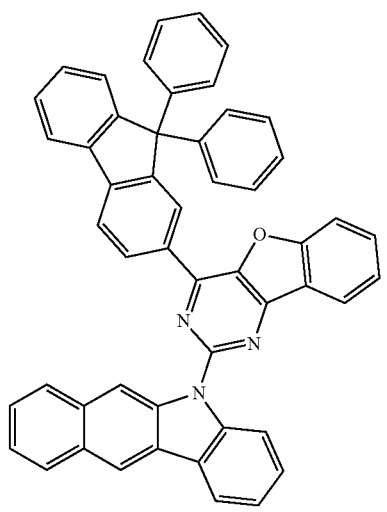
466

467
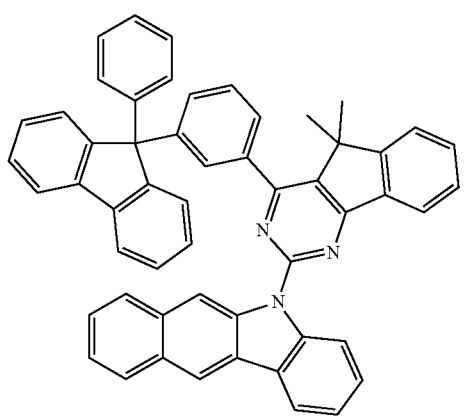
468
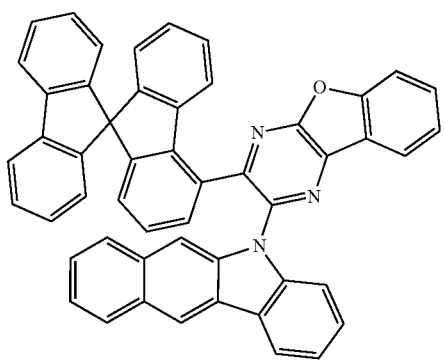
469
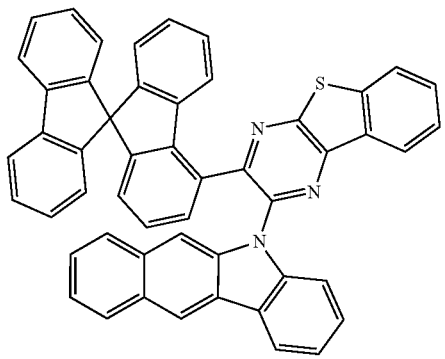
470
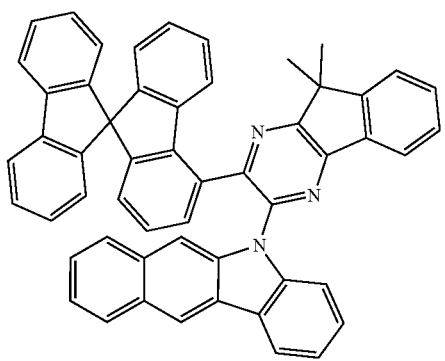
471
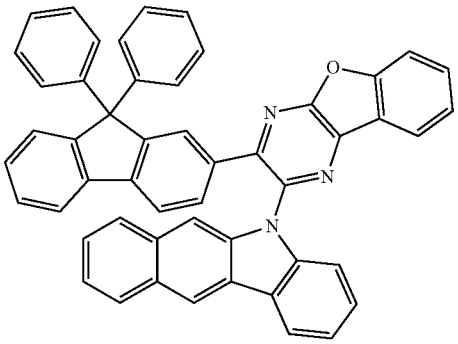
472

473
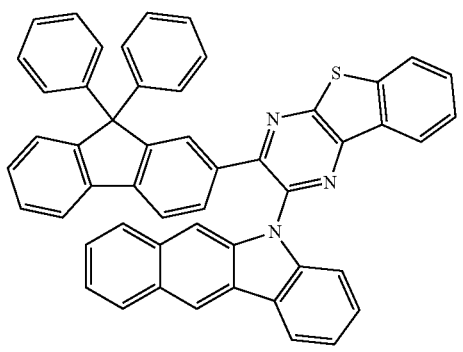
474
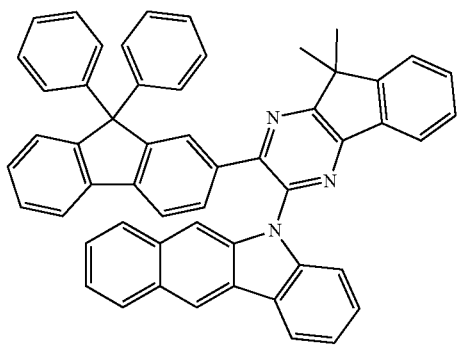
475
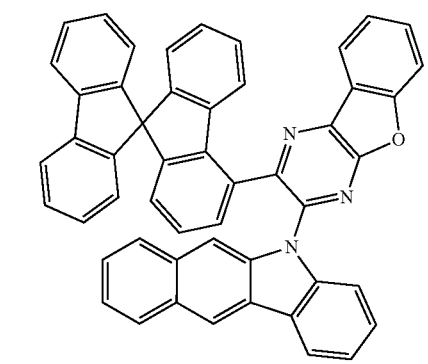
476
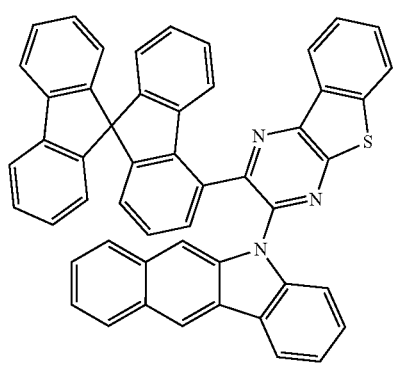
477
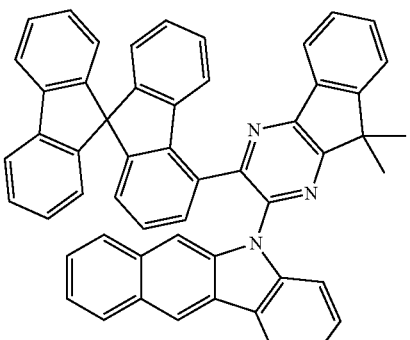
478
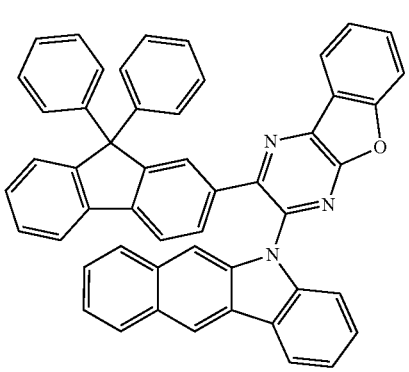
479
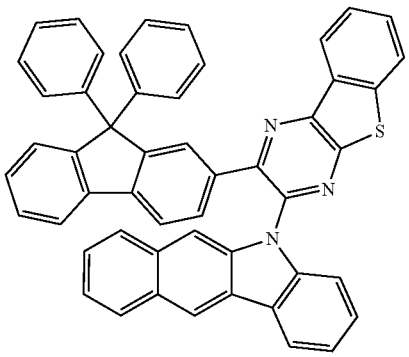
480
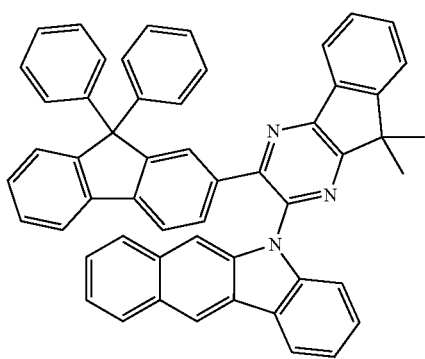

481
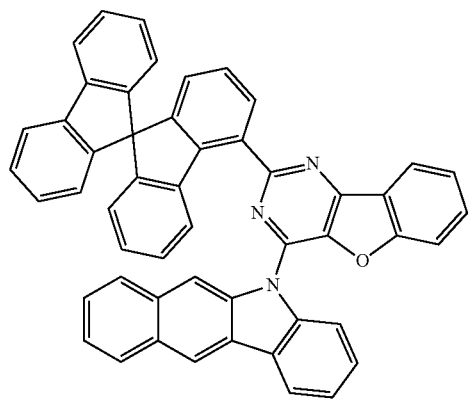
482
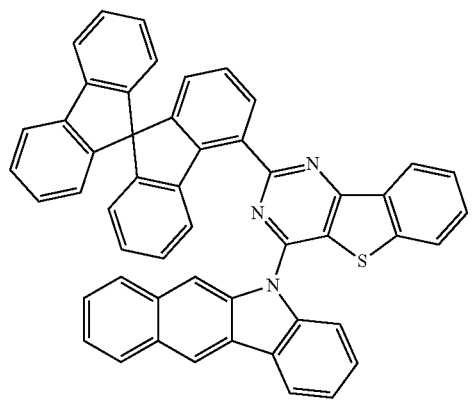
483
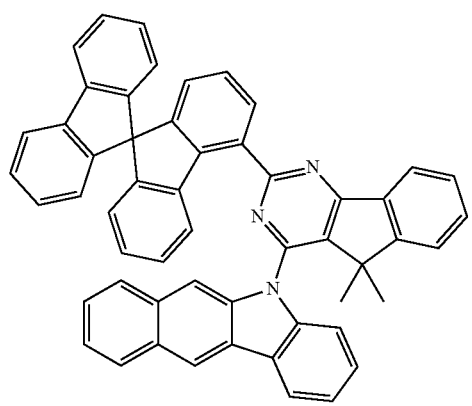
484
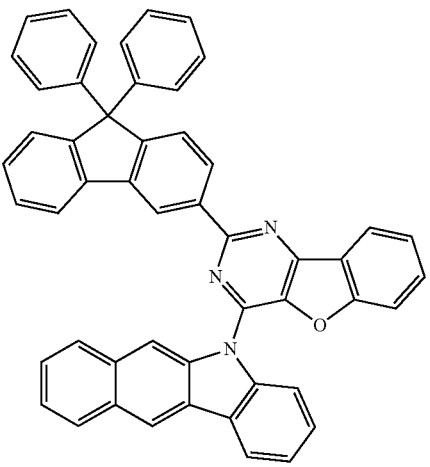
485
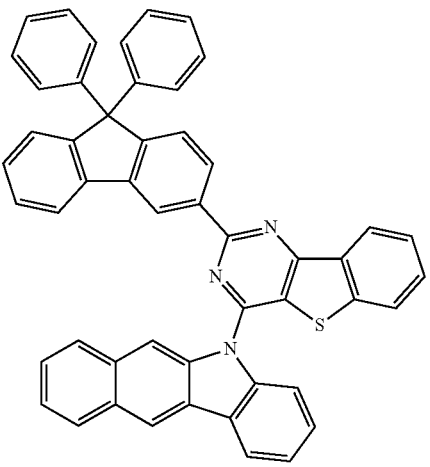
486
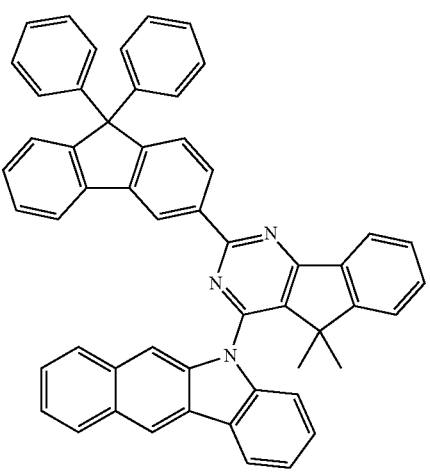

153
-continued
487
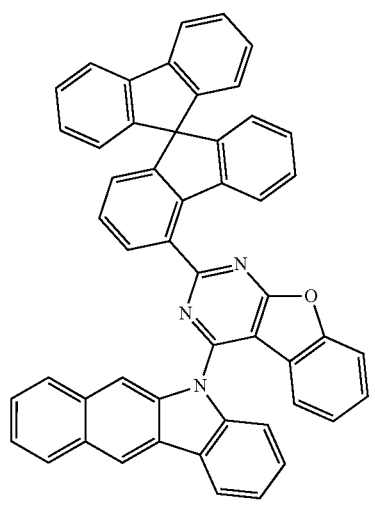
488
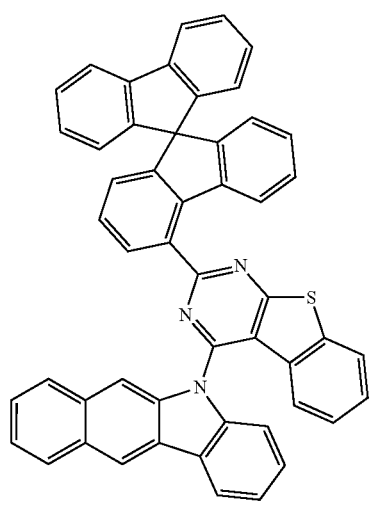
489
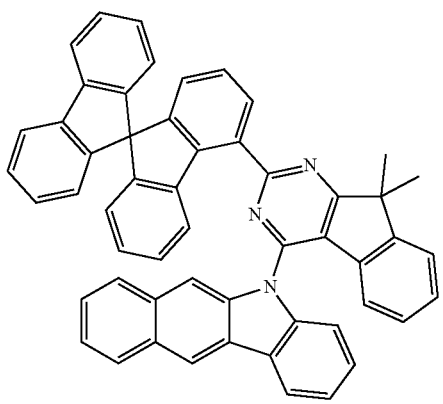
154
-continued
490
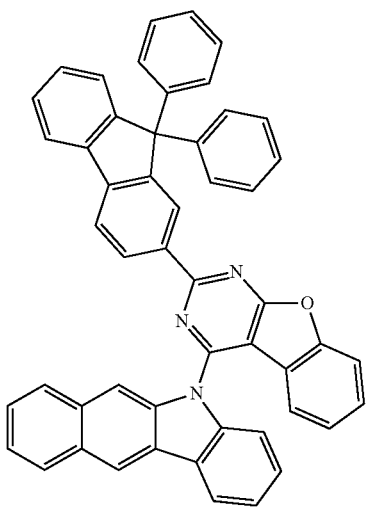
491
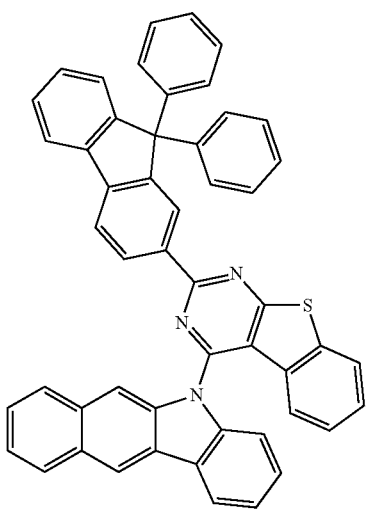
492
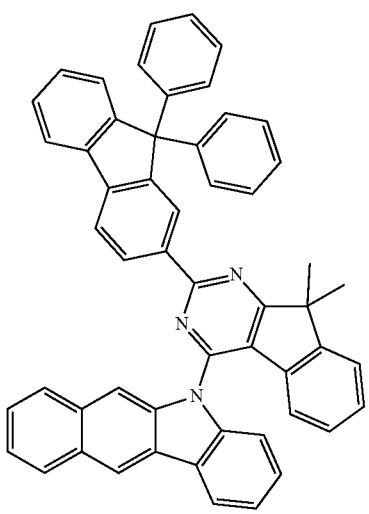

493
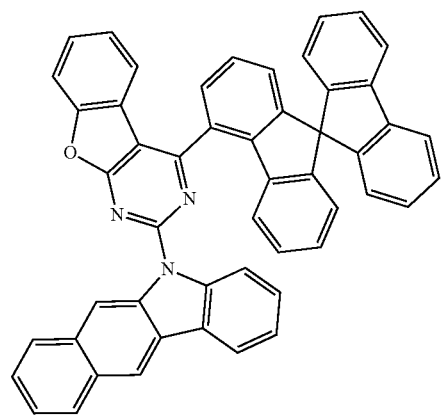
494
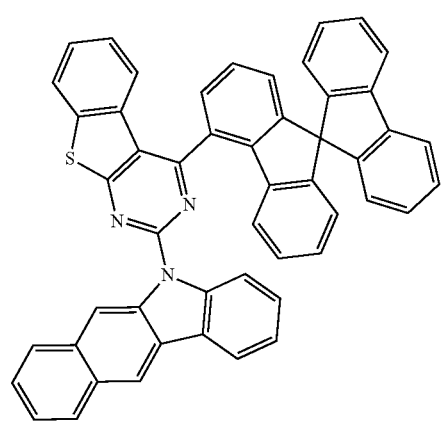
495
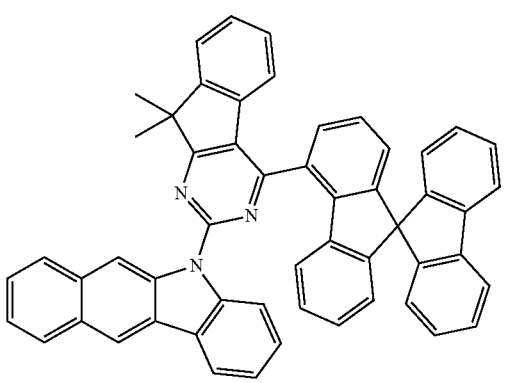
496
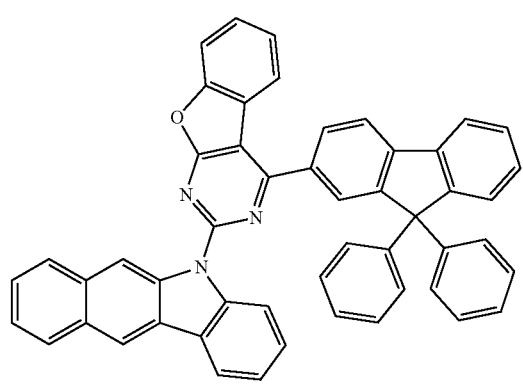
497
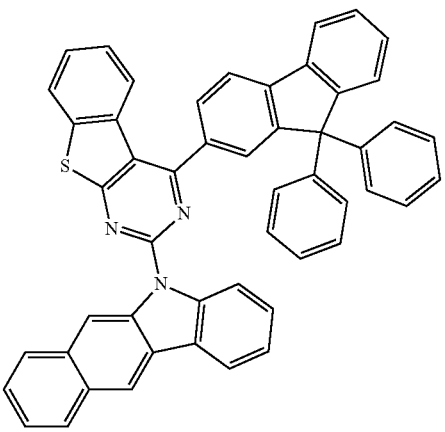
498
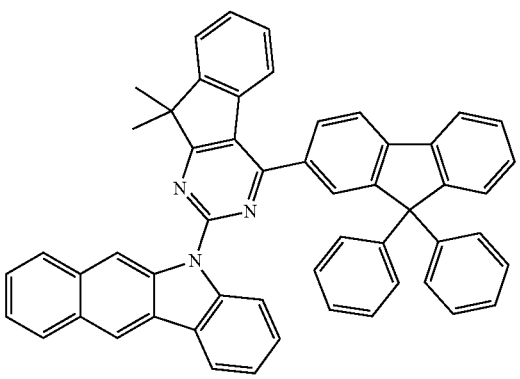
499
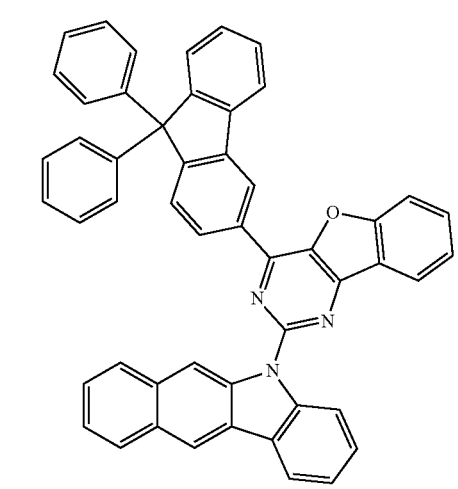

-continued
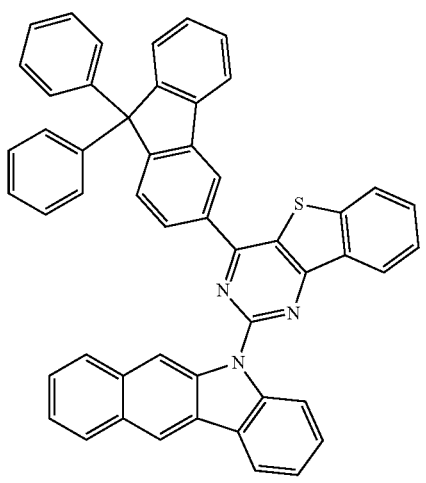
500
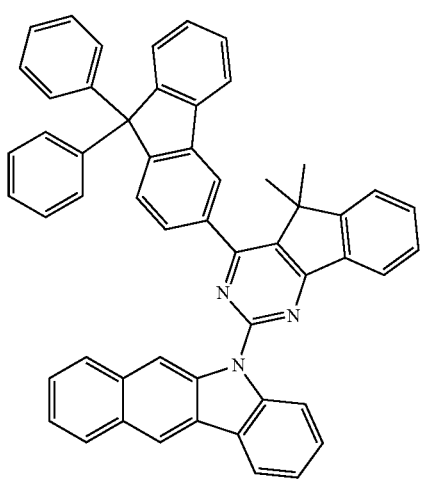
501
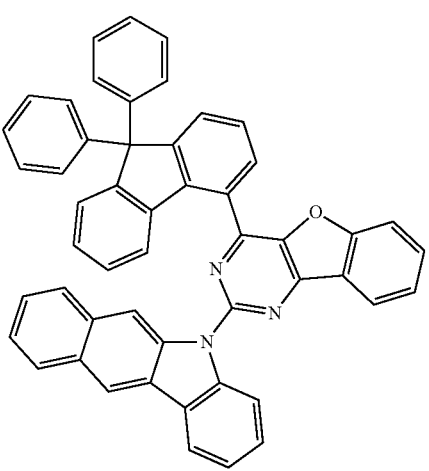
502
-continued
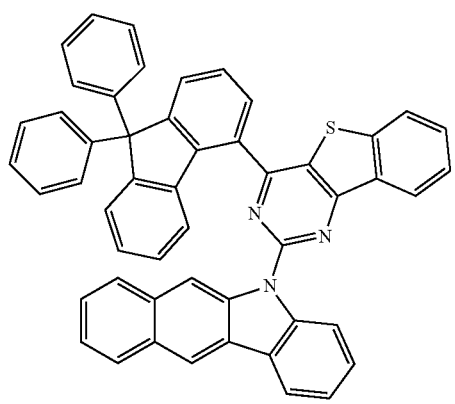
503
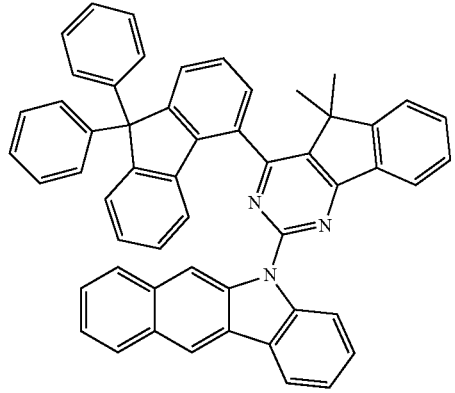
504
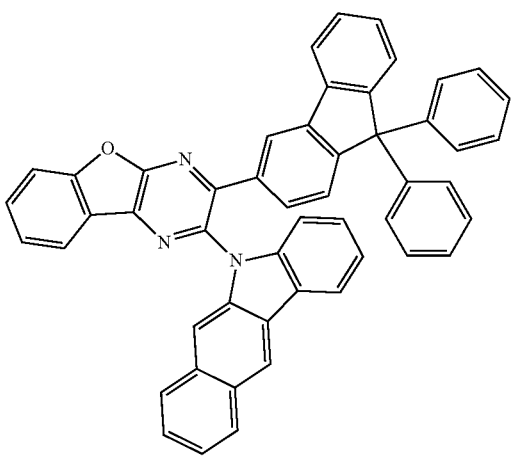
505

506
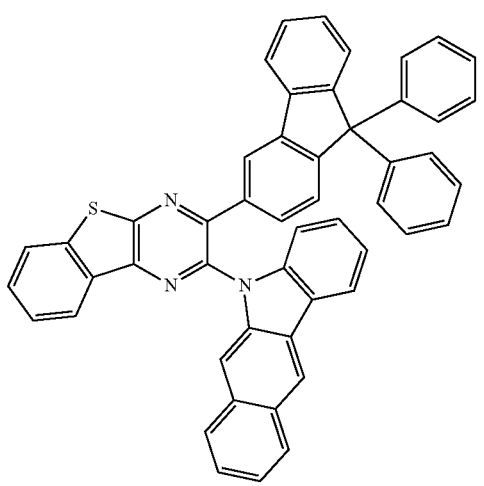
507
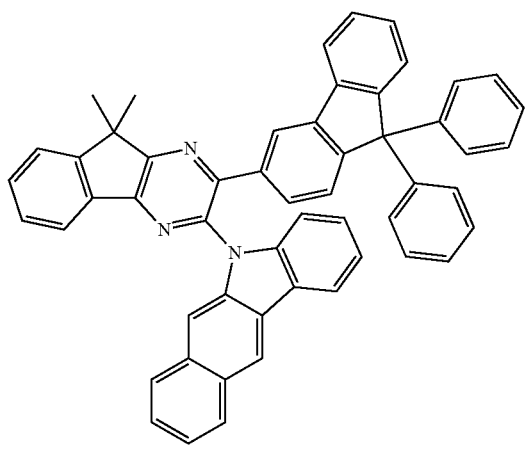
508
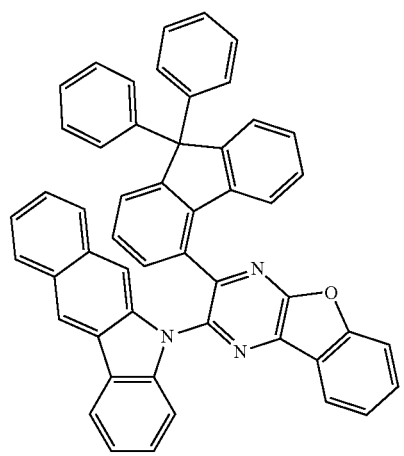
509
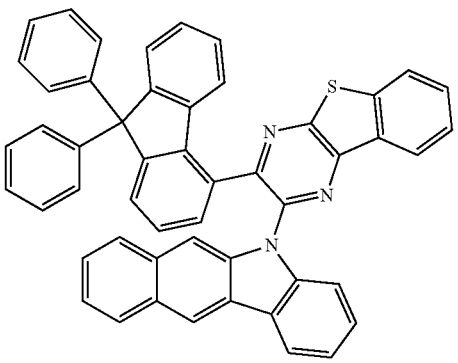
510
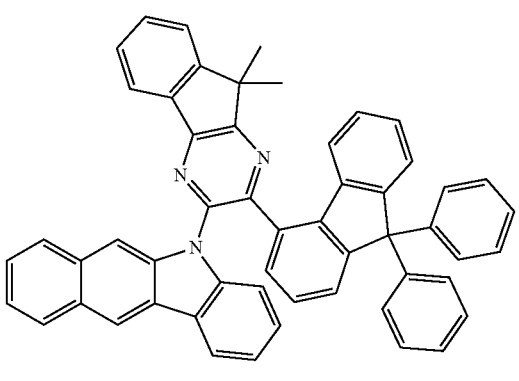
511
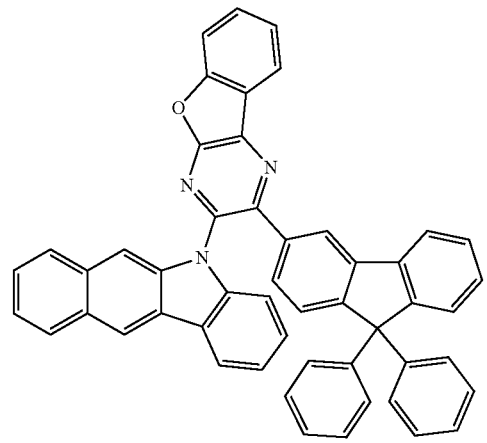
512
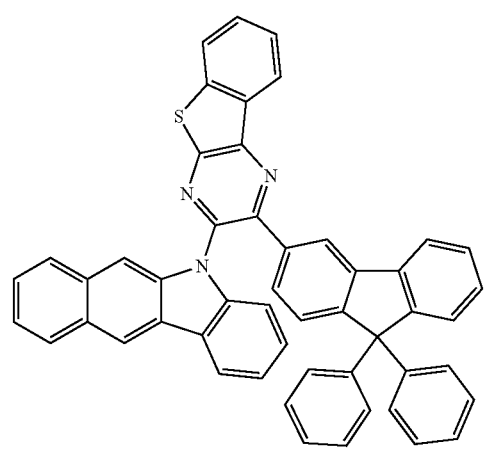

513
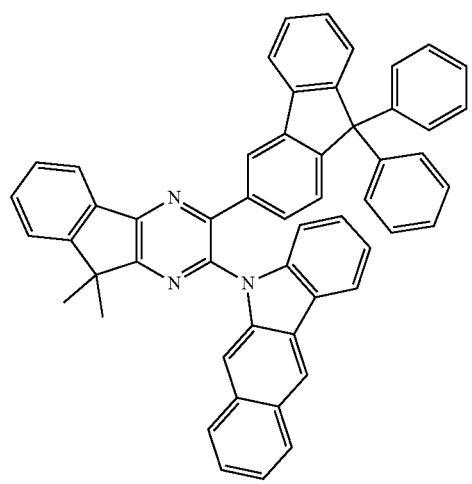
514
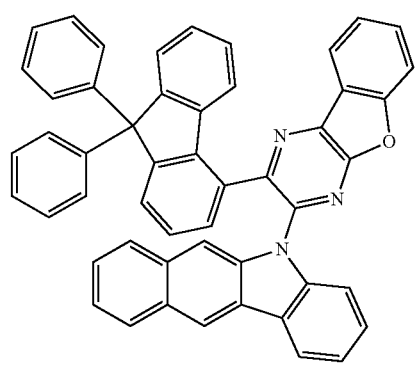
515
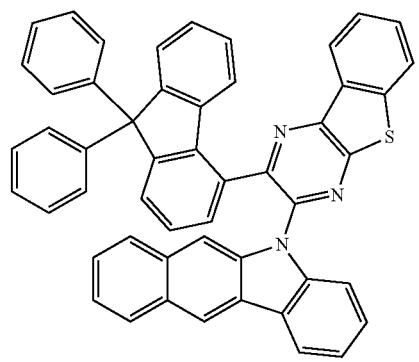
516
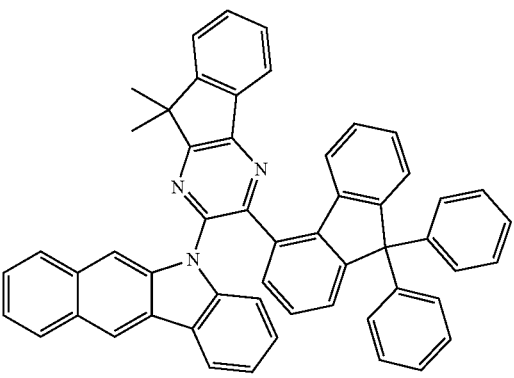
517
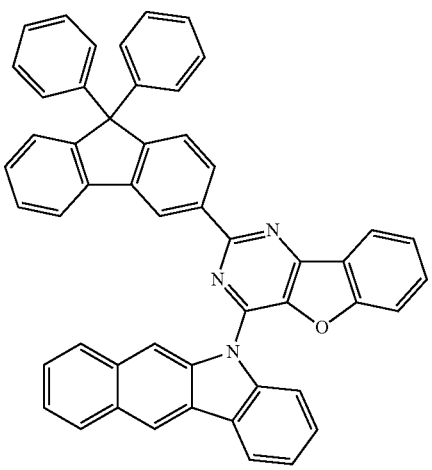
518
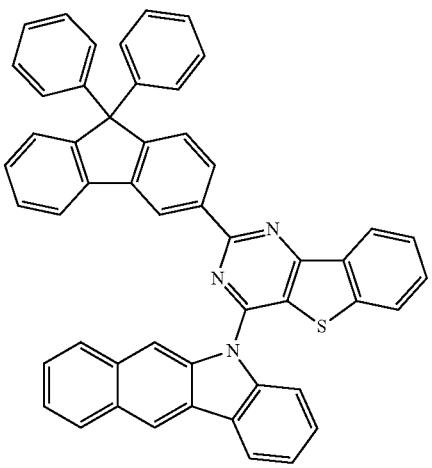
519
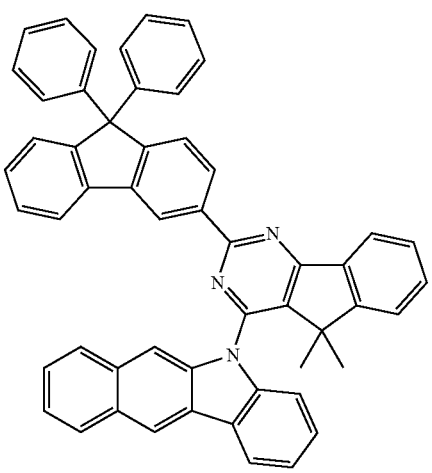

163
-continued
520
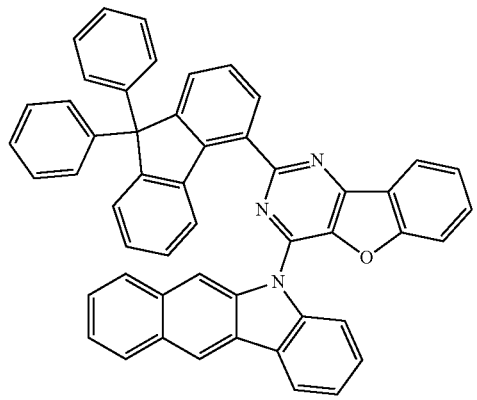
521
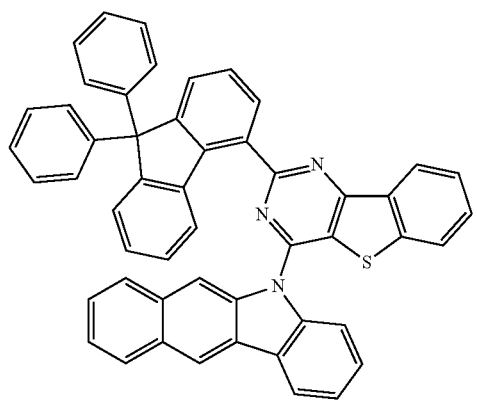
522
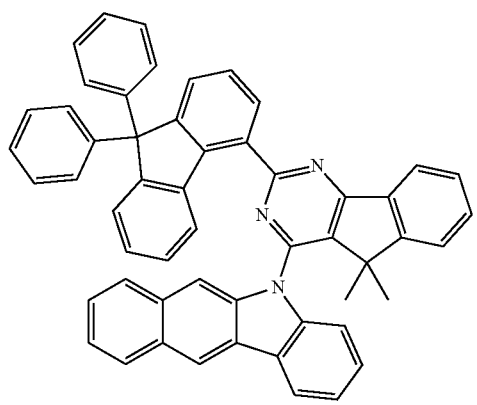
164
-continued
523
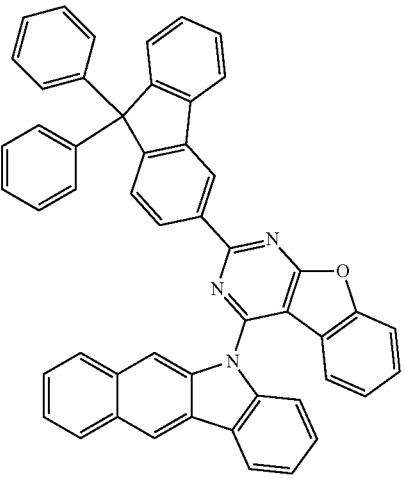
524
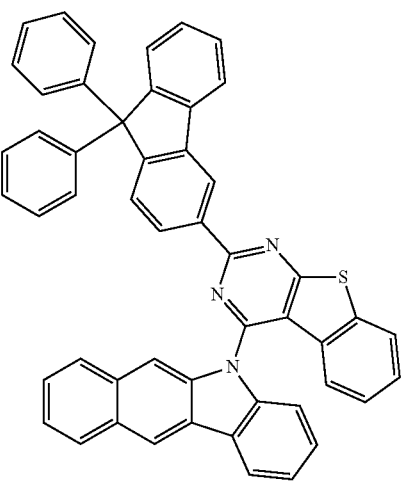
525
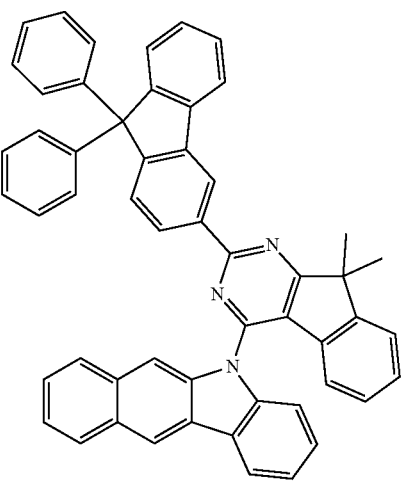

526
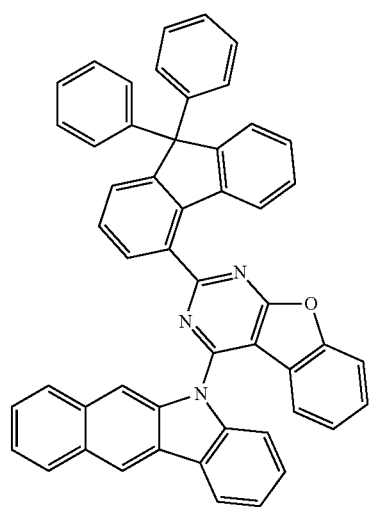
527
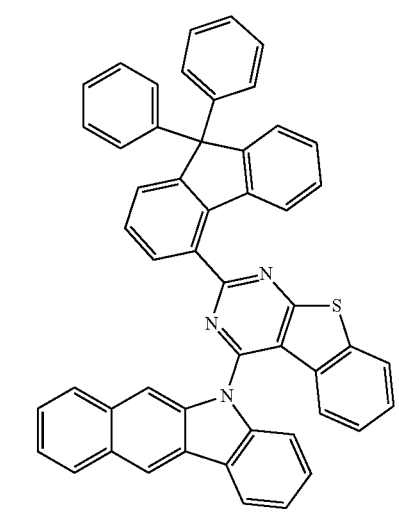
528
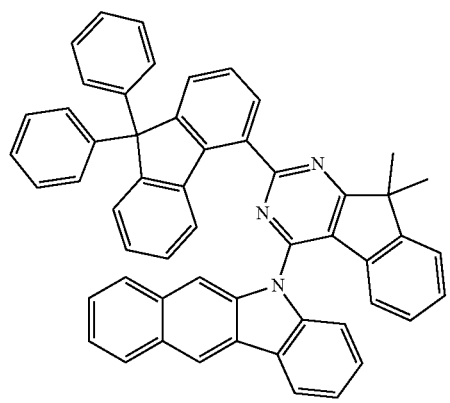
529
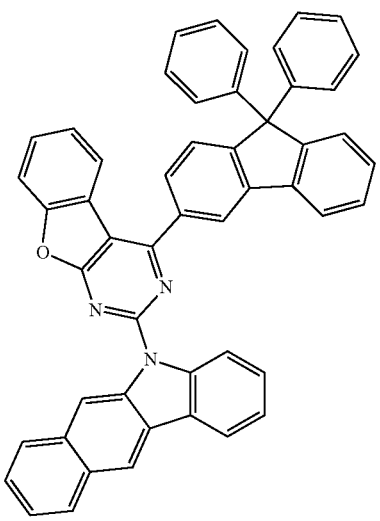
530
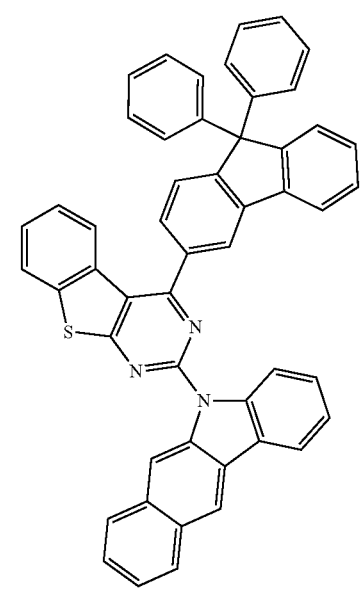
531
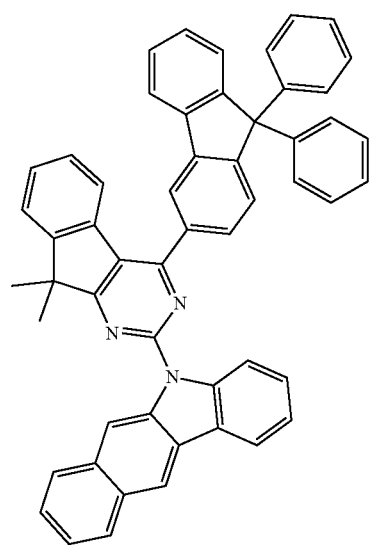

532
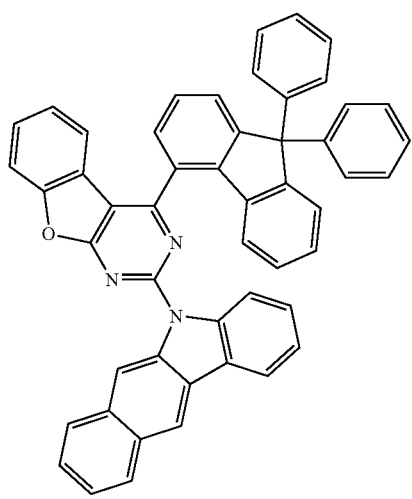
533
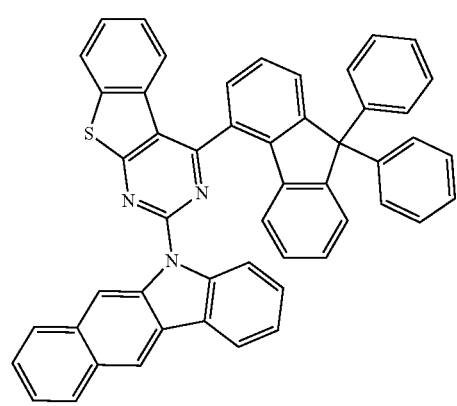
534
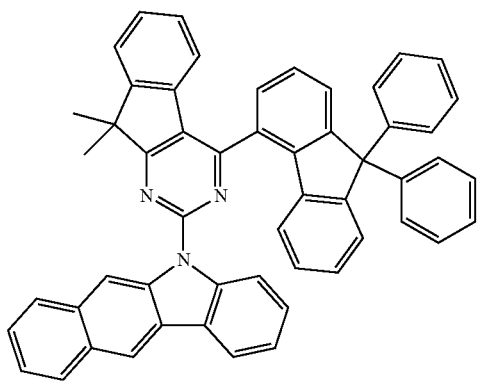
535
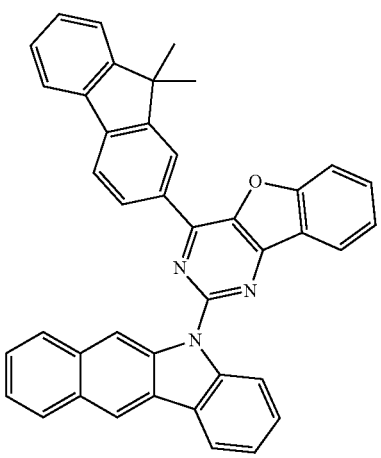
536
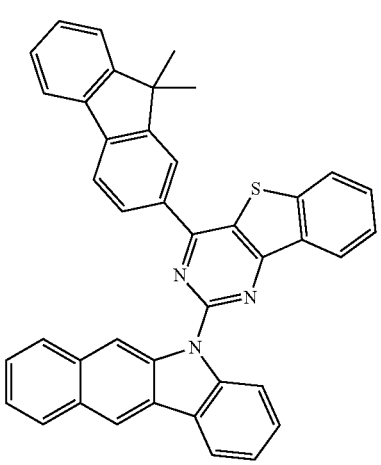
537
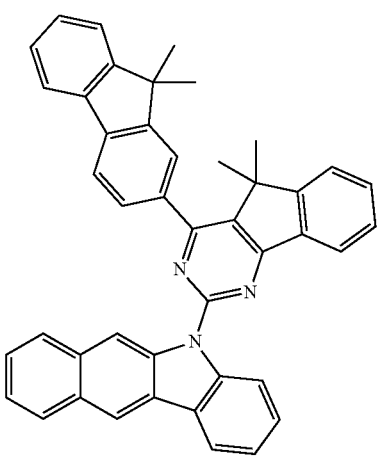

-continued
538
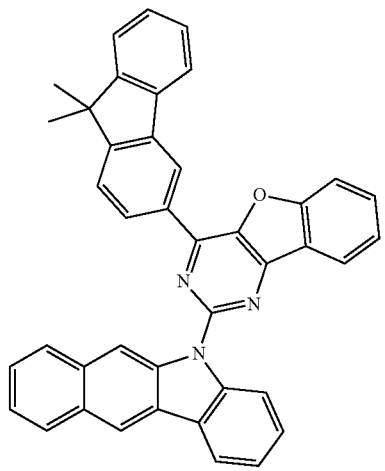
539
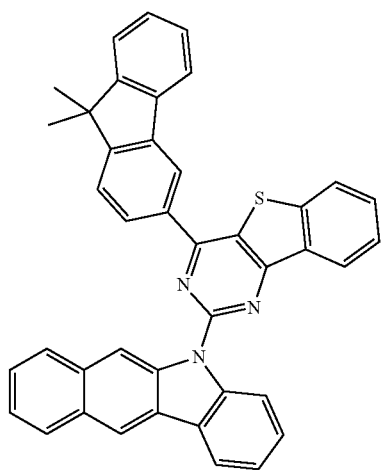
540
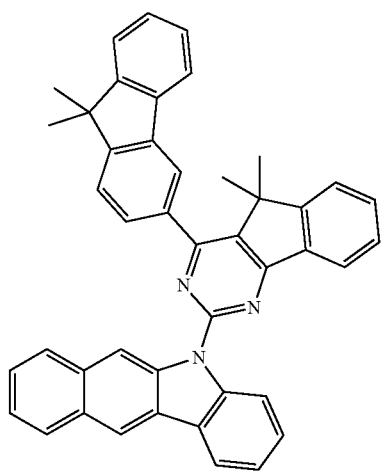
-continued
541
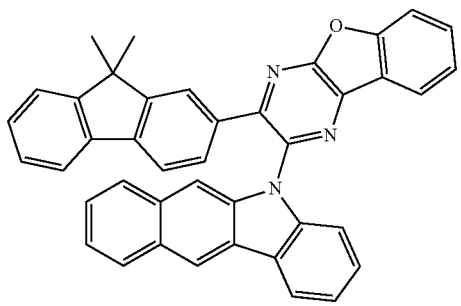
542
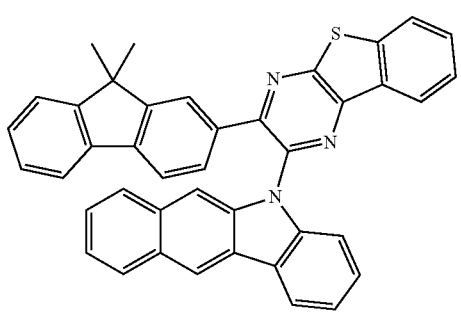
543
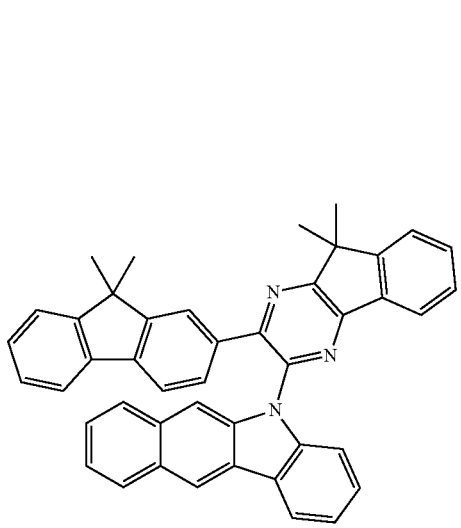
544
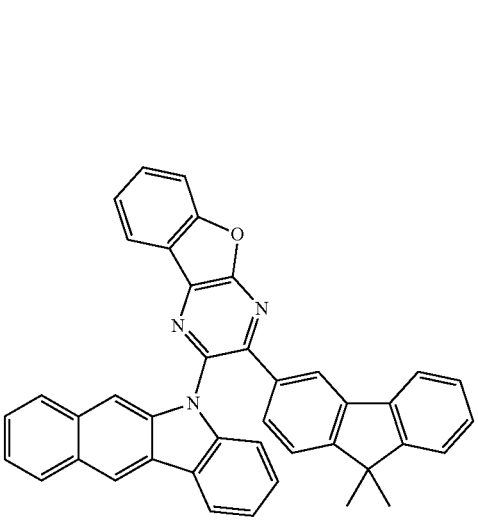

545
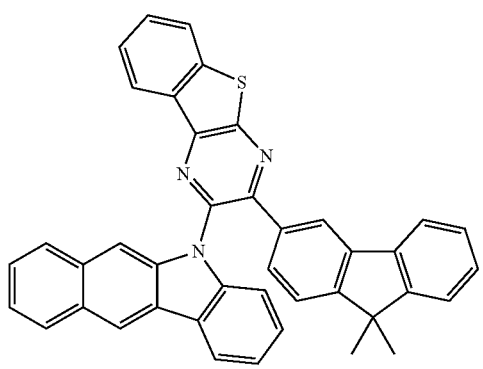
546
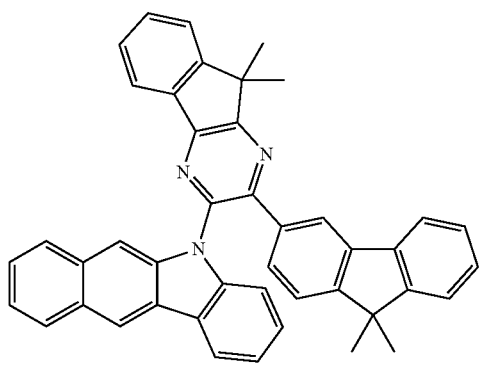
547
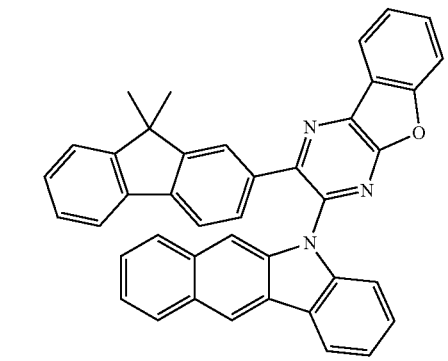
548
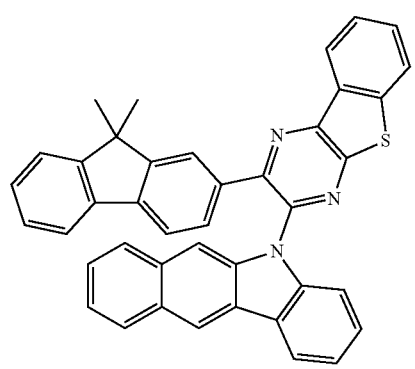
549
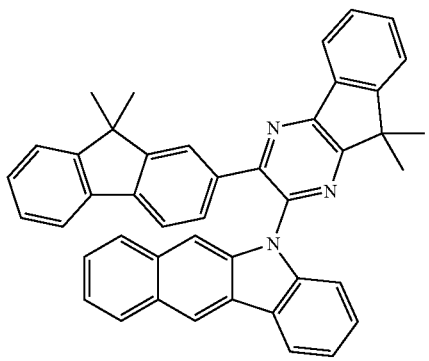
550
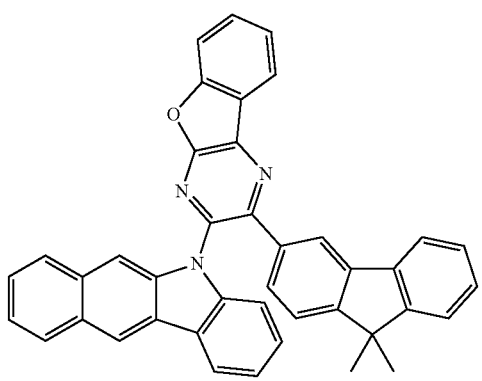
551
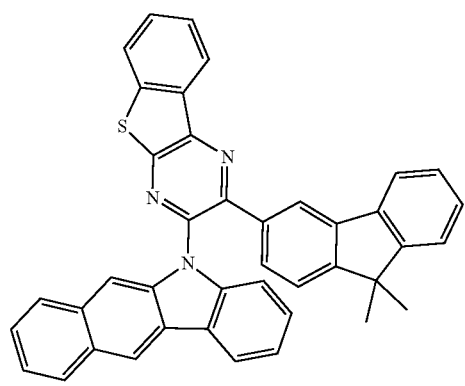
552
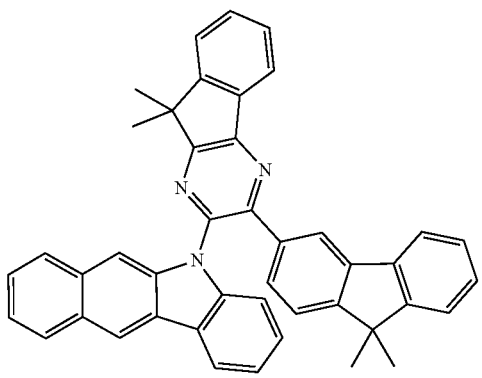

553
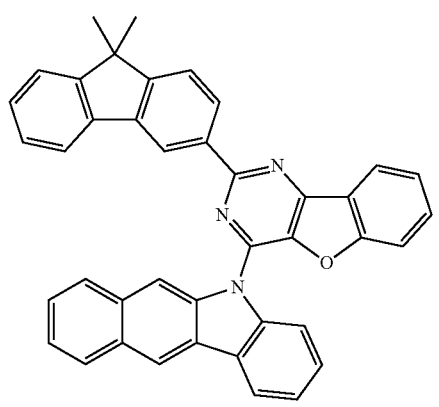
554
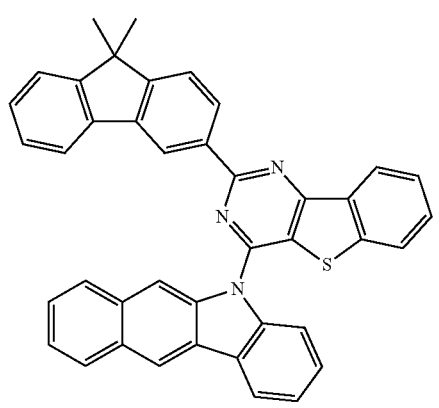
555
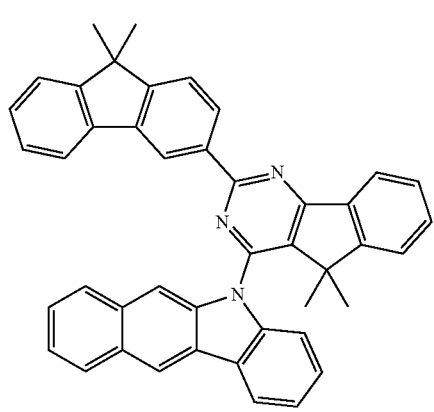
556
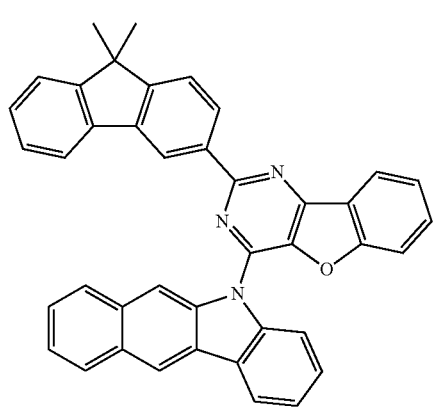
557
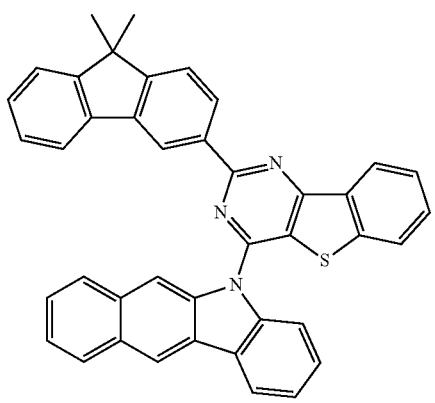
558
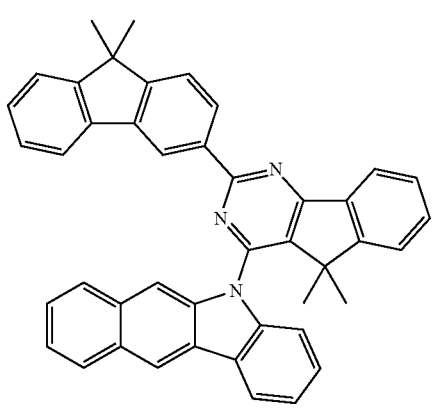
559
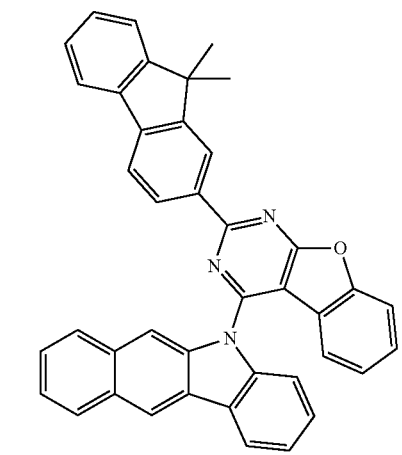

560
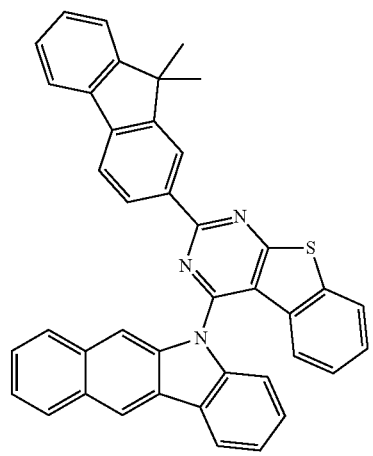
561
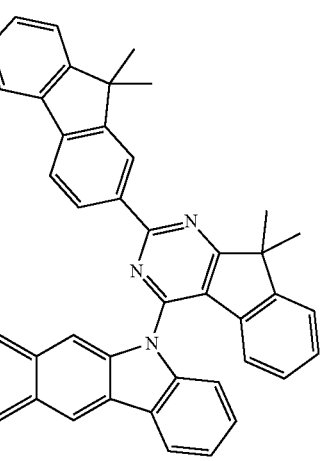
562
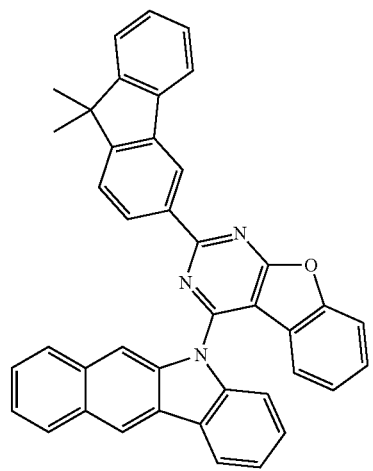
563
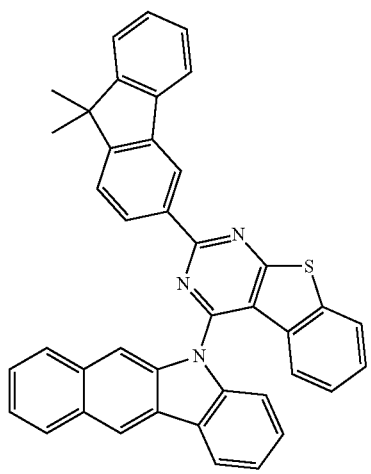
564
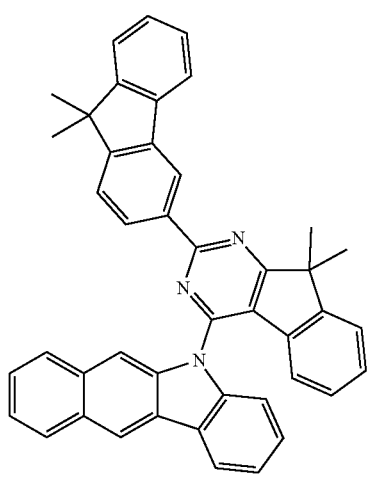
565
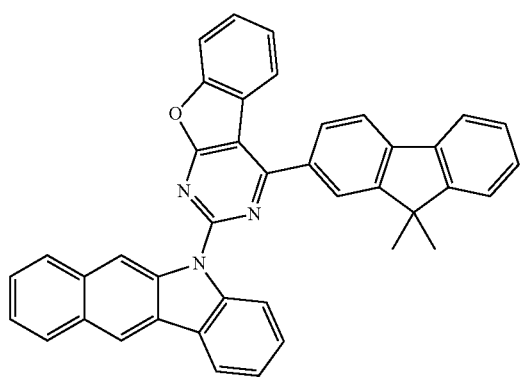

566
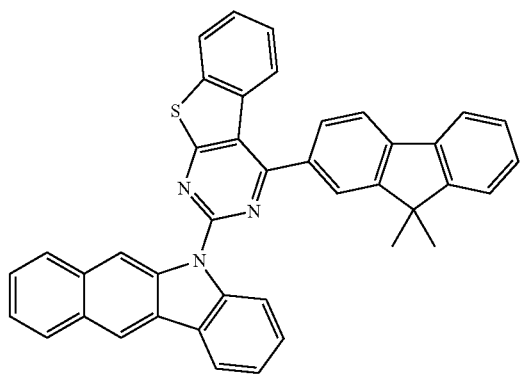
567
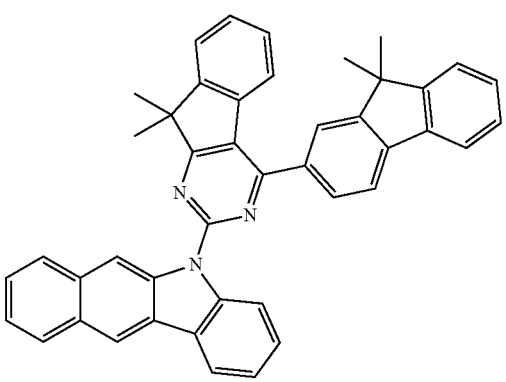
568
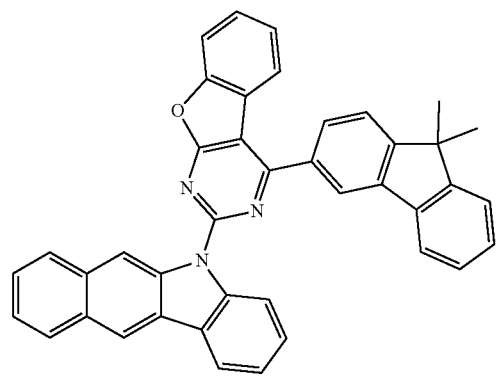
569

570
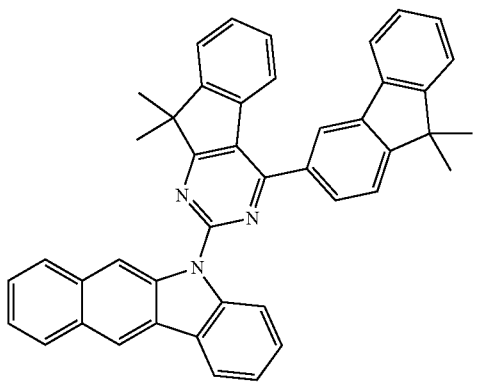
571
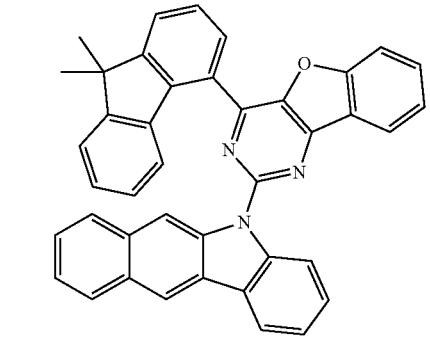
572
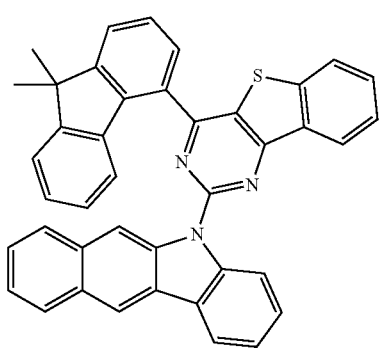
573
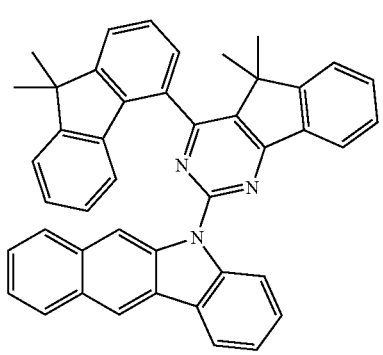

-continued
574
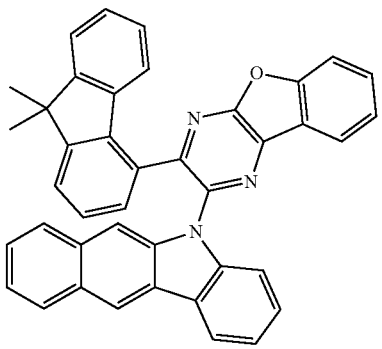
575
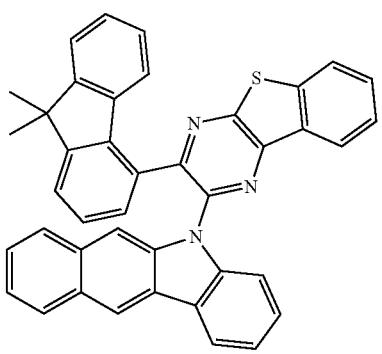
576
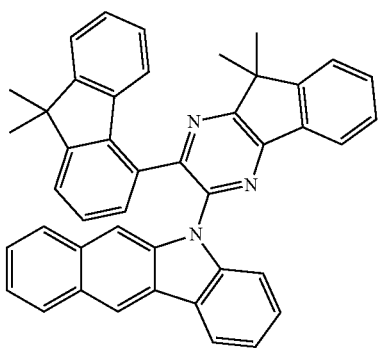
577
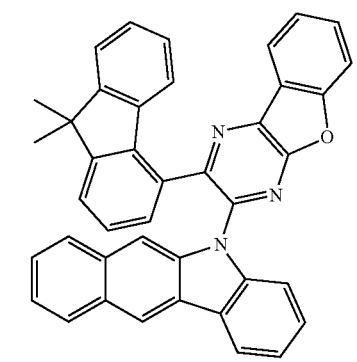
-continued
578
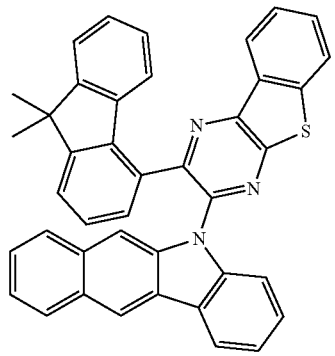
579
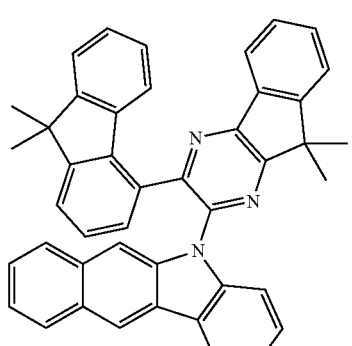
580
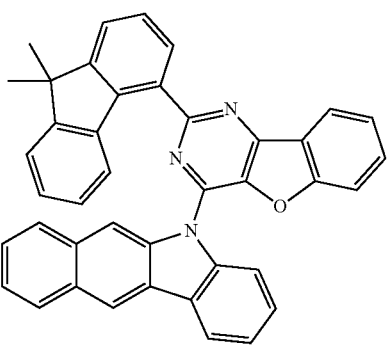
581
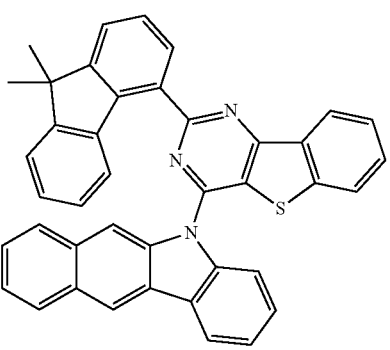

582
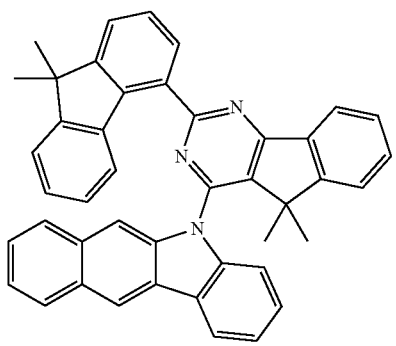
583
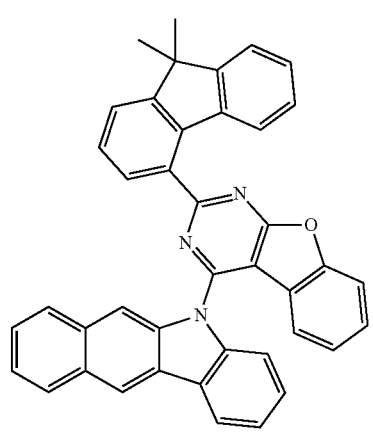
584
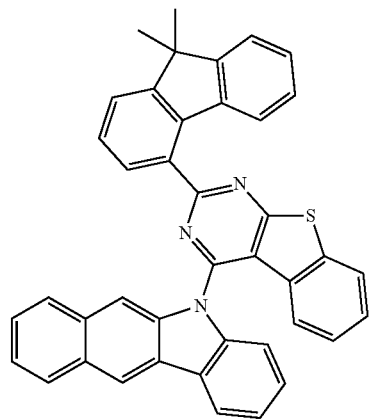
585
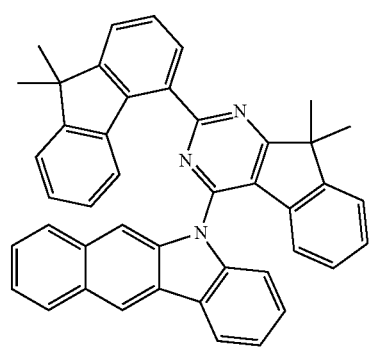
586
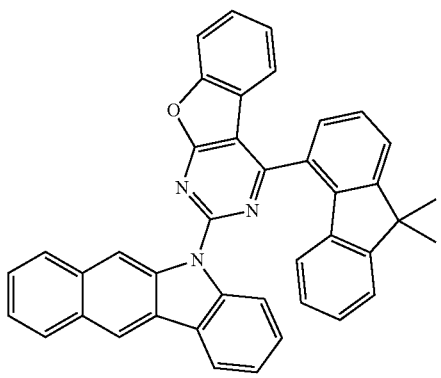
587
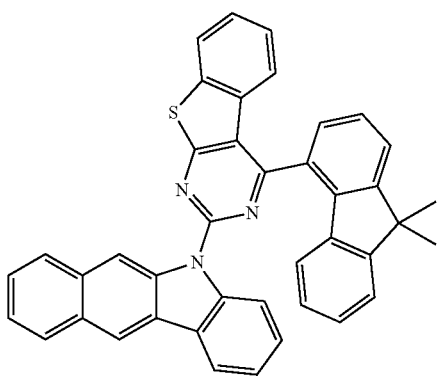
588
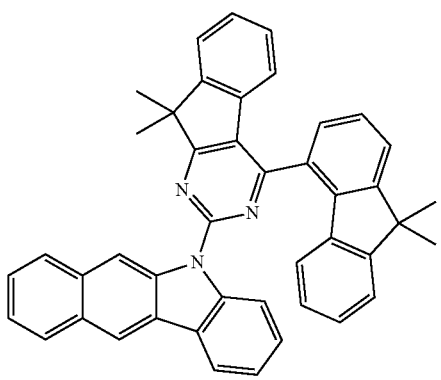

589
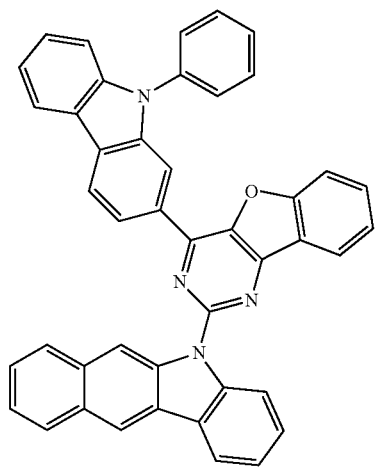
592
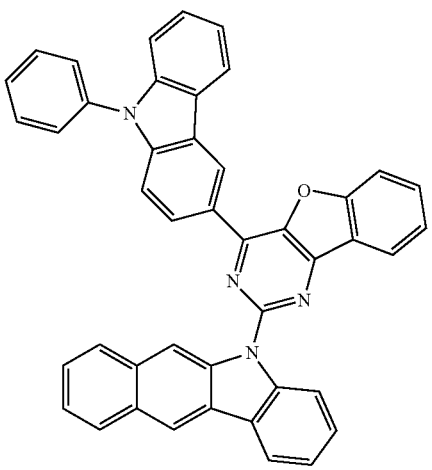
590
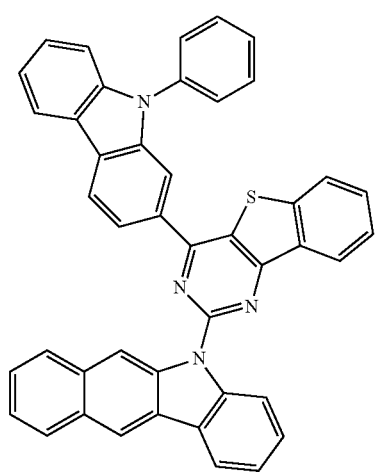
593
591
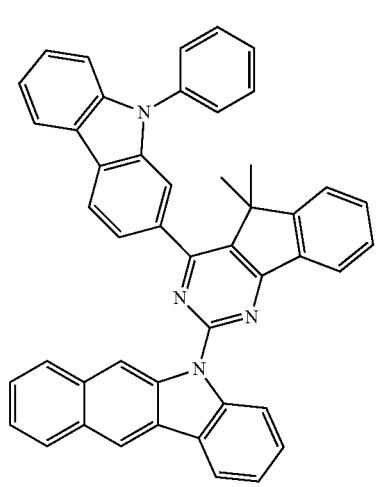
594
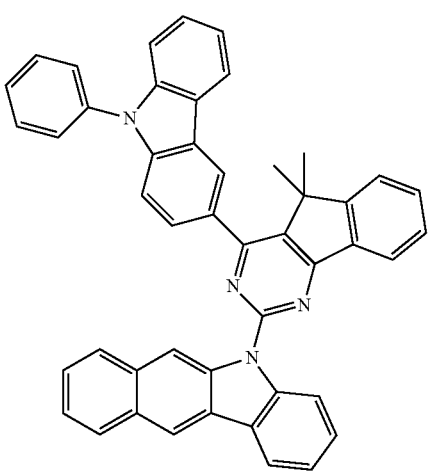

595 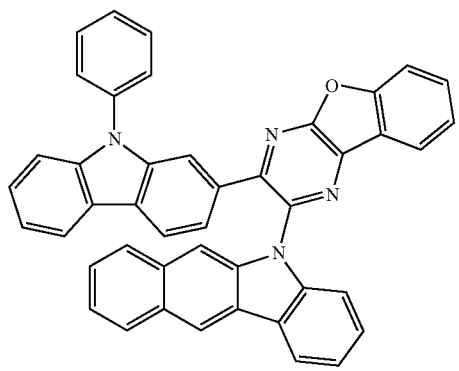
596 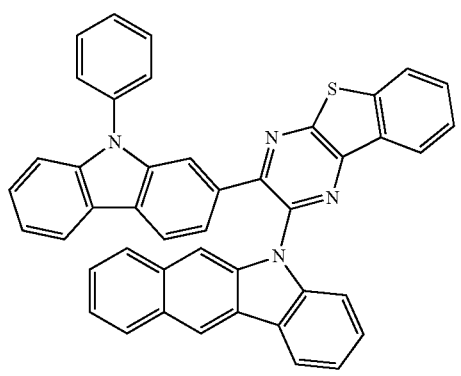
597 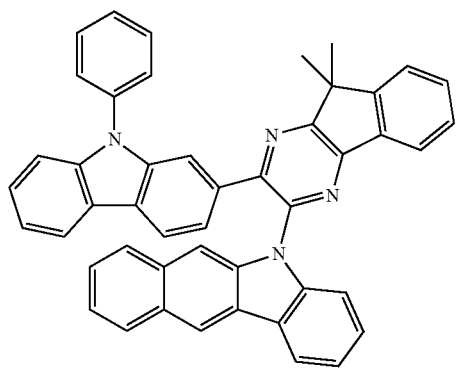
598 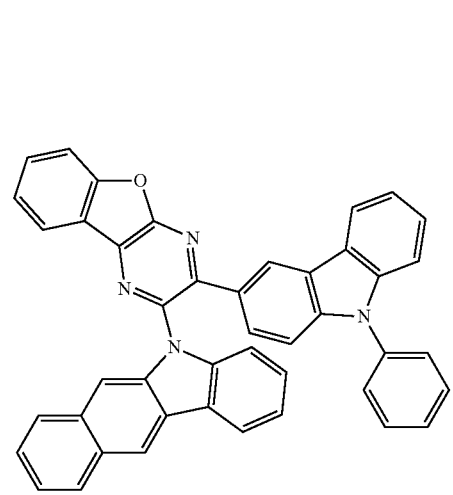
599 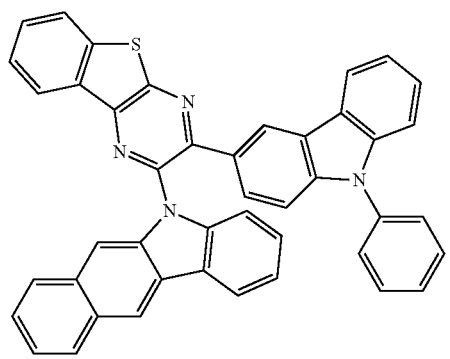
600 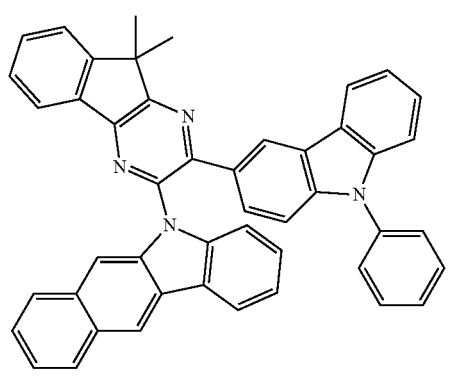
601 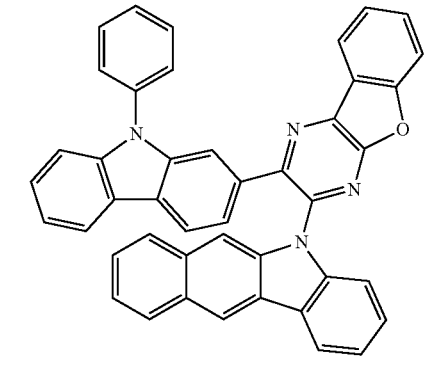
602 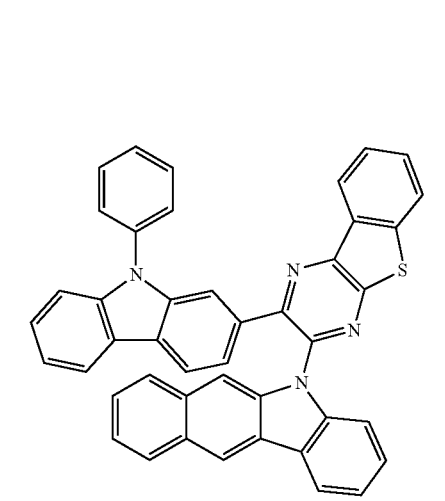

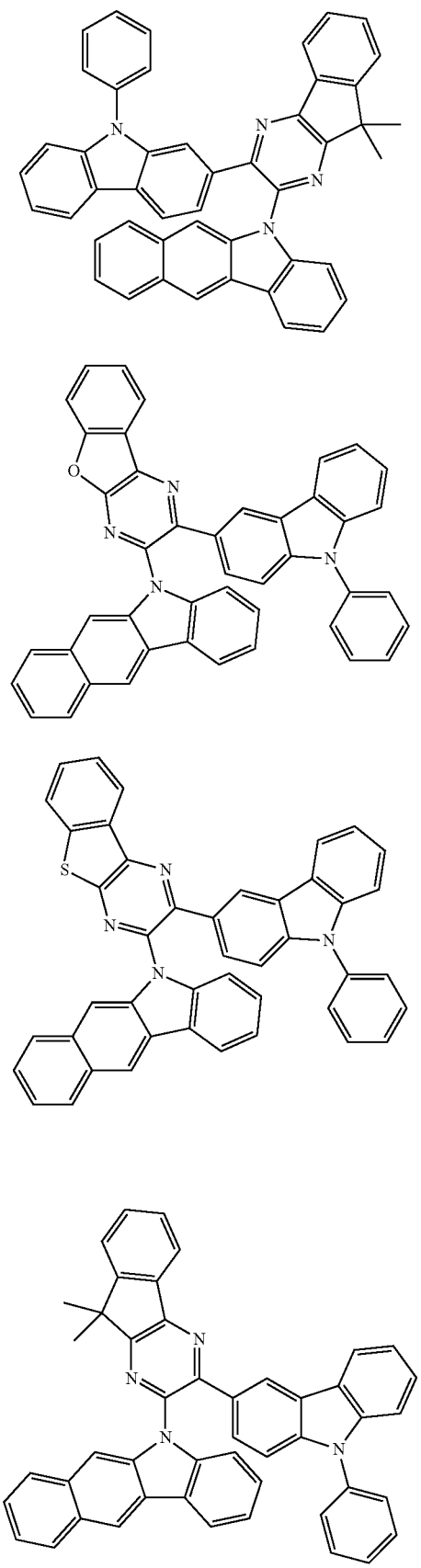
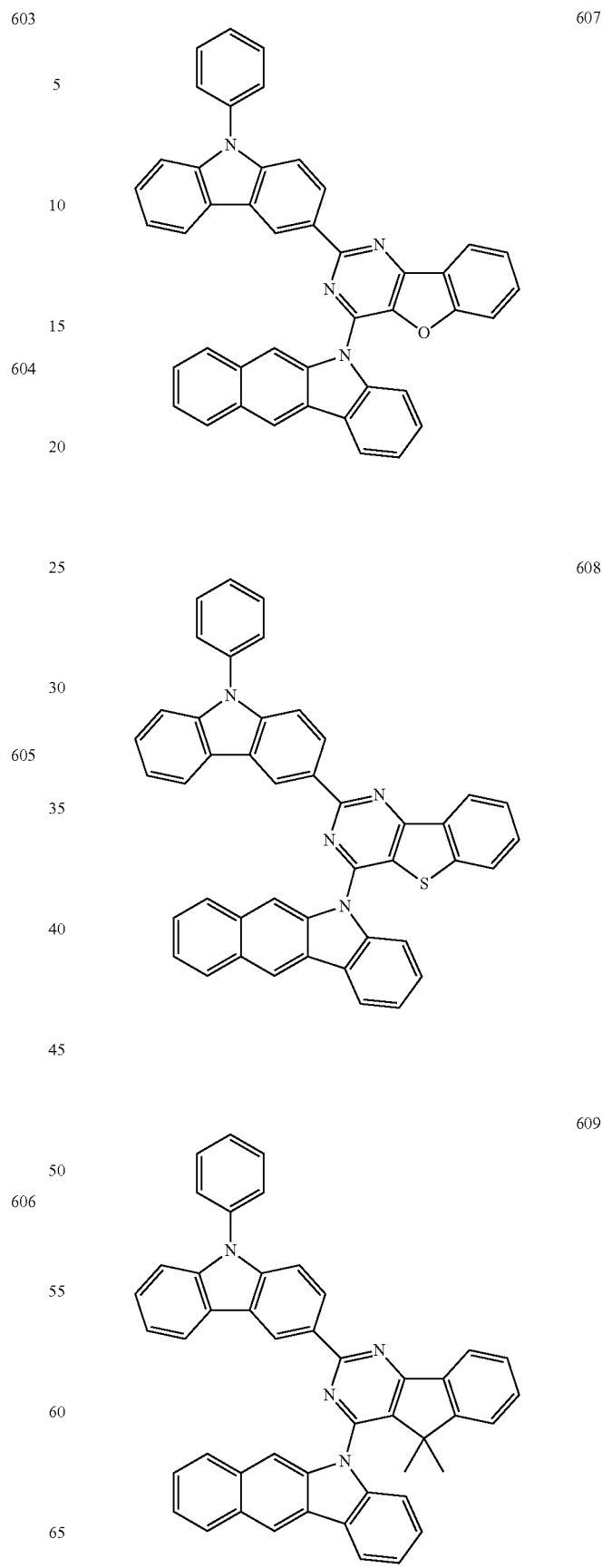

610
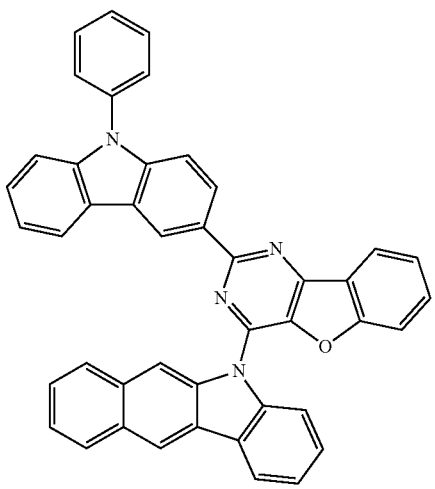
613
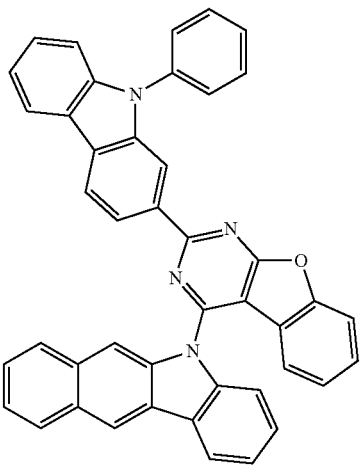
611
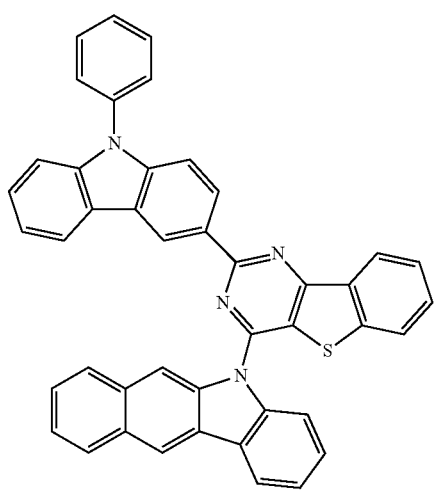
614
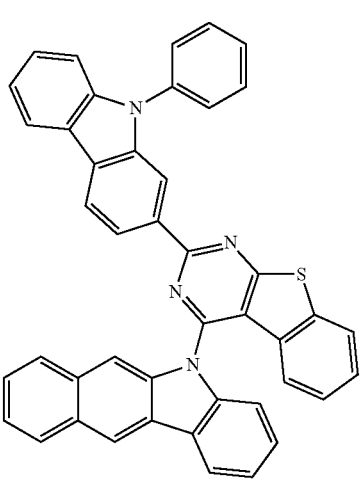
612
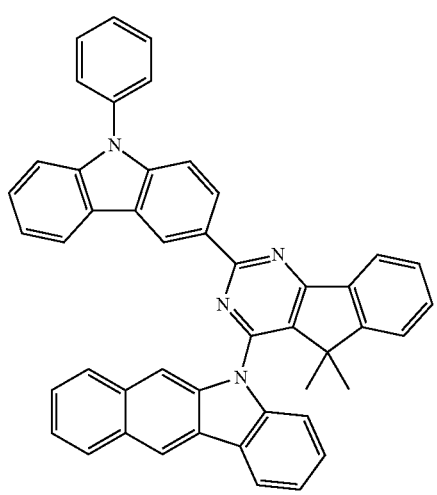
615
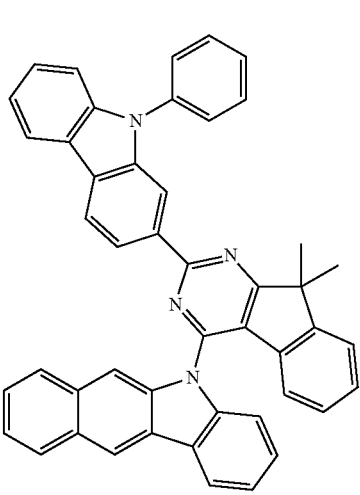

616
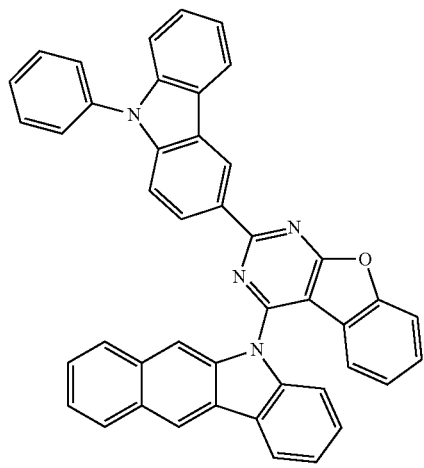
617
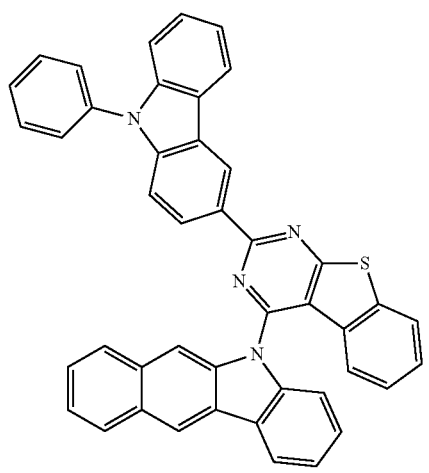
618
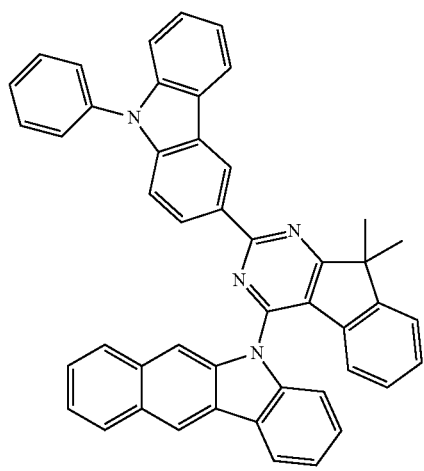
619
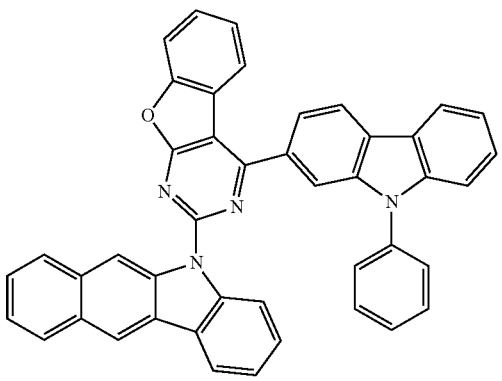
620
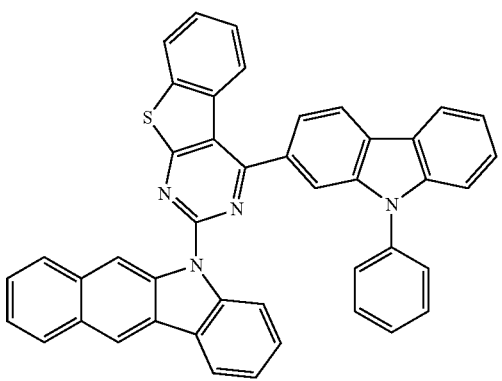
621
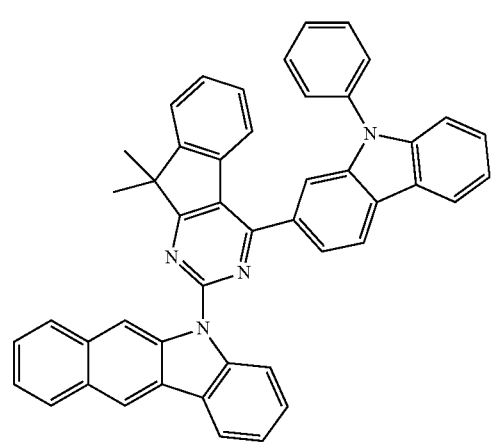
622
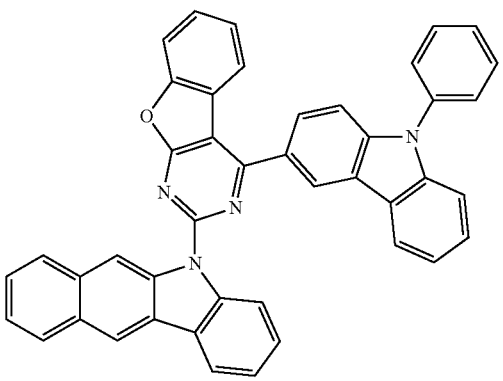

623
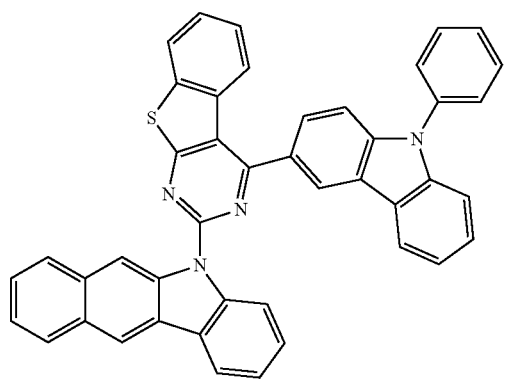
624
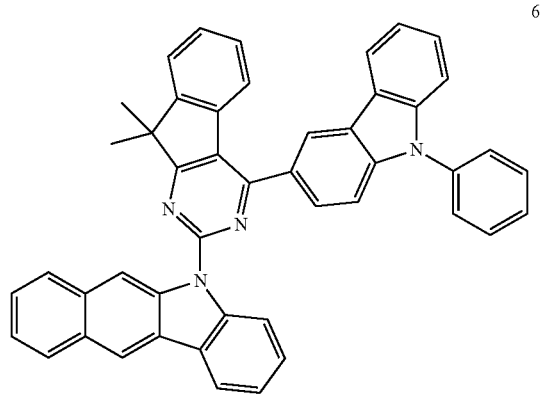
625
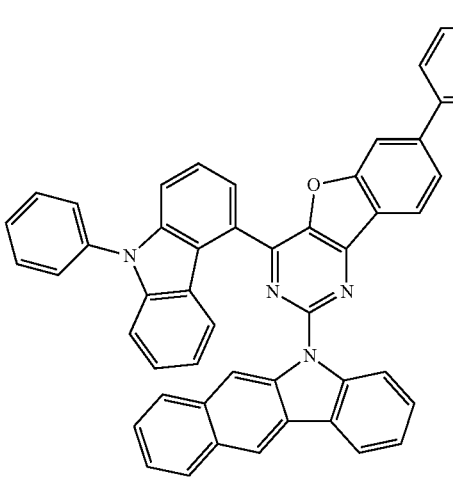
626
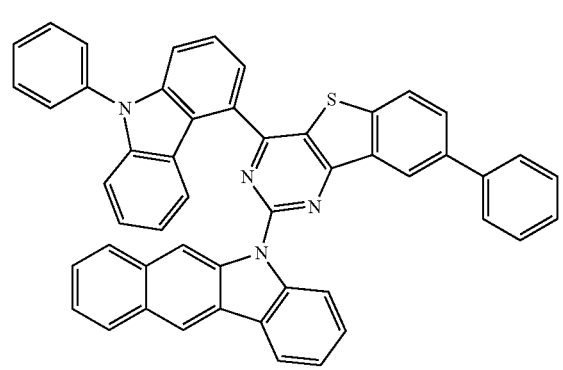
627
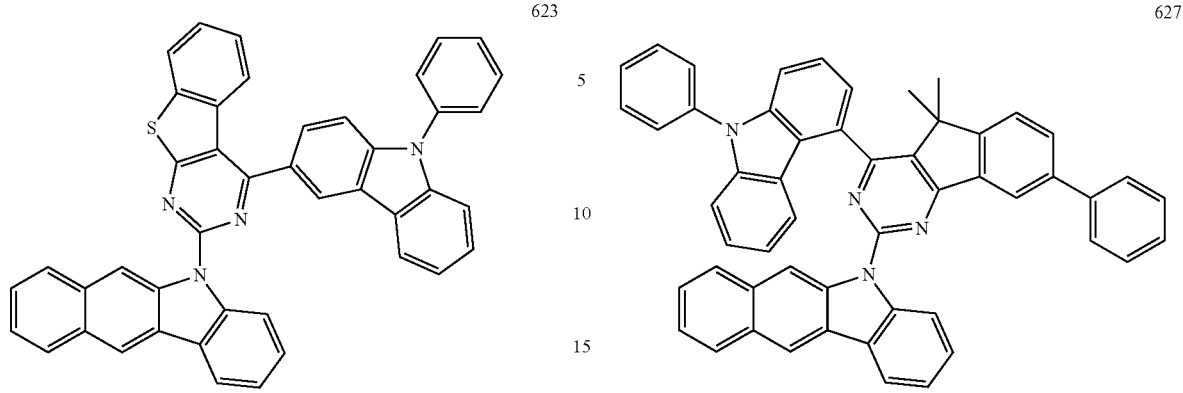
628
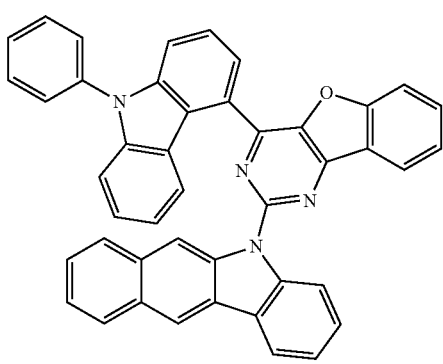
629
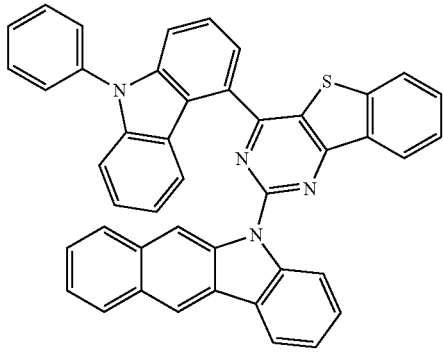
630
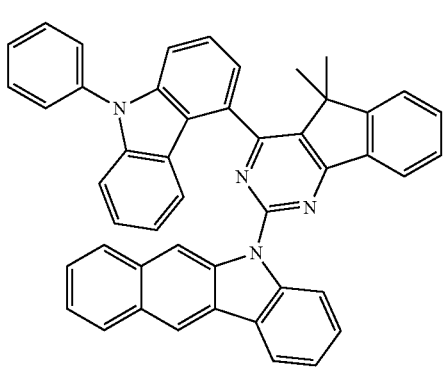

631
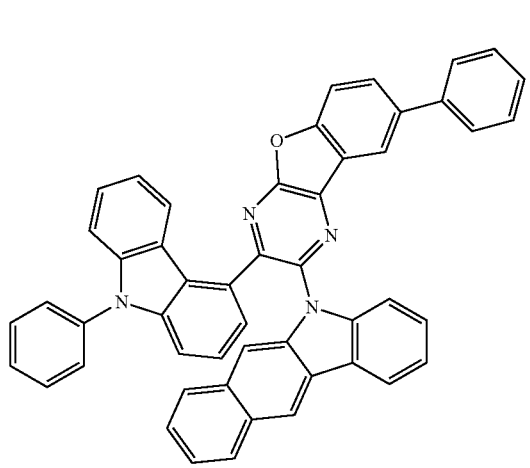
632
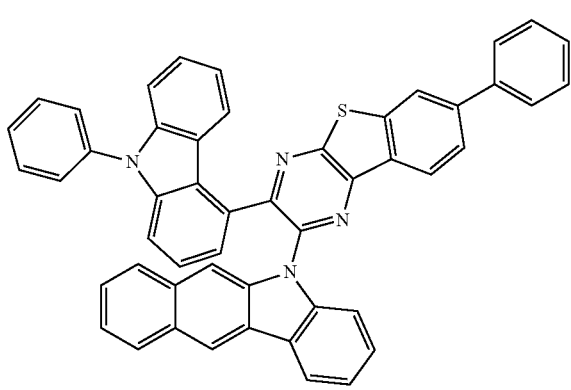
633
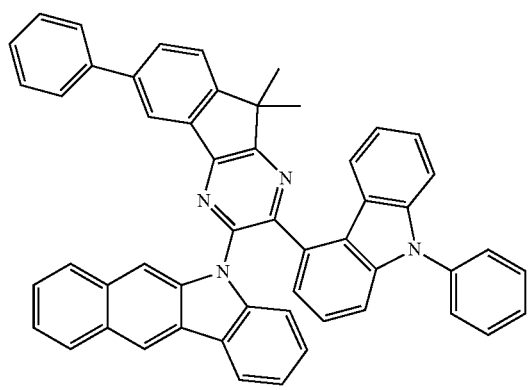
634
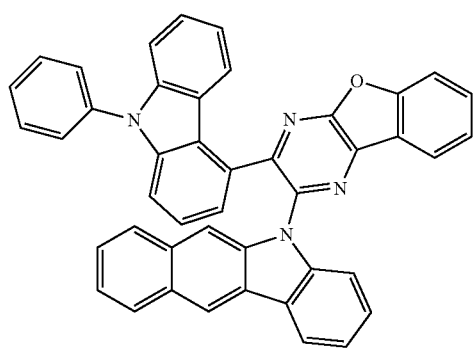
635
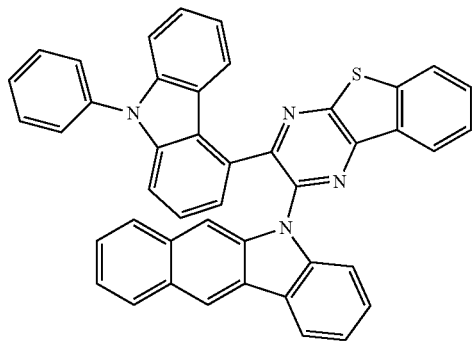
636
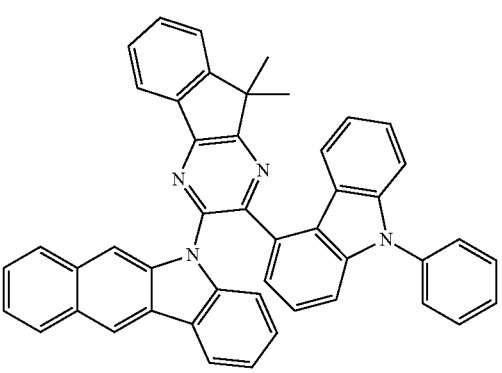
637
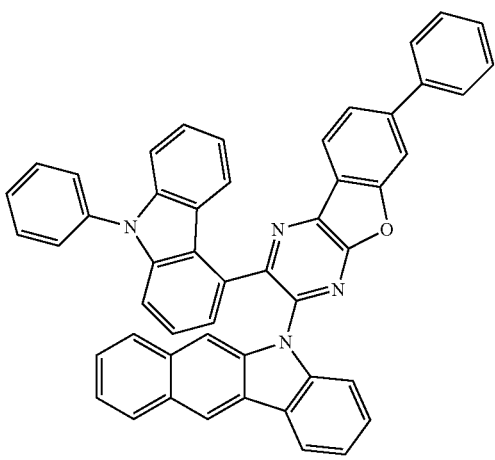

-continued
638
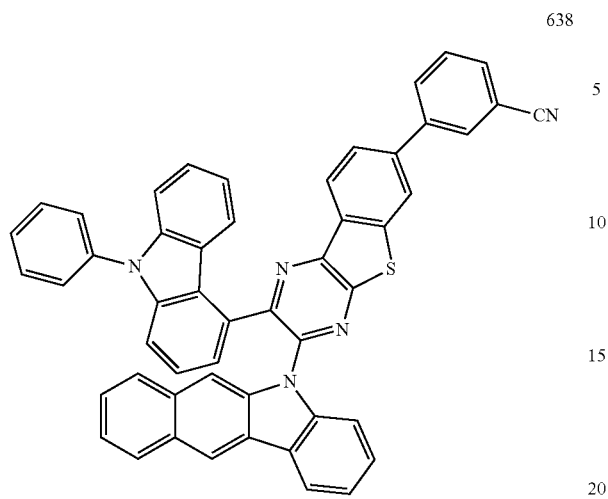
639
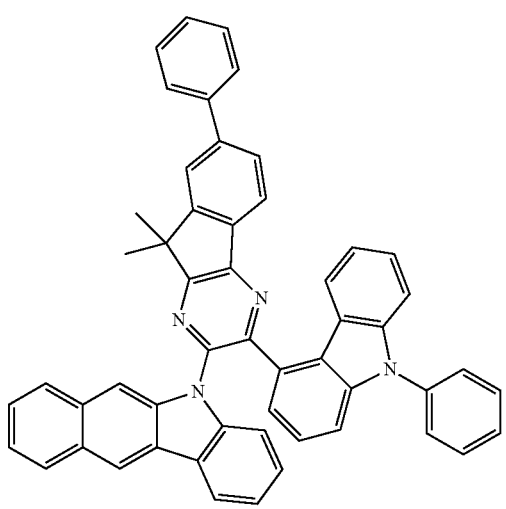
640
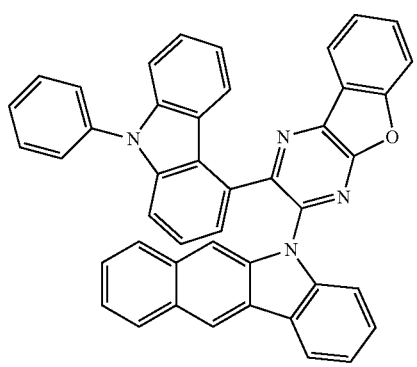
-continued
641
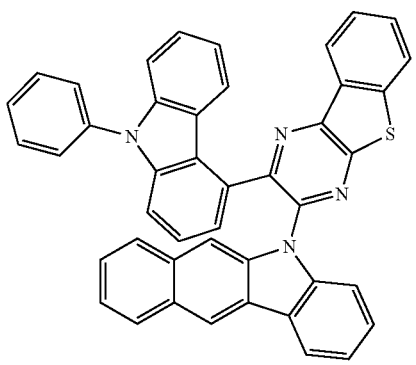
642
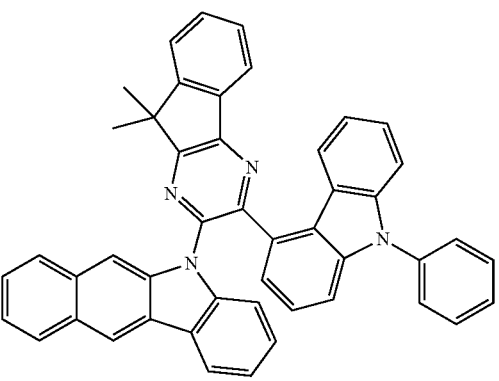
643
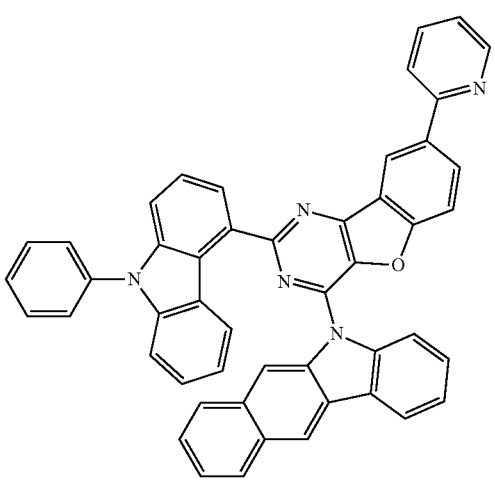

199
-continued
200
-continued
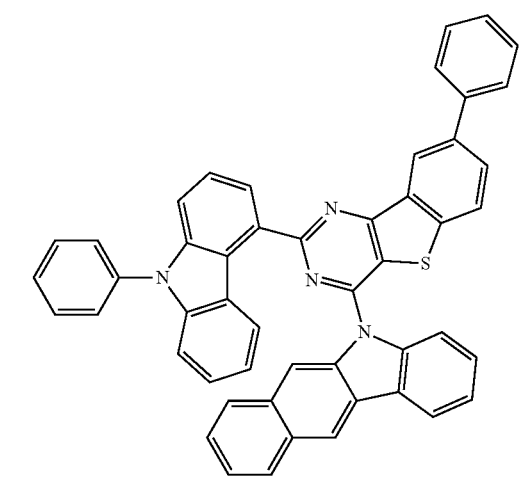
644
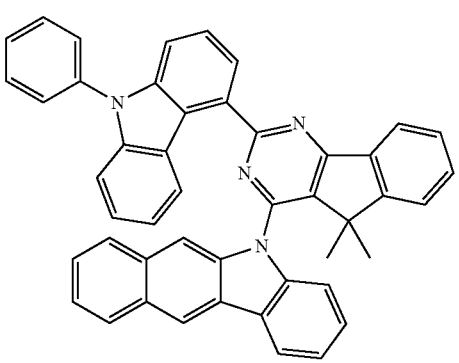
648
645
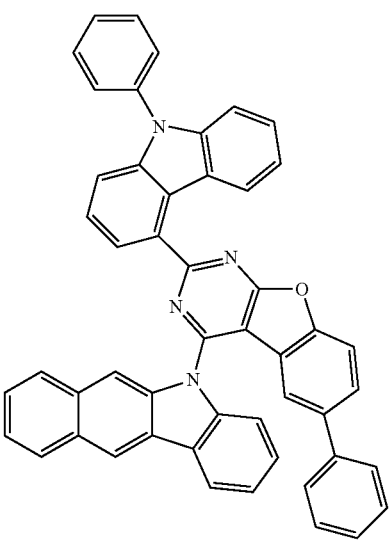
649
646
647
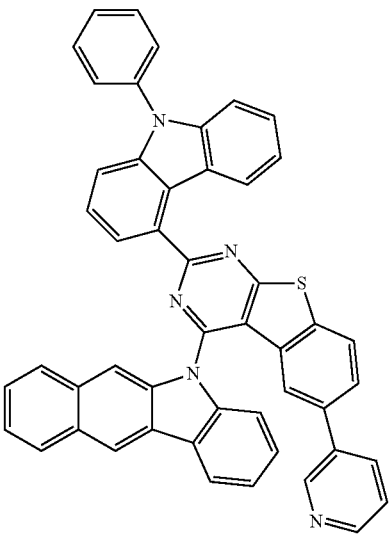
650

201
-continued
651
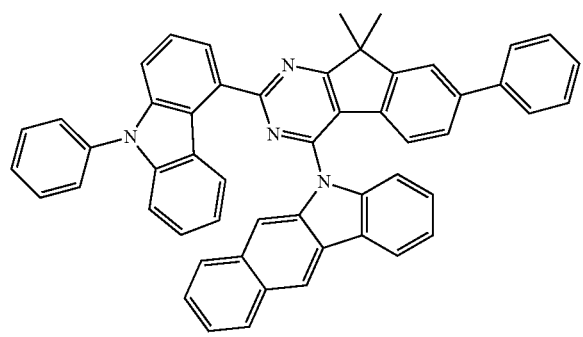
652
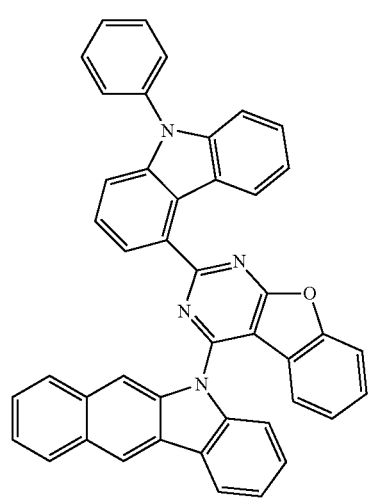
653
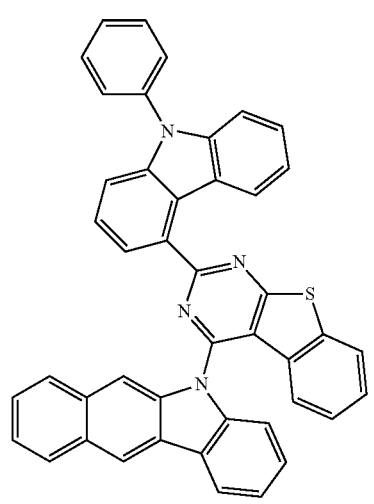
202
-continued
654
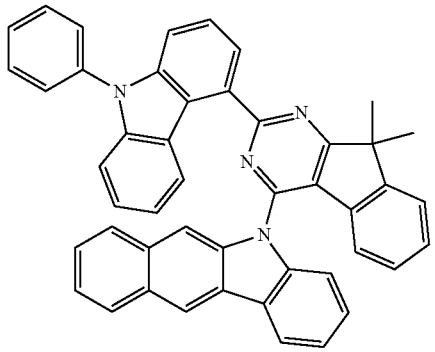
655
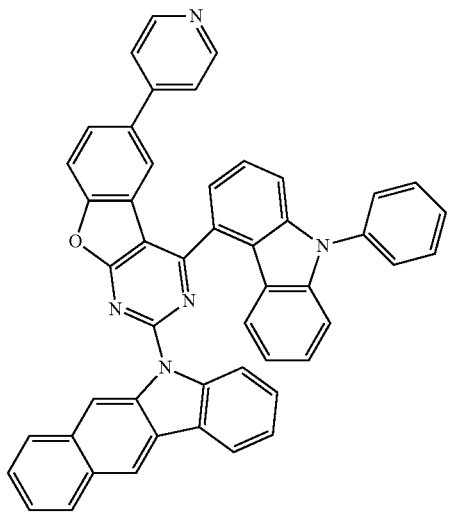
656
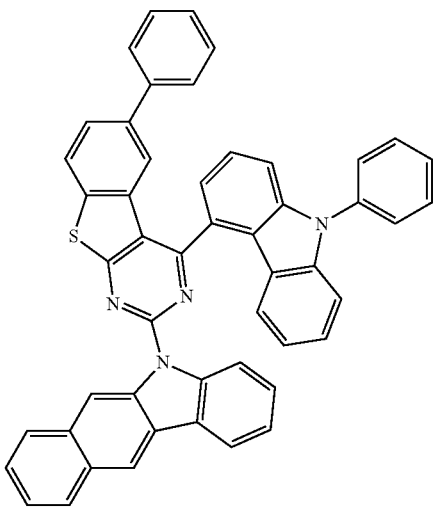

657
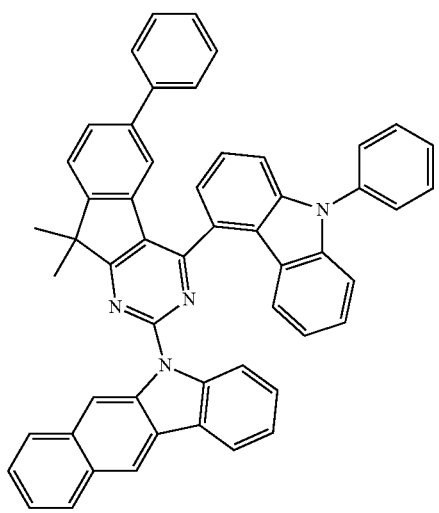
658
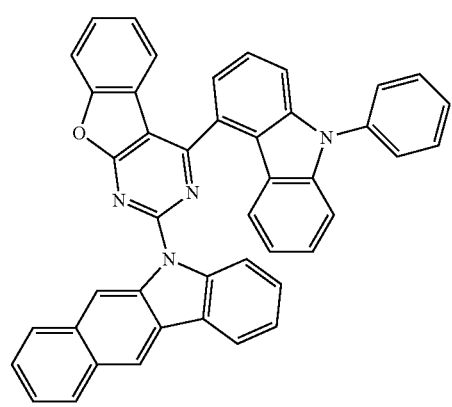
659
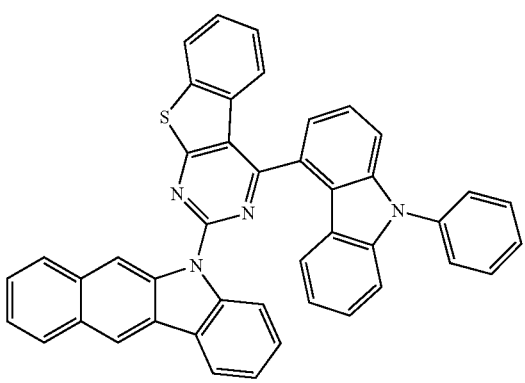
660
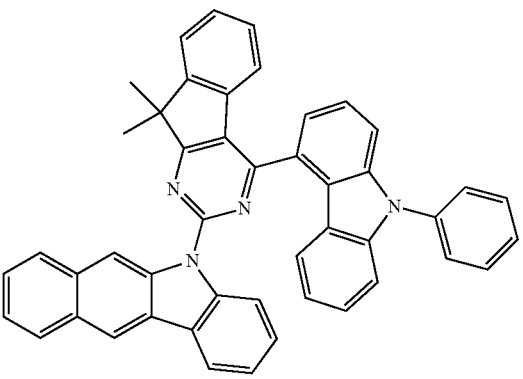
661
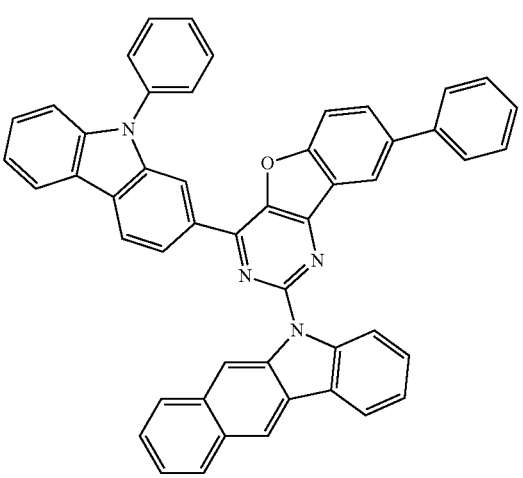
662
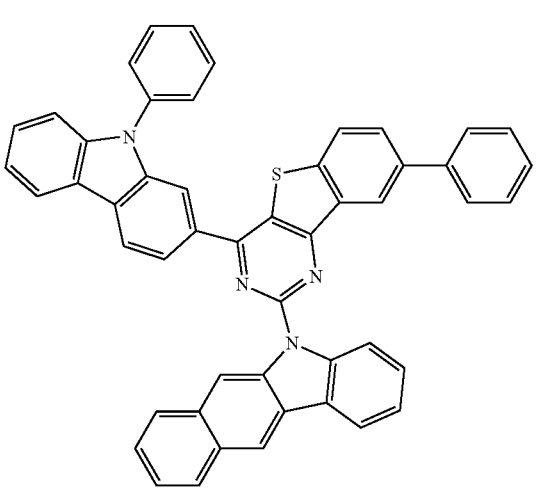

205
663
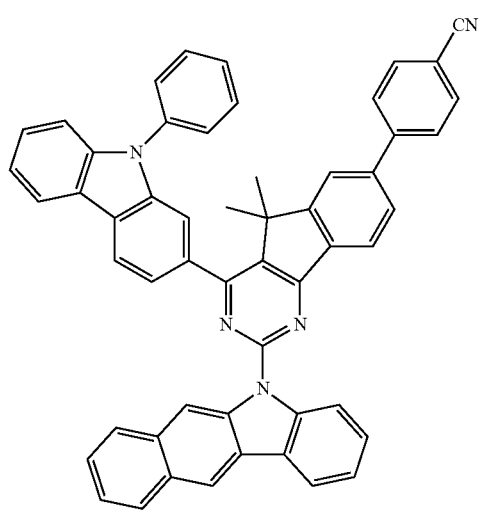
664
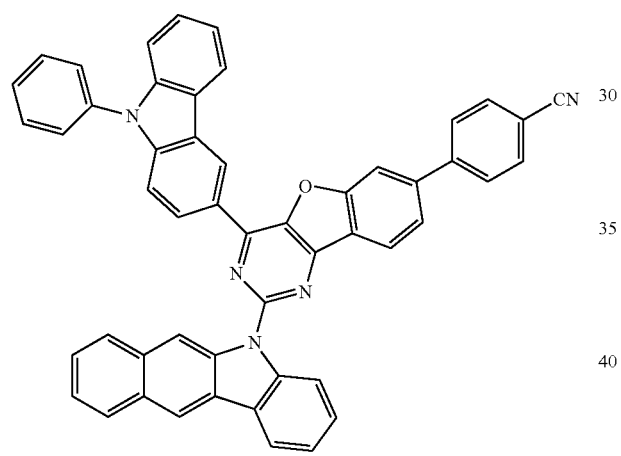
665
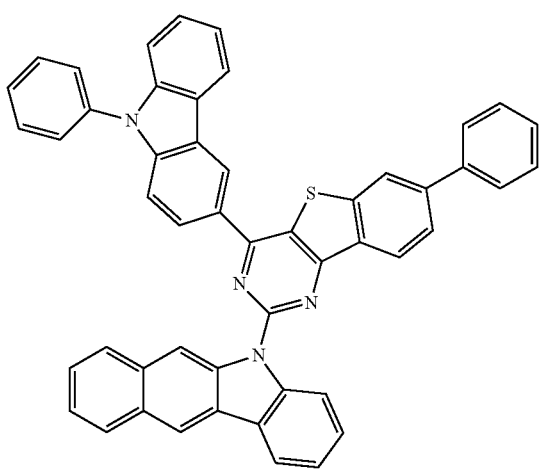
206
666
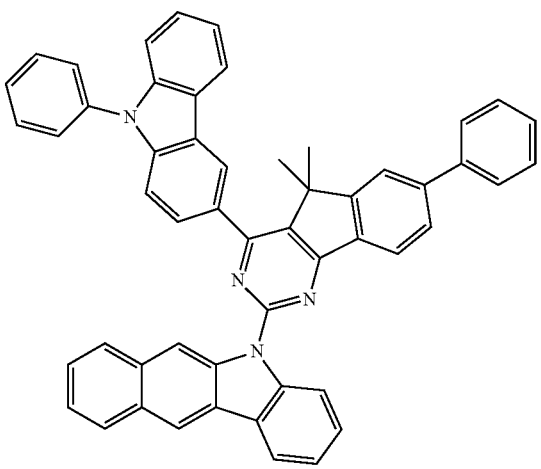
667
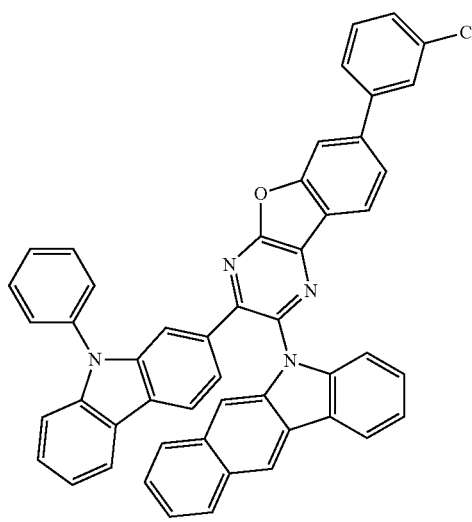
668
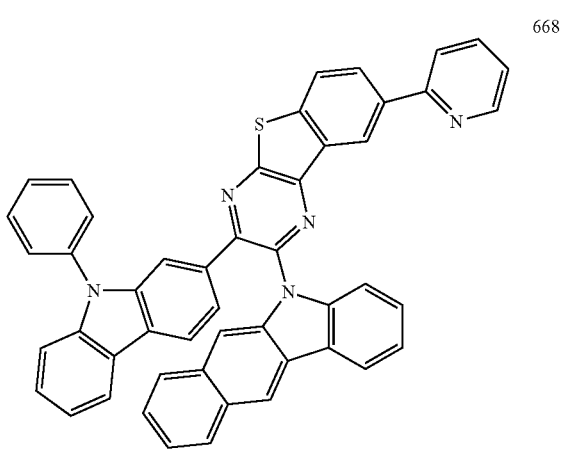

207
-continued
669
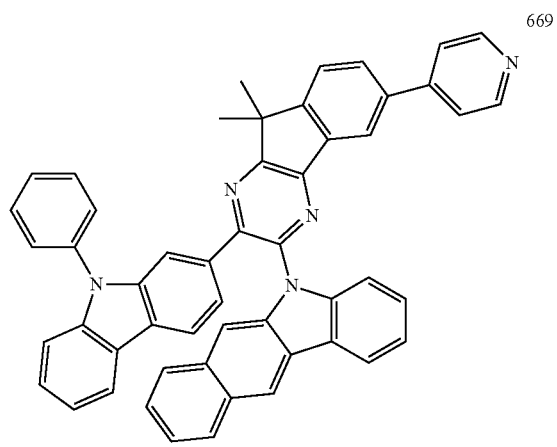
670
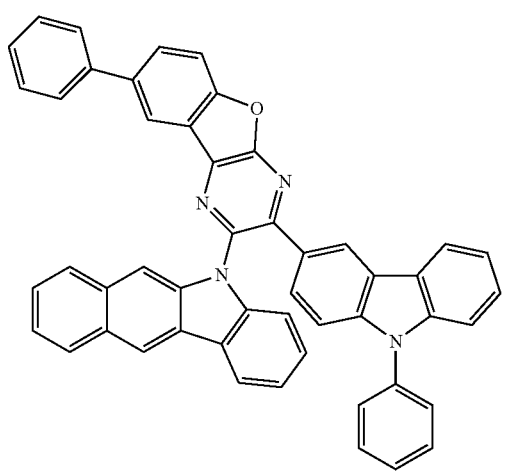
671
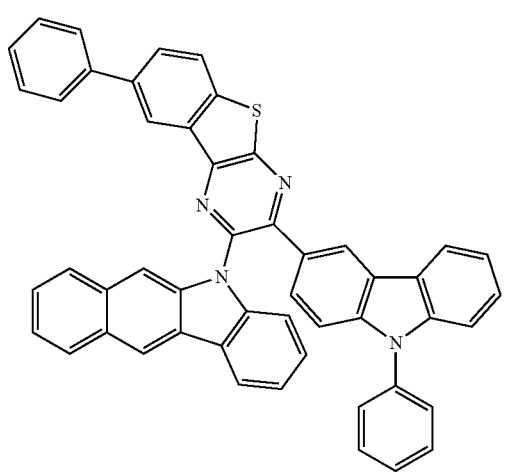
208
-continued
672
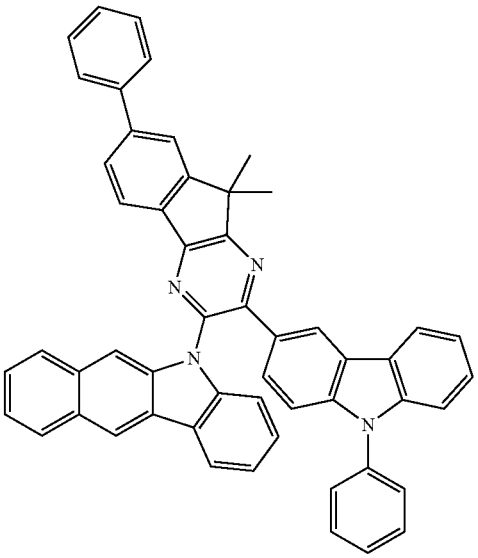
673
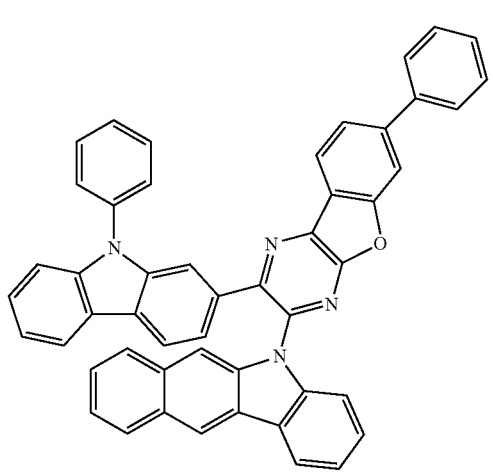
674
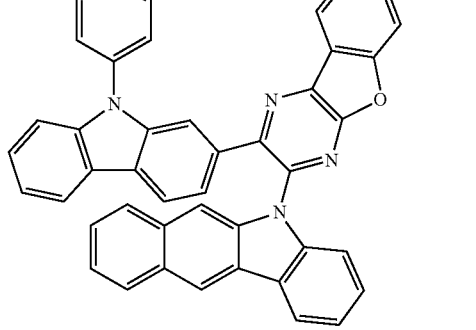

209
-continued
675
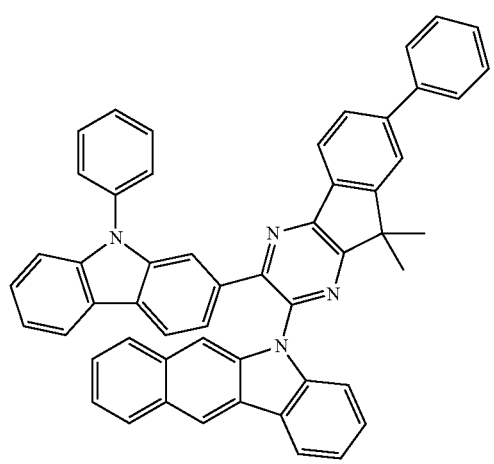
676
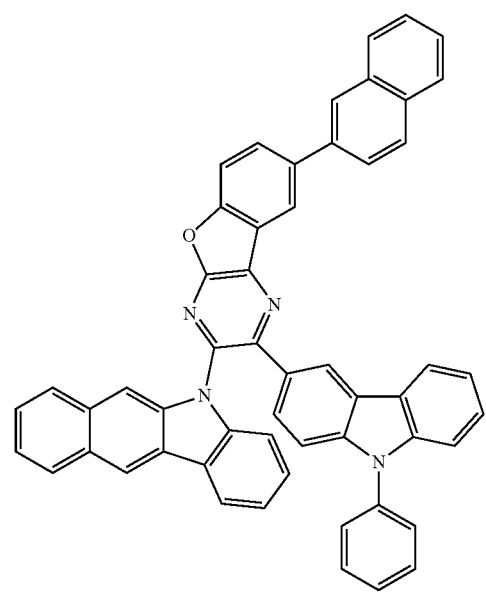
677
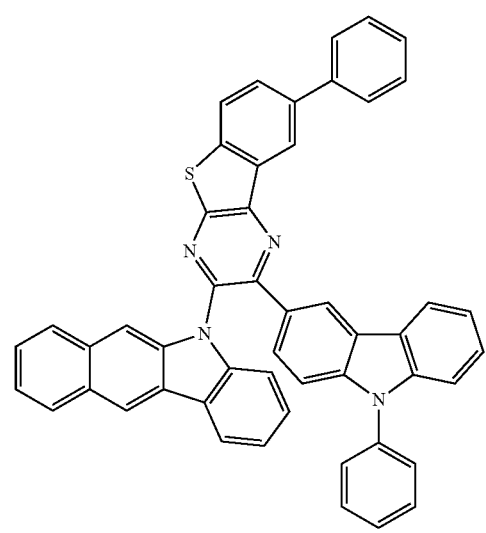
210
-continued
679
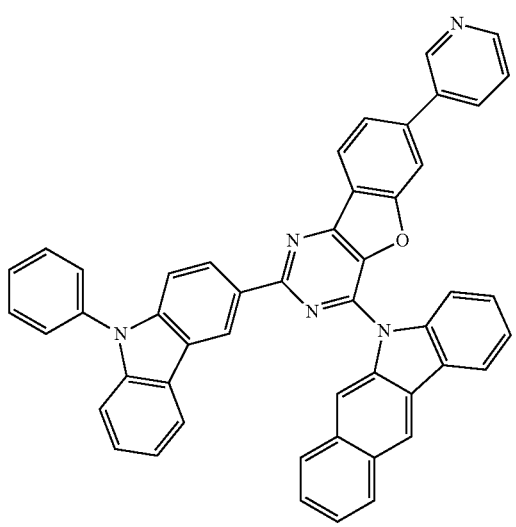
680
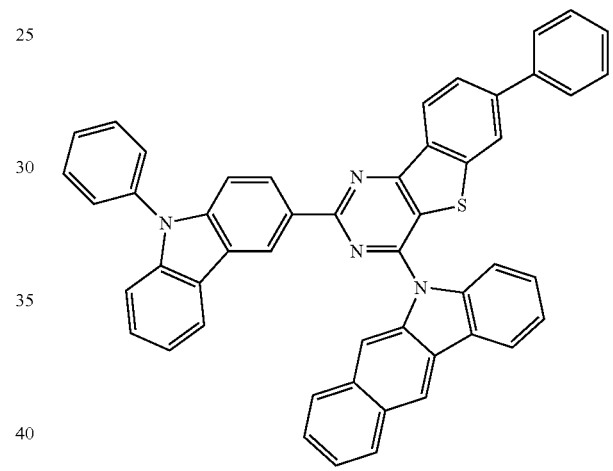
681
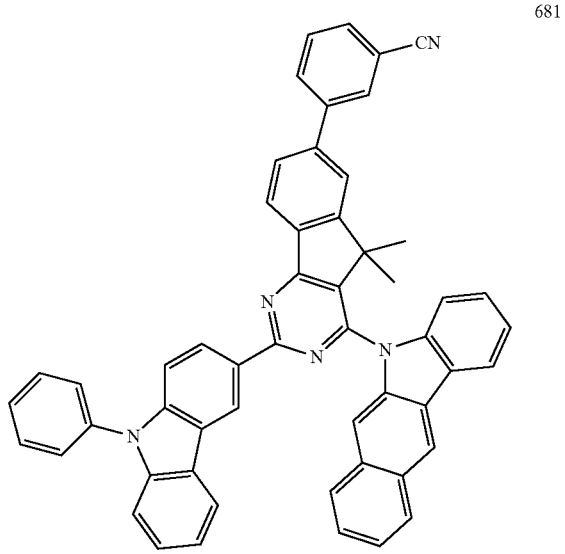

211
-continued
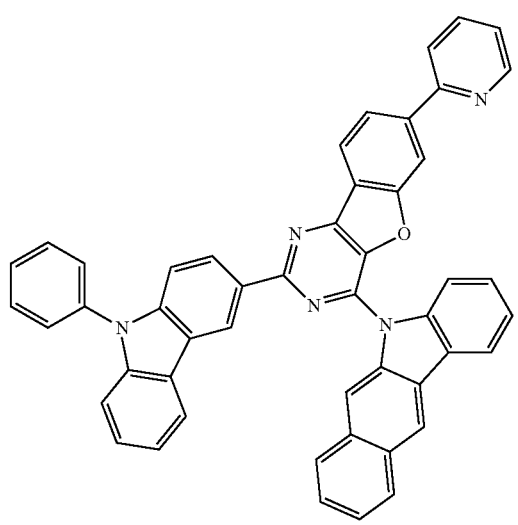
682
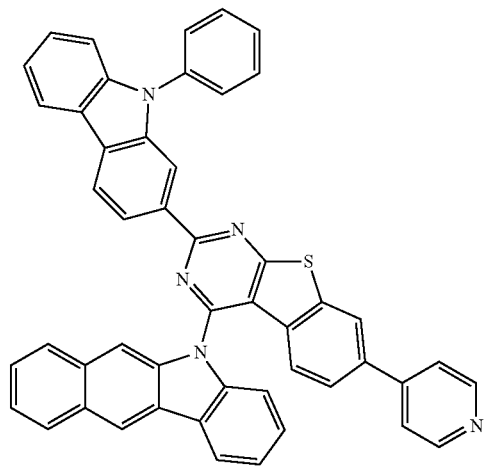
686
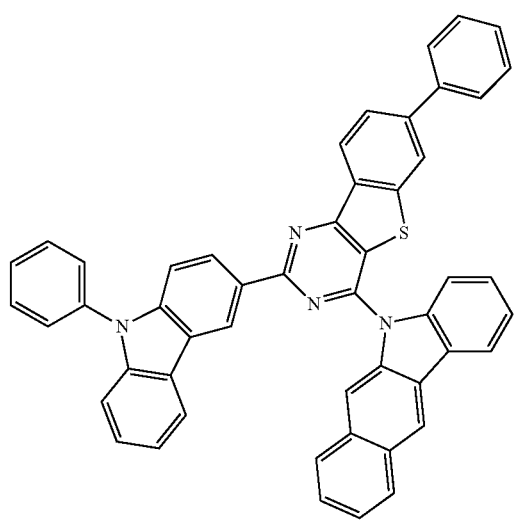
683
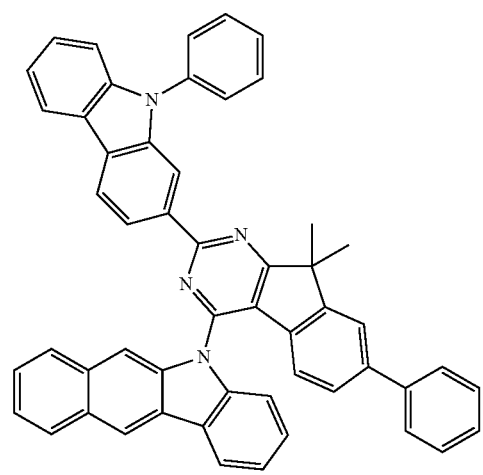
687
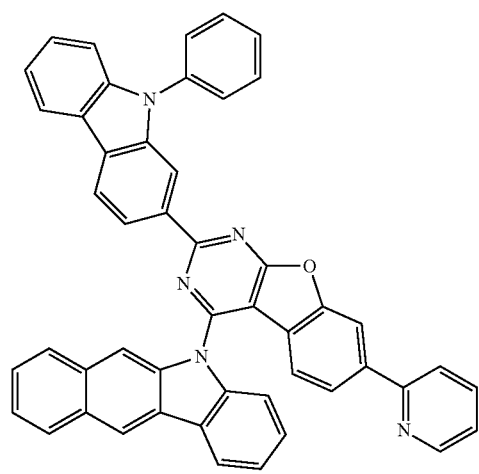
685
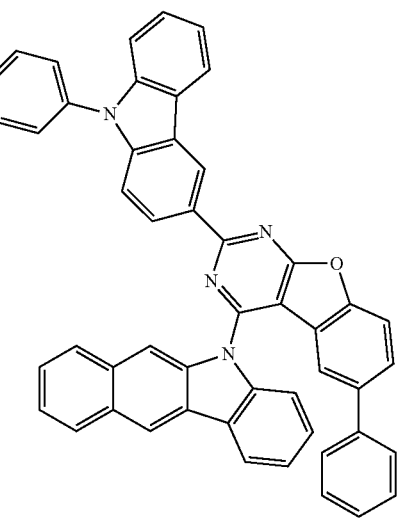
688
212
-continued 689
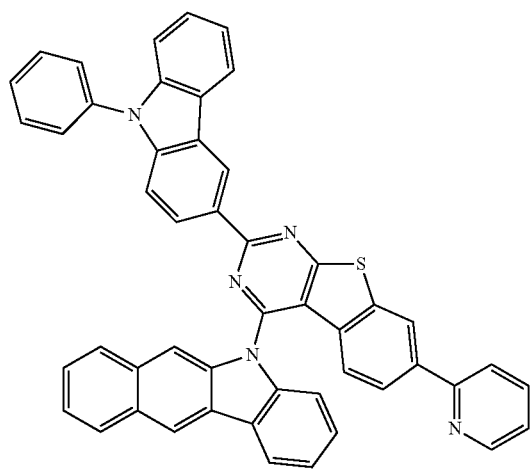
691
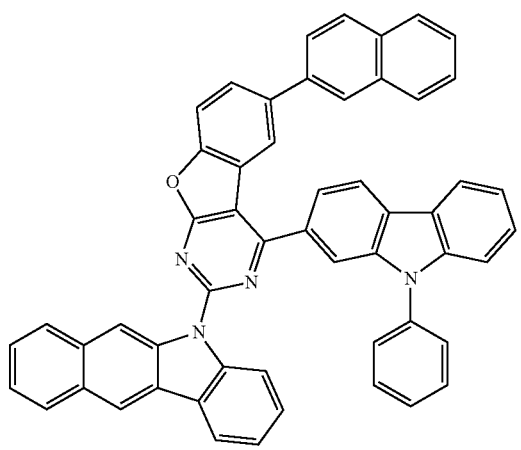
692
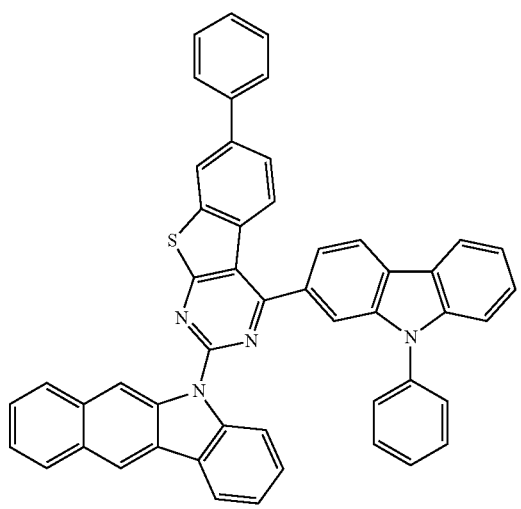
693
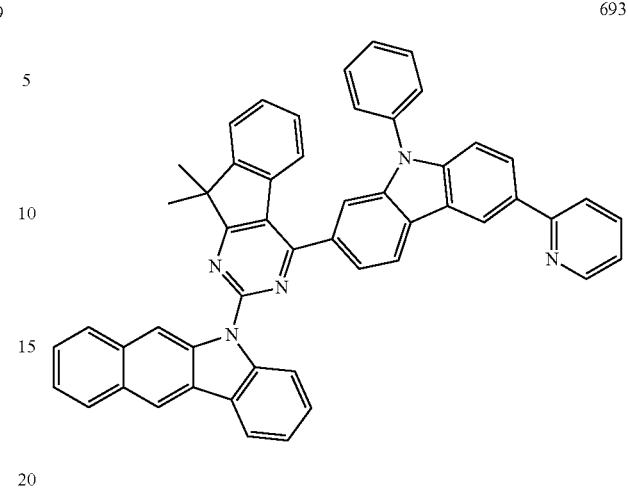
694
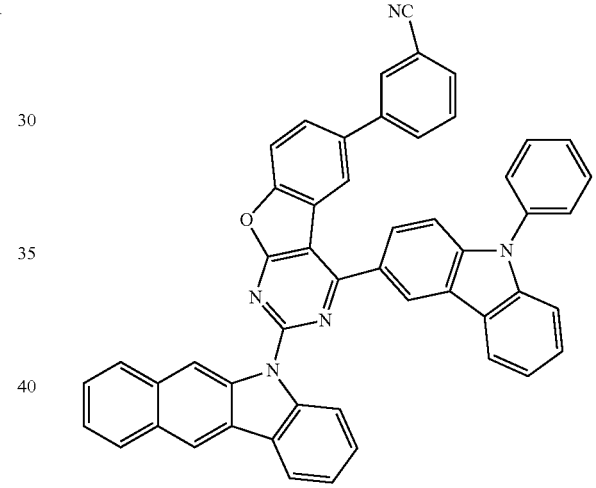
695
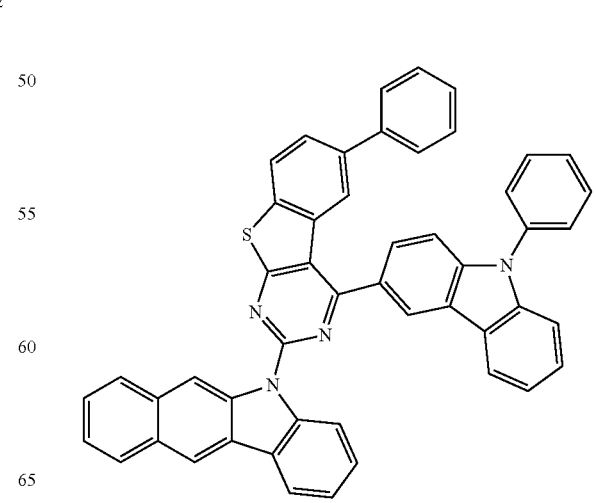

| 678 | 696 |
|---|---|
| 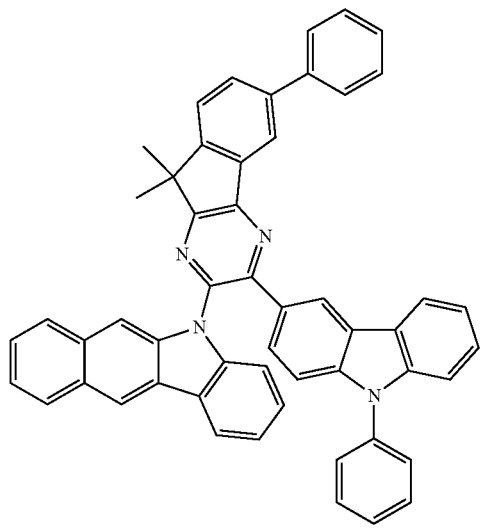 | 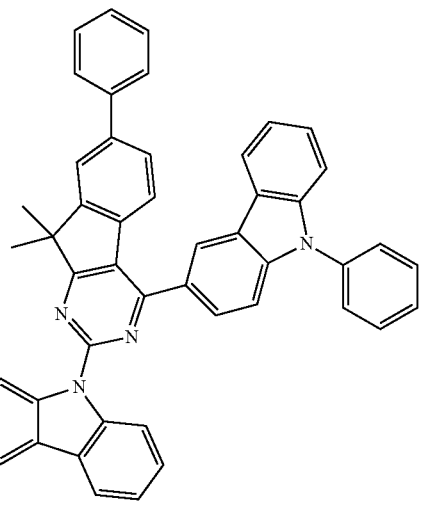 |
| 684 | 697 |
|---|---|
| 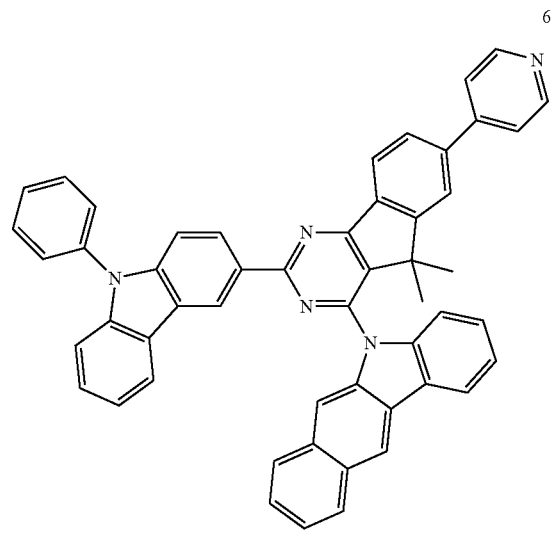 | 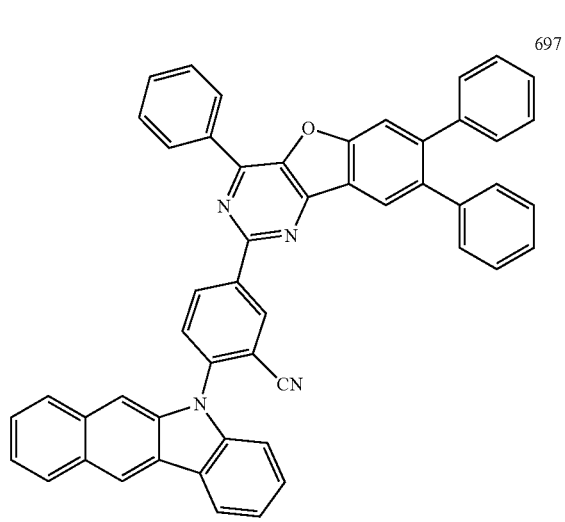 |
| 690 | 698 |
|---|---|
| 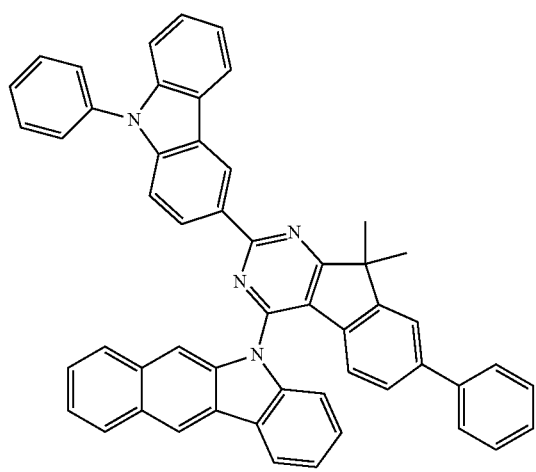 | 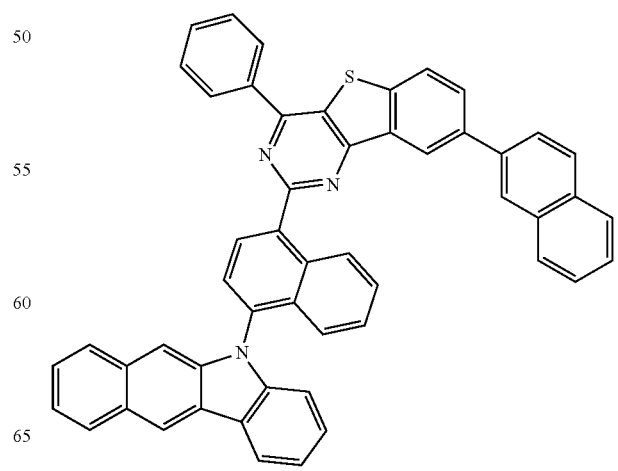 |

-continued
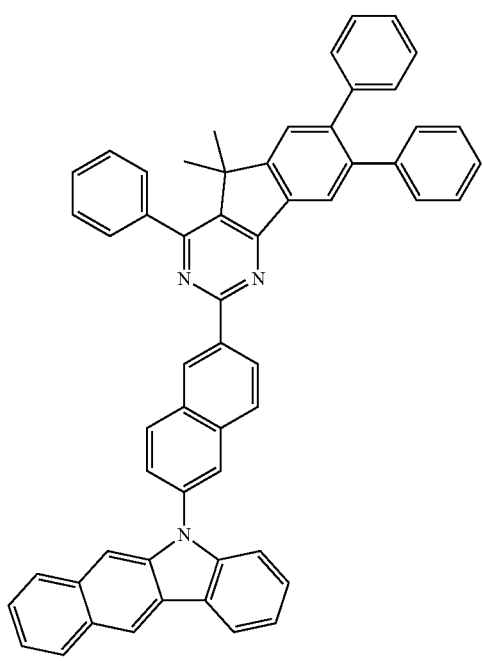
699
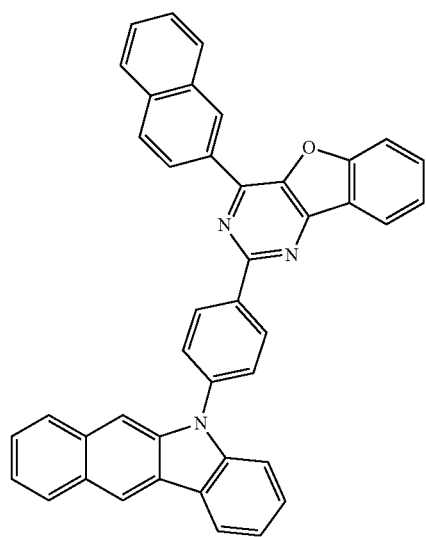
700
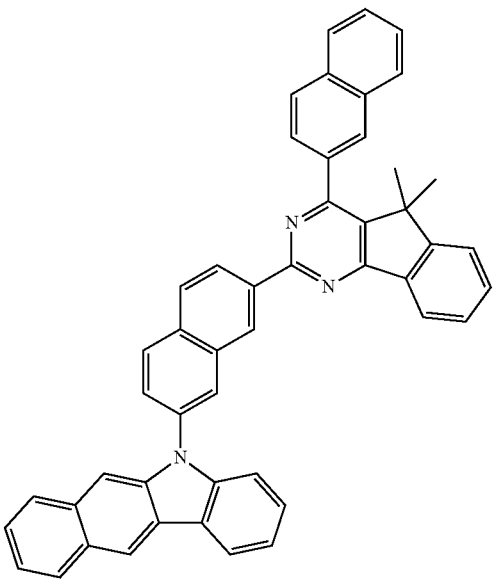
701
702

-continued
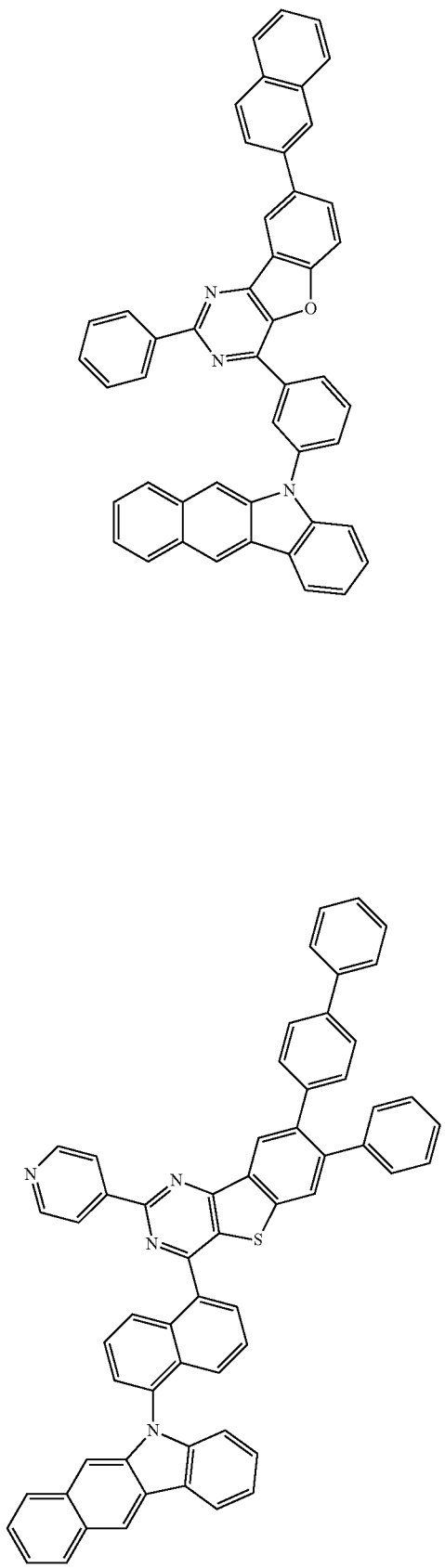
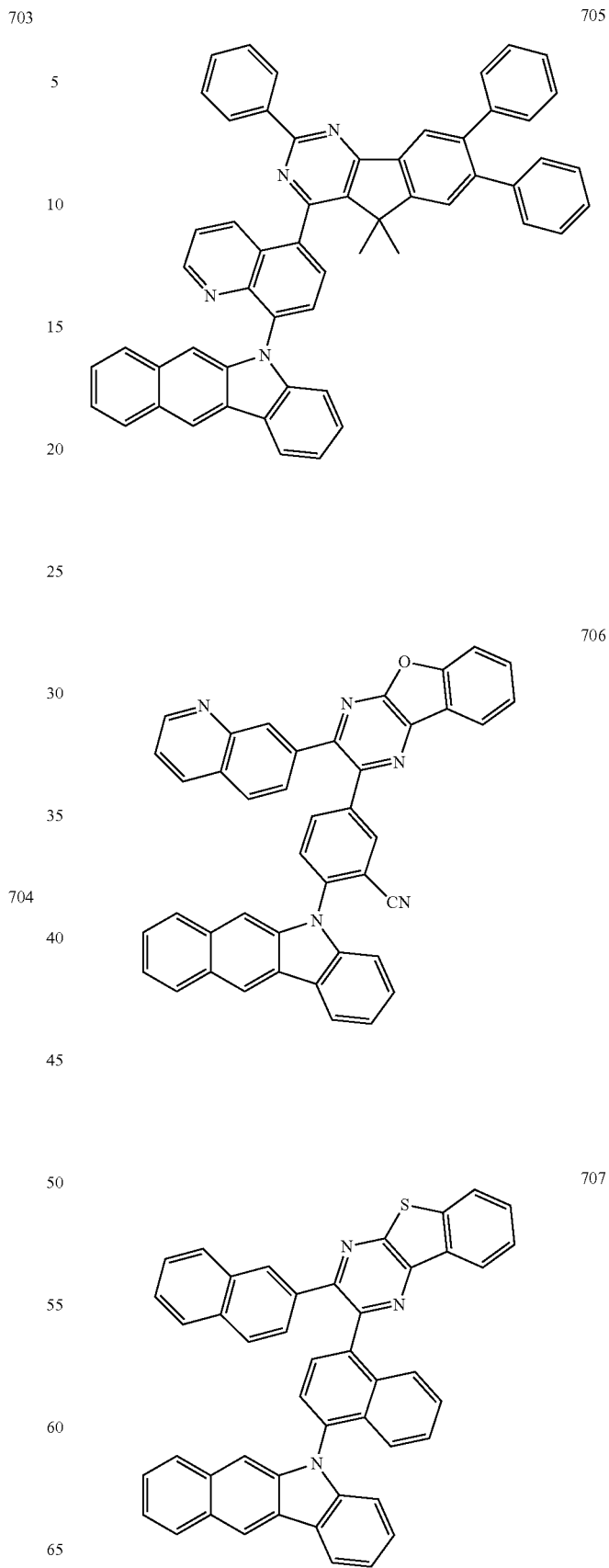

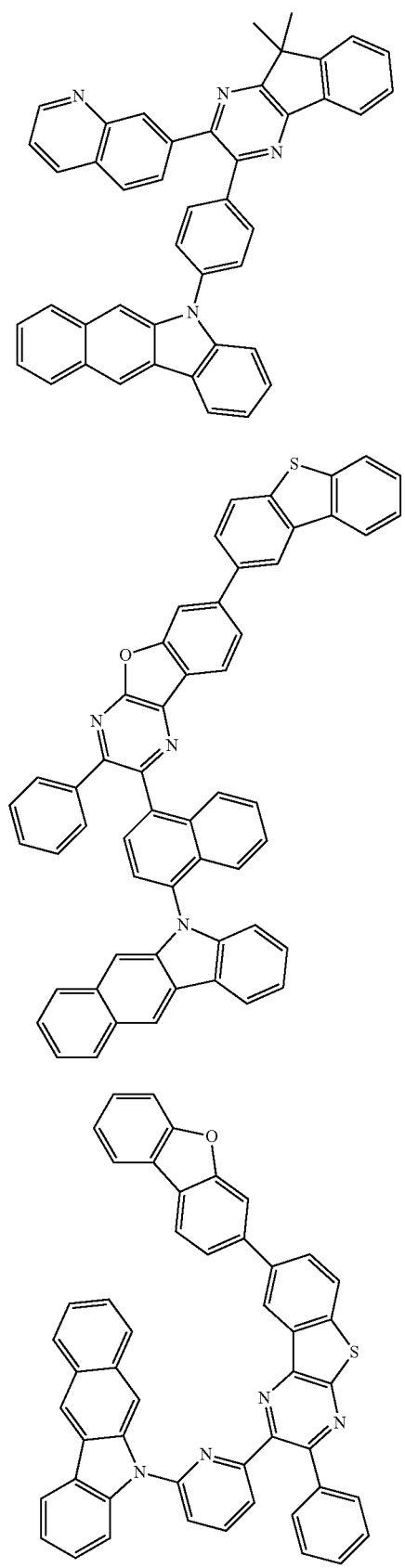
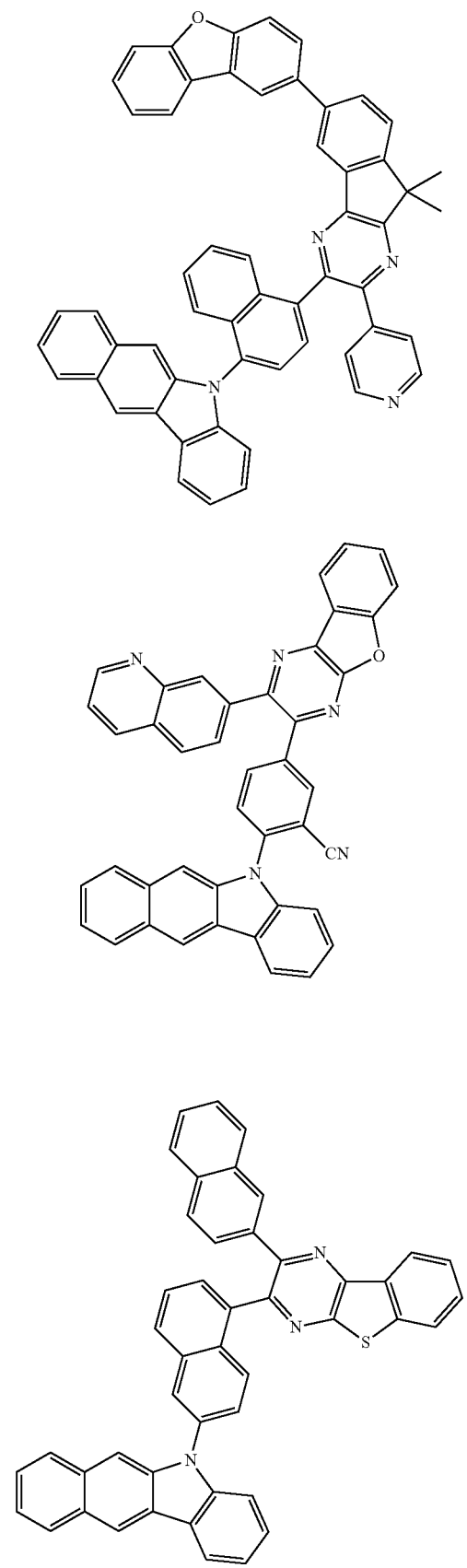

714
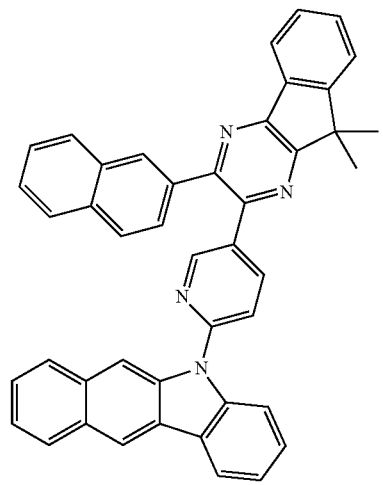
717
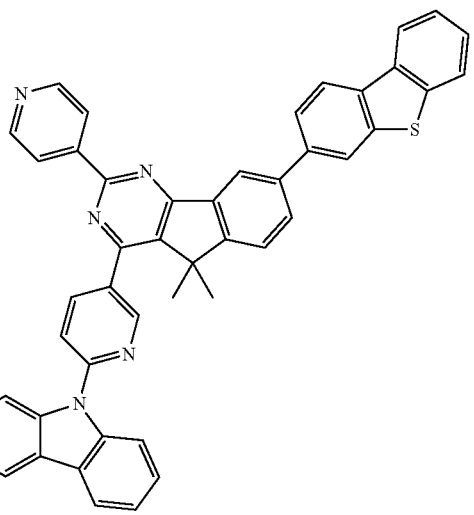
715
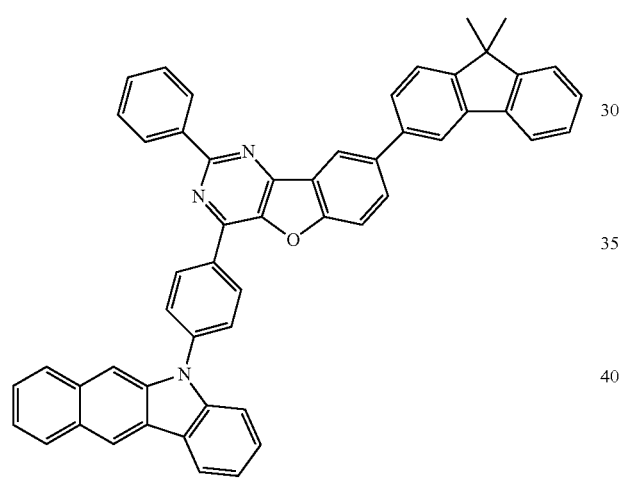
718
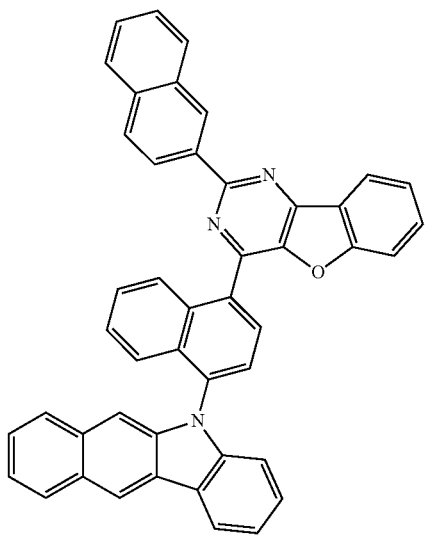
716
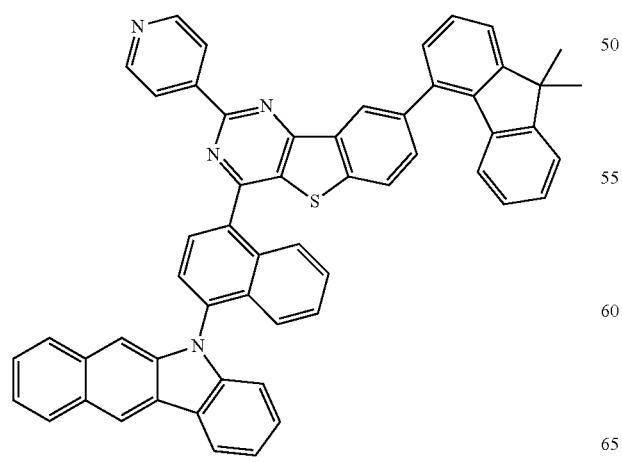
719
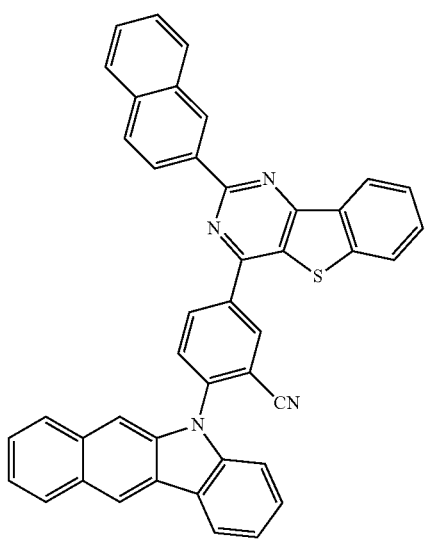

225
-continued
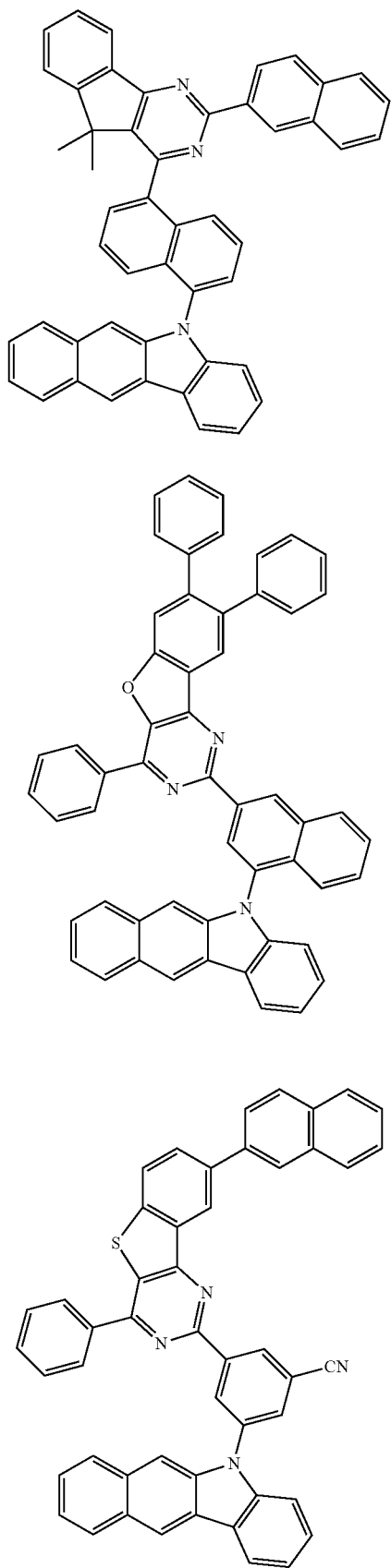
226
-continued
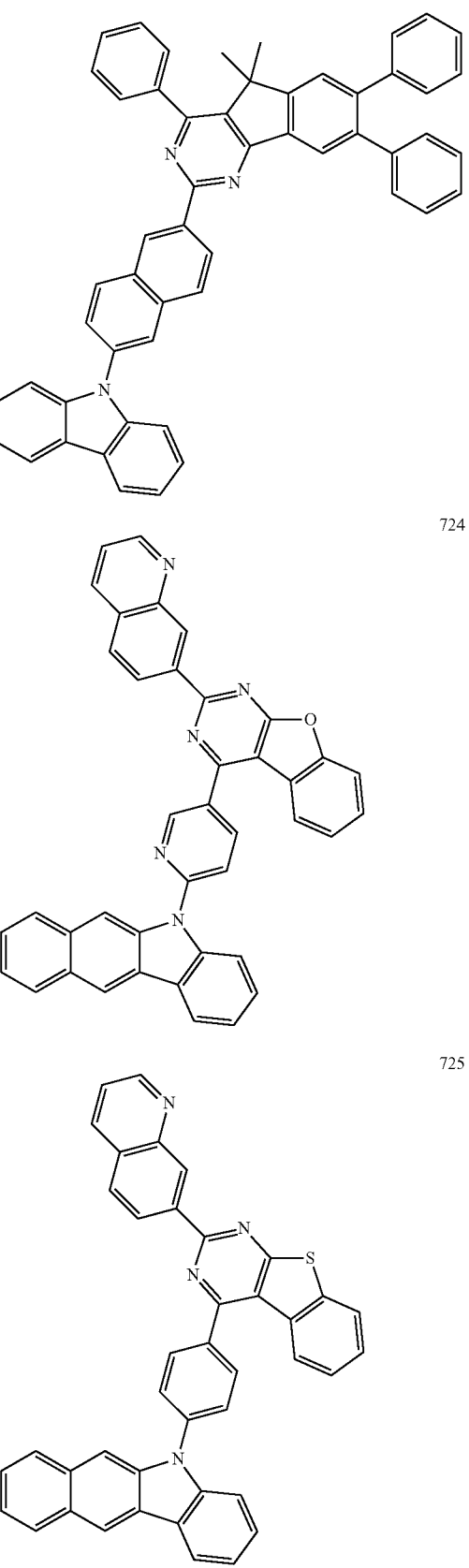

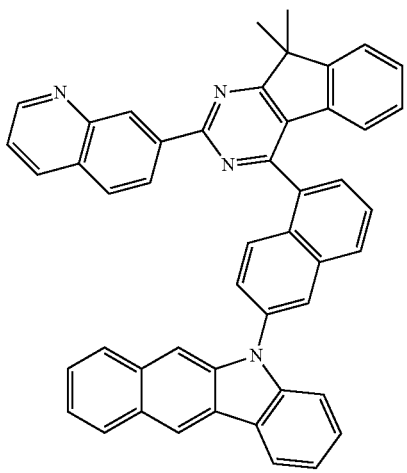
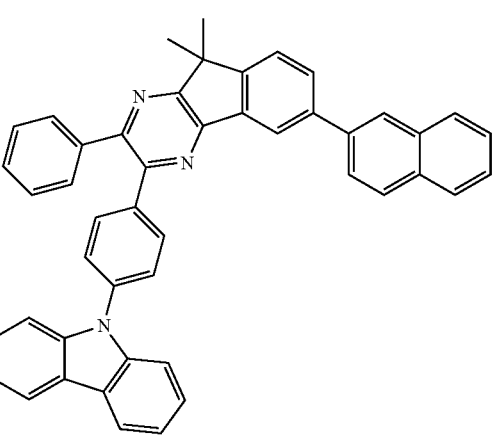
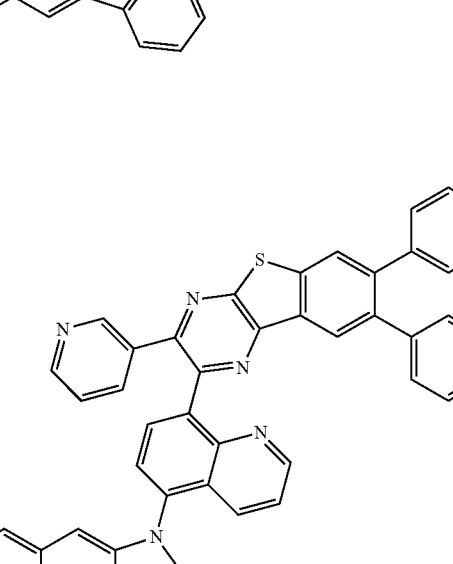

-continued
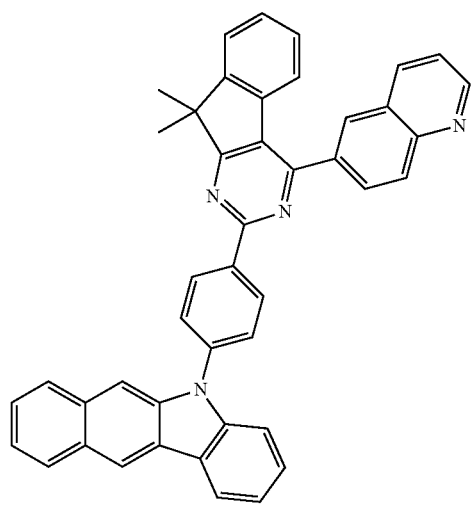
732
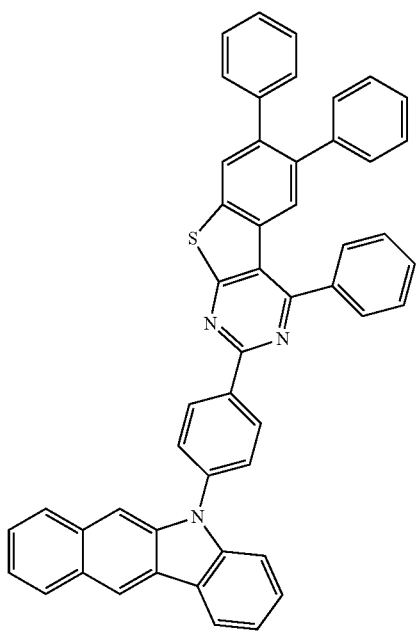
734
733
735

231
-continued
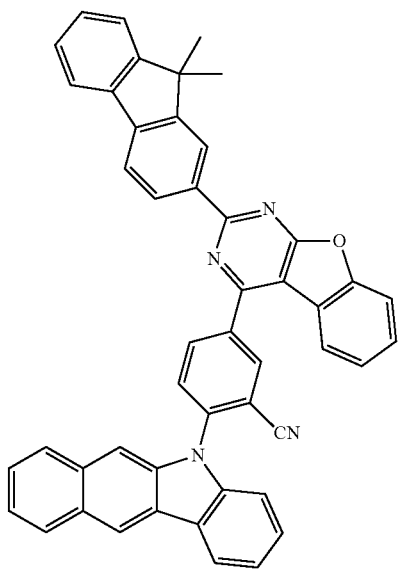
736
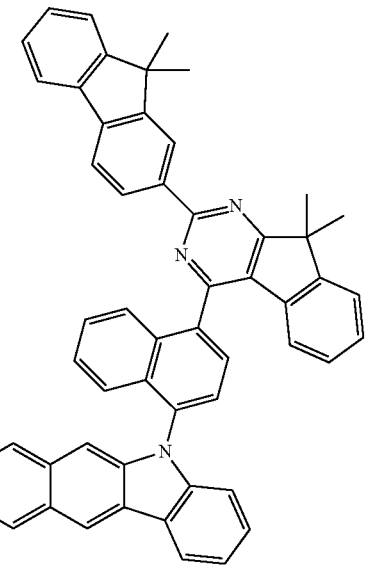
738
737
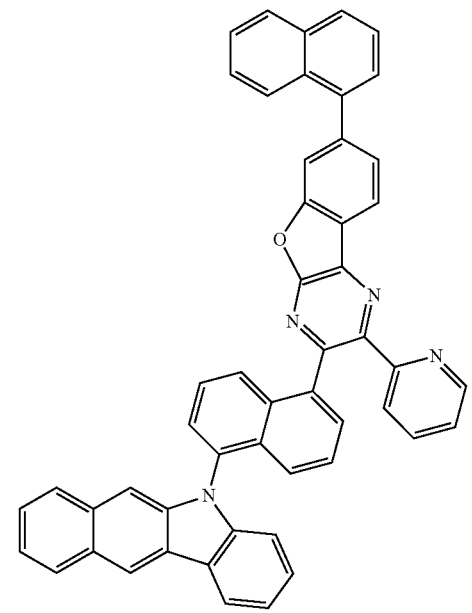
739
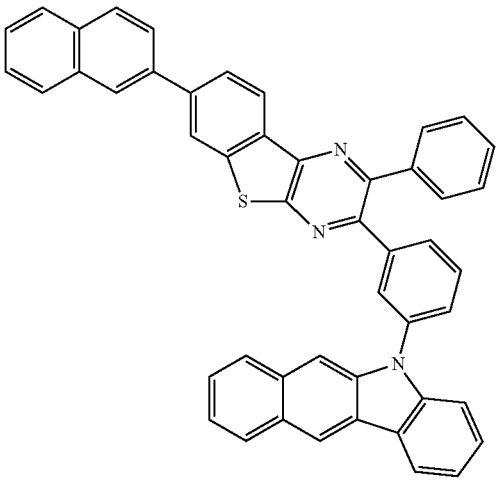
740

741
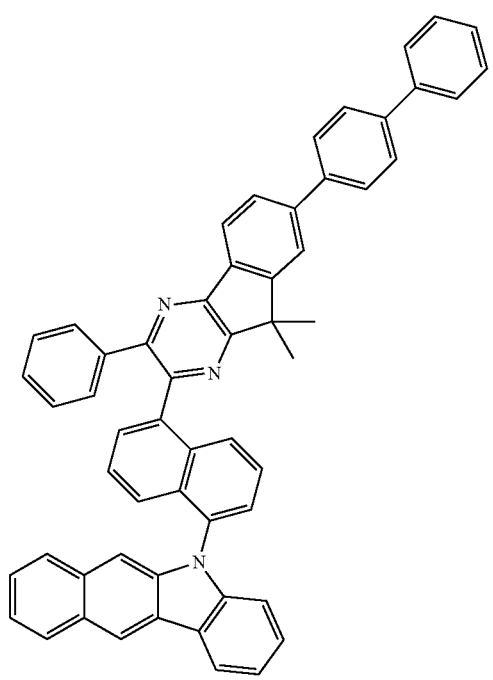
742
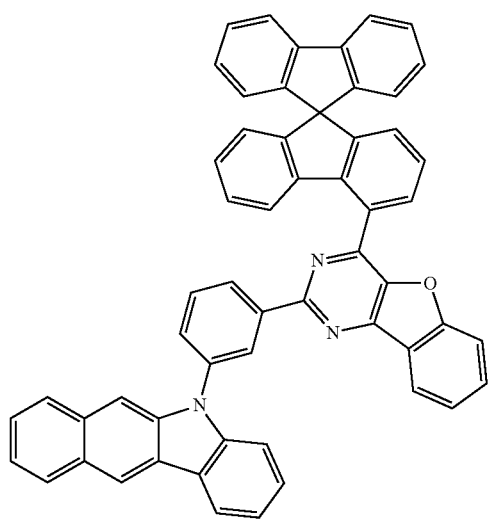
743
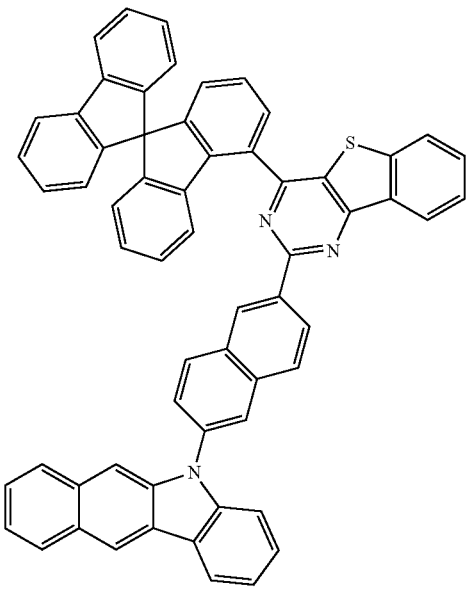
744
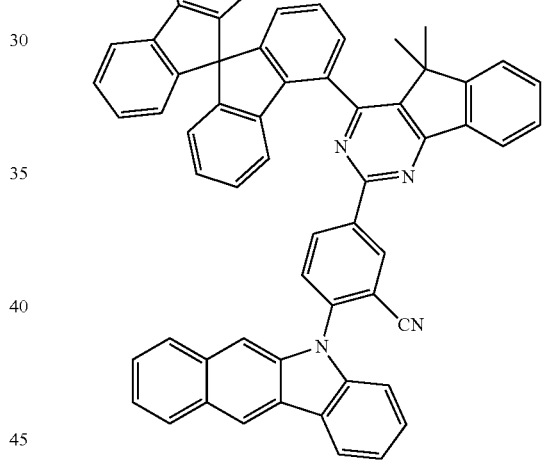
745
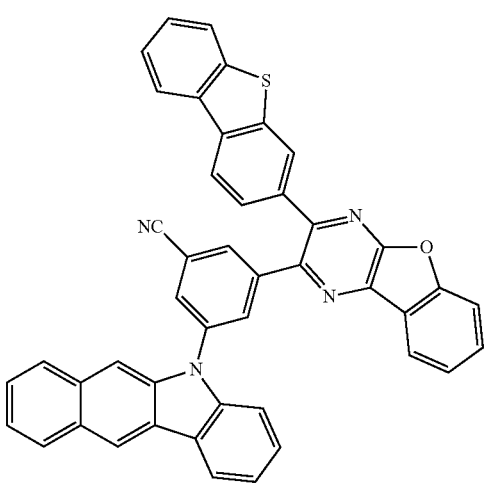

746
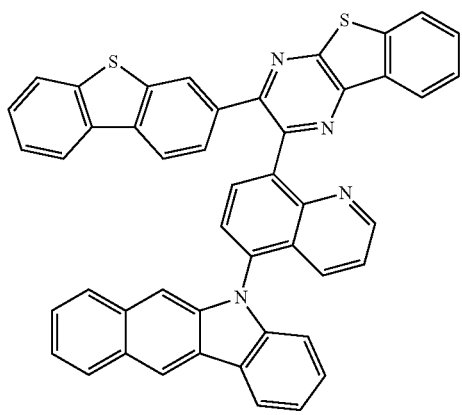
747
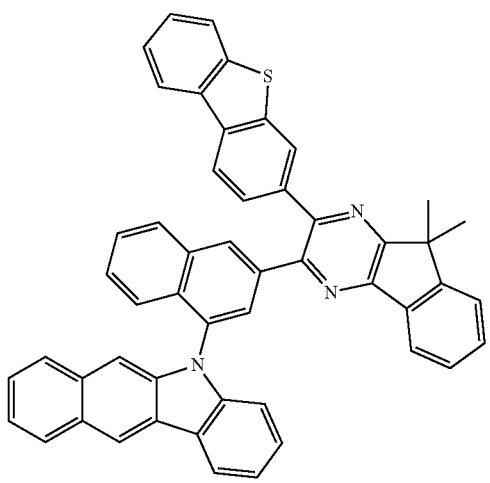
748
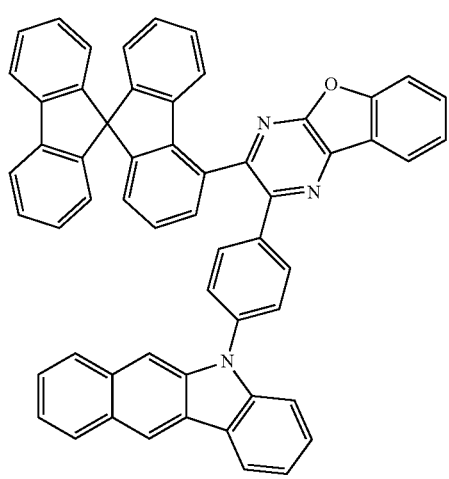
749
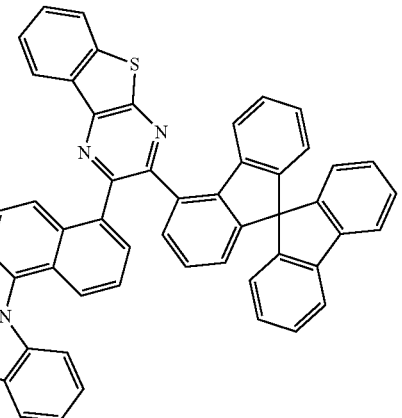
750
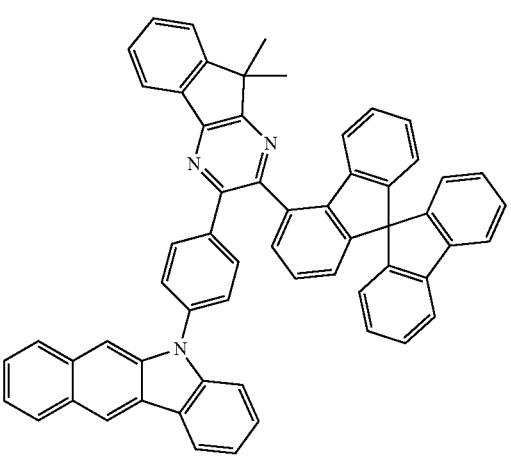
751
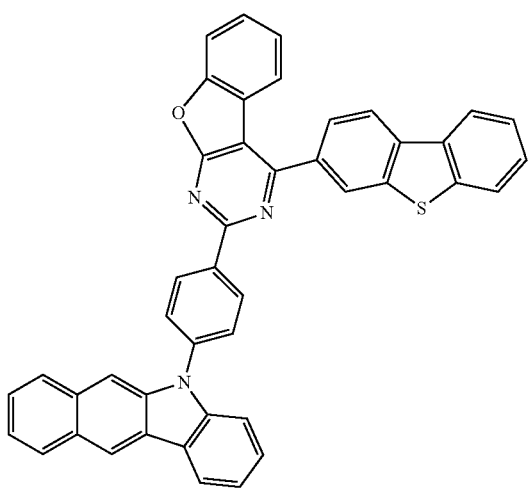

752
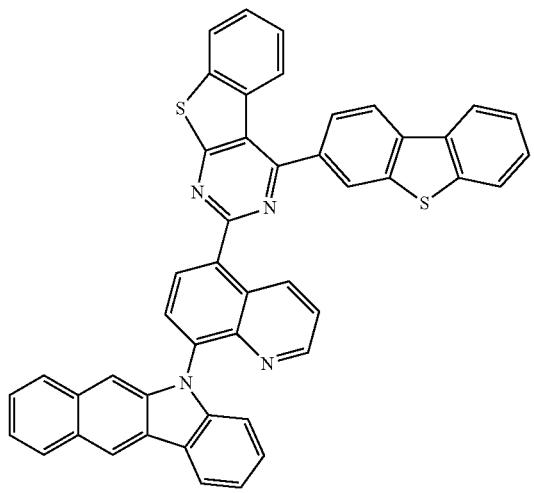
753
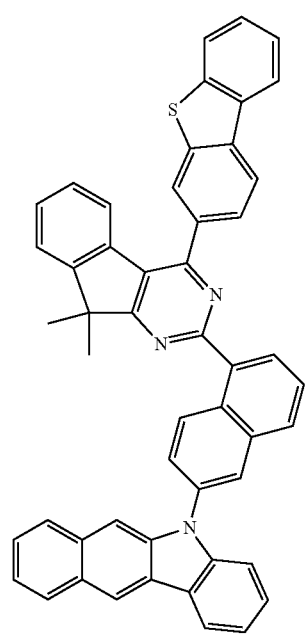
754
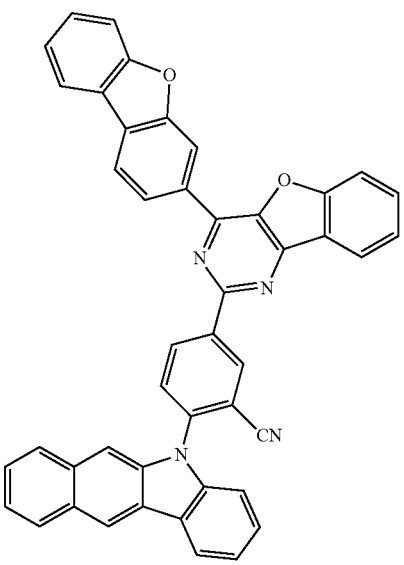
755
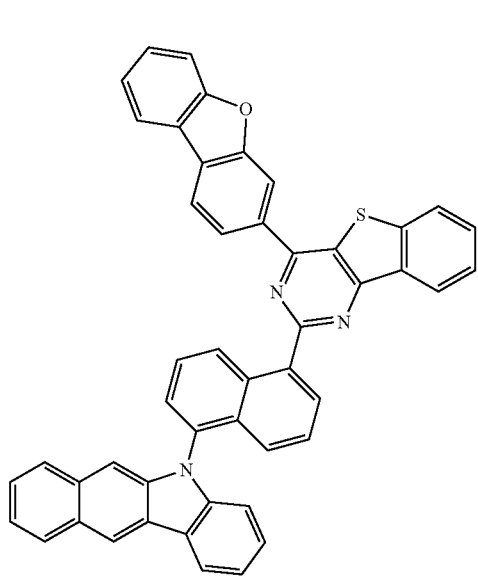

239
-continued
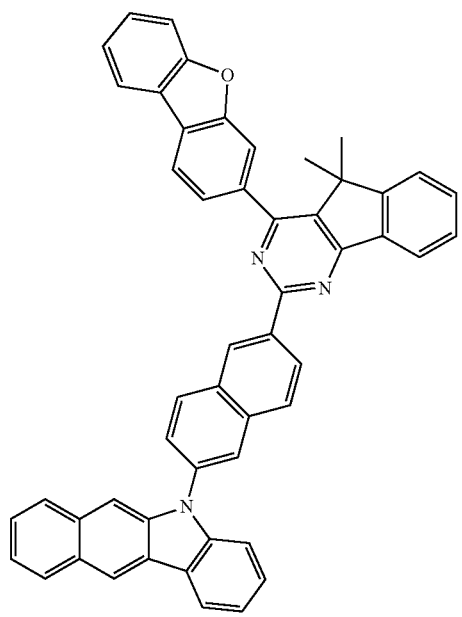
756
240
-continued
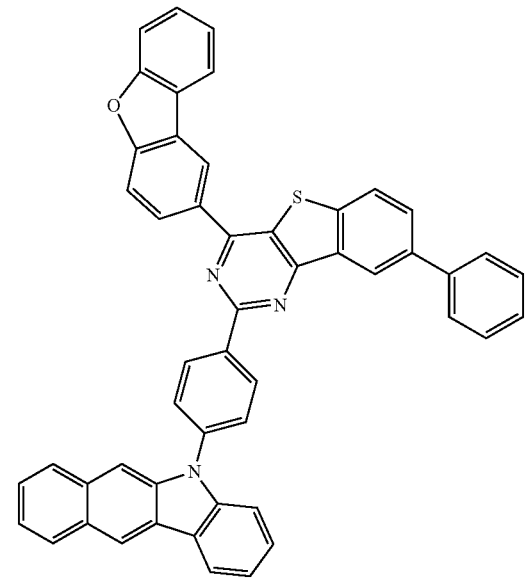
758
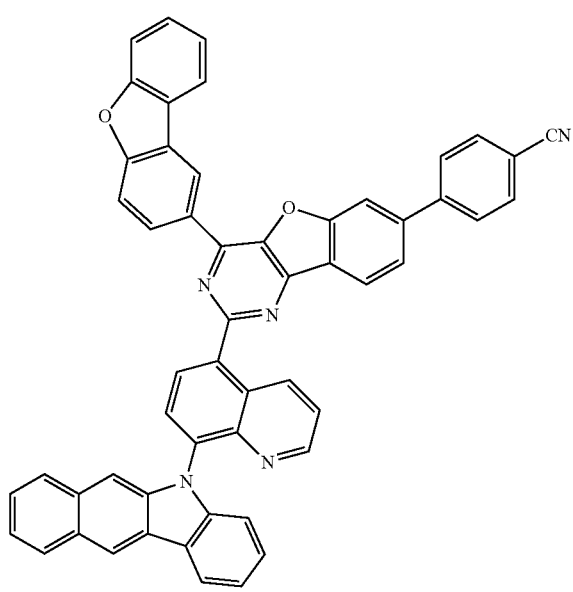
757
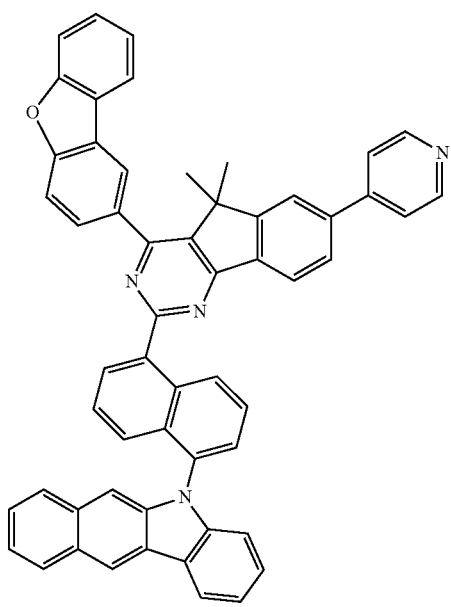
759

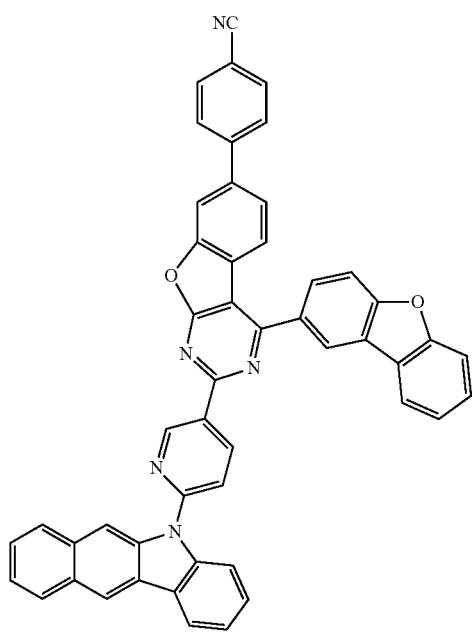
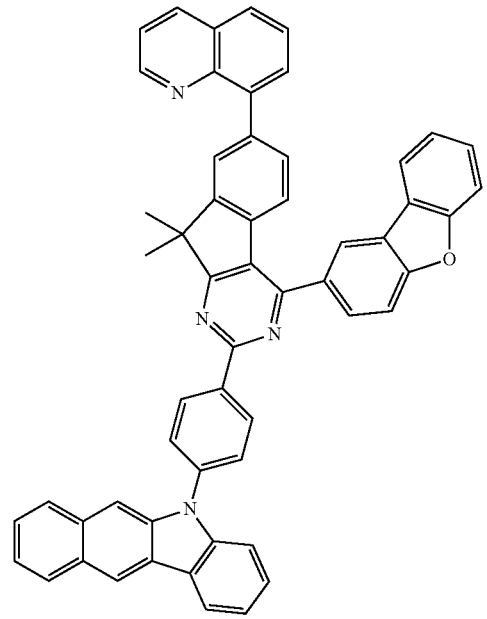
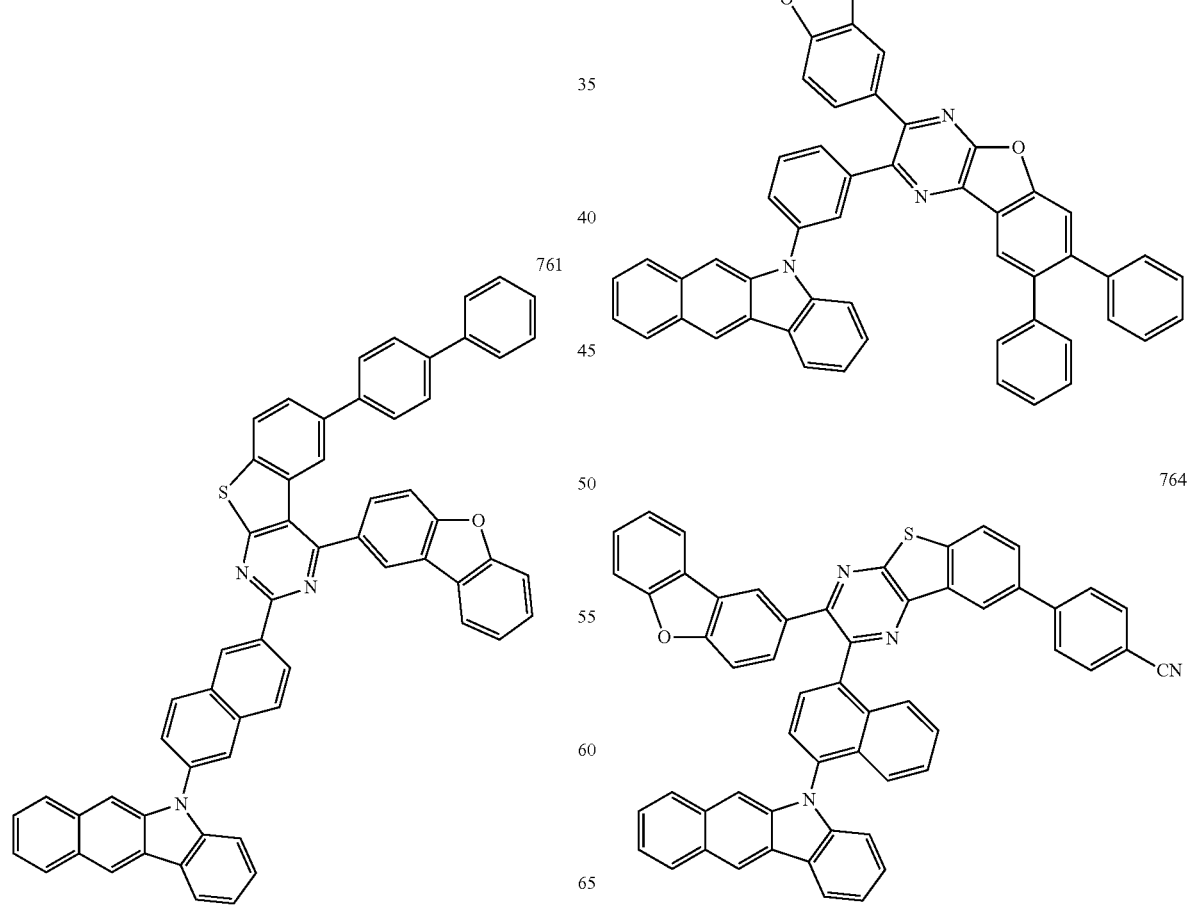

-continued
765
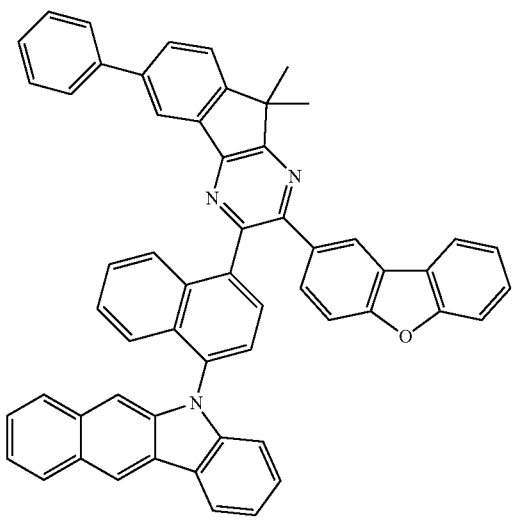
766
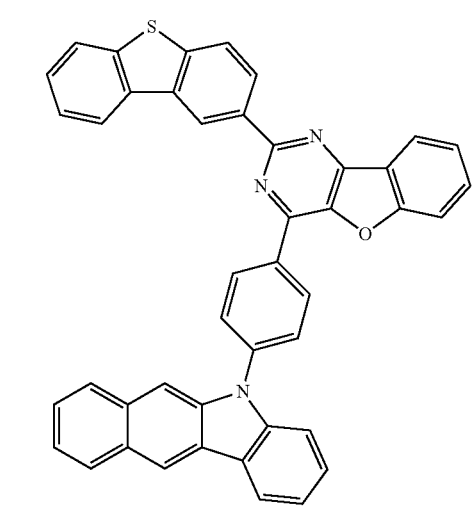
767
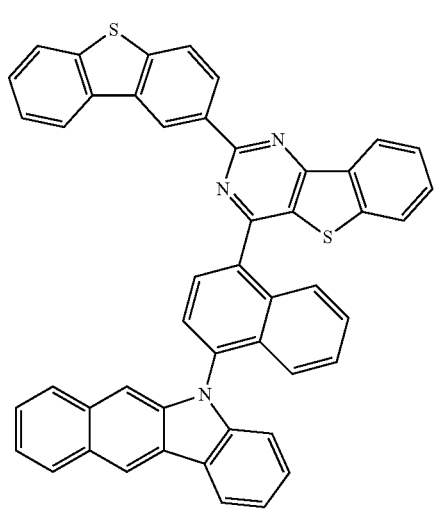
-continued
768
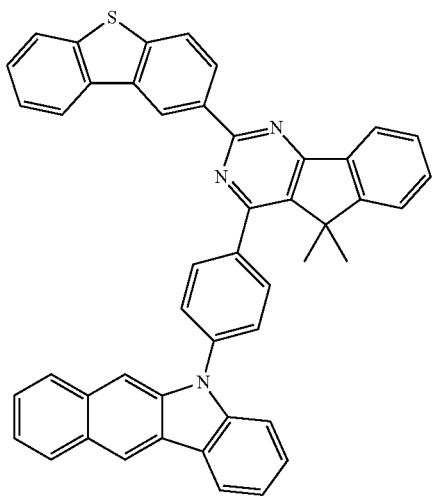
769
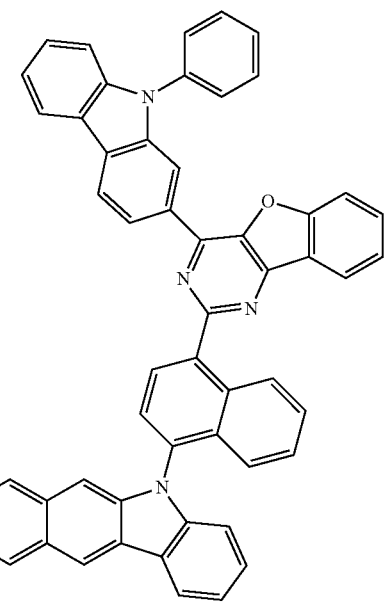
770
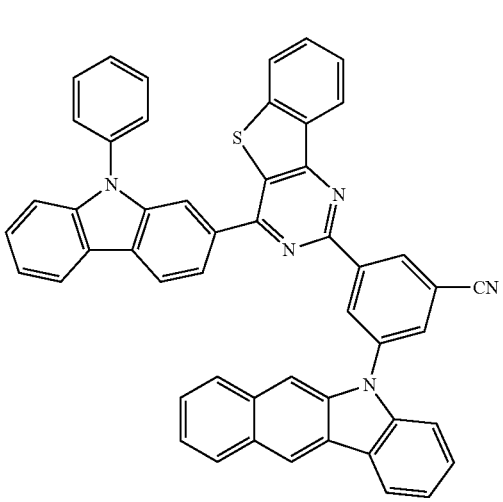

771
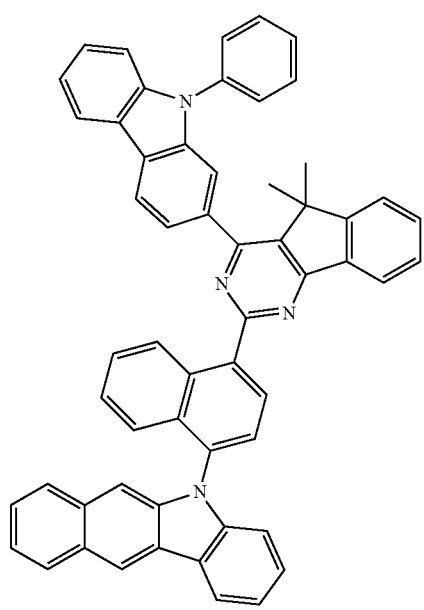
772
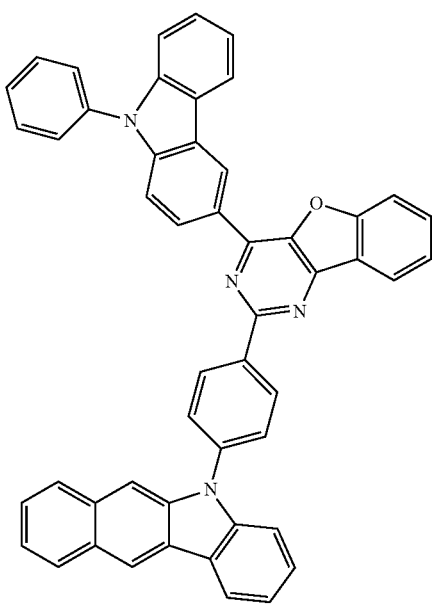
773
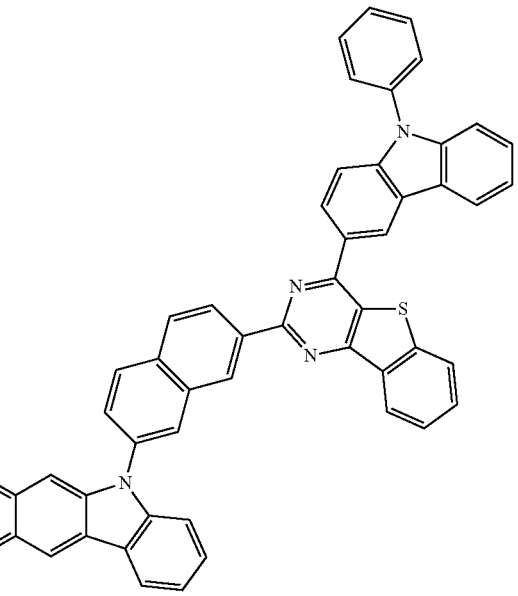
774
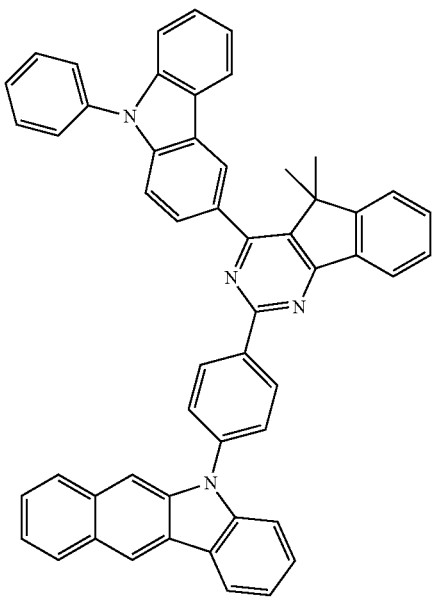

775
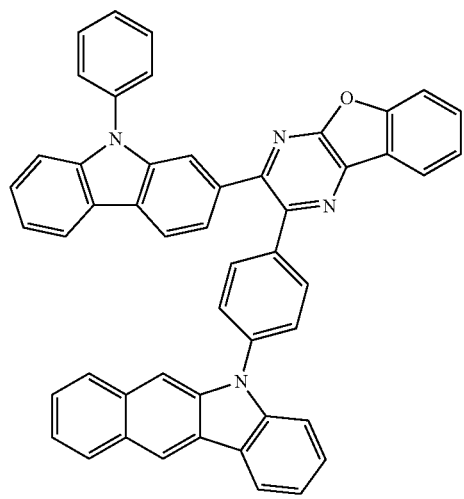
776
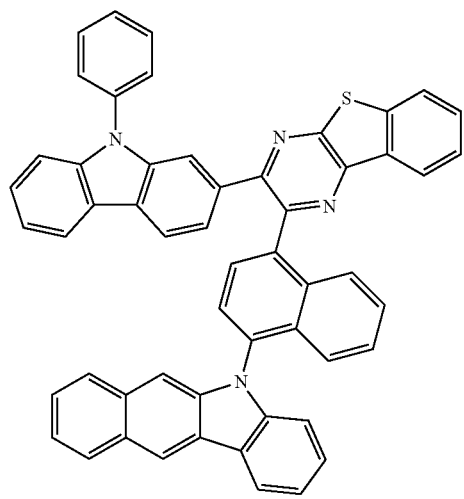
777
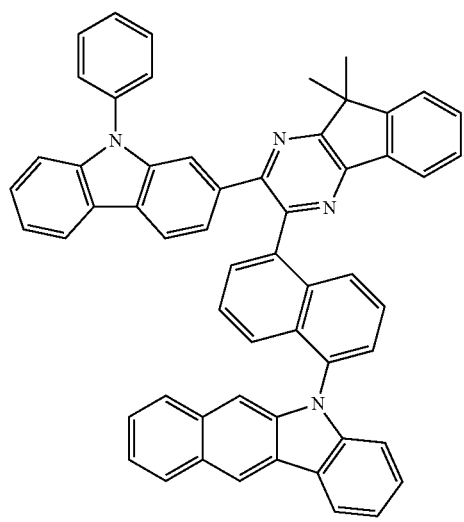
778
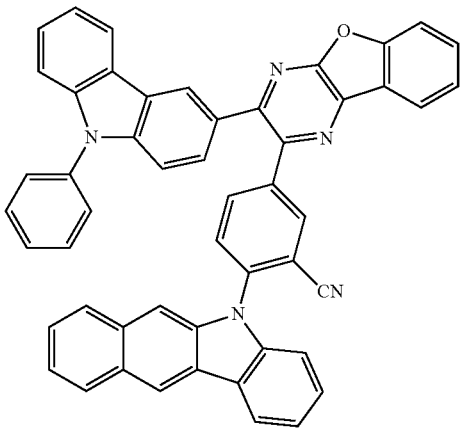
779
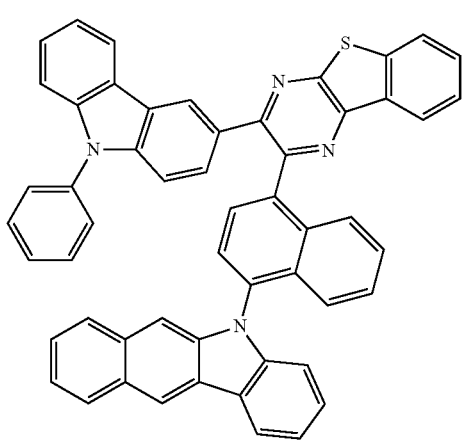
780
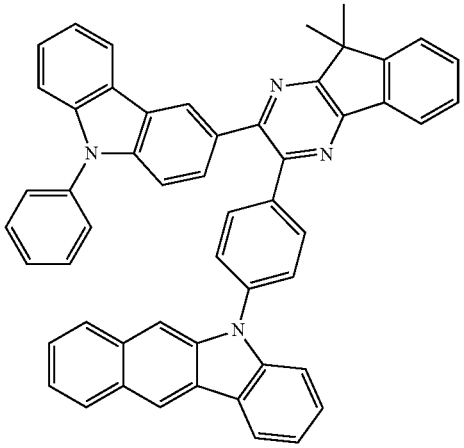

249
-continued
781
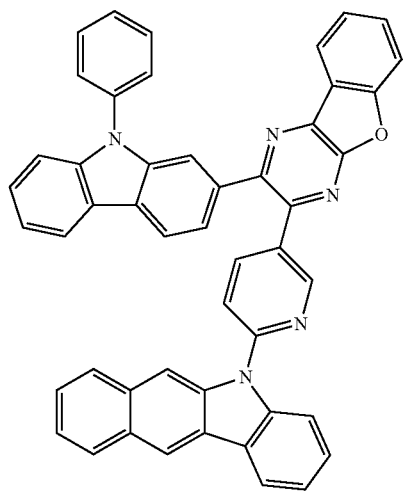
782
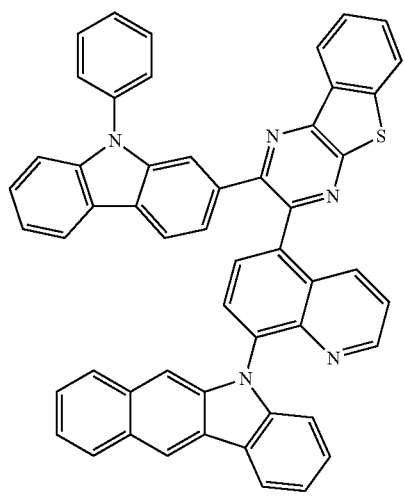
783
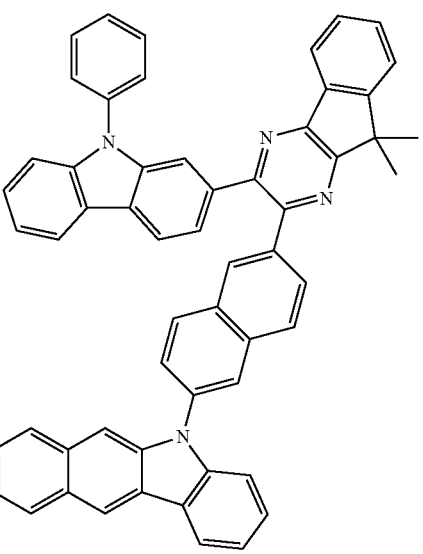
250
-continued
784
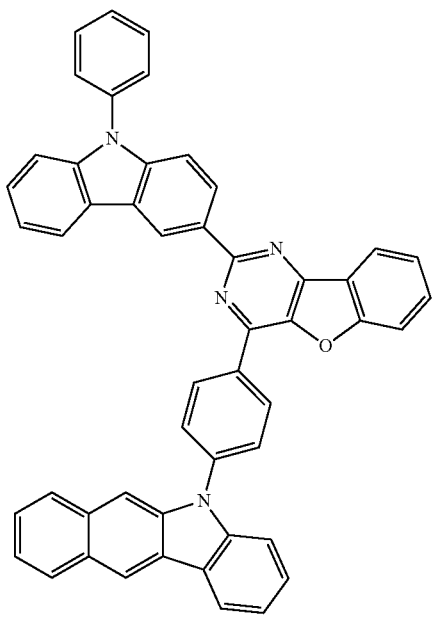
785
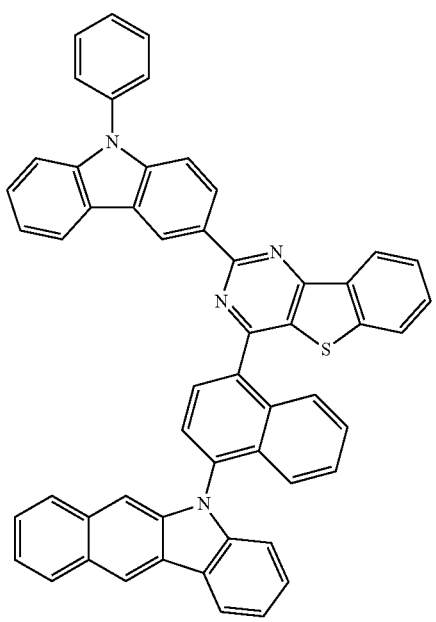

786
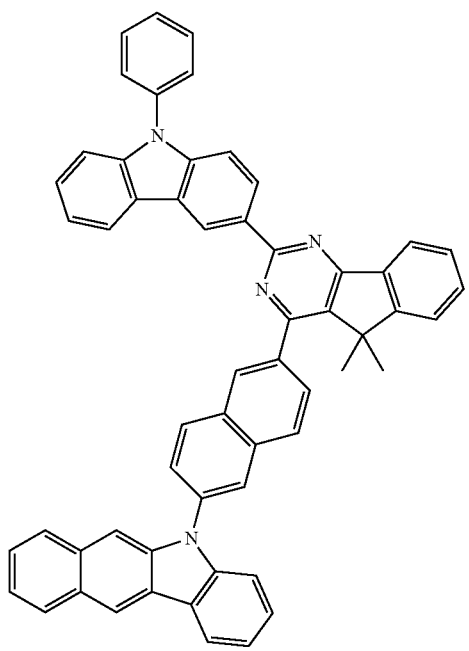
787
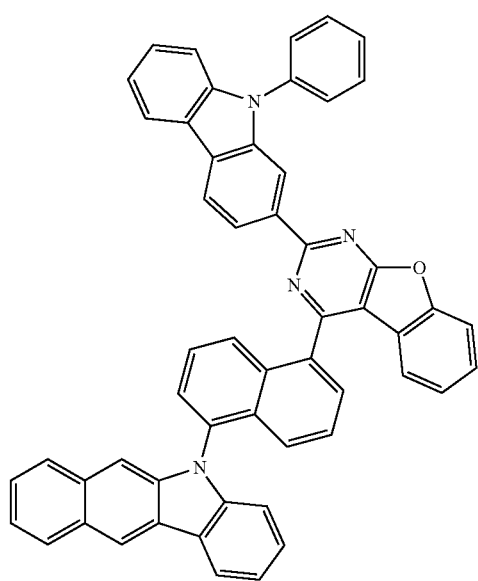
788
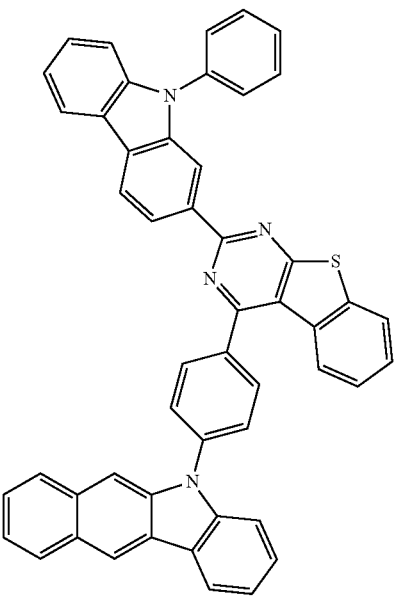
789
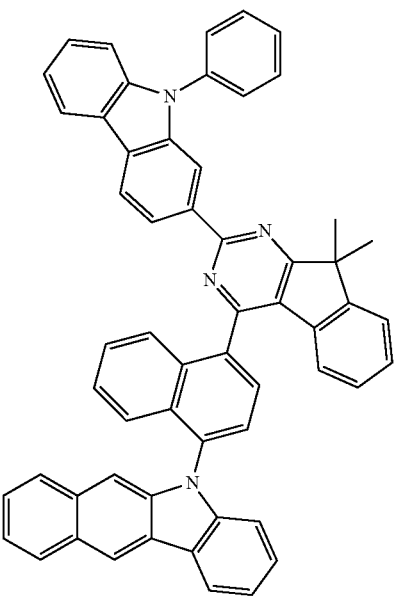

253
-continued
790
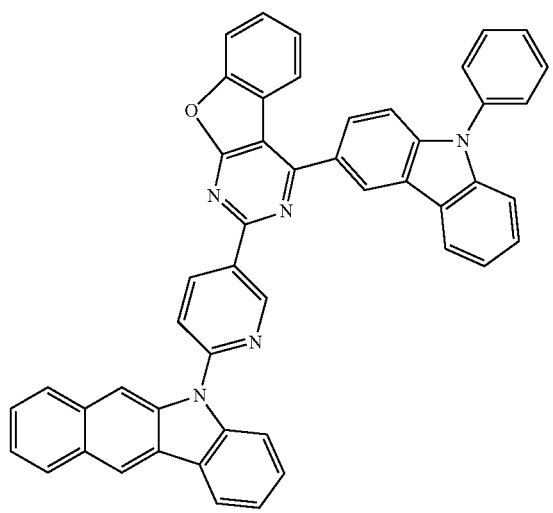
791
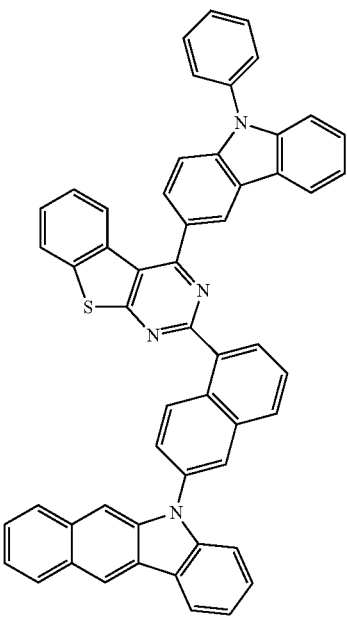
792
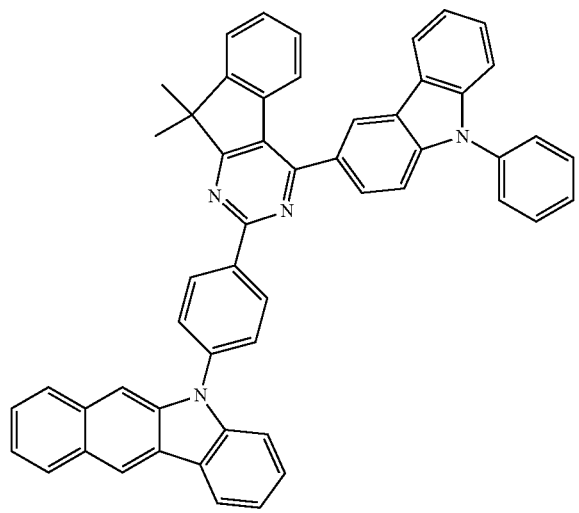
254
-continued
793
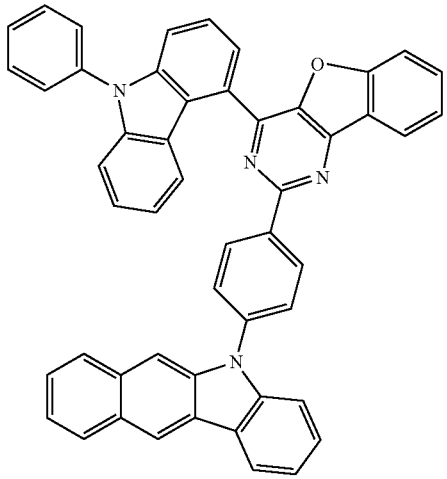
794
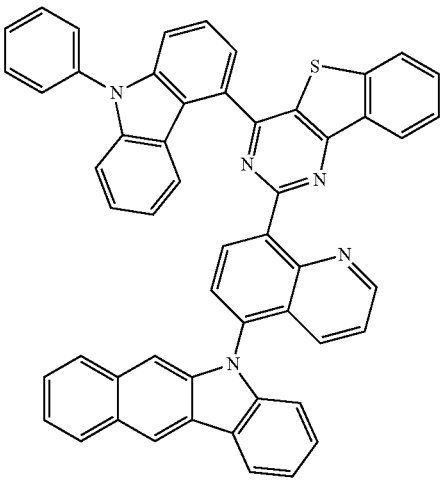
795
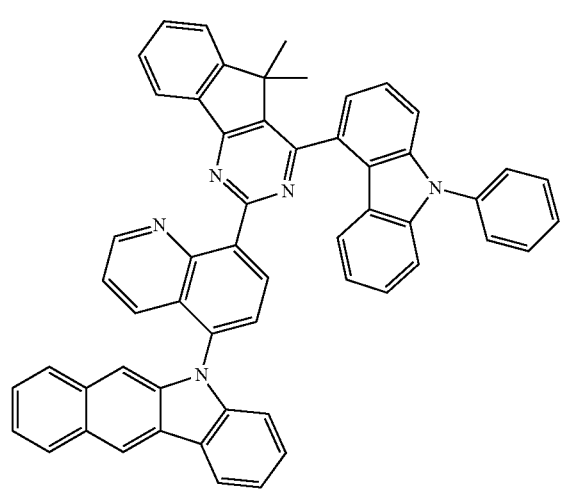

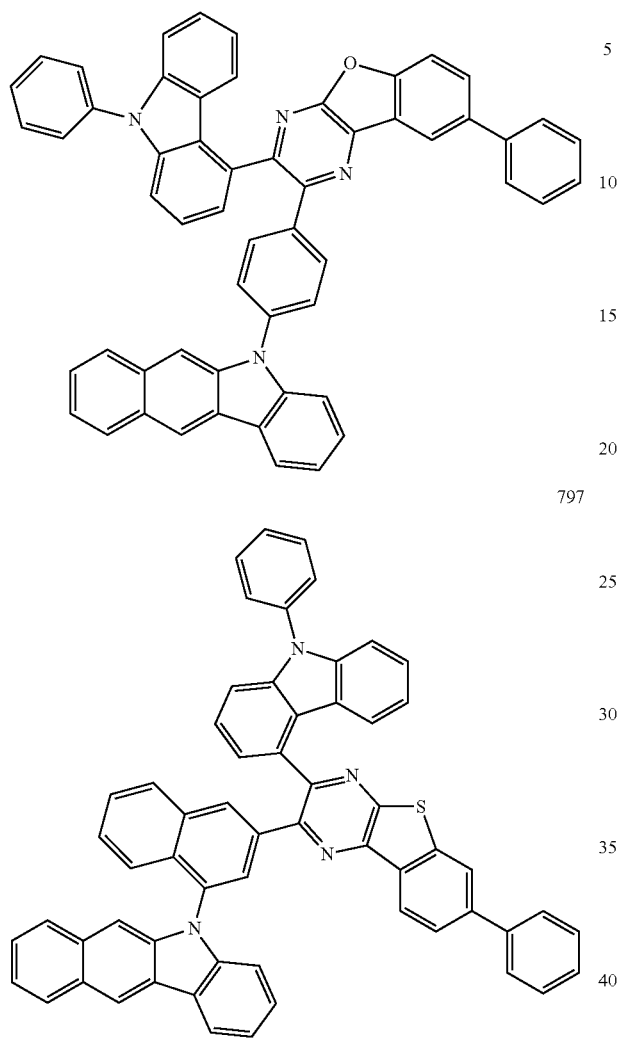
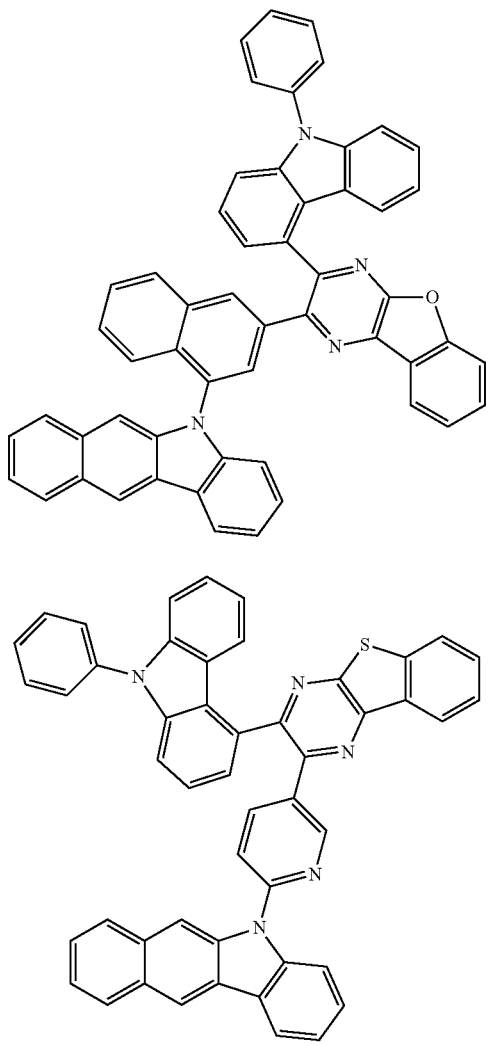
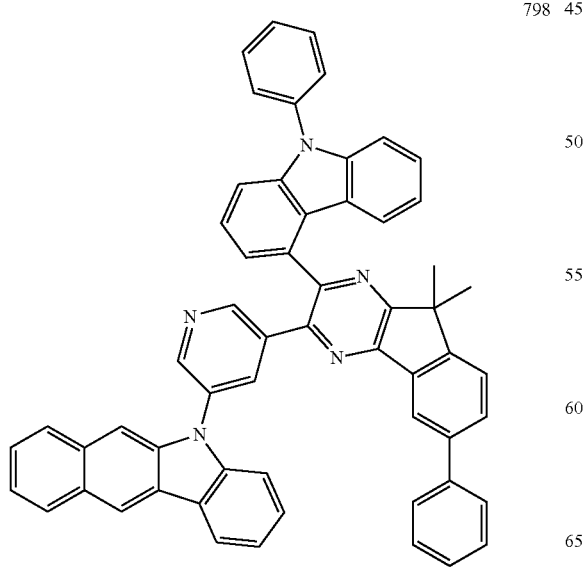
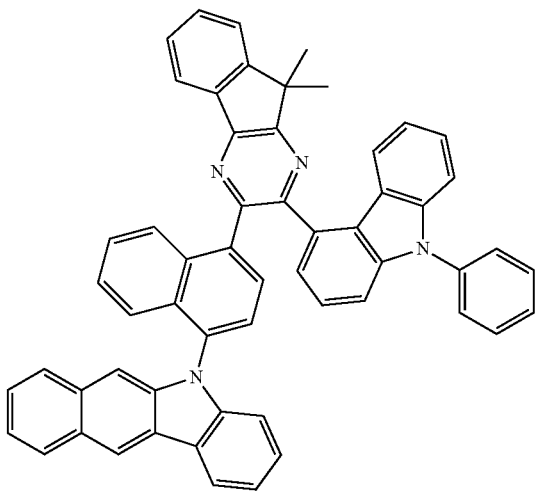

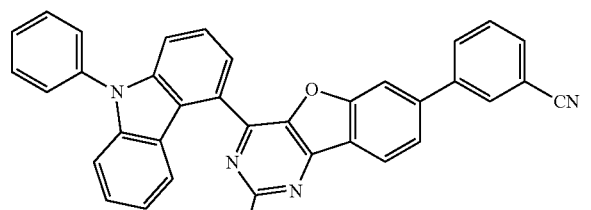
802
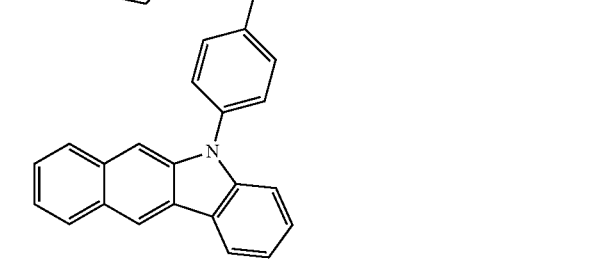
803
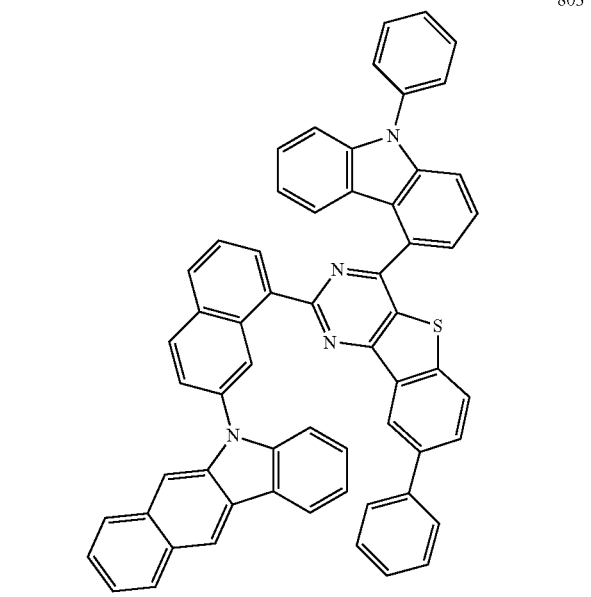
804
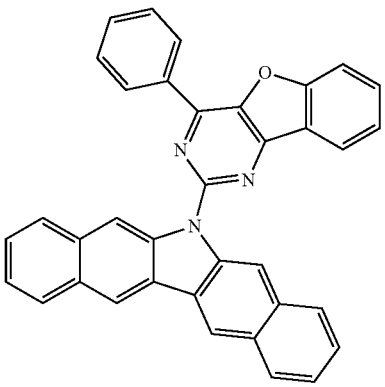
805
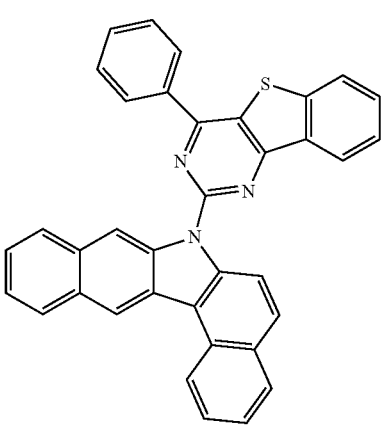
806
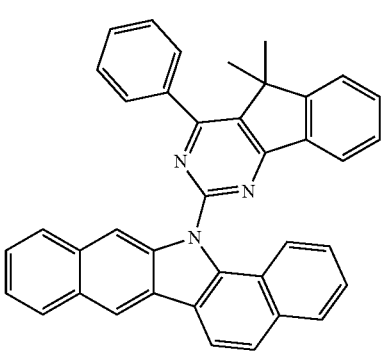
807
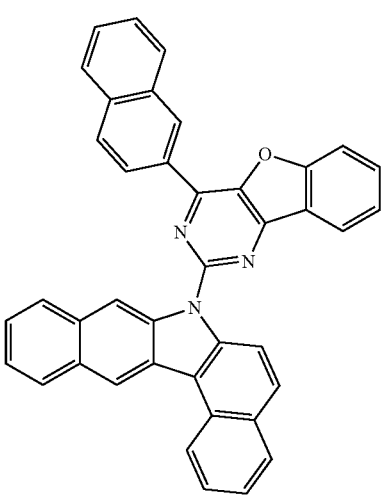
808

259
-continued
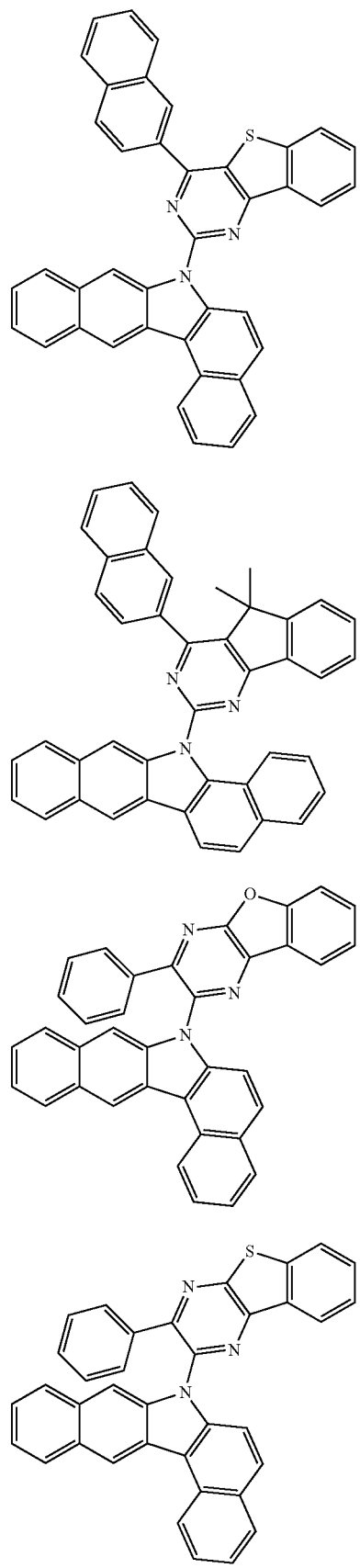
809
810
811
812
260
-continued
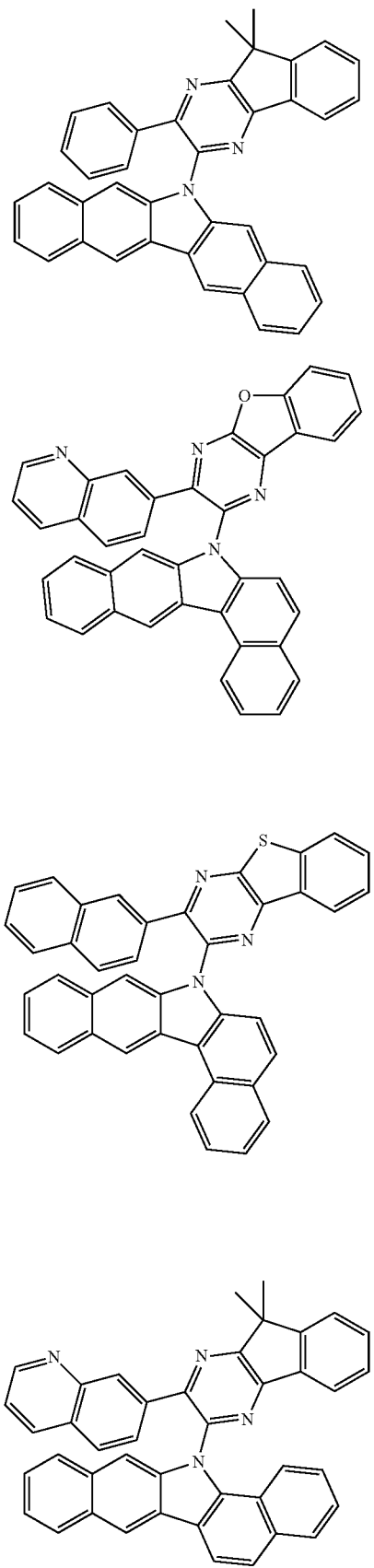
813
814
815
816

-continued
817
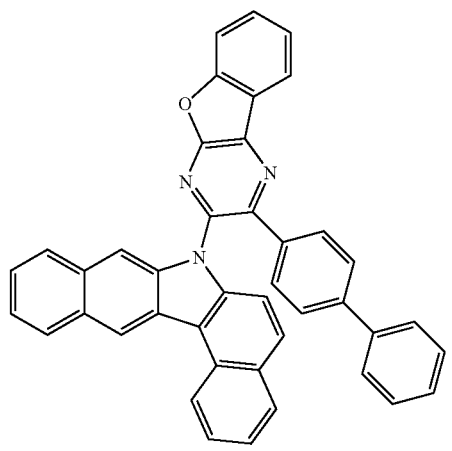
818
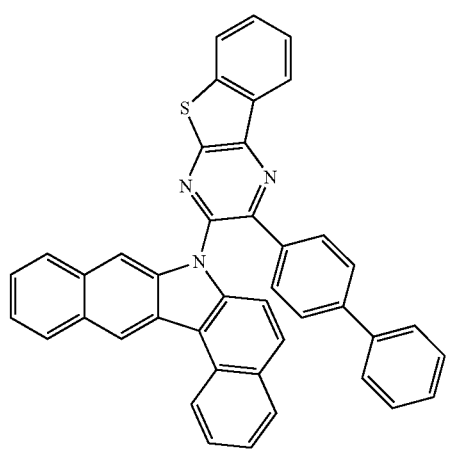
819
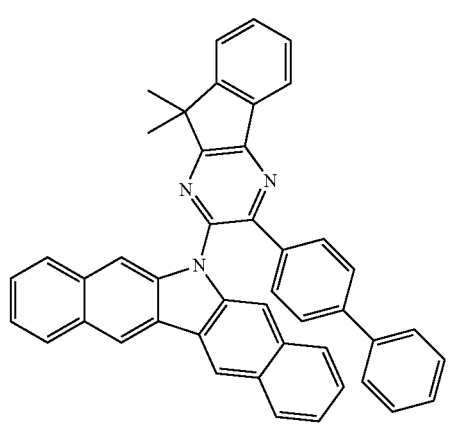
-continued
820
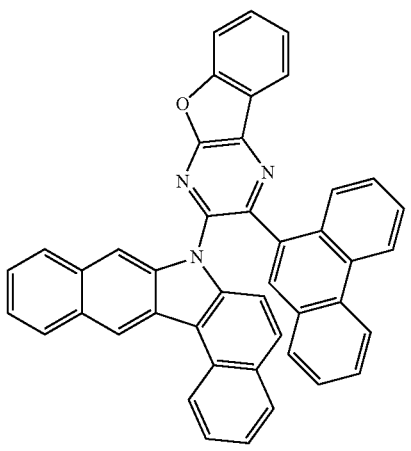
821
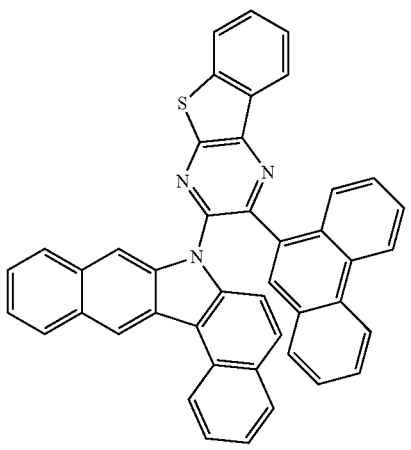
822
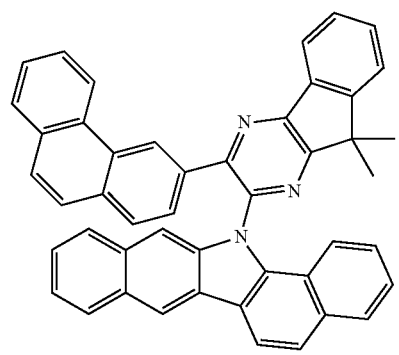
823
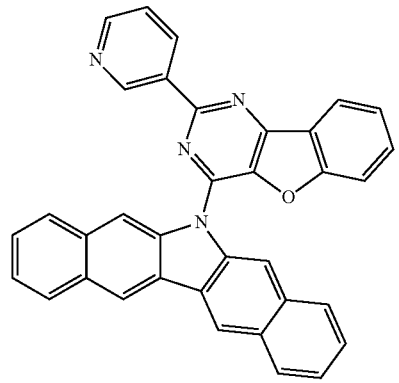

263
-continued
824
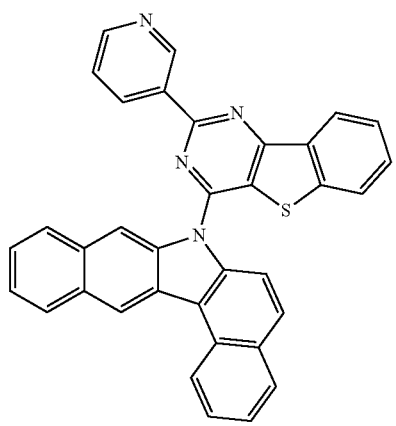
825
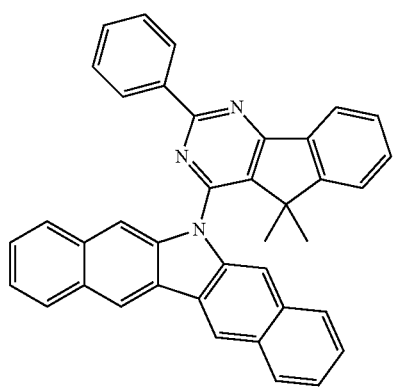
826
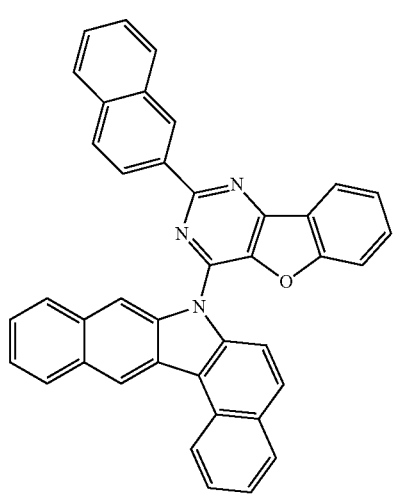
264
-continued
827
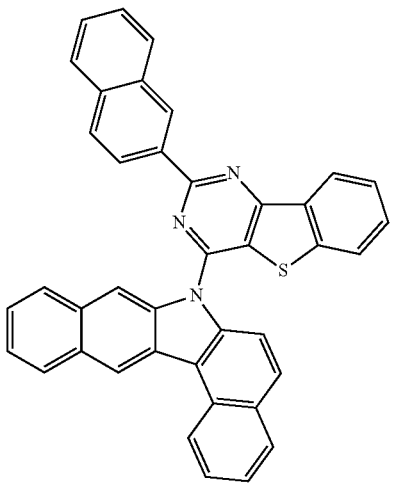
828
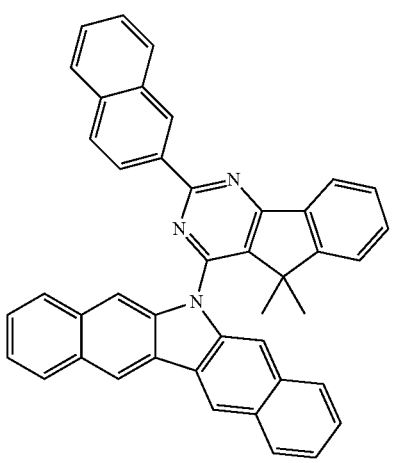
829
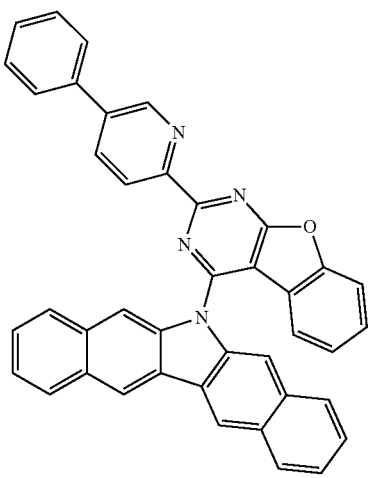

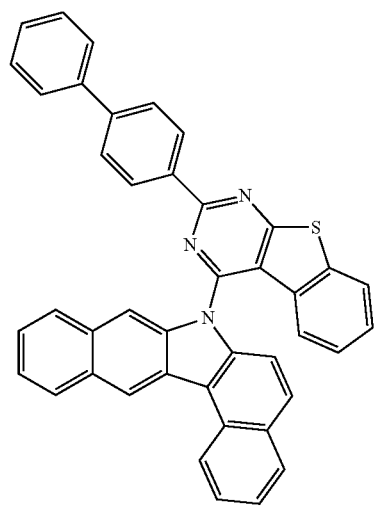
830
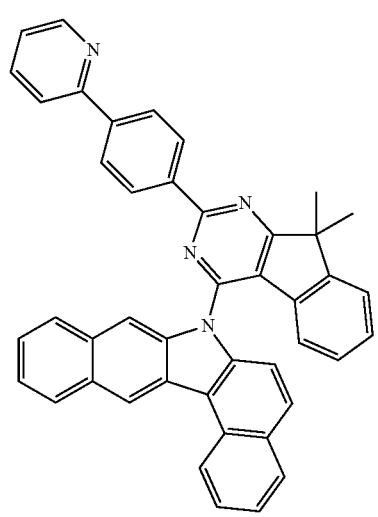
831
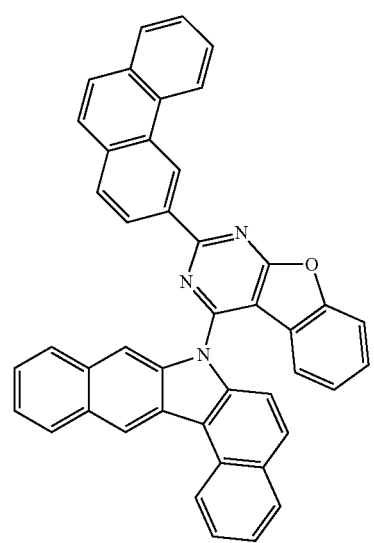
832
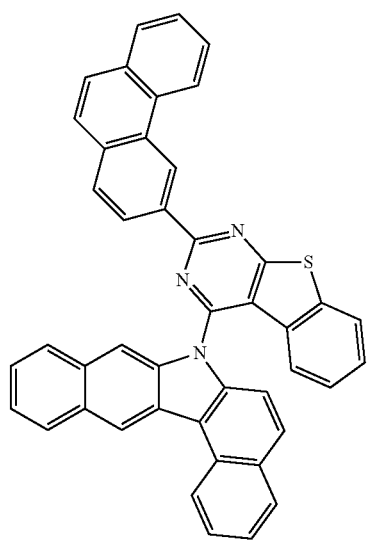
833
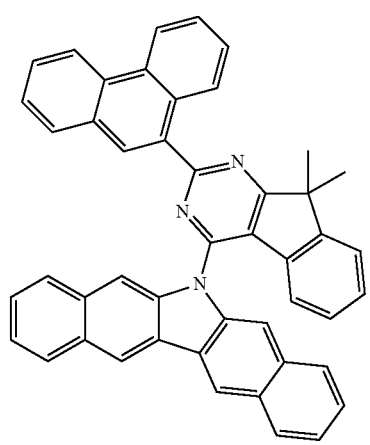
834
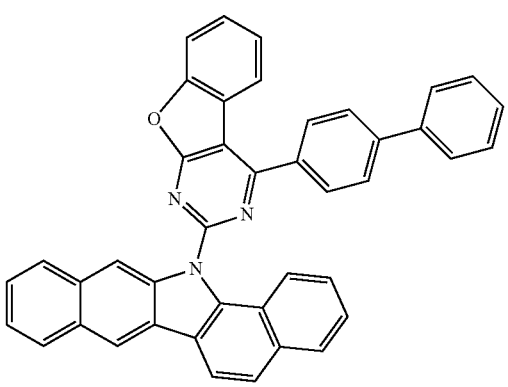
835

836
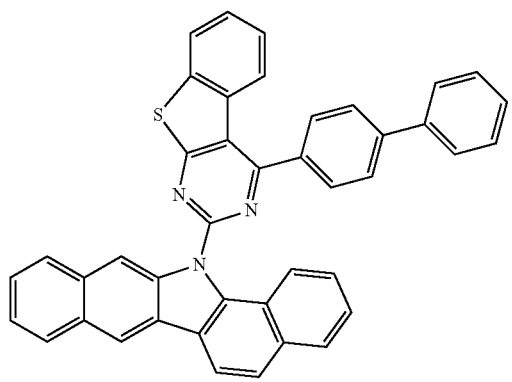
837
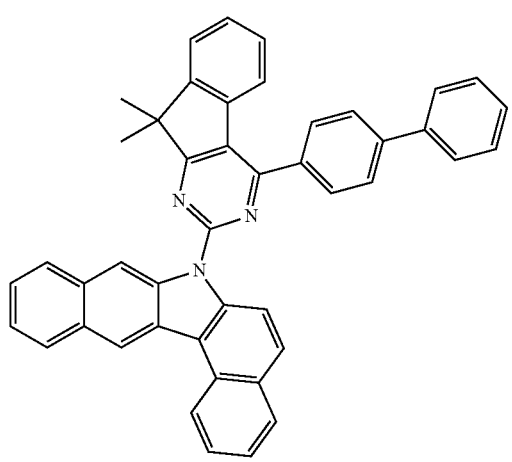
838
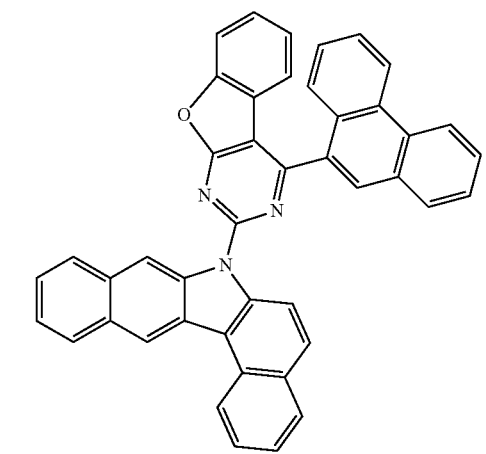
839
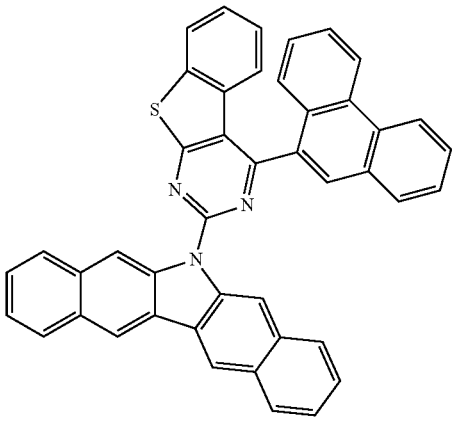
840
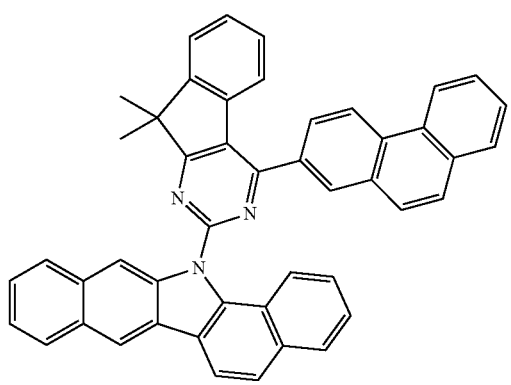
841
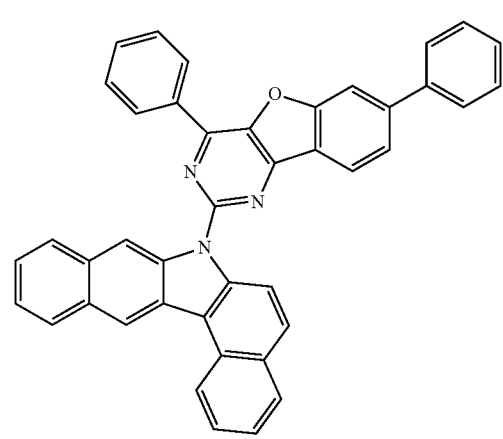
842
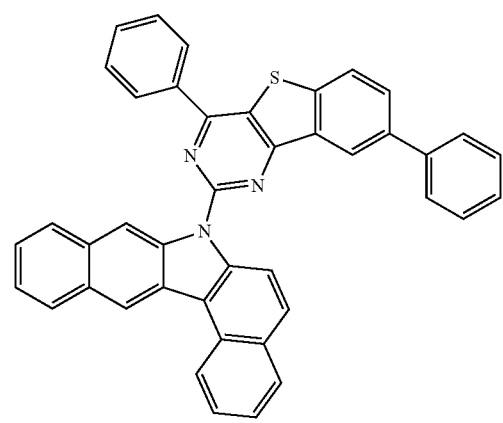

269
-continued
843
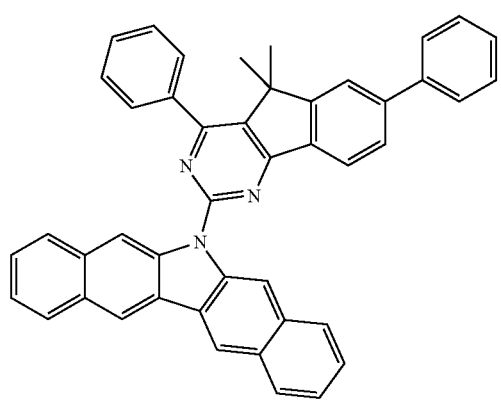
844
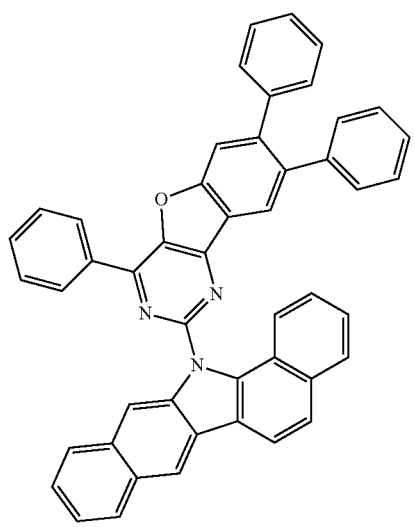
845
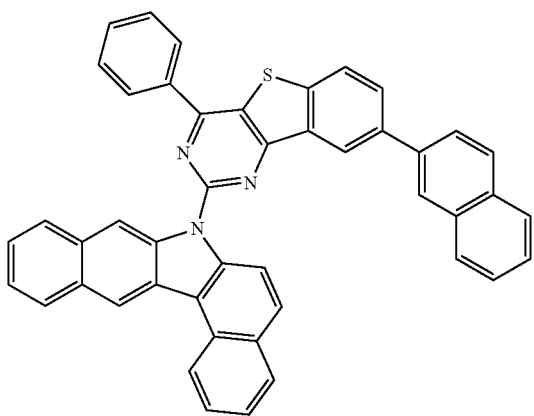
270
-continued
846
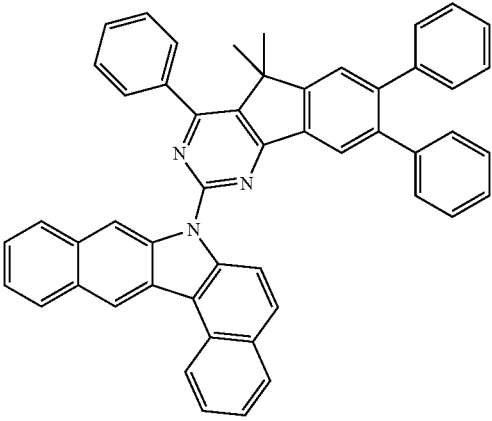
847
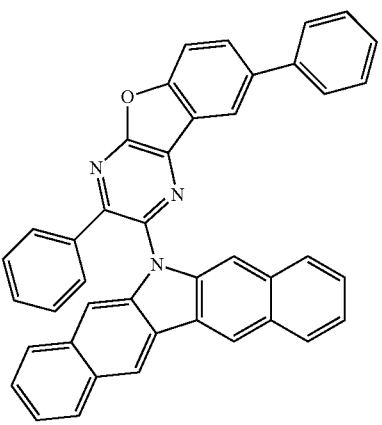
848
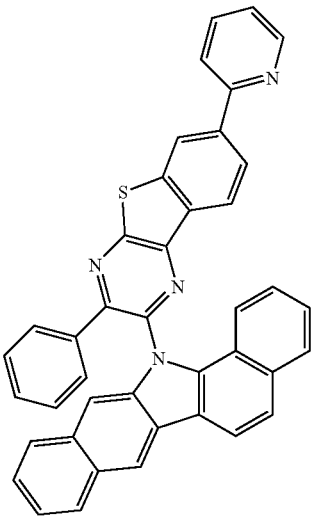

-continued
849
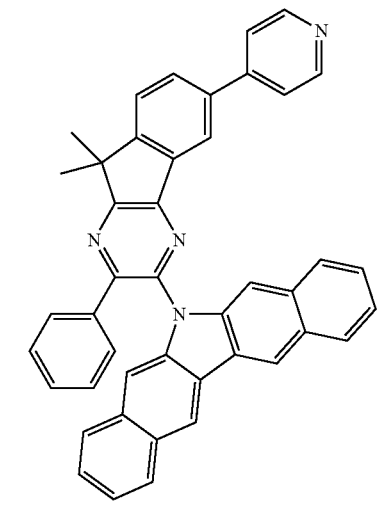
850
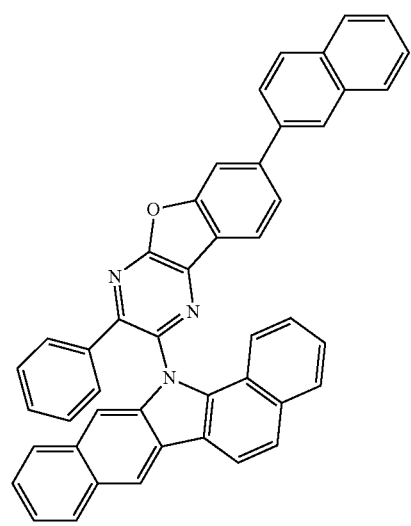
851
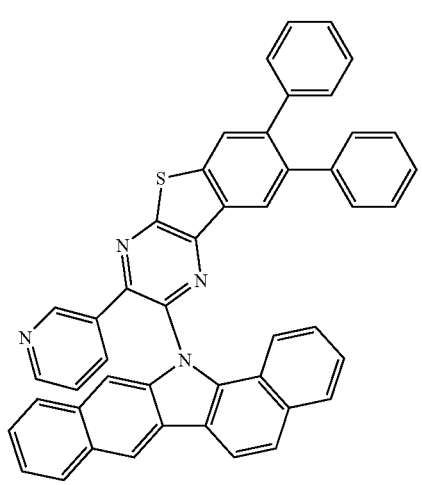
-continued
852
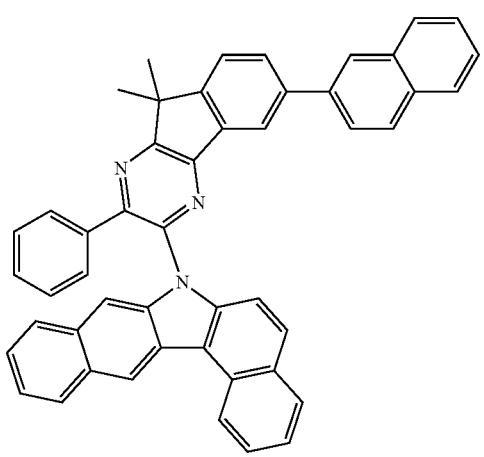
853
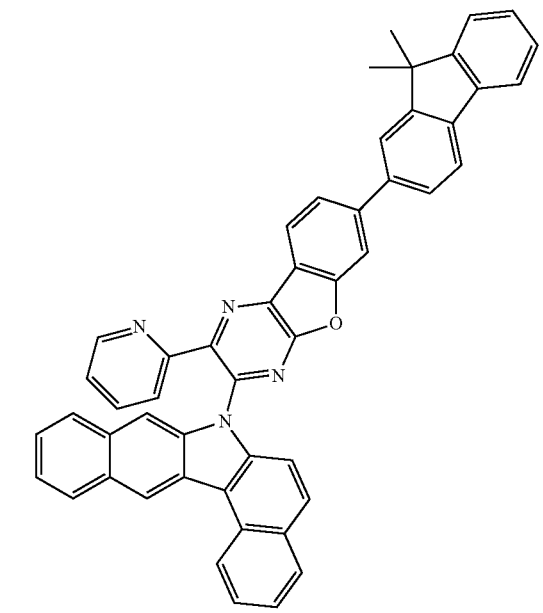
854
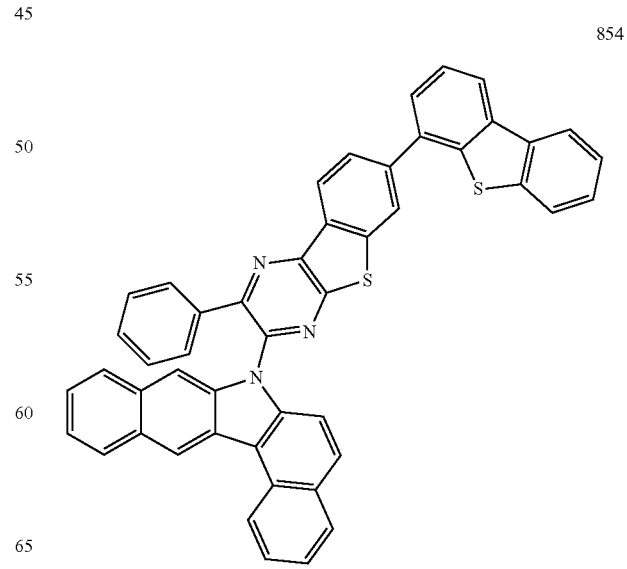

273
-continued
855
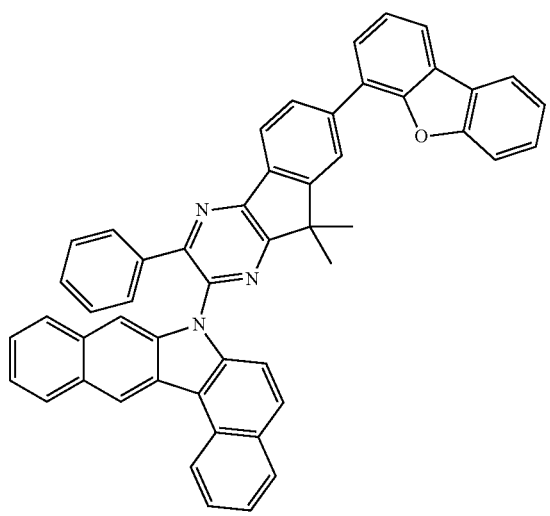
856
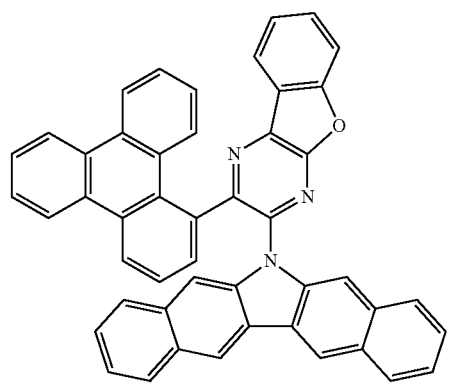
857
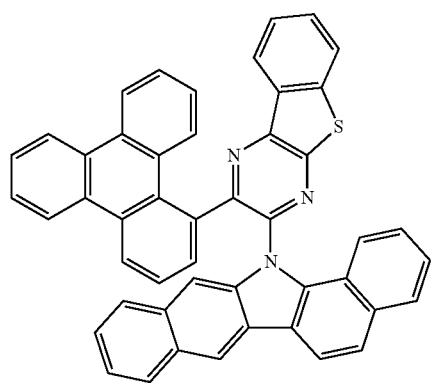
274
-continued
858
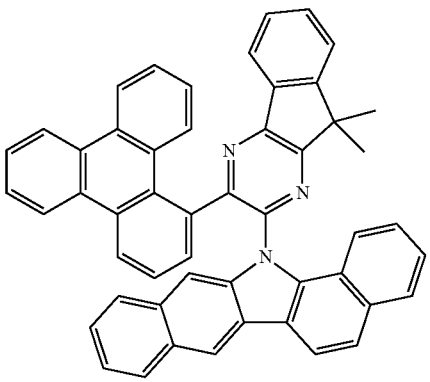
859
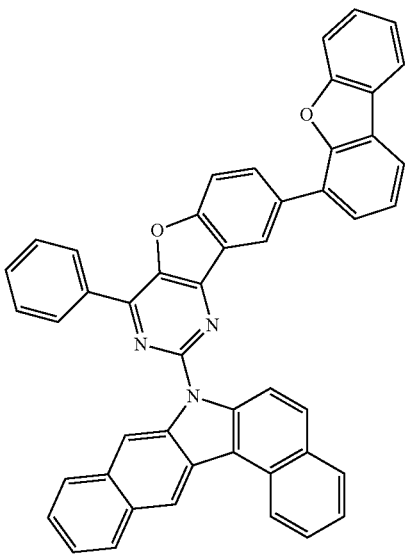
860
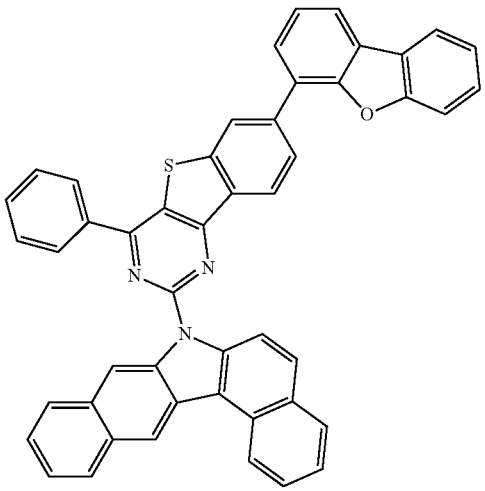

275
-continued
861
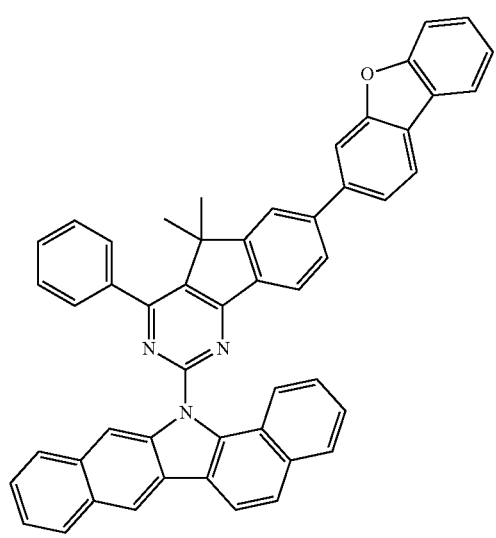
862
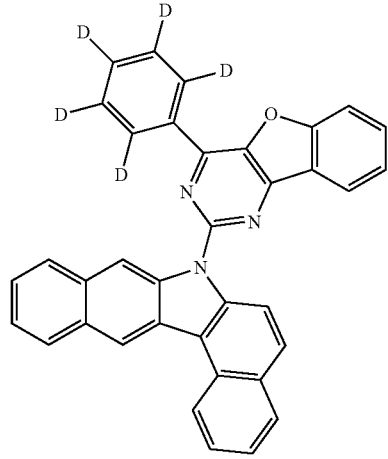
863
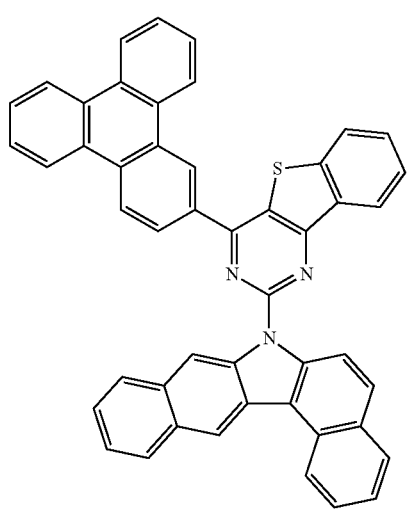
276
-continued
864
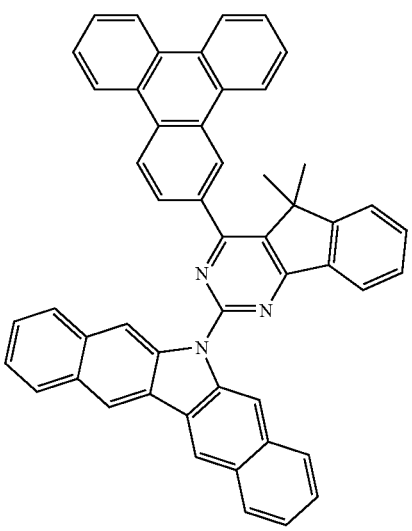
865
866
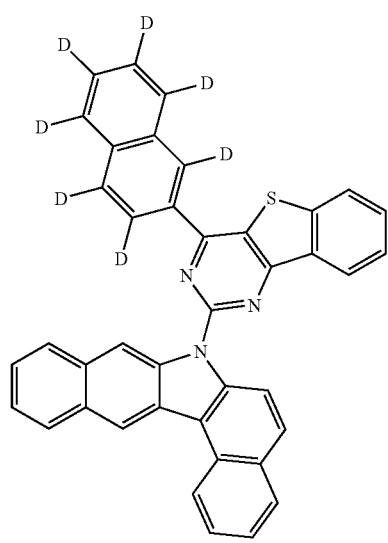

277
-continued
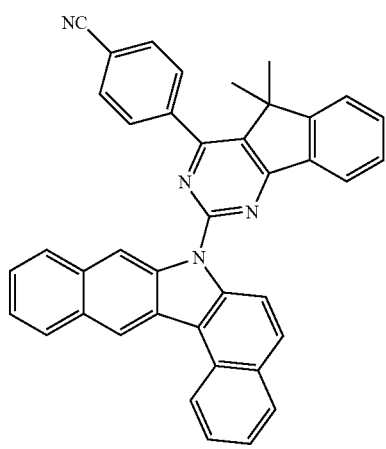
867
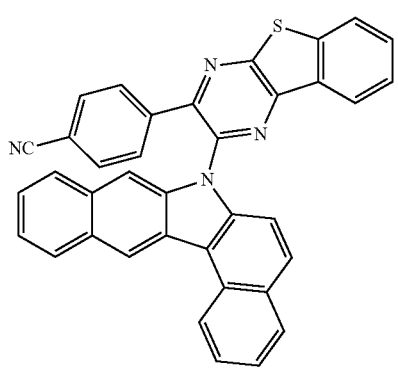
868
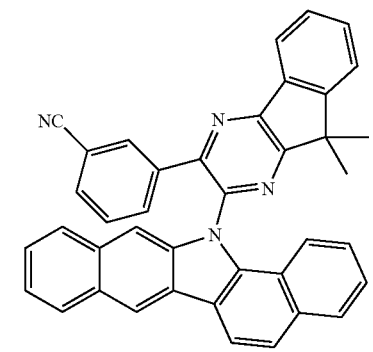
869
278
-continued
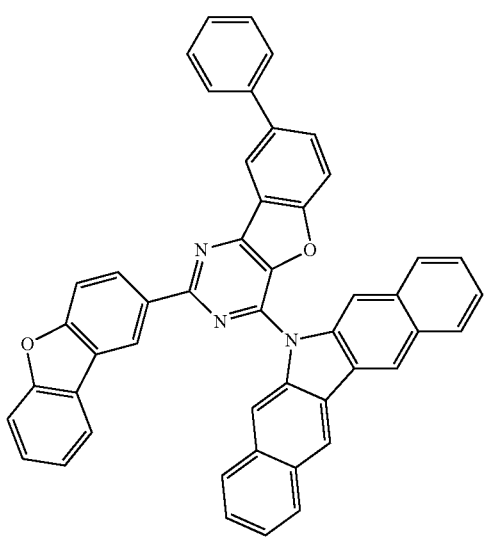
870
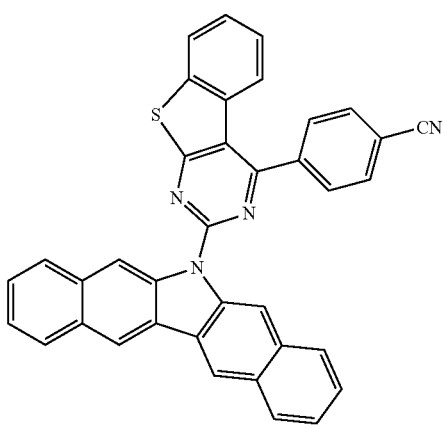
871
872

279
-continued
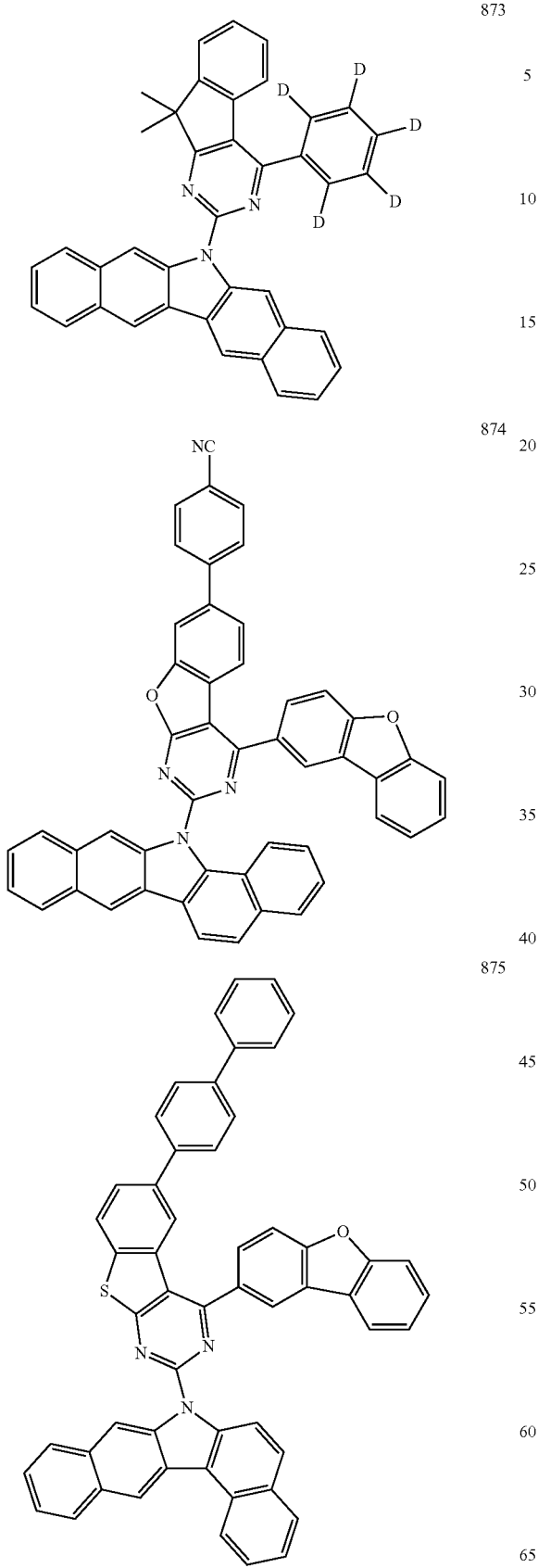
280
-continued

281
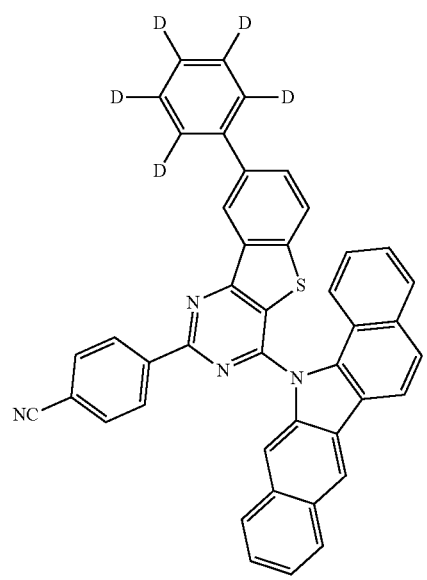
878
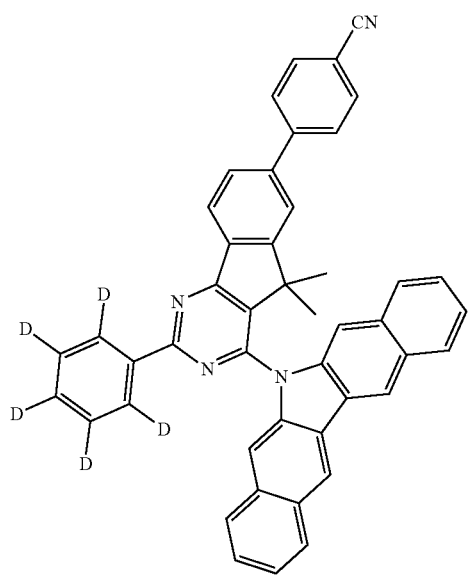
879
282
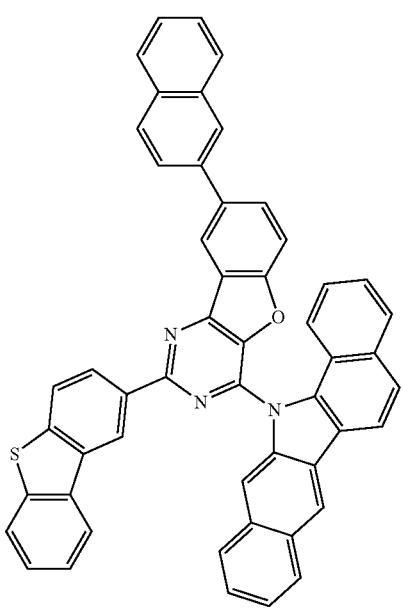
880
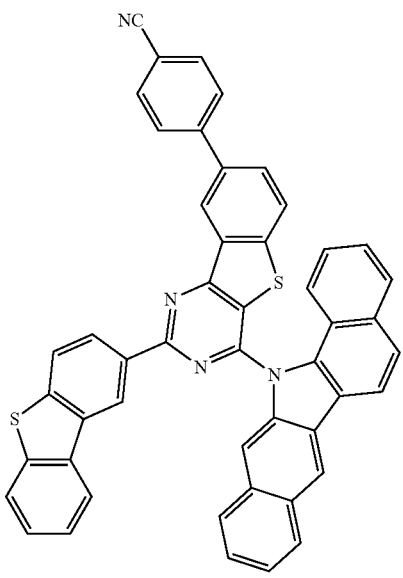
881

882
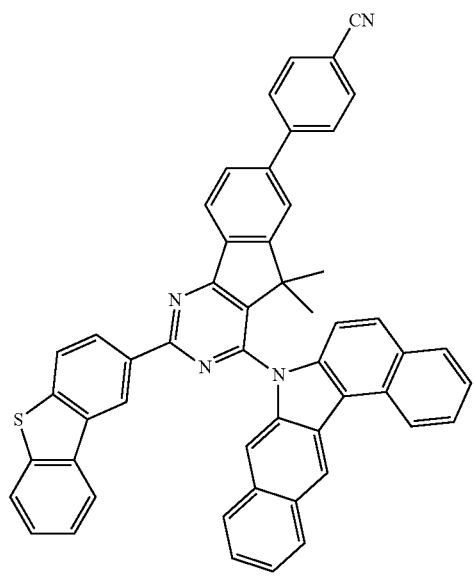
883
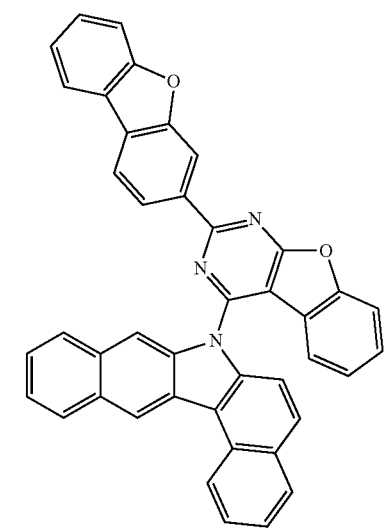
884
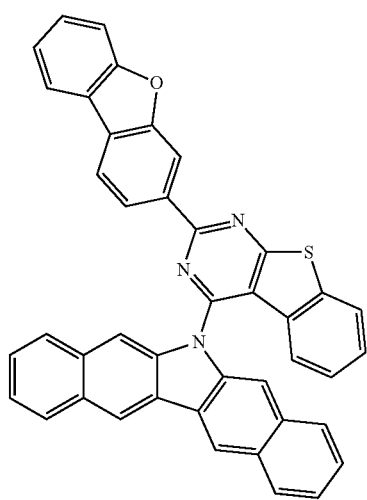
885
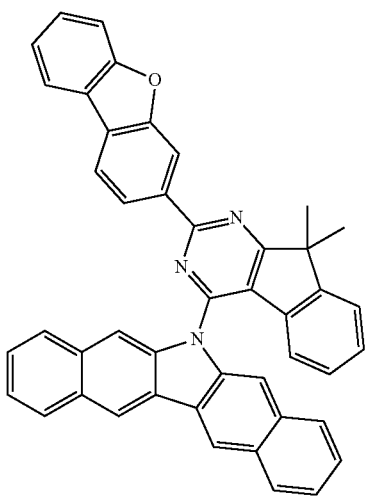
886
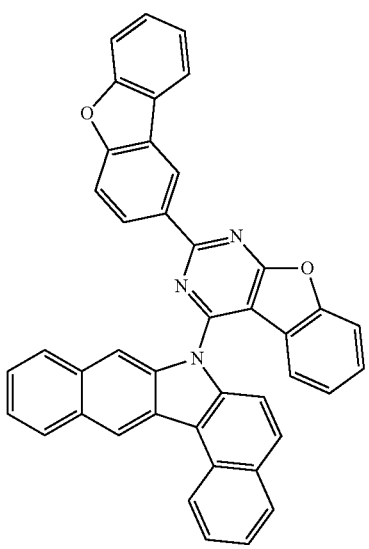
887
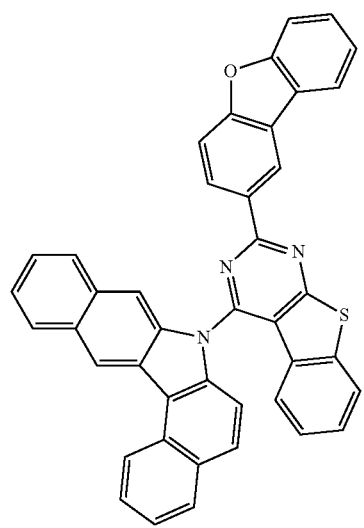

888
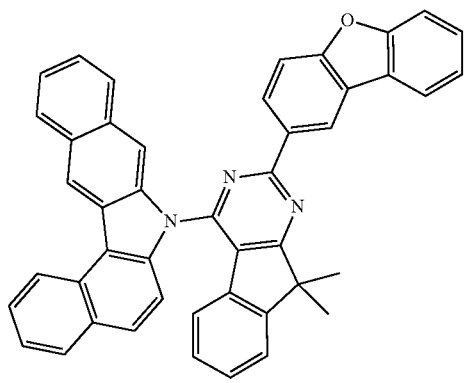
891
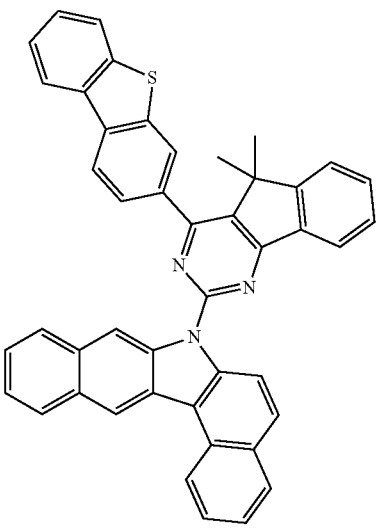
889
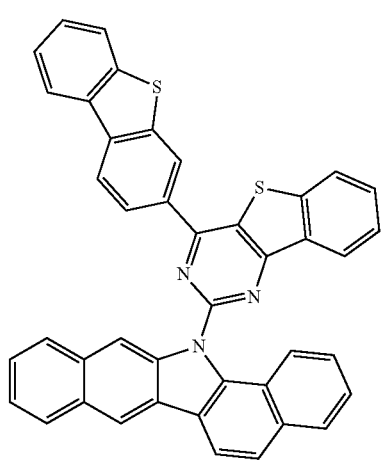
892
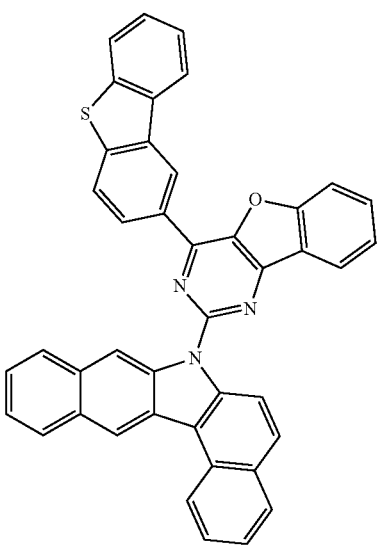
890
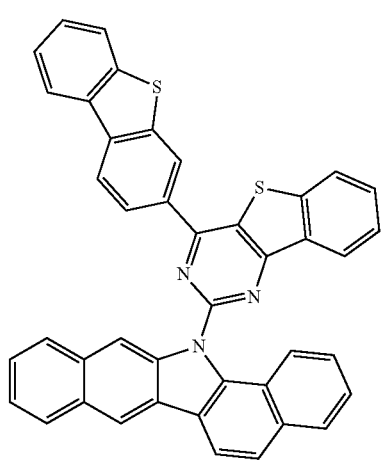
893
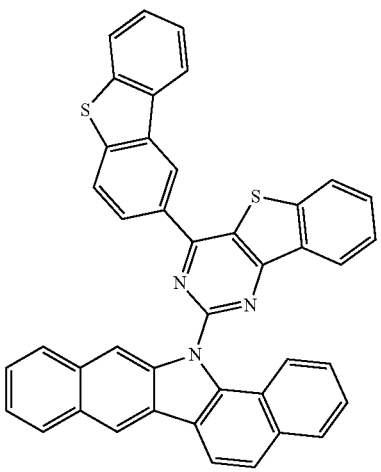

287
-continued
894
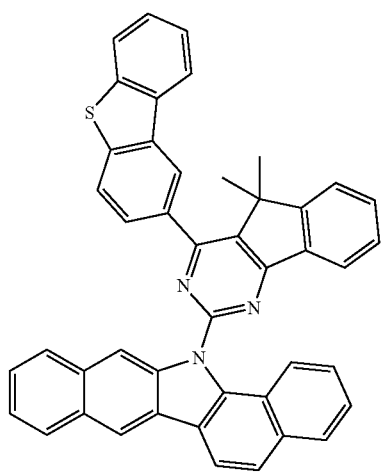
895
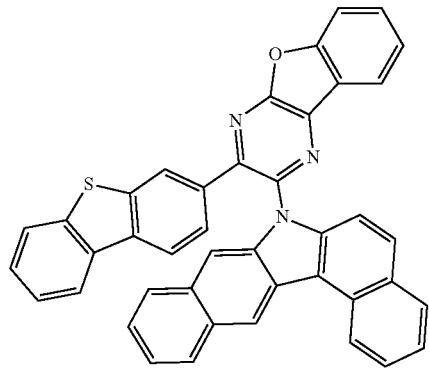
896
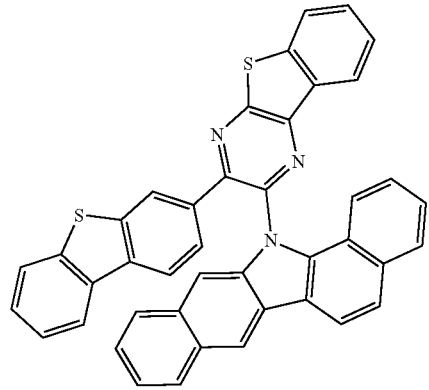
288
-continued
897
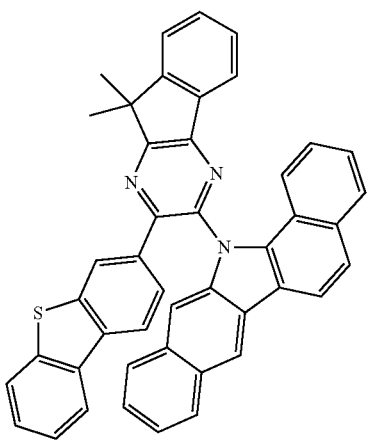
898
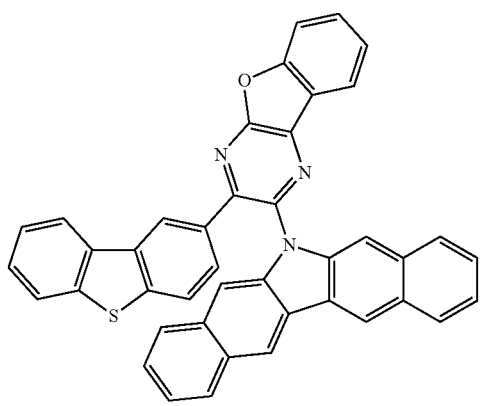
899
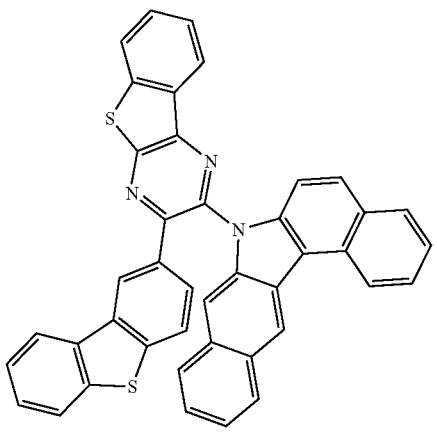

289
-continued
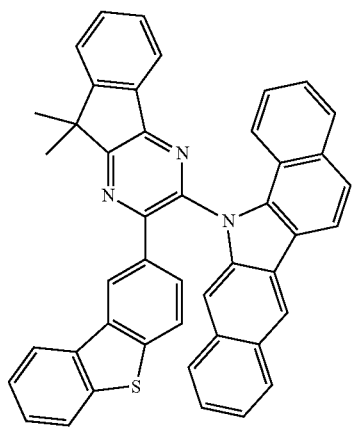
900
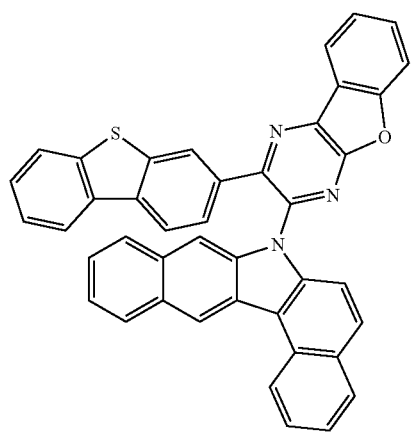
901
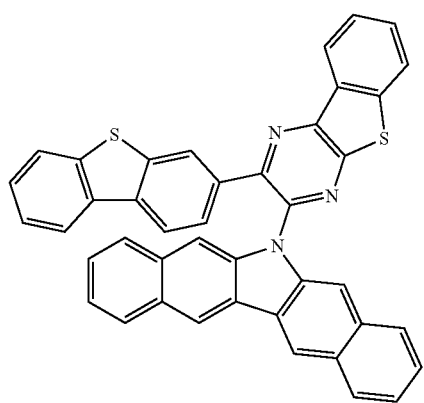
902
290
-continued
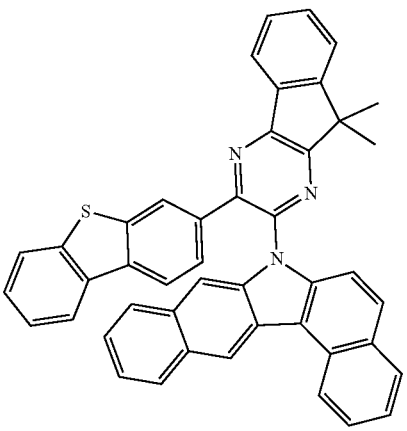
903
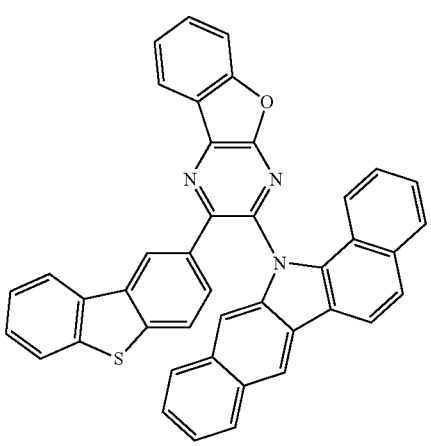
904
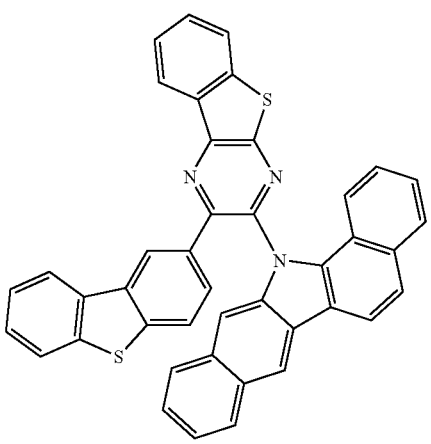
905

906
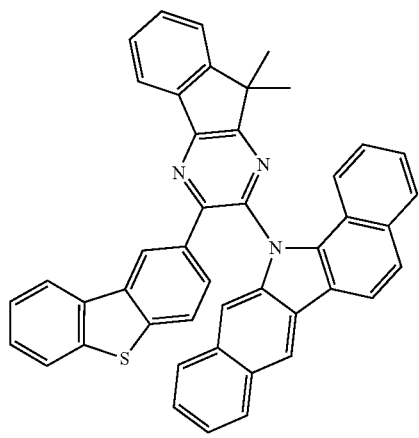
907
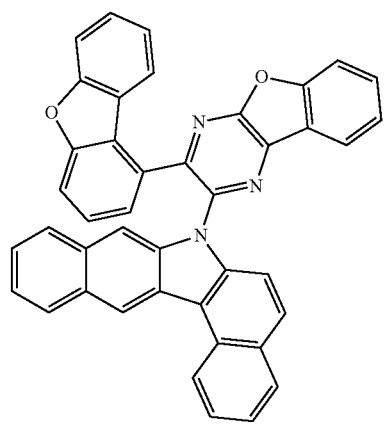
908
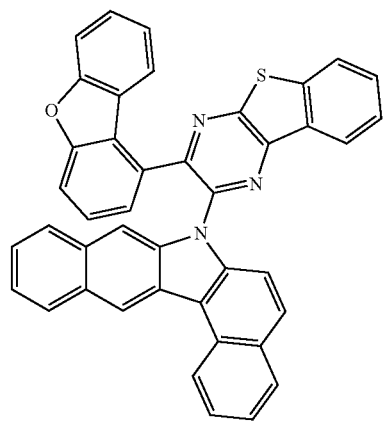
909
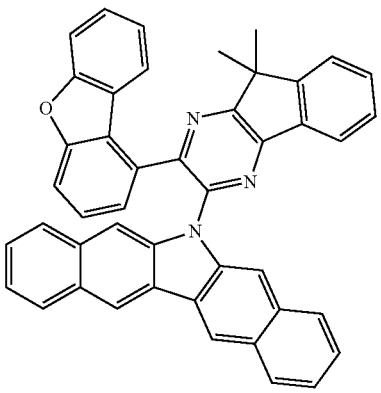
910
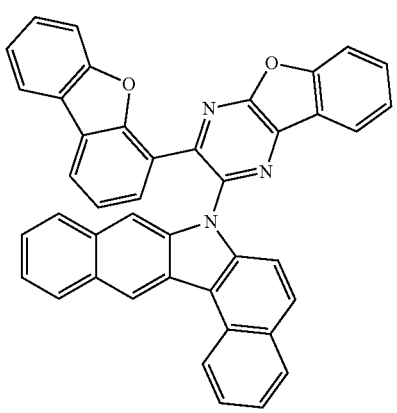
911
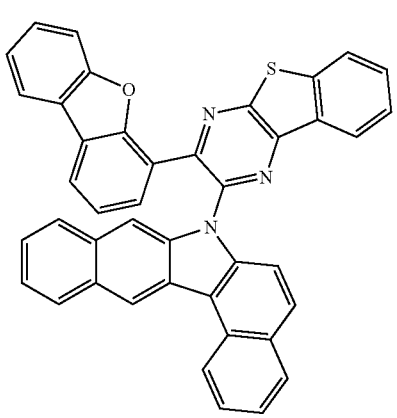
912
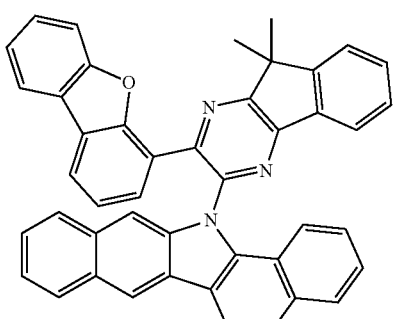

913 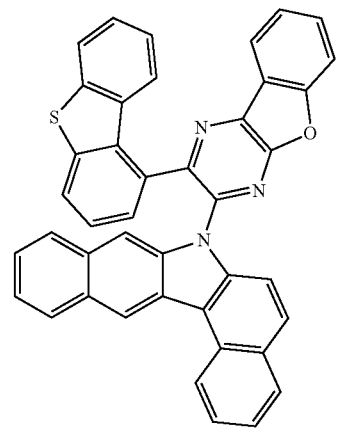
914 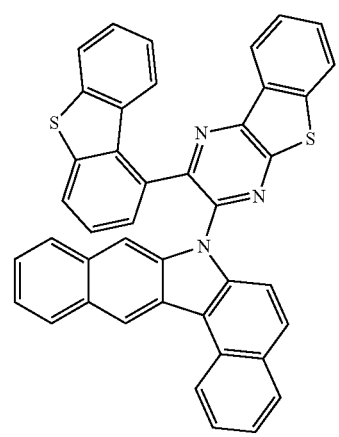
915 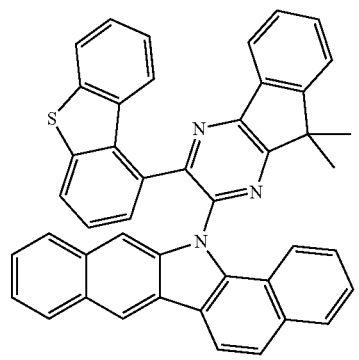
916 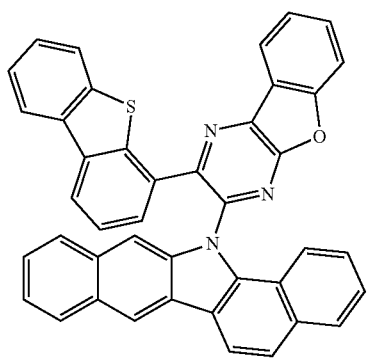
917 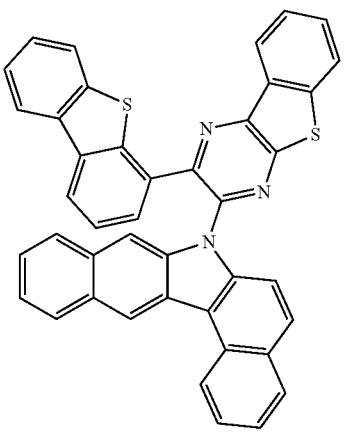
918 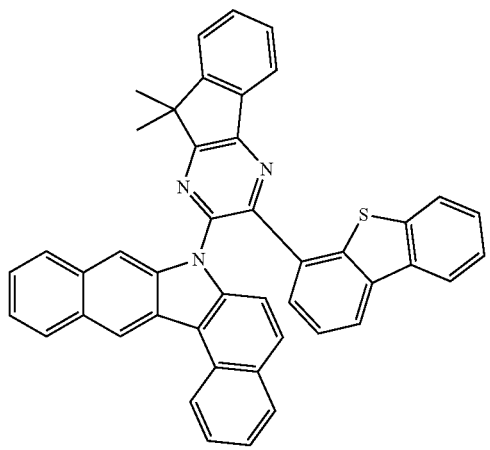
919 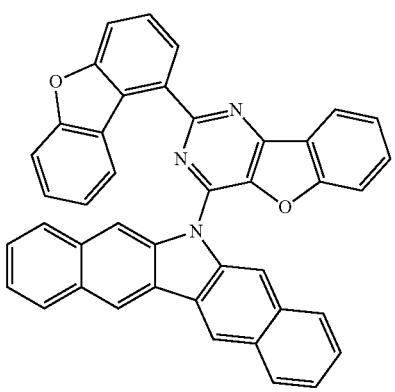

920
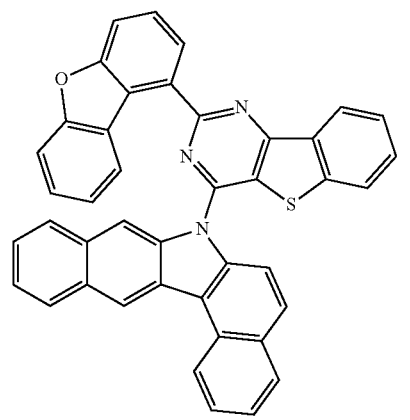
921
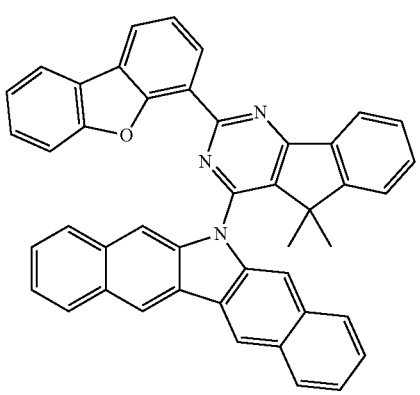
922
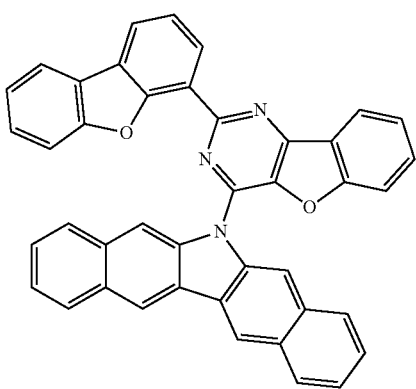
923
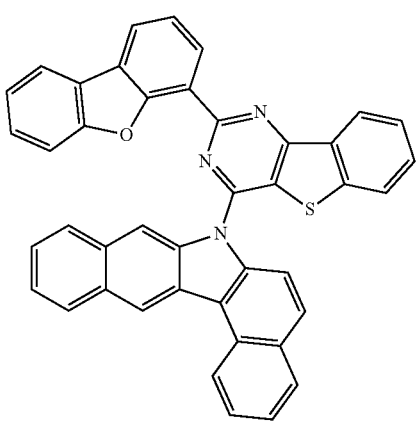
924
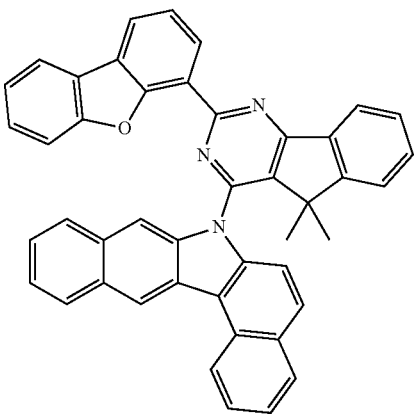
925
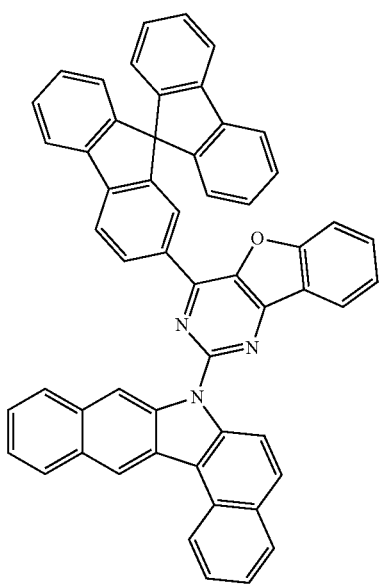
926
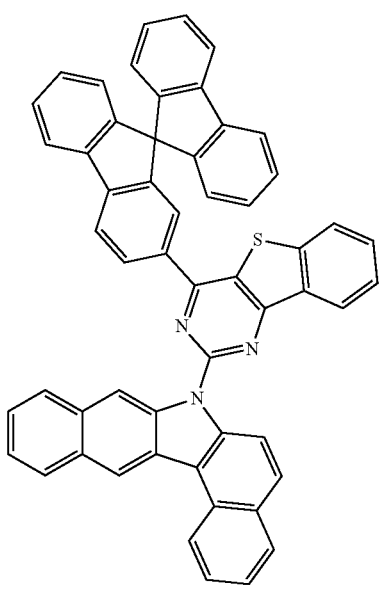

297
-continued
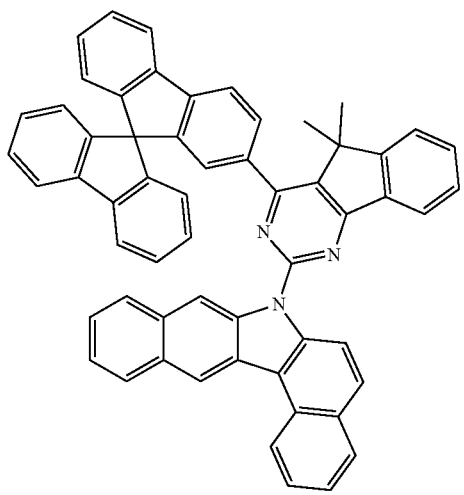
927
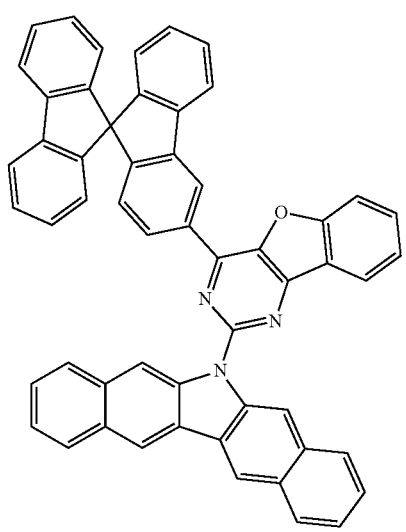
928
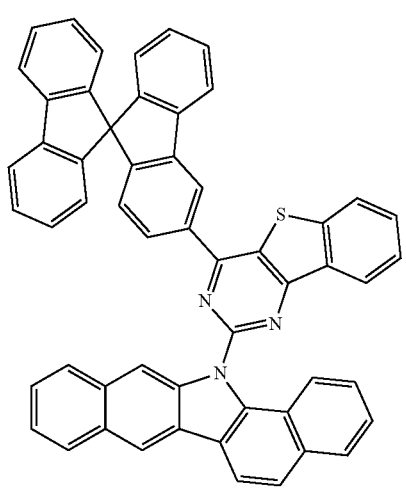
929
298
-continued
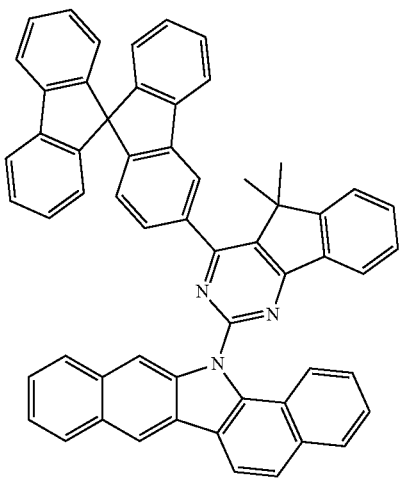
930
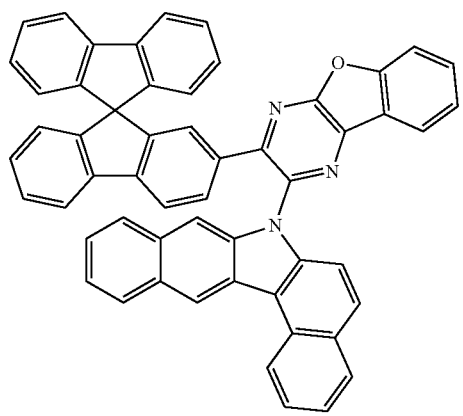
931
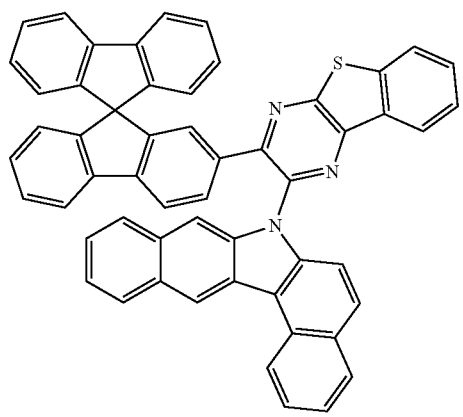
932

299
-continued
300
-continued
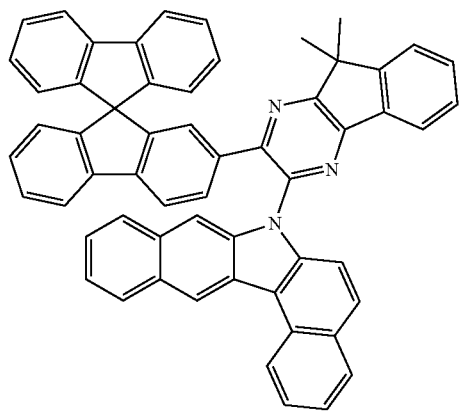
933
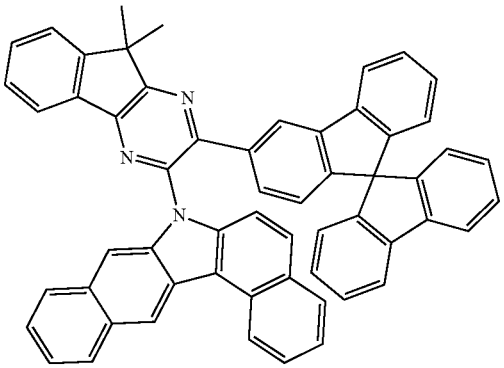
936
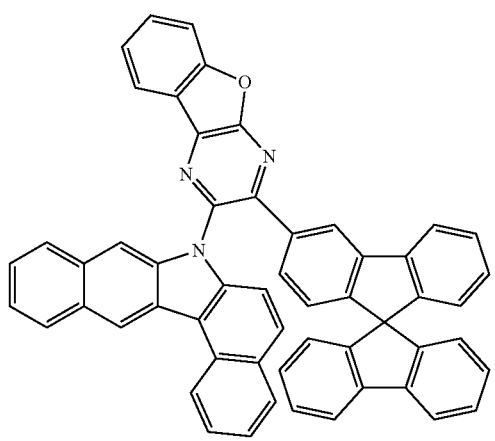
934
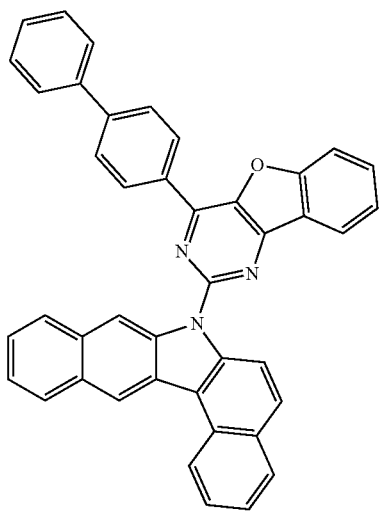
937
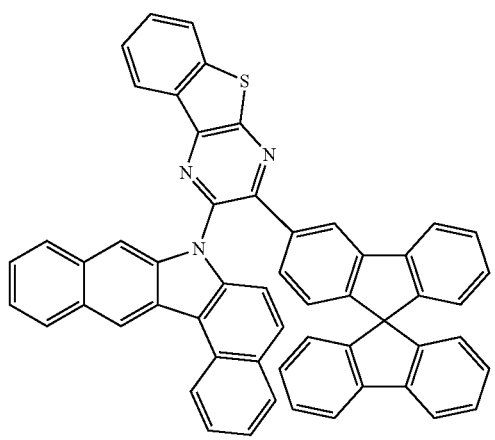
935
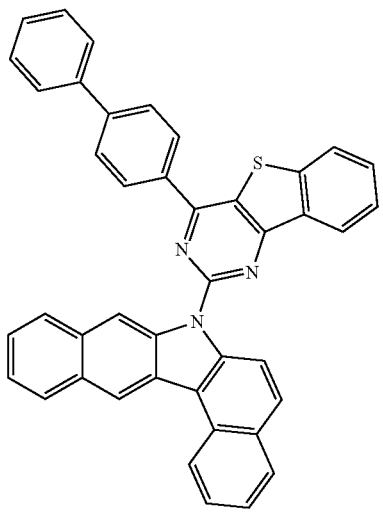
938

301
-continued
939
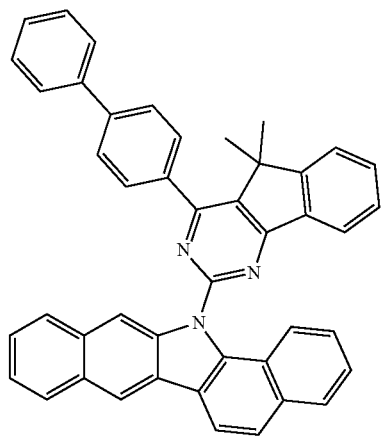
940
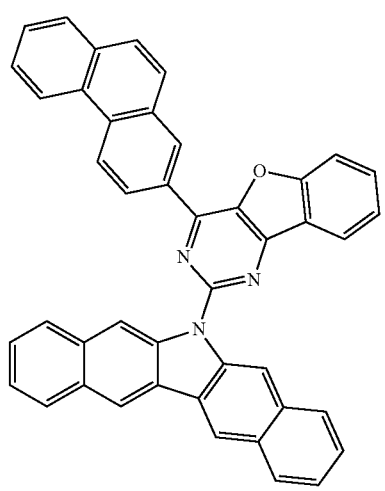
941
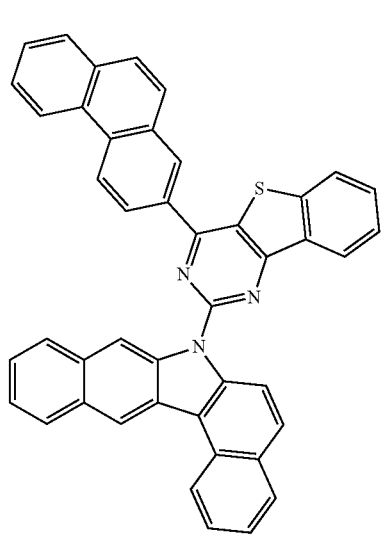
302
-continued
942
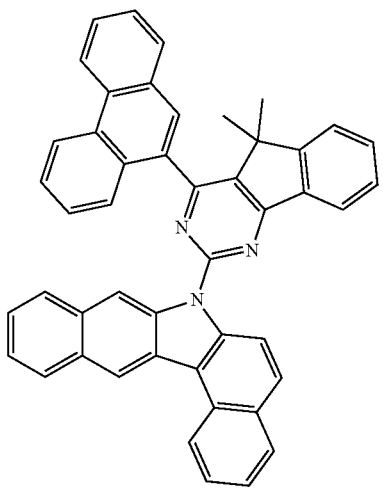
943
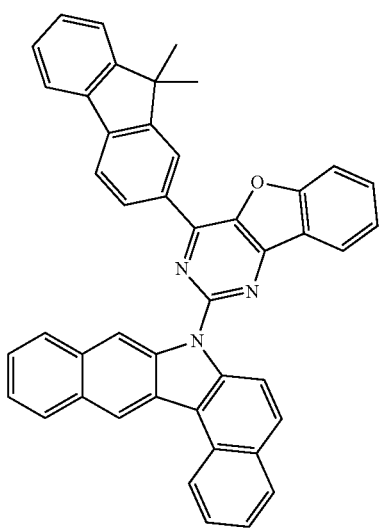
944
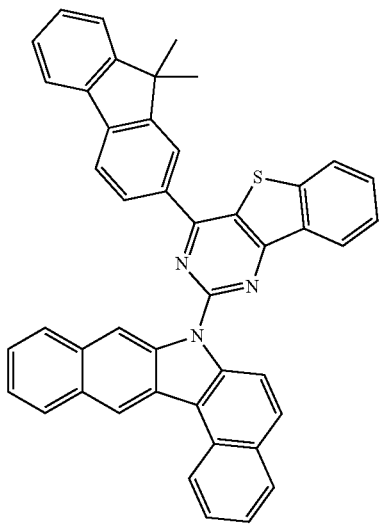

303
-continued
945
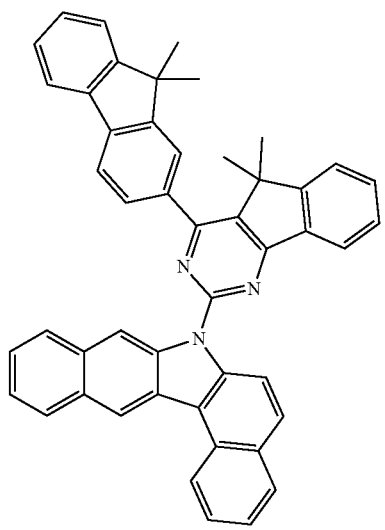
946
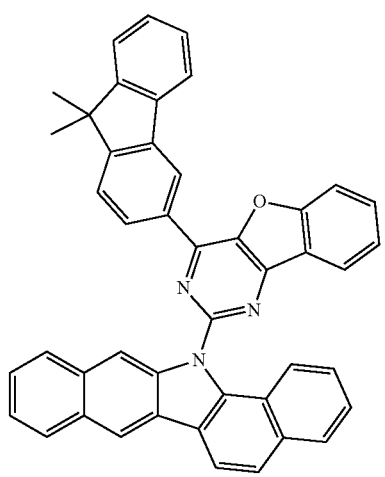
947
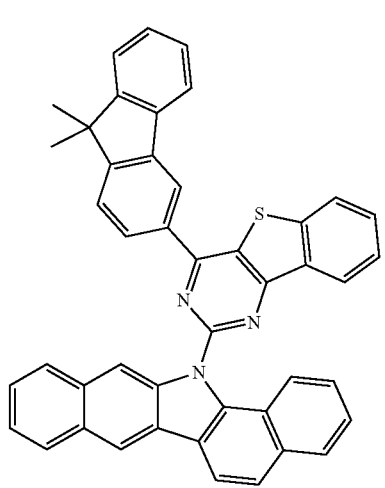
304
-continued
948
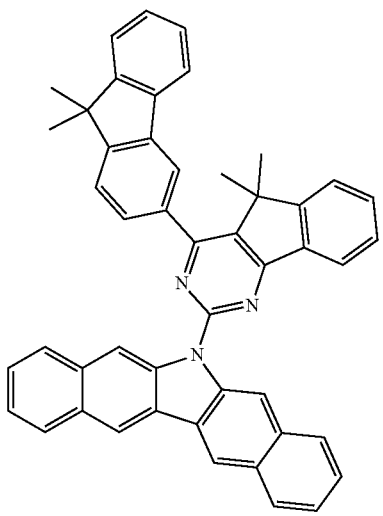
949
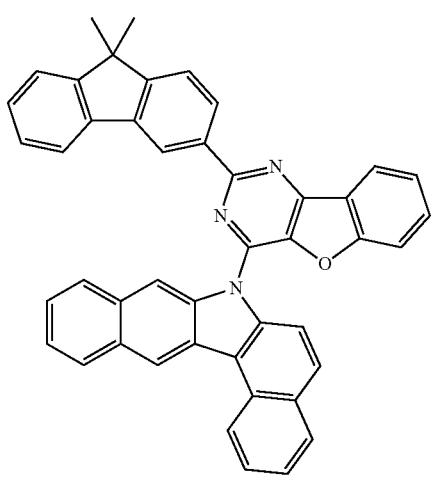
950
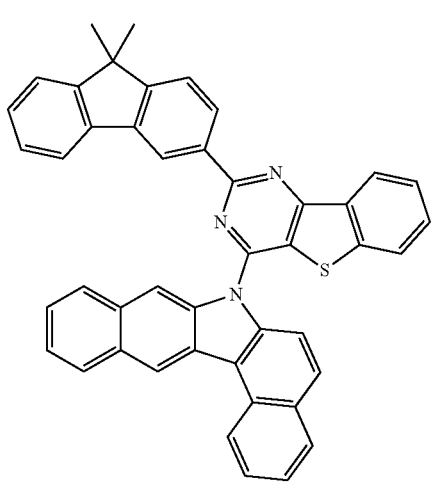

305
-continued
951
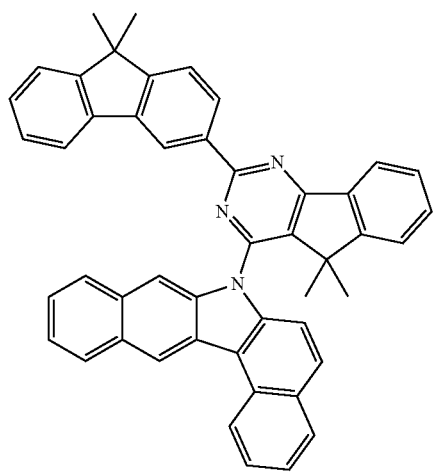
952
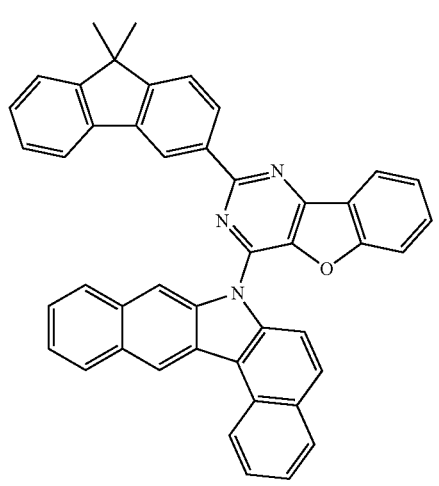
953
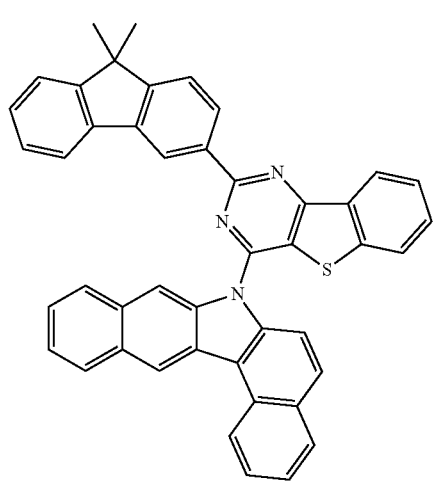
306
-continued
954
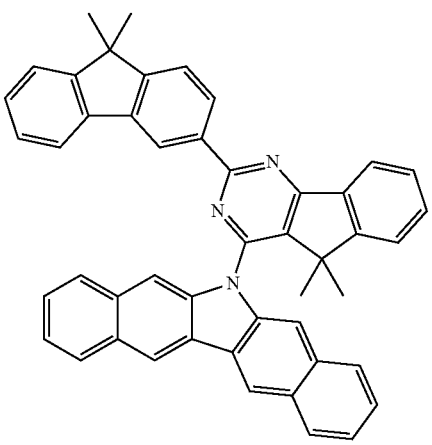
955
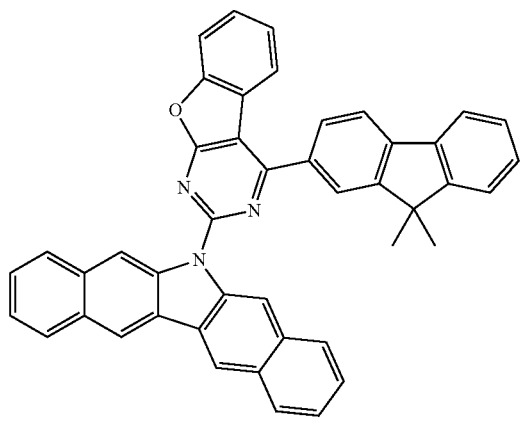
956
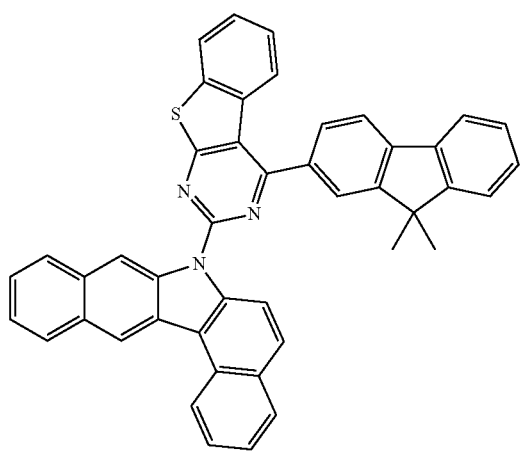

957
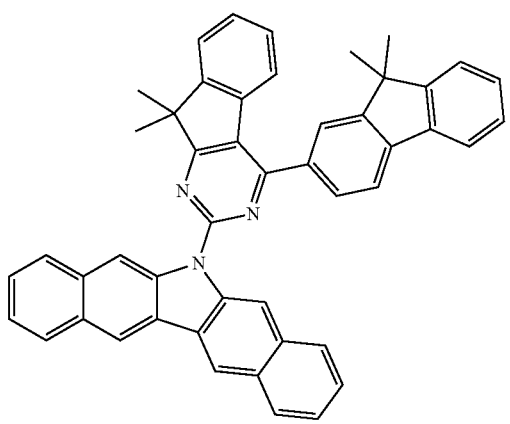
958
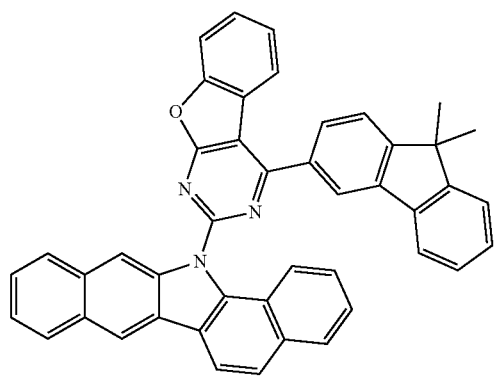
959
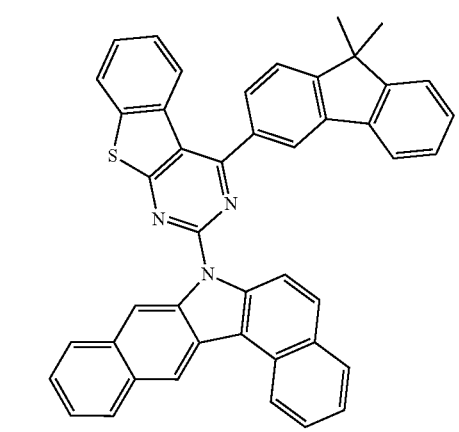
960
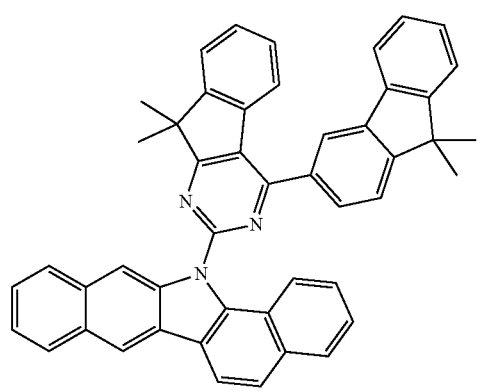
961
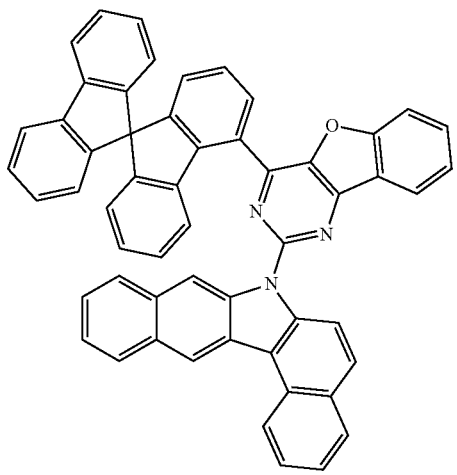
962
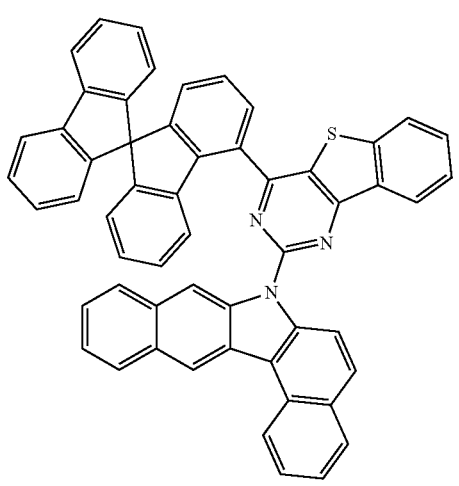
963
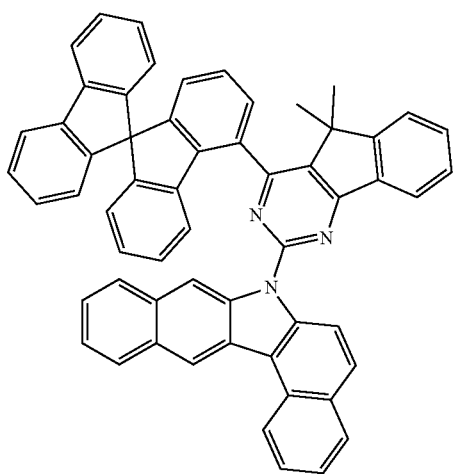

-continued
964
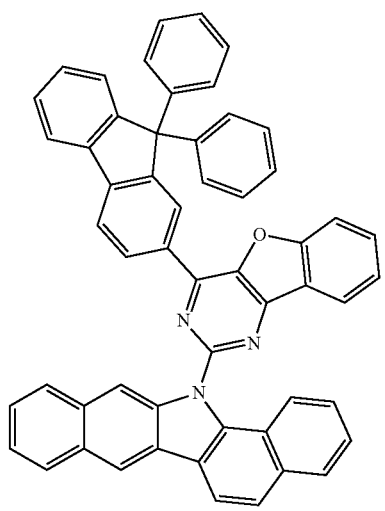
965
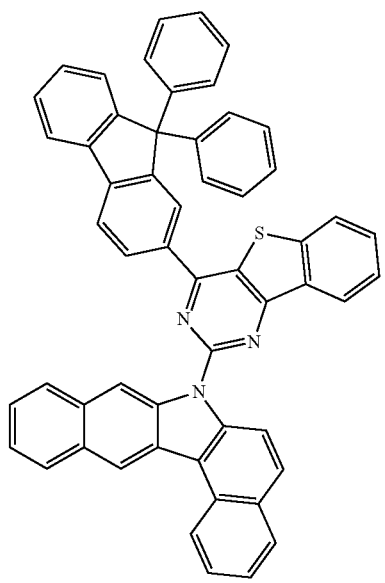
966
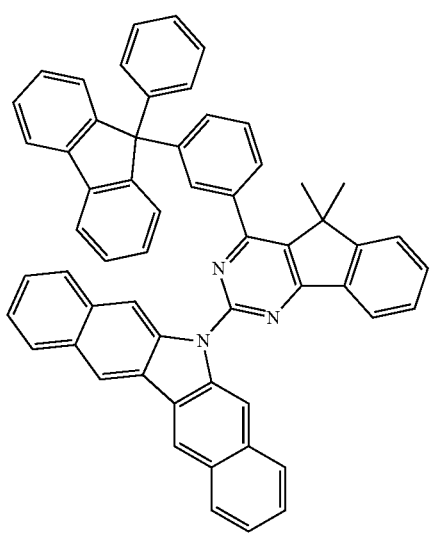
-continued
967
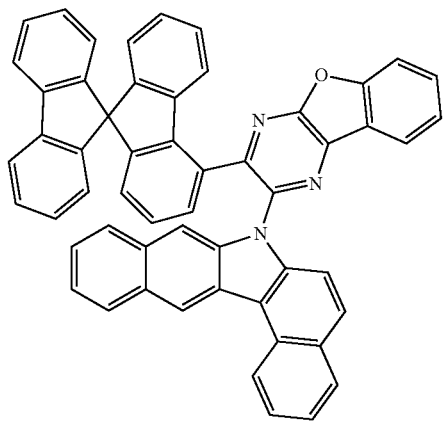
968
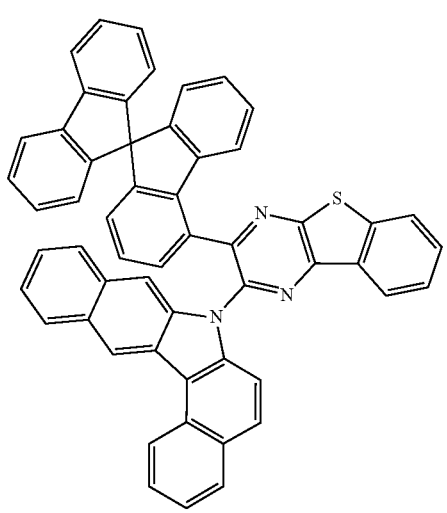
969
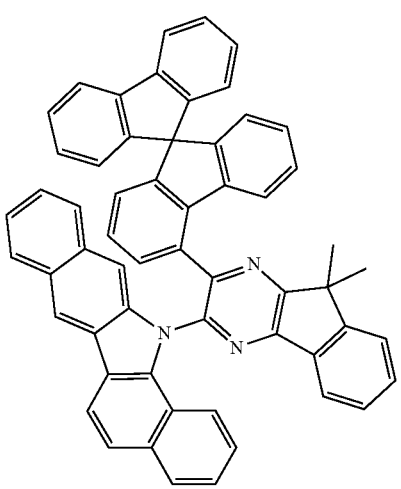

-continued
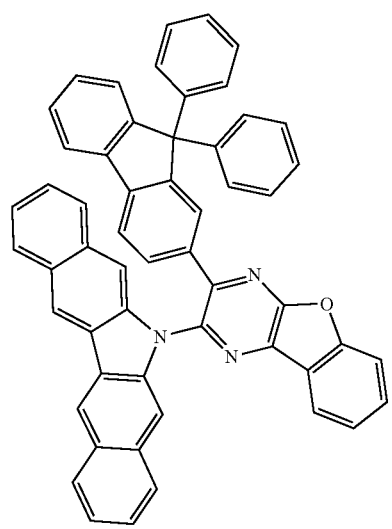
970
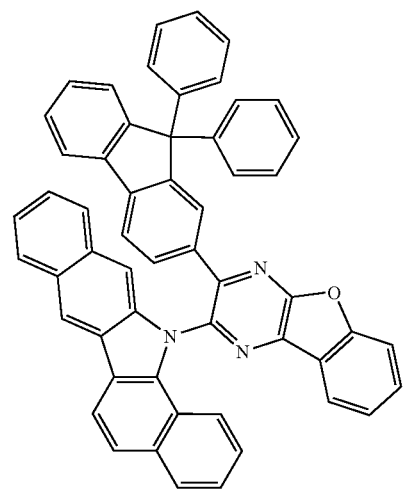
971
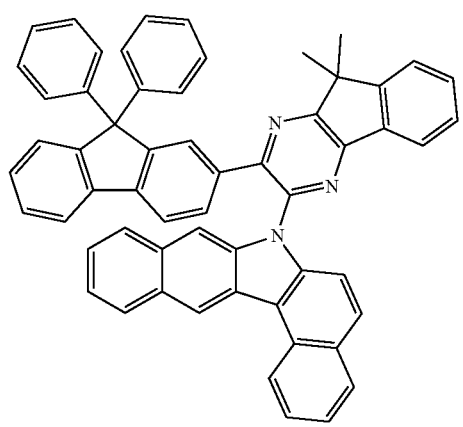
972
-continued
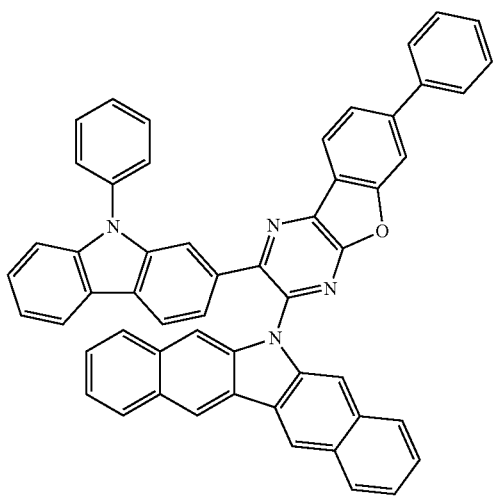
973
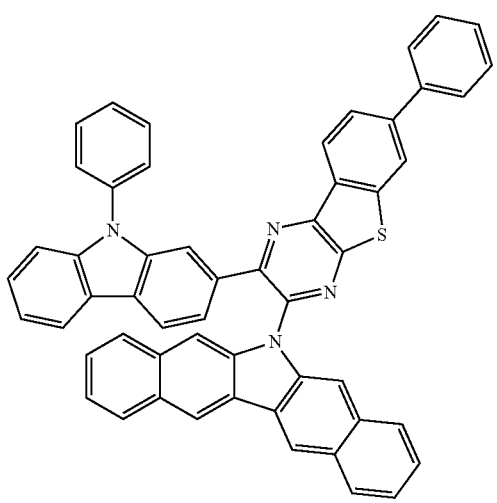
974
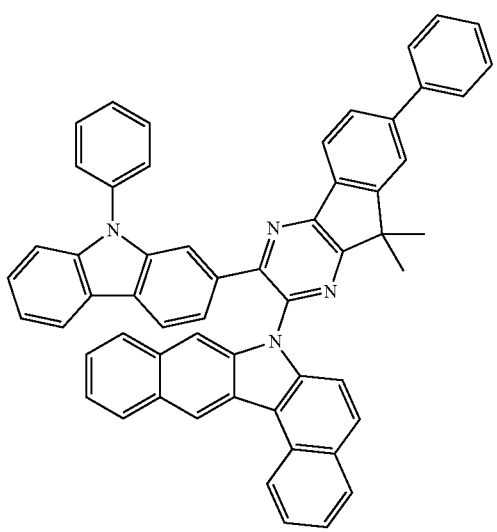
975

976
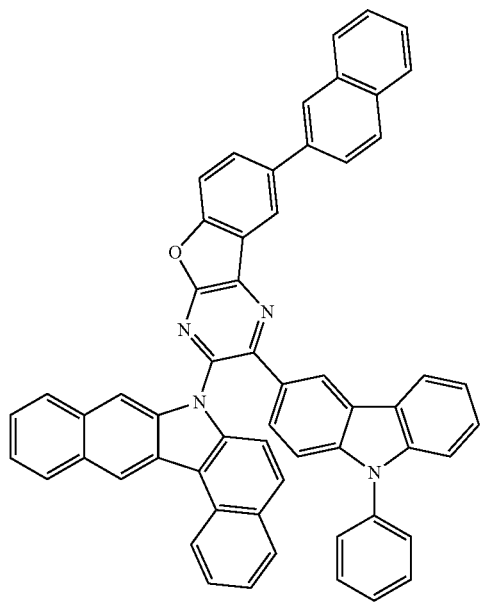
977
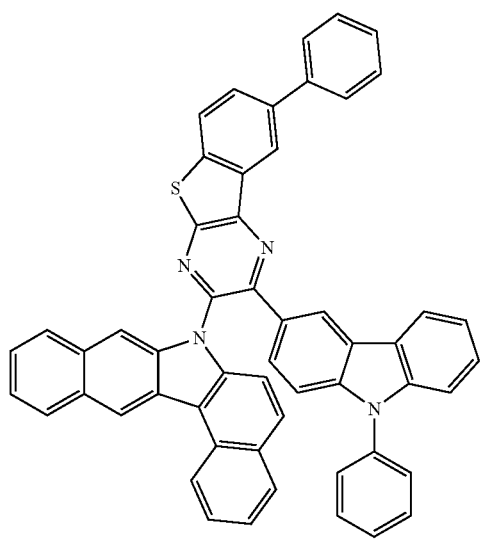
978
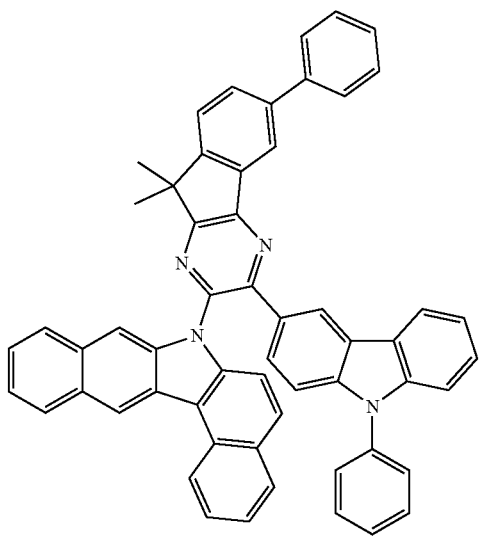
979
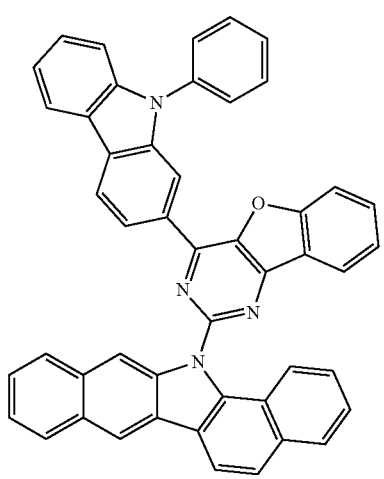
980
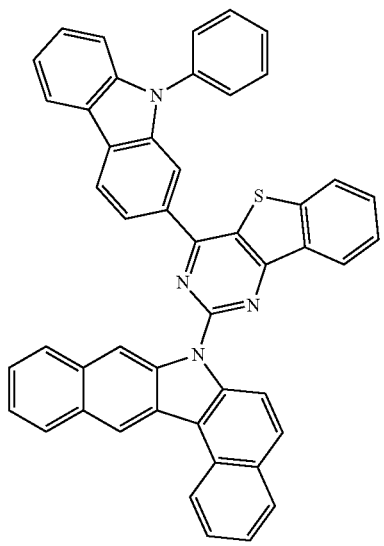

315
-continued
316
-continued
981
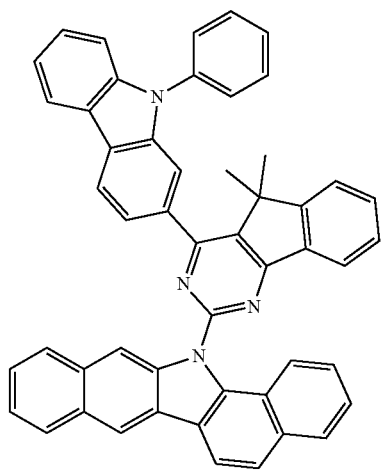
984
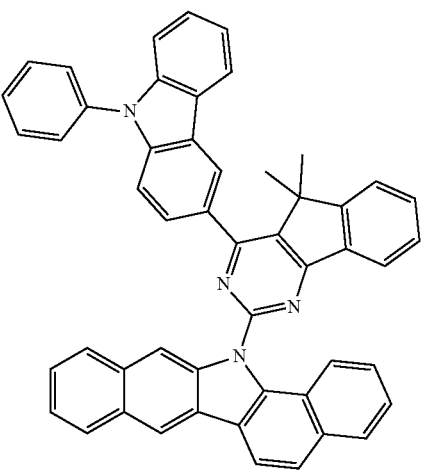
982
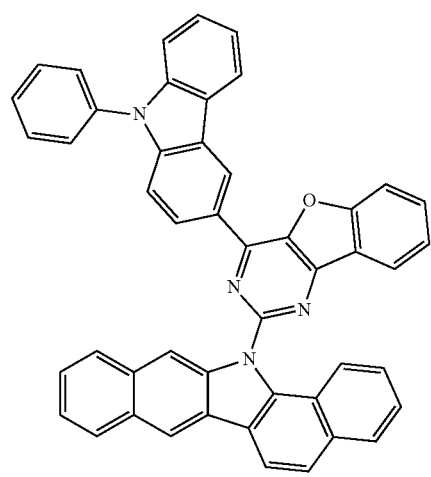
985
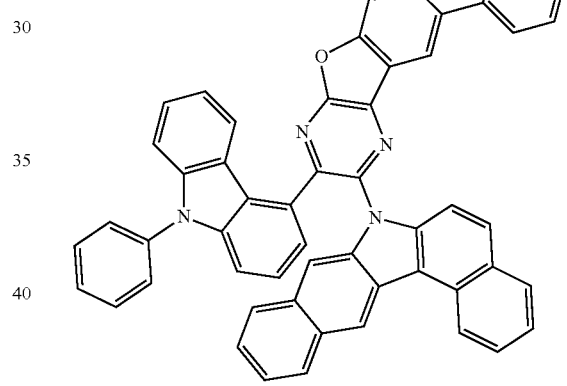
983
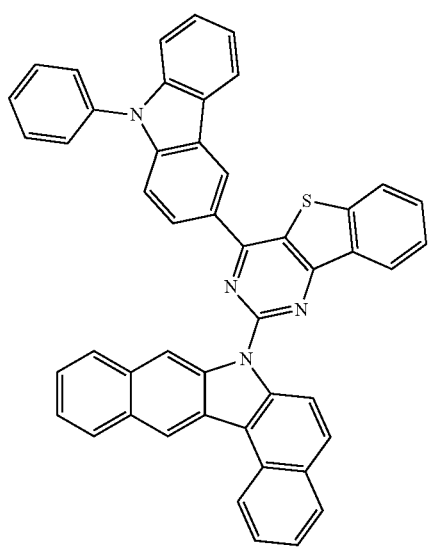
986
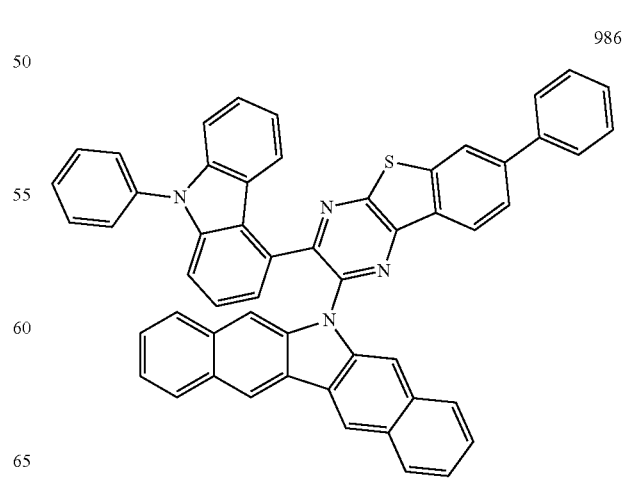

-continued
987
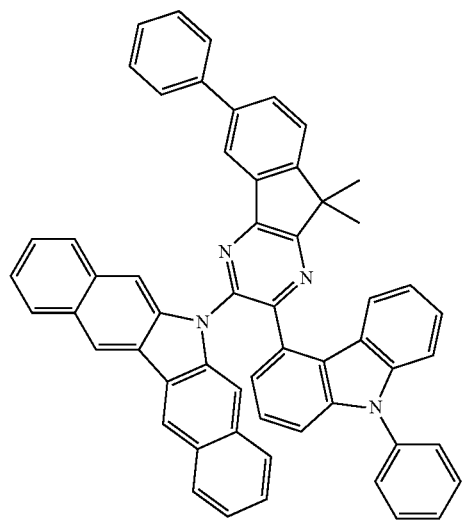
988
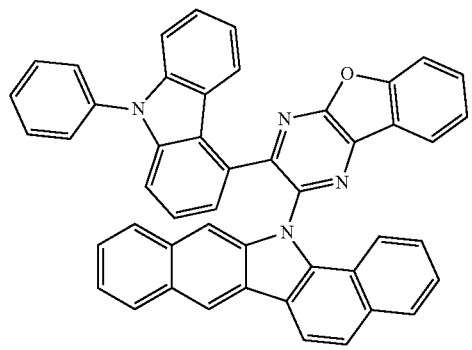
989
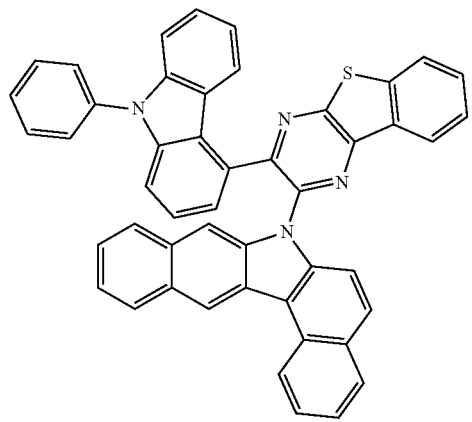
-continued
990
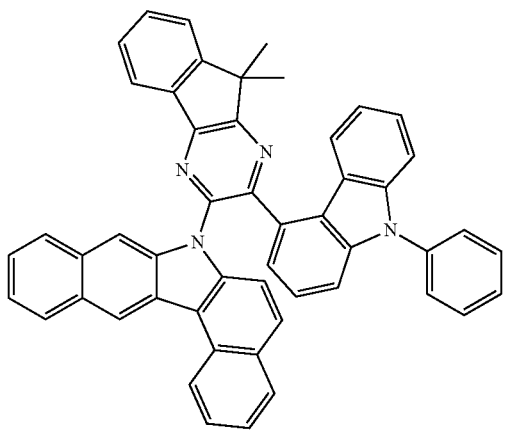
991
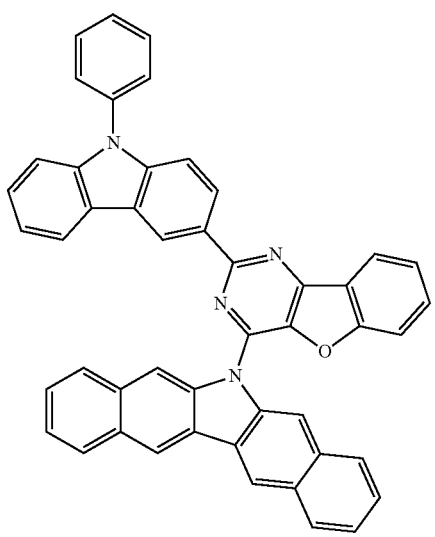
992
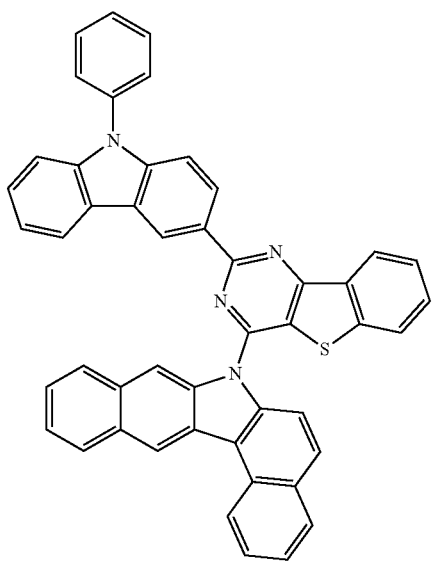

-continued
993
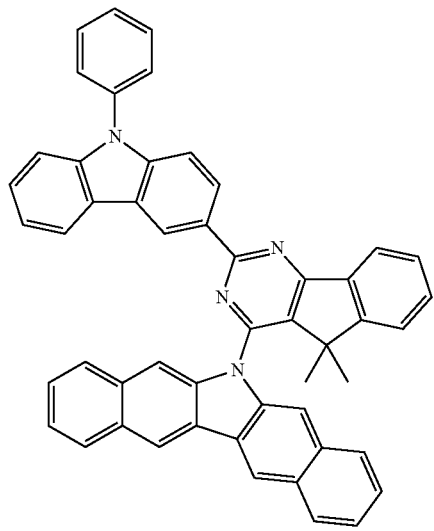
994
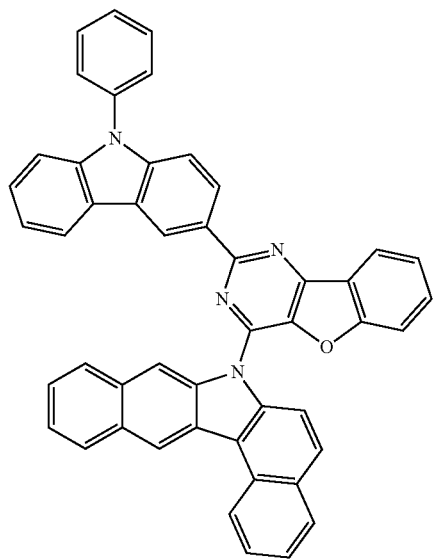
995
-continued
996
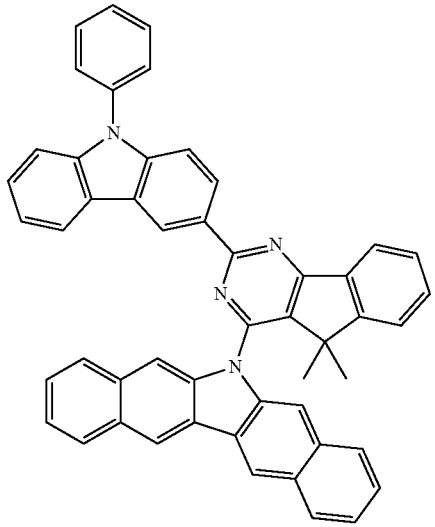
997
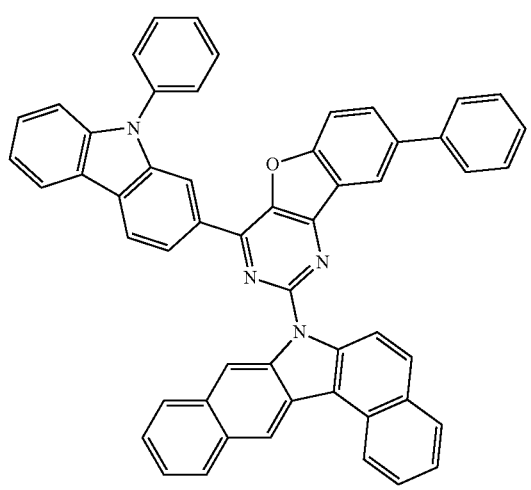
998
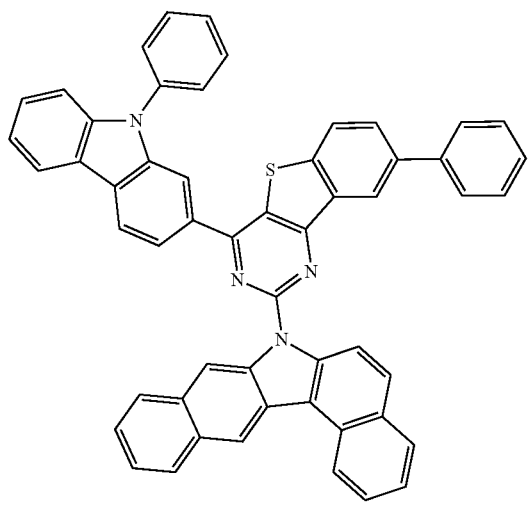

999
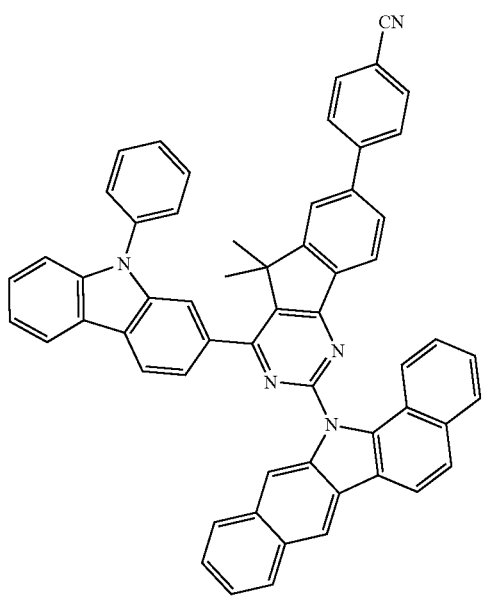
1001
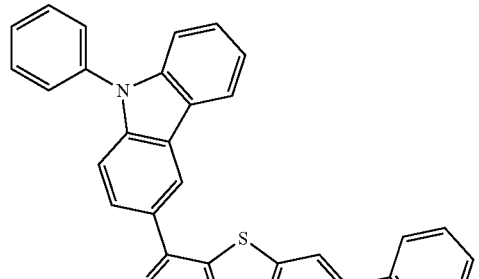
1000
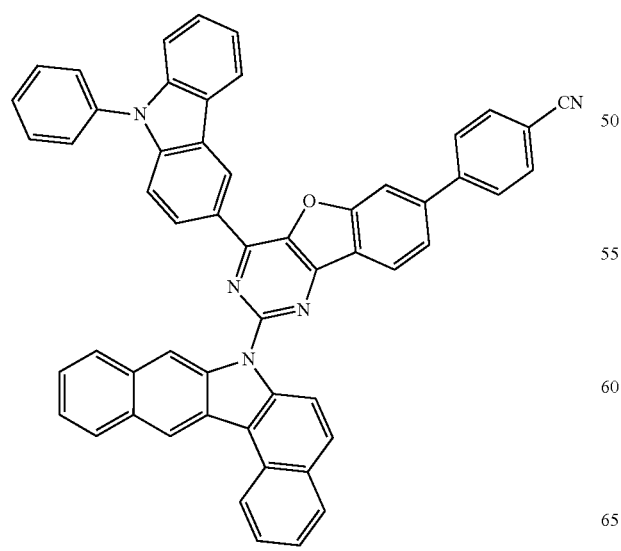
1002
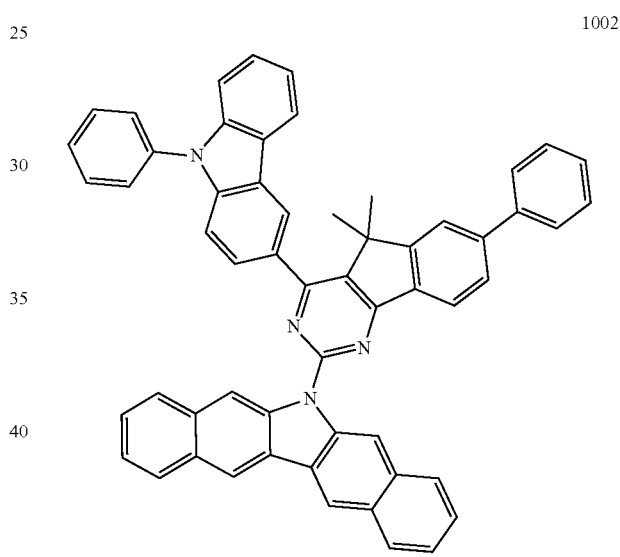
1003
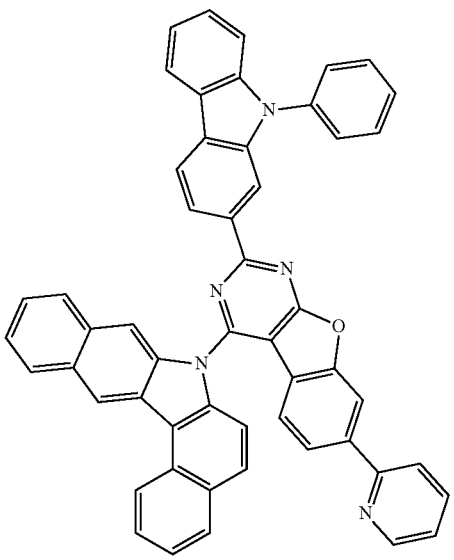

-continued
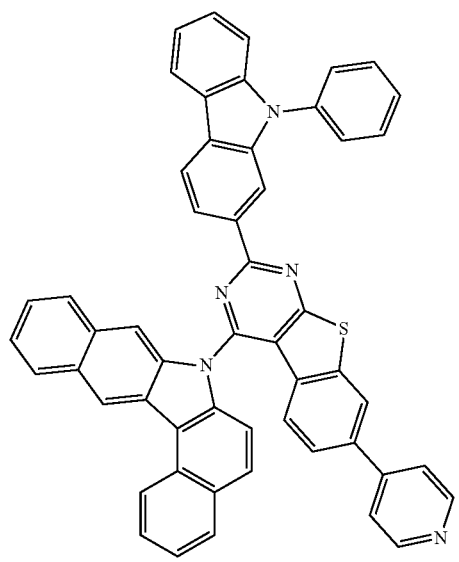
1004
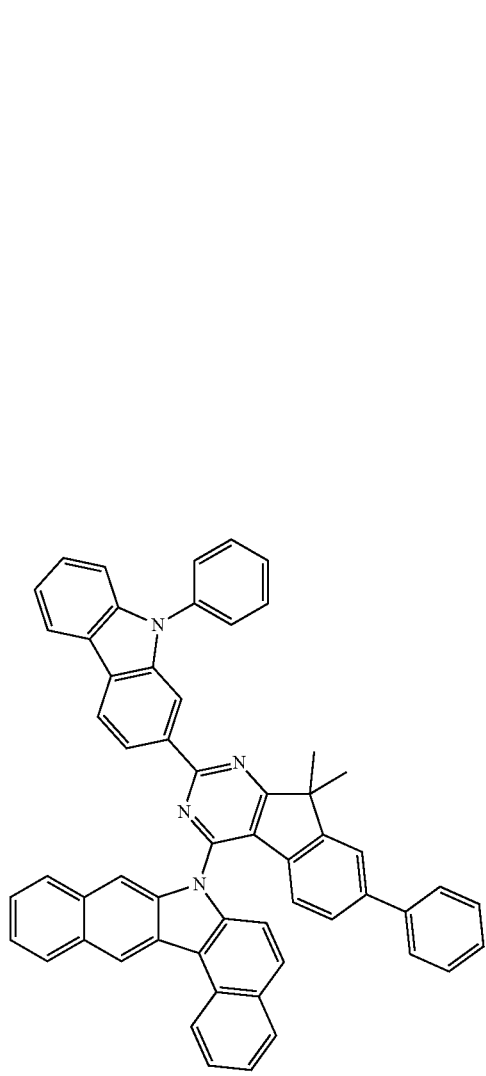
1005
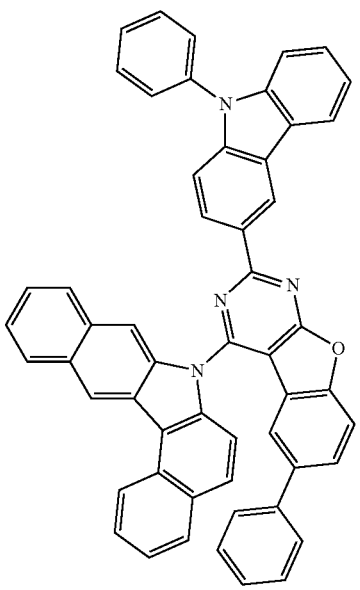
1006
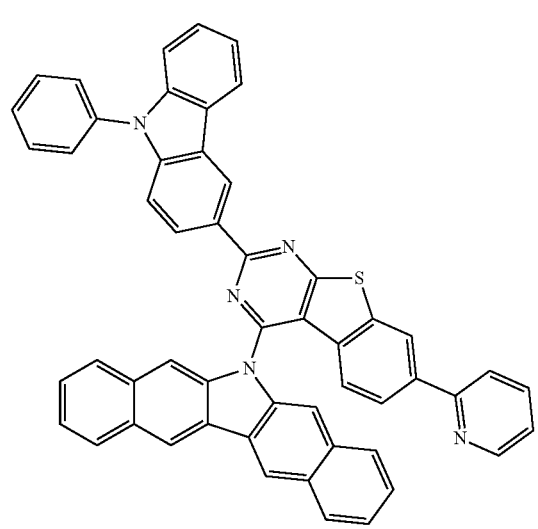
1007
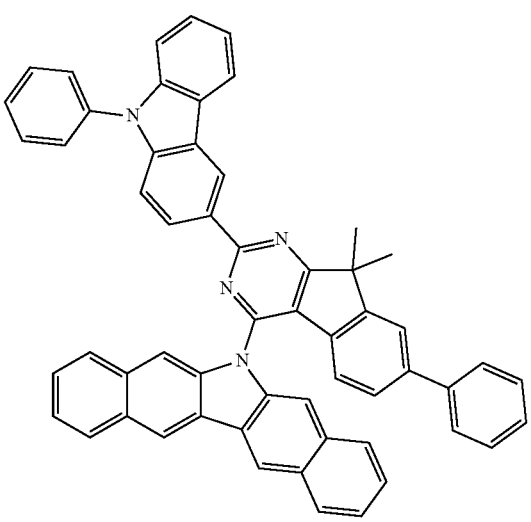
1008

-continued
1009
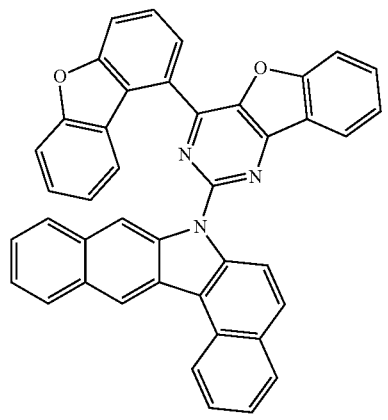
1010
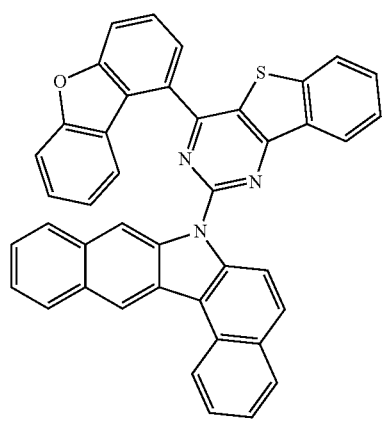
1011
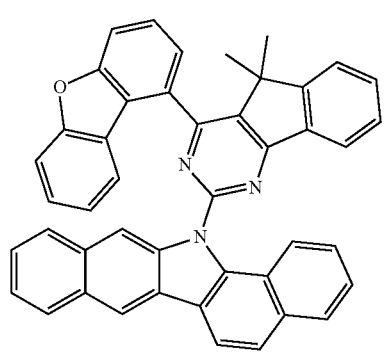
1012
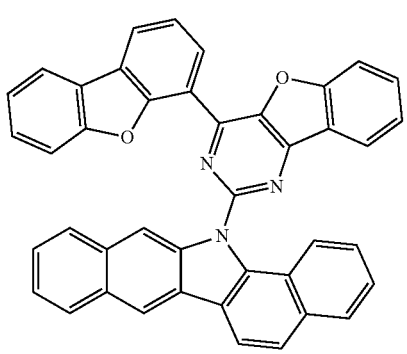
-continued
1013
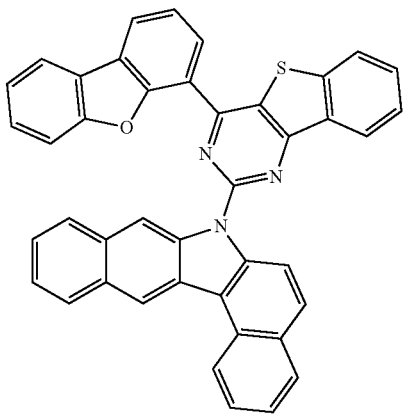
1014
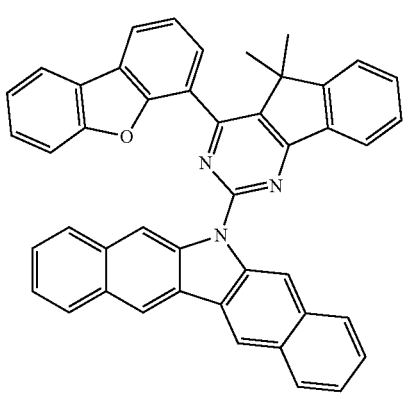
1015
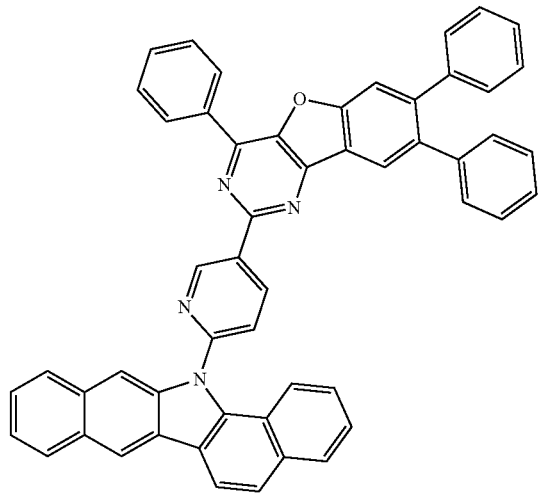

327
-continued
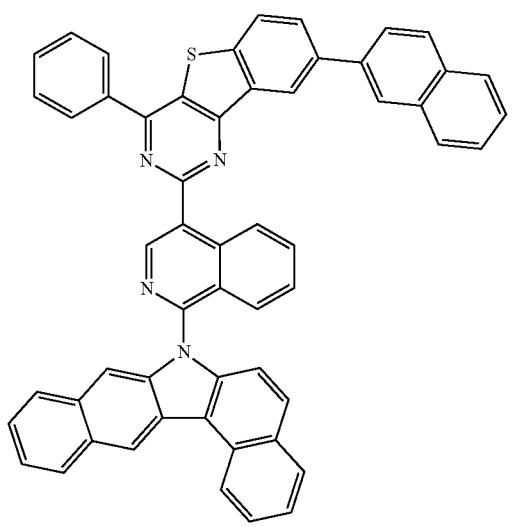
1016
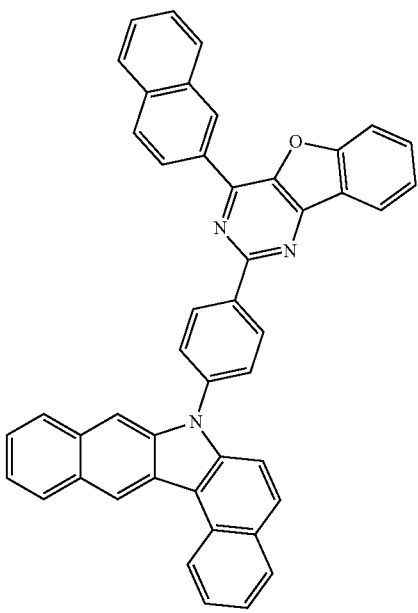
1018
328
-continued
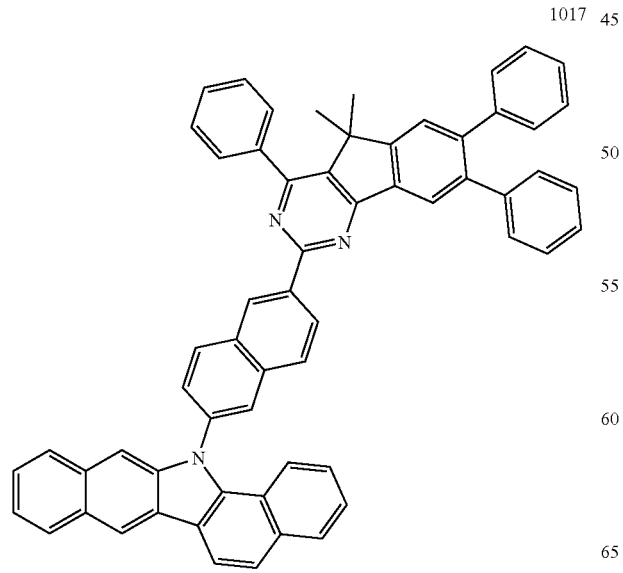
1017
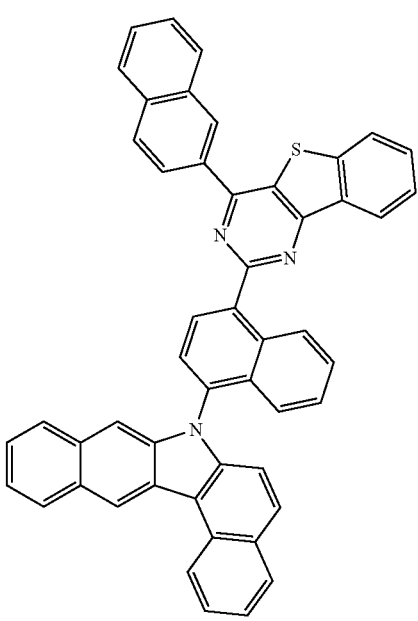
1019

329
-continued
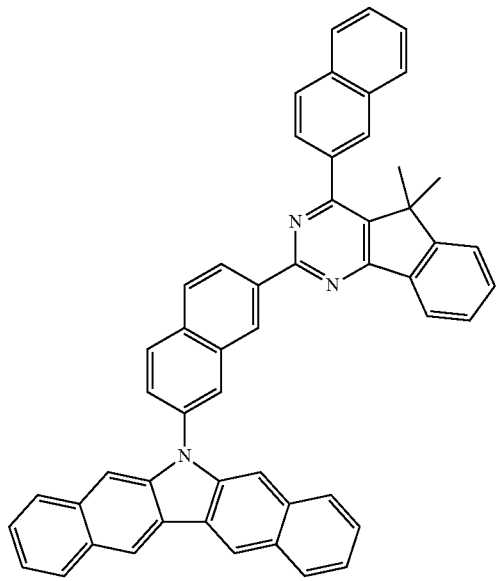
1020
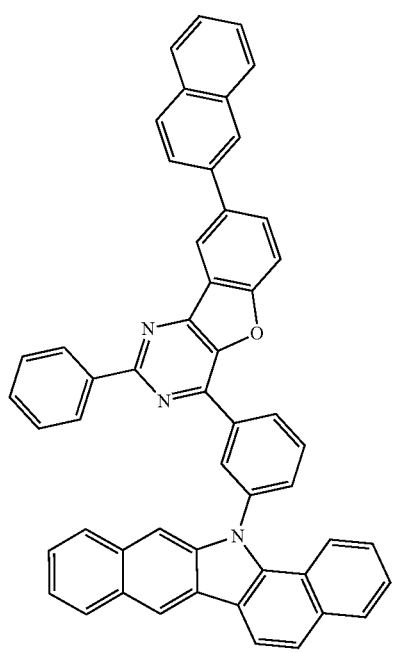
1021
330
-continued
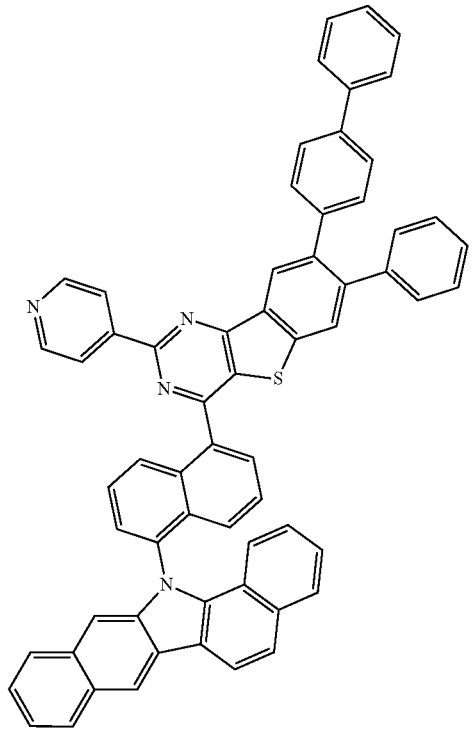
1022
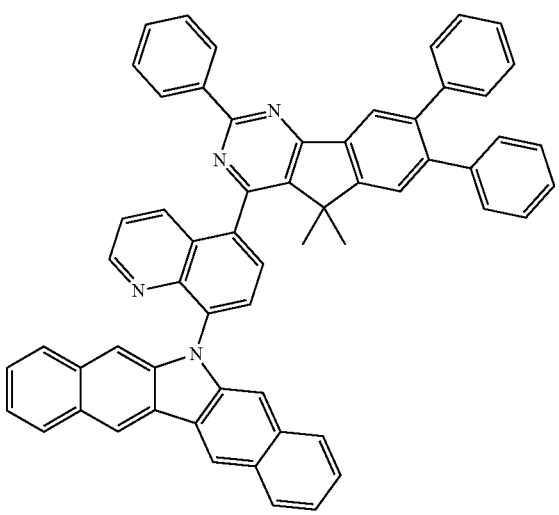
1023

331
-continued
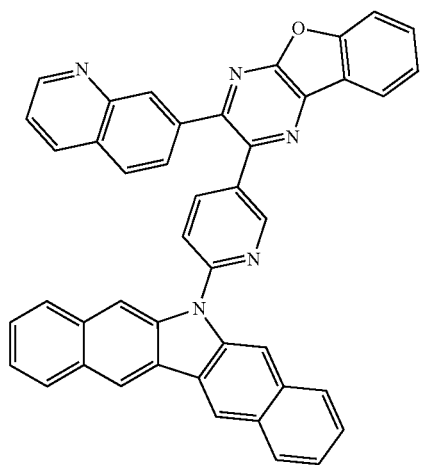
1024
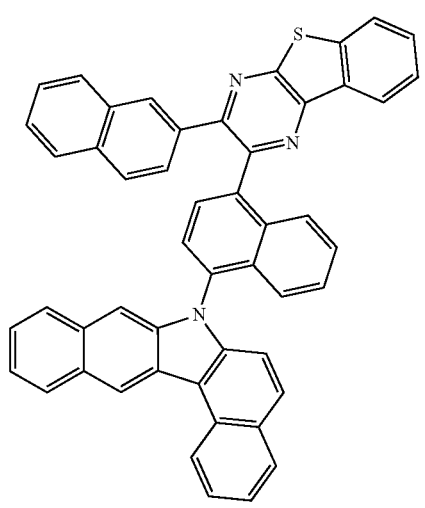
1025
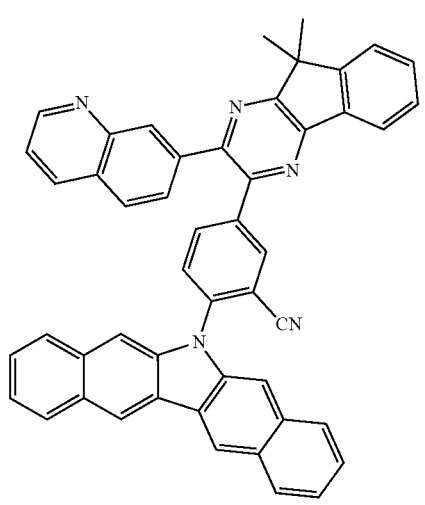
1026
332
-continued
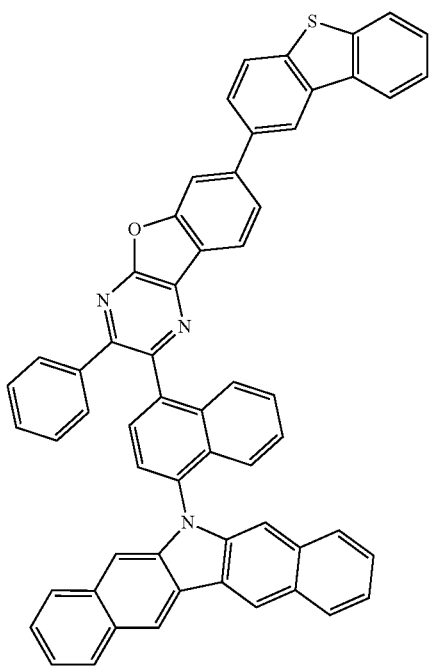
1027
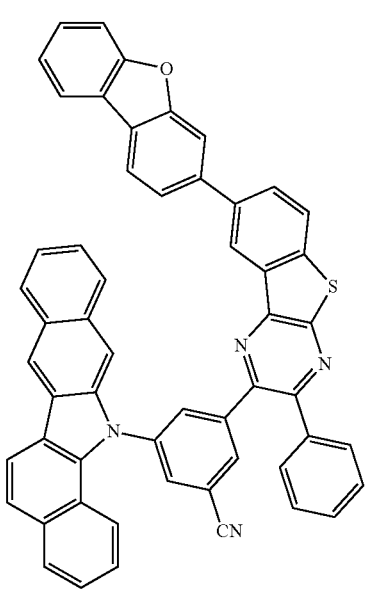
1028

333
-continued
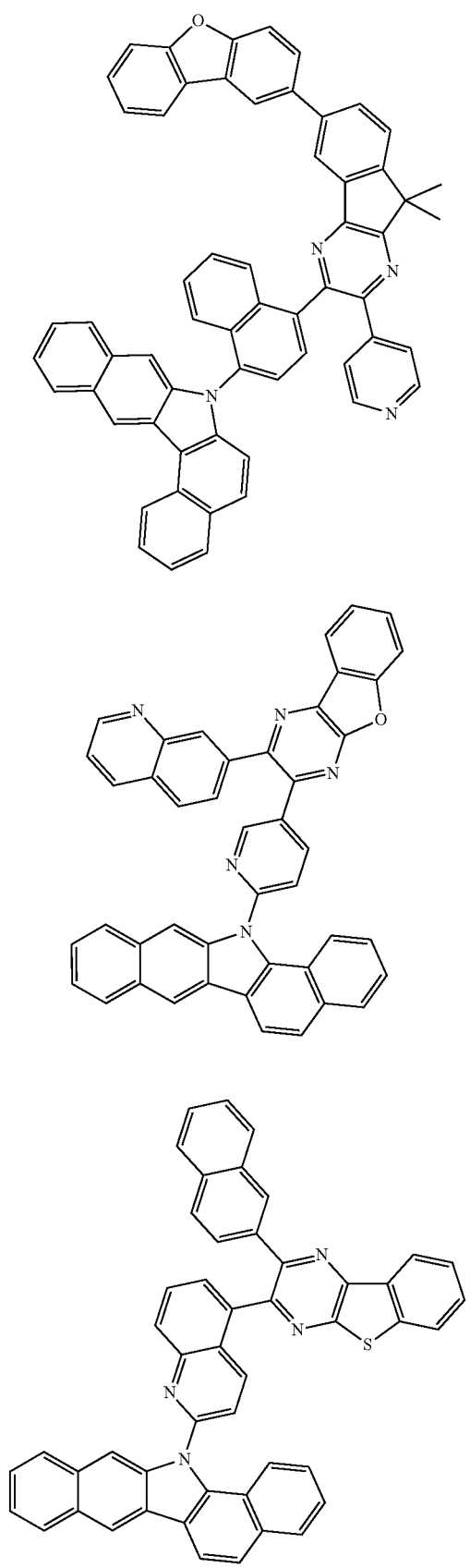
334
-continued

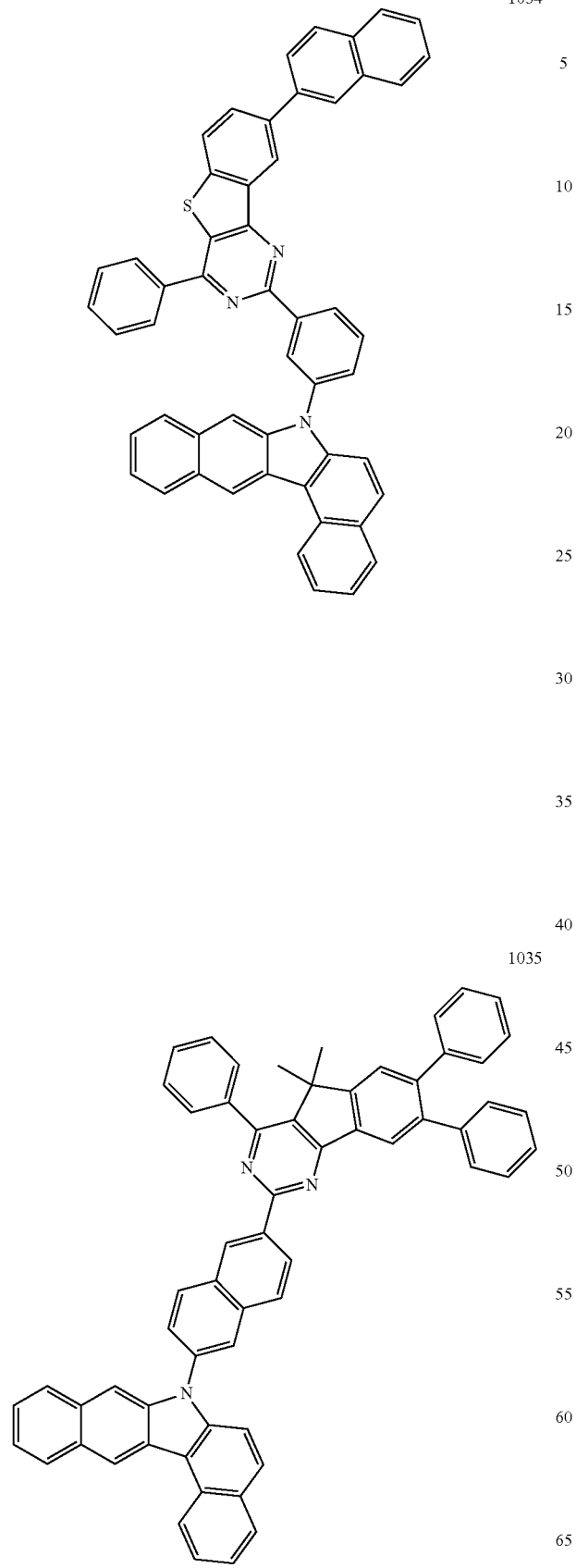
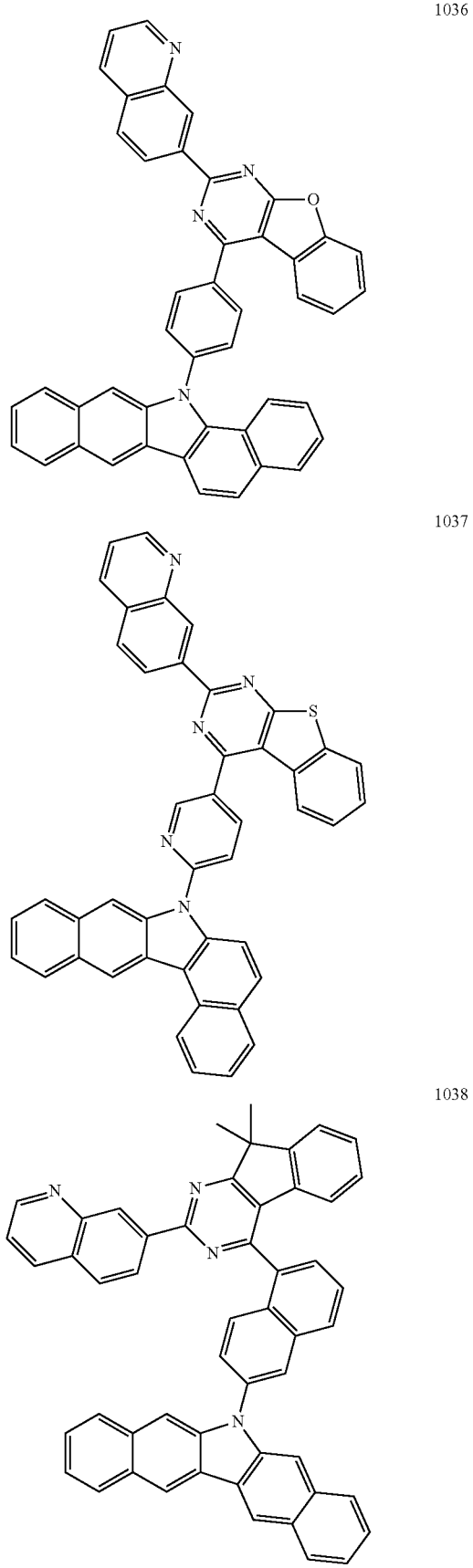

337
-continued
1039
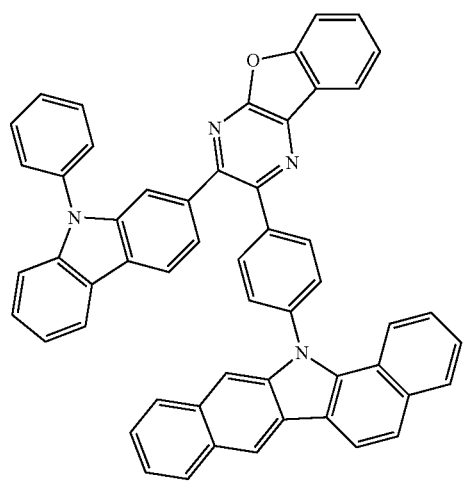
1040
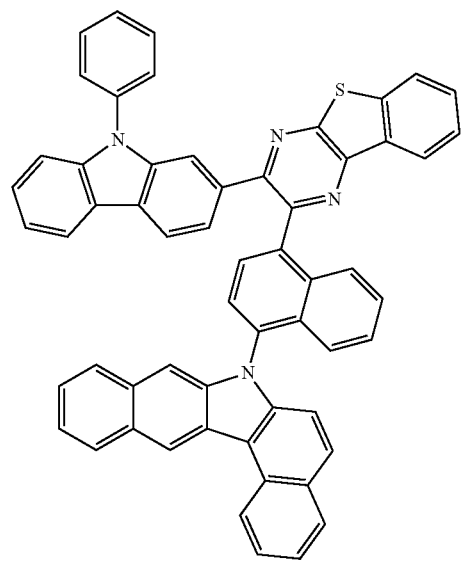
1041
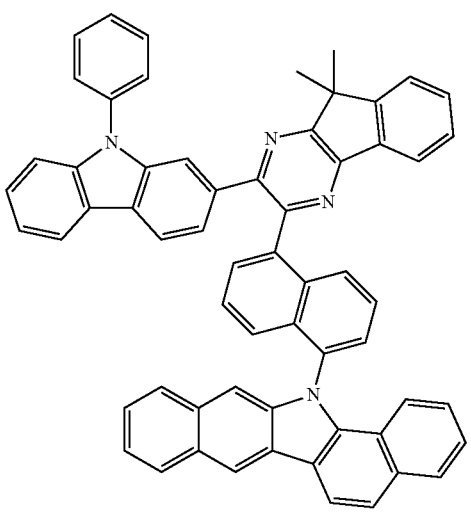
338
-continued
1042
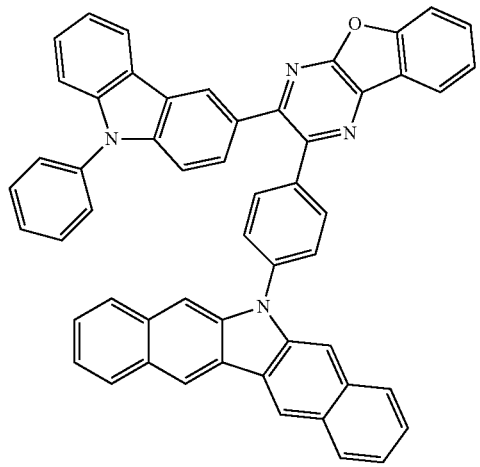
1043
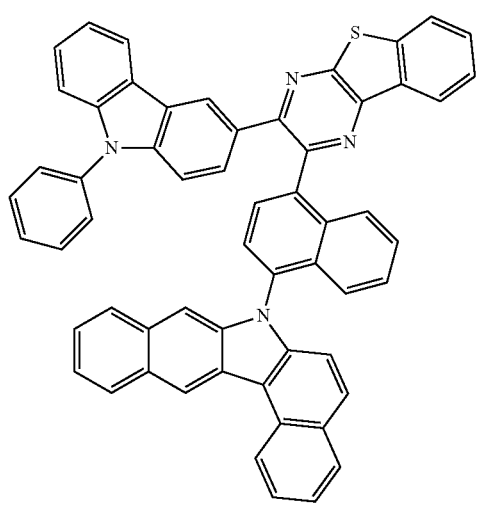
1044
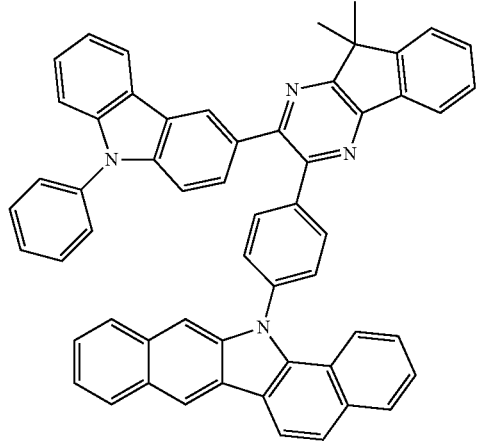

1045
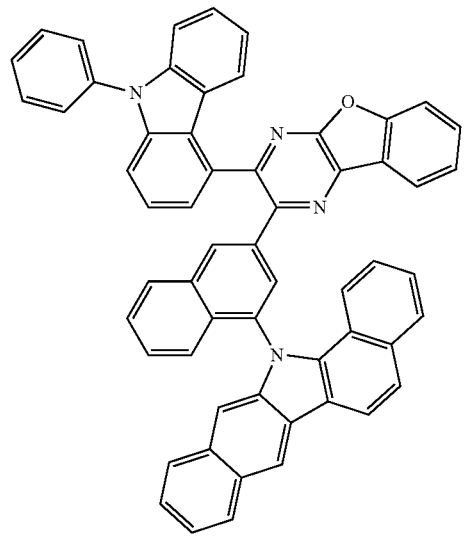
1046
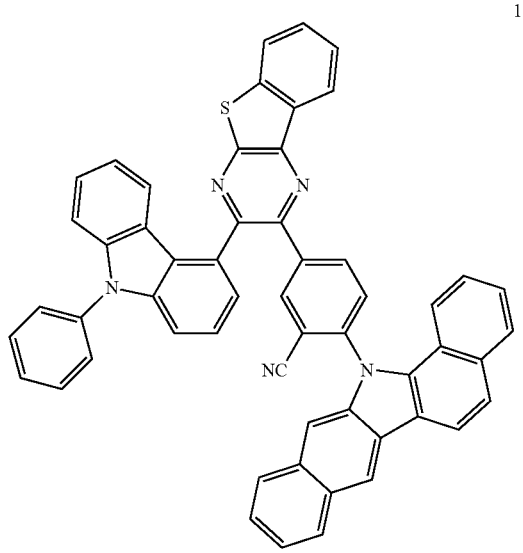
1047
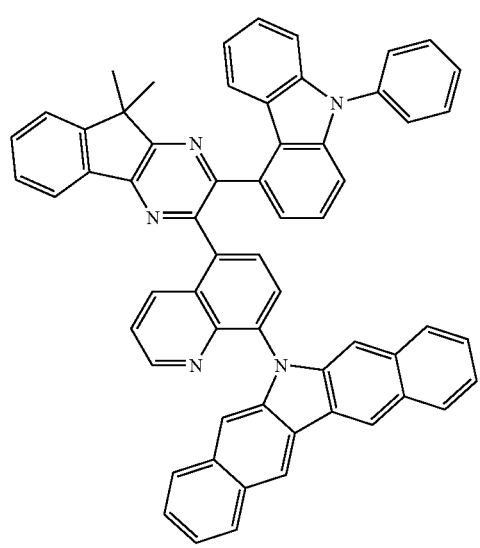
1048
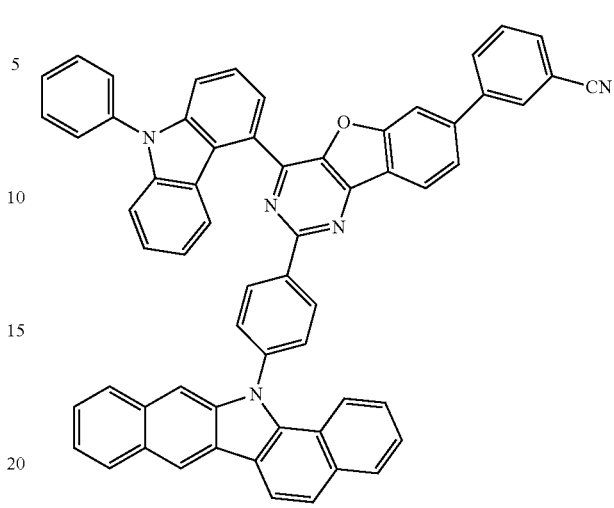
1049
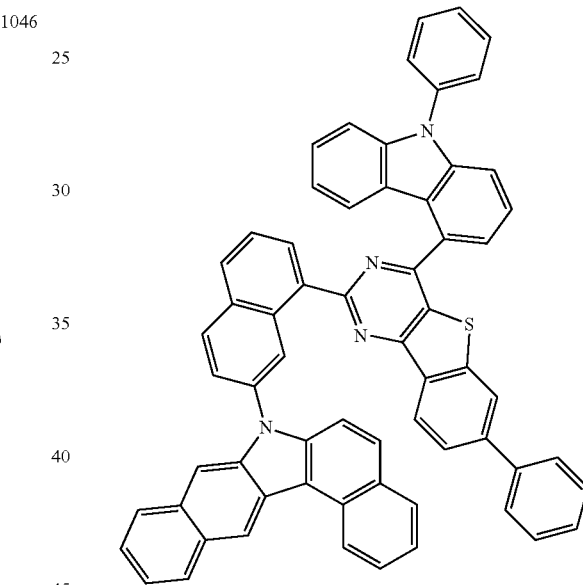
1050
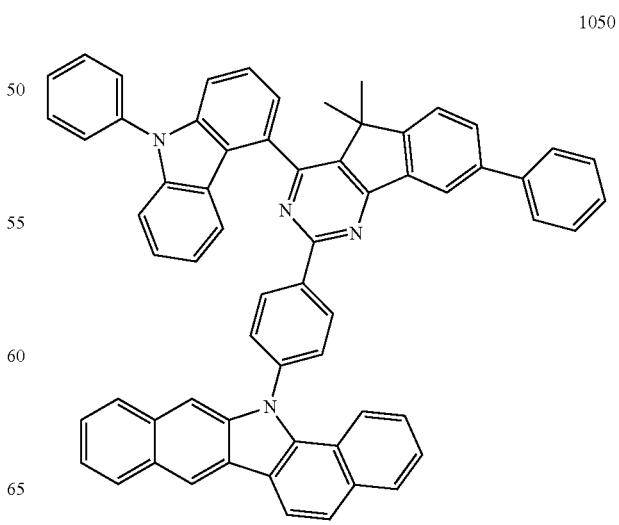

1051
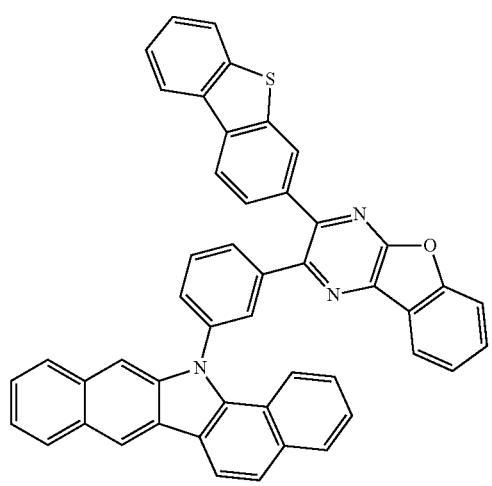
1052
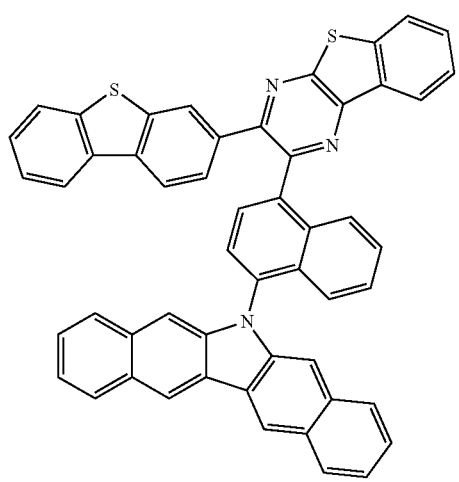
1053
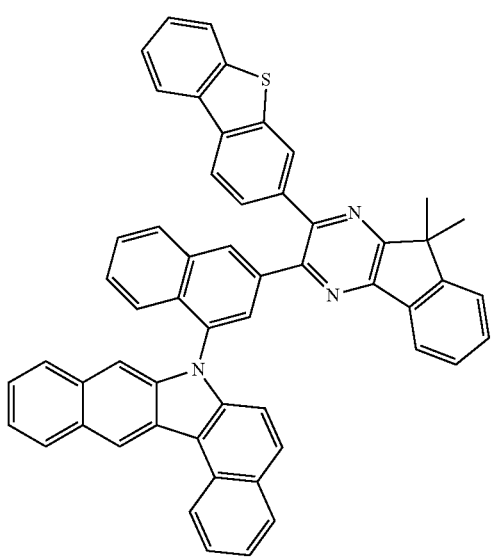
1054
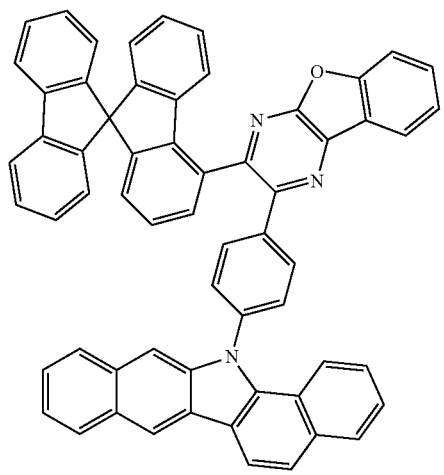
1055
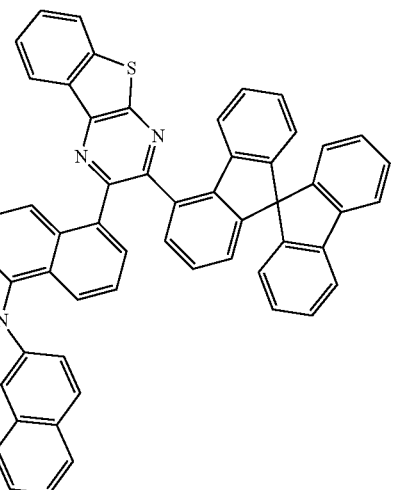
1056
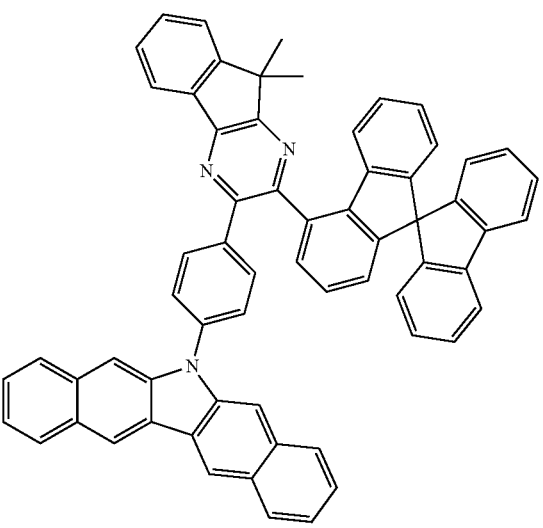

1057
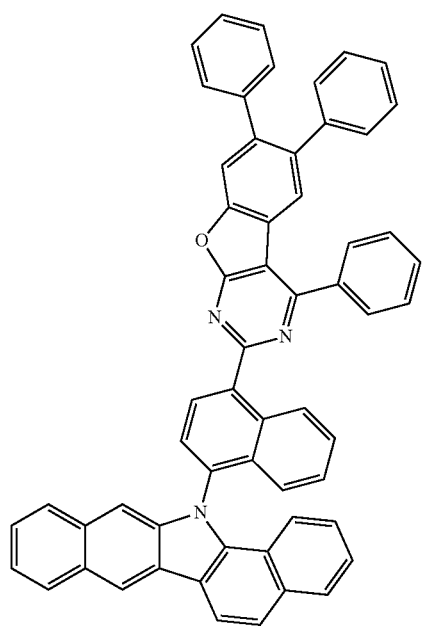
1058
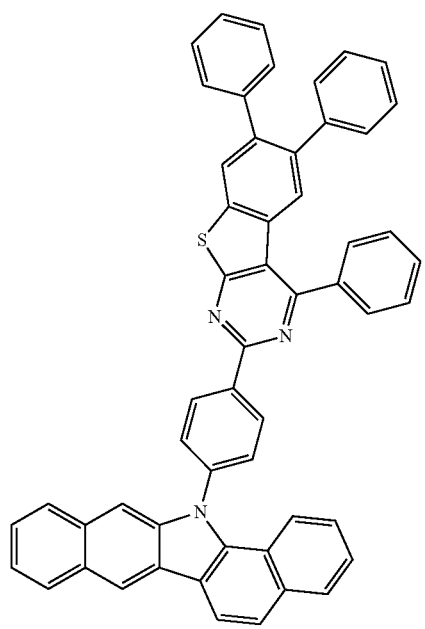
1059
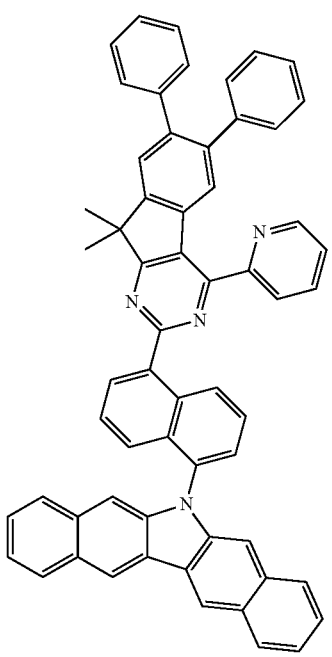
1060
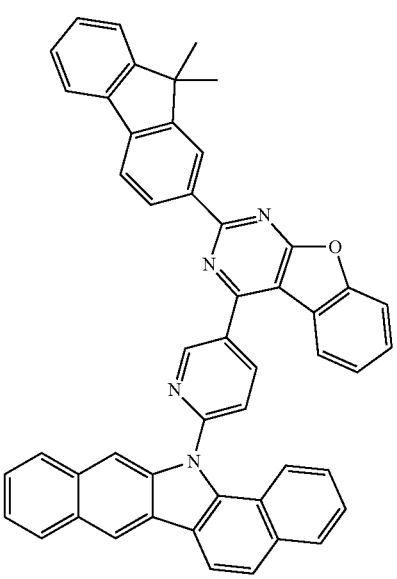

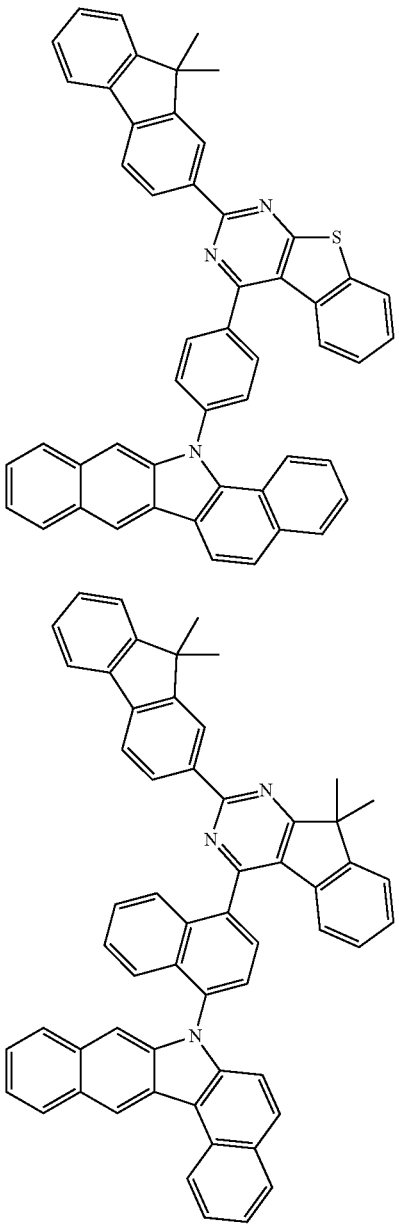

Another embodiment of the present specification provides an organic light emitting device including the compound described above.

One embodiment of the present specification provides an organic light emitting device including a first electrode; a second electrode provided opposite to the first electrode; and one or more organic material layers provided between the first electrode and the second electrode, wherein one or more layers of the one or more organic material layers include the compound.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

The organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the one or more organic material layers include a hole injection layer or a hole transfer layer, and the hole injection layer or the hole transfer layer includes the compound.

In one embodiment of the present specification, the one or more organic material layers include a light emitting layer, and the light emitting layer includes the compound.

In one embodiment of the present specification, the one or more organic material layers include an electron transfer layer or an electron injection layer, and the electron transfer layer or the electron injection layer includes the compound.

In one embodiment of the present specification, the organic light emitting device further includes one, two or more layers selected from the group consisting of a hole injection layer, a hole transfer layer, an electron transfer layer, an electron injection layer, an electron blocking layer and a hole blocking layer.

In one embodiment of the present application, the organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the compound. In one embodiment of the present application, as the two or more organic material layers, two or more may be selected from the group consisting of an electron transfer layer, an electron injection layer, a layer carrying out electron transfer and electron injection at the same time, and a hole blocking layer.

In one embodiment of the present application, the organic material layer includes two or more electron transfer layers, and at least one of the two or more electron transfer layers includes the compound. Specifically, in one embodiment of the present specification, the compound may be included in one of the two or more electron transfer layers, or included in each of the two or more electron transfer layers.

In addition, in one embodiment of the present application, when the compound is included in each of the two or more electron transfer layers, materials other than the compound may be the same as or different from each other.

In one embodiment of the present specification, the organic material layer further includes a hole injection layer or a hole transfer layer including a compound that includes an arylamino group, a carbazole group or a benzocarbazole group in addition to the organic material layer including the compound.

In another embodiment, the organic light emitting device may be an organic light emitting device having a structure in which a first electrode, one or more organic material layers and a second electrode are consecutively laminated on a substrate (normal type).

In another embodiment, the organic light emitting device may be an organic light emitting device having a structure in a reverse direction in which a second electrode, one or more organic material layers and a first electrode are consecutively laminated on a substrate (inverted type).

Figure 2:
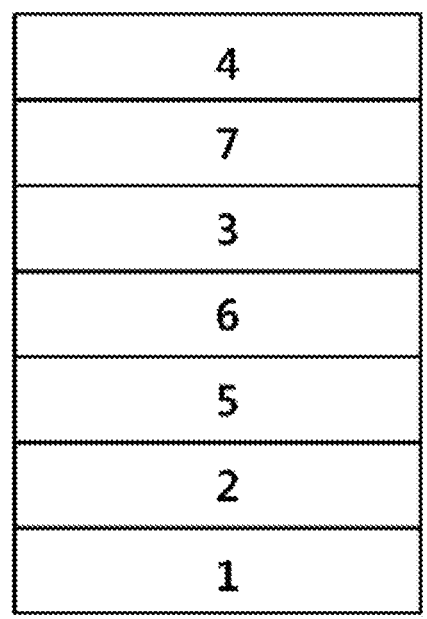
FIG. 2 illustrates an organic light emitting device in which a substrate (1), a first electrode (2), a hole injection layer (5), a hole transfer layer (6), a light emitting layer (3), an electron transfer layer (7) and a second electrode (4) are consecutively laminated.

For example, a structure of the organic light emitting device according to one embodiment of the present specification is illustrated in FIGS. 1 and 2.

FIG. 1 illustrates a structure of the organic light emitting device in which a substrate (1), a first electrode (2), a light emitting layer (3) and a second electrode (4) are consecutively laminated. In such a structure, the compound may be included in the light emitting layer (3).

FIG. 2 illustrates a structure of the organic light emitting device in which a substrate (1), a first electrode (2), a hole injection layer (5), a hole transfer layer (6), a light emitting layer (3), an electron transfer layer (7) and a second electrode (4) are consecutively laminated. In such a structure, the compound may be included in one or more layers of the hole injection layer (5), the hole transfer layer (6), the light emitting layer (3) and the electron transfer layer (7).

In such a structure, the compound may be included in one or more layers of the hole injection layer, the hole transfer layer, the light emitting layer and the electron transfer layer.

The organic light emitting device of the present specification may be manufactured using materials and methods known in the art, except that one or more layers of the organic material layers include the compound of the present specification, that is, the above-mentioned compound.

When the organic light emitting device includes a plurality of organic material layers, the organic material layers may be formed with materials the same as or different from each other.

The organic light emitting device of the present specification may be manufactured using materials and methods known in the art, except that one or more layers of the organic material layers include the above-mentioned compound, that is, the compound represented by Chemical Formula 1.

For example, the organic light emitting device of the present specification may be manufactured by consecutively laminating a first electrode, an organic material layer and a second electrode on a substrate. Herein, the organic light emitting device may be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device may also be manufactured by consecutively depositing a second electrode material, an organic material layer and a first electrode material on a substrate.

In addition, the compound of Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such as method, the organic light emitting device may also be manufactured by consecutively laminating a second electrode material, an organic material layer and a first electrode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the first electrode material, materials having large work function are normally preferred so that hole injection to an organic material layer is smooth. Specific examples of the first electrode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy) thiophene] (PEDOT), polypyrrole and polyaniline, but are not limited thereto.

As the second electrode material, materials having small work function are normally preferred so that electron injection to an organic material layer is smooth. Specific examples of the second electrode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a layer that injects holes from an electrode, and the hole injection material is preferably a compound that has an ability to transfer holes, therefore, has a hole injection effect in a first electrode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of a first electrode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from a first electrode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole series compounds; dimerized styryl compounds; BAlq; 10-hydroxybenzo quinoline-metal compounds; benzoxazole, benzothiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, but the material is not limited thereto.

The dopant material may include compounds as below, but is not limited thereto.

Dp-1
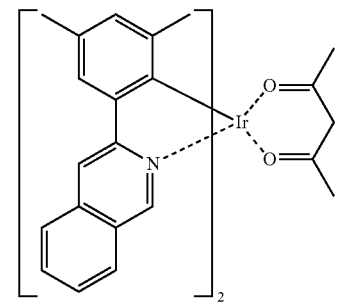

Dp-2

Dp-3

Dp-4
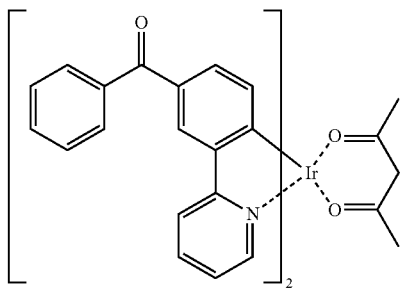

Dp-5
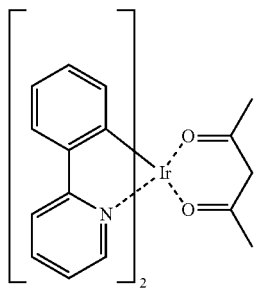

Dp-6
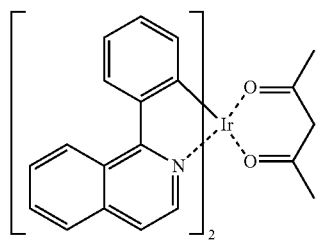

Dp-7
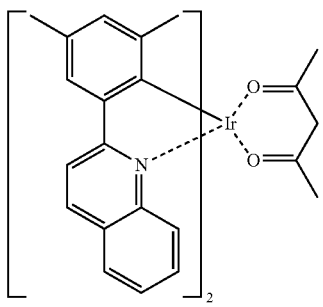

Dp-8
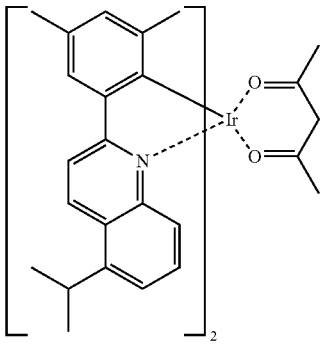

Dp-9
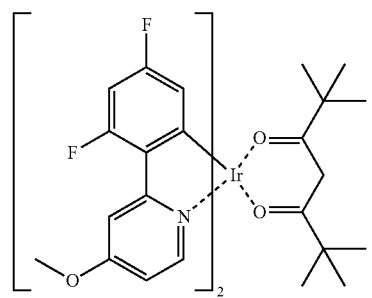
Dp-10
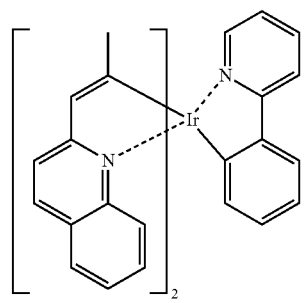
Dp-11
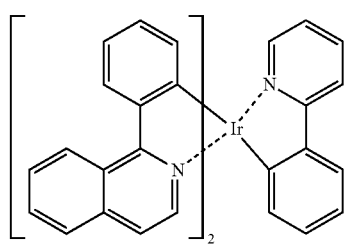
Dp-12
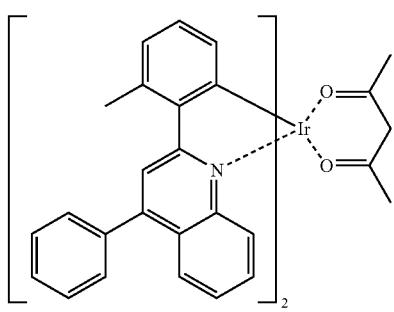
Dp-13
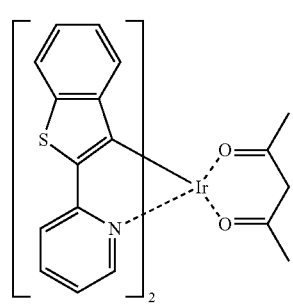
Dp-14
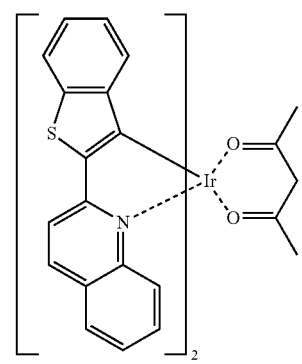
Dp-15
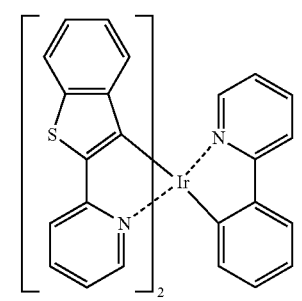
Dp-13
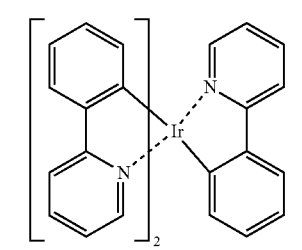
Dp-14
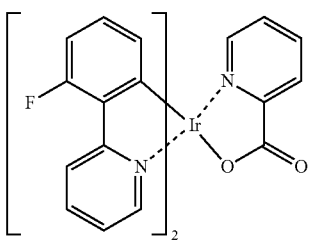
Dp-15
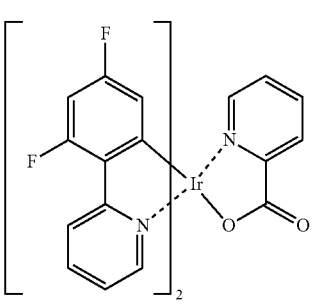

Dp-16
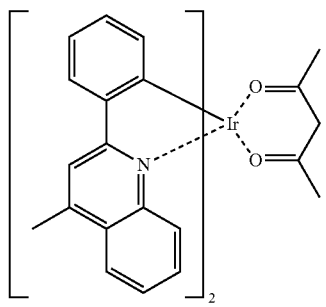
Dp-17
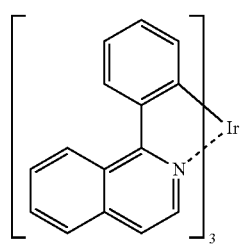
Dp-18
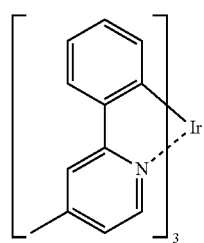
Dp-19
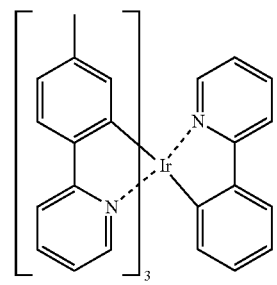
Dp-20
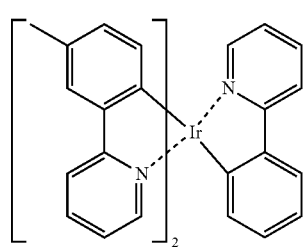
Dp-21
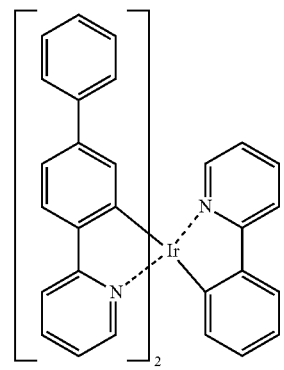
Dp-22
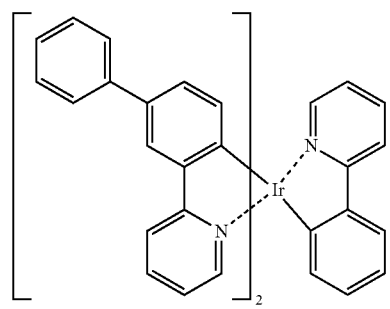
Dp-23
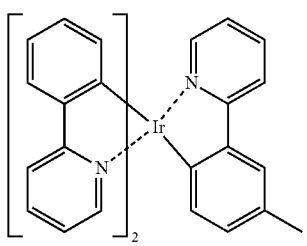
Dp-24
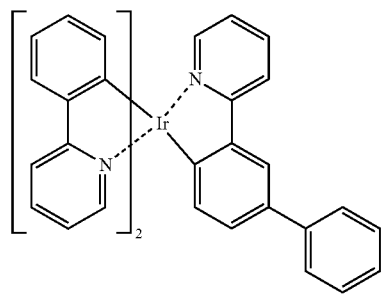
Dp-25
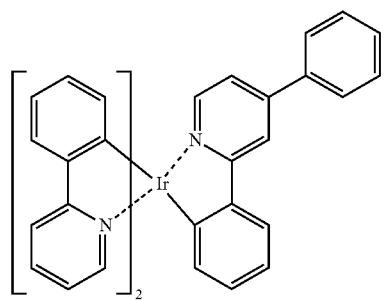

Dp-26
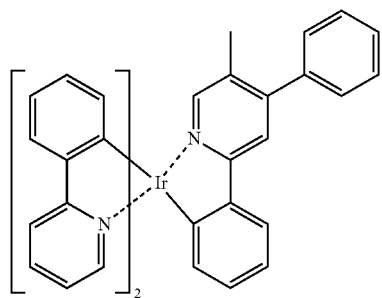
Dp-27
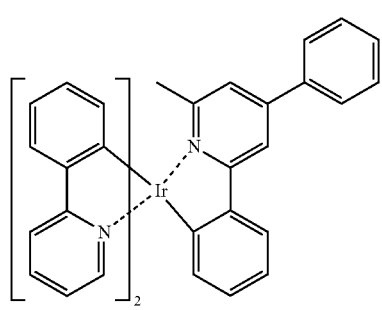
Dp-28
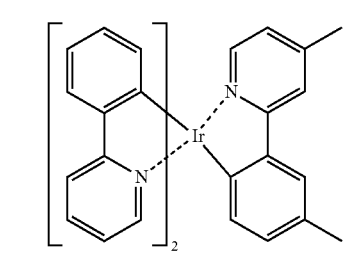
Dp-29
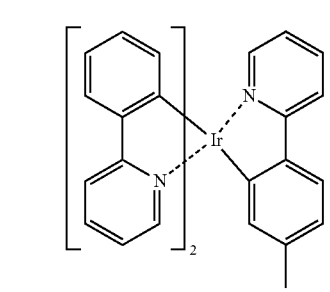
Dp-30
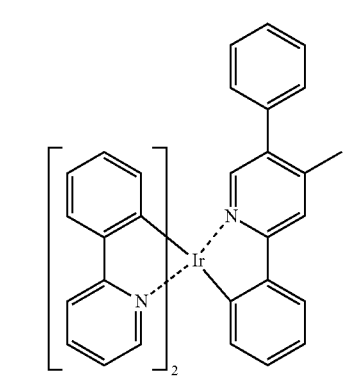
Dp-31
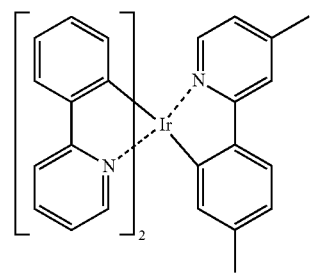
Dp-32
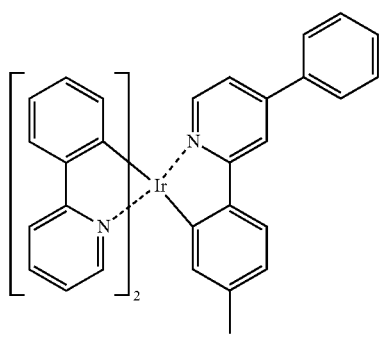
Dp-33
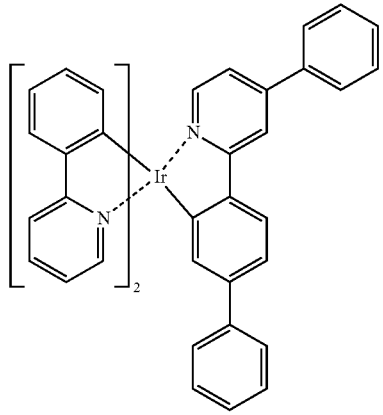
Dp-34
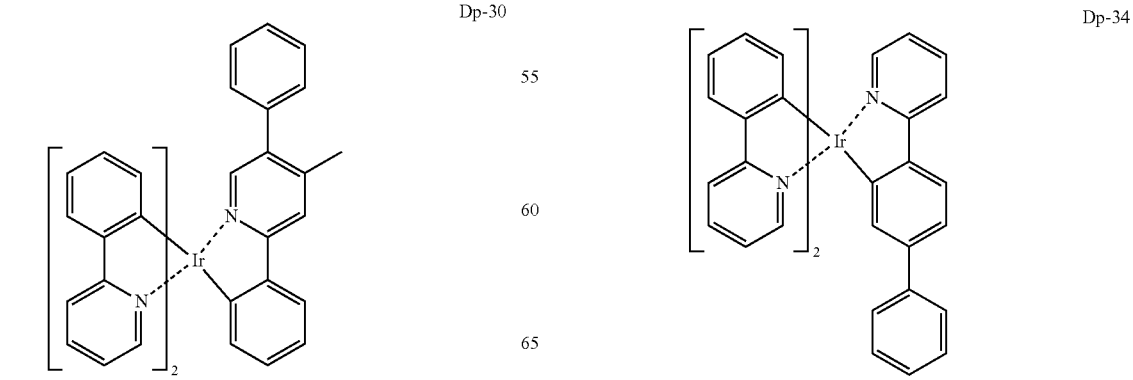

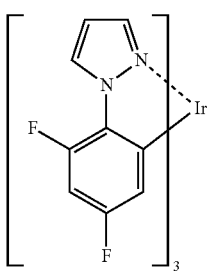

Dp-35

The electron transfer layer is a layer that receives electrons from an electron injection layer and transfers the electrons to a light emitting layer, and as the electron transfer material, materials capable of favorably receiving electrons from a second electrode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a second electrode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a second electrode and may be generally formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification may be a top-emission type, a bottom-emission type or a dual-emission type depending on the materials used.

Methods for preparing the compound of Chemical Formula 1 and manufacturing of an organic light emitting device using the same will be specifically described in the following examples. However, the following examples are for illustrative purposes only, and the scope of the present disclosure is not limited thereby.

The compound of the present disclosure was prepared using a Buchwald-Hartwig coupling reaction, a Heck coupling reaction, a Suzuki coupling reaction and the like as a typical reaction, and evaluations on the device were progressed after purifying and the sublimation purifying all the compounds.

PREPARATION EXAMPLE 1

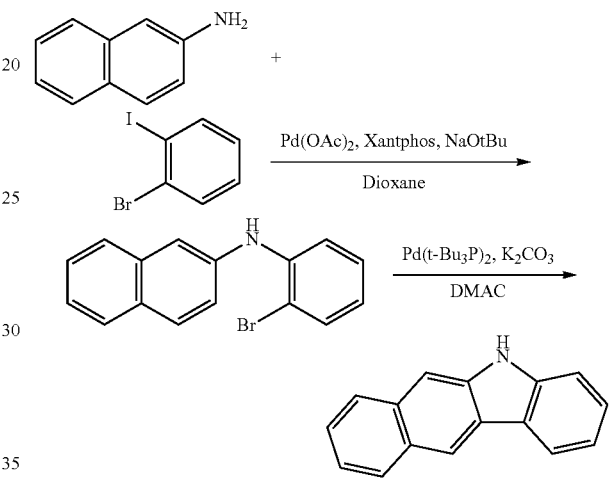

1) Preparation of Chemical Formula a-1

Naphthalen-2-amine (300.0 g, 1.0 eq.), 1-bromo-2-iodobenzene (592.7 g, 1.0 eq.), NaOtBu (302.0 g, 1.5 eq.), Pd(OAc)$_2$ (4.70 g, 0.01 eq.) and Xantphos (12.12 g, 0.01 eq.) were dissolved in 1,4-dioxane (5 L), and the result was stirred under reflux. When the reaction was terminated after 3 hours, the solvent was removed under vacuum. After that, the result was completely dissolved in ethyl acetate, washed with water, and then approximately 70% of the solvent was removed under vacuum again. Under reflux again, crystals were dropped while adding hexane thereto, and the result was cooled and then filtered. This went through column chromatography to obtain Compound a-1 (443.5 g, yield 71%). [M+H]=299

2) Preparation of Chemical Formula a (5H-benzo[b]carbazole)

Pd(t-Bu$_3$P)$_2$ (8.56 g, 0.01 eq.) and K$_2$CO$_3$ (463.2 g, 2.00 eq.) were added to Chemical Formula a-1 (443.5 g, 1.0 eq.) in dimethylacetamide (4 L), and the result was stirred under reflux. After 3 hours, the reaction material was poured into water to drop crystals, and the result was filtered. The filtered solids were completely dissolved in 1,2-dichlorobenzene, then washed with water, and the product-dissolved solution was vacuum concentrated to drop crystals, and the result was cooled and then filtered. This was purified using column chromatography to obtain Chemical Formula a (5H-benzo[b]carbazole) (174.8 g, yield 48%). [M+H]=218

FIG. 3 is a graph showing an 1H-NMR value of Chemical Formula a, and FIG. 4 is a graph showing an MS value of Chemical Formula a.

PREPARATION EXAMPLE 2

Preparation of Chemical Formula b (13H-dibenzo[a,h]carbazole)

13H-dibenzo[a,h]carbazole was synthesized using the same method as the preparation method of Chemical Formula a except that 2-bromo-1-iodonaphthalene was used instead of 1-bromo-2-iodobenzene.

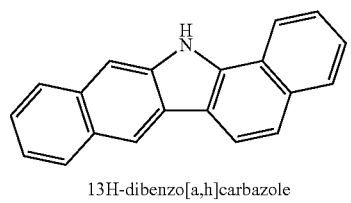 [SMILES: c1ccc2cc3c(cc2c1)[nH]c1c2ccccc2ccc31]

13H-dibenzo[a,h]carbazole

PREPARATION EXAMPLE 3

Preparation of Chemical Formula c (6H-dibenzo[b,h]carbazole)

6H-dibenzo[b,h]carbazole was synthesized using the same method as the preparation method of Chemical Formula a except that 2,3-dibromonaphthalene was used instead of 1-bromo-2-iodobenzene.

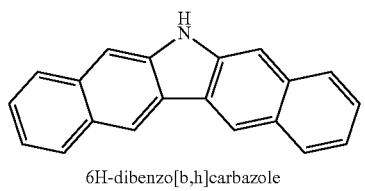 [SMILES: c1ccc2cc3c(cc2c1)[nH]c1cc2ccccc2cc13]

6H-dibenzo[b,h]carbazole

PREPARATION EXAMPLE 4

Preparation of Chemical Formula d (7H-dibenzo[b,g]carbazole)

7H-dibenzo[b,g]carbazole was synthesized using the same method as the preparation method of Chemical Formula a except that 1-bromo-2-iodonaphthalene was used instead of 1-bromo-2-iodobenzene.

FIG. 5 is a graph showing an 1H-NMR value of Chemical Formula d.

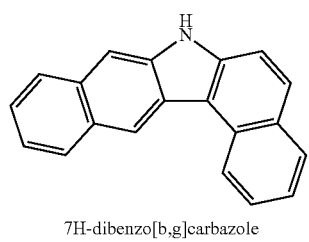 [SMILES: c1ccc2cc3c(cc2c1)[nH]c1ccc2ccccc2c13]

7H-dibenzo[b,g]carbazole

SYNTHESIS EXAMPLE 1

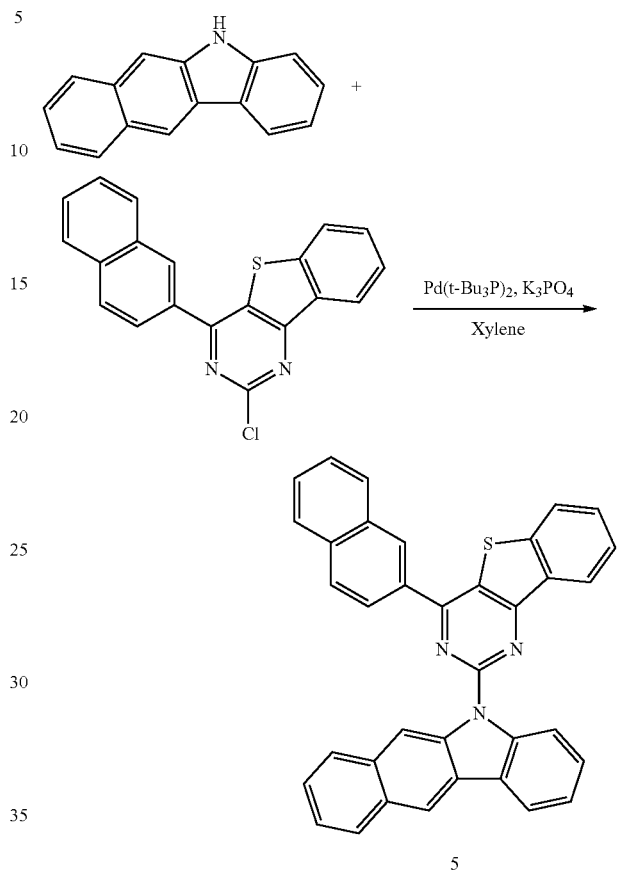

Chemical Formula a (10.0 g, 1.0 eq.), 2-chloro-4-(naphthalen-2-yl)benzo[4,5]thieno[3,2-d]pyrimidine (17.55 g, 1.1 eq.), $K_3PO_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 5 (21.12 g, yield 87%). [M+H]=528

FIG. 6 is a graph showing an 1H-NMR value of Chemical Formula 5.

SYNTHESIS EXAMPLE 2

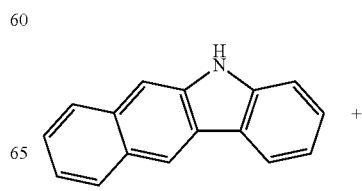

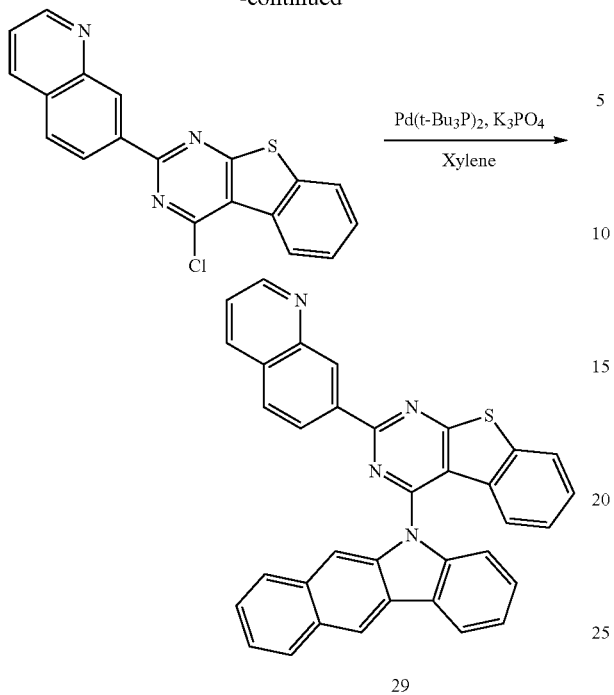

29

Chemical Formula a (10.0 g, 1.0 eq.), 4-chloro-2-(quinolin-7-yl)benzo[4,5]thieno[2,3-d]pyrimidine (17.60 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 29 (17.27 g, yield 71%). [M+H]=529

SYNTHESIS EXAMPLE 3

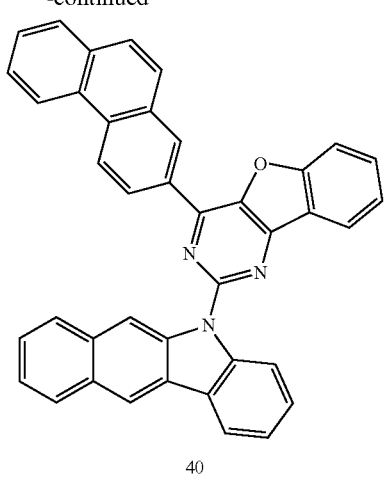

40

Chemical Formula a (10.0 g, 1.0 eq.), 2-chloro-4-(phenanthren-2-yl)benzofuro[3,2-d]pyrimidine (19.28 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 40 (18.87 g, yield 73%). [M+H]=562

FIG. 7 is a graph showing an 1H-NMR value of Chemical Formula 40.

SYNTHESIS EXAMPLE 4

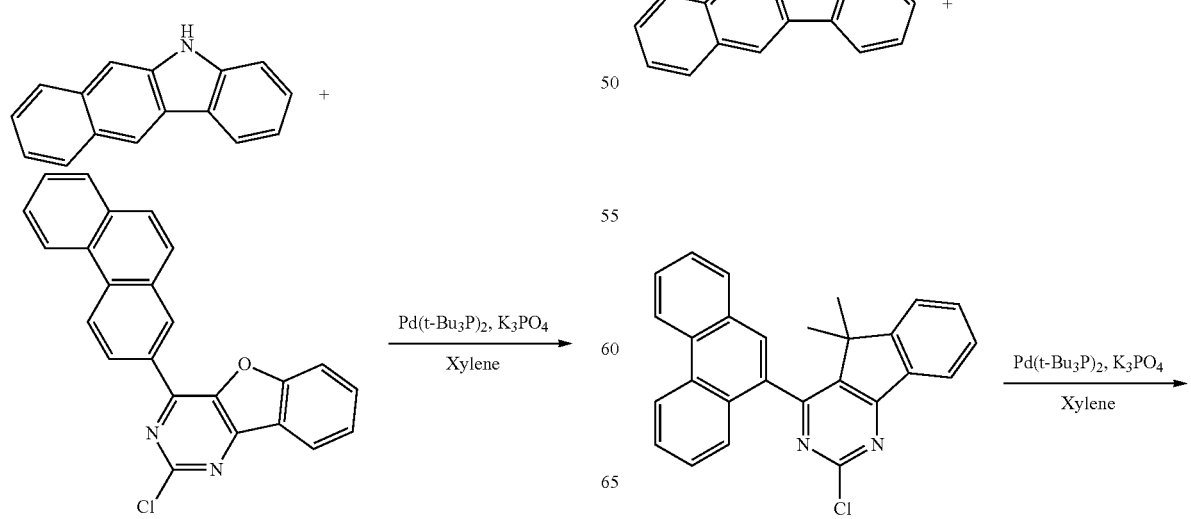

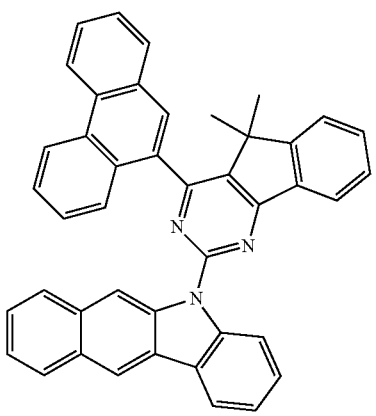

42

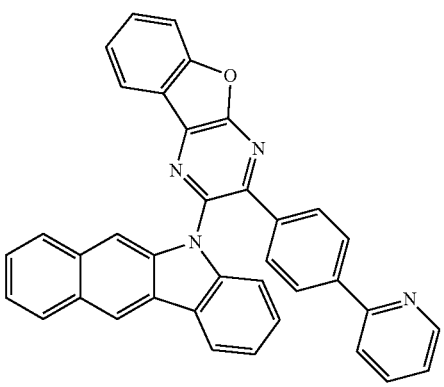

43

Chemical Formula a (10.0 g, 1.0 eq.), 2-chloro-5,5-dimethyl-4-(phenanthren-9-yl)-5H-indeno[1,2-d]pyrimidine (20.60 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 42 (18.93 g, yield 70%). [M+H]=588

Chemical Formula a (10.0 g, 1.0 eq.), 2-chloro-3-(4-(pyridin-2-yl)phenyl)benzofuro[2,3-b]pyrazine (18.11 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 43 (15.86 g, yield 64%). [M+H]=539

SYNTHESIS EXAMPLE 5

SYNTHESIS EXAMPLE 6

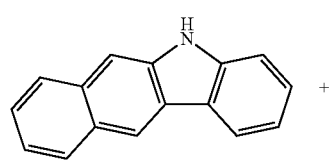

+

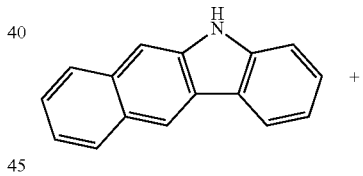

+

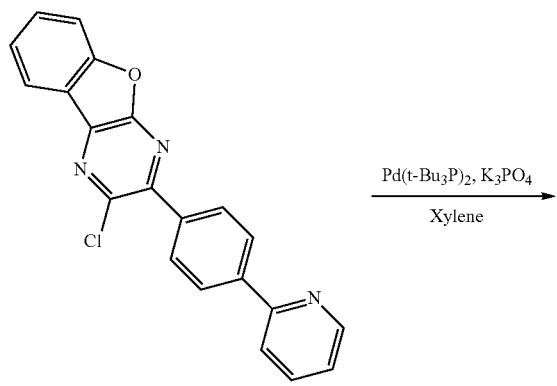

Pd(t-Bu₃P)₂, K₃PO₄
———————→
Xylene

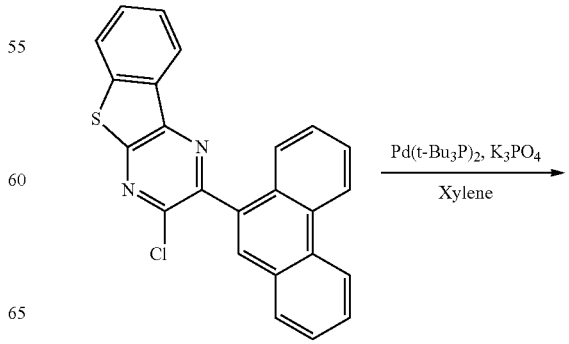

Pd(t-Bu₃P)₂, K₃PO₄
———————→
Xylene

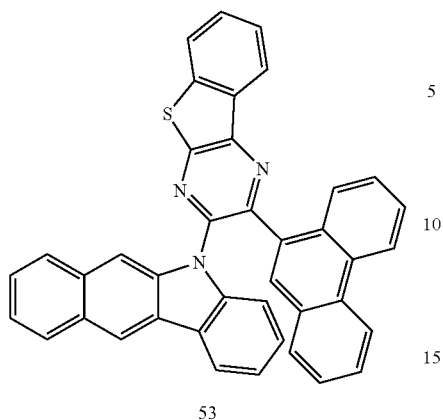

53

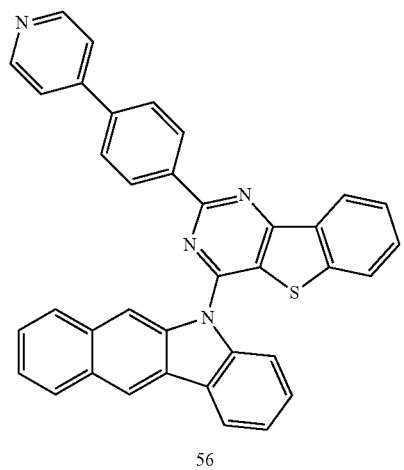

56

Chemical Formula a (10.0 g, 1.0 eq.), 3-chloro-2-(phenanthren-9-yl)benzothieno[2,3-b]pyrazine (20.09 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 53 (16.48 g, yield 62%). [M+H]=578

SYNTHESIS EXAMPLE 7

Chemical Formula a (10.0 g, 1.0 eq.), 4-chloro-2-(4-(pyridin-4-yl)phenyl)benzo[4,5]thieno[3,2-d]pyrimidine (18.92 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 56 (16.59 g, yield 65%). [M+H]=555

SYNTHESIS EXAMPLE 8

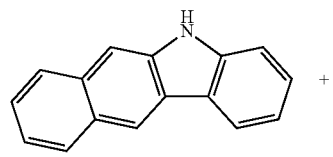 +

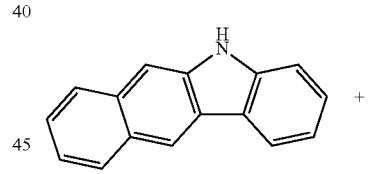 +

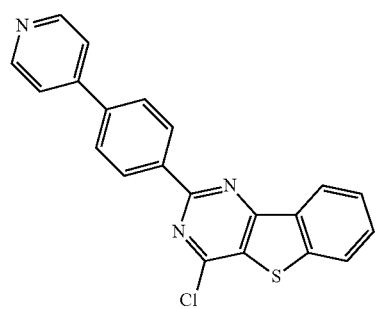

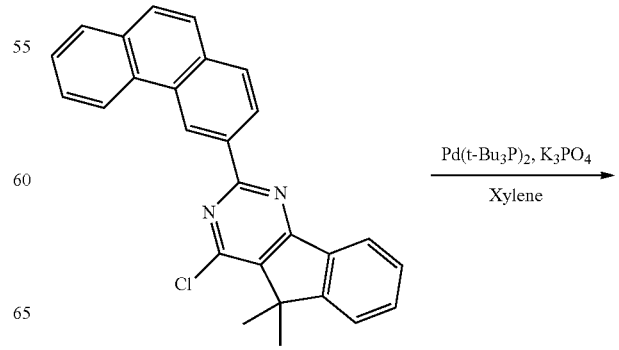

367
-continued

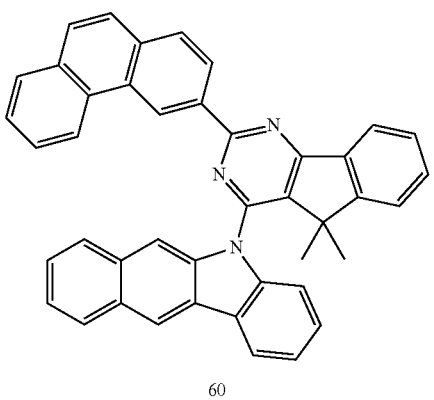

60

368
-continued

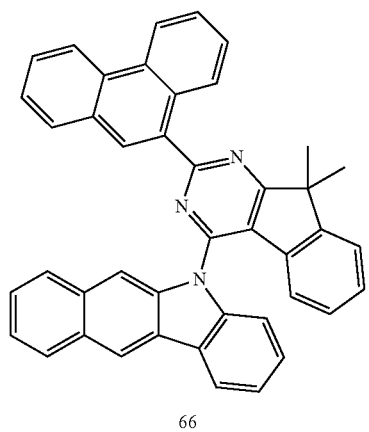

66

Chemical Formula a (10.0 g, 1.0 eq.), 4-chloro-5,5-dimethyl-2-(phenanthren-3-yl)-5H-indeno[1,2-d]pyrimidine (20.60 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 60 (16.50 g, yield 61%). [M+H]=588

SYNTHESIS EXAMPLE 9

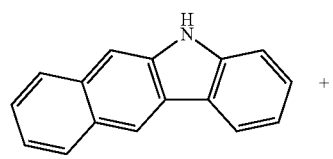

Chemical Formula a (10.0 g, 1.0 eq.), 4-chloro-9,9-dimethyl-2-(phenanthren-9-yl)-9H-indeno[2,1-d]pyrimidine (20.60 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 66 (17.31 g, yield 64%). [M+H]=588

SYNTHESIS EXAMPLE 10

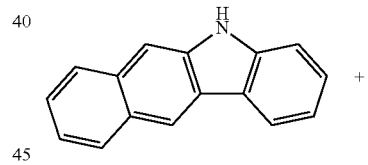

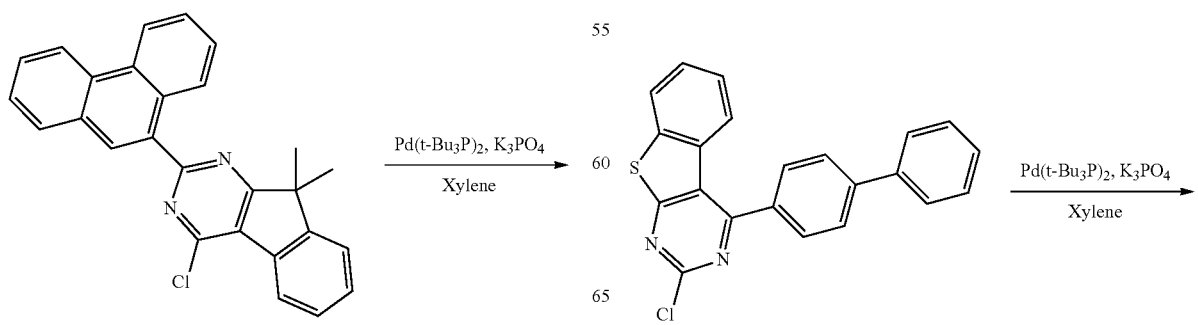

-continued

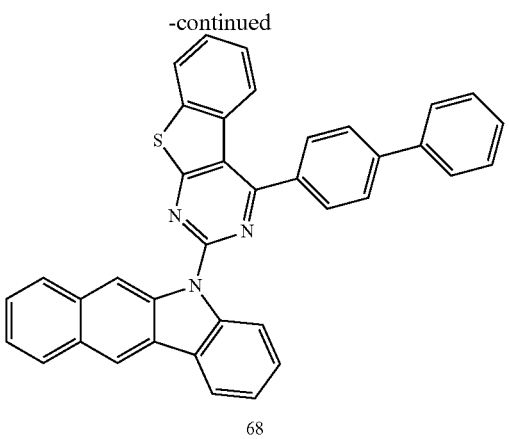

68

Chemical Formula a (10.0 g, 1.0 eq.), 4-([1,1'-biphenyl]-4-yl)-2-chlorobenzo[4,5]thieno[2,3-d]pyrimidine (16.59 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 68 (17.07 g, yield 67%). [M+H]=554

SYNTHESIS EXAMPLE 11

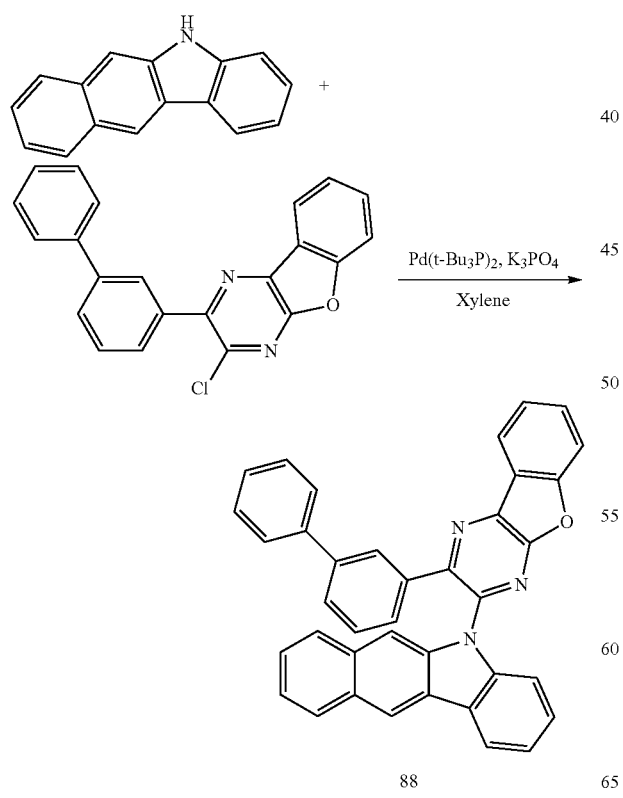

88

Chemical Formula a (10.0 g, 1.0 eq.), 2-([1,1'-biphenyl]-3-yl)-3-chlorobenzofuro[2,3-b]pyrazine (18.06 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 88 (15.58 g, yield 63%). [M+H]=538

SYNTHESIS EXAMPLE 12

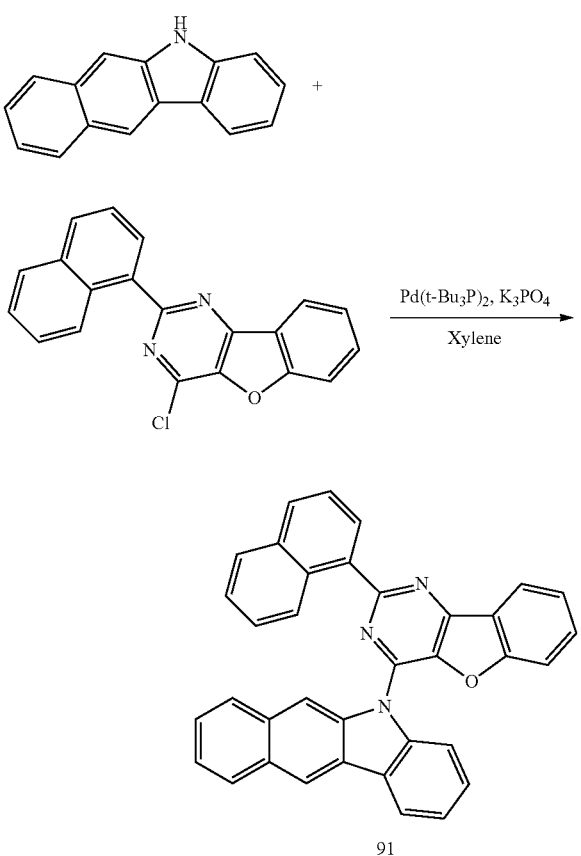

91

Chemical Formula a (10.0 g, 1.0 eq.), 4-chloro-2-(naphthalen-1-yl)benzo[4,5]furo[3,2-d]pyrimidine (16.74 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 91 (15.77 g, yield 67%). [M+H]=512

SYNTHESIS EXAMPLE 13

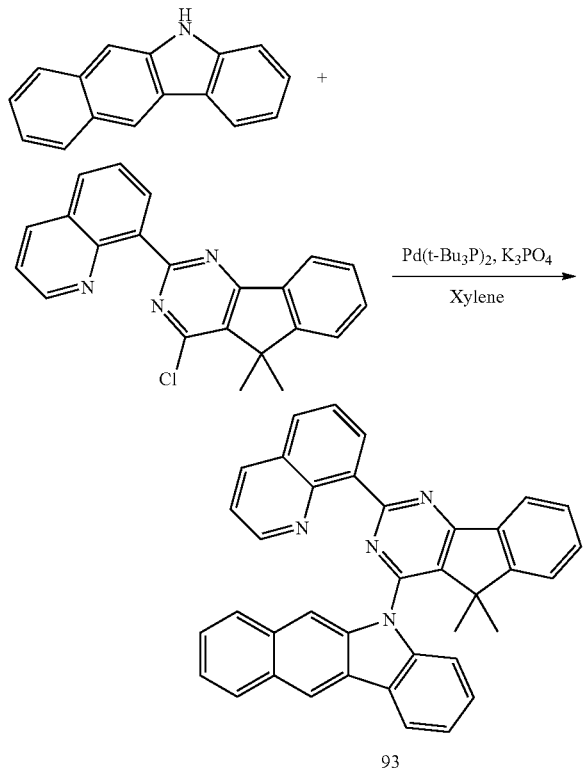

93

Chemical Formula a (10.0 g, 1.0 eq.), 4-chloro-5,5-dimethyl-2-(quinolin-8-yl)-5H-indeno[1,2-d]pyrimidine (18.11 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 93 (16.11 g, yield 65%). [M+H]=539

SYNTHESIS EXAMPLE 14

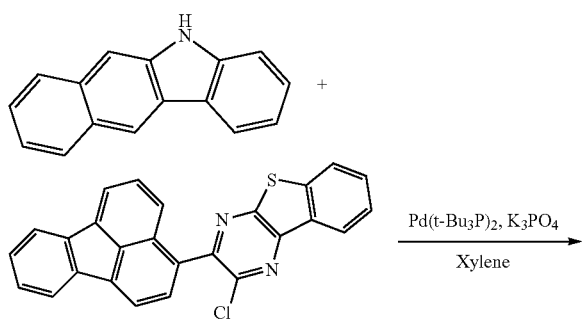

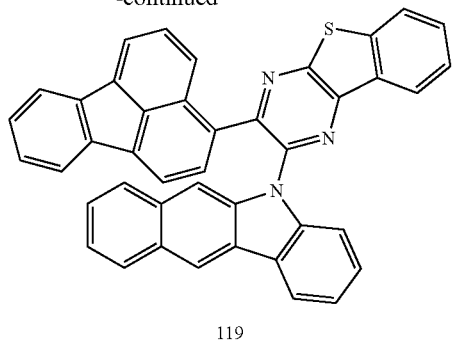

119

Chemical Formula a (10.0 g, 1.0 eq.), 2-chloro-3-(fluoranthen-3-yl)benzo[4,5]thieno[2,3-b]pyrazine (21.30 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 119 (17.72 g, yield 64%). [M+H]=602

SYNTHESIS EXAMPLE 15

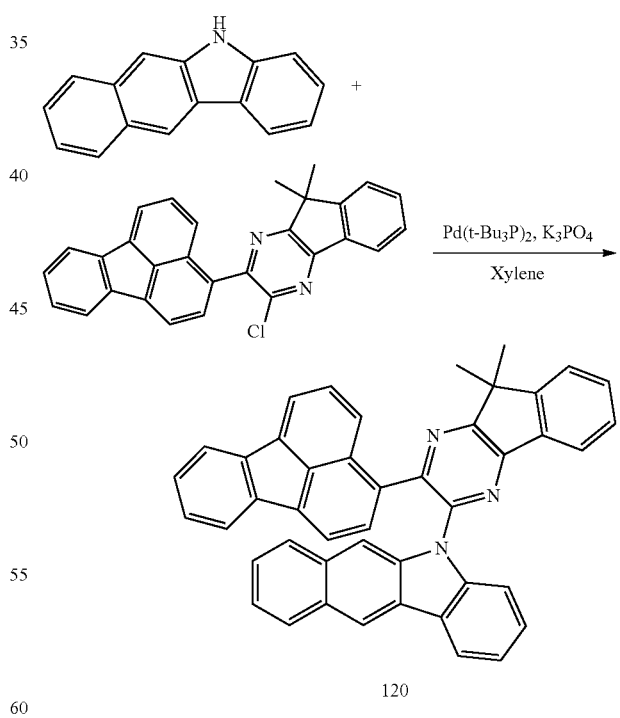

120

Chemical Formula a (10.0 g, 1.0 eq.), 3-chloro-2-(fluoranthen-3-yl)-9,9-dimethyl-9H-indeno[1,2-b]pyrazine (21.81 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 120 (17.17 g, yield 61%). [M+H]=612

SYNTHESIS EXAMPLE 16

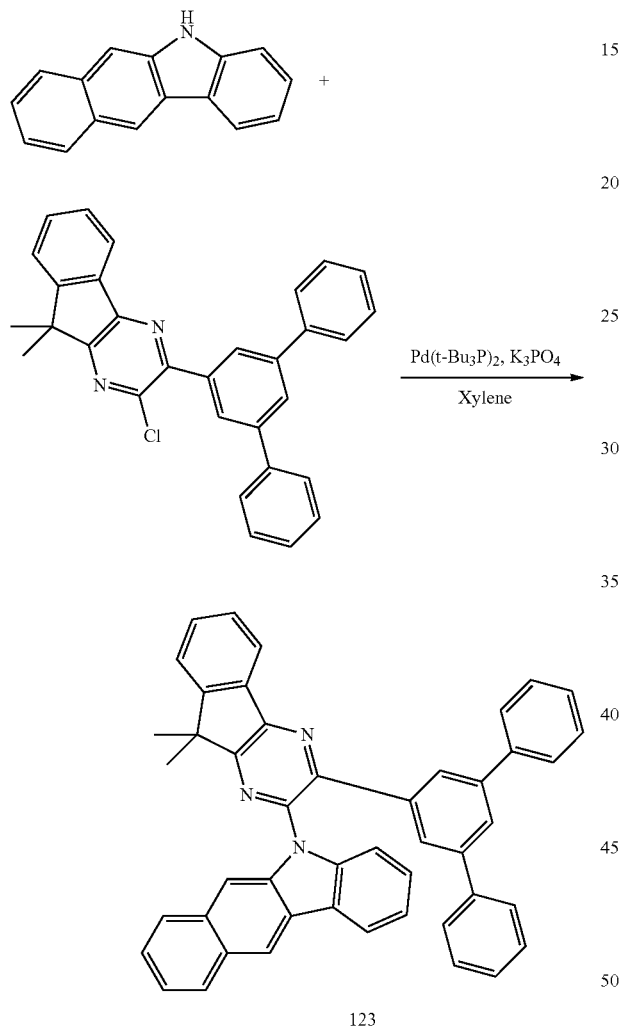

123

Chemical Formula a (10.0 g, 1.0 eq.), 3-([1,1':3',1''-terphenyl]-5'-yl)-2-chloro-9,9-dimethyl-9H-indeno[1,2-b]pyrazine (23.23 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 123 (18.84 g, yield 64%). [M+H]=640

SYNTHESIS EXAMPLE 17

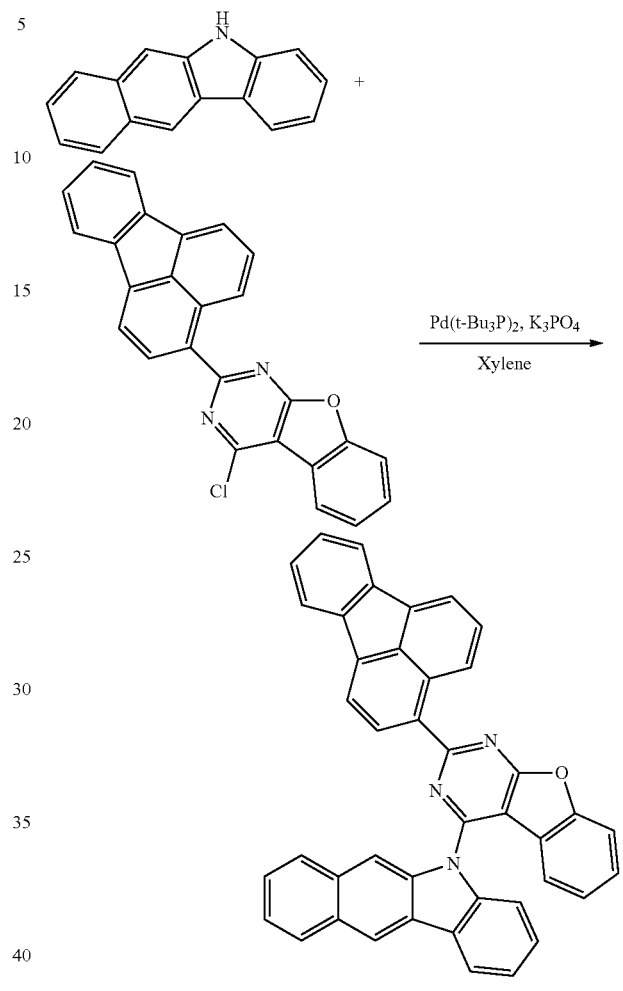

130

Chemical Formula a (10.0 g, 1.0 eq.), 4-chloro-2-(fluoranthen-3-yl)benzofuro[2,3-d]pyrimidine (20.49 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 130 (18.06 g, yield 67%). [M+H]=586

SYNTHESIS EXAMPLE 18

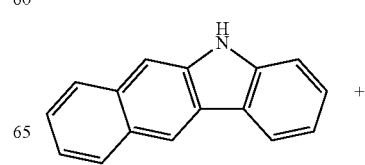

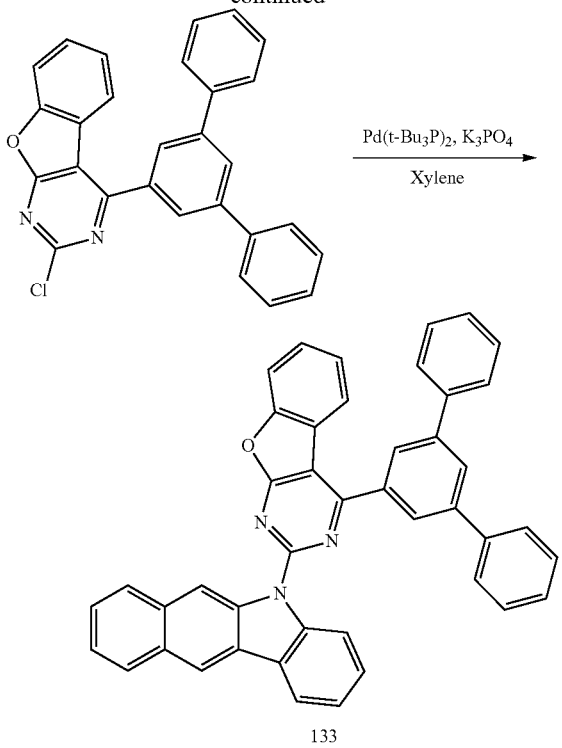

133

Chemical Formula a (10.0 g, 1.0 eq.), 4-([1,1':3',1''-terphenyl]-5'-yl)-2-chlorobenzofuro[2,3-d]pyrimidine (21.91 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 133 (18.36 g, yield 65%). [M+H]=614

SYNTHESIS EXAMPLE 19

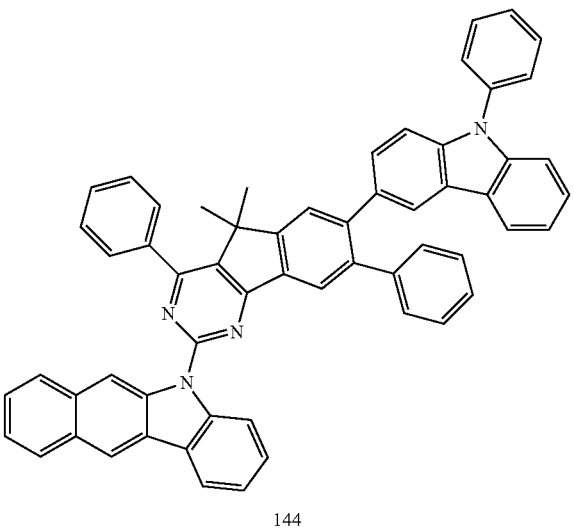

144

Chemical Formula a (10.0 g, 1.0 eq.), 2-chloro-5,5-dimethyl-4,8-diphenyl-7-(9-phenyl-9H-carbazol-3-yl)-5H-indeno[1,2-d]pyrimidine (31.60 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 144 (22.97 g, yield 62%). [M+H]=805

SYNTHESIS EXAMPLE 20

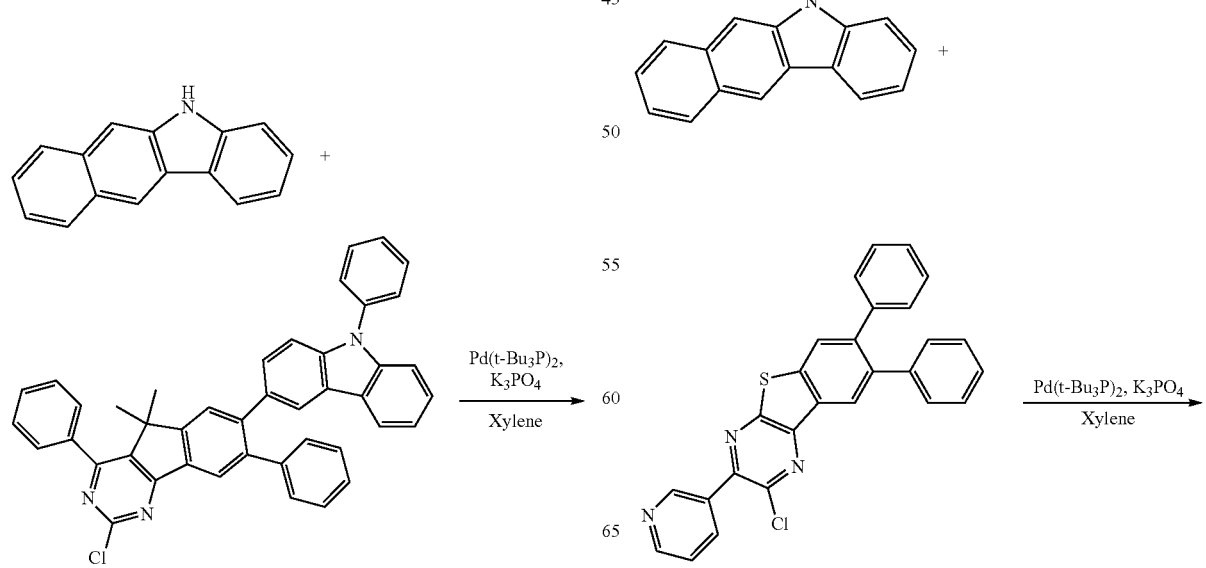

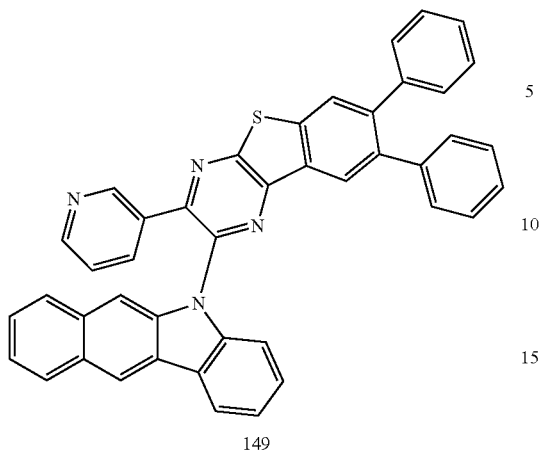

149

Chemical Formula a (10.0 g, 1.0 eq.), 2-chloro-7,8-diphenyl-3-(pyridin-3-yl)benzo[4,5]thieno[2,3-b]pyrazine (22.78 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 149 (17.41 g, yield 60%). [M+H]=631

SYNTHESIS EXAMPLE 21

167

Chemical Formula a (10.0 g, 1.0 eq.), 4-chloro-6-(naphthalen-2-yl)-2,7-diphenylbenzo[4,5]thieno[2,3-d]pyrimidine (22.73 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 167 (19.39 g, yield 62%). [M+H]=680

SYNTHESIS EXAMPLE 22

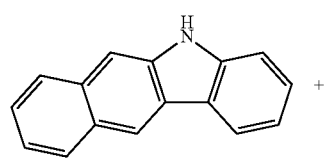 +

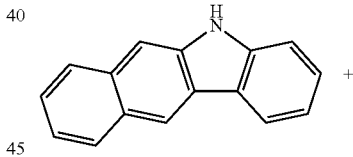 +

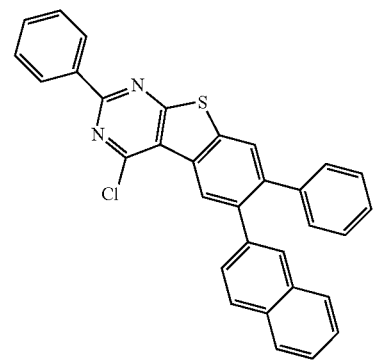

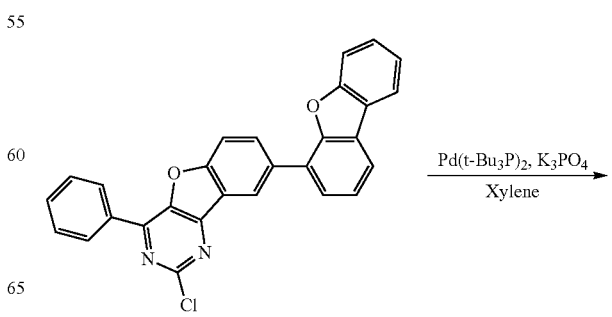

-continued

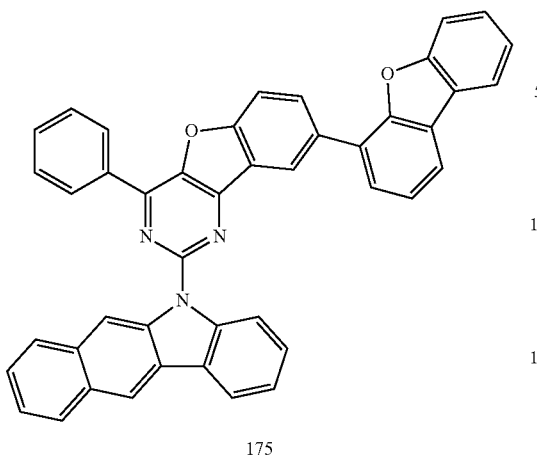

175

Chemical Formula a (10.0 g, 1.0 eq.), 2-chloro-8-(dibenzo[b,d]furan-4-yl)-4-phenylbenzofuro[3,2-d]pyrimidine (22.62 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 175 (18.48 g, yield 64%). [M+H]=628

SYNTHESIS EXAMPLE 23

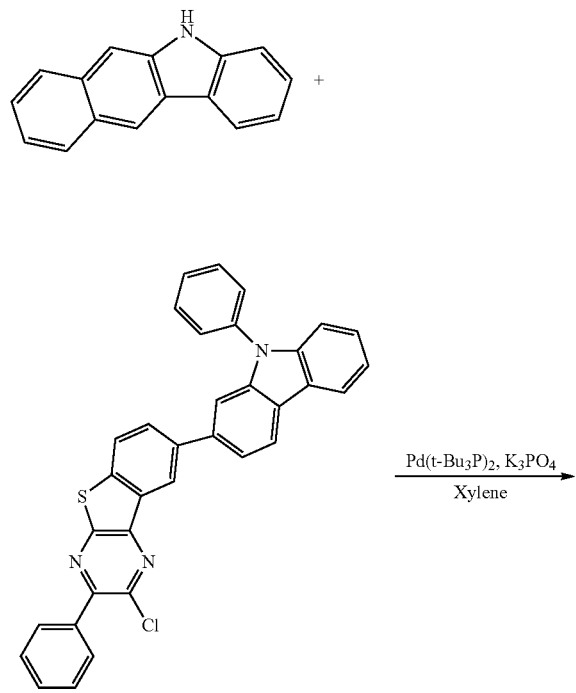

-continued

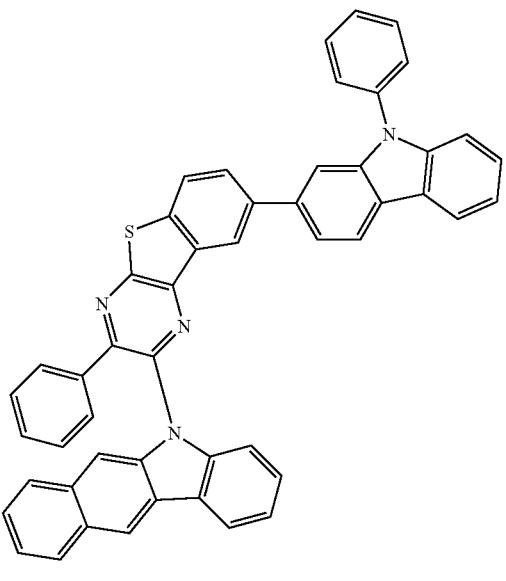

182

Chemical Formula a (10.0 g, 1.0 eq.), 2-chloro-3-phenyl-8-(9-phenyl-9H-carbazol-2-yl)benzo[4,5]thieno[2,3-b]pyrazine (27.24 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 182 (21.17 g, yield 64%). [M+H]=719

SYNTHESIS EXAMPLE 24

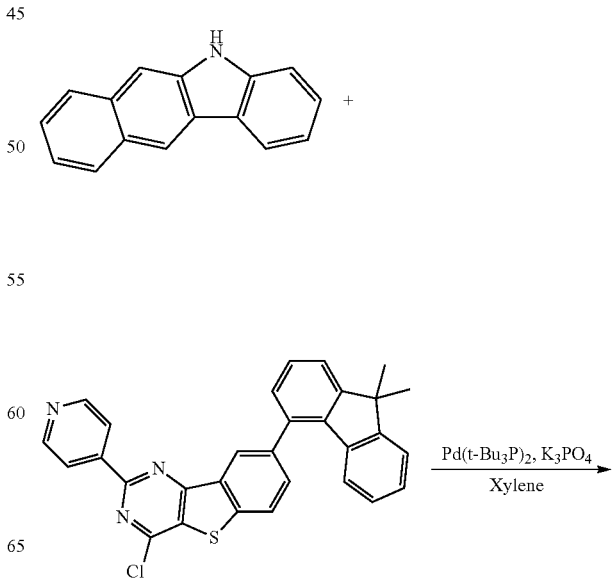

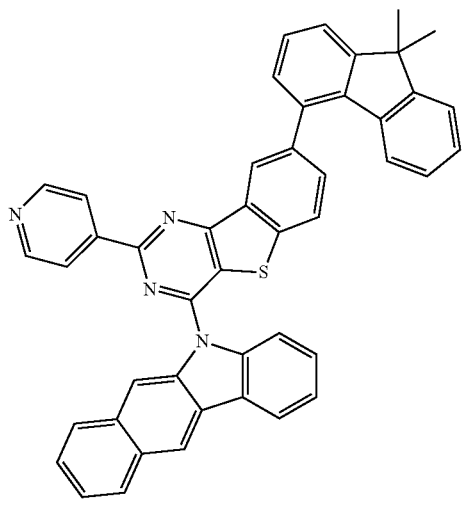

194

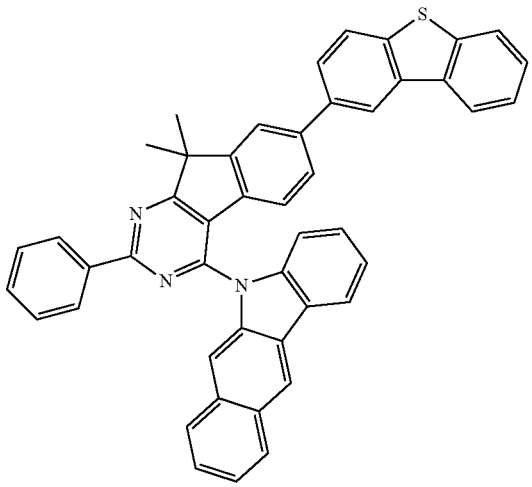

201

Chemical Formula a (10.0 g, 1.0 eq.), 4-chloro-8-(9,9-dimethyl-9H-fluoren-4-yl)-2-(pyridin-4-yl)benzo[4,5]thieno[3,2-d]pyrimidine (24.80 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 194 (19.14 g, yield 62%). [M+H]=671

SYNTHESIS EXAMPLE 25

Chemical Formula a (10.0 g, 1.0 eq.), 4-chloro-7-(dibenzo[b,d]thiophen-2-yl)-9,9-dimethyl-2-phenyl-9H-indeno[2,1-d]pyrimidine (24.75 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 201 (20.65 g, yield 67%). [M+H]=670

SYNTHESIS EXAMPLE 26

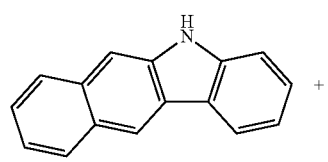

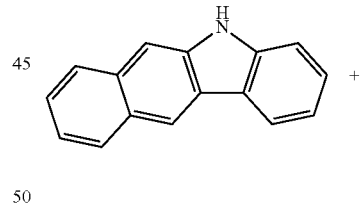

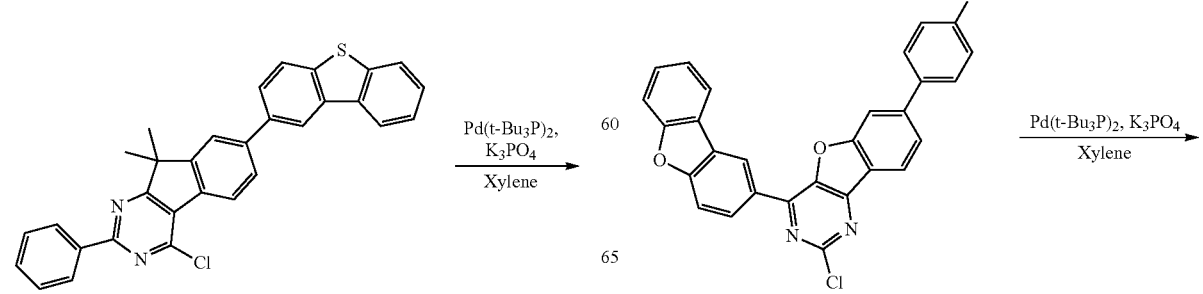

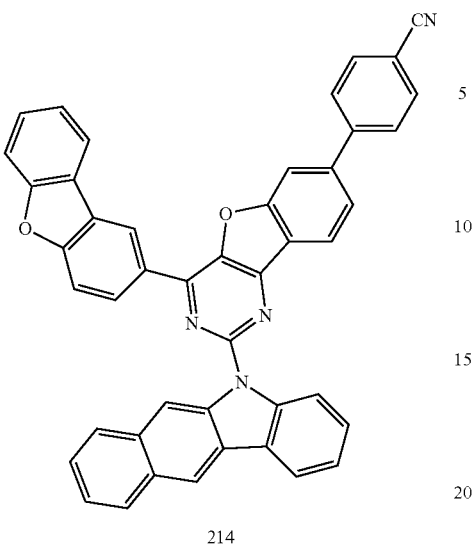

214

Chemical Formula a (10.0 g, 1.0 eq.), 4-(2-chloro-4-(dibenzo[b,d]furan-2-yl)benzofuro[3,2-d]pyrimidin-7-yl)benzonitrile (23.89 g, 1.1 eq.), $K_3PO_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 214 (19.52 g, yield 65%). [M+H]=653

SYNTHESIS EXAMPLE 27

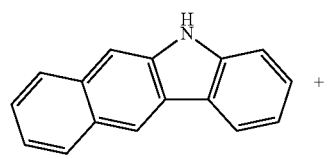

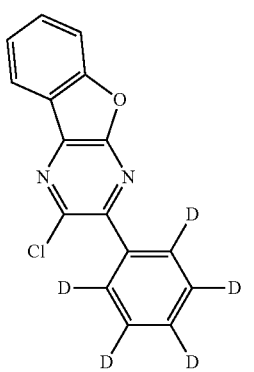

217

Chemical Formula a (10.0 g, 1.0 eq.), 2-chloro-3-(phenyl-d5)benzofuro[2,3-b]pyrazine (14.46 g, 1.1 eq.), $K_3PO_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 217 (14.81 g, yield 69%). [M+H]=467

SYNTHESIS EXAMPLE 28

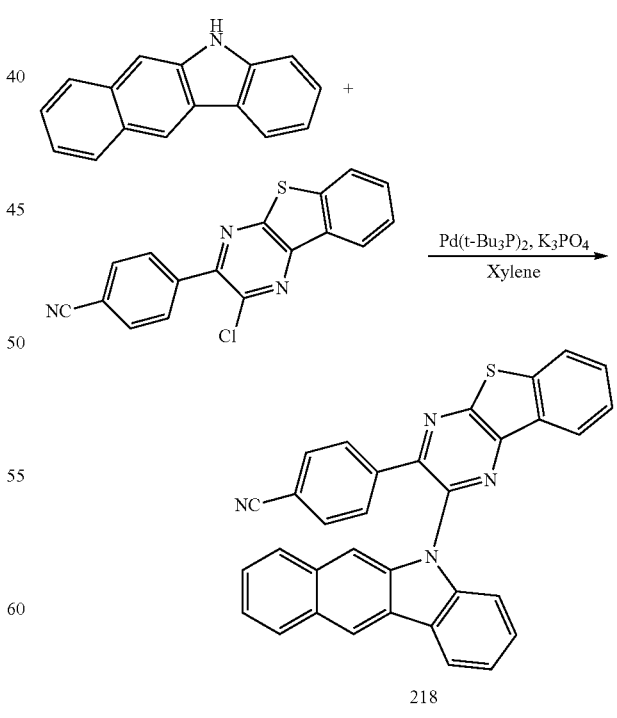

218

Chemical Formula a (10.0 g, 1.0 eq.), 4-(2-chlorobenzo[4,5]thieno[2,3-b]pyrazin-3-yl)benzonitrile (16.29 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 218 (15.73 g, yield 68%). [M+H]=503

SYNTHESIS EXAMPLE 29

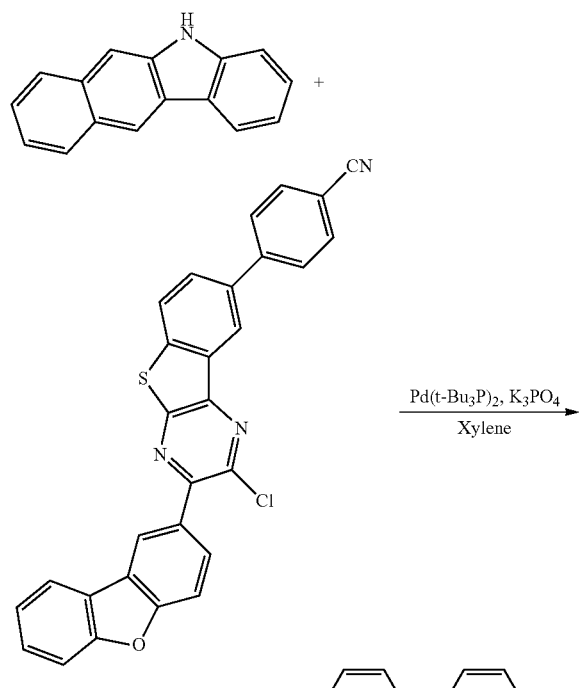

221

Chemical Formula a (10.0 g, 1.0 eq.), 4-(2-chloro-3-(dibenzo[b,d]furan-2-yl)benzo[4,5]thieno[2,3-b]pyrazin-8-yl)benzonitrile (24.80 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 221 (20.62 g, yield 67%). [M+H]=669

SYNTHESIS EXAMPLE 30

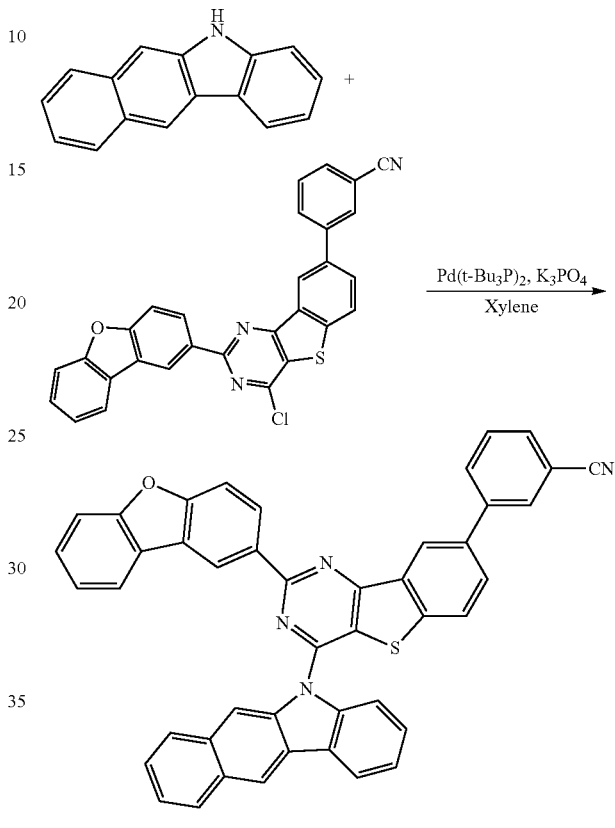

233

Chemical Formula a (10.0 g, 1.0 eq.), 3-(4-chloro-2-(dibenzo[b,d]furan-2-yl)benzo[4,5]thieno[3,2-d]pyrimidin-8-yl)benzonitrile (24.70 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 233 (20.93 g, yield 68%). [M+H]=669

SYNTHESIS EXAMPLE 31

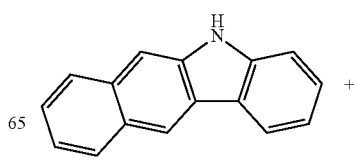

387
-continued

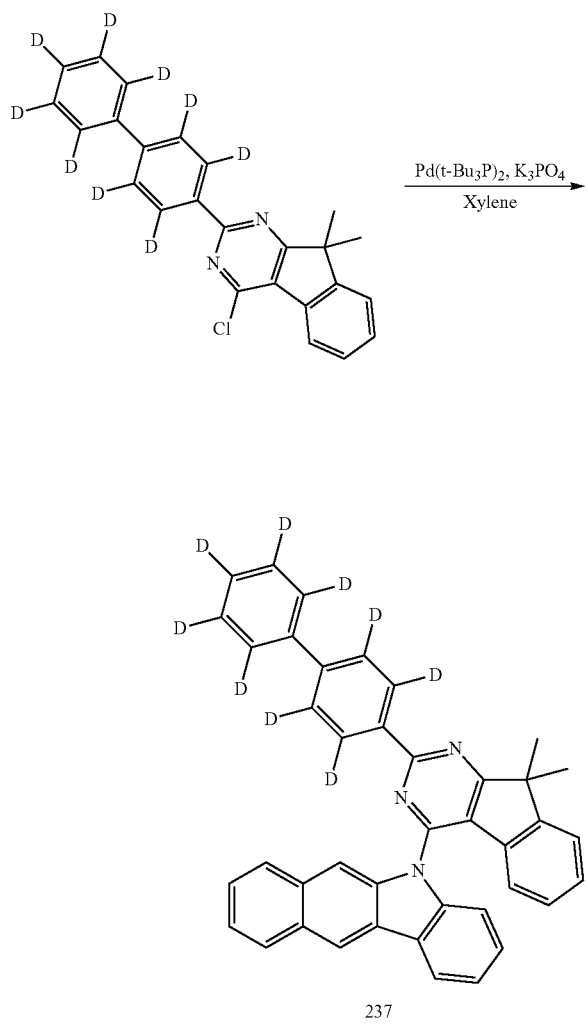

237

388
-continued

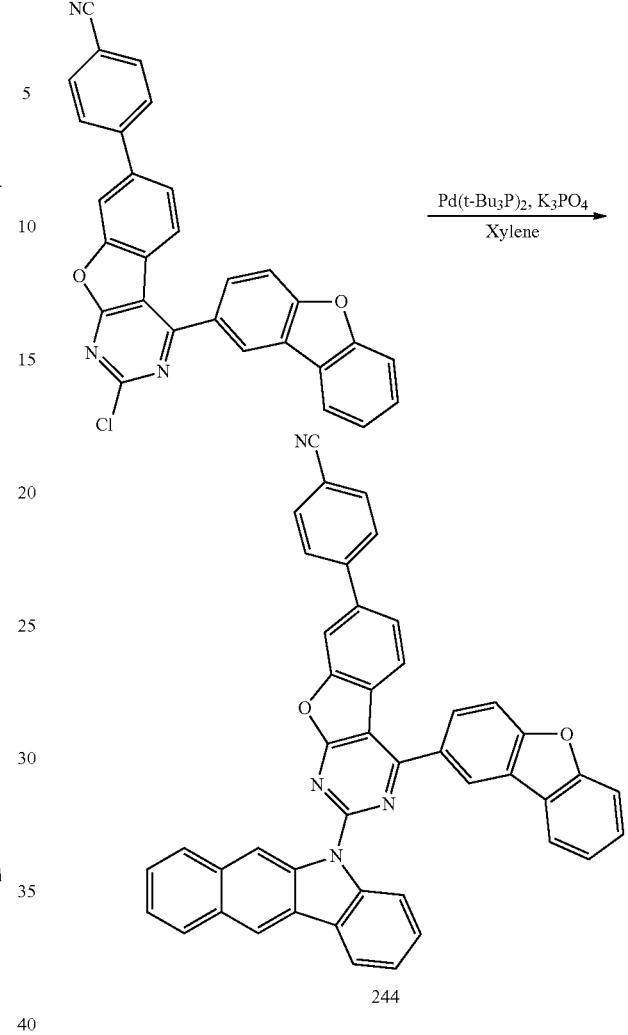

244

Chemical Formula a (10.0 g, 1.0 eq.), 2-([1,1'-biphenyl]-4-yl-d9)-4-chloro-9,9-dimethyl-9H-indeno[2,1-d]pyrimidine (19.84 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 237 (17.92 g, yield 68%). [M+H]=573

SYNTHESIS EXAMPLE 32

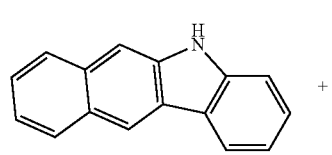

Chemical Formula a (10.0 g, 1.0 eq.), 4-(2-chloro-4-(dibenzo[b,d]furan-2-yl)benzofuro[2,3-d]pyrimidin-7-yl)benzonitrile (23.89 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 244 (19.52 g, yield 65%). [M+H]=574

SYNTHESIS EXAMPLE 33

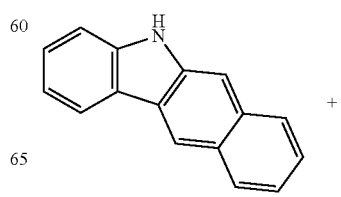

389

-continued

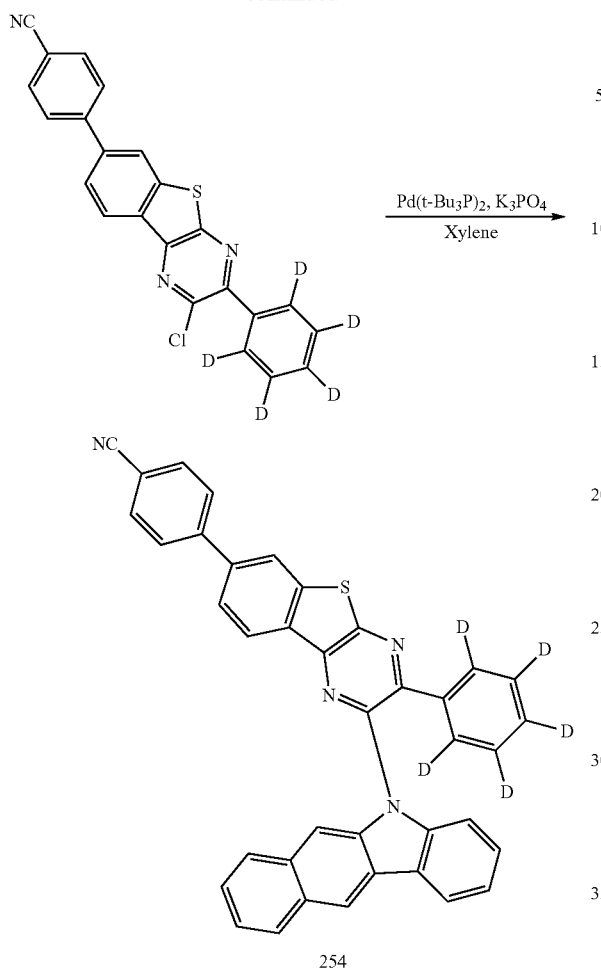

254

390

-continued

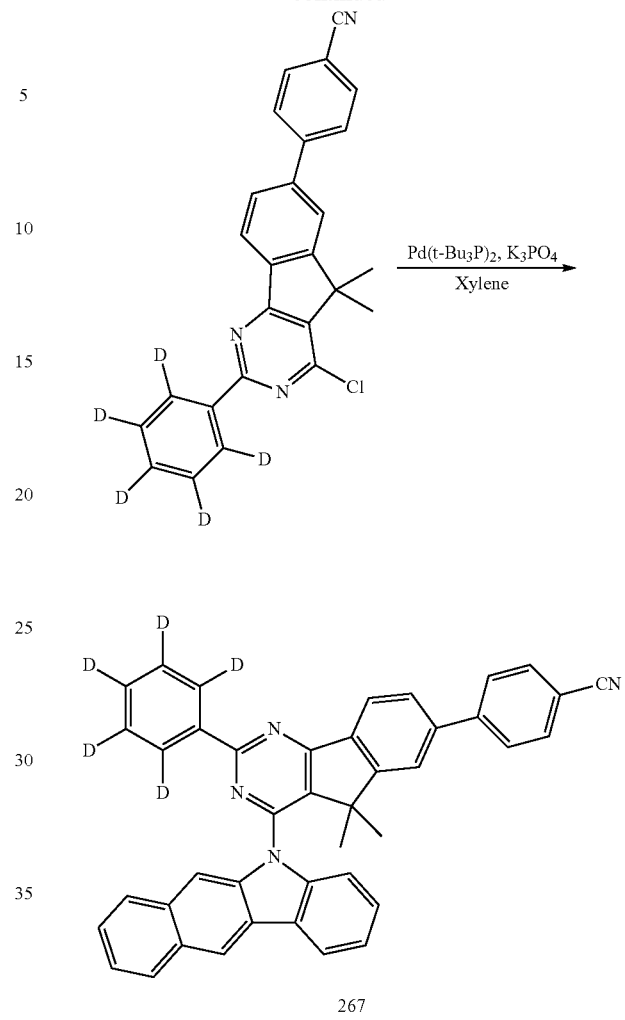

267

Chemical Formula a (10.0 g, 1.0 eq.), 4-(2-chloro-3-(phenyl-d5)benzo[4,5]thieno[2,3-b]pyrazin-7-yl)benzonitrile (20.39 g, 1.1 eq.), $K_3PO_4$ (19.53 g, 2.0 eq.) and Pd(t-$Bu_3P$)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 254 (18.00 g, yield 67%). [M+H]=584

SYNTHESIS EXAMPLE 34

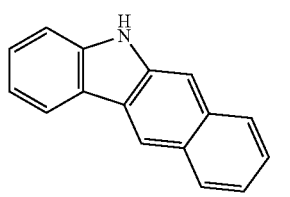 +

Chemical Formula a (10.0 g, 1.0 eq.), 4-(4-chloro-5,5-dimethyl-2-(phenyl-d5)-5H-indeno[1,2-d]pyrimidin-7-yl)benzonitrile (20.90 g, 1.1 eq.), $K_3PO_4$ (15.88 g, 2.0 eq.) and Pd(t-$Bu_3P$)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 267 (17.76 g, yield 65%). [M+H]=594

SYNTHESIS EXAMPLE 35

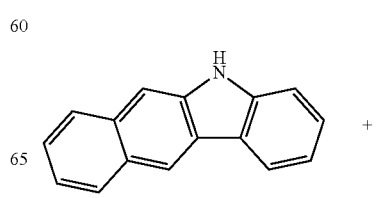 +

391

-continued

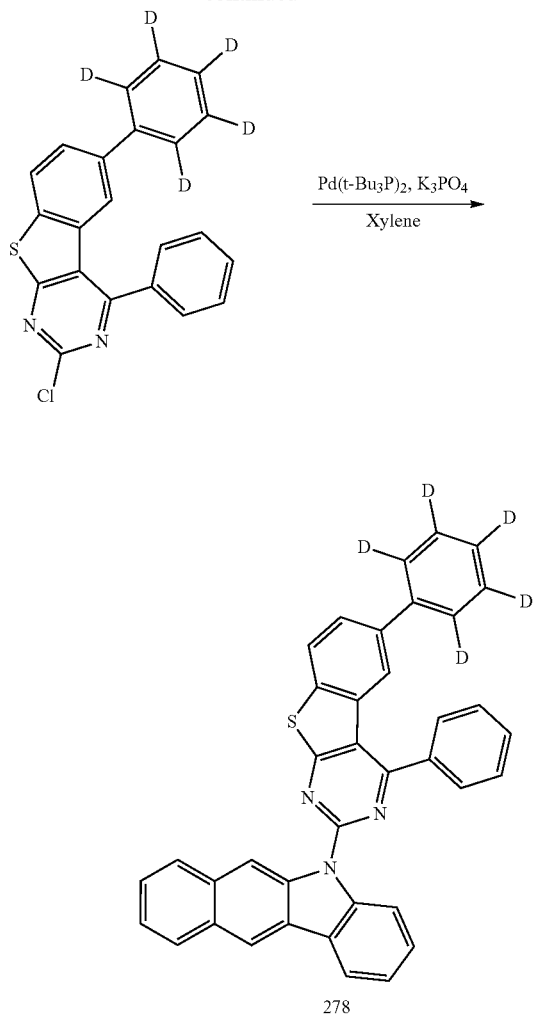

278

Chemical Formula a (10.0 g, 1.0 eq.), 2-chloro-4-phenyl-6-(phenyl-d5)benzo[4,5]thieno[2,3-d]pyrimidine (19.13 g, 1.1 eq.), K$_3$PO$_4$ (15.88 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 278 (17.48 g, yield 68%). [M+H]=559

SYNTHESIS EXAMPLE 36

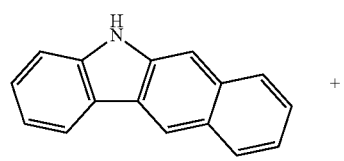

392

-continued

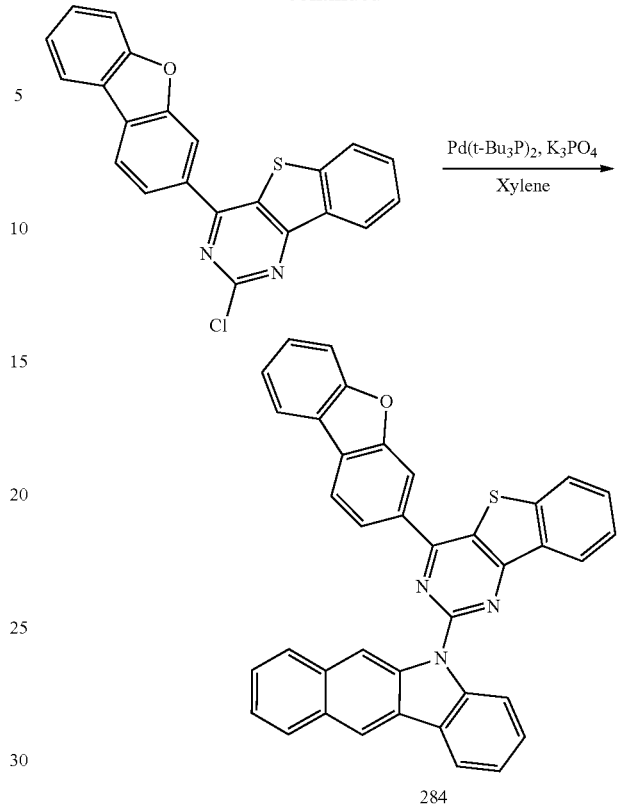

284

Chemical Formula a (10.0 g, 1.0 eq.), 2-chloro-4-(dibenzo[b,d]furan-3-yl)benzo[4,5]thieno[3,2-d]pyrimidine (19.58 g, 1.1 eq.), K$_3$PO$_4$ (15.88 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 284 (16.72 g, yield 64%). [M+H]=568

SYNTHESIS EXAMPLE 37

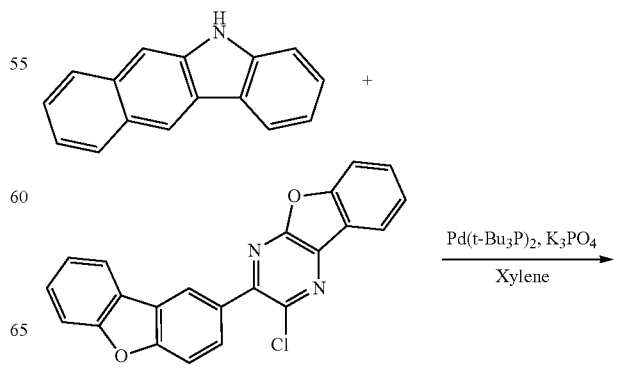

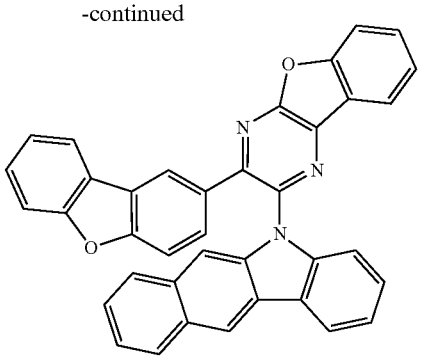

292

Chemical Formula a (10.0 g, 1.0 eq.), 2-chloro-3-(dibenzo[b,d]furan-2-yl)benzofuro[2,3-b]pyrazine (18.77 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 292 (17.01 g, yield 67%). [M+H]=552

SYNTHESIS EXAMPLE 38

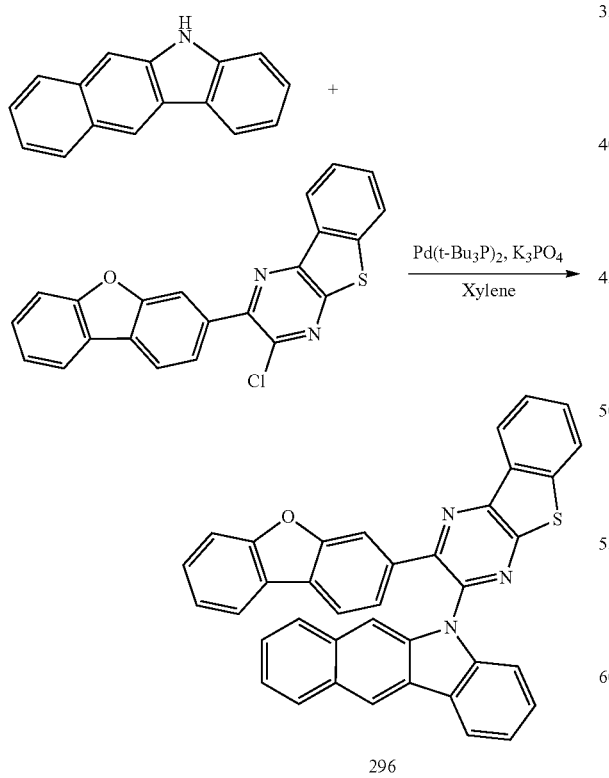

296

Chemical Formula a (10.0 g, 1.0 eq.), 3-chloro-2-(dibenzo[b,d]furan-3-yl)benzo[4,5]thieno[2,3-b]pyrazine (19.58 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 296 (16.98 g, yield 65%). [M+H]=568

SYNTHESIS EXAMPLE 39

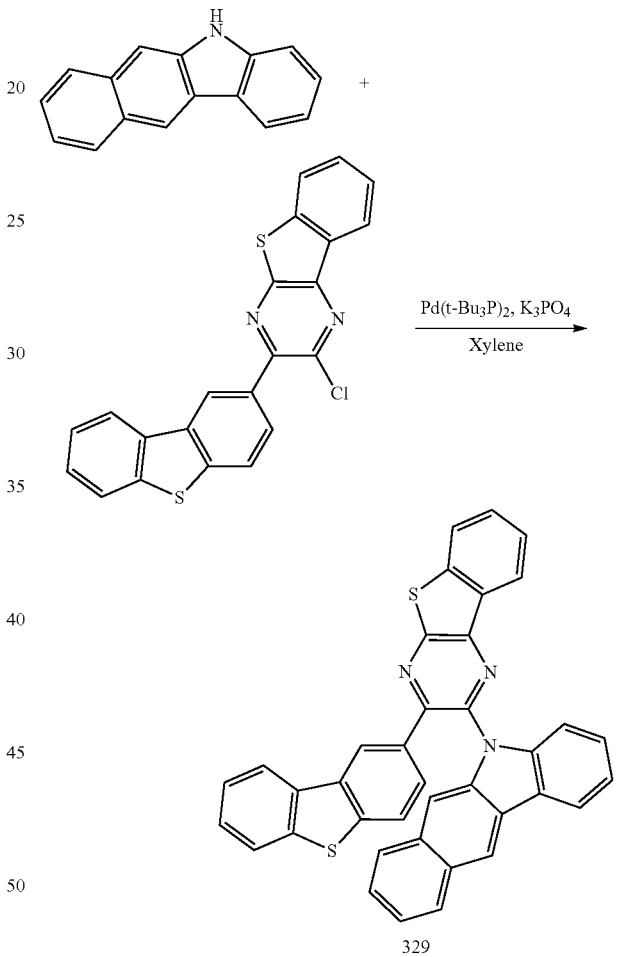

329

Chemical Formula a (10.0 g, 1.0 eq.), 2-chloro-3-(dibenzo[b,d]thiophen-2-yl)benzo[4,5]thieno[2,3-b]pyrazin (20.39 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 329 (17.73 g, yield 66%). [M+H]=584

SYNTHESIS EXAMPLE 40

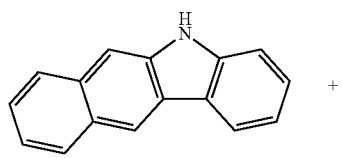

+

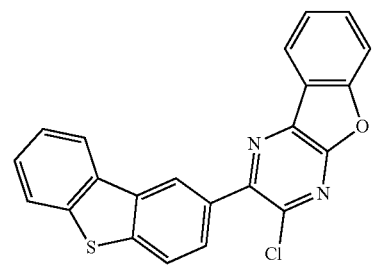

Pd(t-Bu₃P)₂, K₃PO₄ / Xylene →

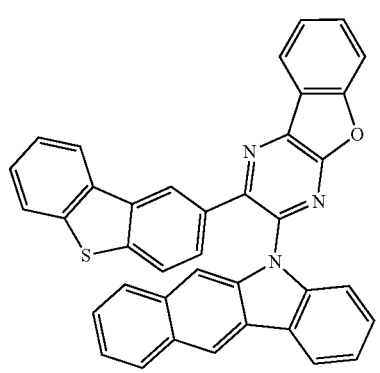

334

Chemical Formula a (10.0 g, 1.0 eq.), 3-chloro-2-(dibenzo[b,d]thiophen-2-yl)benzofuro[2,3-b]pyrazine (19.58 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 334 (17.50 g, yield 67%). [M+H]=568

SYNTHESIS EXAMPLE 41

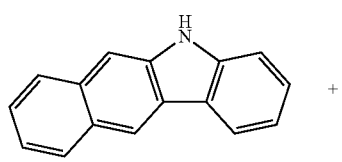

+

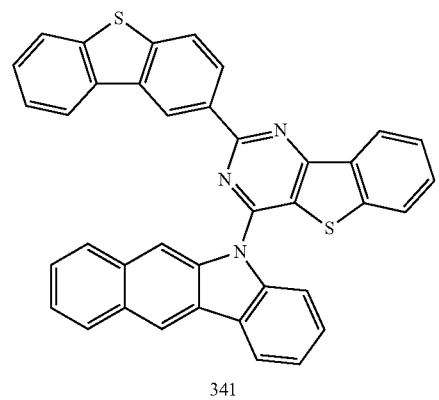

Pd(t-Bu₃P)₂, K₃PO₄ / Xylene →

341

Chemical Formula a (10.0 g, 1.0 eq.), 4-chloro-2-(dibenzo[b,d]thiophen-2-yl)benzo[4,5]thieno[3,2-d]pyrimidine (20.39 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 341 (17.46 g, yield 65%). [M+H]=584

SYNTHESIS EXAMPLE 42

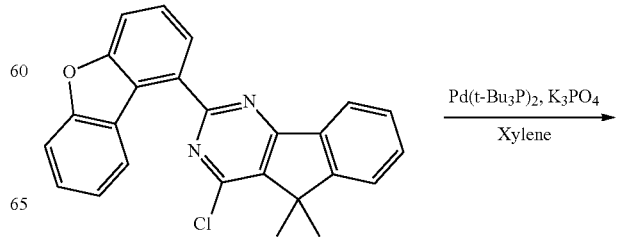

+

Pd(t-Bu₃P)₂, K₃PO₄ / Xylene →

-continued

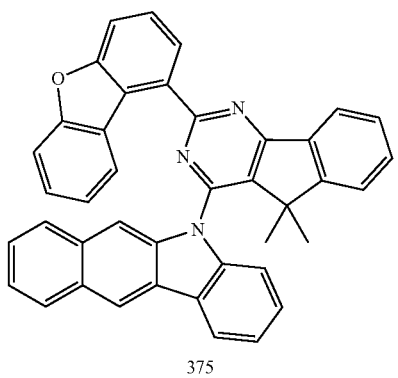

375

-continued

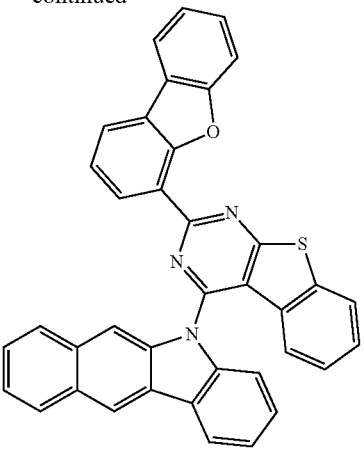

383

Chemical Formula a (10.0 g, 1.0 eq.), 4-chloro-2-(dibenzo[b,d]furan-1-yl)-5,5-dimethyl-5H-indeno[1,2-d]pyrimidine (20.09 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 375 (17.81 g, yield 67%). [M+H]=578

SYNTHESIS EXAMPLE 43

Chemical Formula a (10.0 g, 1.0 eq.), 4-chloro-2-(dibenzo[b,d]furan-4-yl)benzo[4,5]thieno[2,3-d]pyrimidine (19.58 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 383 (17.50 g, yield 67%). [M+H]=568

SYNTHESIS EXAMPLE 44

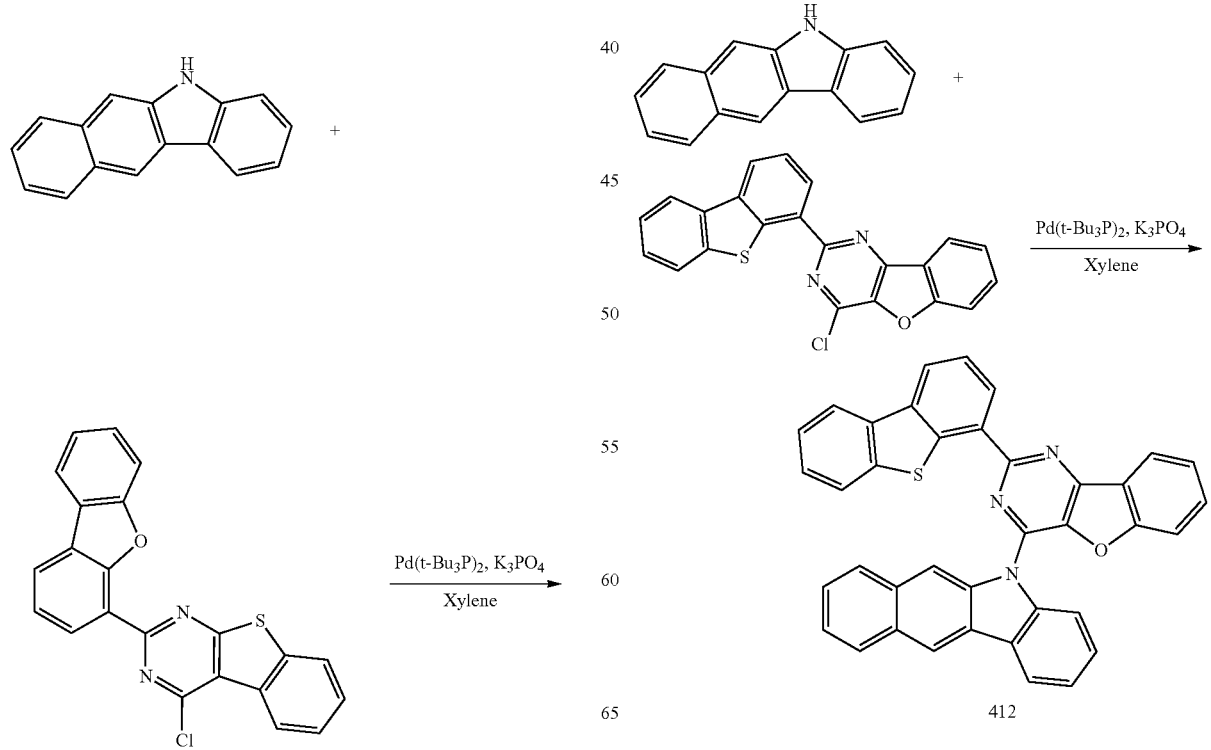

412

Chemical Formula a (10.0 g, 1.0 eq.), 4-chloro-2-(dibenzo[b,d]thiophen-4-yl)benzofuro[3,2-d]pyrimidine (17.25 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 412 (16.98 g, yield 65%). [M+H]=568

SYNTHESIS EXAMPLE 45

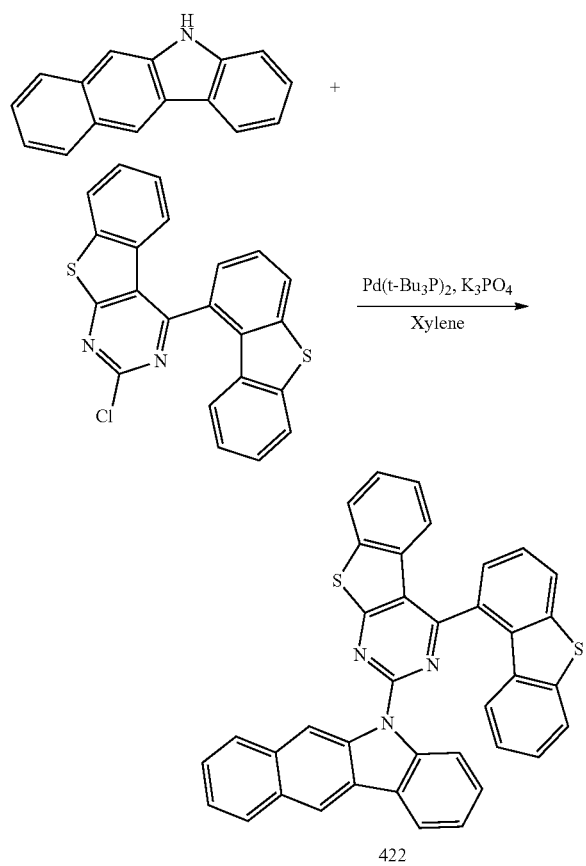

422

Chemical Formula a (10.0 g, 1.0 eq.), 2-chloro-4-(dibenzo[b,d]thiophen-1-yl)benzo[4,5]thieno[2,3-d]pyrimidine (20.39 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 422 (18.26 g, yield 68%). [M+H]=584

SYNTHESIS EXAMPLE 46

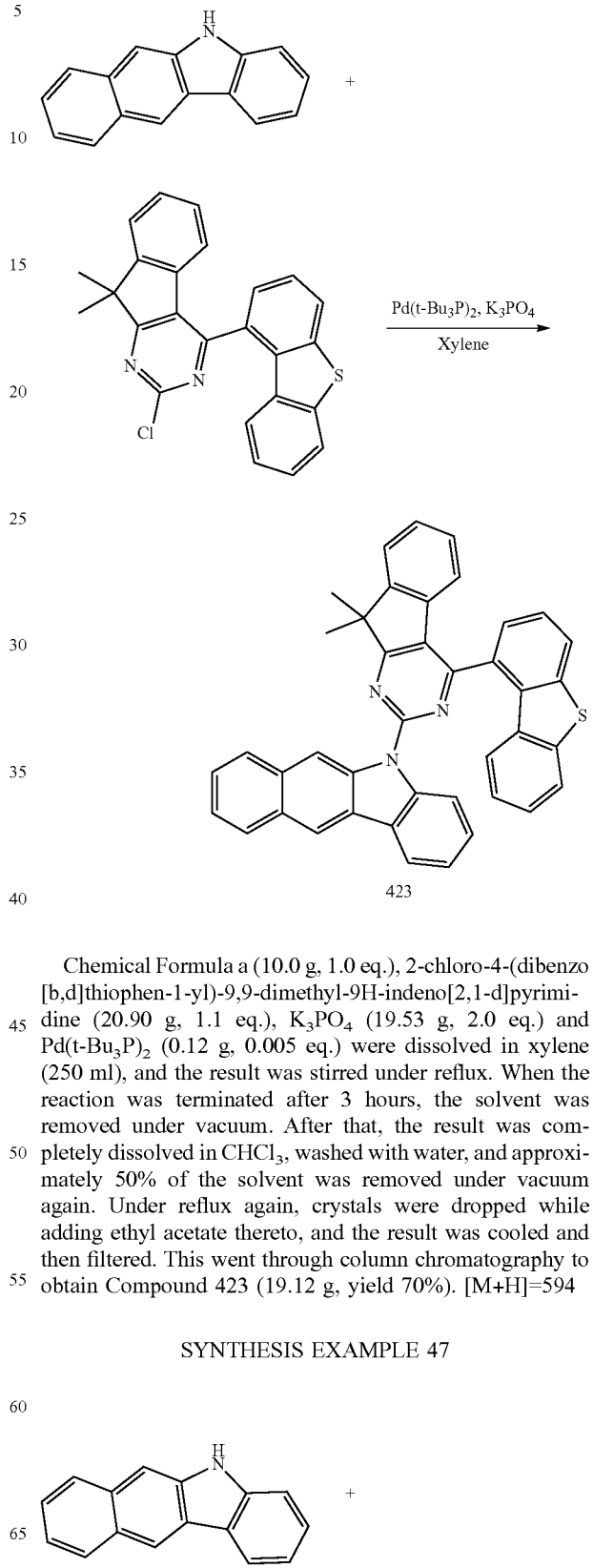

423

Chemical Formula a (10.0 g, 1.0 eq.), 2-chloro-4-(dibenzo[b,d]thiophen-1-yl)-9,9-dimethyl-9H-indeno[2,1-d]pyrimidine (20.90 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 423 (19.12 g, yield 70%). [M+H]=594

SYNTHESIS EXAMPLE 47

401
-continued

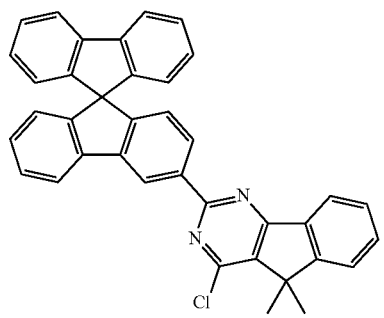

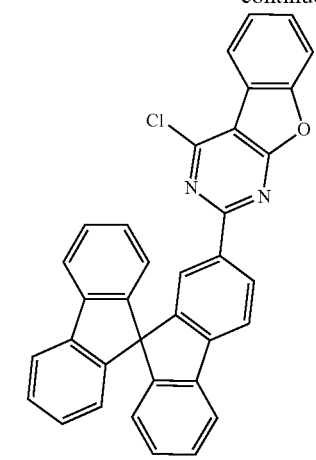

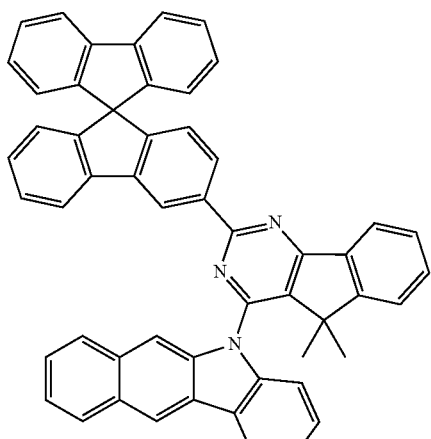

450

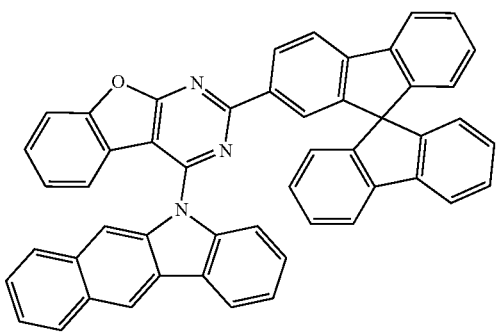

451

Chemical Formula a (10.0 g, 1.0 eq.), 2-(9,9'-spirobi[fluoren]-3-yl)-4-chloro-5,5-dimethyl-5H-indeno[1,2-d]pyrimidine (27.59 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 450 (22.71 g, yield 68%). [M+H]=726

Chemical Formula a (10.0 g, 1.0 eq.), 2-(9,9'-spirobi[fluoren]-2-yl)-4-chlorobenzofuro[2,3-d]pyrimidine (26.27 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 451 (22.22 g, yield 69%). [M+H]=700

FIG. 8 is a graph showing an 1H-NMR value of Chemical Formula 451.

SYNTHESIS EXAMPLE 48

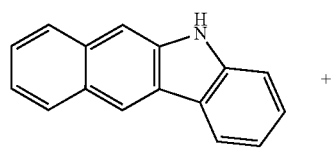 +

SYNTHESIS EXAMPLE 49

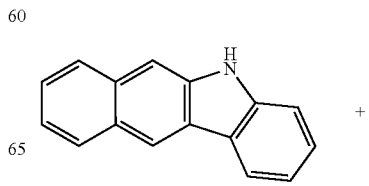 +

-continued

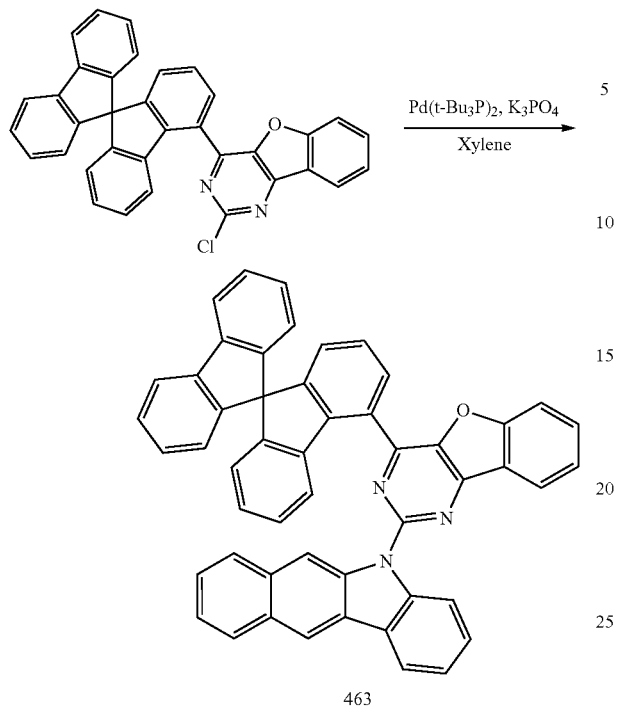

463

Chemical Formula a (10.0 g, 1.0 eq.), 4-(9,9'-spirobi[fluoren]-4-yl)-2-chlorobenzofuro[3,2-d]pyrimidine (26.27 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 463 (20.93 g, yield 65%). [M+H]=700

SYNTHESIS EXAMPLE 50

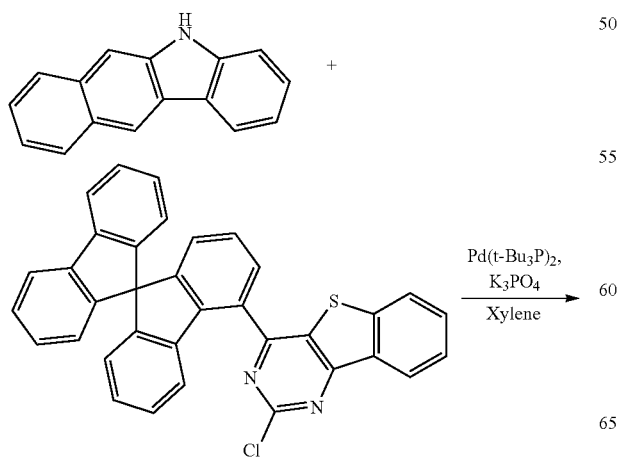

-continued

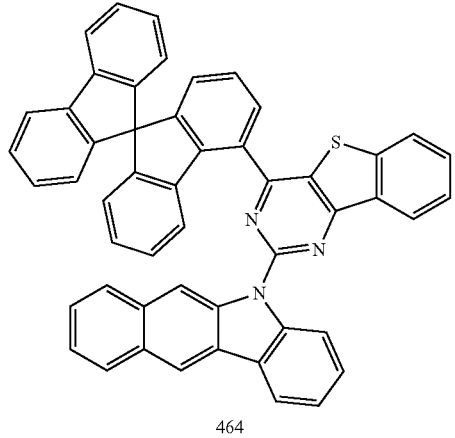

464

Chemical Formula a (10.0 g, 1.0 eq.), 4-(9,9'-spirobi[fluoren]-4-yl)-2-chlorobenzo[4,5]thieno[3,2-d]pyrimidine (27.08 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 464 (22.07 g, yield 67%). [M+H]=716

SYNTHESIS EXAMPLE 51

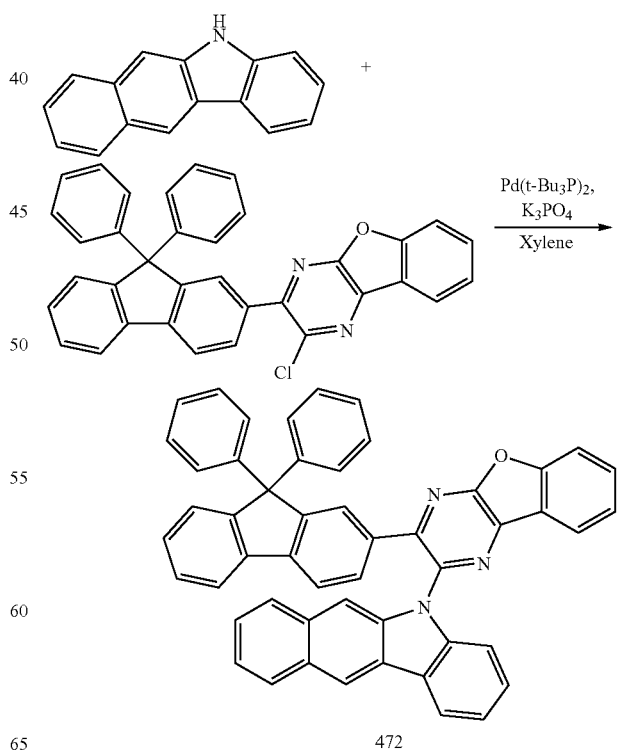

472

Chemical Formula a (10.0 g, 1.0 eq.), 2-chloro-3-(9,9-diphenyl-9H-fluoren-2-yl)benzofuro[2,3-b]pyrazine (26.37 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 472 (21.64 g, yield 67%). [M+H]=702

SYNTHESIS EXAMPLE 52

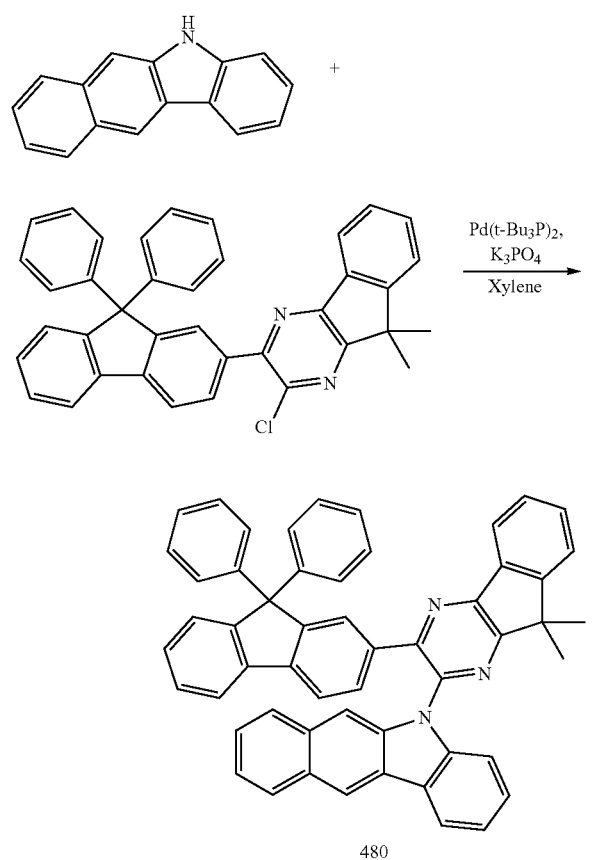

480

Chemical Formula a (10.0 g, 1.0 eq.), 2-chloro-3-(9,9-diphenyl-9H-fluoren-2-yl)-9,9-dimethyl-9H-indeno[1,2-b]pyrazine (27.69 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 480 (23.11 g, yield 69%). [M+H]=728

SYNTHESIS EXAMPLE 53

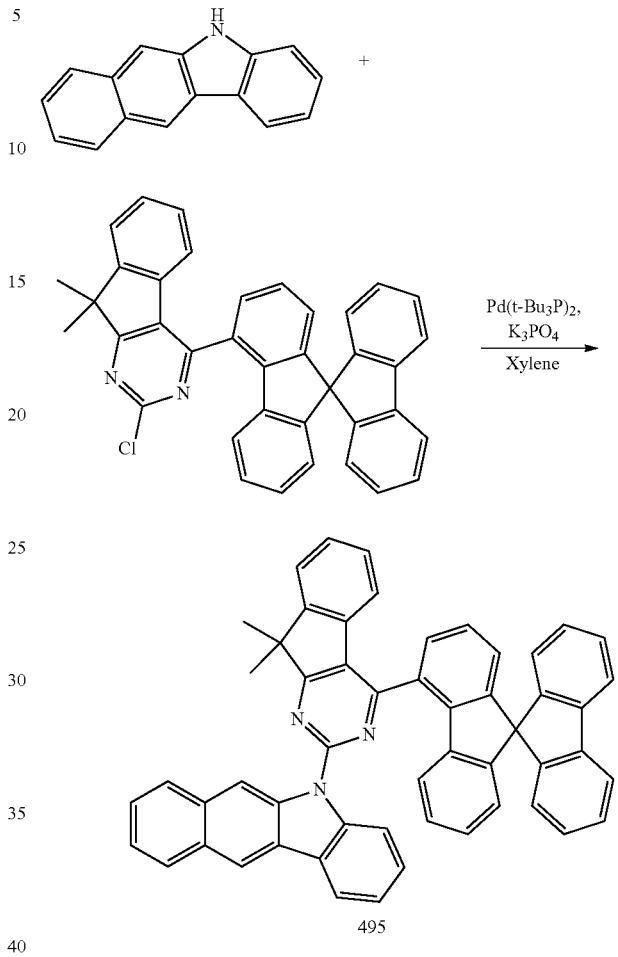

495

Chemical Formula a (10.0 g, 1.0 eq.), 4-(9,9'-spirobi[fluoren]-4-yl)-2-chloro-9,9-dimethyl-9H-indeno[2,1-d]pyrimidine (27.59 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 495 (23.72 g, yield 71%). [M+H]=726

SYNTHESIS EXAMPLE 54

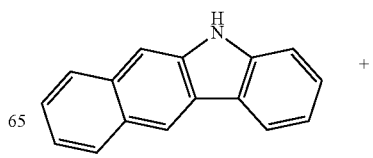

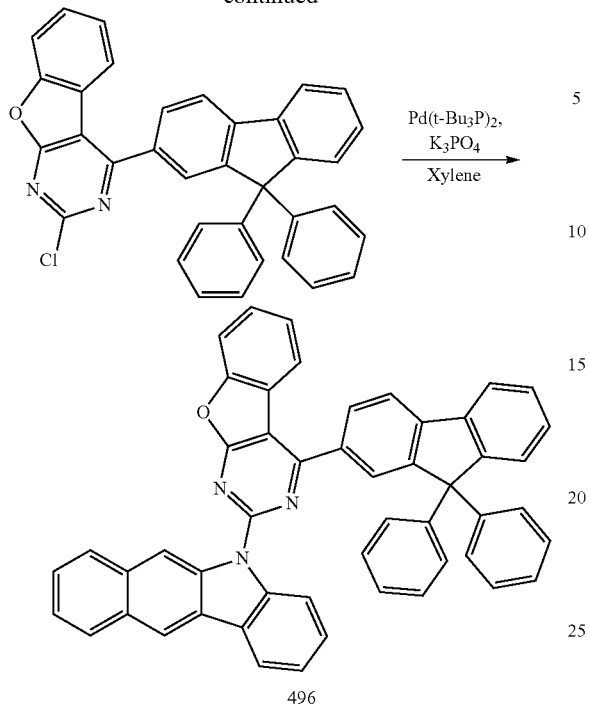

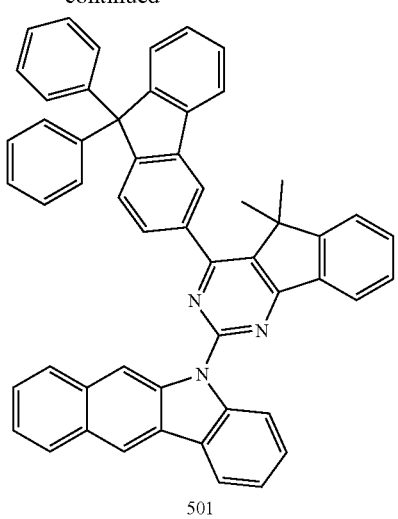

Chemical Formula a (10.0 g, 1.0 eq.), 2-chloro-4-(9,9-diphenyl-9H-fluoren-2-yl)benzofuro[2,3-d]pyrimidine (26.37 g, 1.1 eq.), $K_3PO_4$ (19.53 g, 2.0 eq.) and Pd(t-$Bu_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 496 (22.61 g, yield 70%). [M+H]=702

SYNTHESIS EXAMPLE 55

Chemical Formula a (10.0 g, 1.0 eq.), 2-chloro-4-(9,9-diphenyl-9H-fluoren-3-yl)-5,5-dimethyl-5H-indeno[1,2-d]pyrimidine (27.69 g, 1.1 eq.), $K_3PO_4$ (19.53 g, 2.0 eq.) and Pd(t-$Bu_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 501 (24.12 g, yield 72%). [M+H]=728

SYNTHESIS EXAMPLE 56

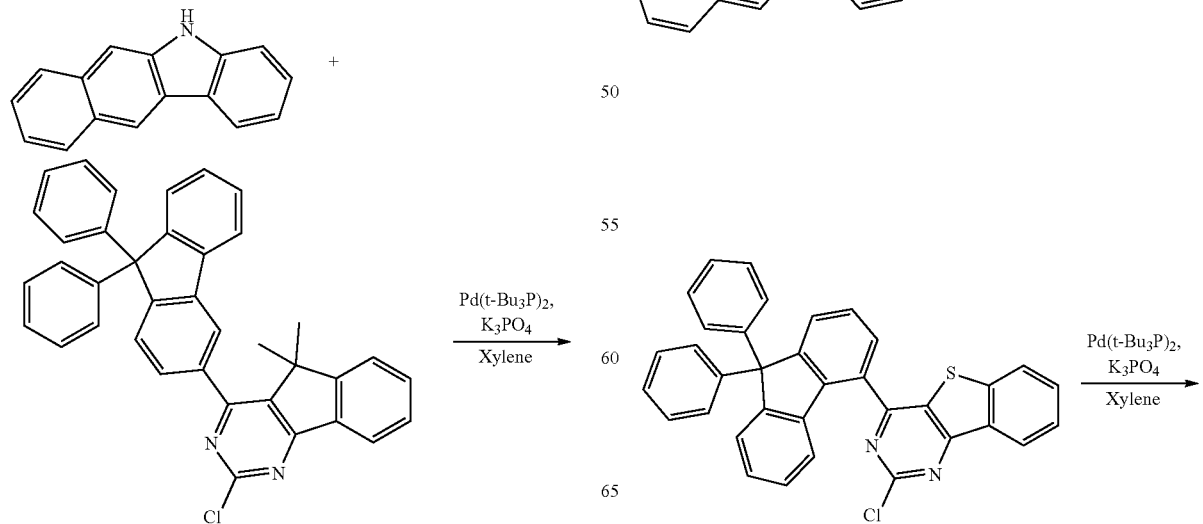

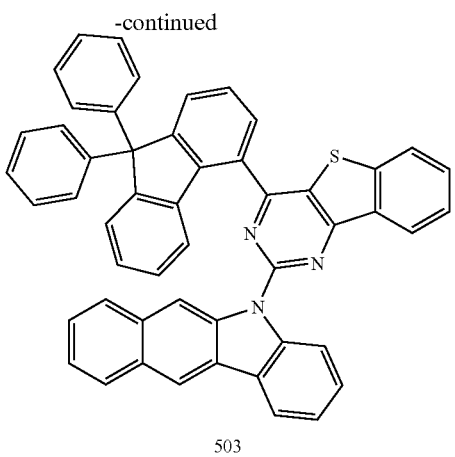

503

Chemical Formula a (10.0 g, 1.0 eq.), 2-chloro-4-(9,9-diphenyl-9H-fluoren-4-yl)benzo[4,5]thieno[3,2-d]pyrimidine (27.19 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 503 (23.12 g, yield 70%). [M+H]=718

SYNTHESIS EXAMPLE 57

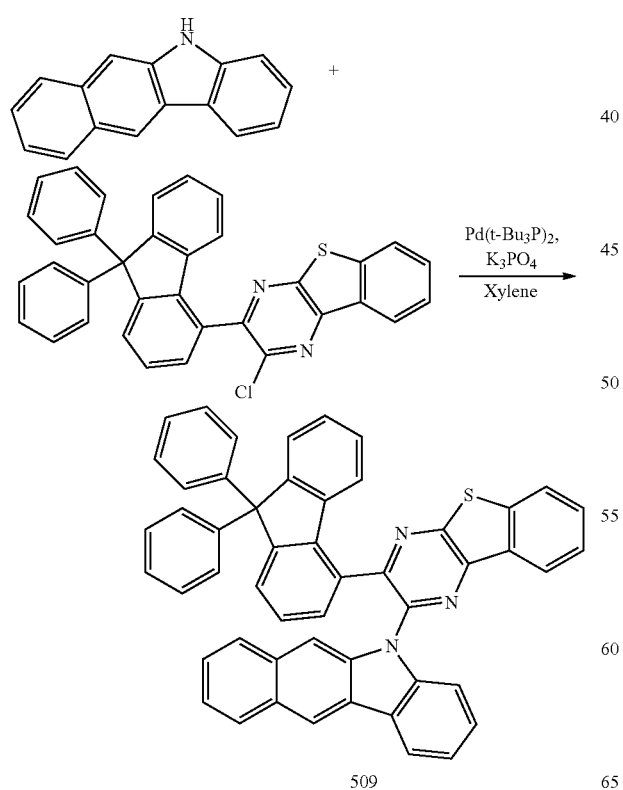

509

Chemical Formula a (10.0 g, 1.0 eq.), 2-chloro-3-(9,9-diphenyl-9H-fluoren-4-yl)benzo[4,5]thieno[2,3-b]pyrazine (27.19 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 509 (23.78 g, yield 72%). [M+H]=718

SYNTHESIS EXAMPLE 58

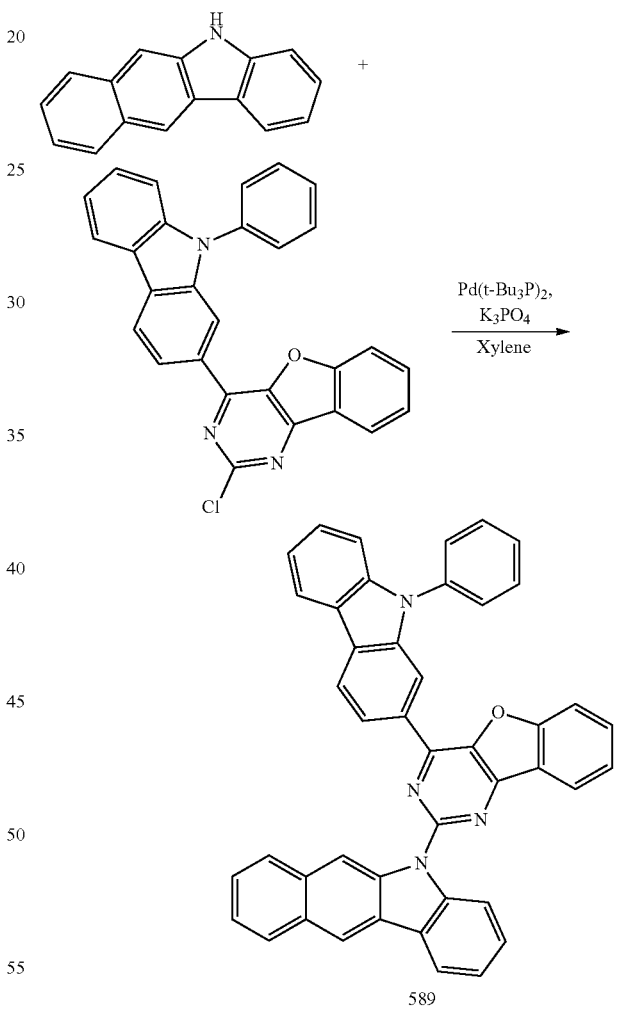

589

Chemical Formula a (10.0 g, 1.0 eq.), 2-chloro-4-(9-phenyl-9H-carbazol-2-yl)benzofuro[3,2-d]pyrimidine (22.57 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 589 (20.19 g, yield 70%). [M+H]=627

SYNTHESIS EXAMPLE 59

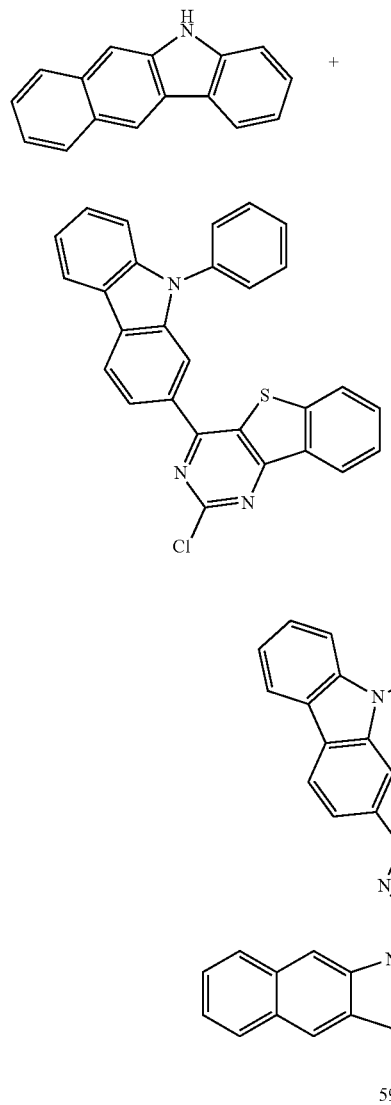

590

Chemical Formula a (10.0 g, 1.0 eq.), 2-chloro-4-(9-phenyl-9H-carbazol-2-yl)benzo[4,5]thieno[3,2-d]pyrimidine (23.38 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 590 (21.01 g, yield 71%). [M+H]=653

SYNTHESIS EXAMPLE 60

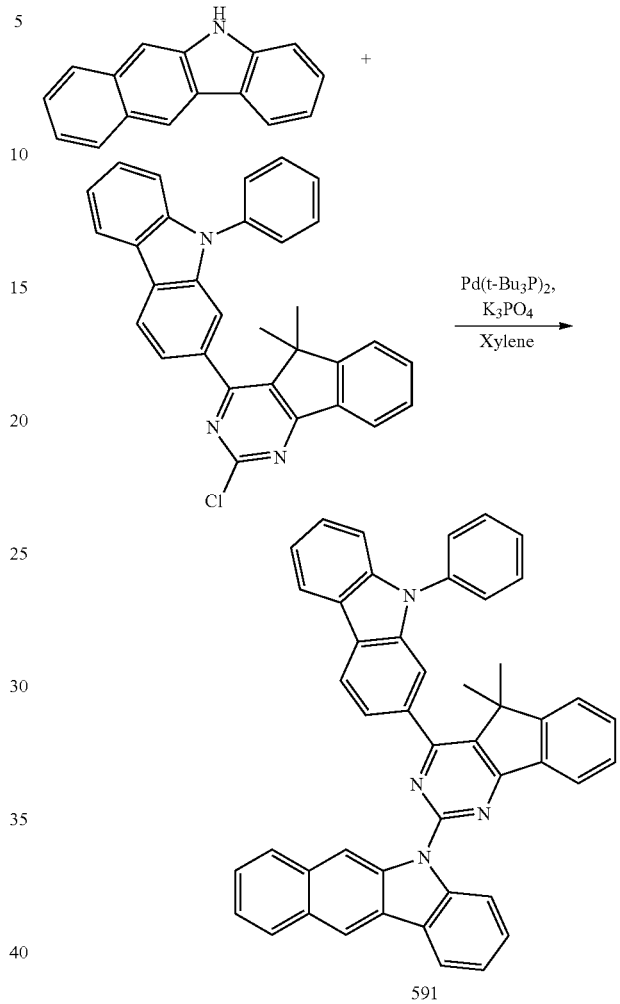

591

Chemical Formula a (10.0 g, 1.0 eq.), 2-chloro-5,5-dimethyl-4-(9-phenyl-9H-carbazol-2-yl)-5H-indeno[1,2-d]pyrimidine (23.89 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 591 (20.43 g, yield 68%). [M+H]=653

SYNTHESIS EXAMPLE 61

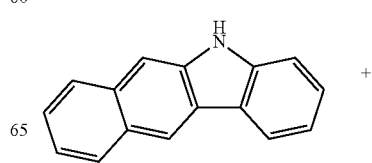

413

-continued

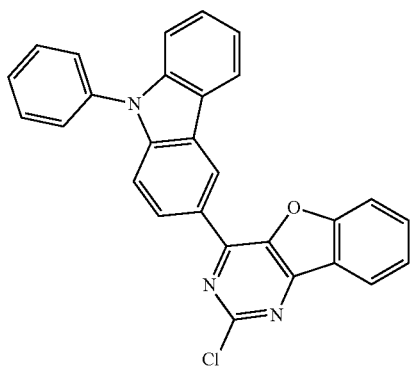

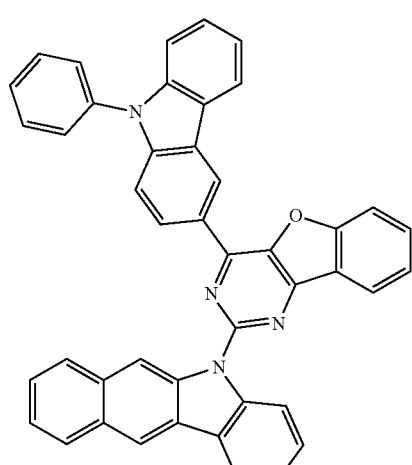
592

Chemical Formula a (10.0 g, 1.0 eq.), 2-chloro-4-(9-phenyl-9H-carbazol-3-yl)benzofuro[3,2-d]pyrimidine (22.57 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 592 (20.19 g, yield 70%). [M+H]=627

SYNTHESIS EXAMPLE 62

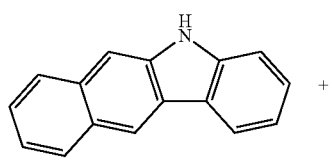

414

-continued

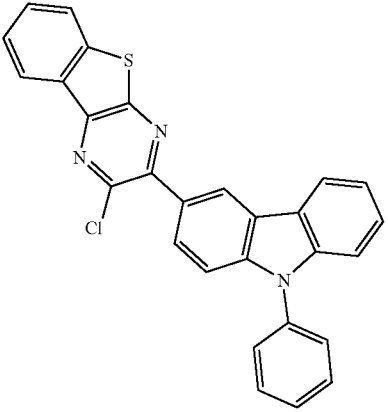

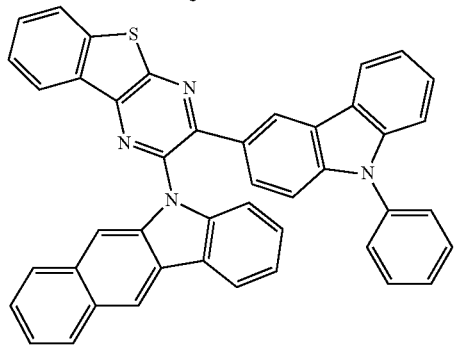
599

Chemical Formula a (10.0 g, 1.0 eq.), 2-chloro-3-(9-phenyl-9H-carbazol-3-yl)benzo[4,5]thieno[2,3-b]pyrazine (23.38 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 599 (21.00 g, yield 71%). [M+H]=643

SYNTHESIS EXAMPLE 63

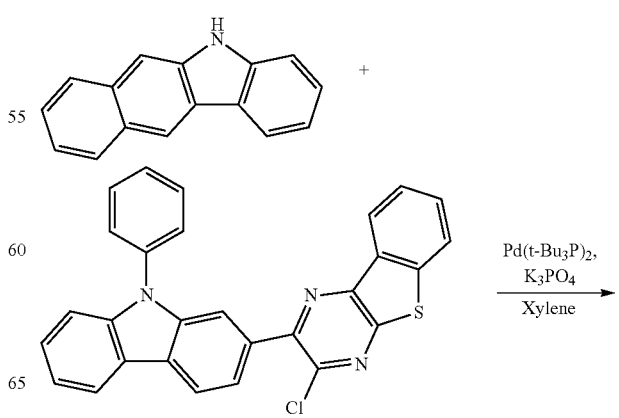

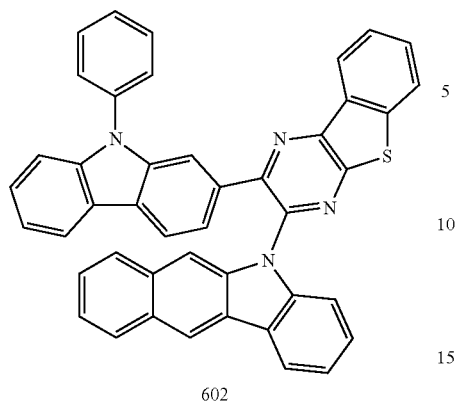

602

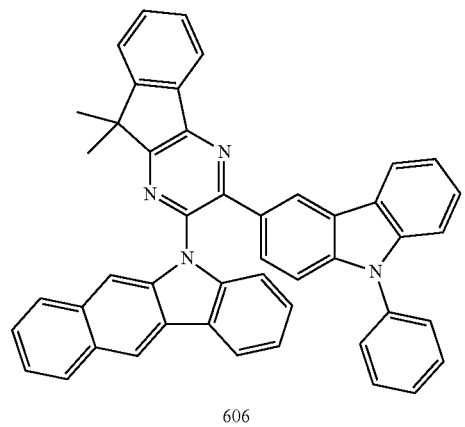

606

Chemical Formula a (10.0 g, 1.0 eq.), 3-chloro-2-(9-phenyl-9H-carbazol-2-yl)benzo[4,5]thieno[2,3-b]pyrazine (23.38 g, 1.1 eq.), $K_3PO_4$ (19.53 g, 2.0 eq.) and Pd(t-$Bu_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 602 (21.00 g, yield 71%). [M+H]=643

SYNTHESIS EXAMPLE 64

Chemical Formula a (10.0 g, 1.0 eq.), 2-chloro-9,9-dimethyl-3-(9-phenyl-9H-carbazol-3-yl)-9H-indeno[1,2-b]pyrazine (23.89 g, 1.1 eq.), $K_3PO_4$ (19.53 g, 2.0 eq.) and Pd(t-$Bu_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 606 (20.43 g, yield 68%). [M+H]=653

SYNTHESIS EXAMPLE 65

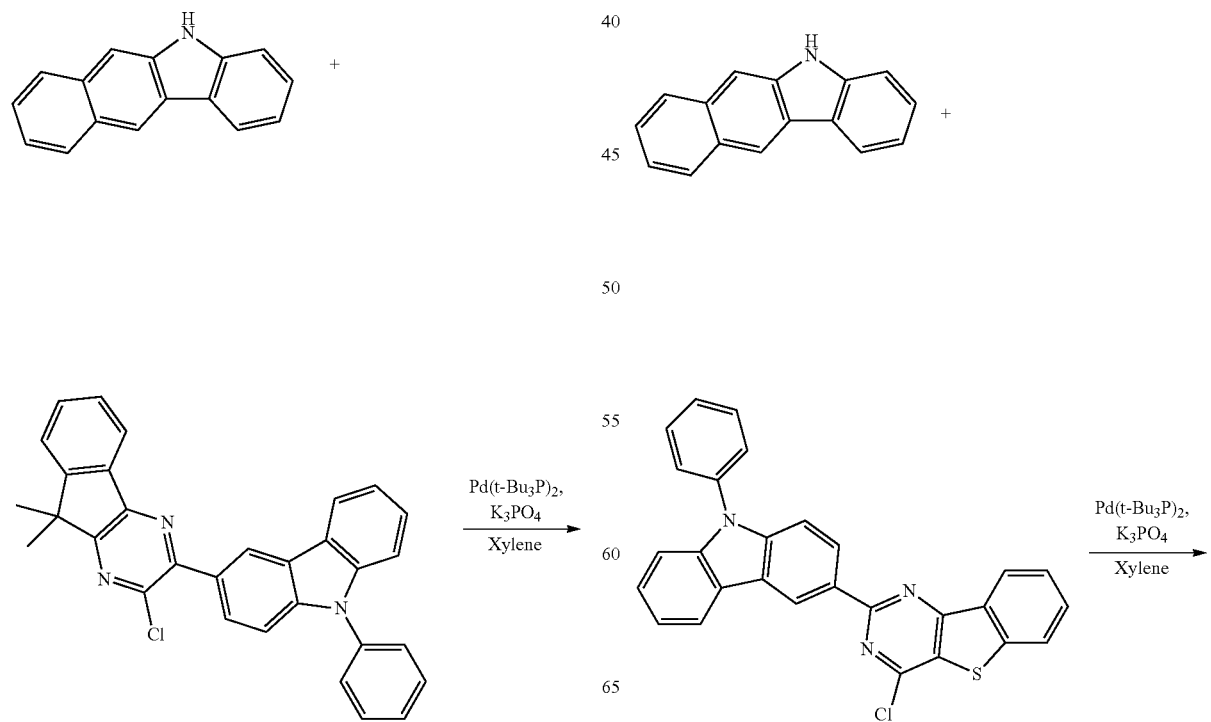

-continued

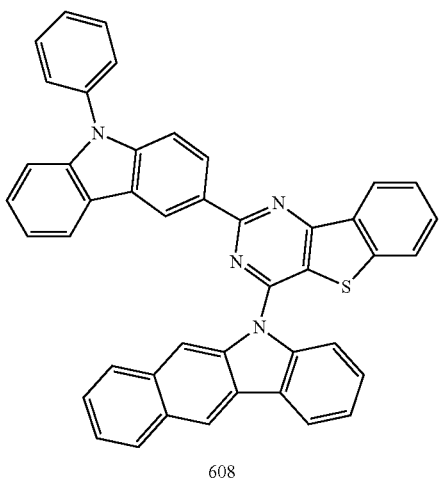

608

-continued

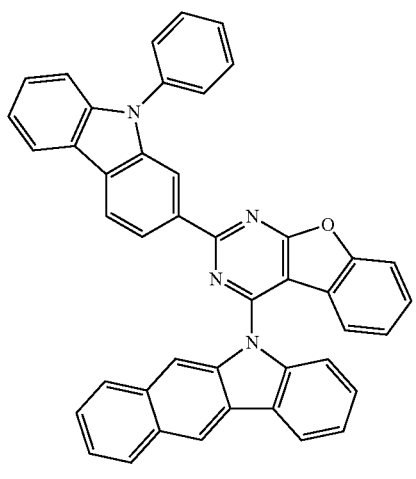

613

Chemical Formula a (10.0 g, 1.0 eq.), 4-chloro-2-(9-phenyl-9H-carbazol-3-yl)benzo[4,5]thieno[3,2-d]pyrimidine (23.38 g, 1.1 eq.), $K_3PO_4$ (19.53 g, 2.0 eq.) and Pd(t-$Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 608 (19.22 g, yield 65%). [M+H]=643

Chemical Formula a (10.0 g, 1.0 eq.), 4-chloro-2-(9-phenyl-9H-carbazol-2-yl)benzofuro[2,3-d]pyrimidine (22.57 g, 1.1 eq.), $K_3PO_4$ (19.53 g, 2.0 eq.) and Pd(t-$Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 613 (18.74 g, yield 65%). [M+H]=627

SYNTHESIS EXAMPLE 66

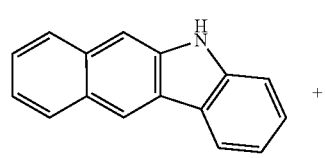 +

SYNTHESIS EXAMPLE 67

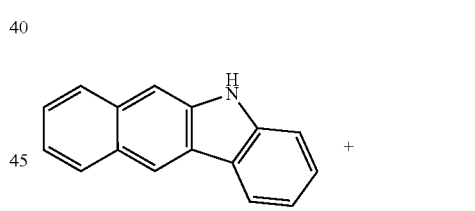 +

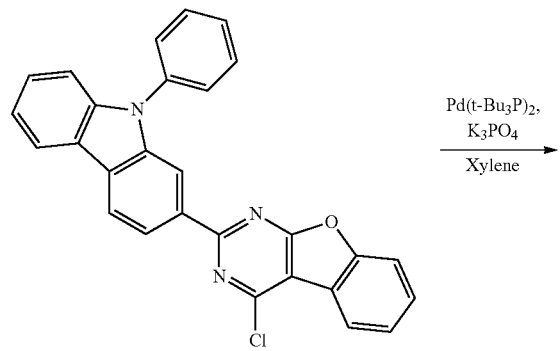

Pd(t-$Bu_3P)_2$,
$K_3PO_4$
———————→
Xylene

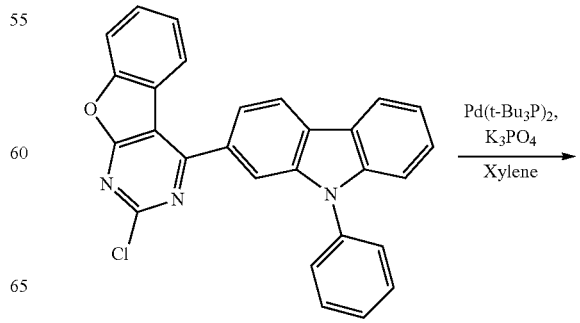

Pd(t-$Bu_3P)_2$,
$K_3PO_4$
———————→
Xylene

419
-continued

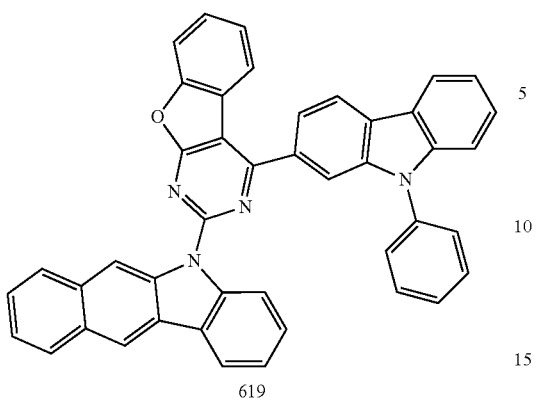

619

420
-continued

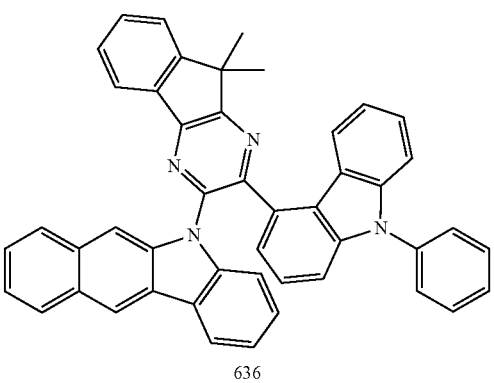

636

Chemical Formula a (10.0 g, 1.0 eq.), 2-chloro-4-(9-phenyl-9H-carbazol-2-yl)benzofuro[2,3-d]pyrimidine (22.57 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 619 (19.32 g, yield 67%). [M+H]=627

Chemical Formula a (10.0 g, 1.0 eq.), 3-chloro-9,9-dimethyl-2-(9-phenyl-9H-carbazol-4-yl)-9H-indeno[1,2-b]pyrazine (23.89 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 636 (20.73 g, yield 69%). [M+H]=653

SYNTHESIS EXAMPLE 68

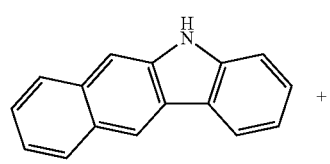

SYNTHESIS EXAMPLE 69

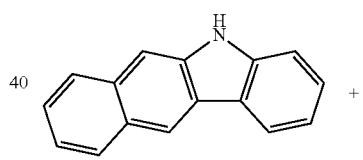

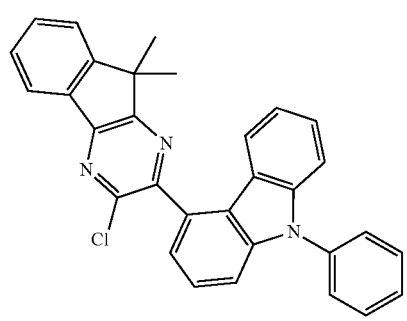

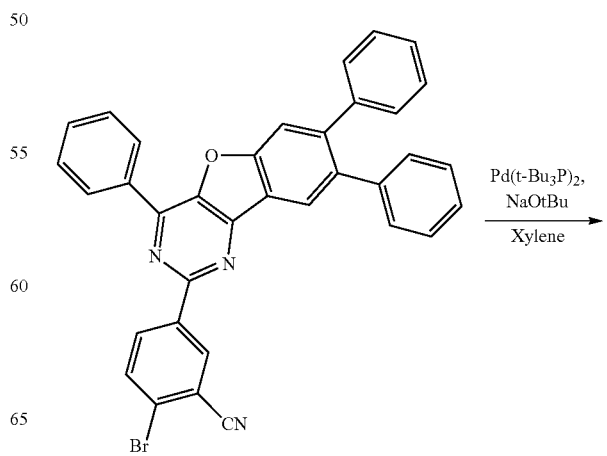

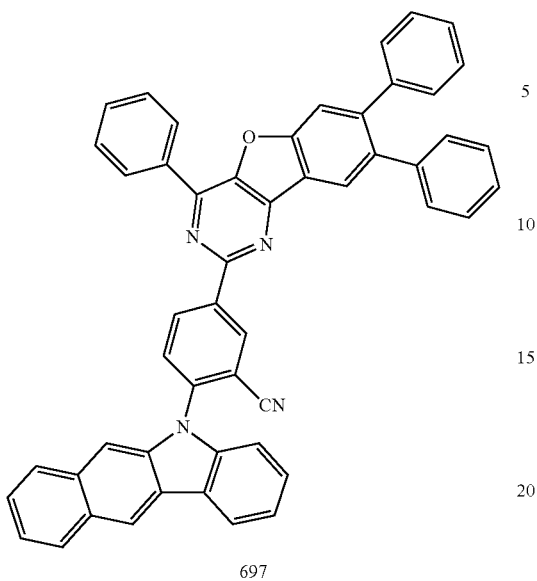

697

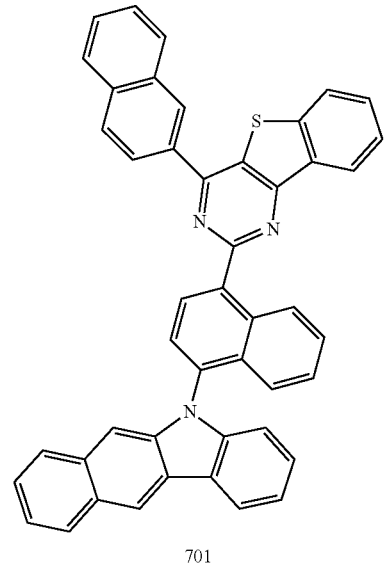

701

Chemical Formula a (10.0 g, 1.0 eq.), 2-bromo-5-(4,7,8-triphenylbenzofuro[3,2-d]pyrimidin-2-yl)benzonitrile (29.28 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 697 (21.38 g, yield 65%). [M+H]=715

Chemical Formula a (10.0 g, 1.0 eq.), 2-(4-bromonaphthalen-1-yl)-4-(naphthalen-2-yl)benzo[4,5]thieno[3,2-d]pyrimidine (26.19 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 701 (20.46 g, yield 68%). [M+H]=654

SYNTHESIS EXAMPLE 70

SYNTHESIS EXAMPLE 71

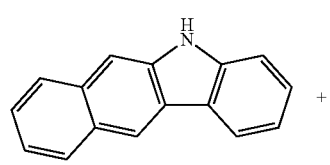

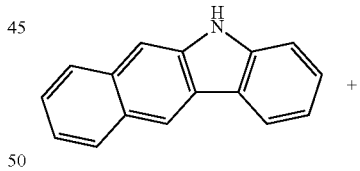

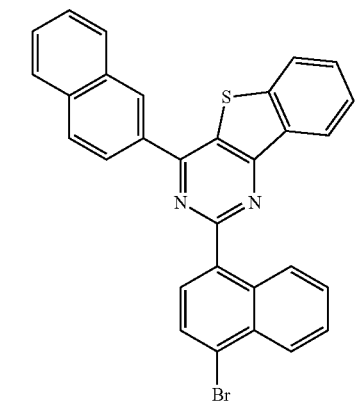

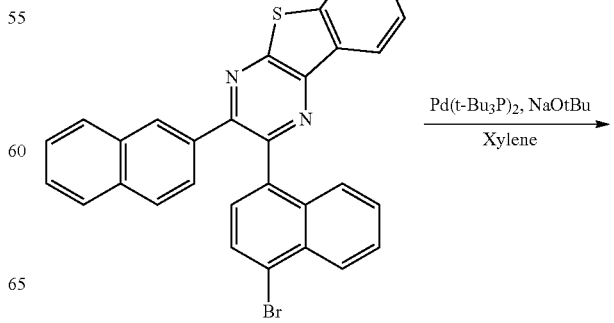

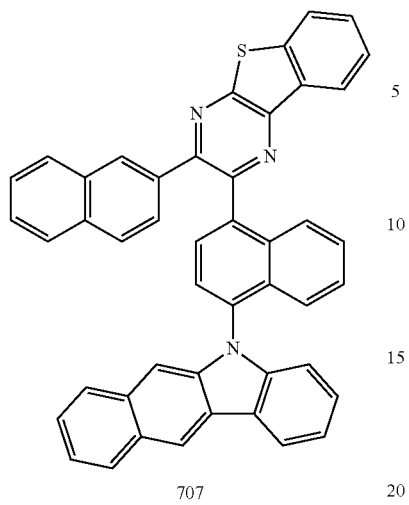

707

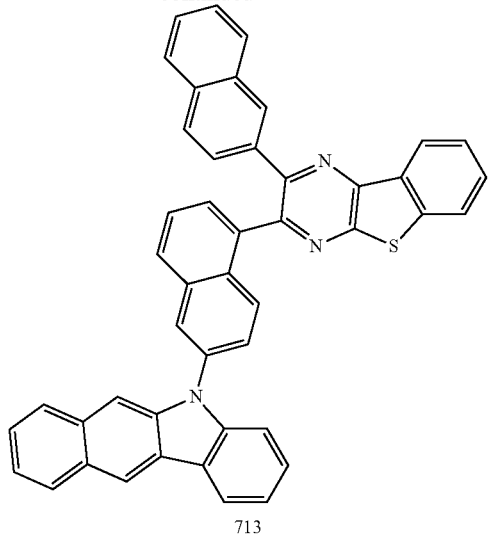

713

Chemical Formula a (10.0 g, 1.0 eq.), 2-(4-bromonaphthalen-1-yl)-3-(naphthalen-2-yl)benzo[4,5]thieno[2,3-b]pyrazine (26.19 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 707 (21.36 g, yield 71%). [M+H]=654

SYNTHESIS EXAMPLE 72

Chemical Formula a (10.0 g, 1.0 eq.), 3-(6-bromonaphthalen-1-yl)-2-(naphthalen-2-yl)benzo[4,5]thieno[2,3-b]pyrazine (26.19 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 713 (20.76 g, yield 69%). [M+H]=654

SYNTHESIS EXAMPLE 73

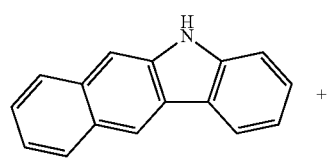

+

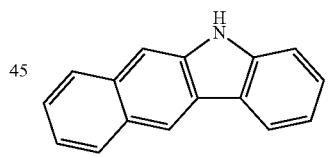

+

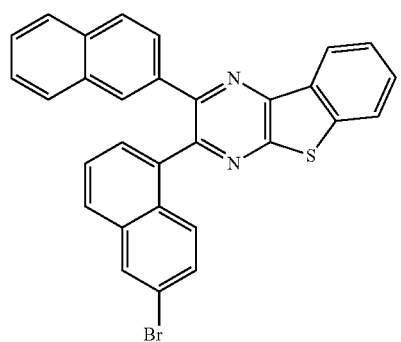

Pd(t-Bu$_3$P)$_2$, NaOtBu
——————→
Xylene

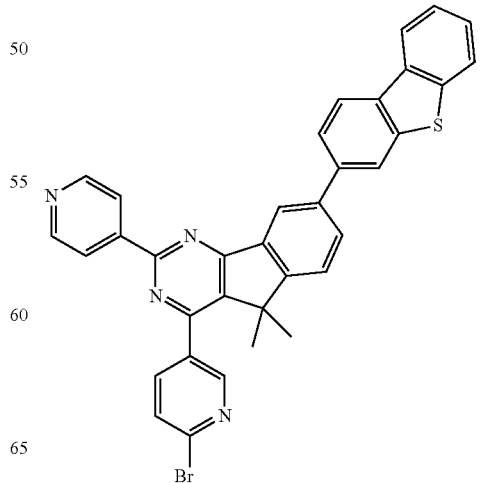

Pd(t-Bu$_3$P)$_2$, NaOtBu
——————→
Xylene

-continued

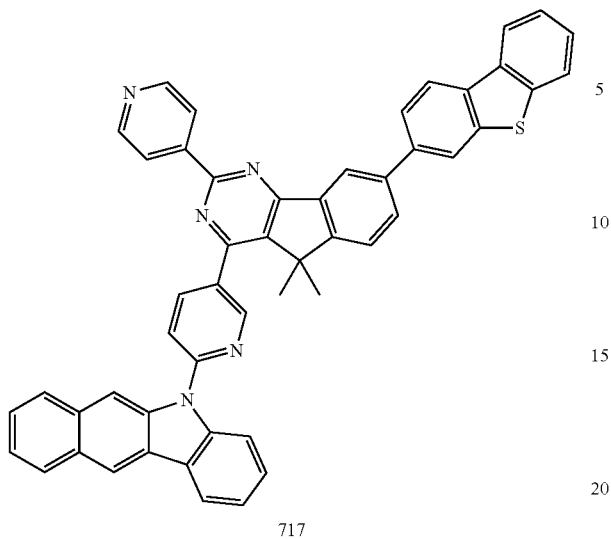
717

-continued

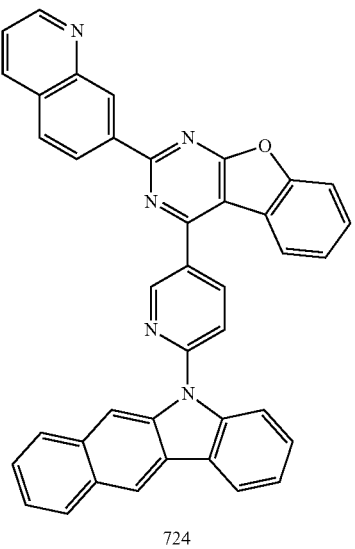
724

Chemical Formula a (10.0 g, 1.0 eq.), 4-(6-bromopyridin-3-yl)-8-(dibenzo[b,d]thiophen-3-yl)-5,5-dimethyl-2-(pyridin-4-yl)-5H-indeno[1,2-d]pyrimidine (30.96 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 717 (24.78 g, yield 72%). [M+H]=745

SYNTHESIS EXAMPLE 74

Chemical Formula a (10.0 g, 1.0 eq.), 4-(6-bromopyridin-3-yl)-2-(quinolin-7-yl)benzofuro[2,3-d]pyrimidine (22.94 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 724 (19.54 g, yield 72%). [M+H]=590

SYNTHESIS EXAMPLE 75

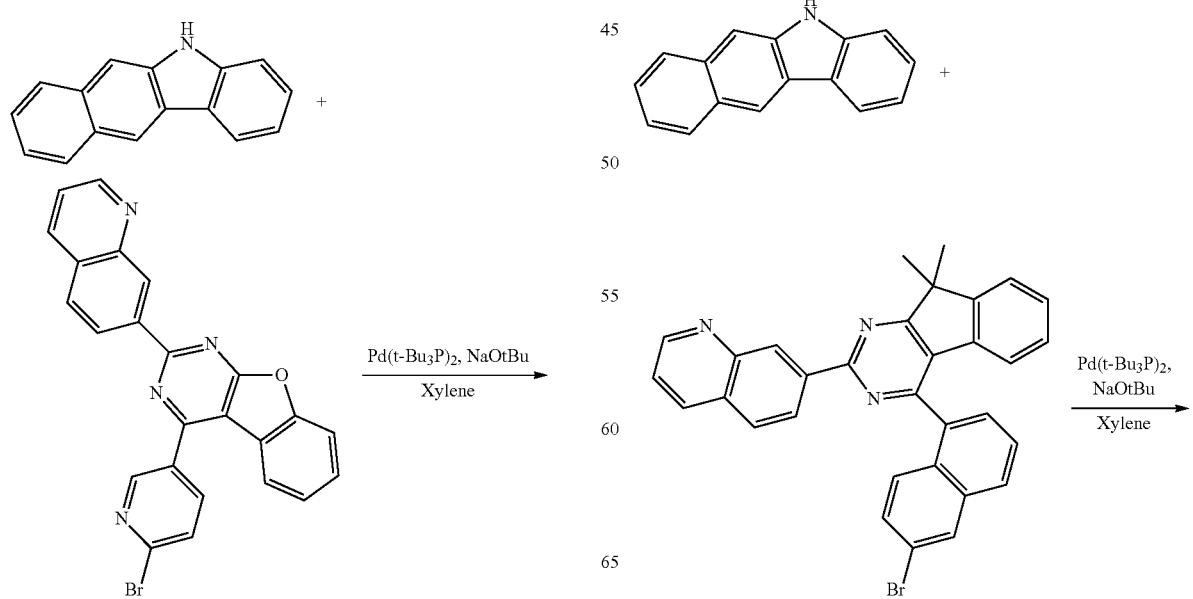

-continued

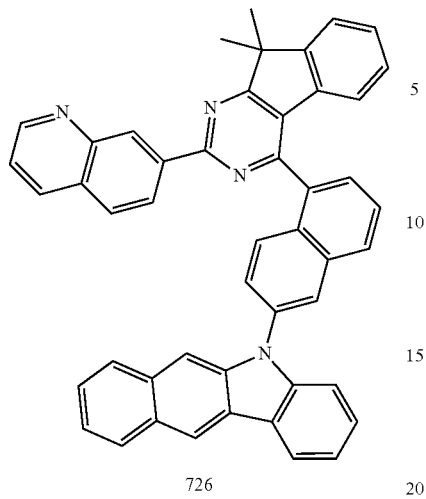

726

Chemical Formula a (10.0 g, 1.0 eq.), 4-(6-bromonaphthalen-1-yl)-9,9-dimethyl-2-(quinolin-7-yl)-9H-indeno[2,1-d]pyrimidine (26.75 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 726 (21.41 g, yield 70%). [M+H]=665

SYNTHESIS EXAMPLE 76

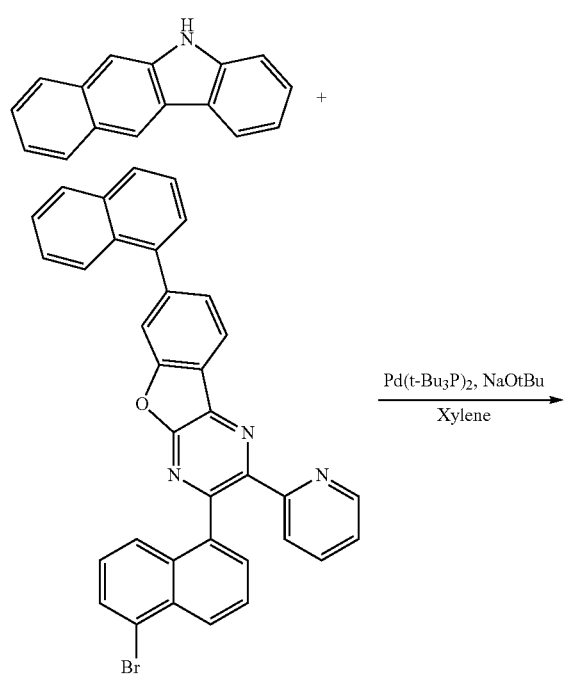

-continued

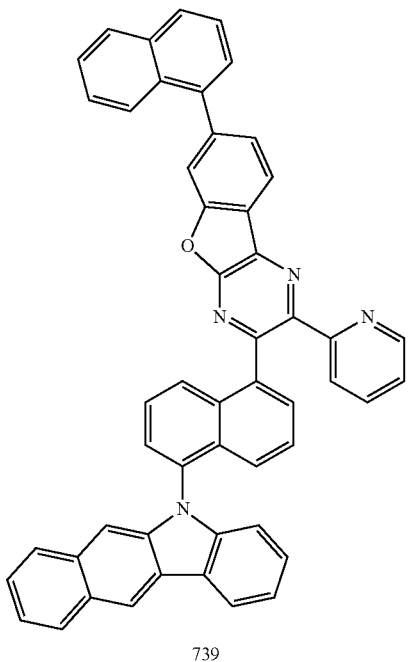

739

Chemical Formula a (10.0 g, 1.0 eq.), 3-(5-bromonaphthalen-1-yl)-7-(naphthalen-1-yl)-2-(pyridin-2-yl)benzofuro[2,3-b]pyrazine (29.28 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 739 (23.68 g, yield 72%). [M+H]=715

SYNTHESIS EXAMPLE 77

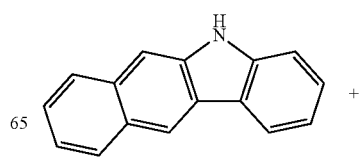

-continued

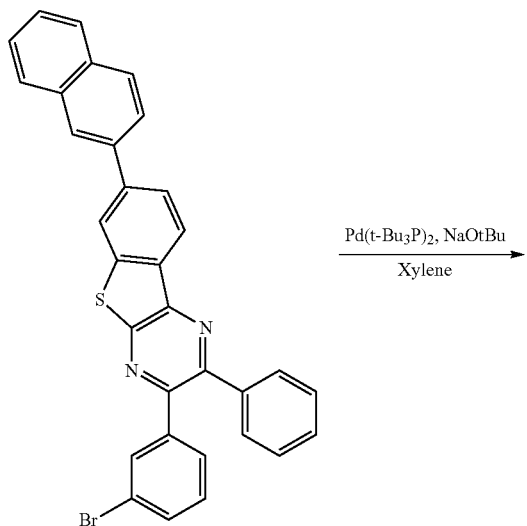

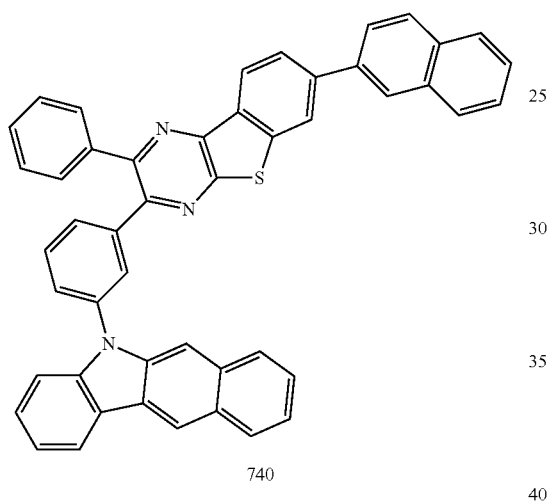

740

Chemical Formula a (10.0 g, 1.0 eq.), 3-(3-bromophenyl)-7-(naphthalen-2-yl)-2-phenylbenzo[4,5]thieno[2,3-b]pyrazine (27.51 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 740 (21.90 g, yield 70%). [M+H]=680

SYNTHESIS EXAMPLE 78

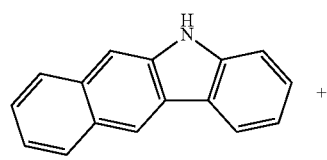 +

-continued

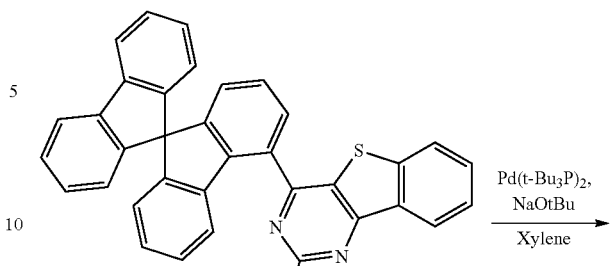

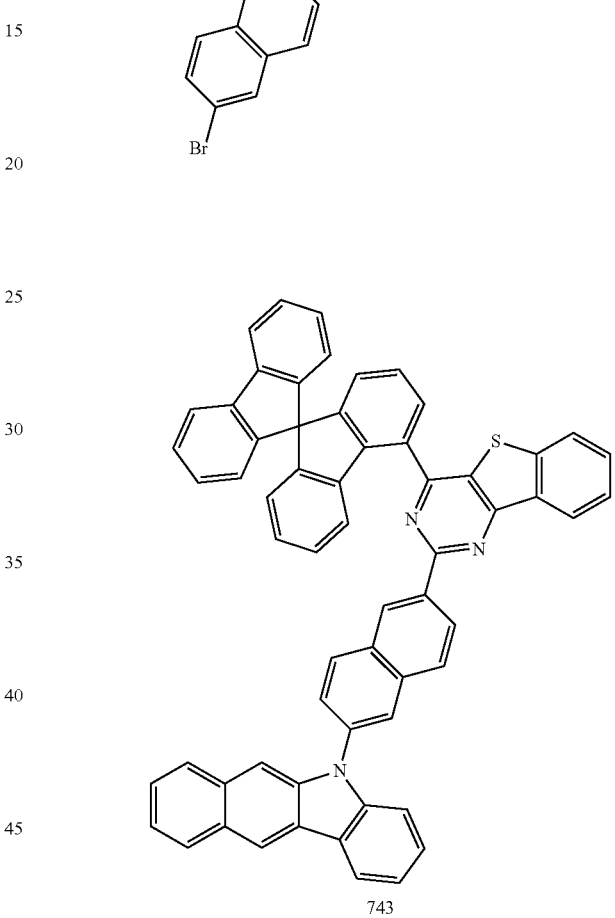

743

Chemical Formula a (10.0 g, 1.0 eq.), 4-(9,9'-spirobi[fluoren]-4-yl)-2-(6-bromonaphthalen-2-yl)benzo[4,5]thieno[3,2-d]pyrimidine (35.72 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 743 (24.80 g, yield 64%). [M+H]=843

SYNTHESIS EXAMPLE 79

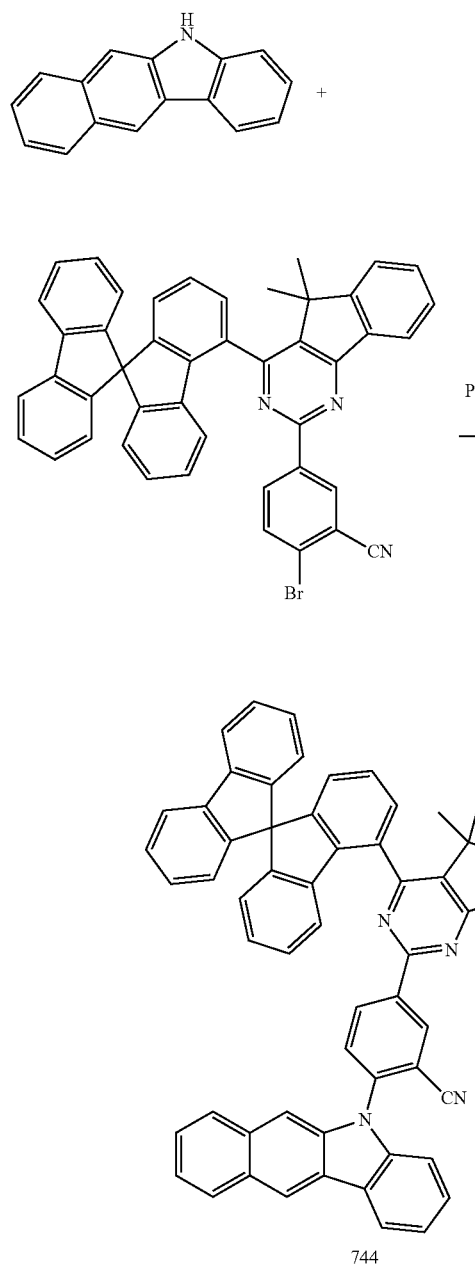

744

Chemical Formula a (10.0 g, 1.0 eq.), 5-(4-(9,9'-spirobi[fluoren]-4-yl)-5,5-dimethyl-5H-indeno[1,2-d]pyrimidin-2-yl)-2-bromobenzonitrile (34.96 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 744 (25.50 g, yield 67%). [M+H]=828

SYNTHESIS EXAMPLE 80

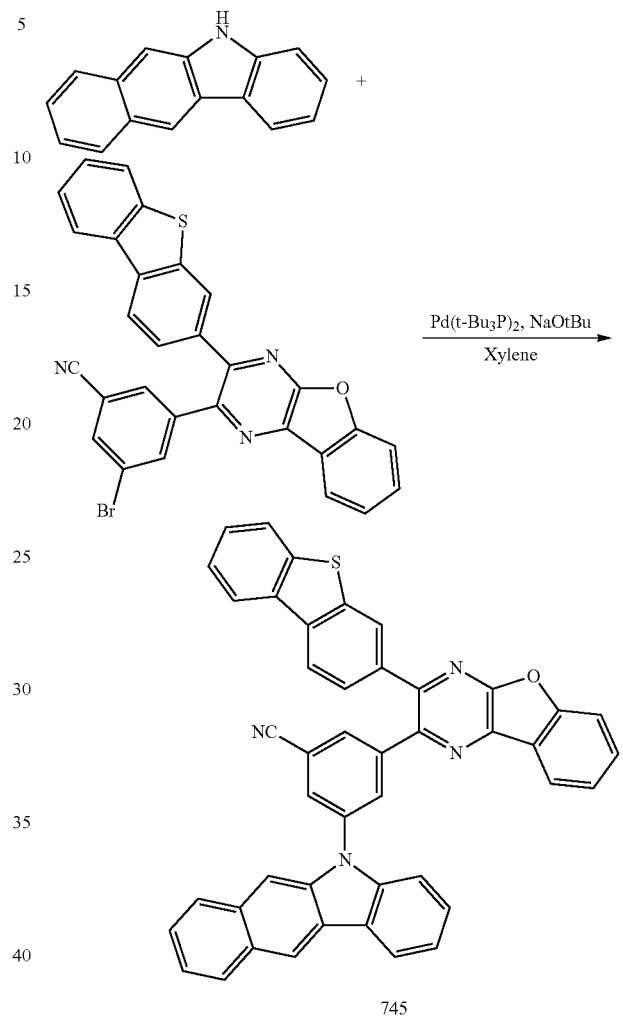

745

Chemical Formula a (10.0 g, 1.0 eq.), 3-bromo-5-(3-(dibenzo[b,d]thiophen-3-yl)benzofuro[2,3-b]pyrazin-2-yl)benzonitrile (26.95 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 745 (19.69 g, yield 64%). [M+H]=669

SYNTHESIS EXAMPLE 81

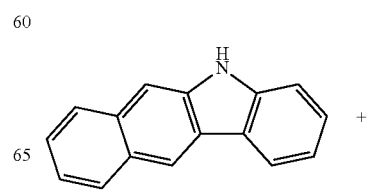

433

-continued

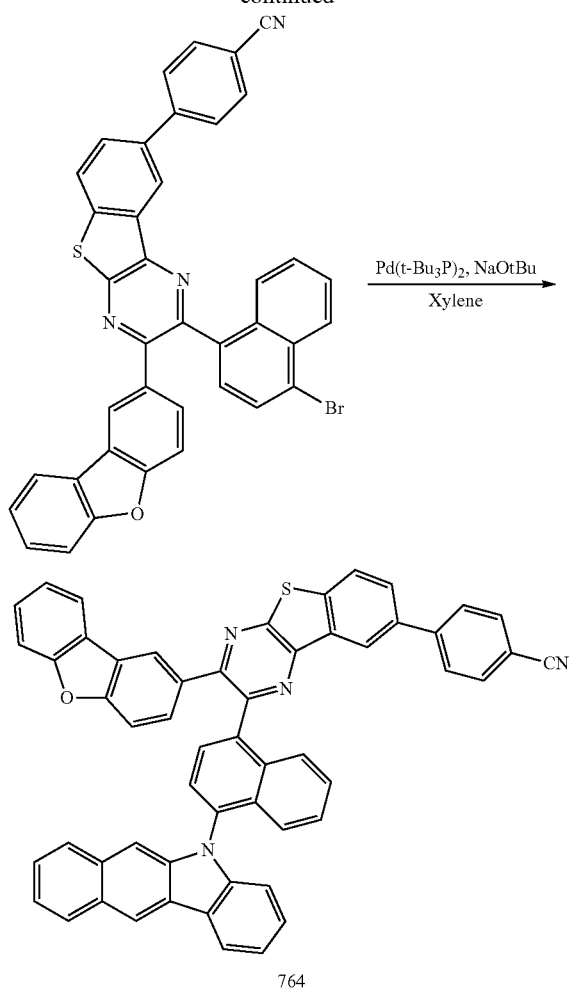

764

434

-continued

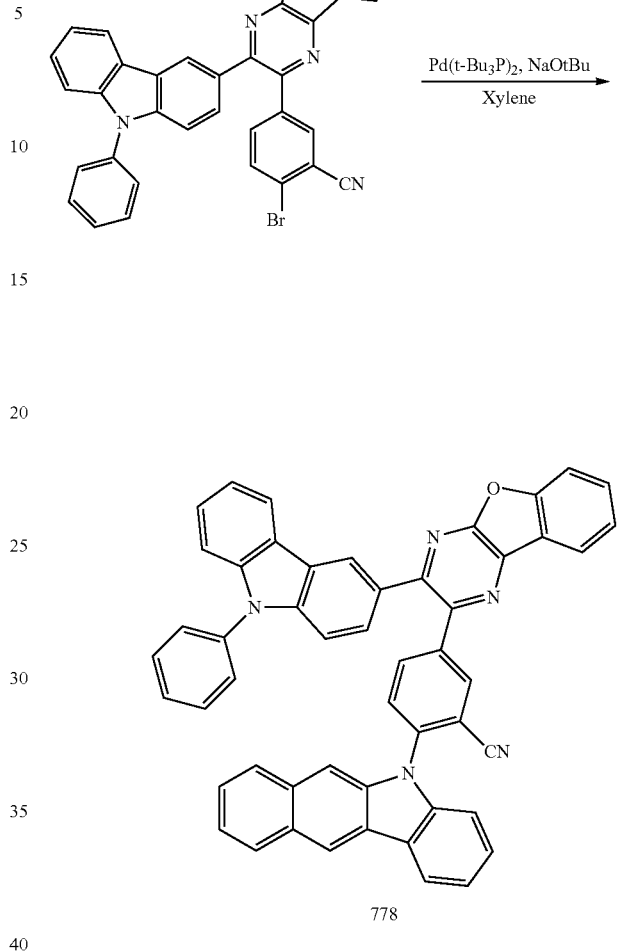

778

Chemical Formula a (10.0 g, 1.0 eq.), 4-(2-(4-bromonaph-thalen-1-yl)-3-(dibenzo[b,d]furan-2-yl)benzo[4,5]thieno[2,3-b]pyrazin-8-yl)benzonitrile (33.34 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 764 (22.31 g, yield 61%). [M+H]=795

Chemical Formula a (10.0 g, 1.0 eq.), 2-bromo-5-(3-(9-phenyl-9H-carbazol-3-yl)benzofuro[2,3-b]pyrazin-2-yl) benzonitrile (29.94 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 778 (21.10 g, yield 63%). [M+H]=728

SYNTHESIS EXAMPLE 82

SYNTHESIS EXAMPLE 83

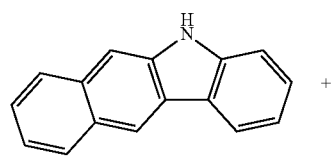 +

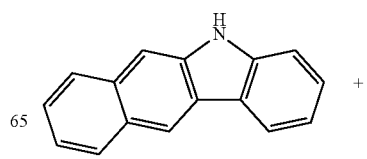 +

435

-continued

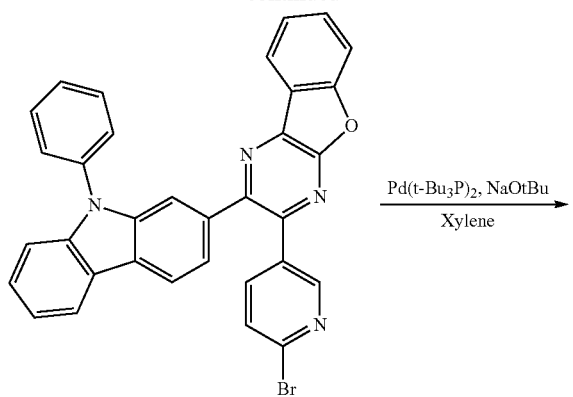

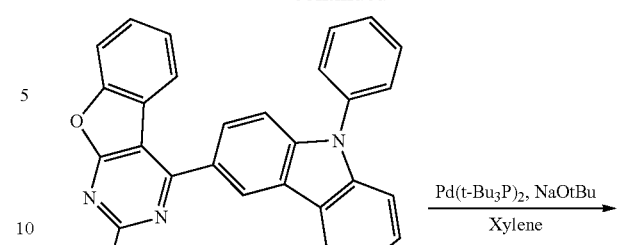

436

-continued

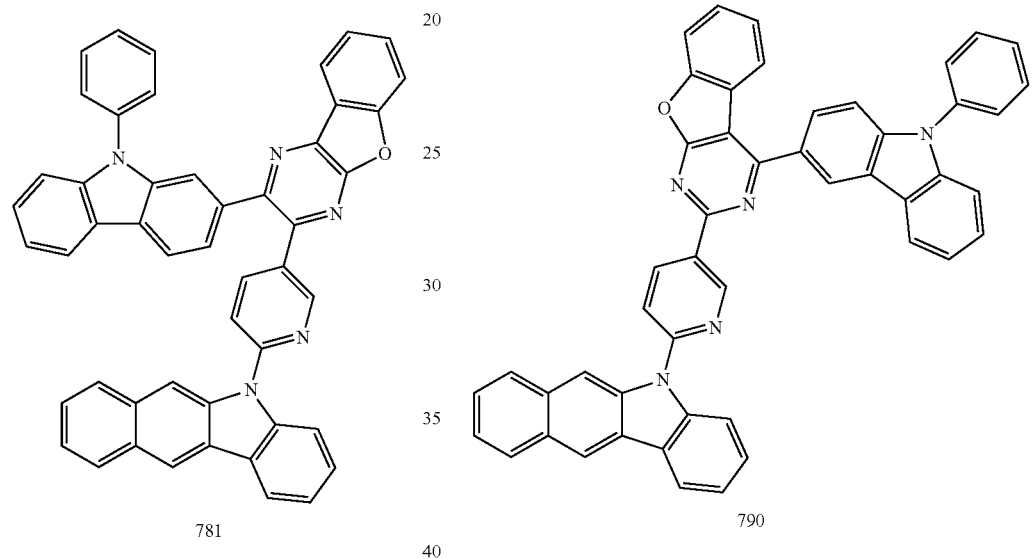

Chemical Formula a (10.0 g, 1.0 eq.), 3-(6-bromopyridin-3-yl)-2-(9-phenyl-9H-carbazol-2-yl)benzofuro[2,3-b]pyrazine (28.72 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 781 (20.73 g, yield 64%). [M+H]=704

SYNTHESIS EXAMPLE 84

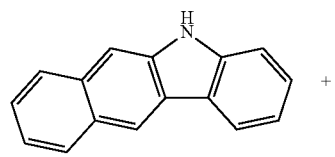

Chemical Formula a (10.0 g, 1.0 eq.), 2-(6-bromopyridin-3-yl)-4-(9-phenyl-9H-carbazol-3-yl)benzofuro[2,3-d]pyrimidine (28.729 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 790 (21.70 g, yield 67%). [M+H]=704

SYNTHESIS EXAMPLE 85

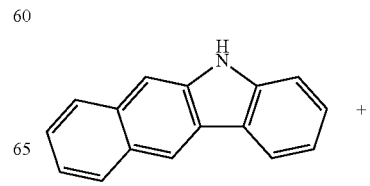

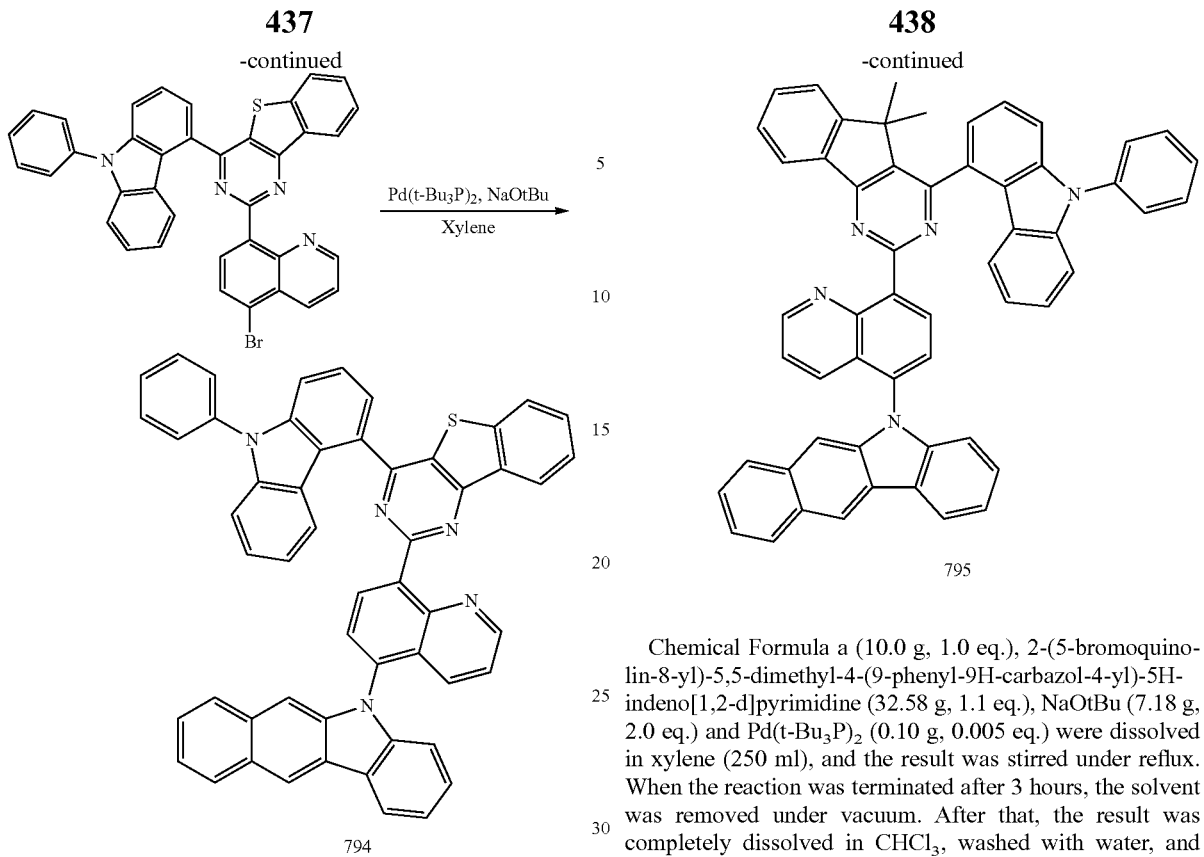

Chemical Formula a (10.0 g, 1.0 eq.), 2-(5-bromoquinolin-8-yl)-4-(9-phenyl-9H-carbazol-4-yl)benzo[4,5]thieno[3,2-d]pyrimidine (32.07 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 794 (23.03 g, yield 65%). [M+H]=770

SYNTHESIS EXAMPLE 86

Chemical Formula a (10.0 g, 1.0 eq.), 2-(5-bromoquinolin-8-yl)-5,5-dimethyl-4-(9-phenyl-9H-carbazol-4-yl)-5H-indeno[1,2-d]pyrimidine (32.58 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 795 (23.33 g, yield 67%). [M+H]=780

SYNTHESIS EXAMPLE 87

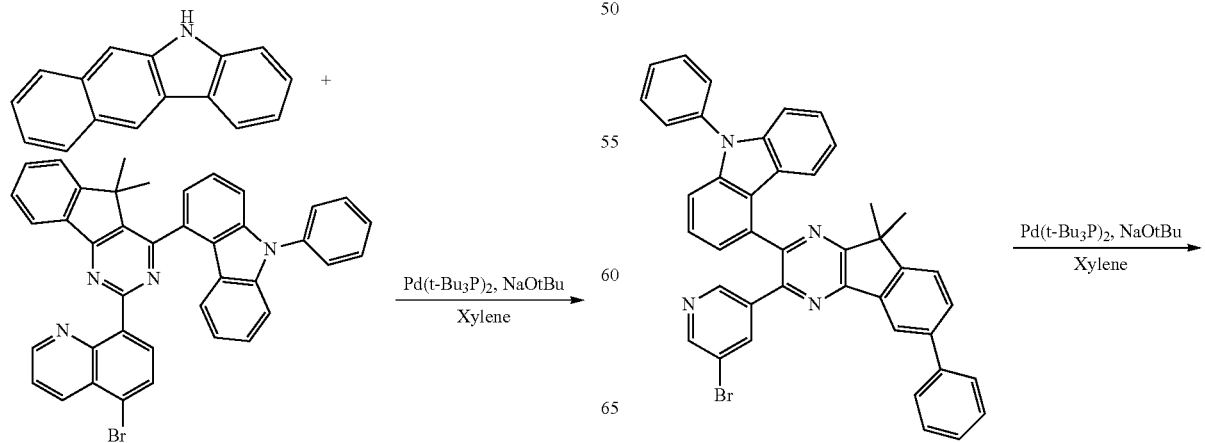

439
-continued

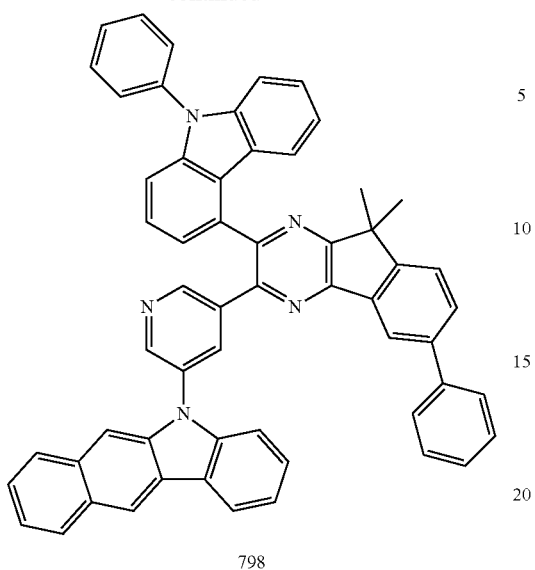

798

440
-continued

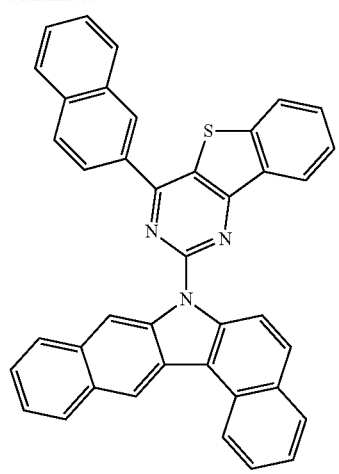

809

Chemical Formula a (10.0 g, 1.0 eq.), 3-(5-bromopyridin-3-yl)-9,9-dimethyl-6-phenyl-2-(9-phenyl-9H-carbazol-4-yl)-9H-indeno[1,2-b]pyrazine (33.90 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 798 (24.85 g, yield 67%). [M+H]=806

SYNTHESIS EXAMPLE 88

Chemical Formula d (10.0 g, 1.0 eq.), 2-chloro-4-(naphthalen-2-yl)benzo[4,5]thieno[3,2-d]pyrimidine (17.55 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 809 (18.34 g, yield 69%). [M+H]=578

FIG. 9 is a graph showing an 1H-NMR value of Chemical Formula 809.

SYNTHESIS EXAMPLE 89

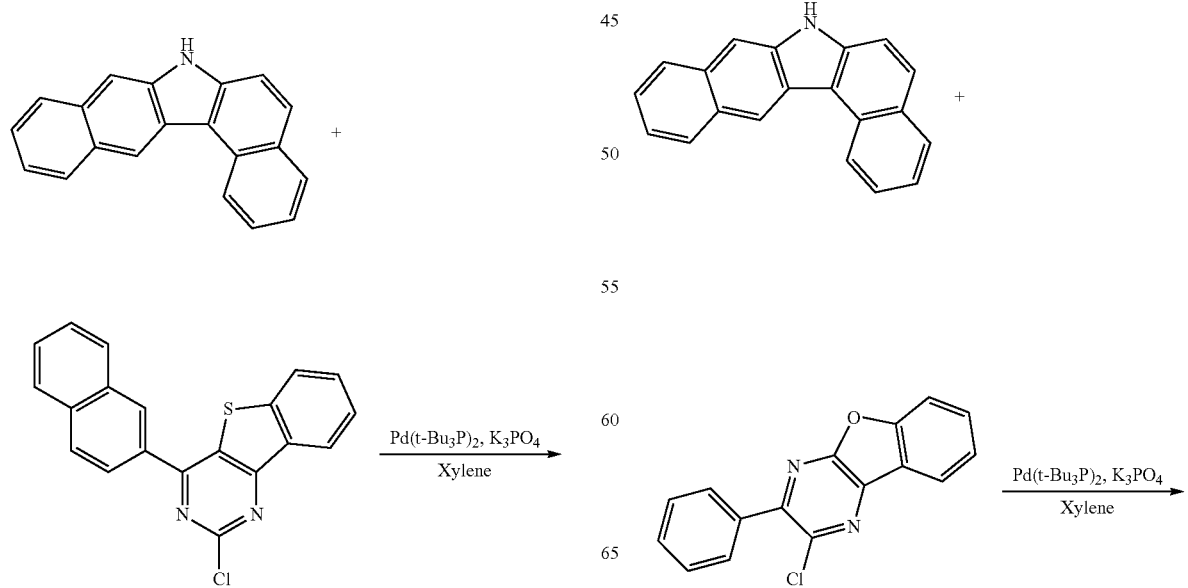

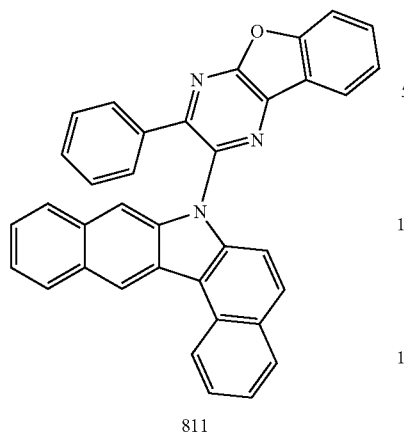

811

Chemical Formula d (10.0 g, 1.0 eq.), 2-chloro-3-phenyl-benzofuro[2,3-b]pyrazine (17.25 g, 1.1 eq.), K$_3$PO$_4$ (14.21 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 811 (15.06 g, yield 64%). [M+H]=512

SYNTHESIS EXAMPLE 90

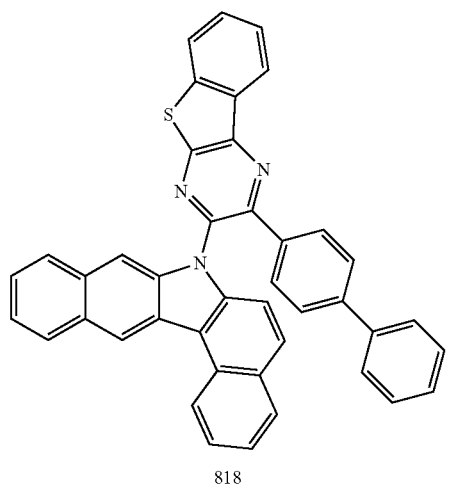

818

Chemical Formula d (10.0 g, 1.0 eq.), 2-([1,1'-biphenyl]-4-yl)-3-chlorobenzo[4,5]thieno[2,3-b]pyrazine (18.87 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 818 (18.61 g, yield 67%). [M+H]=604

SYNTHESIS EXAMPLE 91

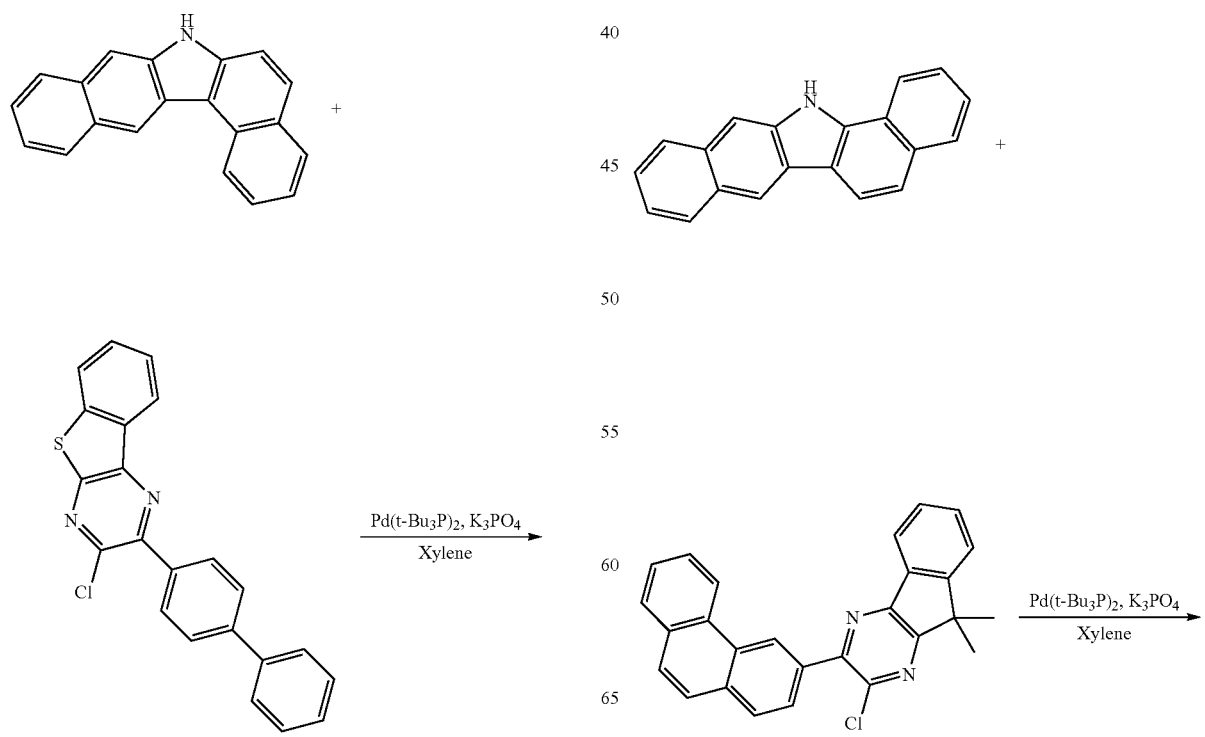

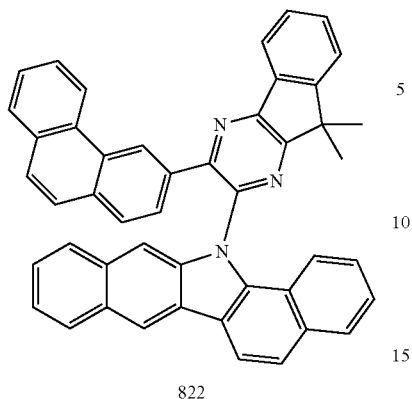

822

Chemical Formula b (10.0 g, 1.0 eq.), 2-chloro-9,9-dimethyl-3-(phenanthren-3-yl)-9H-indeno[1,2-b]pyrazine (20.60 g, 1.1 eq.), $K_3PO_4$ (19.53 g, 2.0 eq.) and Pd(t-$Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 822 (19.08 g, yield 65%). [M+H]=638

SYNTHESIS EXAMPLE 92

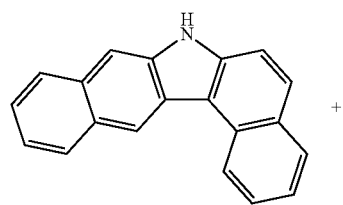

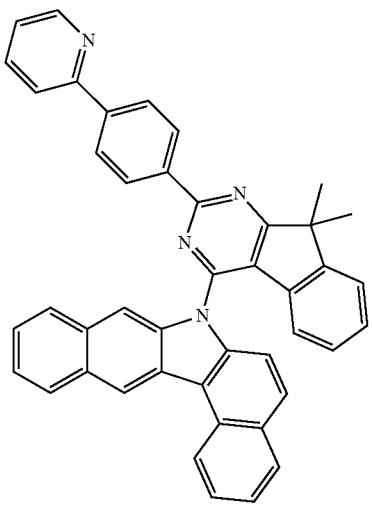

831

Chemical Formula d (10.0 g, 1.0 eq.), 4-chloro-9,9-dimethyl-2-(4-(pyridin-2-yl)phenyl)-9H-indeno[2,1-d]pyrimidine (19.43 g, 1.1 eq.), $K_3PO_4$ (19.53 g, 2.0 eq.) and Pd(t-$Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 831 (19.24 g, yield 68%). [M+H]=615

SYNTHESIS EXAMPLE 93

-continued

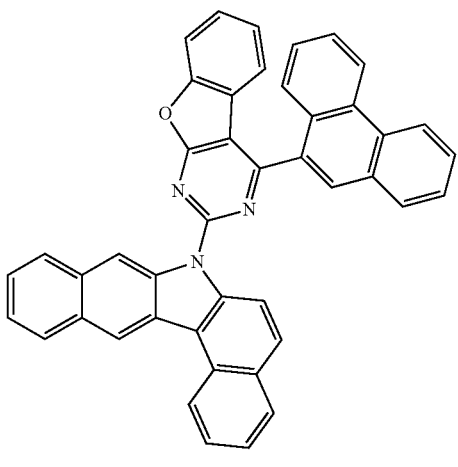

838

Chemical Formula d (10.0 g, 1.0 eq.), 2-chloro-4-(phenanthren-9-yl)benzofuro[2,3-d]pyrimidine (19.28 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 838 (18.30 g, yield 65%). [M+H]=612

SYNTHESIS EXAMPLE 94

-continued

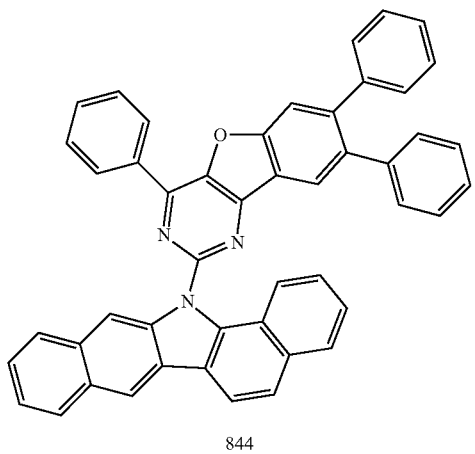

844

Chemical Formula b (10.0 g, 1.0 eq.), 2-chloro-4,7,8-triphenylbenzofuro[3,2-d]pyrimidine (21.91 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 844 (20.46 g, yield 67%). [M+H]=664

SYNTHESIS EXAMPLE 95

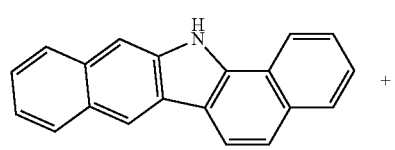 +

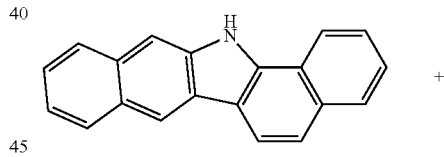 +

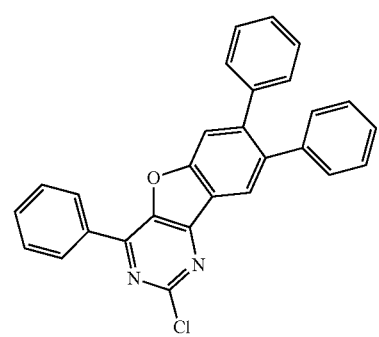 $\xrightarrow{\text{Pd(t-Bu}_3\text{P)}_2, \text{K}_3\text{PO}_4}{\text{Xylene}}$

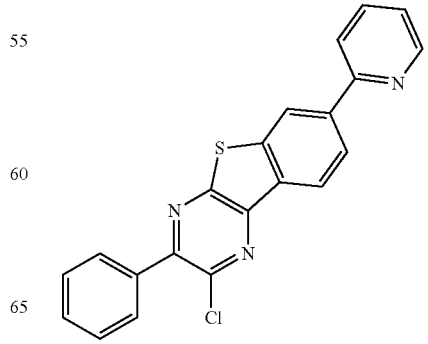 $\xrightarrow{\text{Pd(t-Bu}_3\text{P)}_2, \text{K}_3\text{PO}_4}{\text{Xylene}}$ -continued

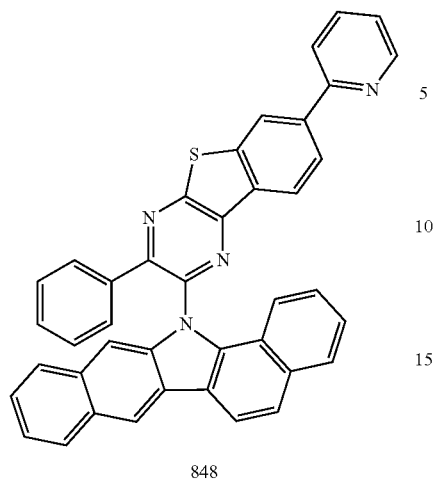

848

Chemical Formula b (10.0 g, 1.0 eq.), 2-chloro-3-phenyl-7-(pyridin-2-yl)benzo[4,5]thieno[2,3-b]pyrazine (18.92 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 848 (18.09 g, yield 65%). [M+H]=605

SYNTHESIS EXAMPLE 96

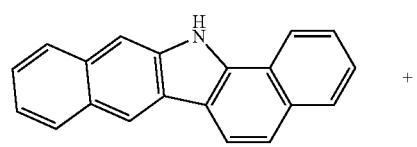

+

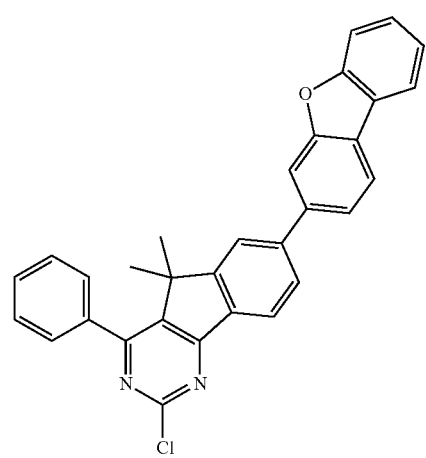

-continued

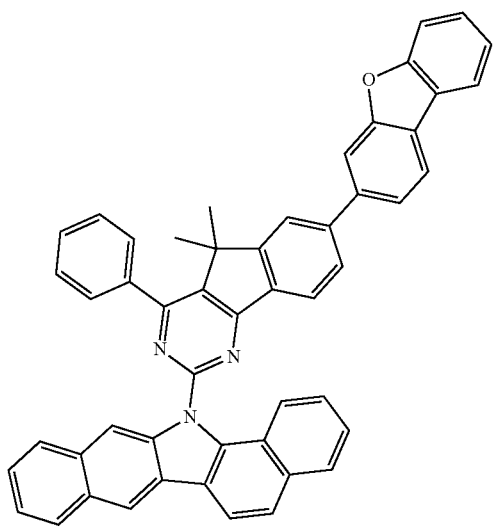

861

Chemical Formula b (10.0 g, 1.0 eq.), 2-chloro-7-(dibenzo[b,d]furan-3-yl)-5,5-dimethyl-4-phenyl-5H-indeno[1,2-d]pyrimidine (23.94 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 861 (21.38 g, yield 66%). [M+H]=704

SYNTHESIS EXAMPLE 97

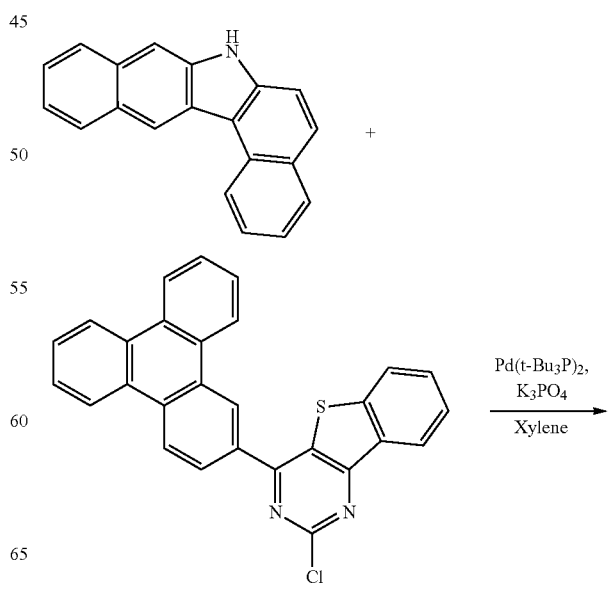

Chemical Formula d (10.0 g, 1.0 eq.), 2-chloro-4-(triphenylen-2-yl)benzo[4,5]thieno[3,2-d]pyrimidine (22.62 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 863 (19.96 g, yield 64%). [M+H]=678

SYNTHESIS EXAMPLE 98

Chemical Formula d (10.0 g, 1.0 eq.), 2-chloro-4-(naphthalen-2-yl-d7)benzo[4,5]thieno[3,2-d]pyrimidine (17.91 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 866 (16.14 g, yield 60%). [M+H]=585

SYNTHESIS EXAMPLE 99

-continued

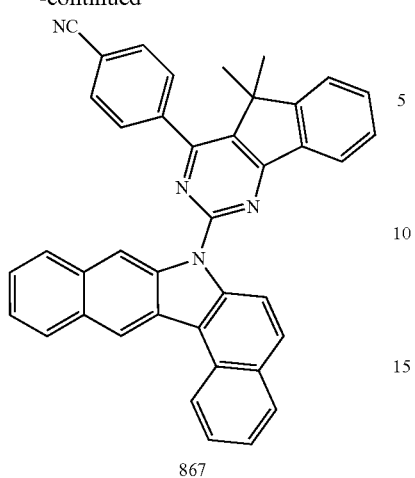

867

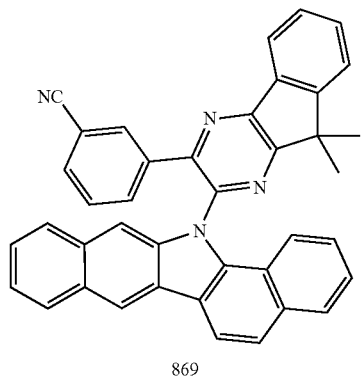

869

Chemical Formula d (10.0 g, 1.0 eq.), 4-(2-chloro-5,5-dimethyl-5H-indeno[1,2-d]pyrimidin-4-yl)benzonitrile (16.79 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 867 (17.35 g, yield 67%). [M+H]=563

Chemical Formula b (10.0 g, 1.0 eq.), 3-(2-chloro-9,9-dimethyl-9H-indeno[1,2-b]pyrazin-3-yl)benzonitrile (16.79 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 869 (16.57 g, yield 64%). [M+H]=563

SYNTHESIS EXAMPLE 100

SYNTHESIS EXAMPLE 101

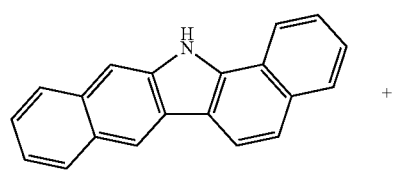

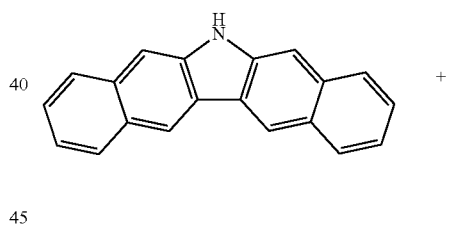

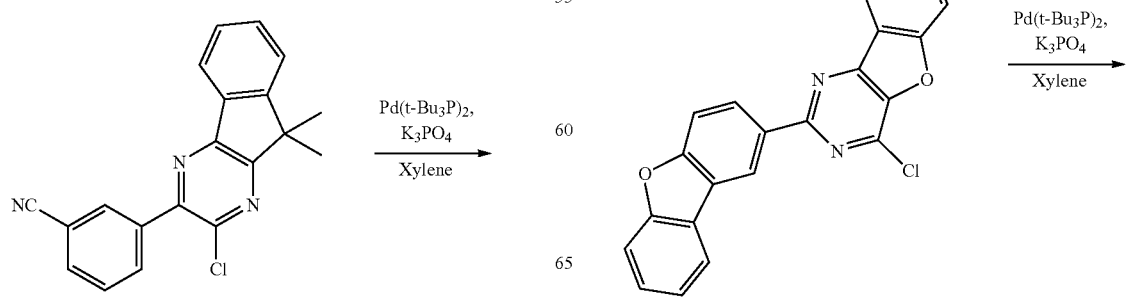

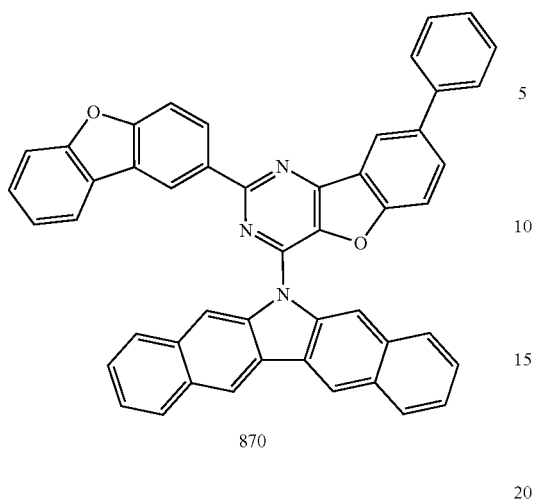

870

Chemical Formula c (10.0 g, 1.0 eq.), 4-chloro-2-(dibenzo[b,d]furan-2-yl)-8-phenylbenzofuro[3,2-d]pyrimidine (22.62 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 870 (20.90 g, yield 67%). [M+H]=678

SYNTHESIS EXAMPLE 102

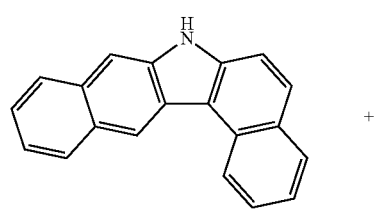

871

Chemical Formula d (10.0 g, 1.0 eq.), 2-chloro-4-(phenyl-d5)benzofuro[2,3-d]pyrimidine (14.46 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 871 (17.83 g, yield 75%). [M+H]=517

SYNTHESIS EXAMPLE 103

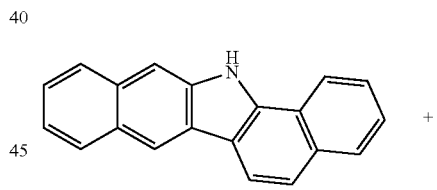

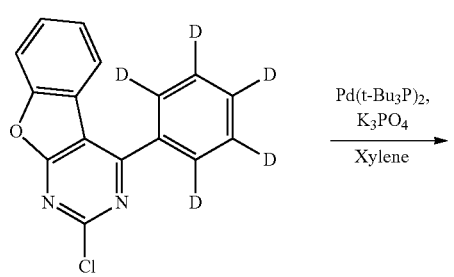

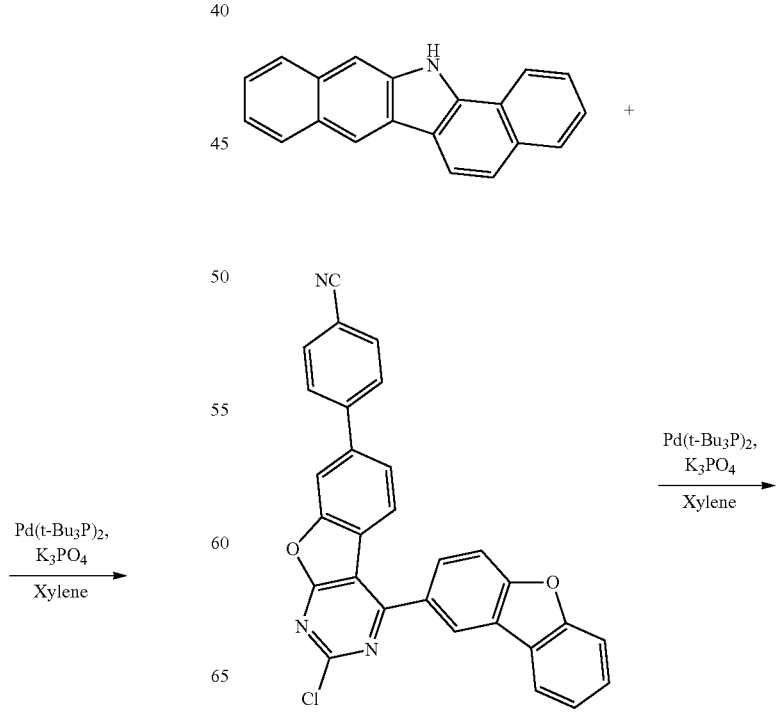

455
-continued

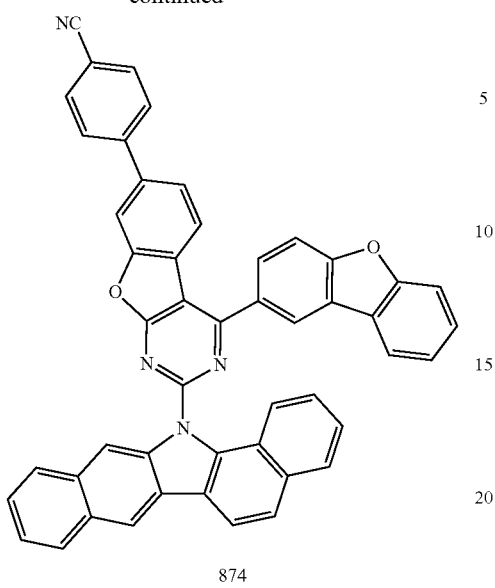

874

456
-continued

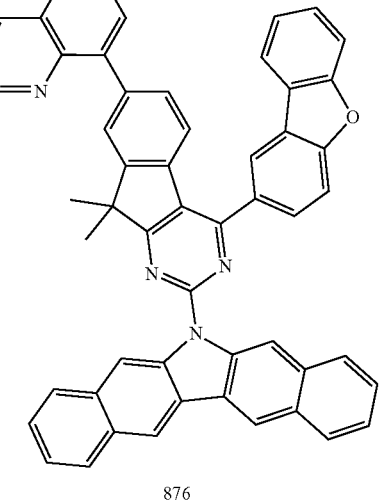

876

Chemical Formula b (10.0 g, 1.0 eq.), 4-(2-chloro-4-(dibenzo[b,d]furan-2-yl)benzofuro[2,3-d]pyrimidin-7-yl) benzonitrile (23.89 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 874 (21.67 g, yield 67%). [M+H]=703

SYNTHESIS EXAMPLE 104

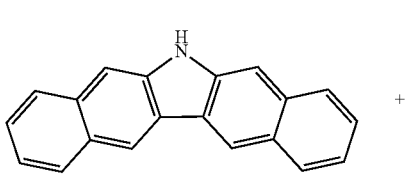

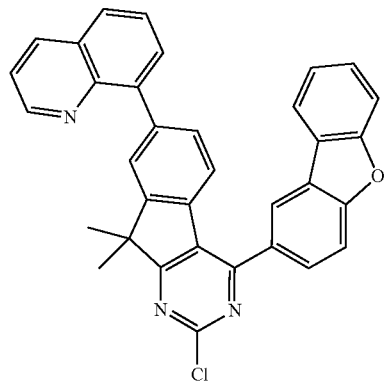

Chemical Formula c (10.0 g, 1.0 eq.), 2-chloro-4-(dibenzo[b,d]furan-2-yl)-9,9-dimethyl-7-(quinolin-8-yl)-9H-indeno[2,1-d]pyrimidine (26.53 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 876 (22.58 g, yield 65%). [M+H]=634

SYNTHESIS EXAMPLE 105

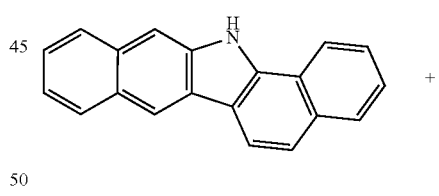

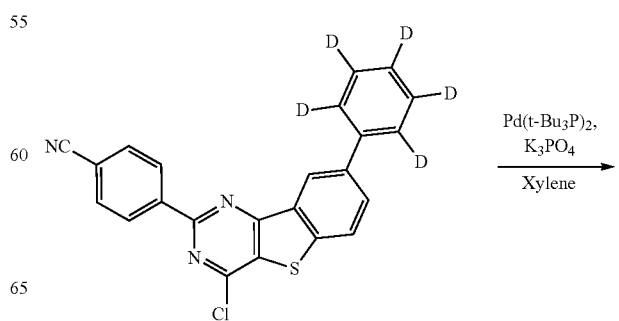

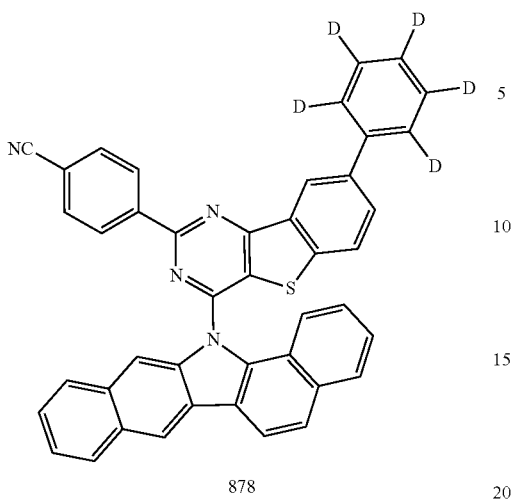

878

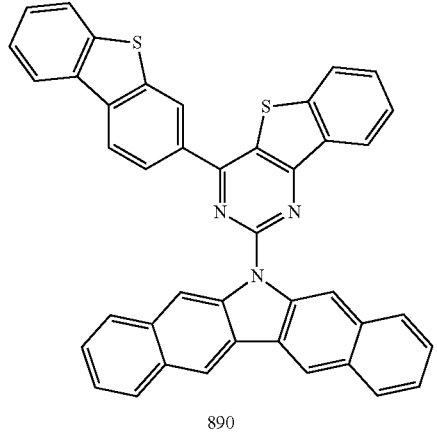

890

Chemical Formula b (10.0 g, 1.0 eq.), 4-(4-chloro-8-(phenyl-d5)benzo[4,5]thieno[3,2-d]pyrimidin-2-yl)benzonitrile (20.39 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 878 (18.96 g, yield 65%). [M+H]=634

Chemical Formula c (10.0 g, 1.0 eq.), 2-chloro-4-(dibenzo[b,d]thiophen-3-yl)benzo[4,5]thieno[3,2-d]pyrimidine (20.39 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 890 (18.08 g, yield 62%). [M+H]=634

SYNTHESIS EXAMPLE 106

SYNTHESIS EXAMPLE 107

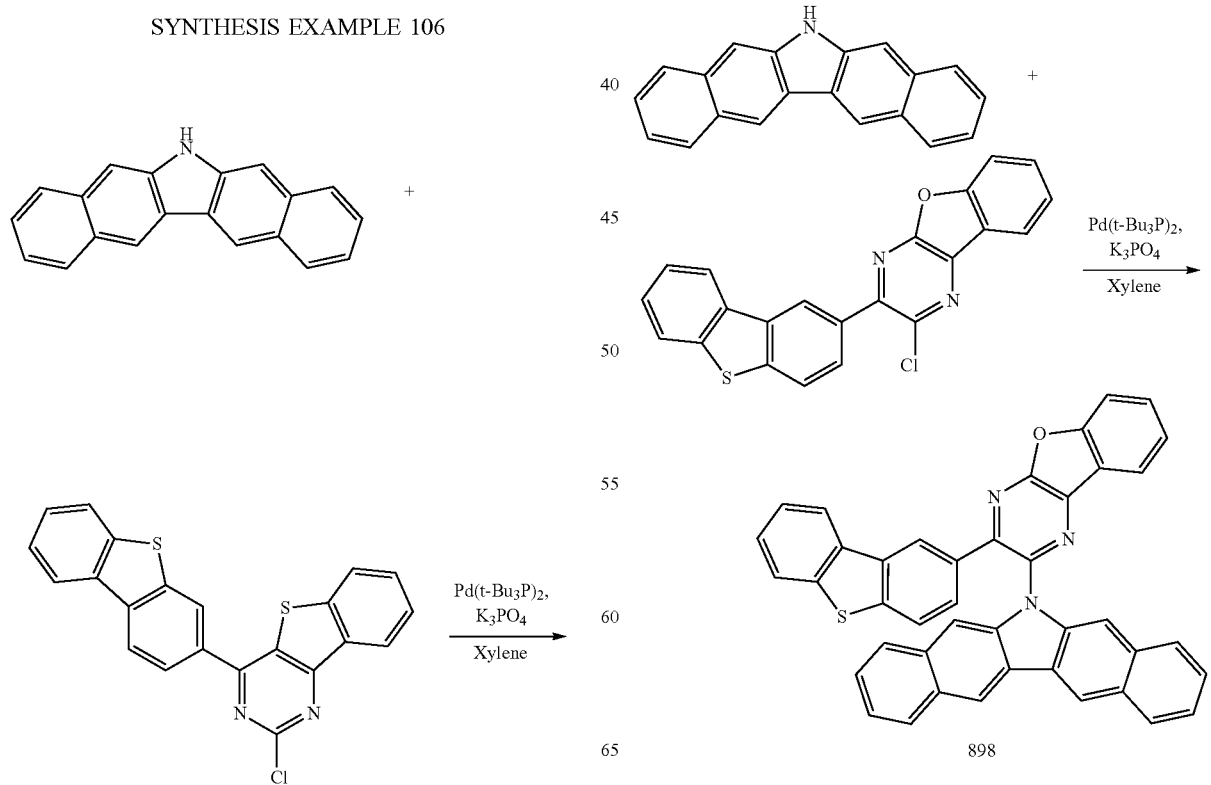

898

459

Chemical Formula c (10.0 g, 1.0 eq.), 2-chloro-3-(dibenzo[b,d]thiophen-2-yl)benzofuro[2,3-b]pyrazine (19.58 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 898 (18.19 g, yield 64%). [M+H]=618

SYNTHESIS EXAMPLE 108

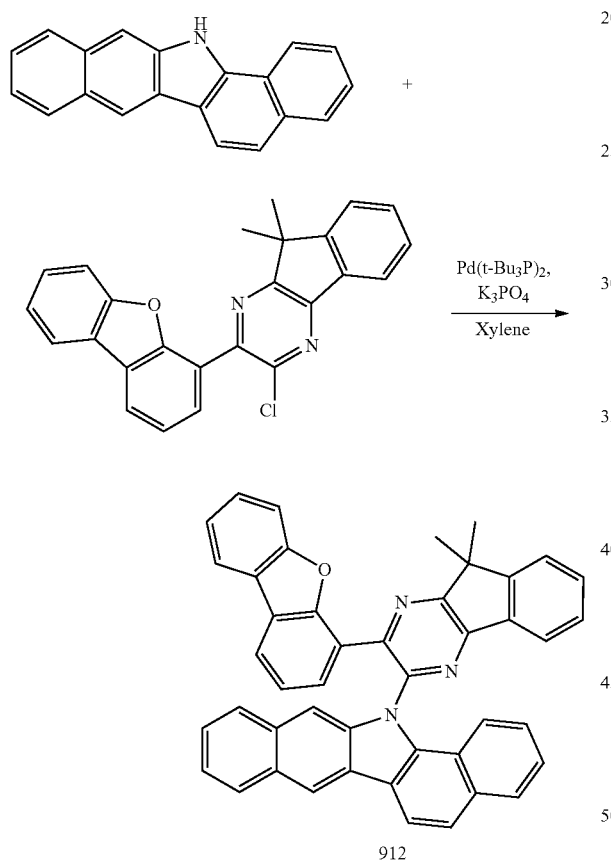

912

Chemical Formula b (10.0 g, 1.0 eq.), 3-chloro-2-(dibenzo[b,d]furan-4-yl)-9,9-dimethyl-9H-indeno[1,2-b]pyrazine (20.09 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 912 (19.35 g, yield 67%). [M+H]=628

460

SYNTHESIS EXAMPLE 109

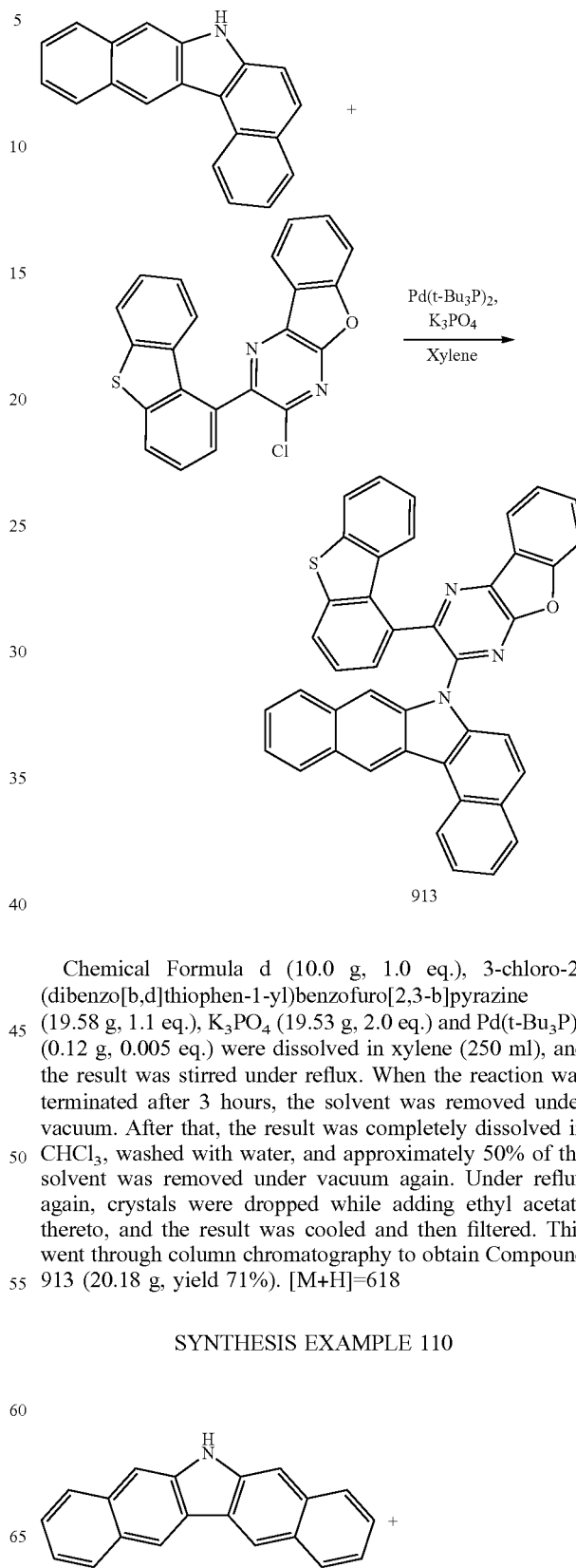

913

Chemical Formula d (10.0 g, 1.0 eq.), 3-chloro-2-(dibenzo[b,d]thiophen-1-yl)benzofuro[2,3-b]pyrazine (19.58 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 913 (20.18 g, yield 71%). [M+H]=618

SYNTHESIS EXAMPLE 110

-continued

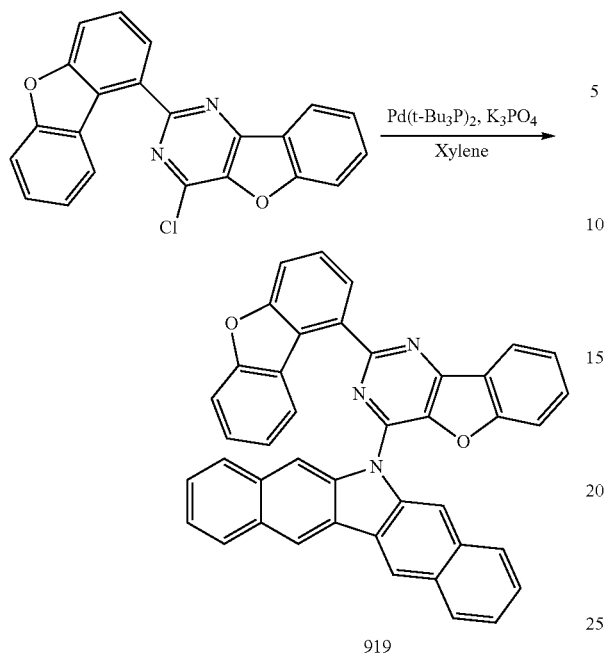

919

Chemical Formula c (10.0 g, 1.0 eq.), 4-chloro-2-(dibenzo[b,d]furan-1-yl)benzofuro[3,2-d]pyrimidine (18.77 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 919 (19.38 g, yield 70%). [M+H]=602

SYNTHESIS EXAMPLE 111

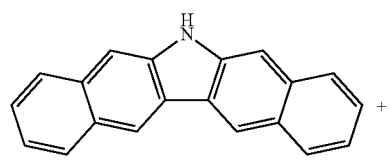

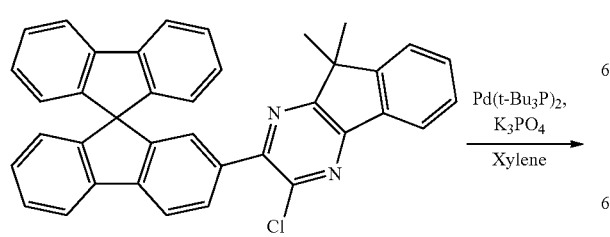

-continued

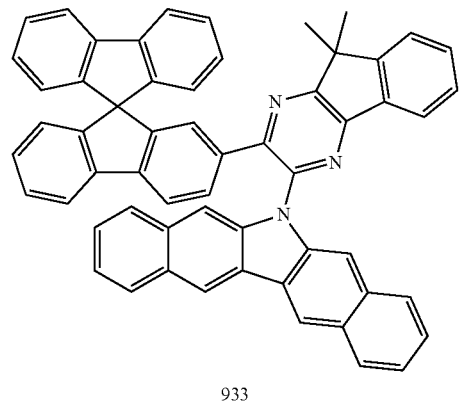

933

Chemical Formula c (10.0 g, 1.0 eq.), 2-(9,9'-spirobi[fluoren]-2-yl)-3-chloro-9,9-dimethyl-9H-indeno[1,2-b]pyrazine (27.59 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 933 (23.92 g, yield 67%). [M+H]=776

SYNTHESIS EXAMPLE 112

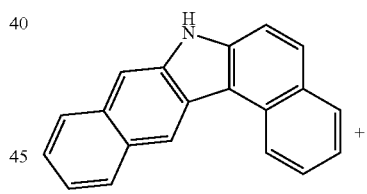

463

-continued

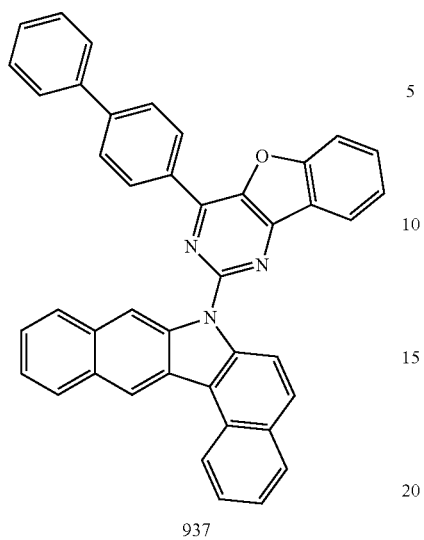

937

Chemical Formula d (10.0 g, 1.0 eq.), 4-([1,1'-biphenyl]-4-yl)-2-chlorobenzofuro[3,2-d]pyrimidine (18.06 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 937 (19.47 g, yield 72%). [M+H]=588

SYNTHESIS EXAMPLE 113

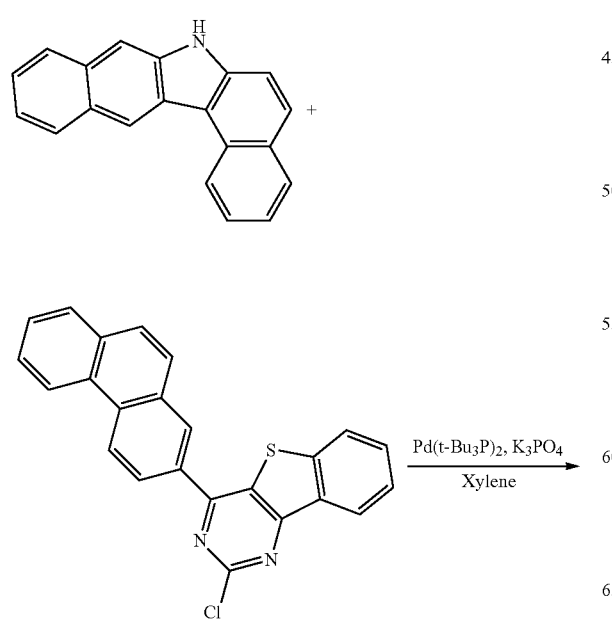

464

-continued

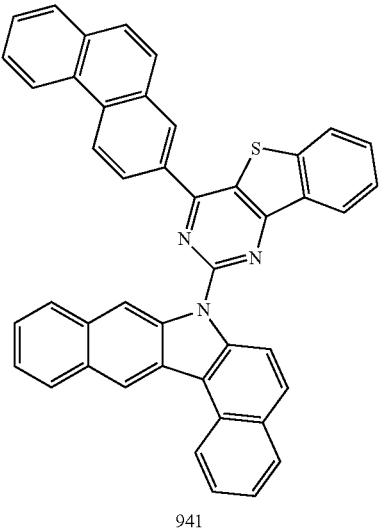

941

Chemical Formula d (10.0 g, 1.0 eq.), 2-chloro-4-(phenanthren-2-yl)benzo[4,5]thieno[3,2-d]pyrimidine (20.09 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 941 (21.38 g, yield 74%). [M+H]=628

SYNTHESIS EXAMPLE 114

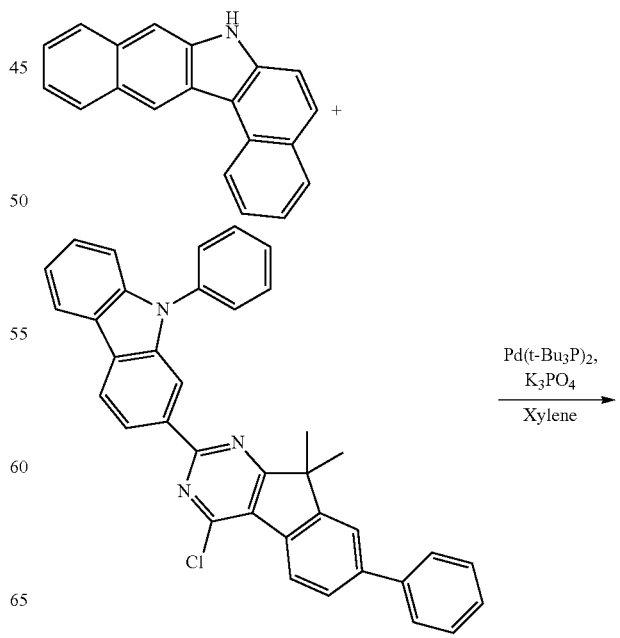

465

-continued

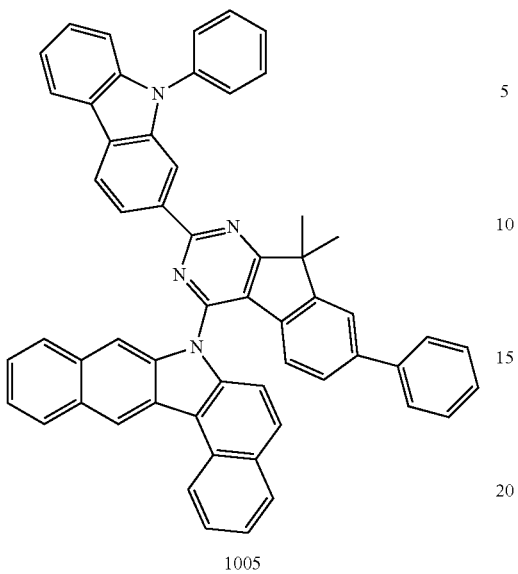

1005

Chemical Formula d (10.0 g, 1.0 eq.), 4-chloro-9,9-dimethyl-7-phenyl-2-(9-phenyl-9H-carbazol-2-yl)-9H-indeno[2,1-d]pyrimidine (27.74 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 1005 (27.74 g, yield 63%). [M+H]=779

SYNTHESIS EXAMPLE 115

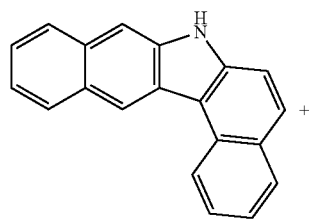

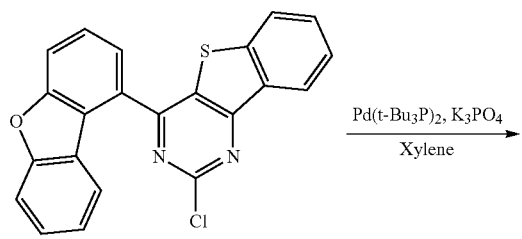

466

-continued

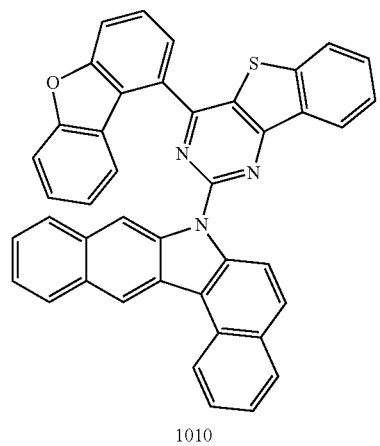

1010

Chemical Formula d (10.0 g, 1.0 eq.), 2-chloro-4-(dibenzo[b,d]furan-1-yl)benzo[4,5]thieno[3,2-d]pyrimidine (15.91 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 1010 (15.25 g, yield 66%). [M+H]=618

SYNTHESIS EXAMPLE 116

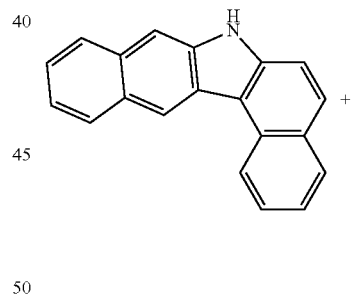

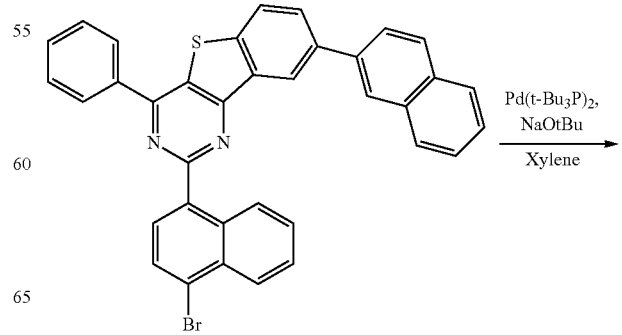

-continued

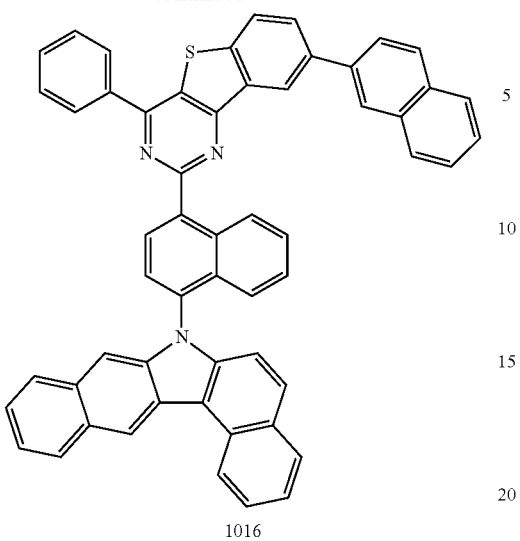

1016

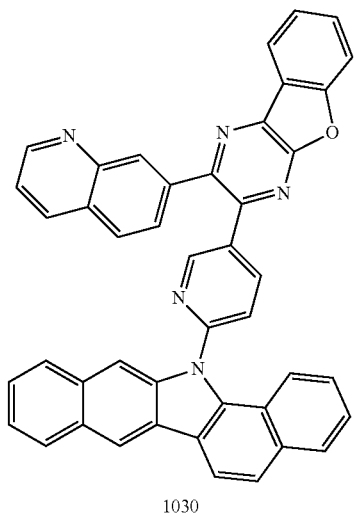

1030

Chemical Formula d (10.0 g, 1.0 eq.), 2-(4-bromonaphthalen-1-yl)-8-(naphthalen-2-yl)-4-phenylbenzo[4,5]thieno[3,2-d]pyrimidine (24.42 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1016 (17.79 g, yield 61%). [M+H]=780

Chemical Formula b (10.0 g, 1.0 eq.), 3-(6-bromopyridin-3-yl)-2-(quinolin-7-yl)benzofuro[2,3-b]pyrazine (24.83 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1030 (18.61 g, yield 63%). [M+H]=640

SYNTHESIS EXAMPLE 118

SYNTHESIS EXAMPLE 117

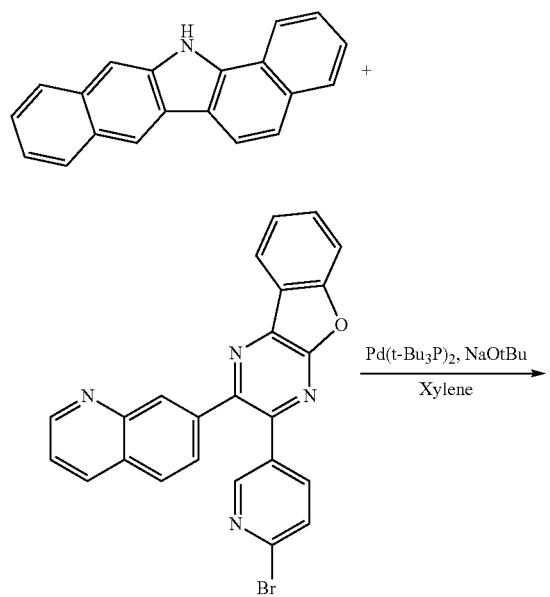

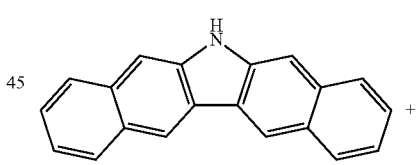

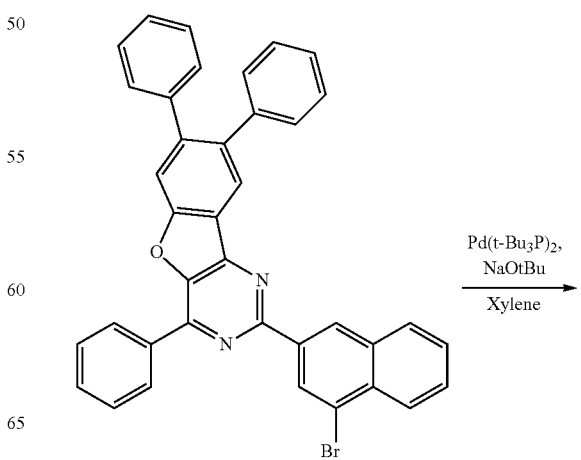

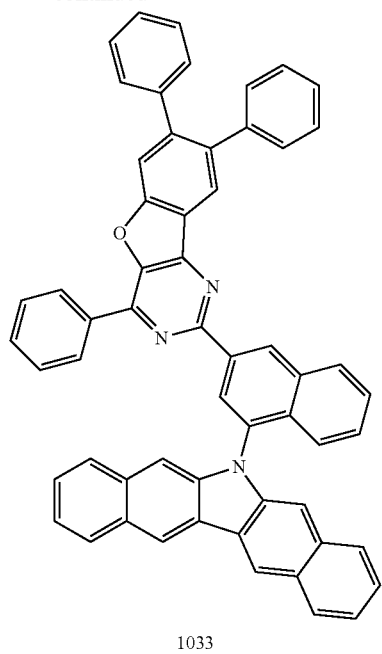

1033

Chemical Formula c (10.0 g, 1.0 eq.), 2-(4-bromonaphthalen-2-yl)-4,7,8-triphenylbenzofuro[3,2-d]pyrimidine (18.65 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1033 (15.55 g, yield 65%). [M+H]=790

SYNTHESIS EXAMPLE 119

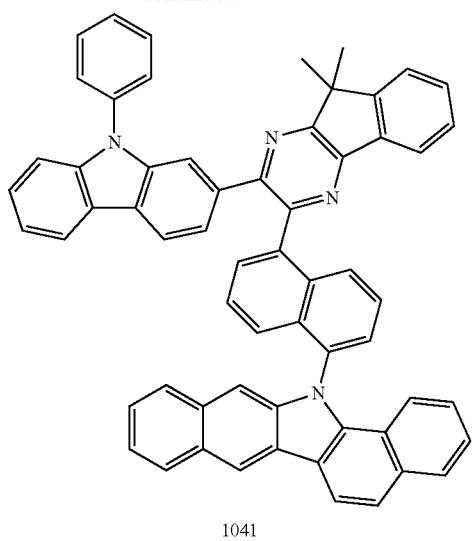

1041

Chemical Formula b (10.0 g, 1.0 eq.), 3-(5-bromonaphthalen-1-yl)-9,9-dimethyl-2-(9-phenyl-9H-carbazol-2-yl)-9H-indeno[1,2-b]pyrazine (26.44 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1041 (18.91 g, yield 61%). [M+H]=830

SYNTHESIS EXAMPLE 120

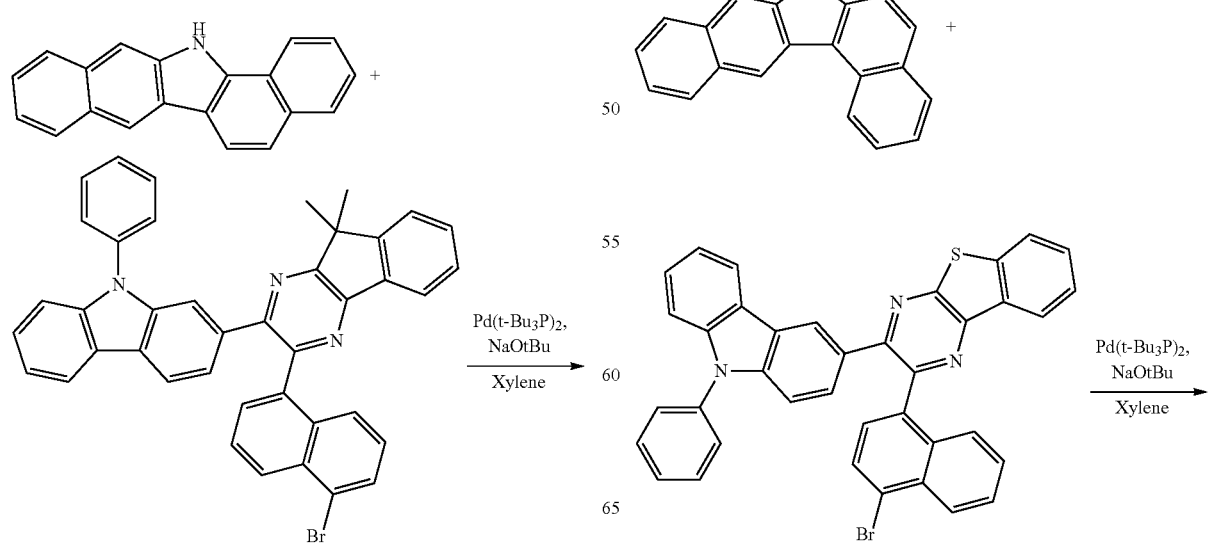

-continued

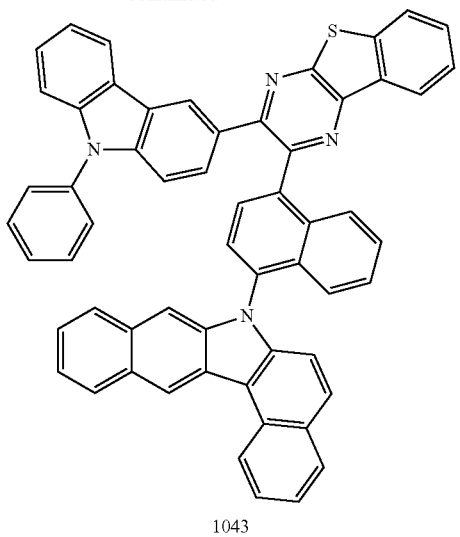

1043

Chemical Formula d (10.0 g, 1.0 eq.), 2-(4-bromonaphthalen-1-yl)-3-(9-phenyl-9H-carbazol-3-yl)benzo[4,5]thieno[2,3-b]pyrazine (26.02 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1043 (19.91 g, yield 65%). [M+H]=820

SYNTHESIS EXAMPLE 121

-continued

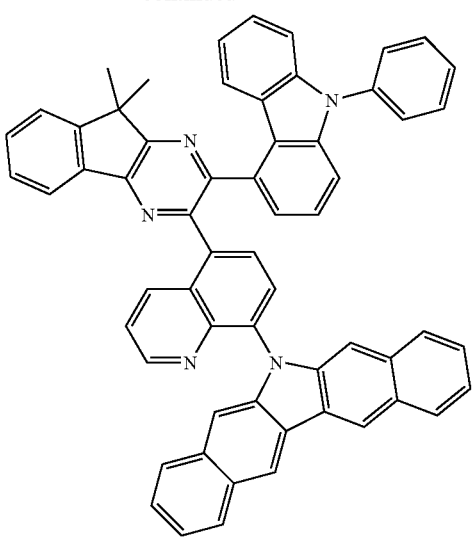

1047

Chemical Formula c (10.0 g, 1.0 eq.), 3-(8-bromoquinolin-5-yl)-9,9-dimethyl-2-(9-phenyl-9H-carbazol-4-yl)-9H-indeno[1,2-b]pyrazine (26.48 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1047 (19.24 g, yield 62%). [M+H]=831

SYNTHESIS EXAMPLE 122

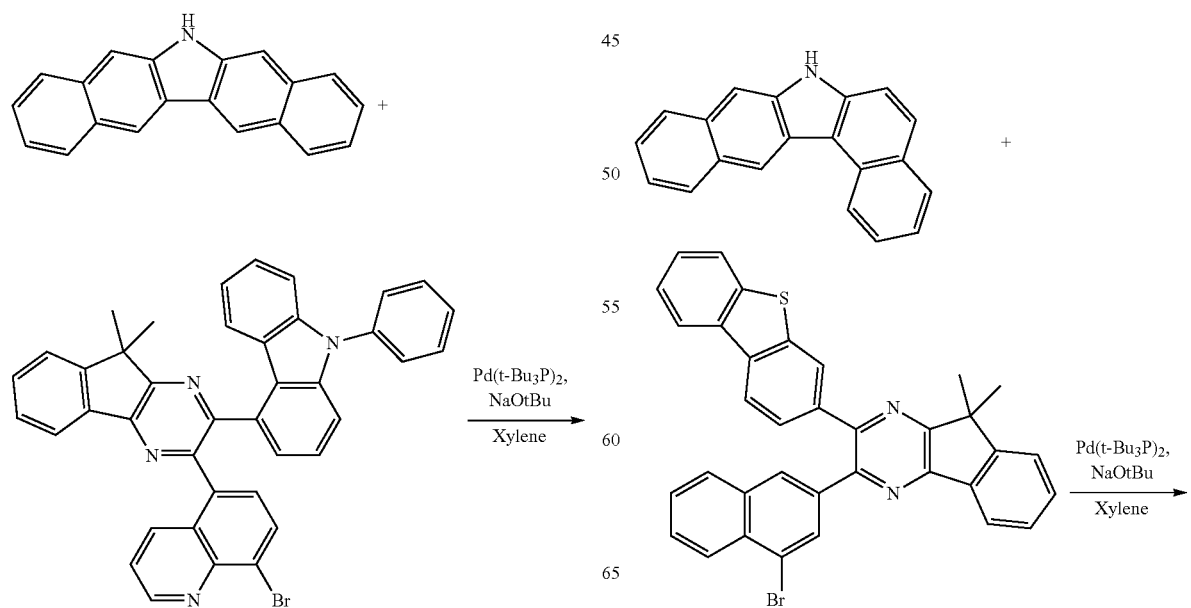

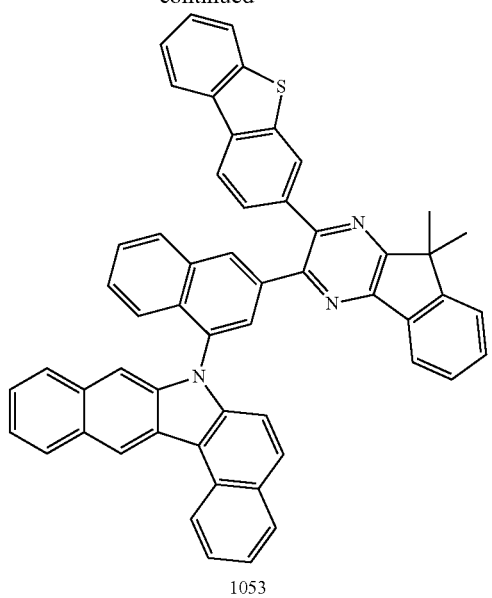

1053

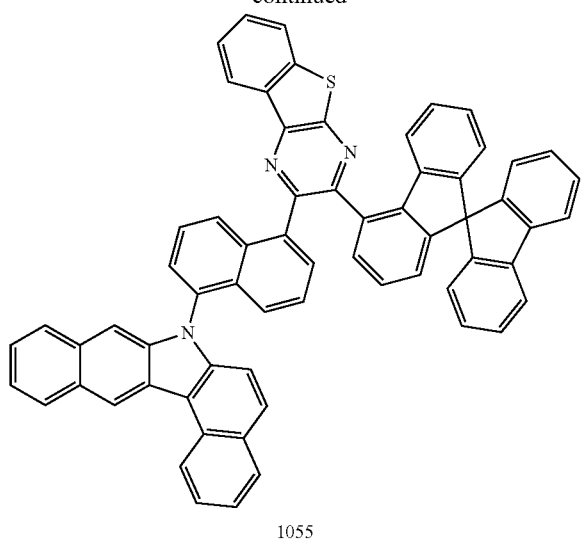

1055

Chemical Formula d (10.0 g, 1.0 eq.), 3-(4-bromonaphthalen-2-yl)-2-(dibenzo[b,d]thiophen-3-yl)-9,9-dimethyl-9H-indeno[1,2-b]pyrazine (24.01 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1053 (18.72 g, yield 65%). [M+H]=770

SYNTHESIS EXAMPLE 123

Chemical Formula d (10.0 g, 1.0 eq.), 3-(9,9'-spirobi[fluoren]-4-yl)-2-(5-bromonaphthalen-1-yl)benzo[4,5]thieno[2,3-b]pyrazine (29.03 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1055 (20.35 g, yield 61%). [M+H]=893

SYNTHESIS EXAMPLE 124

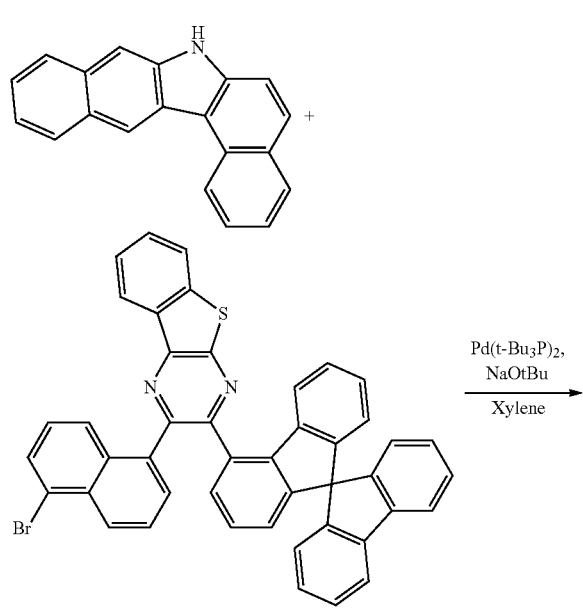

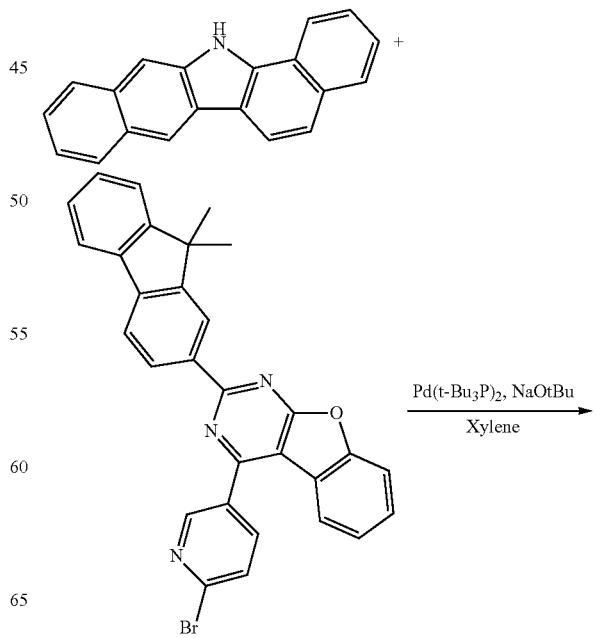

-continued

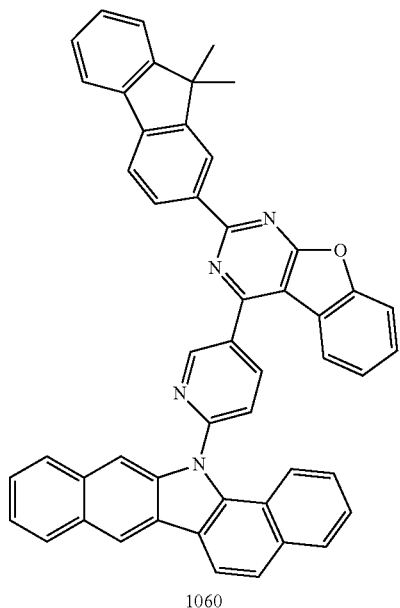

1060

Chemical Formula b (10.0 g, 1.0 eq.), 4-(6-bromopyridin-3-yl)-2-(9,9-dimethyl-9H-fluoren-2-yl)benzofuro[2,3-d]pyrimidine (21.33 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1060 (16.87 g, yield 64%). [M+H]=705

COMPARATIVE EXAMPLE 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 Compound was formed to a thickness of 1150 Å as a hole injection layer with the following A-1 Compound being p-doped in a concentration of 1.5%. A hole transfer layer having a film thickness of 800 Å was formed by vacuum depositing the following HT-1 Compound on the hole injection layer. Subsequently, an electron blocking layer was formed by vacuum depositing the following EB-1 Compound on the hole transfer layer to a film thickness of 150 Å. Then, on the EB-1 deposited film, a red light emitting layer having a thickness of 400 Å was formed by vacuum depositing the following RH-1 Compound and the following Dp-7 Compound in a weight ratio of 98:2. On the light emitting layer, a hole blocking layer was formed by vacuum depositing the following HB-1 Compound to a film thickness of 30 Å. Then, on the hole blocking layer, an electron injection and transfer layer was formed to a thickness of 300 Å by vacuum depositing the following ET-1 Compound and the following LiQ Compound in a weight ratio of 2:1. A cathode was formed on the electron injection and transfer layer by depositing lithium fluoride (LiF) to a thickness of 12 Å and aluminum to a thickness of 1,000 Å in consecutive order.

HI-1

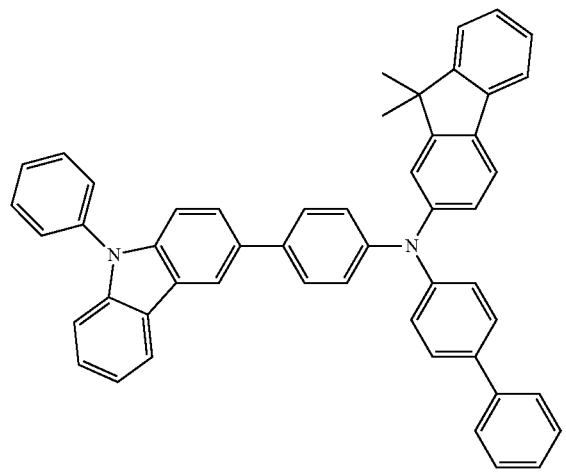

A-1

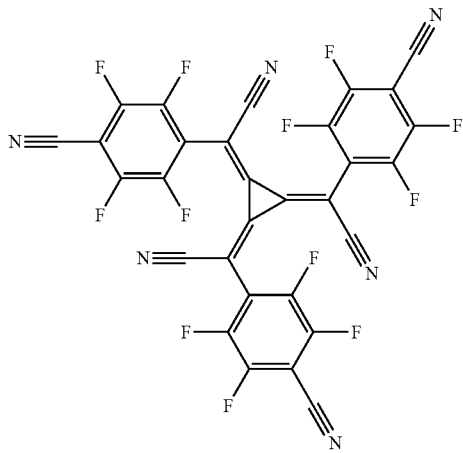

-continued
HT-1
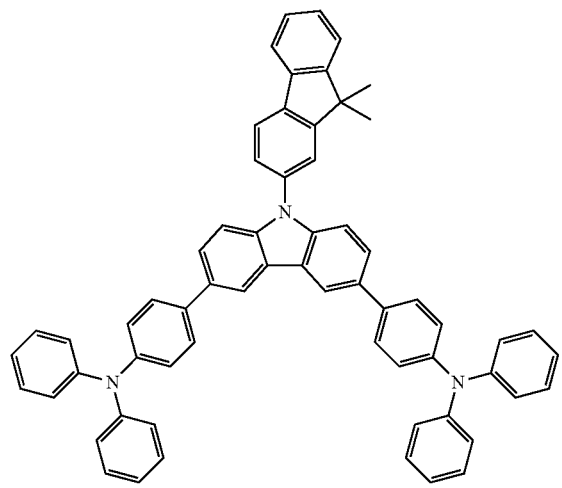
EB-1
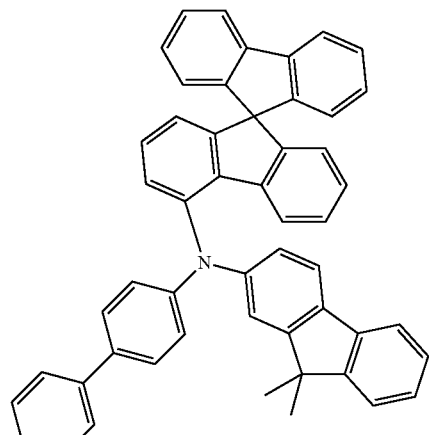
RH-1
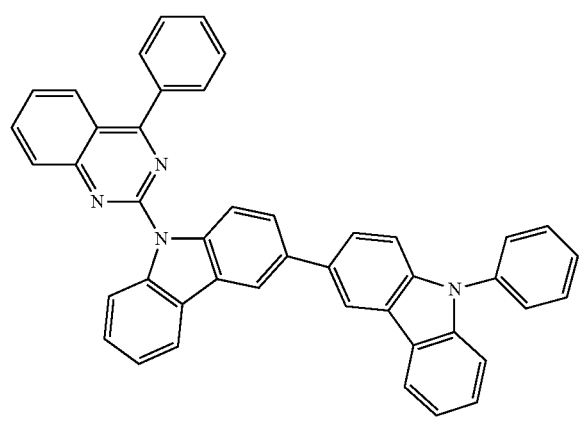
Dp-7
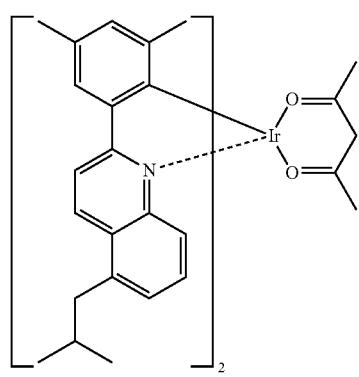
HB-1
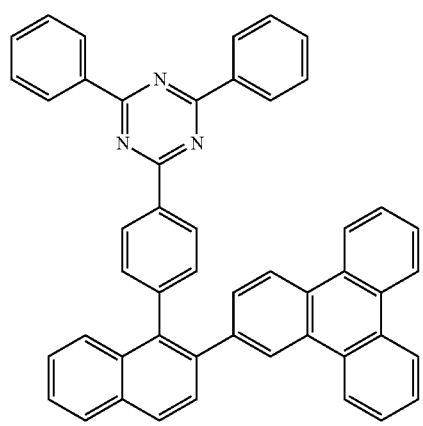

ET-1
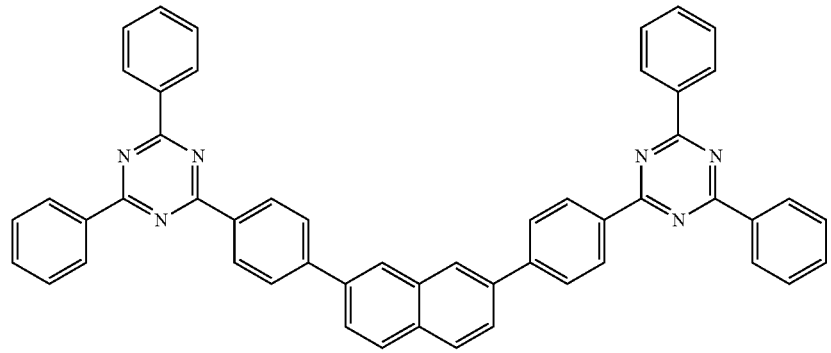
LiQ
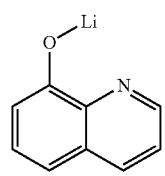
RH-2
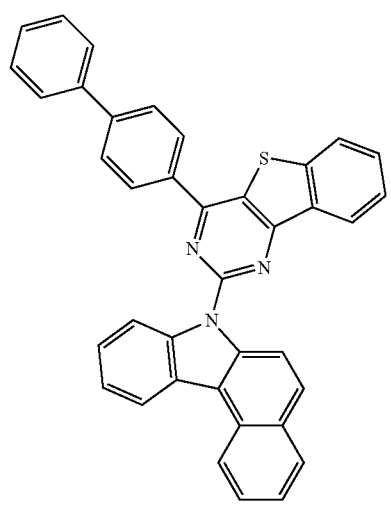
RH-3
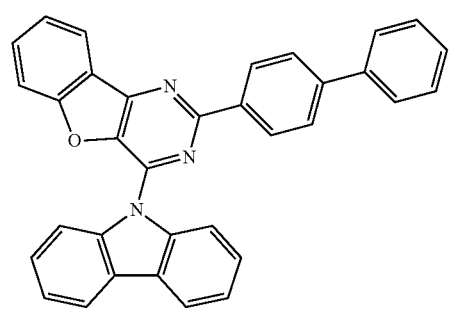
RH-4
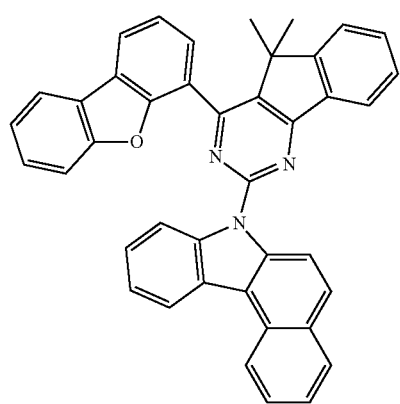

-continued
RH-5
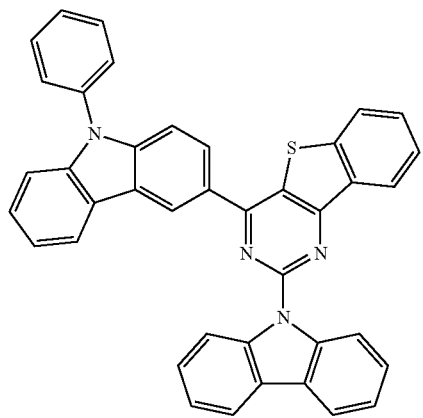
RH-6
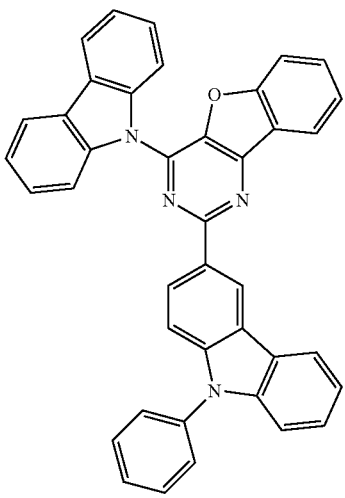
RH-7
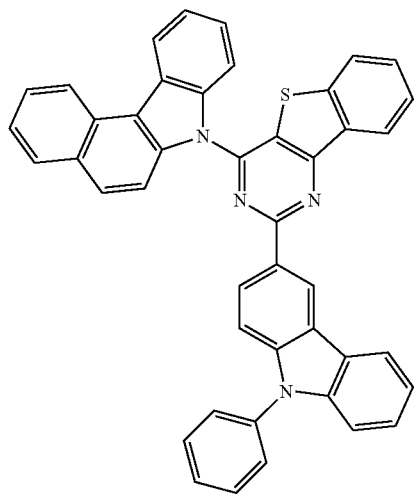
RH-8
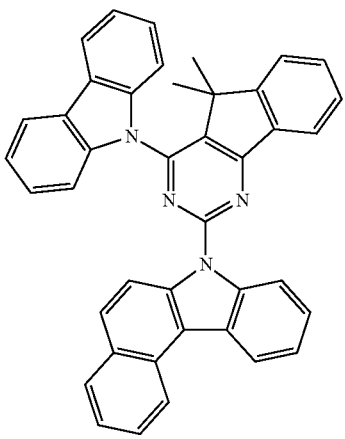
RH-9
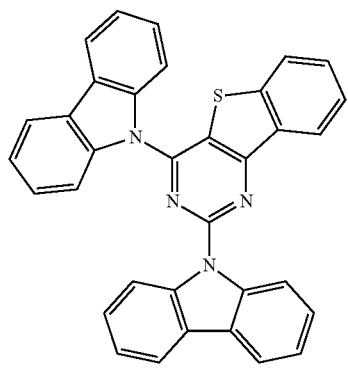
RH-10
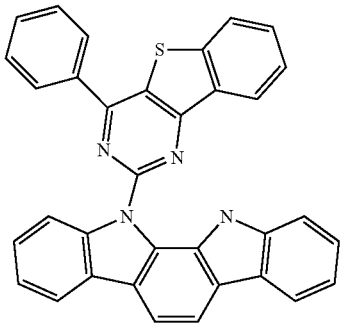

-continued
RH-11
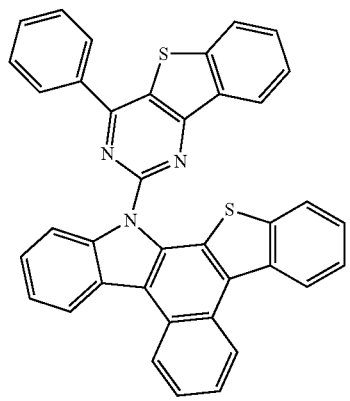
RH-12
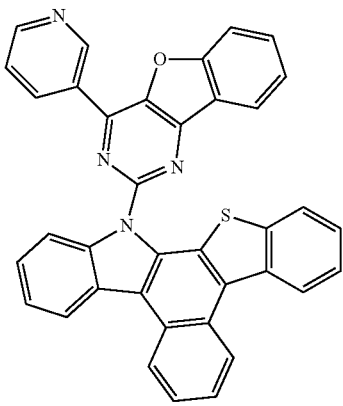
RH-13
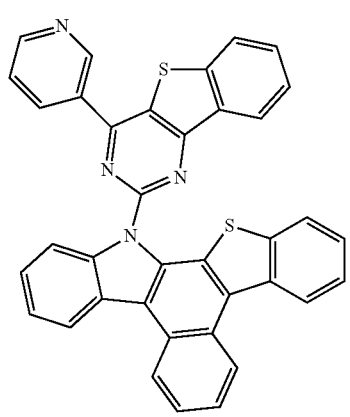
RH-14
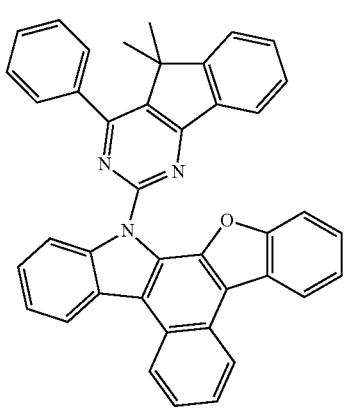
RH-15
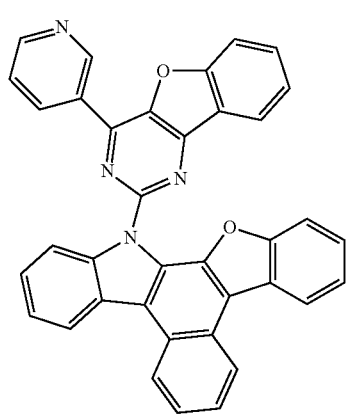
RH-16
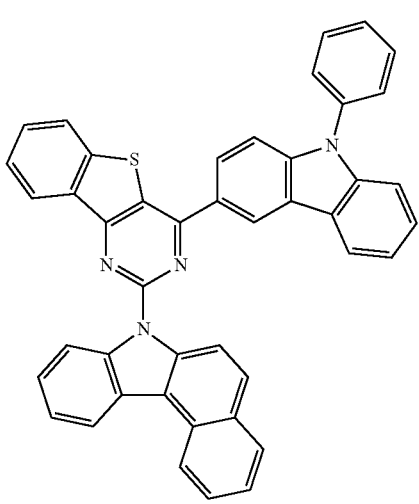

-continued
RH-17
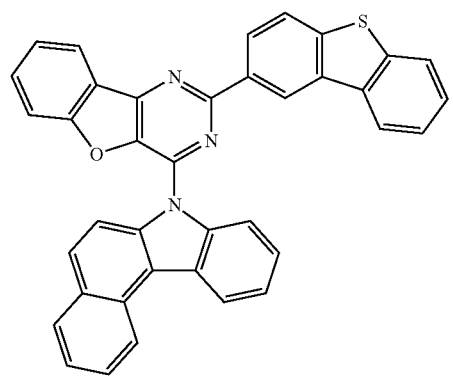
RH-18
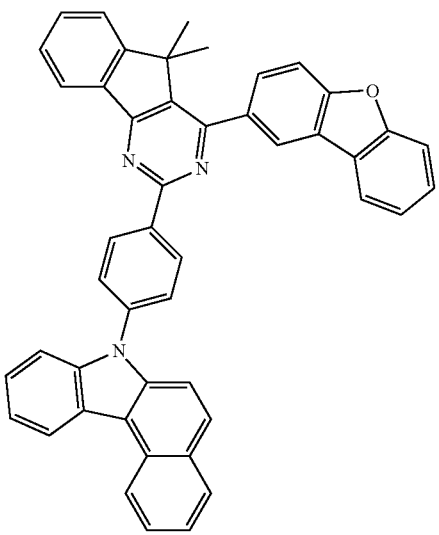
RH-19
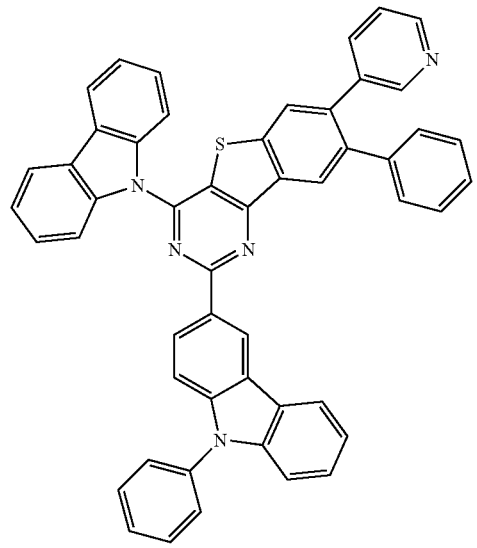
RH-20
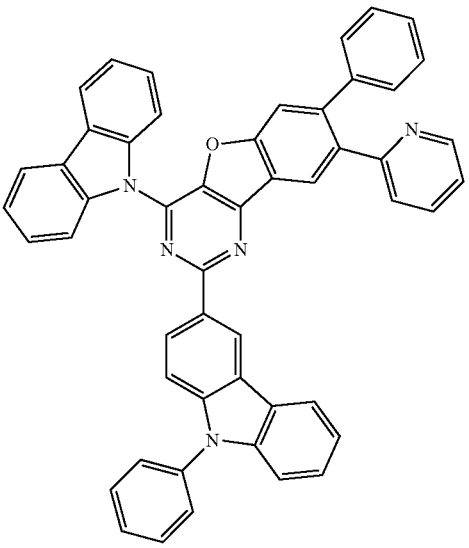
RH-21
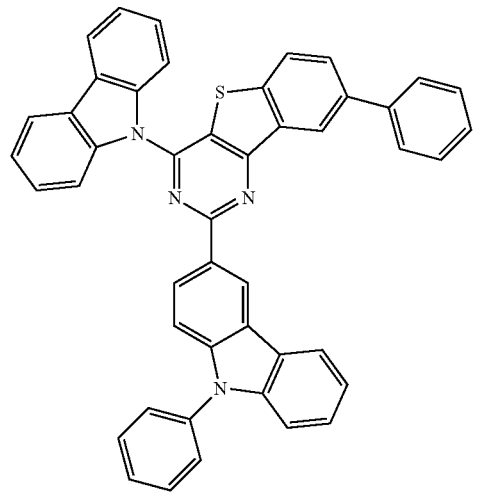
RH-22
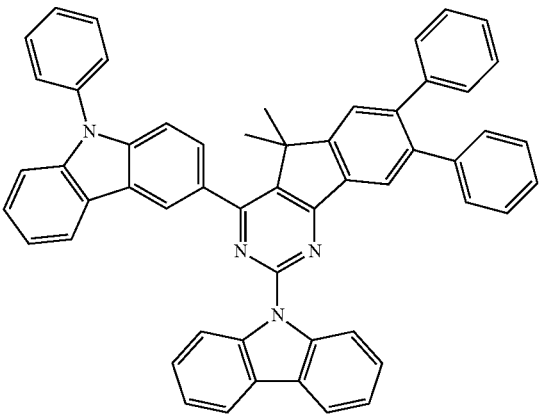

-continued
RH-23
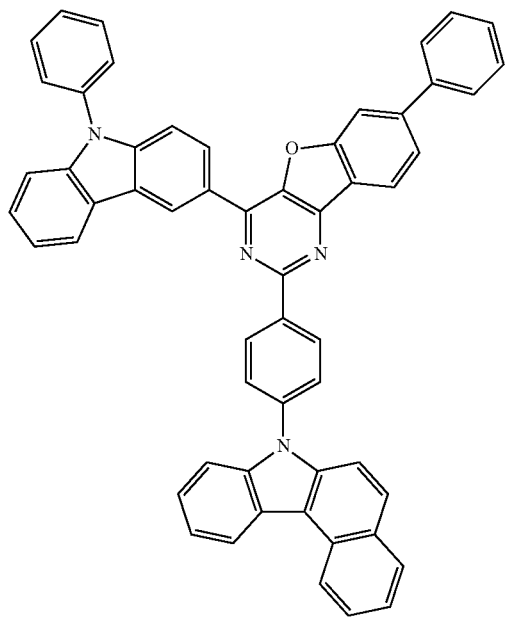
RH-24
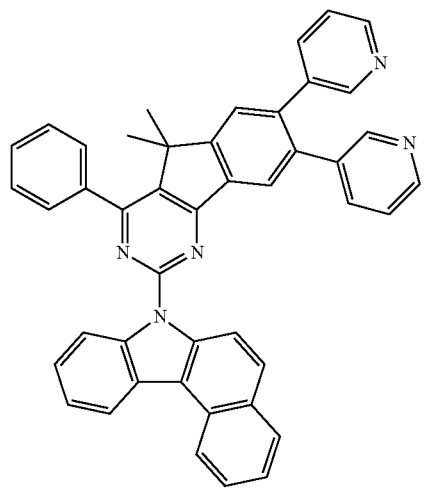
RH-25
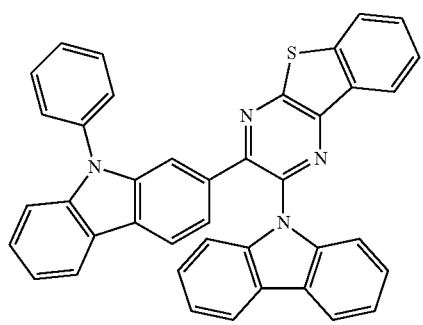
RH-26
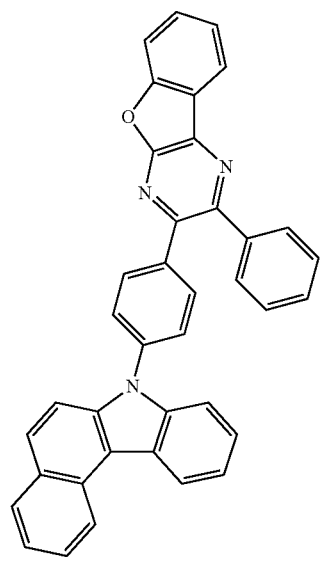
RH-27
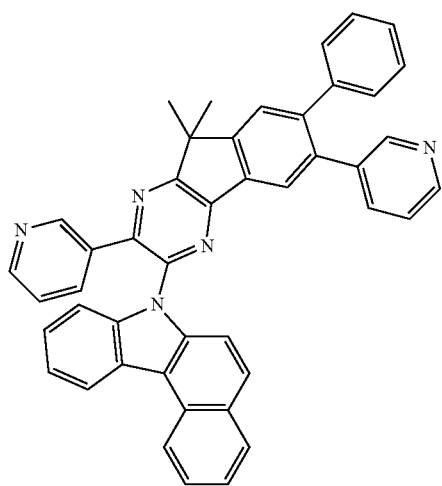
RH-28
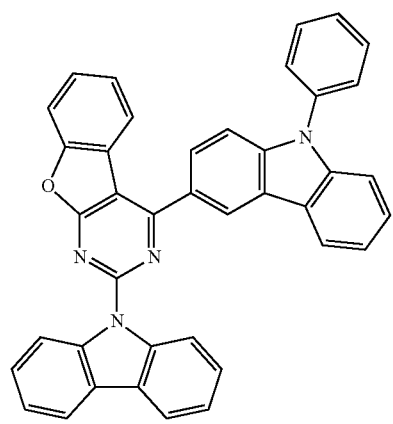

-continued
RH-29
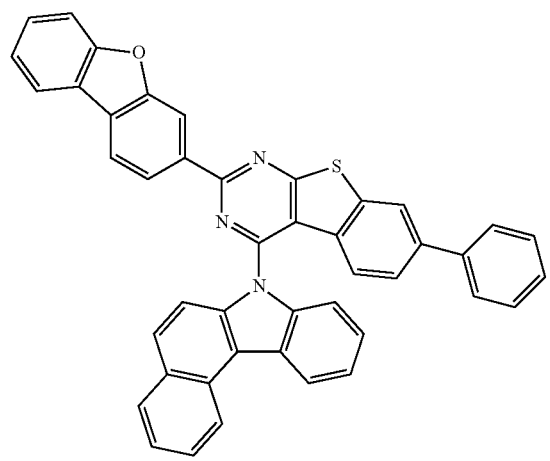
RH-30
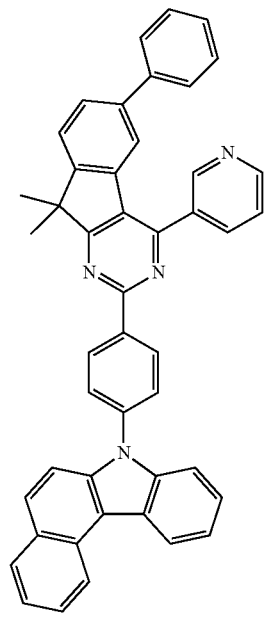
RH-31
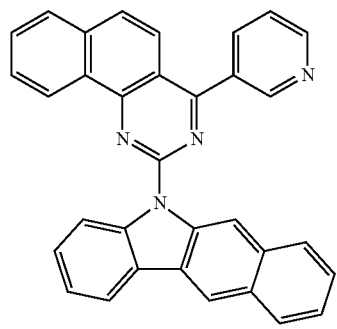
RH-32
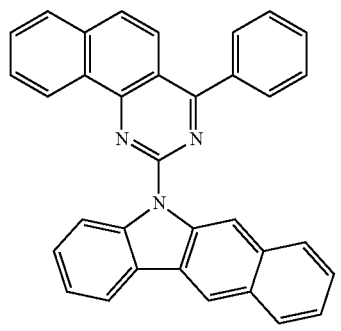
RH-33
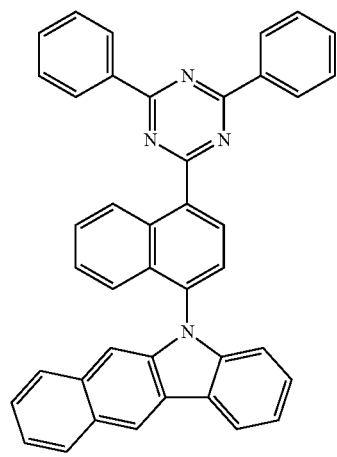
RH-34
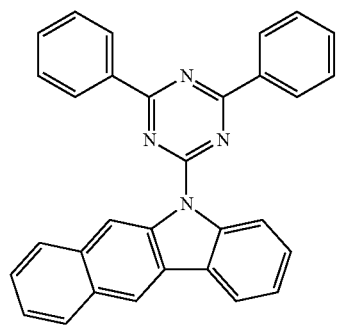

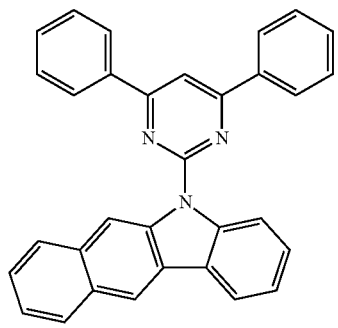

RH-35

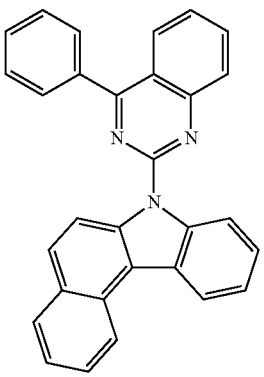

RH-36

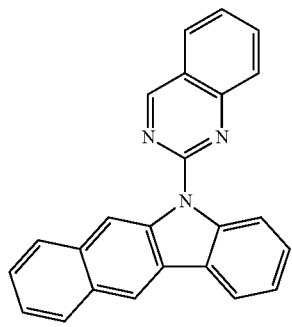

RH-37

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-6}$ torr.

EXAMPLE 1 TO EXAMPLE 124

Organic light emitting devices were manufactured in the same manner as in Comparative Example 1 except that, in organic light emitting device of Comparative Example 1, compounds described in the following Table 1 were each used instead of RH-1.

COMPARATIVE EXAMPLE 2 TO COMPARATIVE EXAMPLE 37

Organic light emitting devices were manufactured in the same manner as in Comparative Example 1 except that, in organic light emitting device of Comparative Example 1, compounds described in the following Table 1 were each used instead of RH-1.

When a current was applied to the organic light emitting devices manufactured in Example 1 to Example 124, and Comparative Example 1 to Comparative Example 37, a voltage, efficiency and a lifetime were measured, and the results are shown in the following Table 1. T95 means time taken for the luminance decreasing to 95% from its initial luminance (5000 nit).

TABLE 1

| Category | Material | Driving Voltage (V) | Efficiency (cd/A) | Lifetime T95 (hr) | Light Emitting Color |
|---|---|---|---|---|---|
| Comparative Example 1 | RH-1 | 4.55 | 33.1 | 191 | Red |
| Example 1 | Compound 5 | 4.22 | 35.5 | 275 | Red |
| Example 2 | Compound 29 | 4.29 | 36.7 | 290 | Red |
| Example 3 | Compound 40 | 3.98 | 39.4 | 305 | Red |
| Example 4 | Compound 42 | 3.89 | 40.5 | 316 | Red |
| Example 5 | Compound 43 | 3.91 | 38.1 | 301 | Red |
| Example 6 | Compound 53 | 3.95 | 39.8 | 305 | Red |
| Example 7 | Compound 56 | 4.07 | 37.6 | 311 | Red |
| Example 8 | Compound 60 | 4.05 | 38.4 | 297 | Red |
| Example 9 | Compound 66 | 4.20 | 39.9 | 285 | Red |
| Example 10 | Compound 68 | 3.94 | 38.1 | 320 | Red |
| Example 11 | Compound 88 | 4.21 | 39.1 | 307 | Red |
| Example 12 | Compound 91 | 4.17 | 39.5 | 295 | Red |
| Example 13 | Compound 93 | 3.80 | 38.7 | 297 | Red |
| Example 14 | Compound 119 | 3.81 | 40.5 | 286 | Red |
| Example 15 | Compound 120 | 4.03 | 40.7 | 335 | Red |
| Example 16 | Compound 123 | 3.91 | 40.5 | 257 | Red |

TABLE 1-continued

| Category | Material | Driving Voltage (V) | Efficiency (cd/A) | Lifetime T95 (hr) | Light Emitting Color |
|---|---|---|---|---|---|
| Example 17 | Compound 130 | 3.95 | 39.1 | 293 | Red |
| Example 18 | Compound 133 | 3.97 | 39.7 | 273 | Red |
| Example 19 | Compound 144 | 3.98 | 41.3 | 289 | Red |
| Example 20 | Compound 149 | 4.11 | 39.3 | 301 | Red |
| Example 21 | Compound 167 | 3.90 | 39.1 | 274 | Red |
| Example 22 | Compound 175 | 3.95 | 39.7 | 275 | Red |
| Example 23 | Compound 182 | 4.06 | 37.3 | 280 | Red |
| Example 24 | Compound 194 | 4.01 | 38.8 | 267 | Red |
| Example 25 | Compound 201 | 4.13 | 37.3 | 313 | Red |
| Example 26 | Compound 214 | 3.75 | 40.3 | 341 | Red |
| Example 27 | Compound 217 | 4.25 | 38.3 | 326 | Red |
| Example 28 | Compound 218 | 3.87 | 42.7 | 310 | Red |
| Example 29 | Compound 221 | 3.79 | 40.3 | 332 | Red |
| Example 30 | Compound 233 | 3.82 | 42.3 | 357 | Red |
| Example 31 | Compound 237 | 3.89 | 40.8 | 290 | Red |
| Example 32 | Compound 244 | 3.80 | 41.1 | 341 | Red |
| Example 33 | Compound 254 | 3.99 | 36.9 | 290 | Red |
| Example 34 | Compound 267 | 4.05 | 37.7 | 314 | Red |
| Example 35 | Compound 278 | 4.09 | 38.1 | 262 | Red |
| Example 36 | Compound 284 | 3.82 | 40.1 | 324 | Red |
| Example 37 | Compound 292 | 3.97 | 41.5 | 319 | Red |
| Example 38 | Compound 296 | 3.90 | 40.0 | 330 | Red |
| Example 39 | Compound 329 | 3.85 | 41.4 | 353 | Red |
| Example 40 | Compound 334 | 3.91 | 40.6 | 371 | Red |
| Example 41 | Compound 341 | 3.99 | 39.1 | 349 | Red |
| Example 42 | Compound 375 | 3.96 | 40.5 | 340 | Red |
| Example 43 | Compound 383 | 3.81 | 42.1 | 329 | Red |
| Example 44 | Compound 412 | 3.75 | 43.4 | 357 | Red |
| Example 45 | Compound 422 | 3.70 | 41.0 | 372 | Red |
| Example 46 | Compound 423 | 3.73 | 40.3 | 334 | Red |
| Example 47 | Compound 450 | 3.86 | 42.8 | 339 | Red |
| Example 48 | Compound 451 | 3.85 | 39.8 | 350 | Red |
| Example 49 | Compound 463 | 3.81 | 37.9 | 324 | Red |
| Example 50 | Compound 464 | 3.92 | 35.5 | 319 | Red |
| Example 51 | Compound 472 | 3.97 | 35.0 | 328 | Red |
| Example 52 | Compound 480 | 3.90 | 41.3 | 342 | Red |
| Example 53 | Compound 495 | 3.84 | 39.3 | 310 | Red |
| Example 54 | Compound 496 | 3.87 | 42.3 | 337 | Red |
| Example 55 | Compound 501 | 3.90 | 40.8 | 321 | Red |
| Example 56 | Compound 503 | 3.71 | 42.7 | 325 | Red |
| Example 57 | Compound 509 | 3.74 | 40.5 | 329 | Red |
| Example 58 | Compound 589 | 3.77 | 38.1 | 342 | Red |
| Example 59 | Compound 590 | 3.75 | 42.7 | 365 | Red |
| Example 60 | Compound 591 | 3.89 | 41.1 | 347 | Red |
| Example 61 | Compound 592 | 3.80 | 39.5 | 323 | Red |
| Example 62 | Compound 599 | 3.99 | 39.5 | 360 | Red |
| Example 63 | Compound 602 | 4.02 | 38.7 | 357 | Red |
| Example 64 | Compound 606 | 3.91 | 37.5 | 341 | Red |
| Example 65 | Compound 608 | 3.95 | 38.1 | 332 | Red |
| Example 66 | Compound 613 | 3.90 | 38.7 | 348 | Red |
| Example 67 | Compound 619 | 3.93 | 40.3 | 337 | Red |
| Example 68 | Compound 636 | 3.84 | 38.3 | 341 | Red |
| Example 69 | Compound 697 | 4.23 | 35.1 | 273 | Red |
| Example 70 | Compound 701 | 3.68 | 38.7 | 295 | Red |
| Example 71 | Compound 707 | 3.65 | 39.3 | 285 | Red |
| Example 72 | Compound 713 | 4.20 | 37.8 | 267 | Red |
| Example 73 | Compound 717 | 4.15 | 38.3 | 234 | Red |
| Example 74 | Compound 724 | 3.99 | 37.3 | 241 | Red |
| Example 75 | Compound 726 | 4.13 | 39.3 | 307 | Red |
| Example 76 | Compound 739 | 4.07 | 38.7 | 273 | Red |
| Example 77 | Compound 740 | 4.01 | 39.3 | 232 | Red |
| Example 78 | Compound 743 | 4.11 | 40.3 | 226 | Red |
| Example 79 | Compound 744 | 4.04 | 39.8 | 243 | Red |
| Example 80 | Compound 745 | 4.10 | 40.1 | 238 | Red |
| Example 81 | Compound 764 | 3.74 | 40.9 | 291 | Red |
| Example 82 | Compound 778 | 4.00 | 39.7 | 265 | Red |
| Example 83 | Compound 781 | 3.91 | 38.1 | 260 | Red |
| Example 84 | Compound 790 | 3.99 | 37.5 | 257 | Red |
| Example 85 | Compound 794 | 4.17 | 40.0 | 288 | Red |
| Example 86 | Compound 795 | 4.11 | 40.5 | 293 | Red |
| Example 87 | Compound 798 | 4.07 | 41.2 | 269 | Red |
| Example 88 | Compound 809 | 3.82 | 40.4 | 339 | Red |
| Example 89 | Compound 811 | 3.94 | 37.1 | 249 | Red |
| Example 90 | Compound 818 | 3.95 | 40.1 | 311 | Red |
| Example 91 | Compound 822 | 3.99 | 42.2 | 293 | Red |
| Example 92 | Compound 831 | 3.87 | 43.1 | 280 | Red |

TABLE 1-continued

| Category | Material | Driving Voltage (V) | Efficiency (cd/A) | Lifetime T95 (hr) | Light Emitting Color |
|---|---|---|---|---|---|
| Example 93 | Compound 838 | 3.73 | 42.0 | 297 | Red |
| Example 94 | Compound 844 | 3.84 | 40.4 | 281 | Red |
| Example 95 | Compound 848 | 3.80 | 43.7 | 282 | Red |
| Example 96 | Compound 861 | 4.01 | 38.6 | 272 | Red |
| Example 97 | Compound 863 | 3.88 | 39.3 | 352 | Red |
| Example 98 | Compound 866 | 3.96 | 36.3 | 291 | Red |
| Example 99 | Compound 867 | 3.81 | 37.8 | 284 | Red |
| Example 100 | Compound 869 | 3.99 | 41.3 | 313 | Red |
| Example 101 | Compound 870 | 3.80 | 42.3 | 330 | Red |
| Example 102 | Compound 871 | 4.05 | 40.3 | 360 | Red |
| Example 103 | Compound 874 | 3.90 | 40.5 | 371 | Red |
| Example 104 | Compound 876 | 4.01 | 41.7 | 350 | Red |
| Example 105 | Compound 878 | 4.06 | 42.5 | 271 | Red |
| Example 106 | Compound 890 | 3.87 | 41.4 | 357 | Red |
| Example 107 | Compound 898 | 3.89 | 39.7 | 351 | Red |
| Example 108 | Compound 912 | 3.90 | 40.1 | 321 | Red |
| Example 109 | Compound 913 | 3.97 | 40.0 | 357 | Red |
| Example 110 | Compound 919 | 3.92 | 42.7 | 315 | Red |
| Example 111 | Compound 933 | 3.95 | 39.5 | 327 | Red |
| Example 112 | Compound 937 | 3.90 | 39.9 | 323 | Red |
| Example 113 | Compound 941 | 3.94 | 38.7 | 336 | Red |
| Example 114 | Compound 1005 | 3.94 | 41.3 | 328 | Red |
| Example 115 | Compound 1010 | 4.00 | 39.3 | 354 | Red |
| Example 116 | Compound 1016 | 4.05 | 37.1 | 292 | Red |
| Example 117 | Compound 1030 | 4.19 | 39.7 | 251 | Red |
| Example 118 | Compound 1033 | 4.24 | 39.3 | 245 | Red |
| Example 119 | Compound 1041 | 4.21 | 38.8 | 267 | Red |
| Example 120 | Compound 1043 | 3.93 | 39.5 | 304 | Red |
| Example 121 | Compound 1047 | 4.16 | 37.4 | 261 | Red |
| Example 122 | Compound 1053 | 4.11 | 39.0 | 277 | Red |
| Example 123 | Compound 1055 | 4.20 | 41.7 | 250 | Red |
| Example 124 | Compound 1060 | 4.25 | 40.1 | 243 | Red |
| Comparative Example 2 | RH-2 | 4.43 | 35.2 | 182 | Red |
| Comparative Example 3 | RH-3 | 4.50 | 34.1 | 205 | Red |
| Comparative Example 4 | RH-4 | 4.40 | 34.1 | 206 | Red |
| Comparative Example 5 | RH-5 | 4.58 | 35.0 | 217 | Red |
| Comparative Example 6 | RH-6 | 4.41 | 33.4 | 179 | Red |
| Comparative Example 7 | RH-7 | 4.67 | 29.7 | 161 | Red |
| Comparative Example 8 | RH-8 | 4.41 | 34.0 | 163 | Red |
| Comparative Example 9 | RH-9 | 4.39 | 35.7 | 184 | Red |
| Comparative Example 10 | RH-10 | 4.51 | 33.3 | 204 | Red |
| Comparative Example 11 | RH-11 | 4.43 | 35.2 | 208 | Red |
| Comparative Example 12 | RH-12 | 4.33 | 34.2 | 171 | Red |
| Comparative Example 13 | RH-13 | 4.51 | 35.1 | 180 | Red |
| Comparative Example 14 | RH-14 | 4.40 | 34.1 | 161 | Red |
| Comparative Example 15 | RH-15 | 4.58 | 31.0 | 177 | Red |
| Comparative Example 16 | RH-16 | 4.31 | 30.4 | 201 | Red |
| Comparative Example 17 | RH-17 | 4.47 | 29.7 | 140 | Red |
| Comparative Example 18 | RH-18 | 4.21 | 32.0 | 169 | Red |
| Comparative Example 19 | RH-19 | 4.29 | 35.7 | 184 | Red |
| Comparative Example 20 | RH-20 | 4.31 | 31.3 | 103 | Red |
| Comparative Example 21 | RH-21 | 4.23 | 35.2 | 97 | Red |
| Comparative Example 22 | RH-22 | 4.33 | 36.2 | 207 | Red |
| Comparative Example 23 | RH-23 | 4.51 | 34.1 | 176 | Red |
| Comparative Example 24 | RH-24 | 4.30 | 37.1 | 167 | Red |
| Comparative Example 25 | RH-25 | 4.47 | 34.0 | 179 | Red |
| Comparative Example 26 | RH-26 | 4.45 | 32.4 | 190 | Red |
| Comparative Example 27 | RH-27 | 4.37 | 29.7 | 131 | Red |
| Comparative Example 28 | RH-28 | 4.41 | 32.0 | 197 | Red |
| Comparative Example 29 | RH-29 | 4.39 | 33.7 | 137 | Red |
| Comparative Example 30 | RH-30 | 4.61 | 31.0 | 169 | Red |
| Comparative Example 31 | RH-31 | 4.13 | 37.7 | 196 | Red |
| Comparative Example 32 | RH-32 | 4.10 | 35.6 | 162 | Red |
| Comparative Example 33 | RH-33 | 4.15 | 35.1 | 161 | Red |
| Comparative Example 34 | RH-34 | 4.19 | 34.7 | 144 | Red |
| Comparative Example 35 | RH-35 | 4.11 | 35.0 | 133 | Red |
| Comparative Example 36 | RH-36 | 4.71 | 32.1 | 126 | Red |
| Comparative Example 37 | RH-37 | 4.41 | 28.4 | 97 | Red |

When applying a current to the organic light emitting devices manufactured in Examples 1 to 124 and Comparative Examples 1 to 37, results of Table 1 were obtained. The red organic light emitting device of Comparative Example 1 used materials that have been widely used in the art, and had a structure using Compound [EB-1] as an electron blocking layer and using RH-1/Dp-7 as a red light emitting layer. Comparative Examples 2 to 37 manufactured organic light emitting devices using RH-2 to RH-37 instead of RH-1. When examining the results of Table 1, it was seen that, when using the compound of the present disclosure as a host of a red light emitting layer, energy transfer from a host to a red dopant was well achieved from the fact that a driving voltage decreased closer to as much as 30% and efficiency increased by 30% or greater compared to the materials in the comparative examples. In addition, it was seen that lifetime properties were greatly improved by a factor of two or more while maintaining high efficiency. This may ultimately be due to the fact that the compounds of the present disclosure have higher stability for electrons and holes compared to the compounds of the comparative examples. As a result, it can be identified that, when using the compound of the present disclosure as a host of a red light emitting layer, a driving voltage, light emission efficiency and lifetime properties of an organic light emitting device are improved.

The invention claimed is:

1. A compound represented by the following Chemical Formula 1:

[Chemical Formula 1]

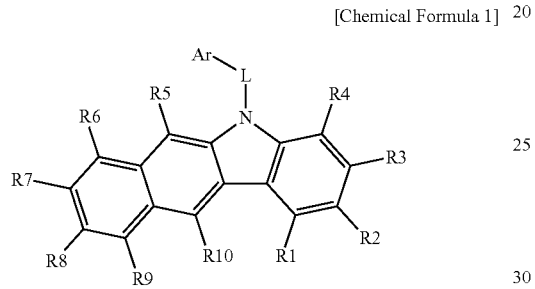

wherein in Chemical Formula 1,

R1 to R4 are hydrogen; deuterium; or bonded to adjacent group among R1 to R4 to form an aryl group having 6 to 60 carbon atoms, R5 to R10 are each independently hydrogen or deuterium, L is a direct bond; a substituted or unsubstituted arylene group; or a substituted or unsubstituted heterocyclic group, and Ar is represented by the following Chemical Formula 2,

[Chemical Formula 2]

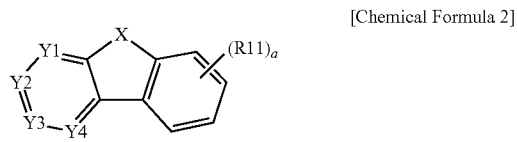

in Chemical Formula 2, two of Y1 to Y4 are N, and the remaining two are C which is a bonding site to L and CR, X is O or S, R and R11 are each independently hydrogen; deuterium; a halogen group; a nitrile group; a nitro group; a hydroxyl group; an aryloxy group; an alkylthioxy group; an arylthioxy group; an alkylsulfoxy group; an arylsulfoxy group; a silyl group; a boron group; a substituted or unsubstituted alkyl group; a substituted or unsubstituted cycloalkyl group; a substituted or unsubstituted alkenyl group; a substituted or unsubstituted aryl group; a substituted or unsubstituted aralkyl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted heterocyclic group, a is an integer of 1 to 4, and when a is 2 or greater, two or more R11s are the same as or different from each other.

2. The compound of claim 1, wherein Chemical Formula 1 is represented by any one selected from among the following Chemical Formulae 1-1 to 1-3:

[Chemical Formula 1-1]

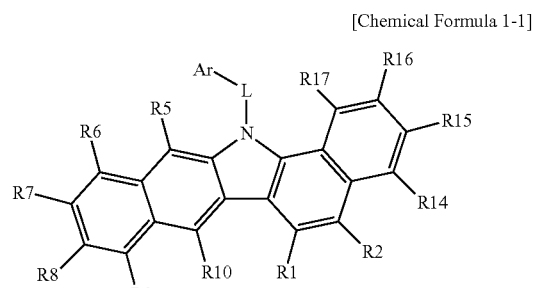

[Chemical Formula 1-2]

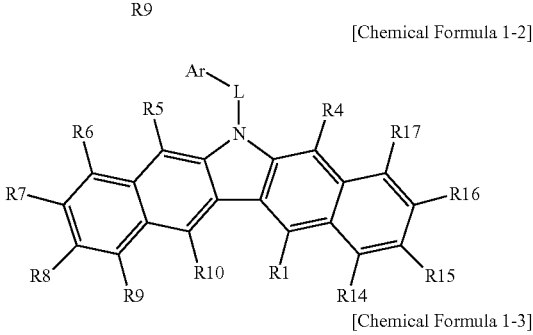

[Chemical Formula 1-3]

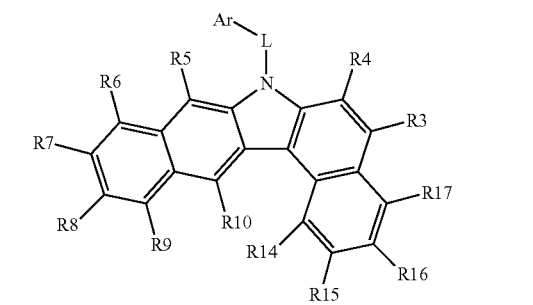

wherein in Chemical Formulae 1-1 to 1-3,

R1 to R10, Ar and L have the same definitions as in claim 1, and

R14 to R17 are each independently hydrogen or deuterium.

3. The compound of claim 1, wherein R is a substituted or unsubstituted aryl group; or a substituted or unsubstituted heterocyclic group.

4. The compound of claim 1, wherein Chemical Formula 2 is represented by any one selected from among the following Chemical Formulae 2-1 and 2-2:

[Chemical Formula 2-1]

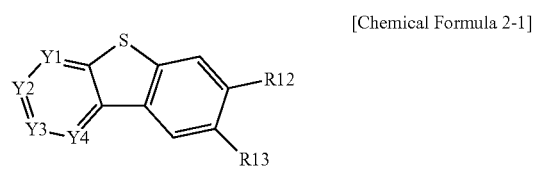

[Chemical Formula 2-2]
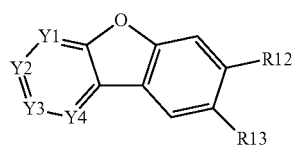
wherein in Chemical Formulae 2-1 and 2-2,
Y1 to Y4 are the same as in claim 1, and R12 and R13 each independently have the same definition as R11 of claim 1.
5. The compound of claim 1, wherein the compound represented by Chemical Formula 1 is selected from among the following compounds:
1
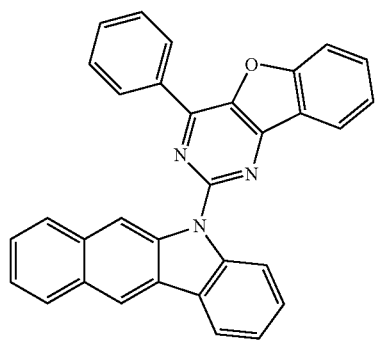
2
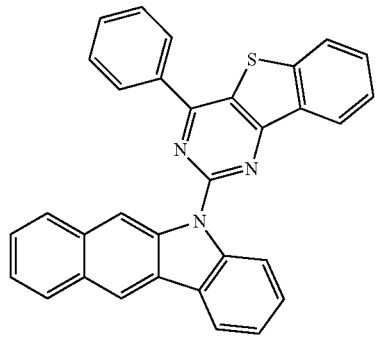
4
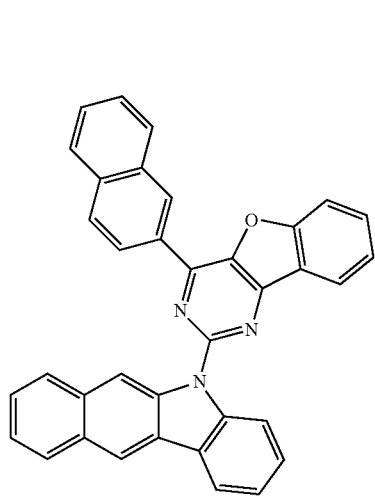
5
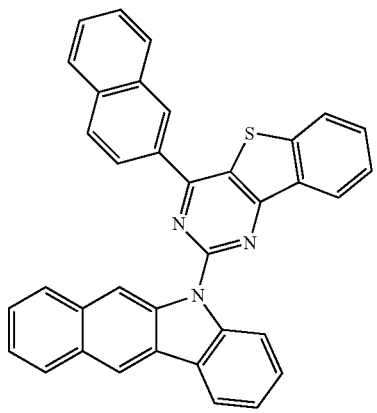
7
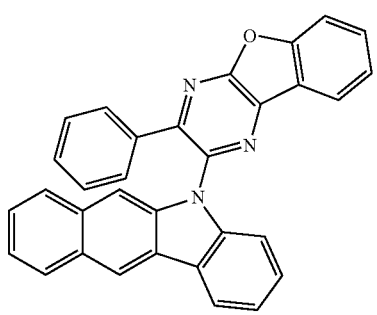
8
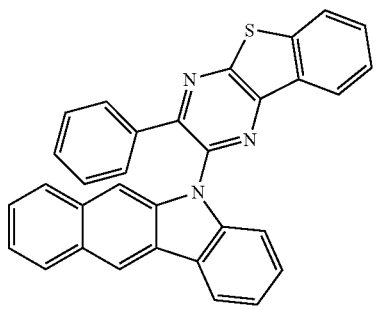
10
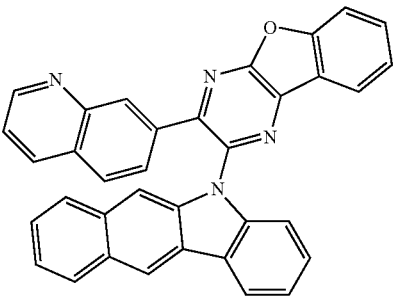
11
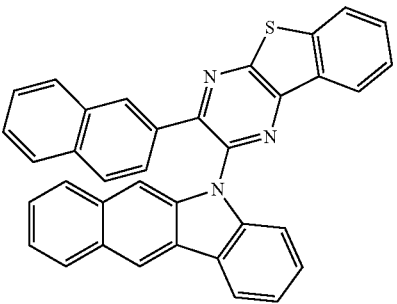

13
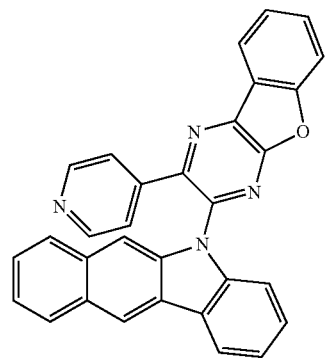
14
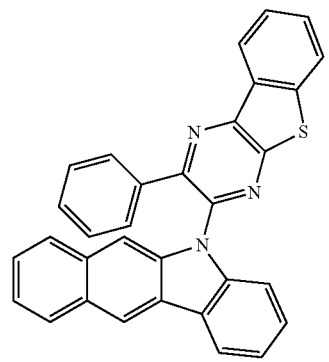
16
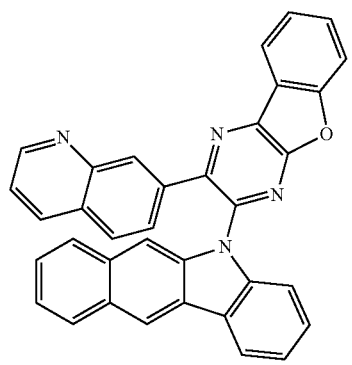
17
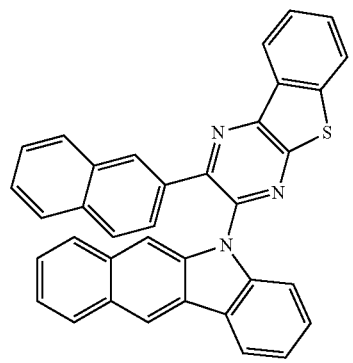
19
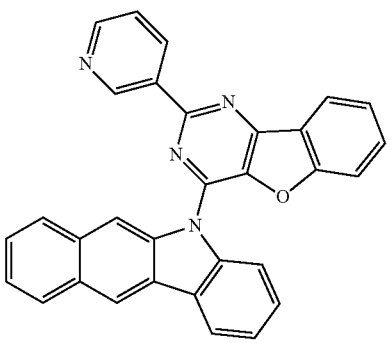
20
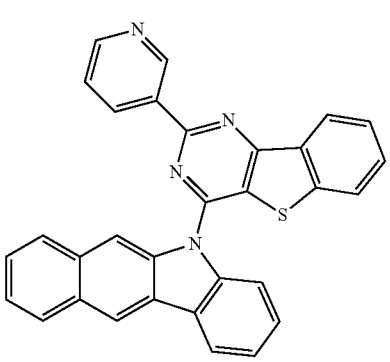
22
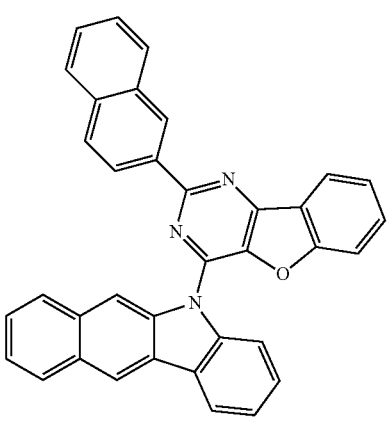
23
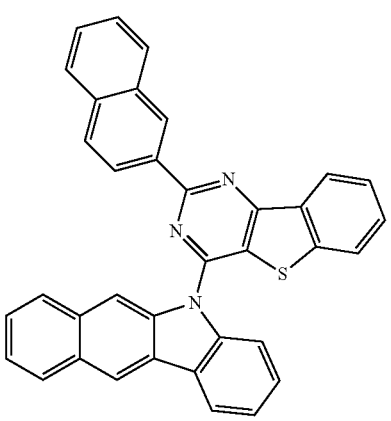

503
-continued
25
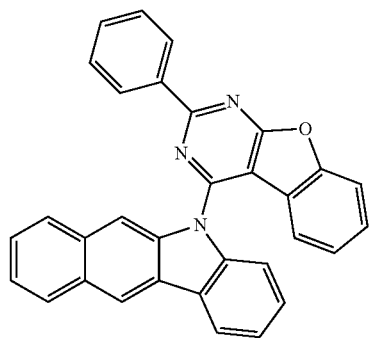
26
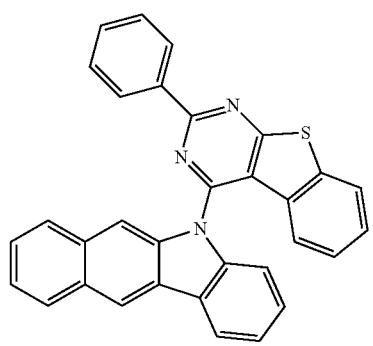
28
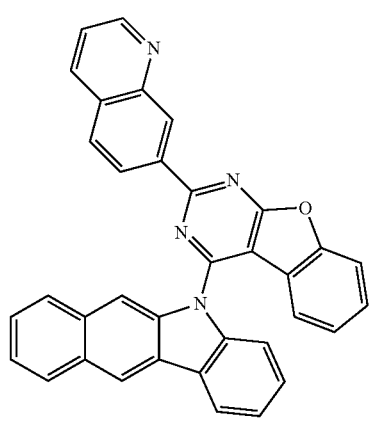
29
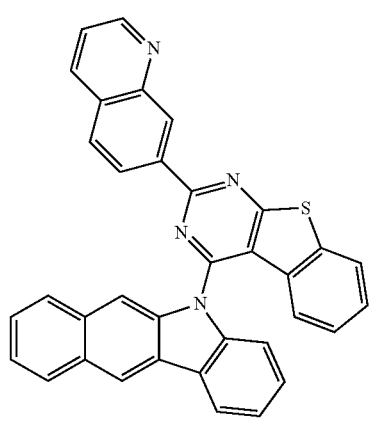
504
-continued
31
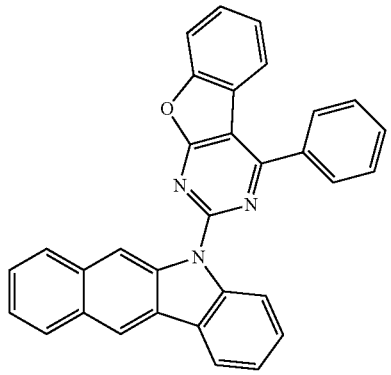
32
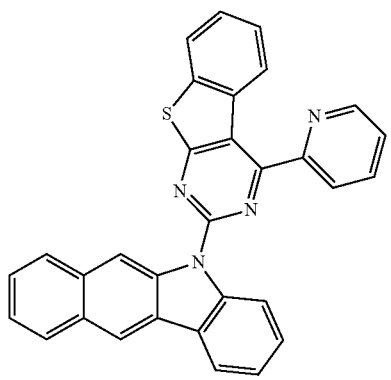
34
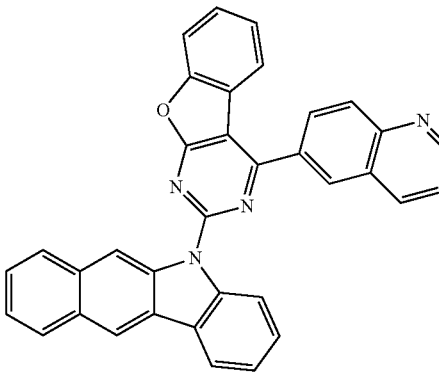
35
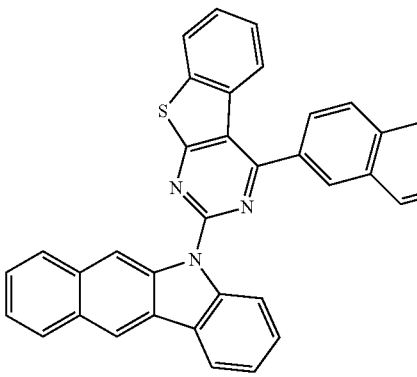

37
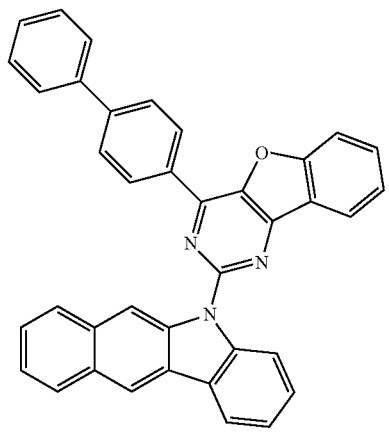
38
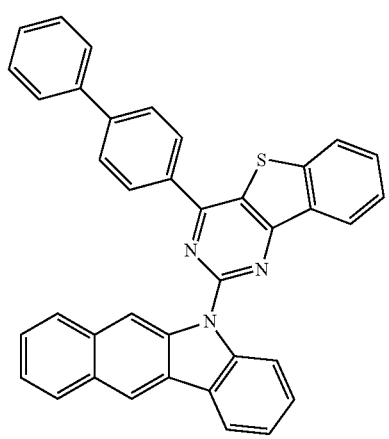
40
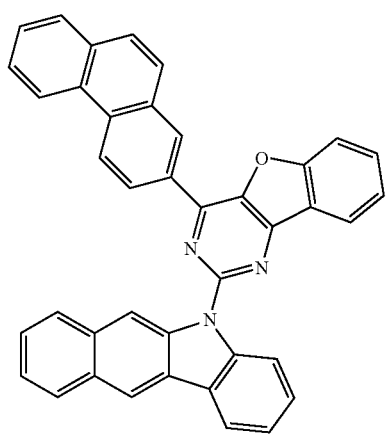
41
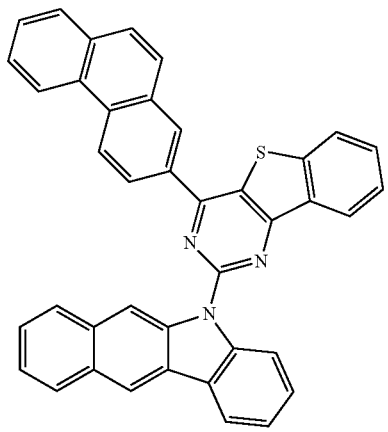
43
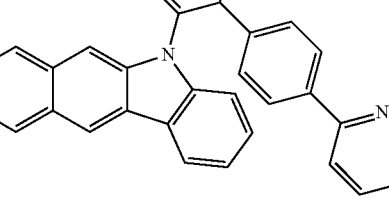
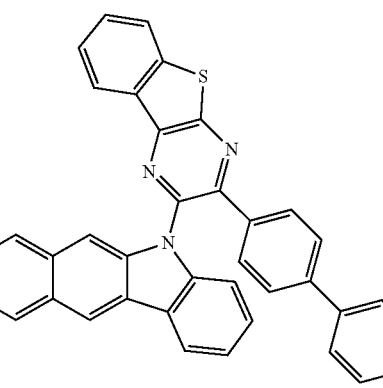
44
46
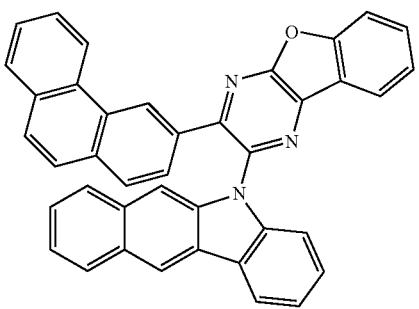

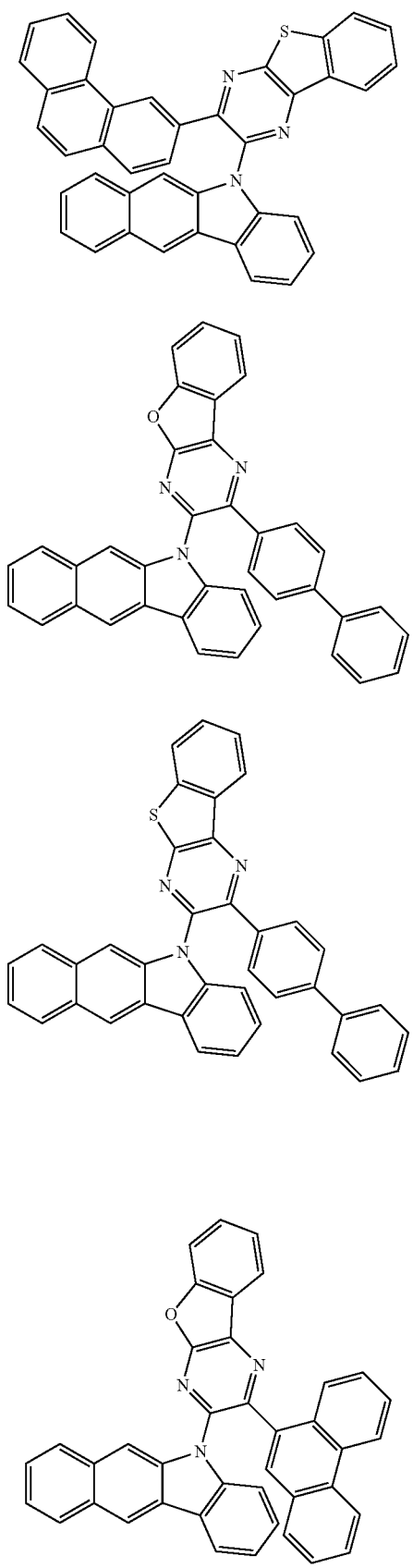

-continued
59
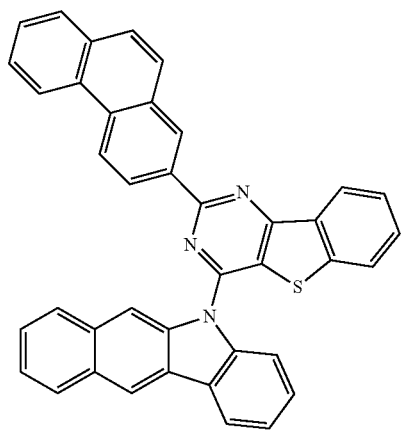
61
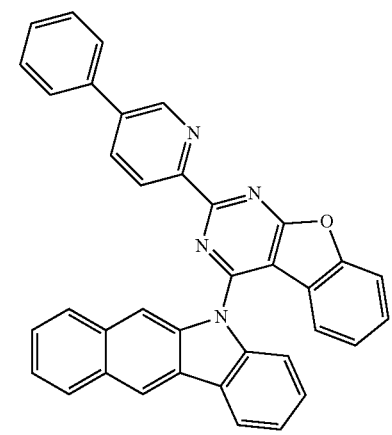
62
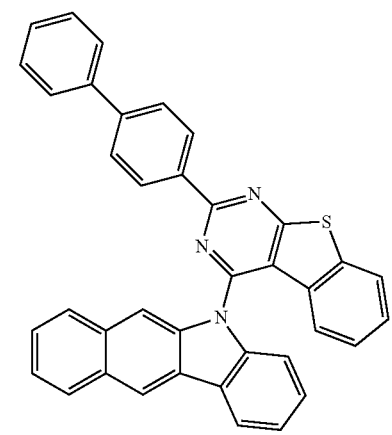
-continued
64
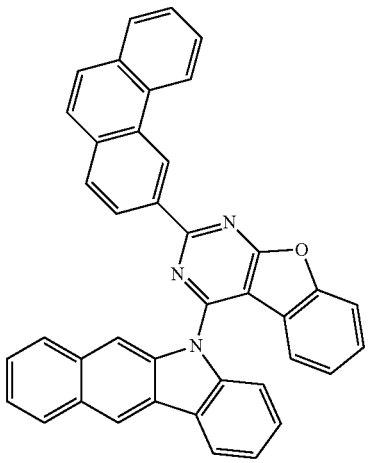
65
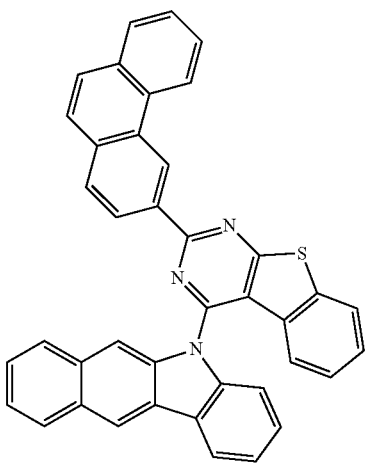
67
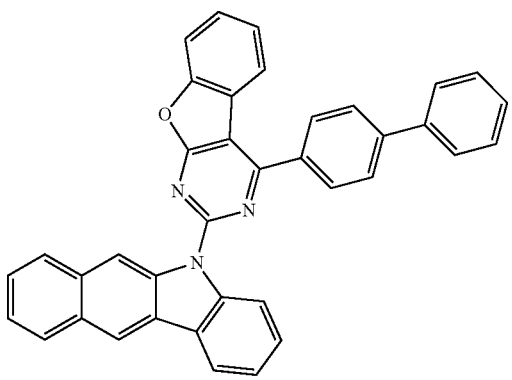

511
-continued
68
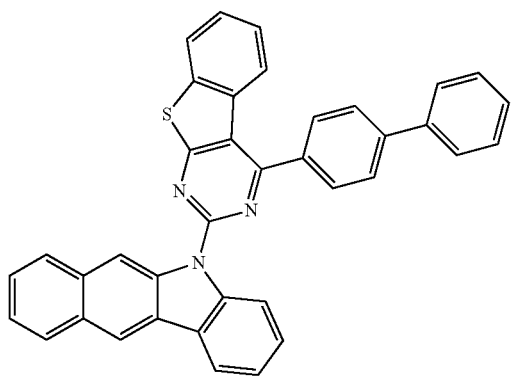
70
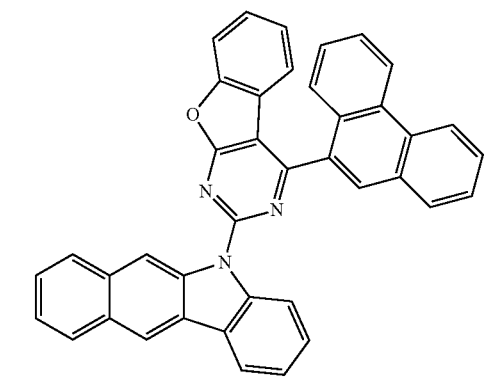
71
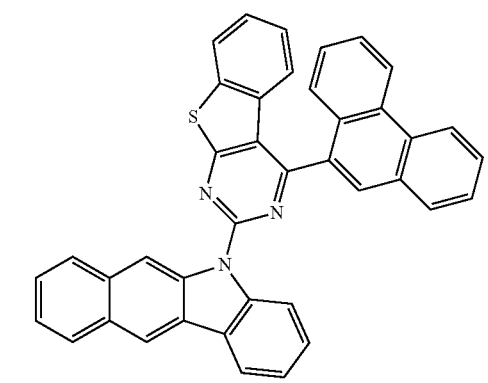
73
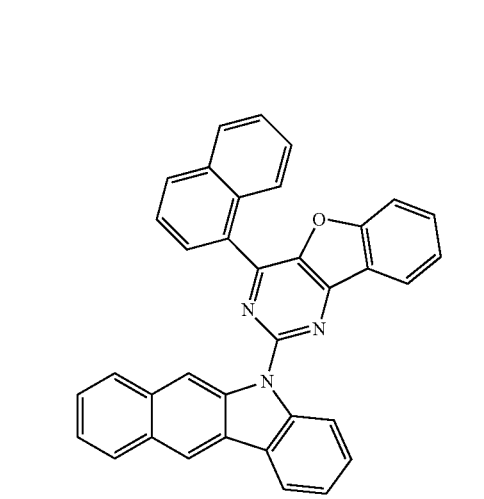
512
-continued
74
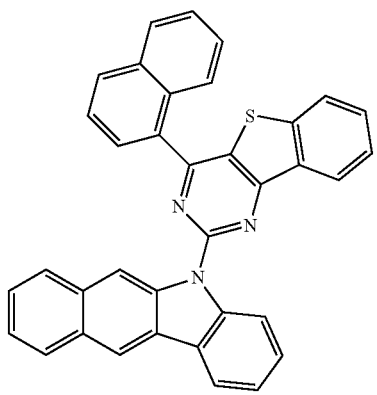
76
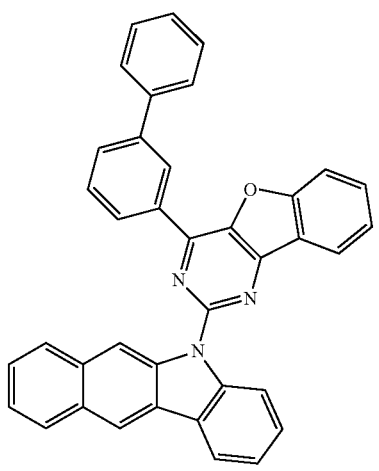
77
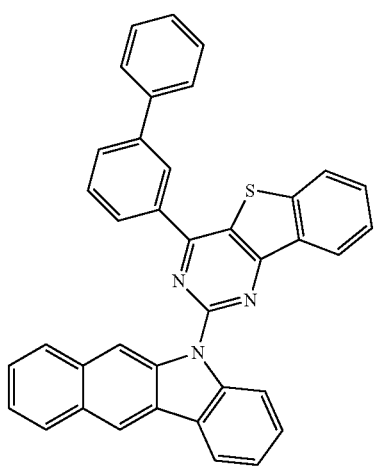
79
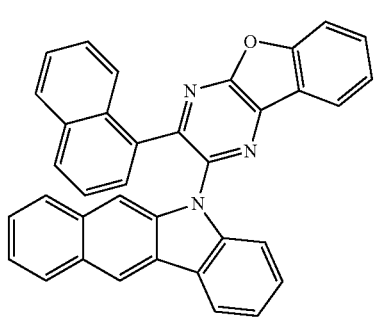

513
-continued
80
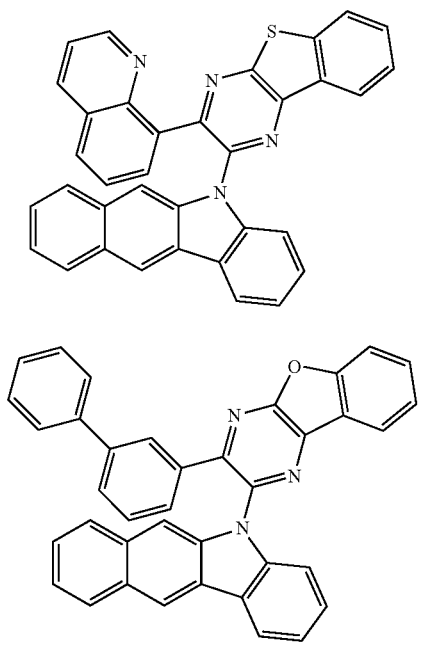
82
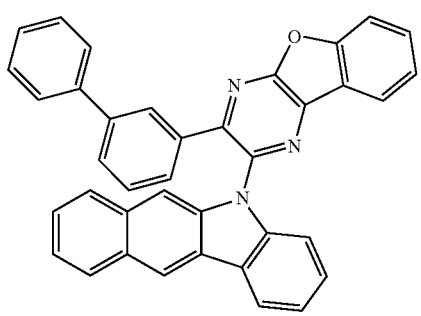
83
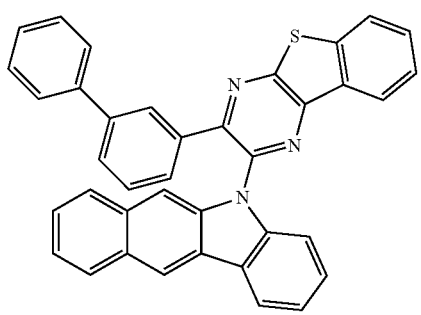
85
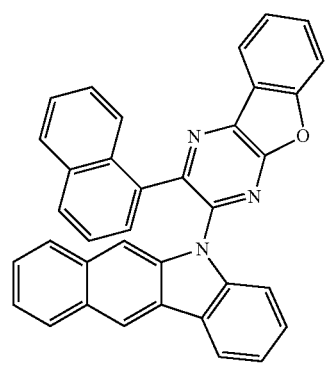
514
-continued
86
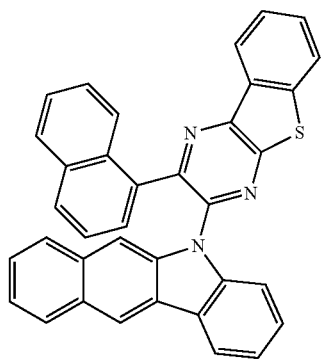
88
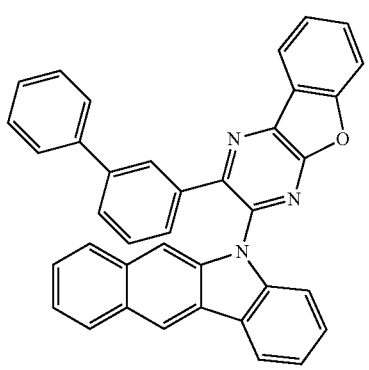
89
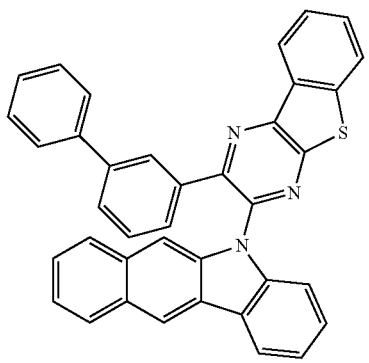
91
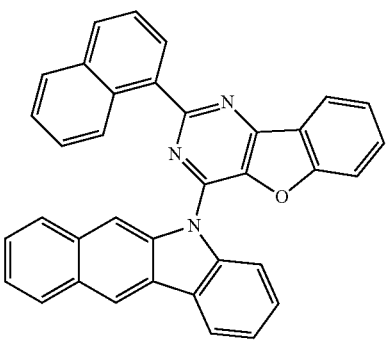

515
-continued
92
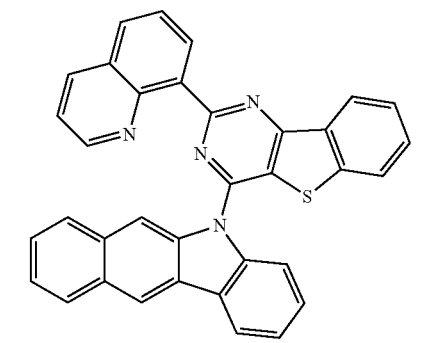
94
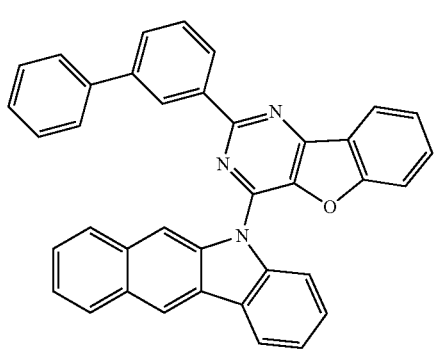
95
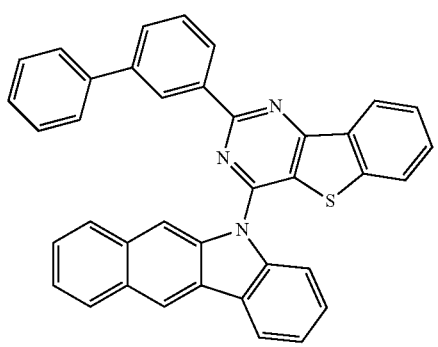
97
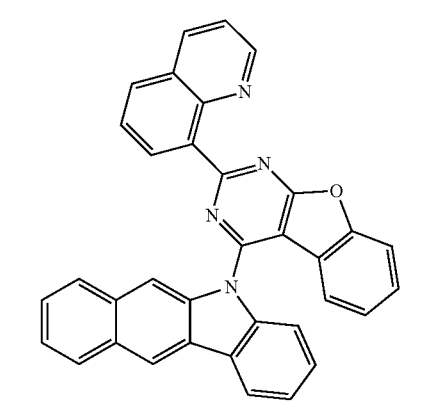
516
-continued
98
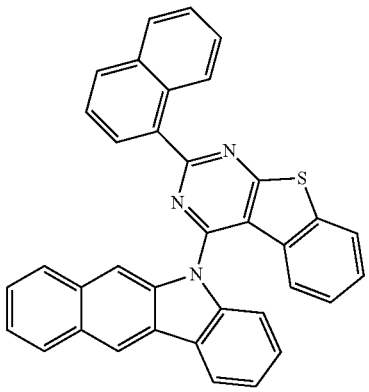
100
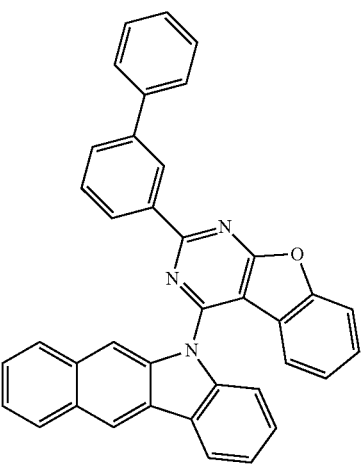
101
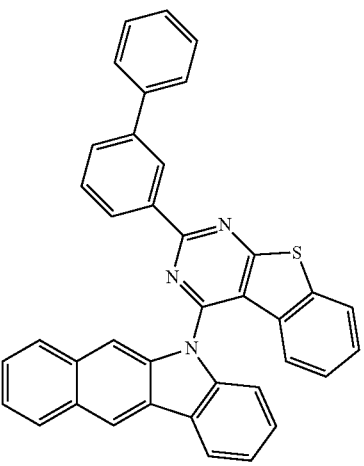

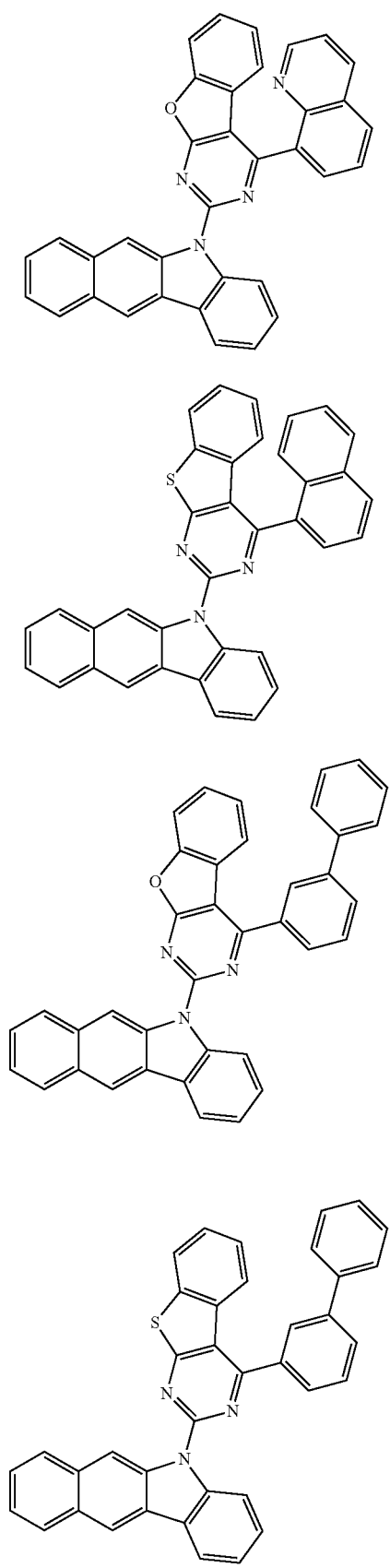
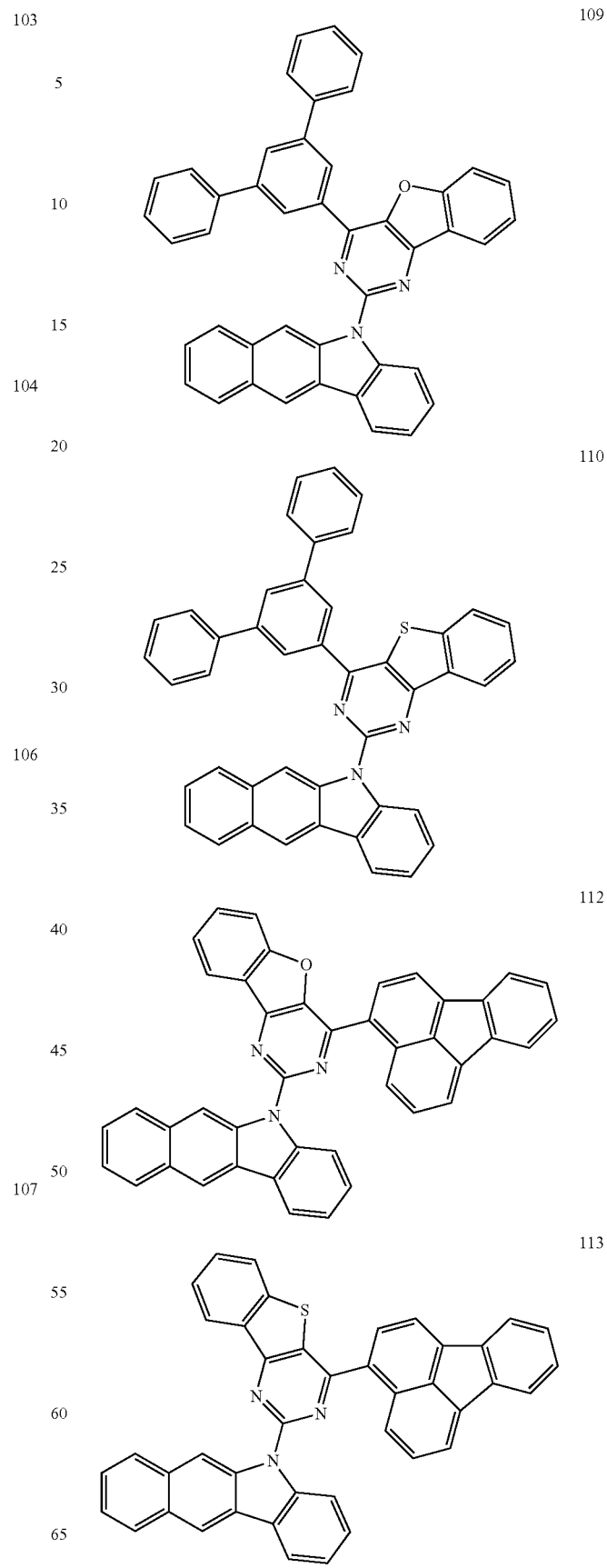

-continued
115
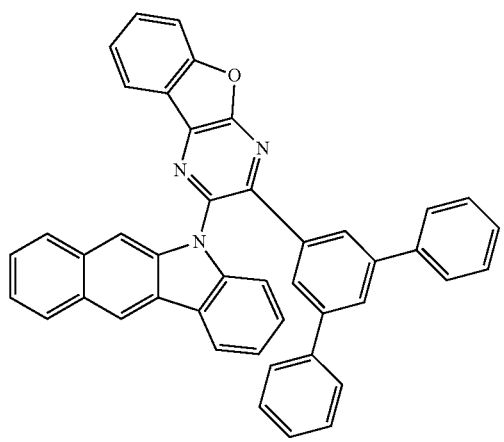
116
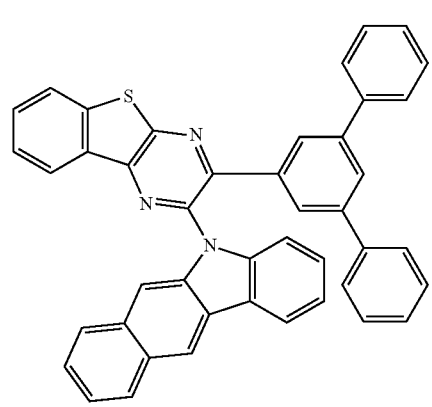
118
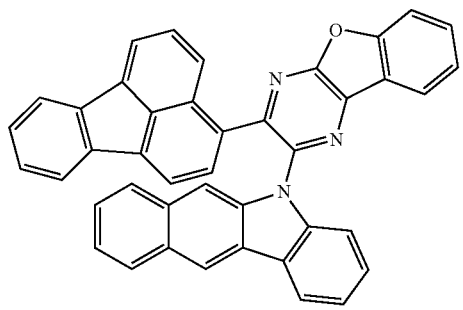
119
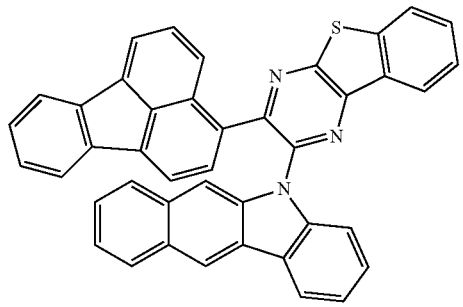
-continued
121
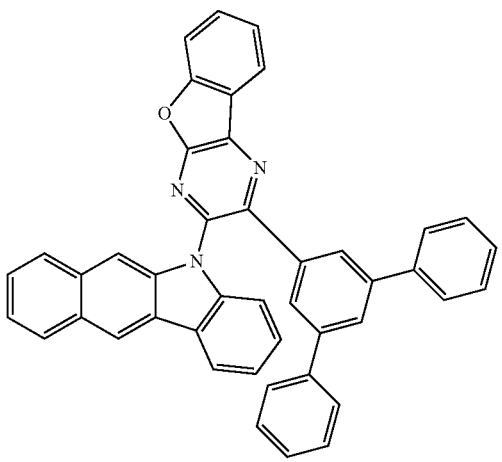
122
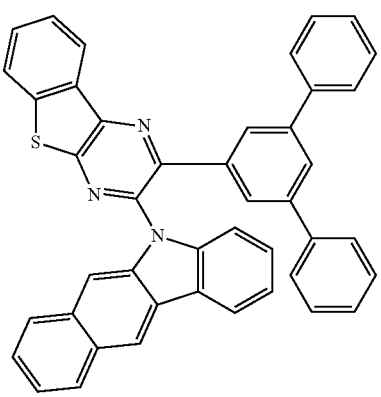
124
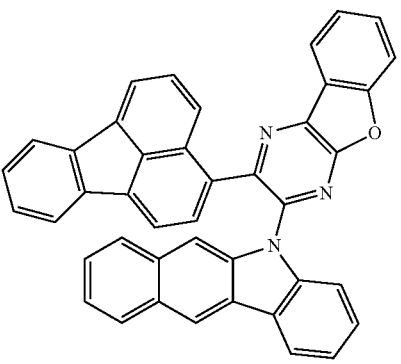
125
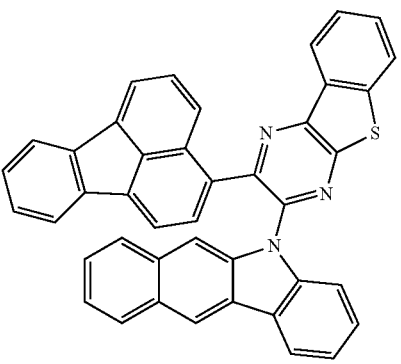

127
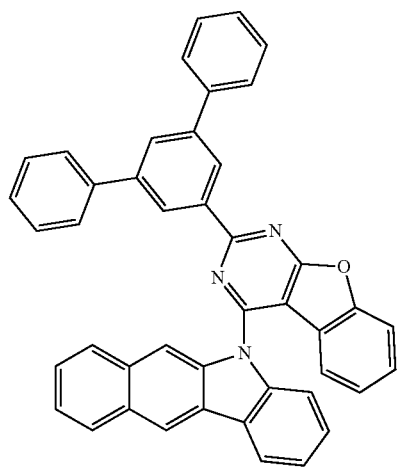
128
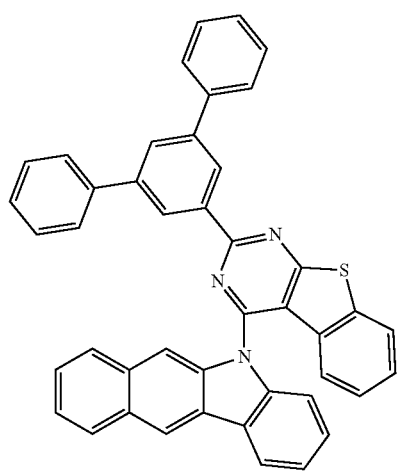
130
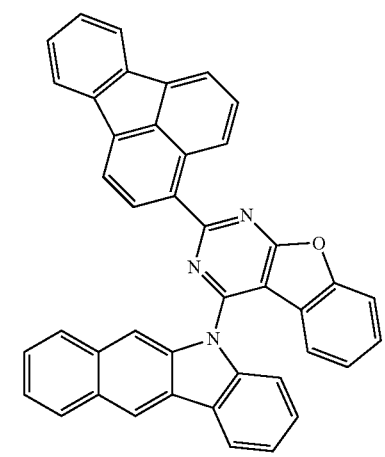
131
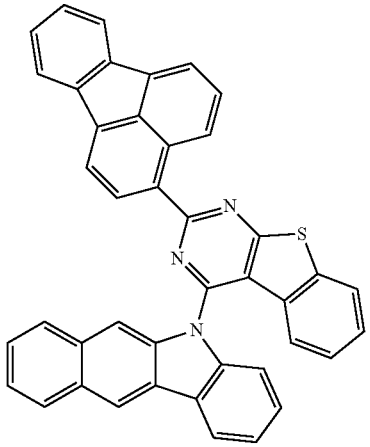
133
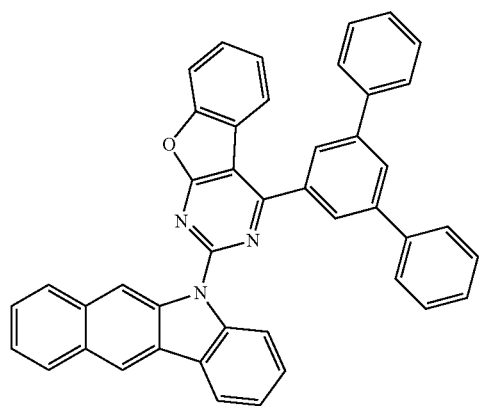
134
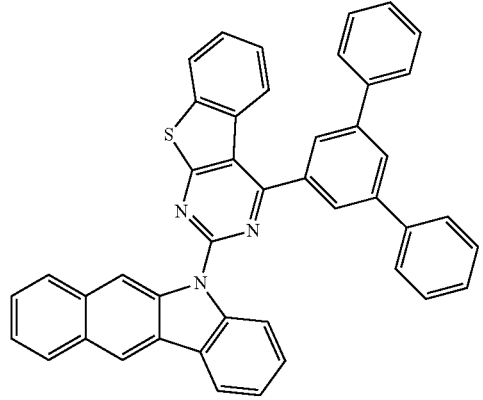
136
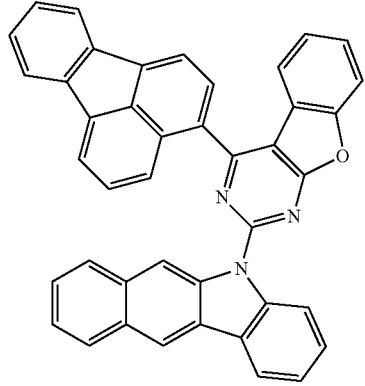

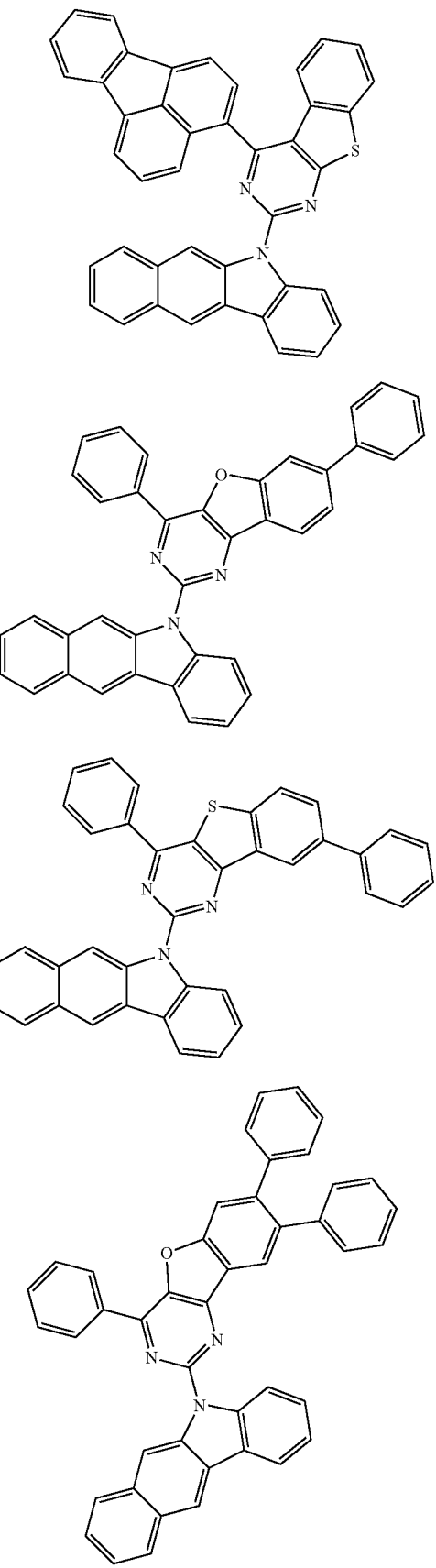
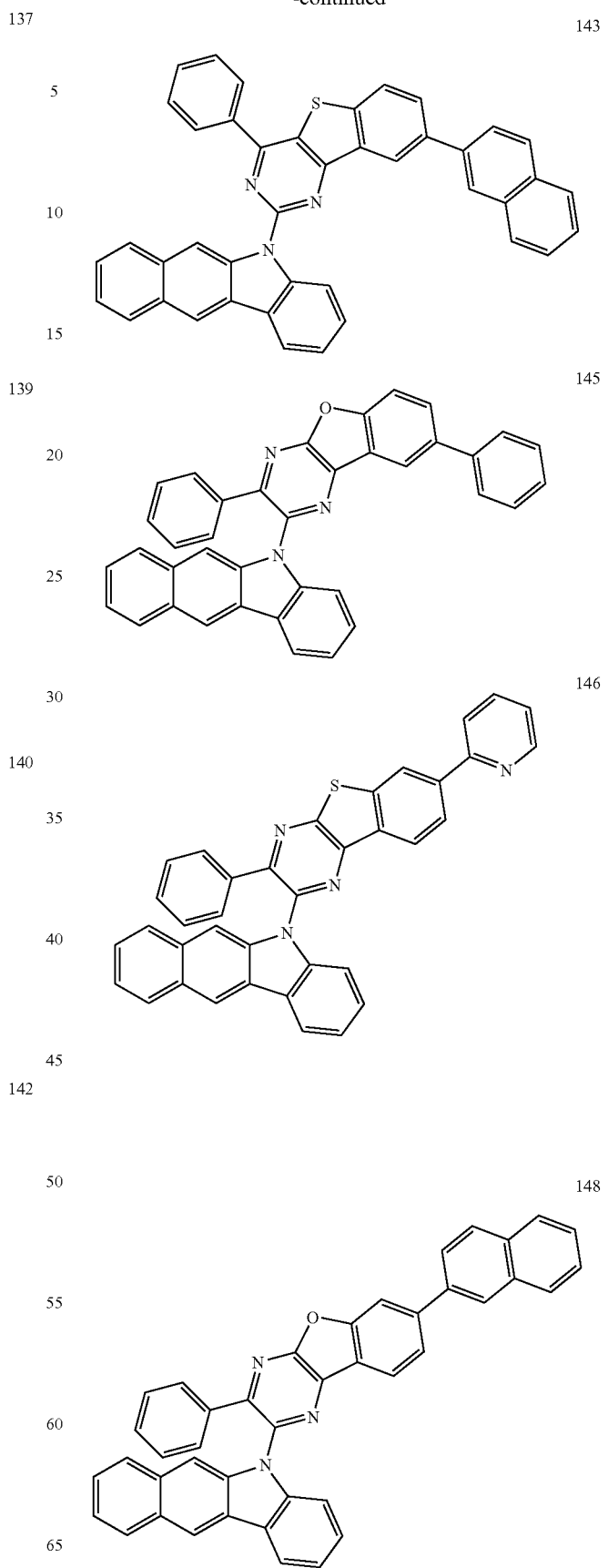

-continued
149
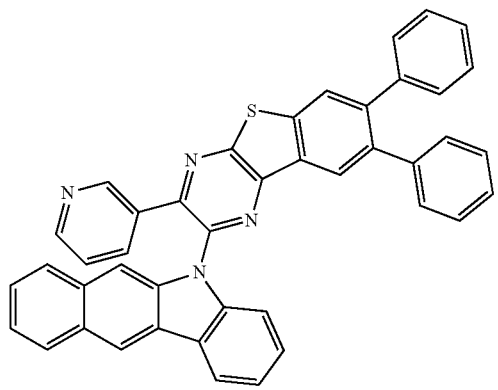
151
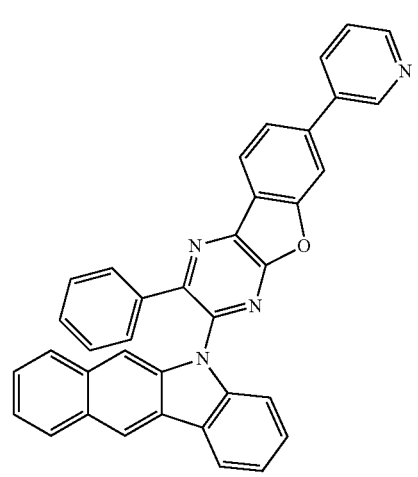
152
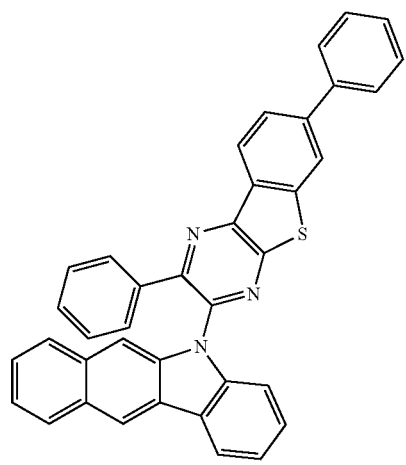
-continued
154
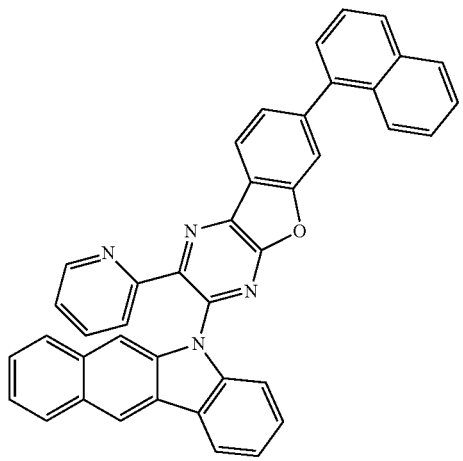
155
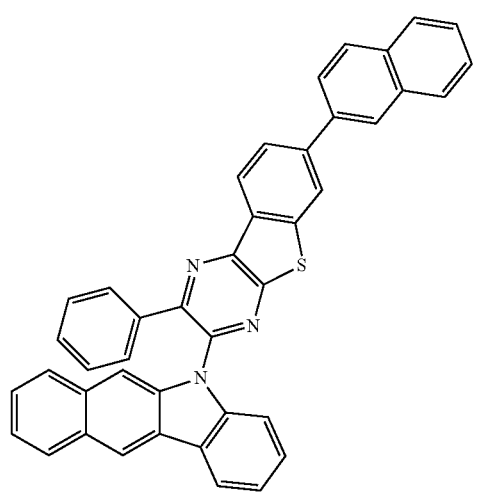
157
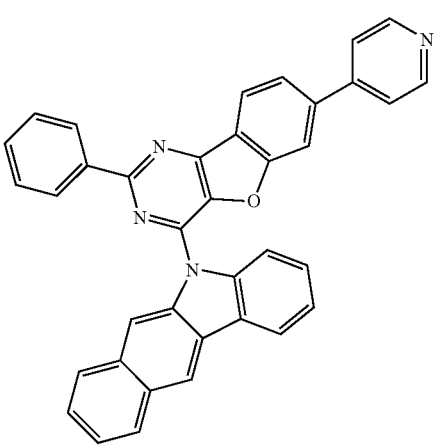

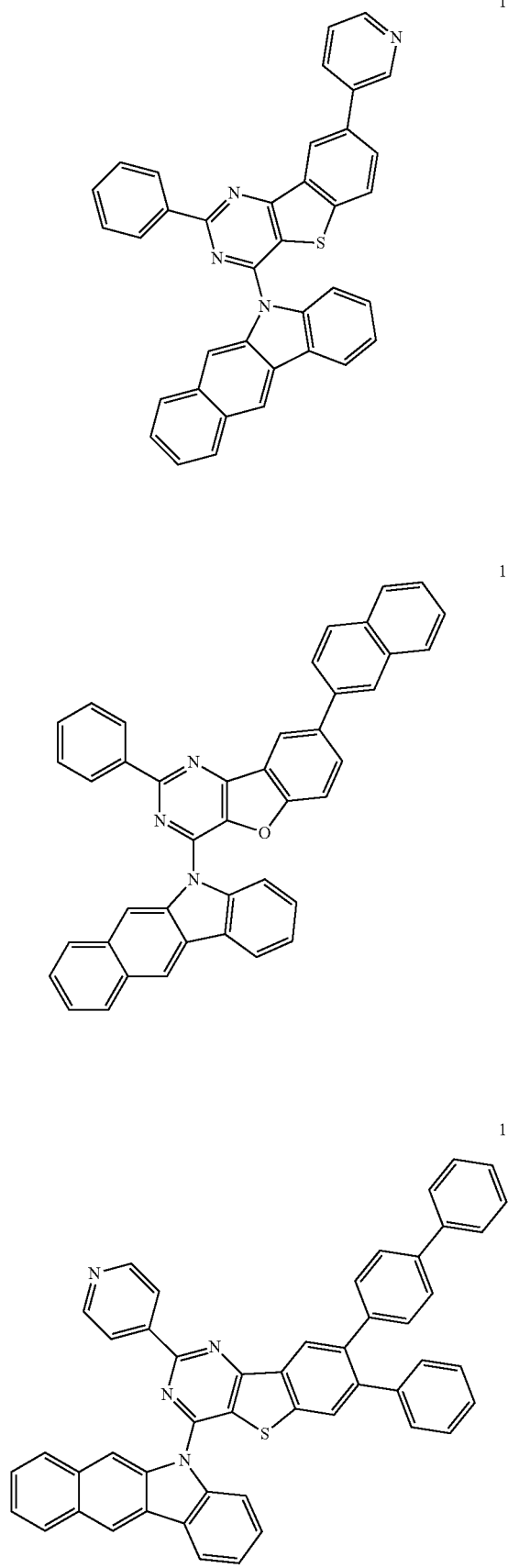
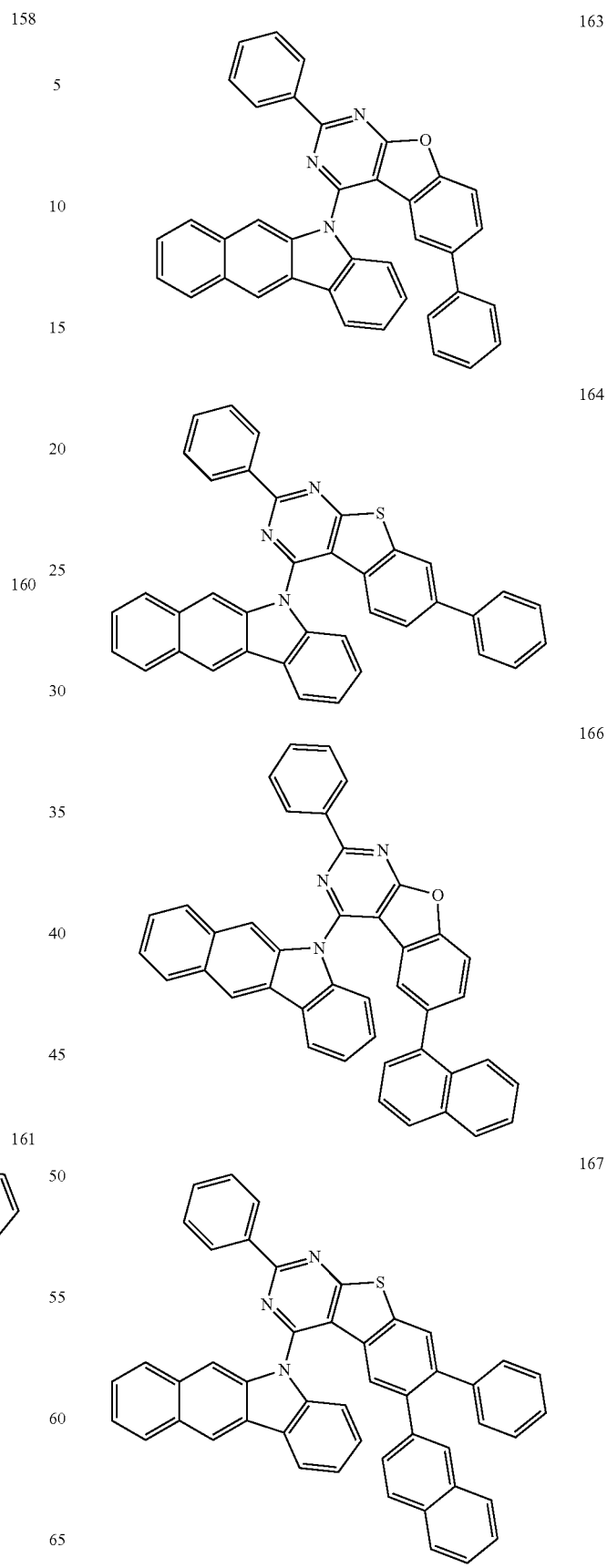

529
-continued
169
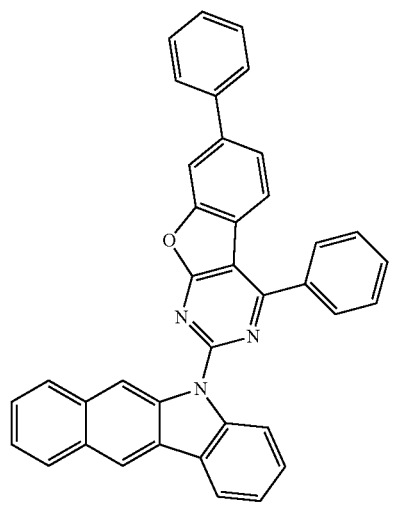
170
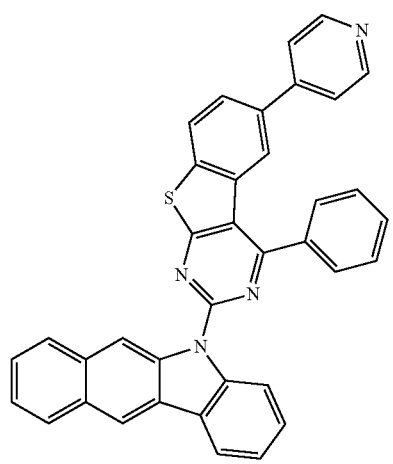
172
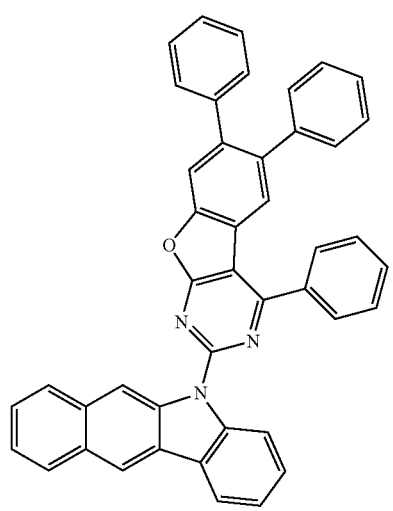
530
-continued
173
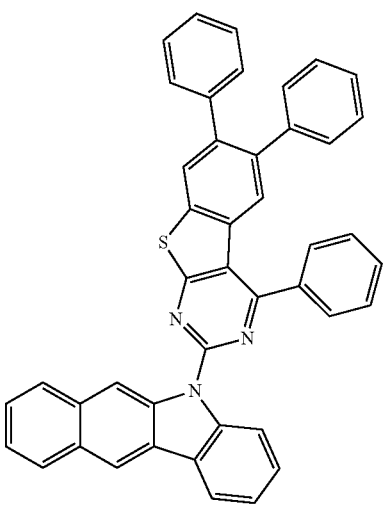
175
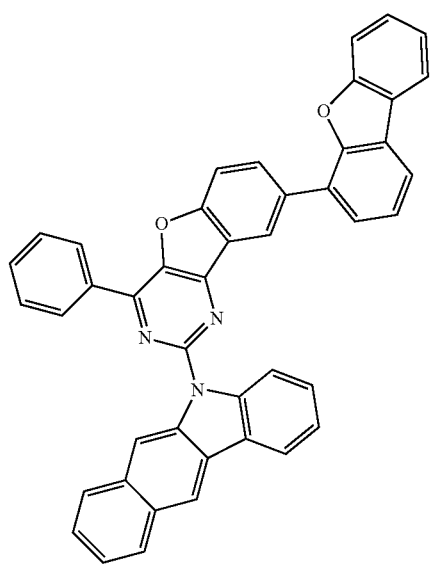
176
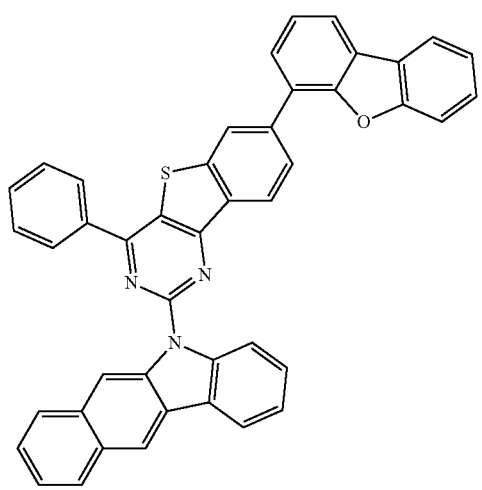

178
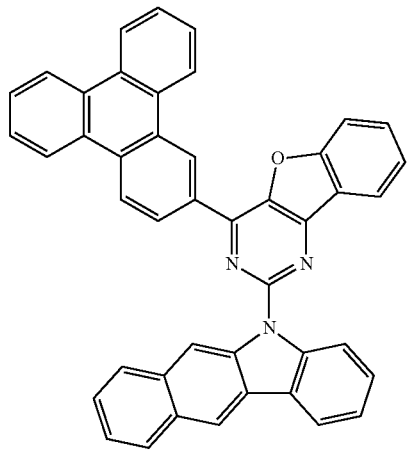
179
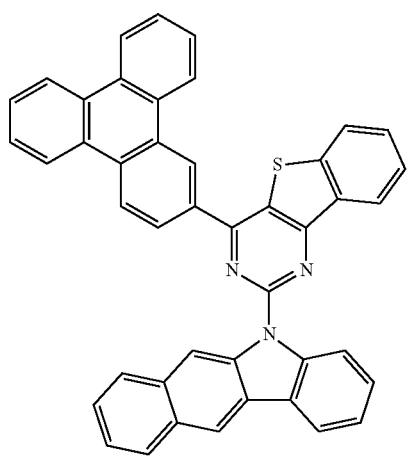
181
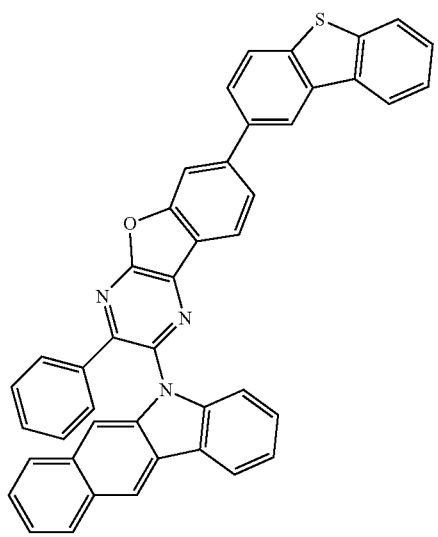
182
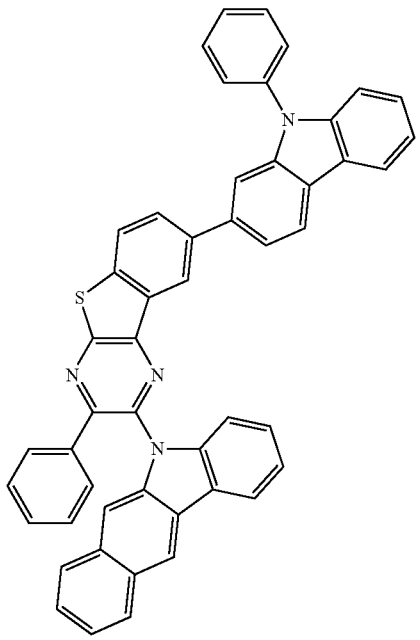
184
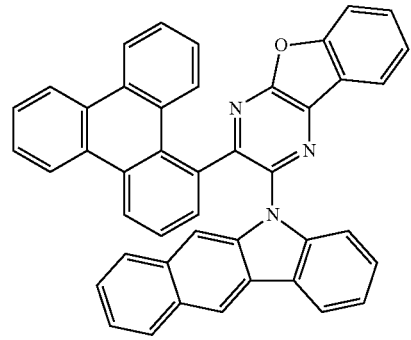
185
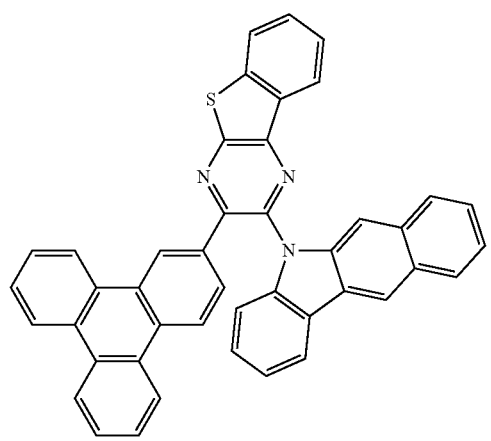

533
-continued
534
-continued
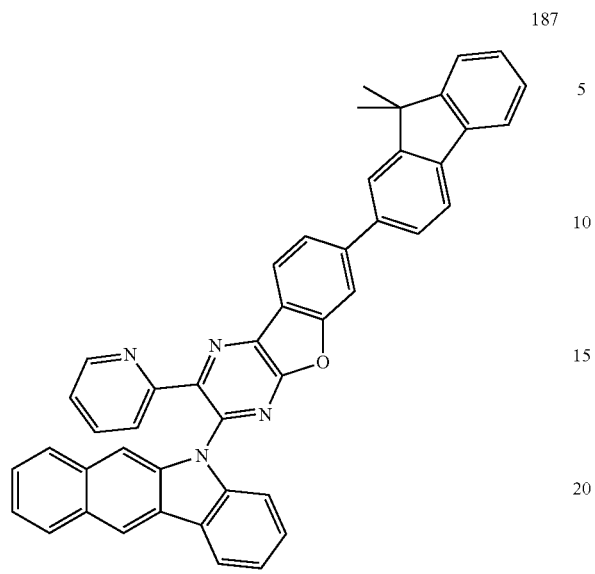
187
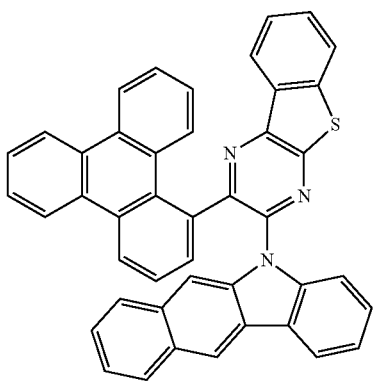
191
188
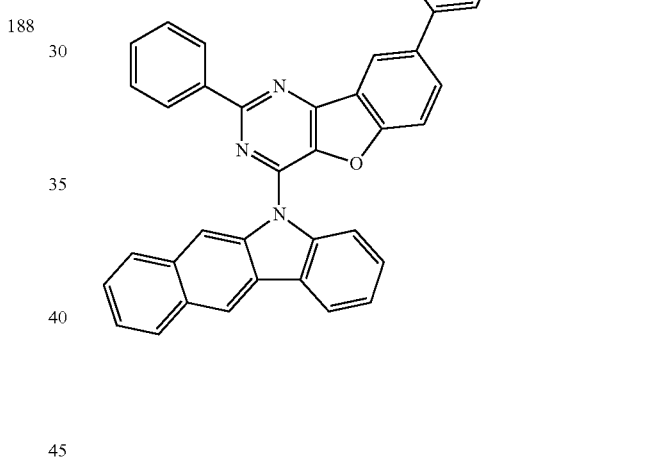
193
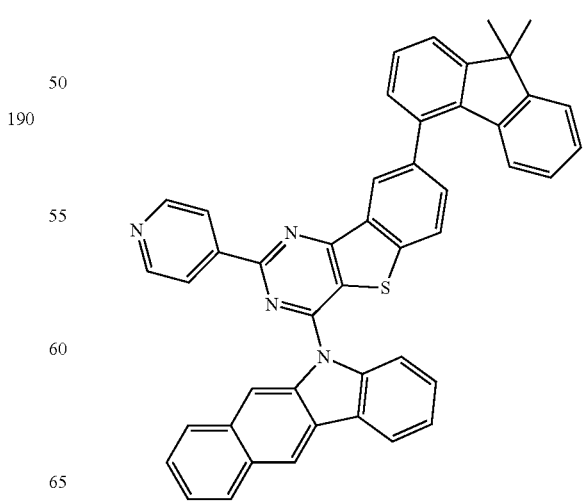
190
194

196
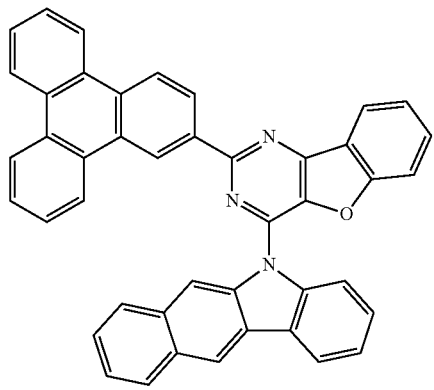
197
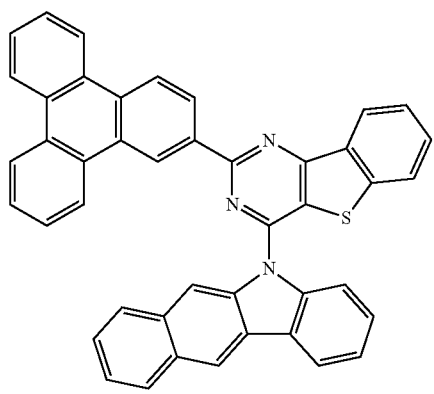
199
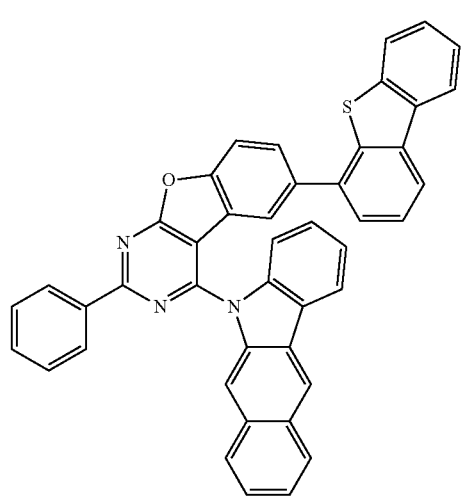
200
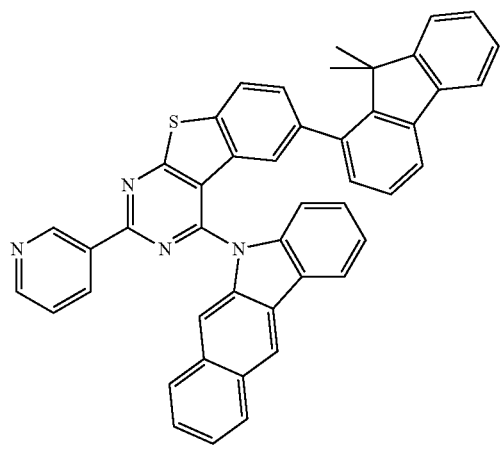
202
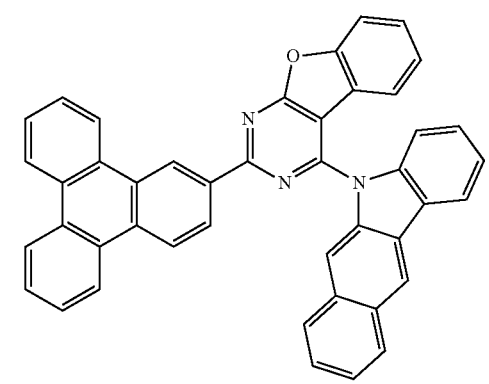
203
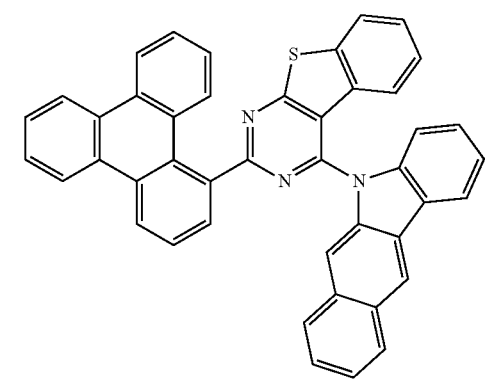

205 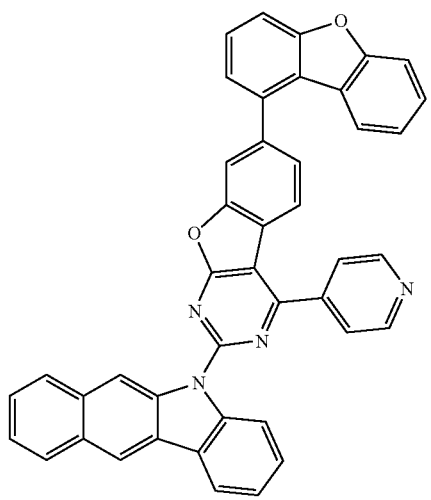
206 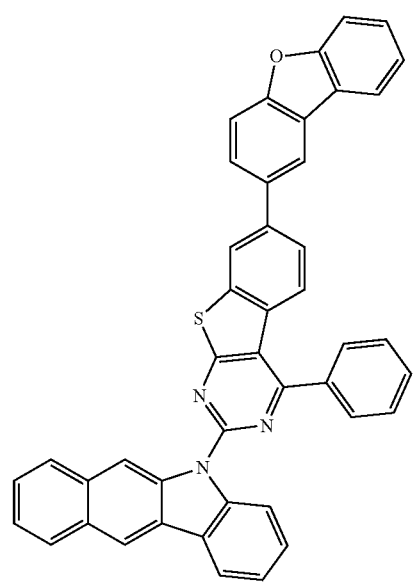
208 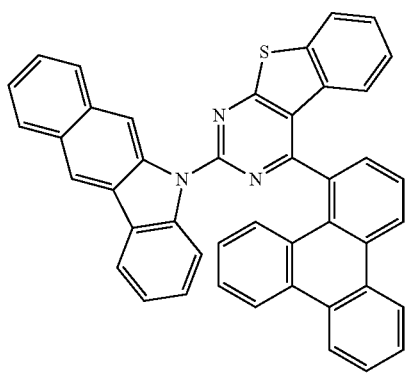
209 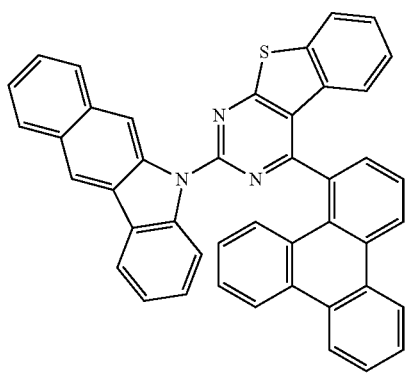
211 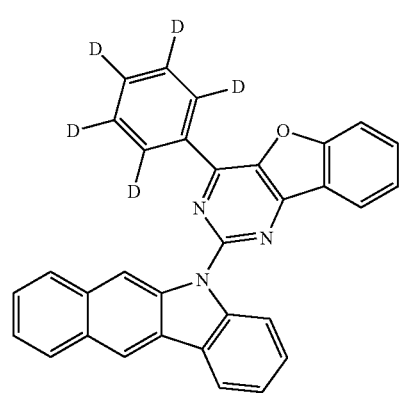
212 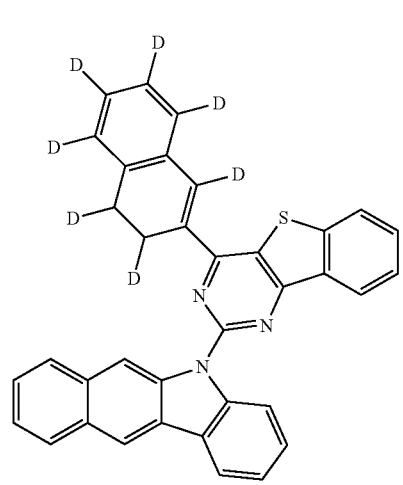

214
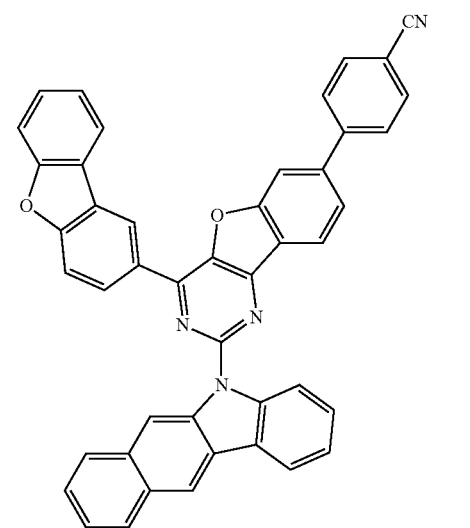
215
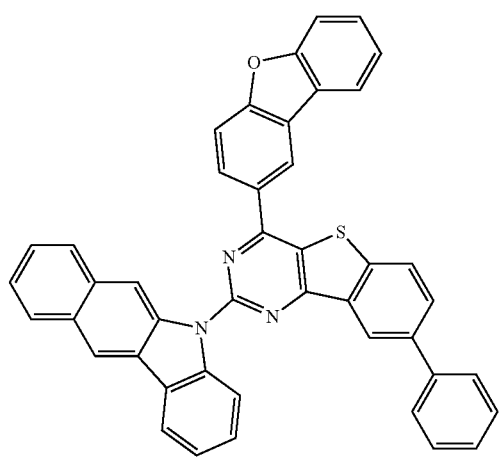
217
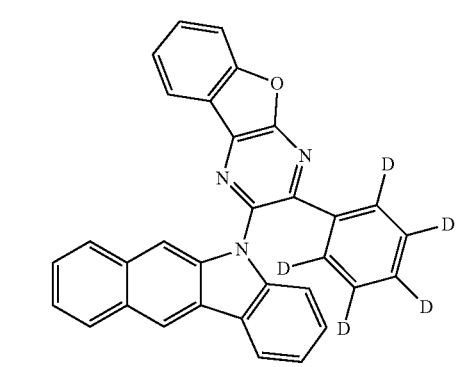
218
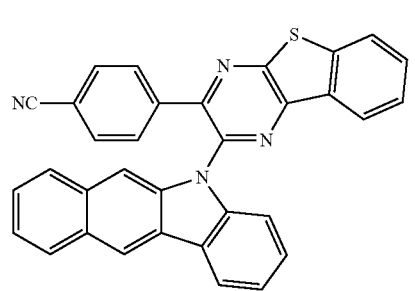
220
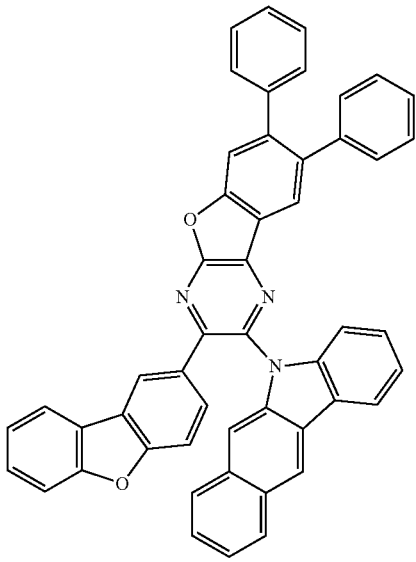
221
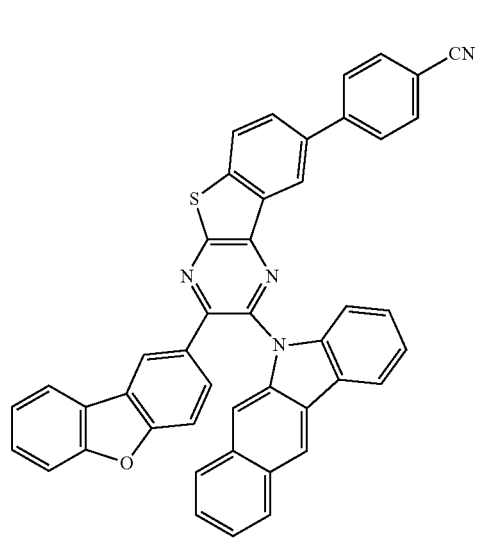
223
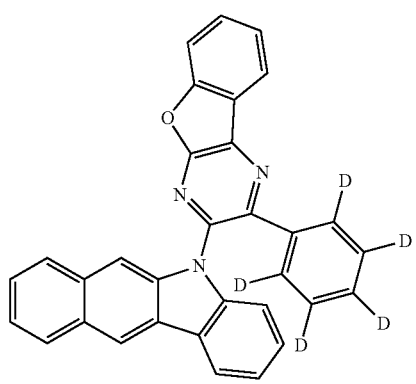

224
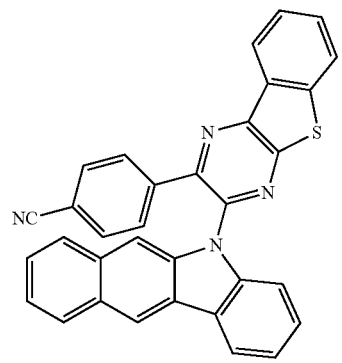
226
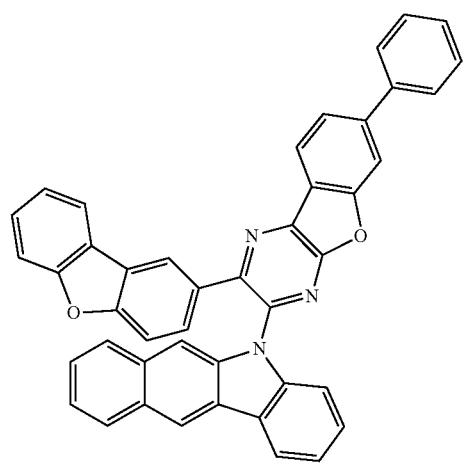
227
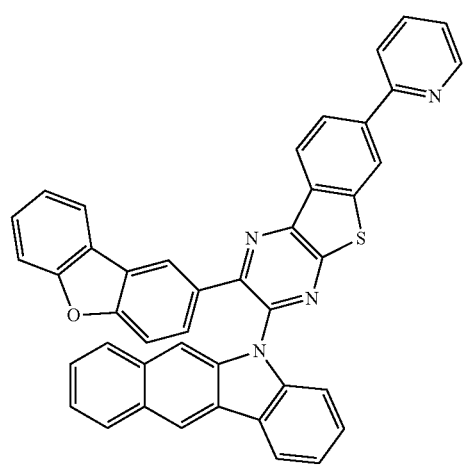
229
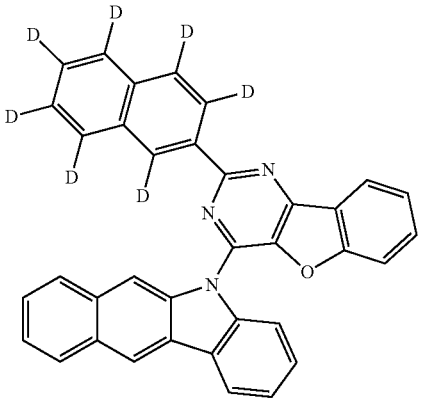
230
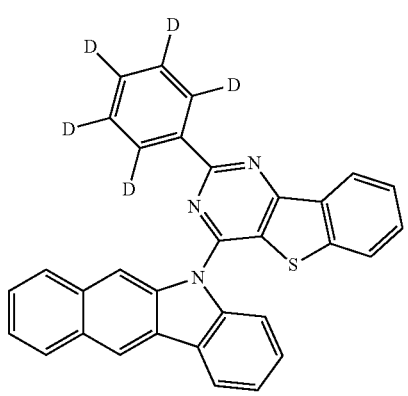
232
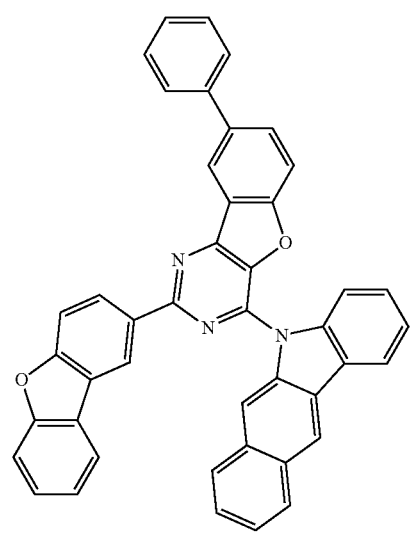

-continued
233
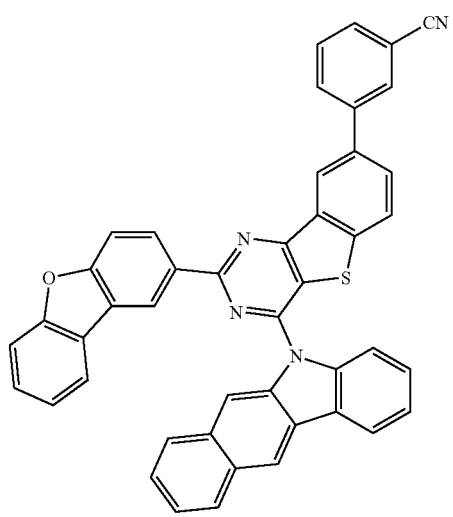
235
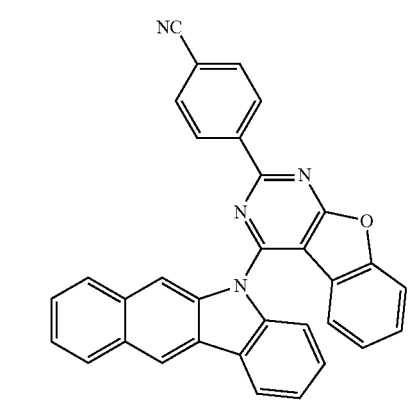
236
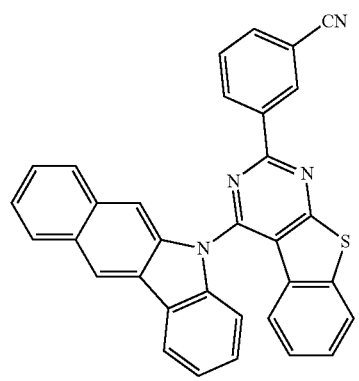
-continued
238
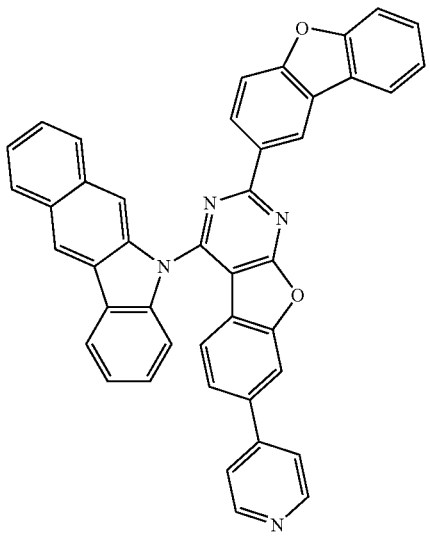
239
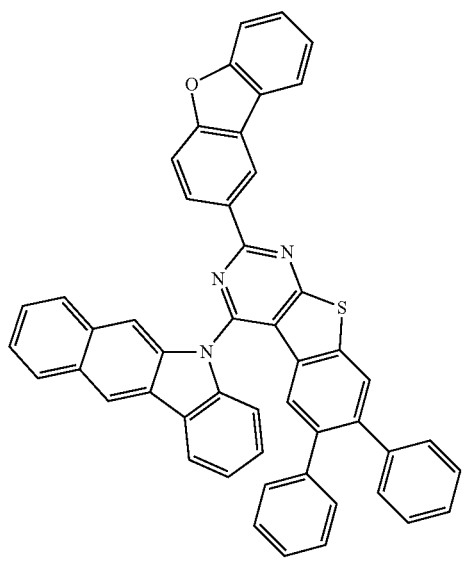
241
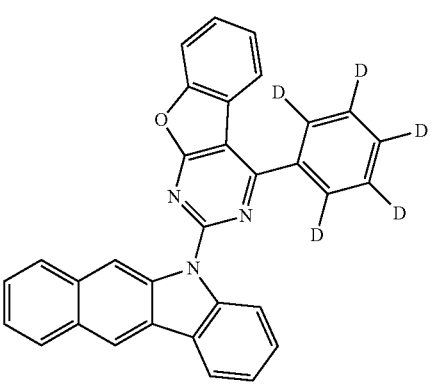

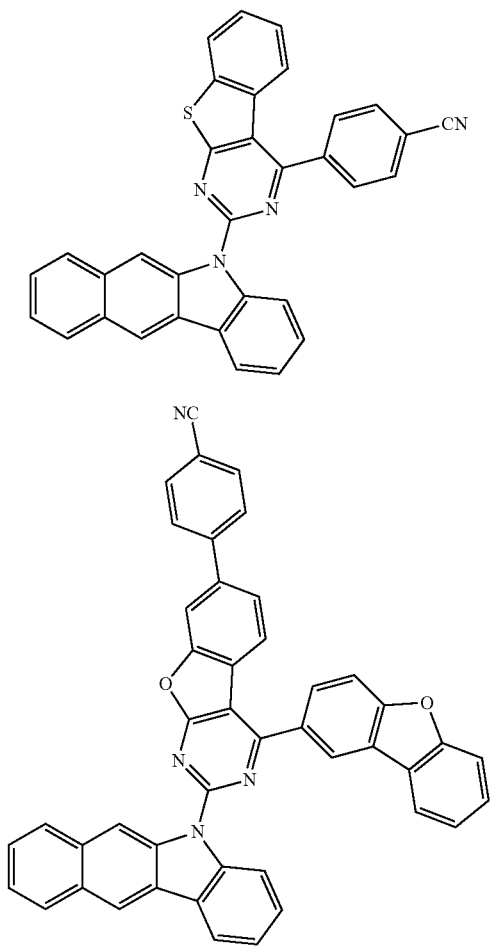
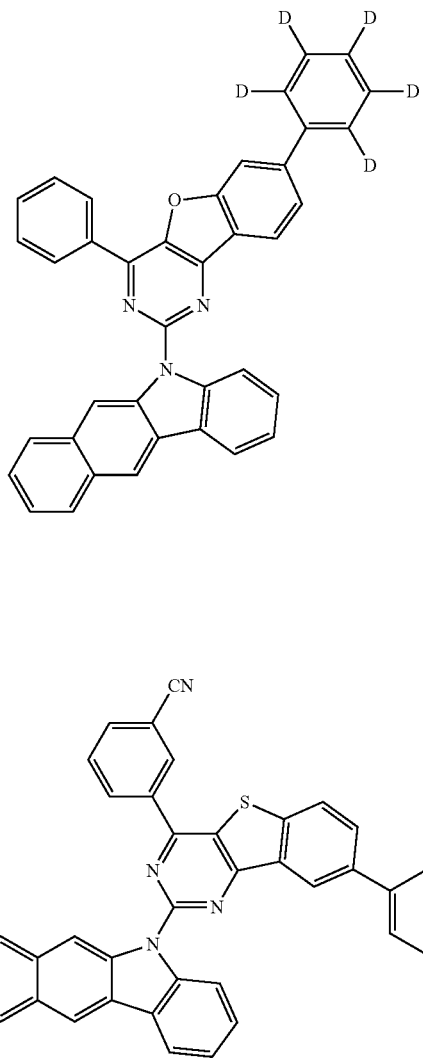
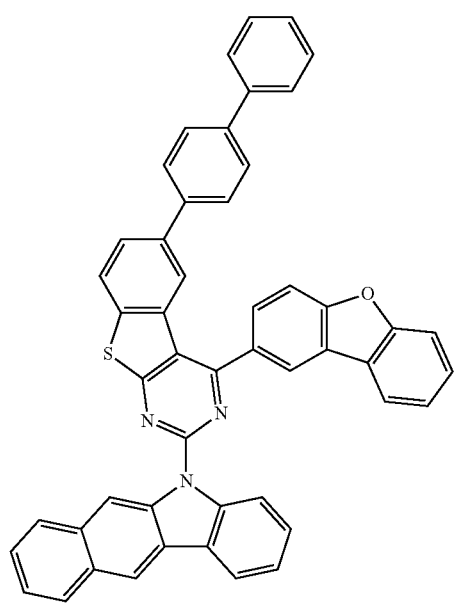
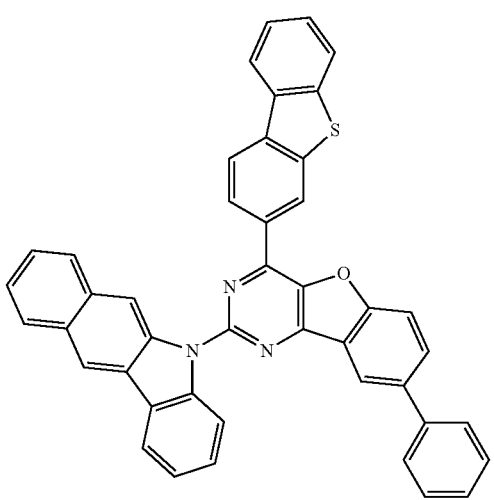

251
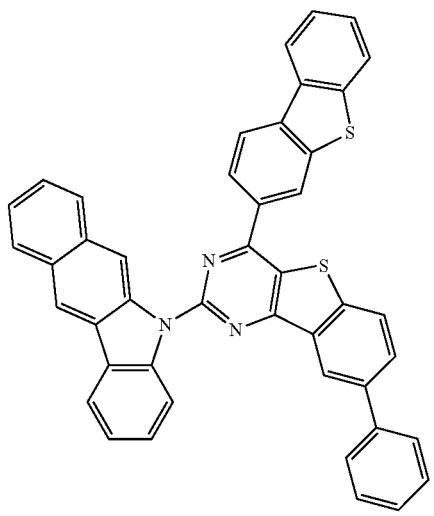
253
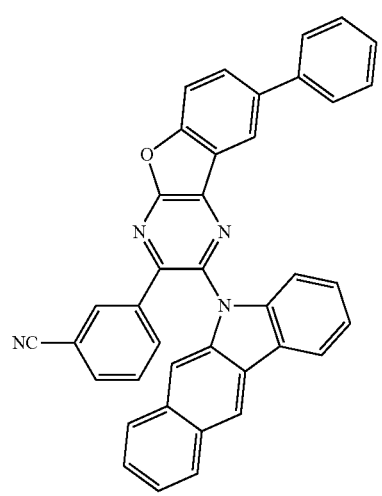
254
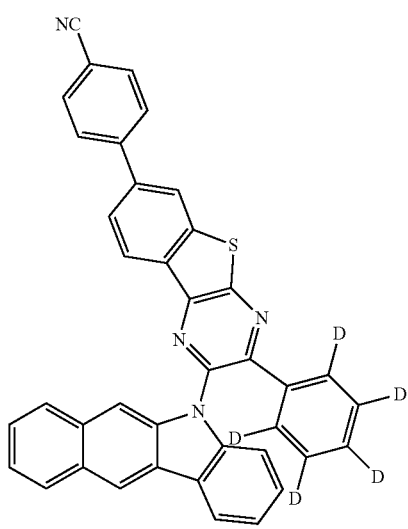
256
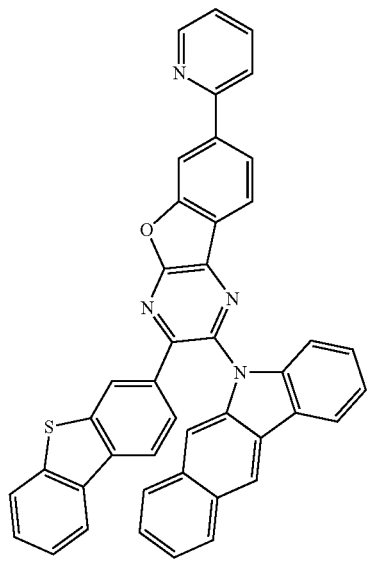
257
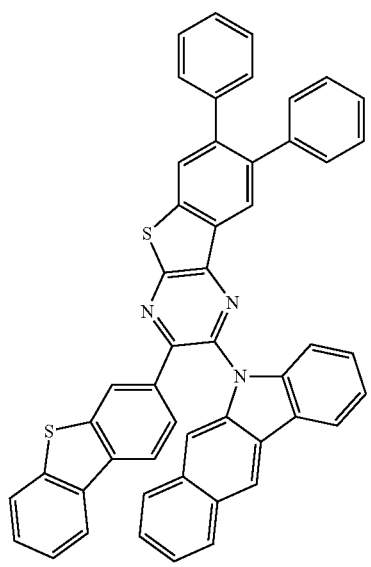
259
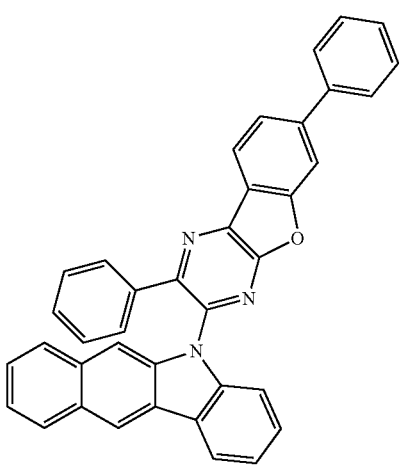

260
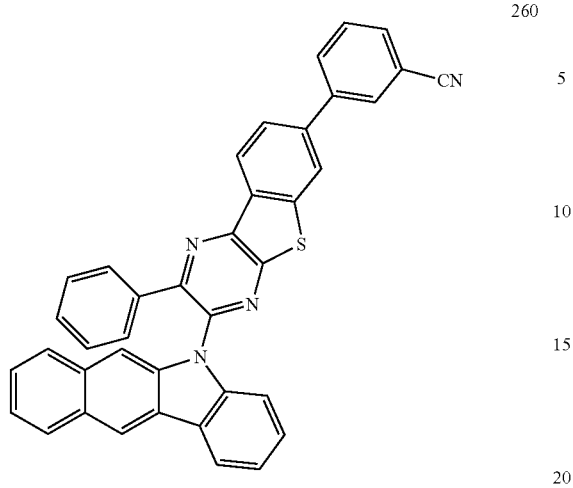
265
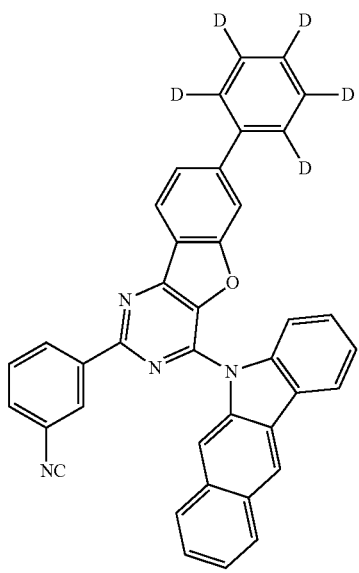
262
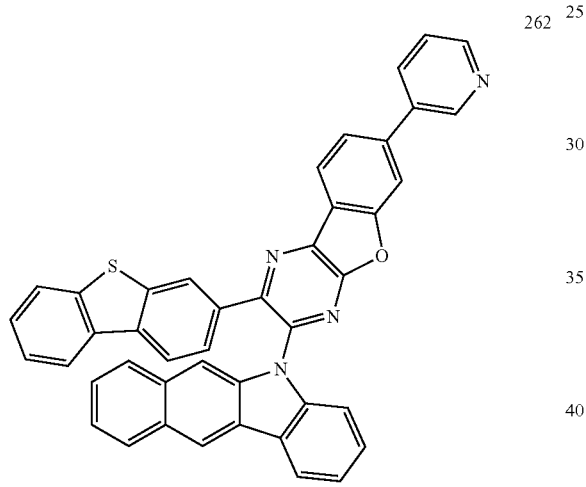
263
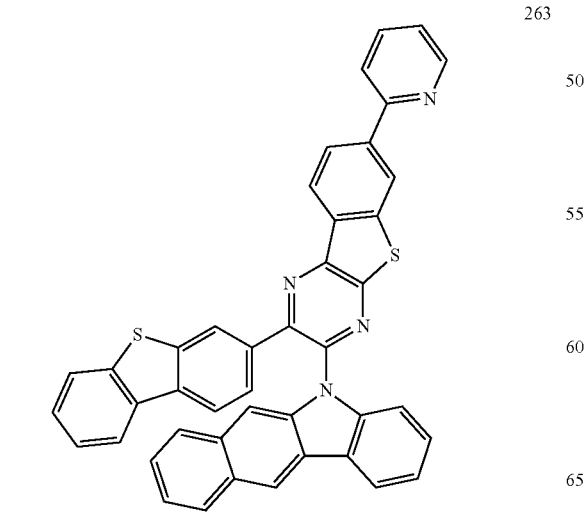
266
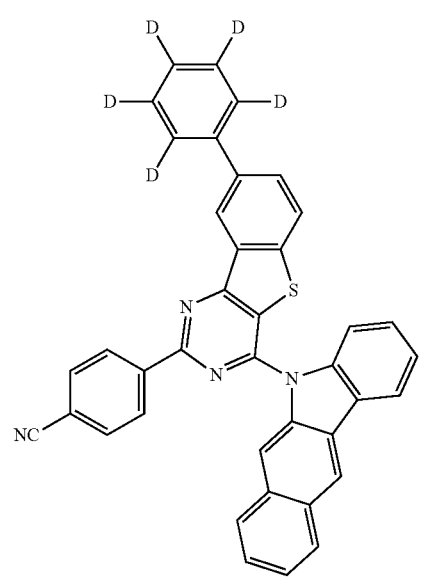

551
-continued
268
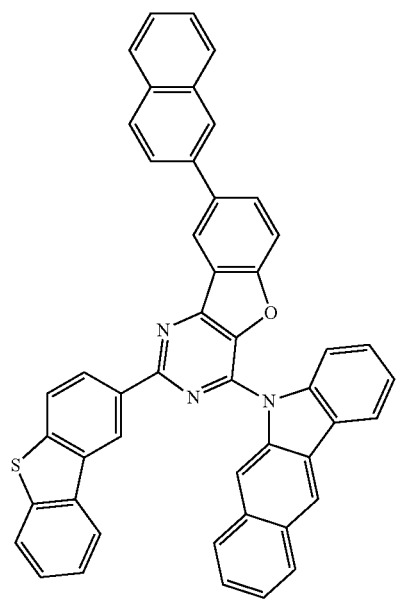
269
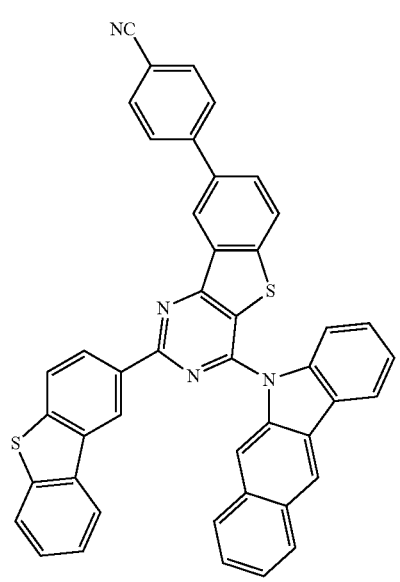
271
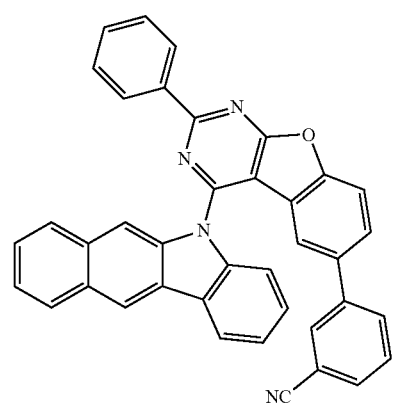
552
-continued
272
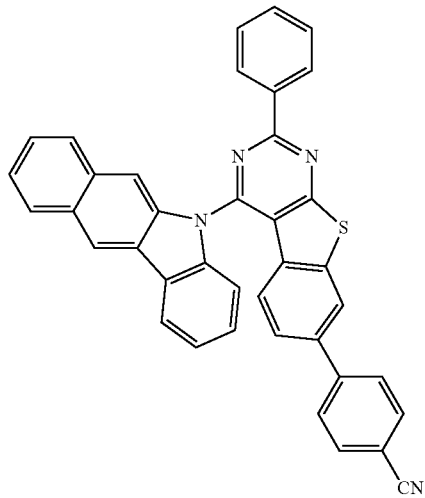
274
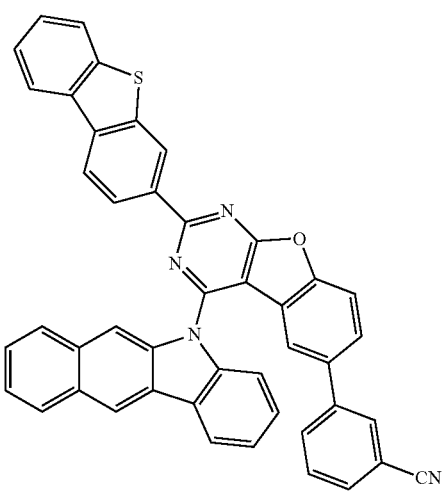
275
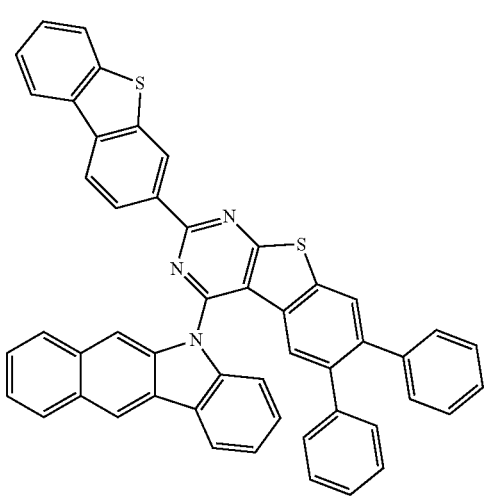

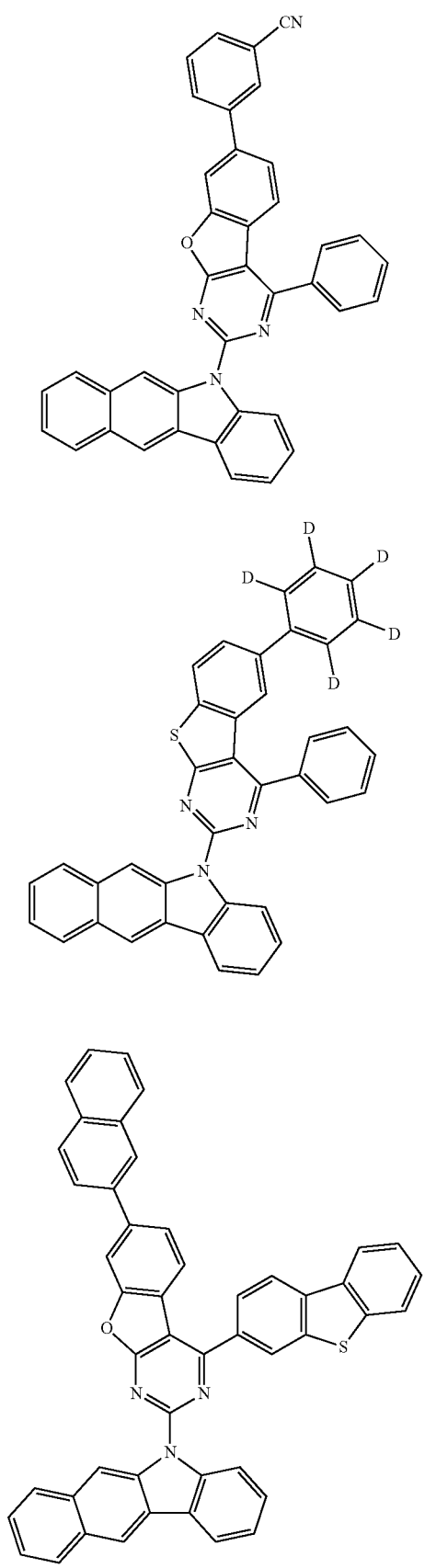
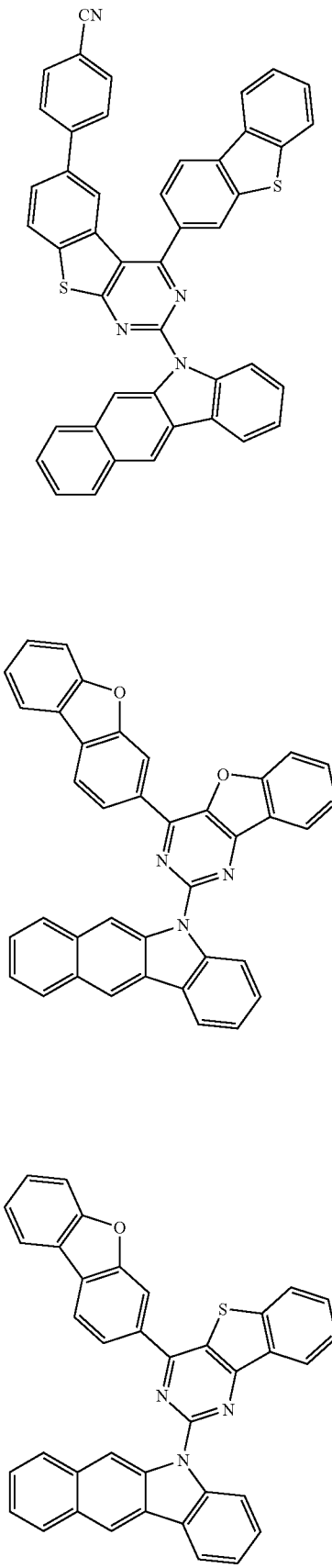

286
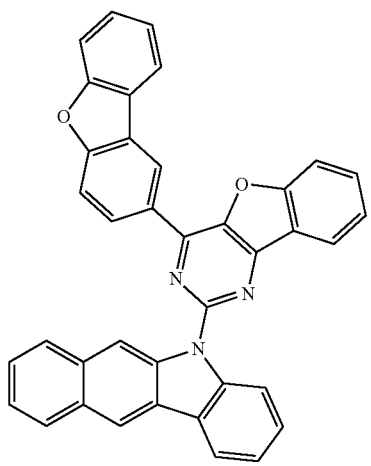
287
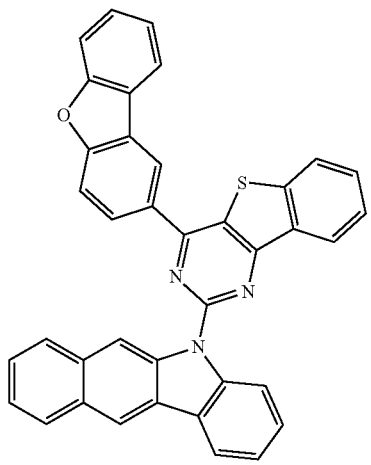
289
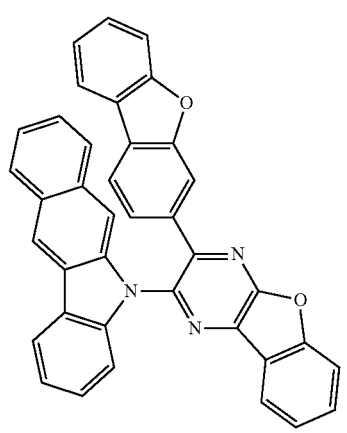
290
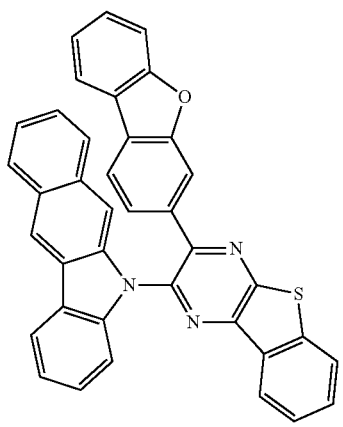
292
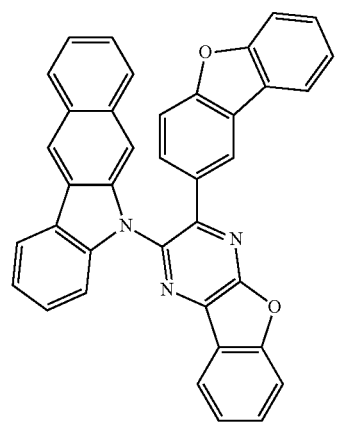
293
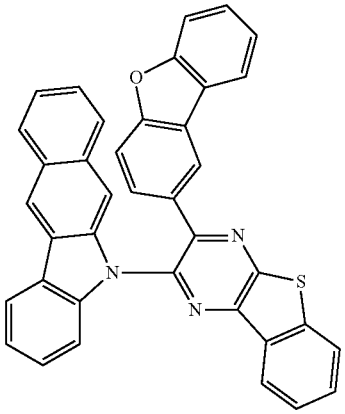

295
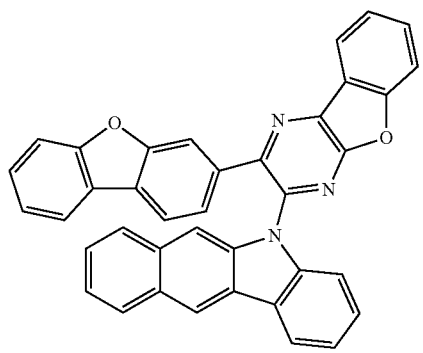
296
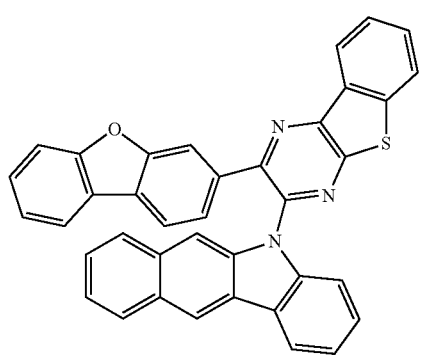
298
301
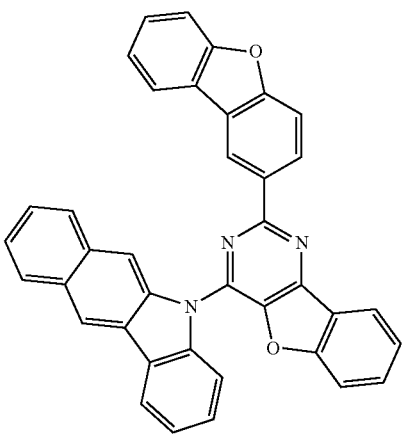
302
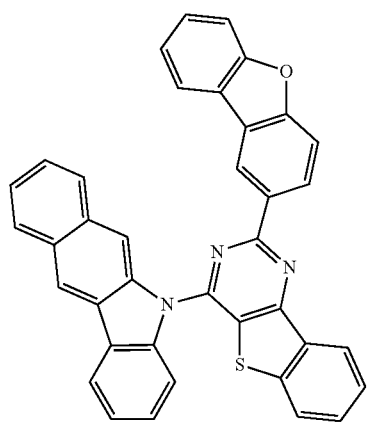
299
304
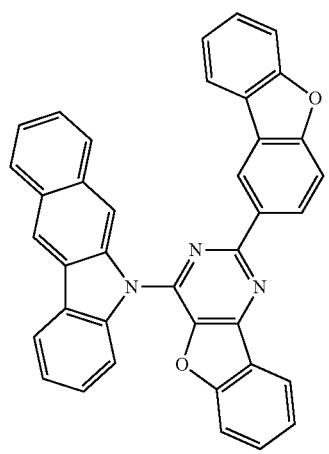

559
-continued
305
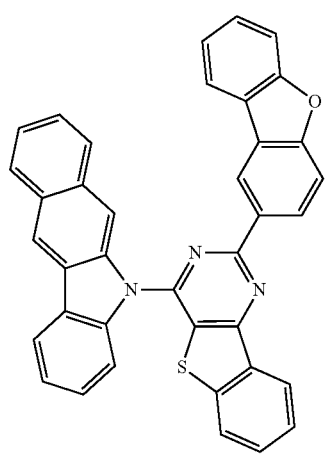
307
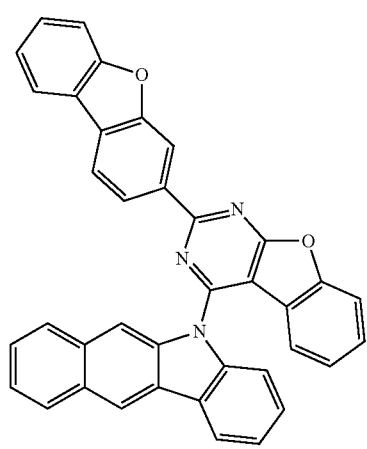
308
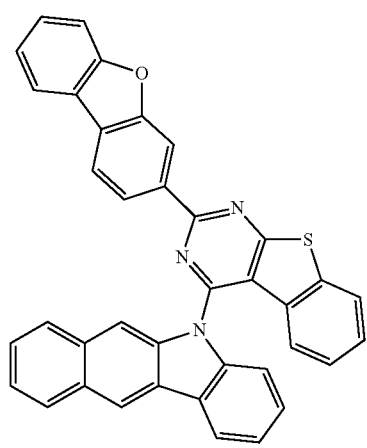
560
-continued
310
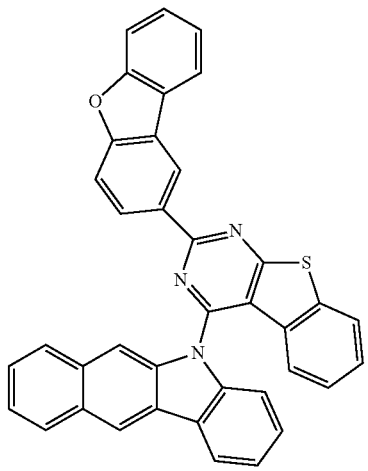
311
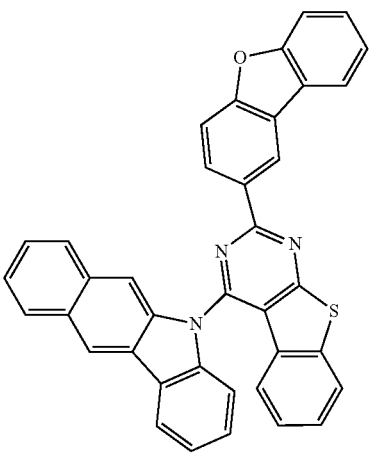
313
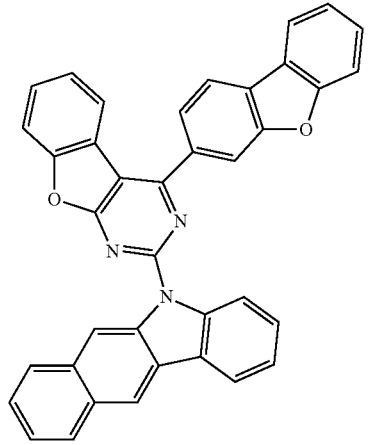

-continued
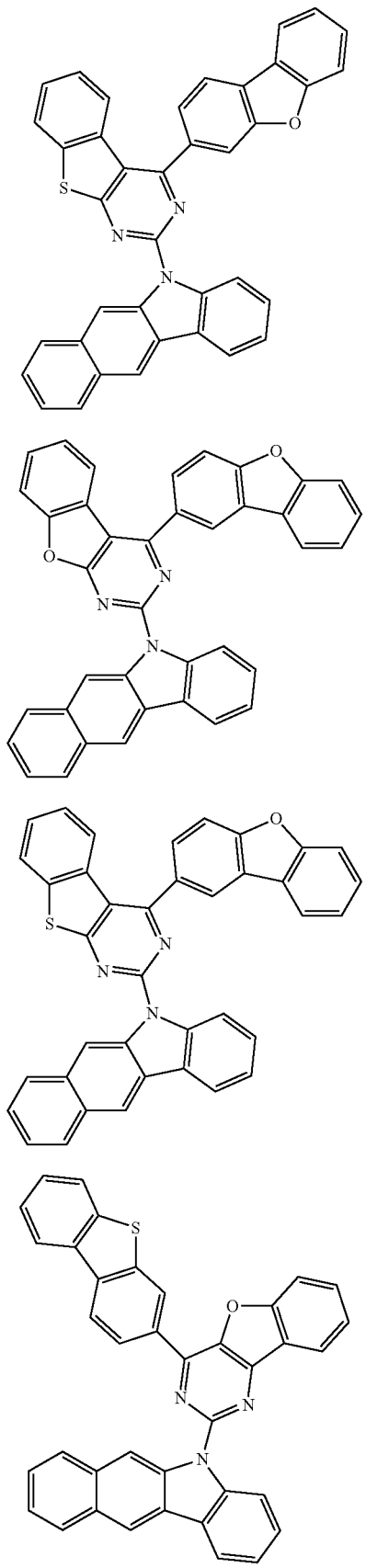
-continued
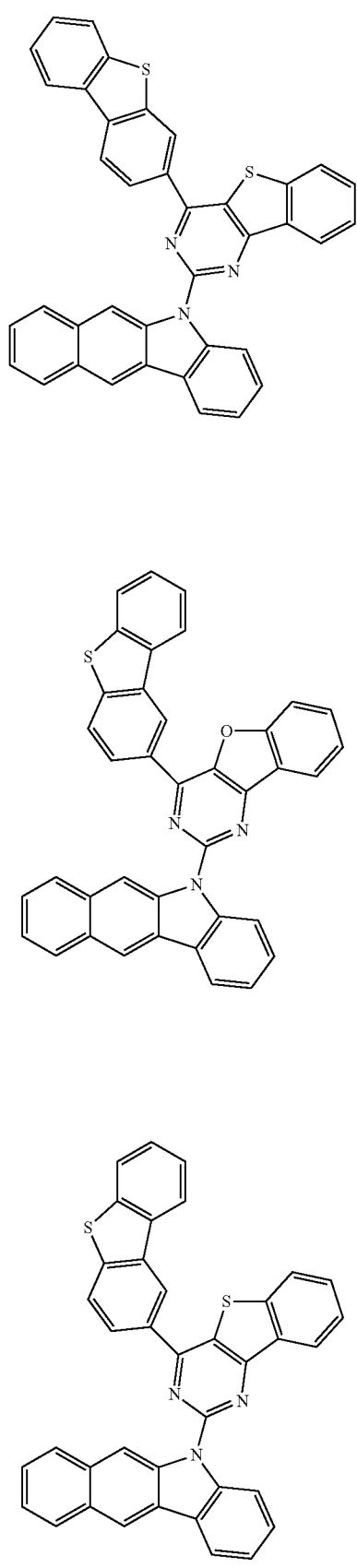

325
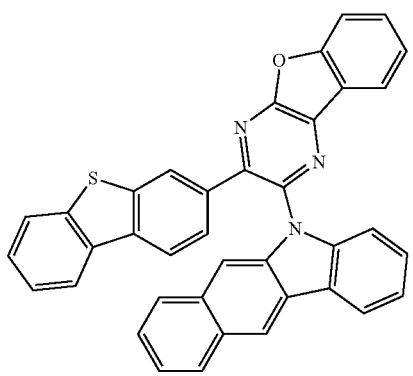
326
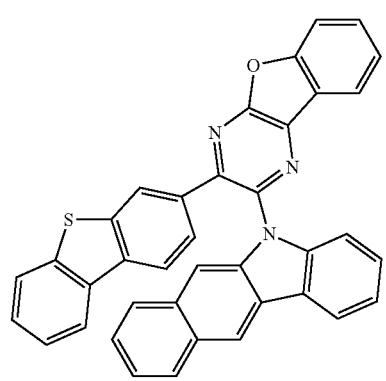
328
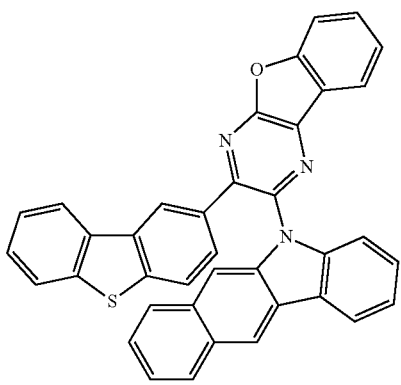
329
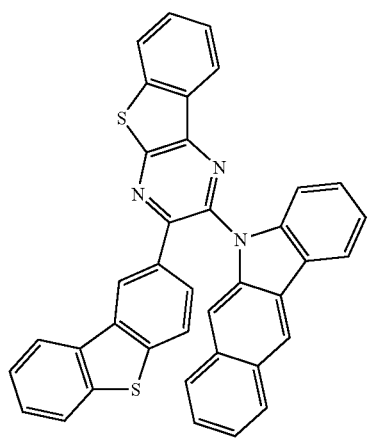
331
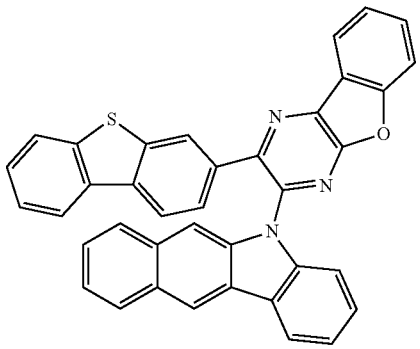
332
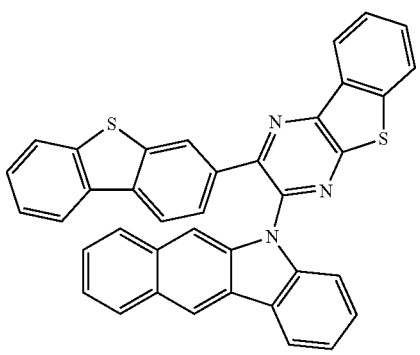
334
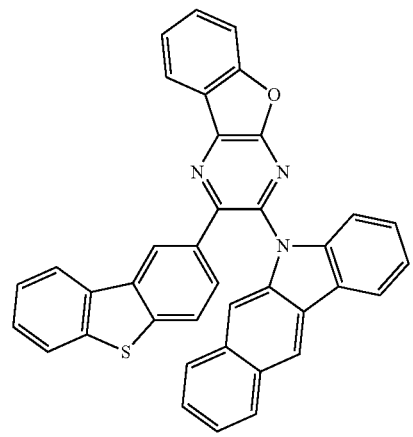
335
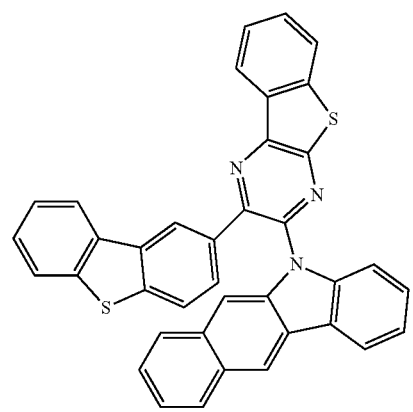

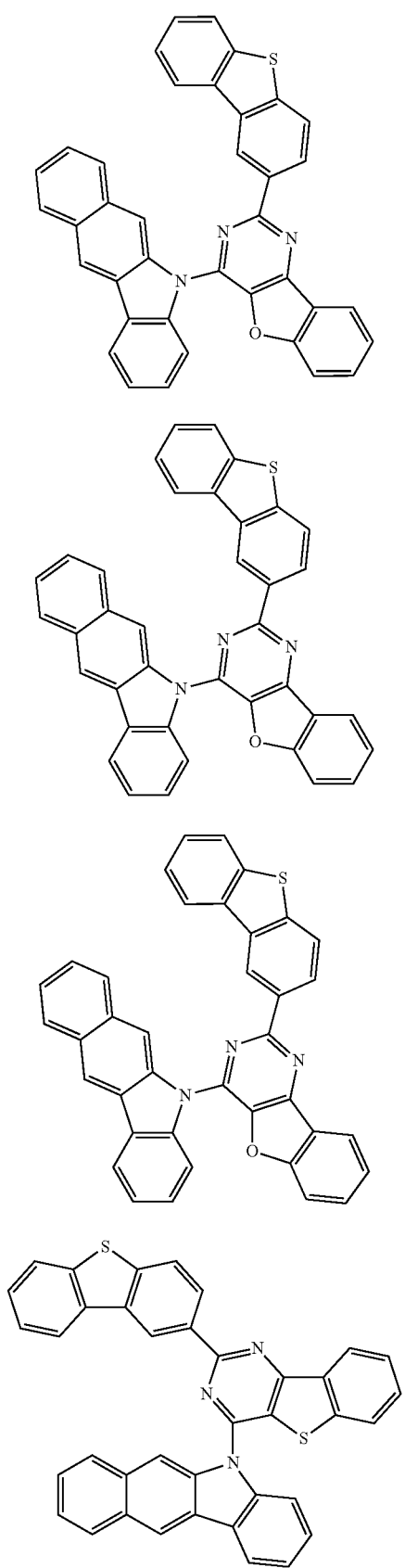
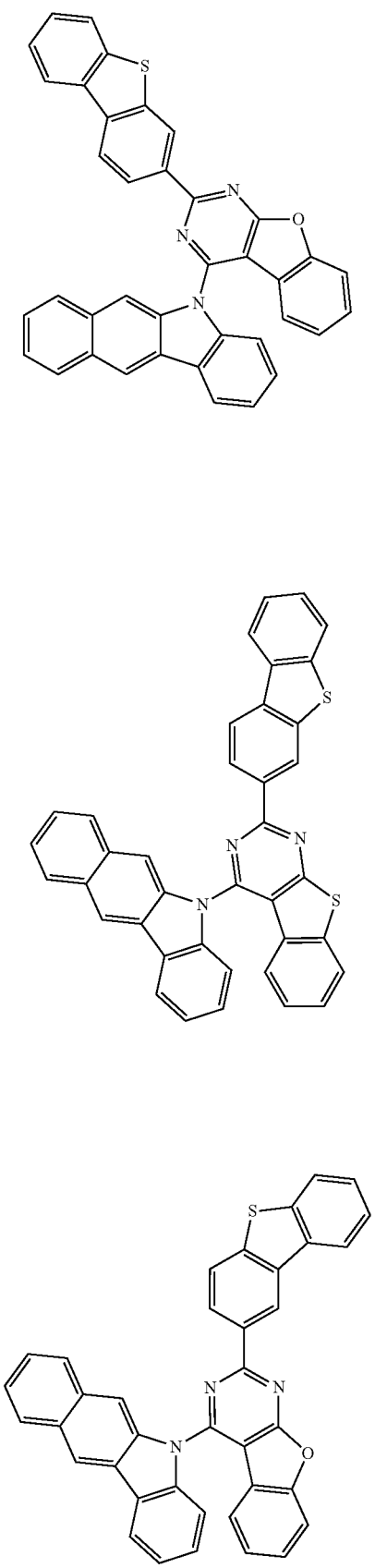

347
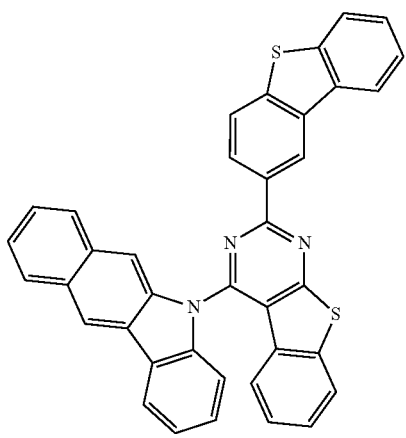
349
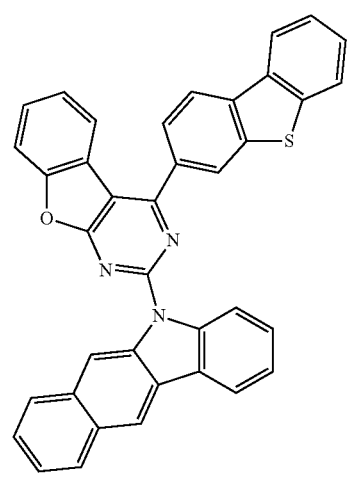
350
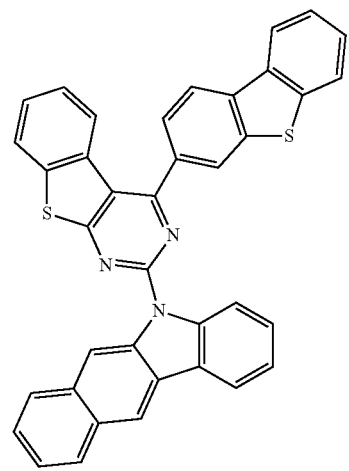
352
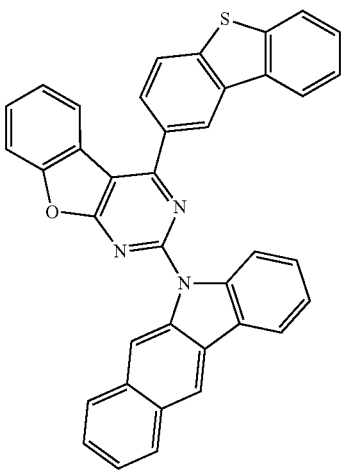
353
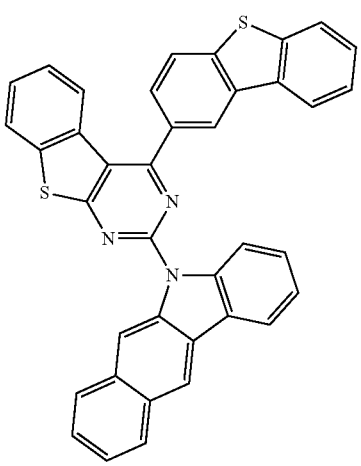
355
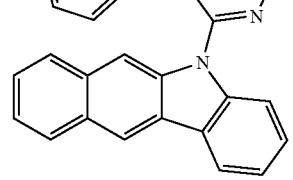
356
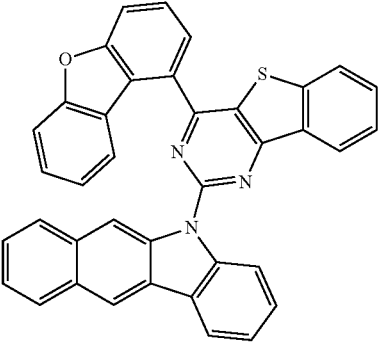

358
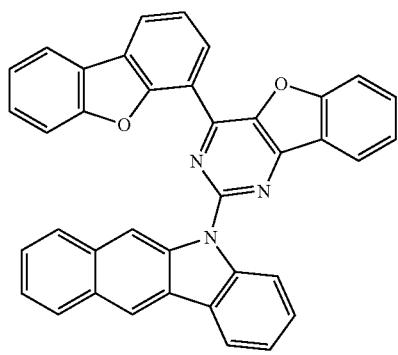
359
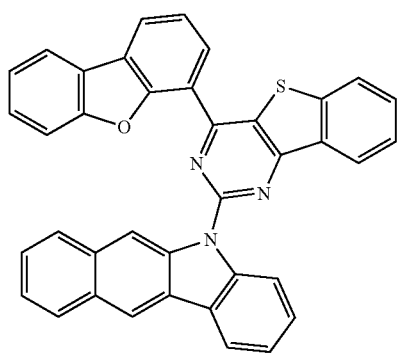
361
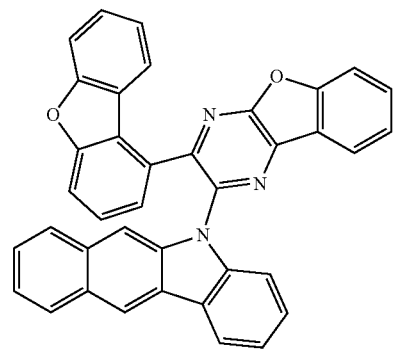
362
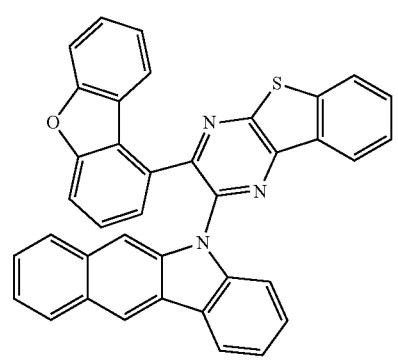
364
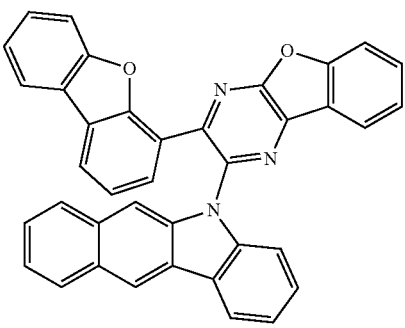
365
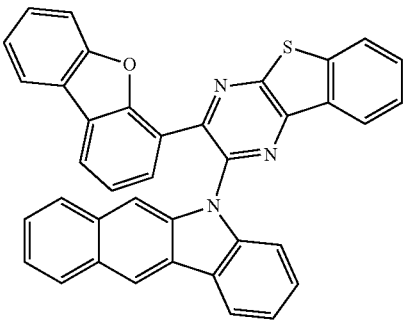
367
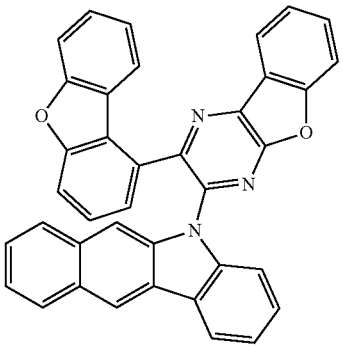
368
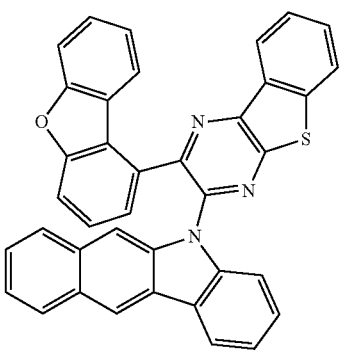

571
-continued
370
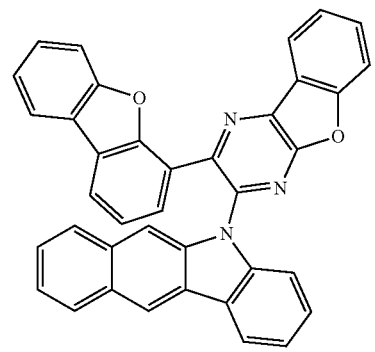
371
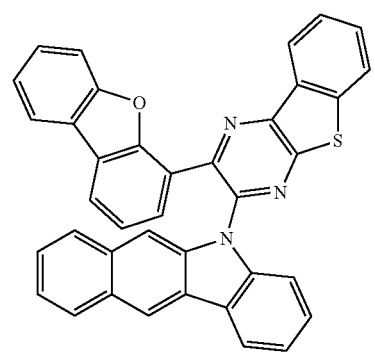
373
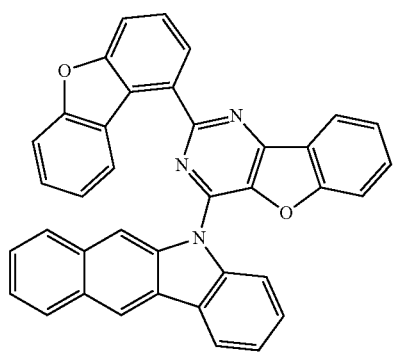
374
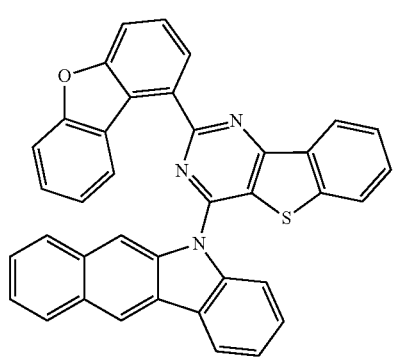
572
-continued
376
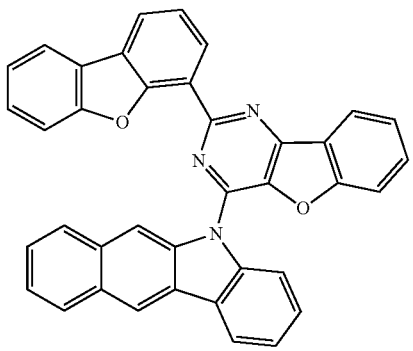
377
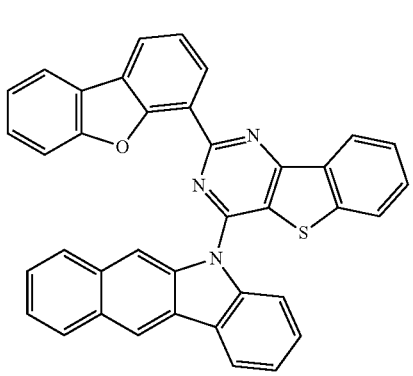
379
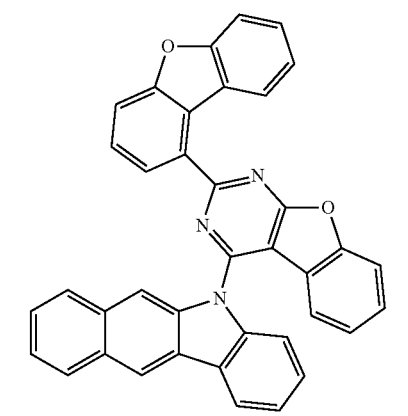
380
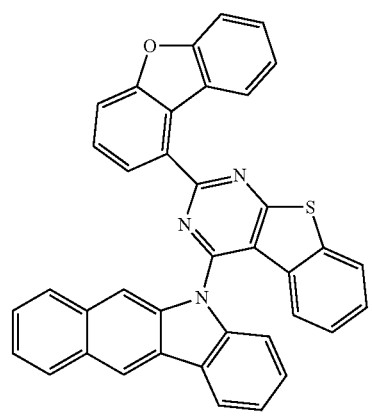

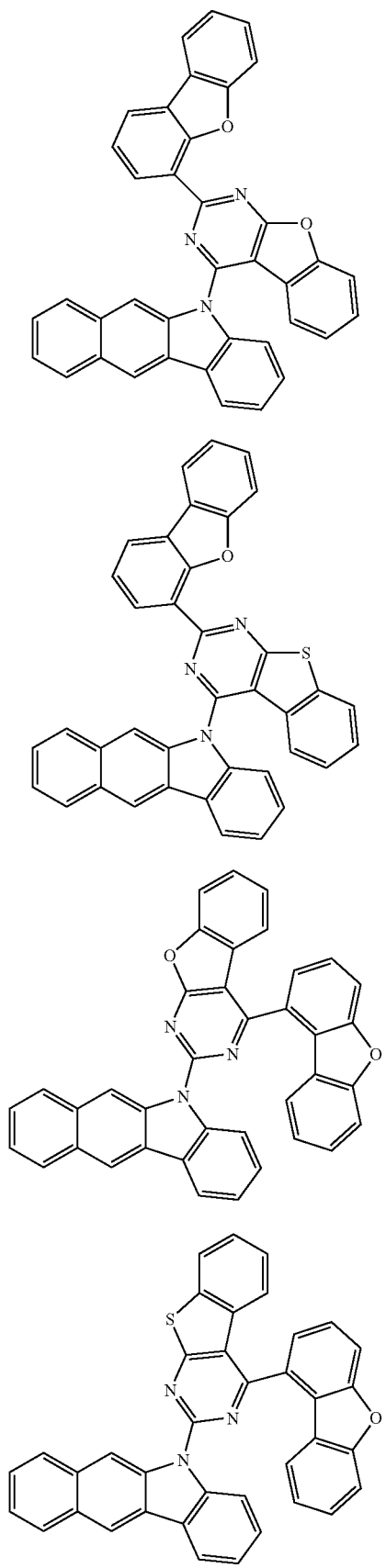
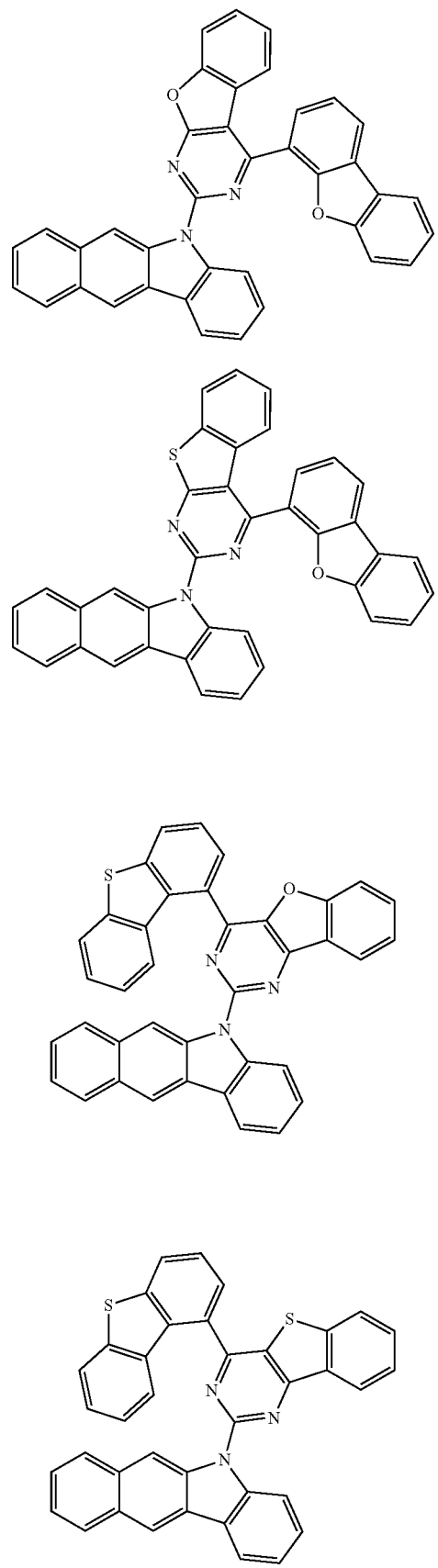

575
-continued
394
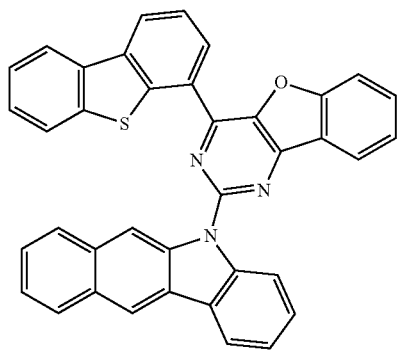
395
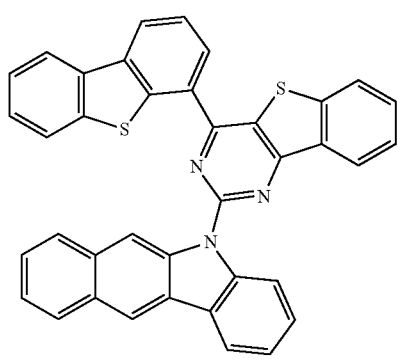
397
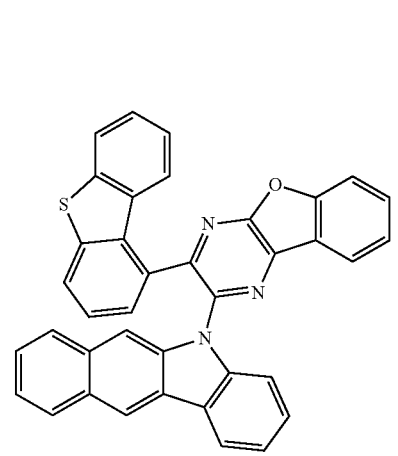
398
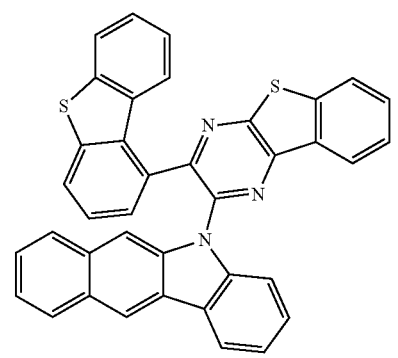
576
-continued
400
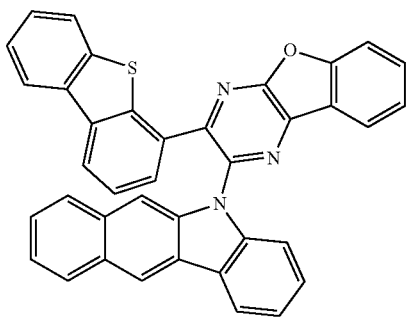
401
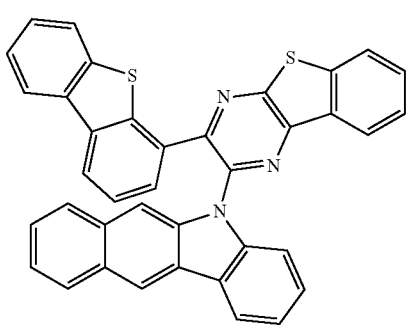
403
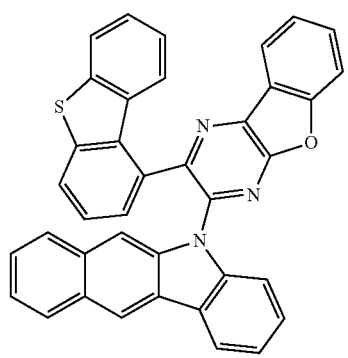
404
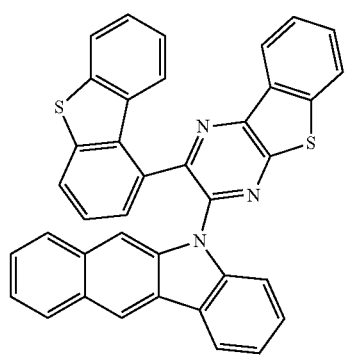

406
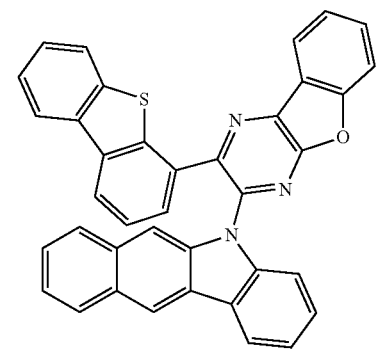
407
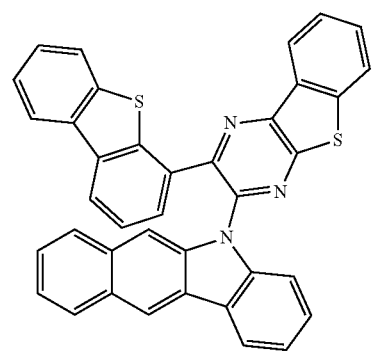
409
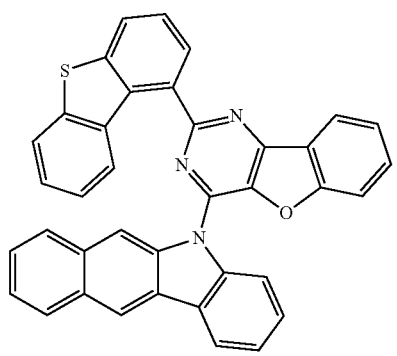
410
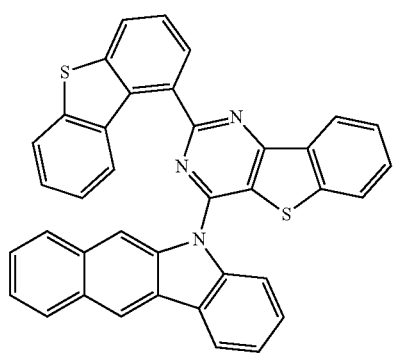
412
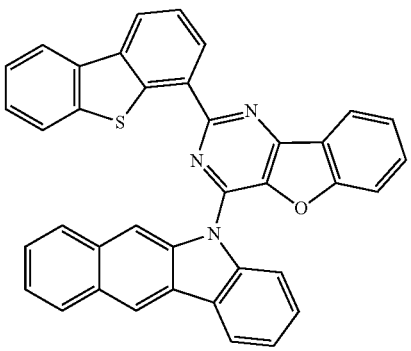
413
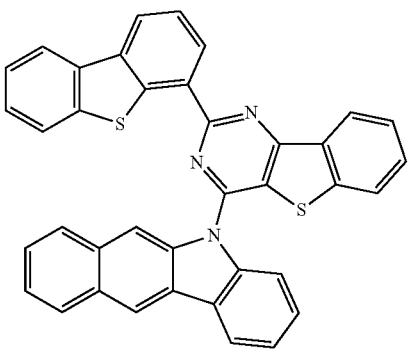
415
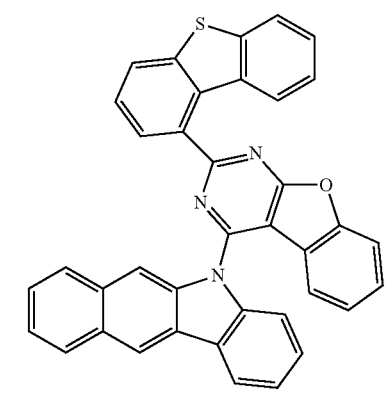
416
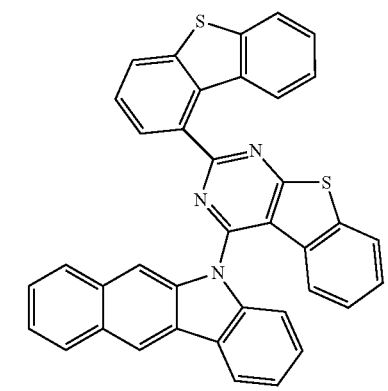

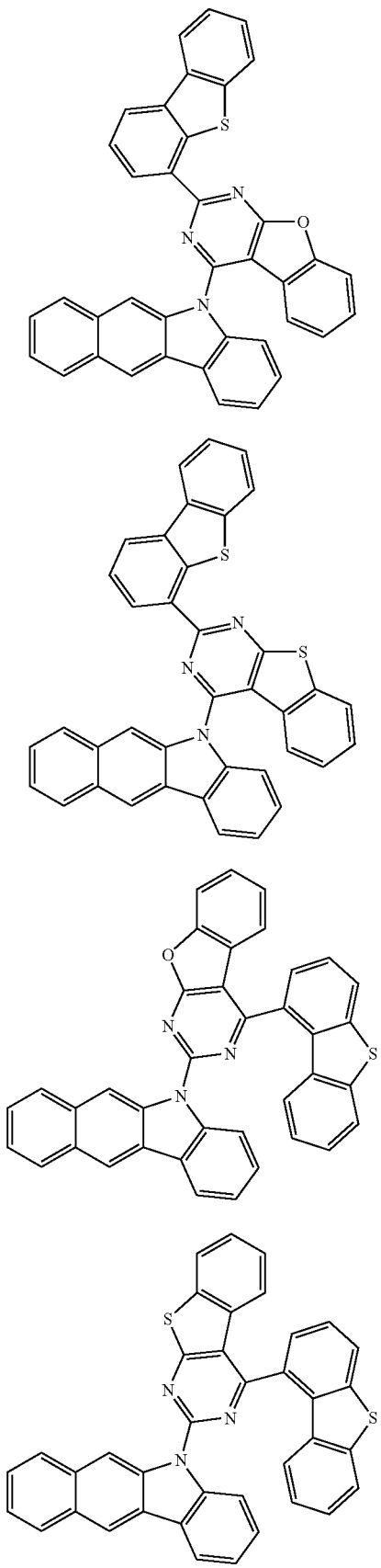
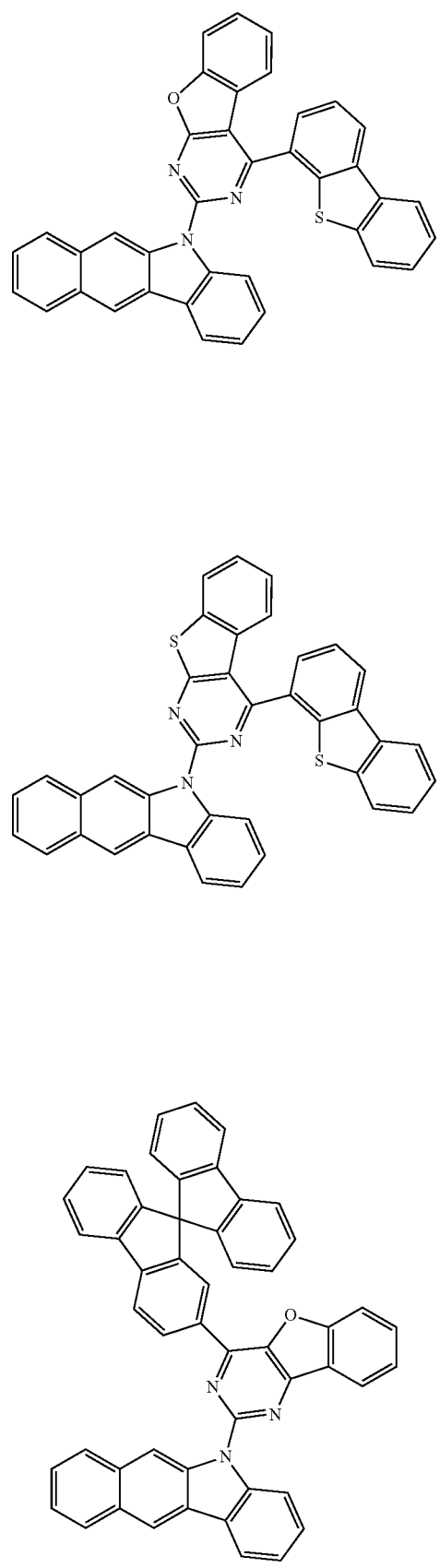

428
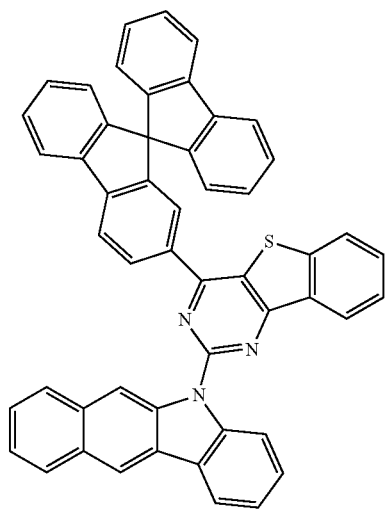
430
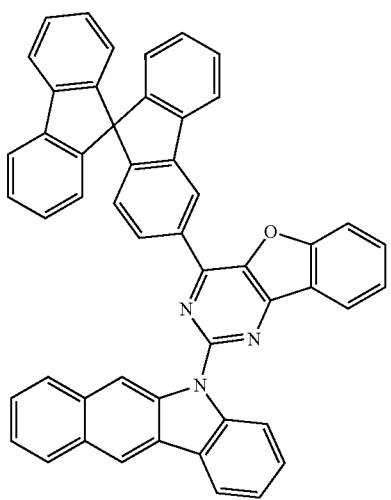
431
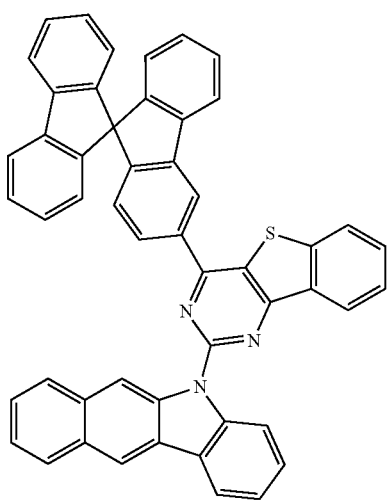
433
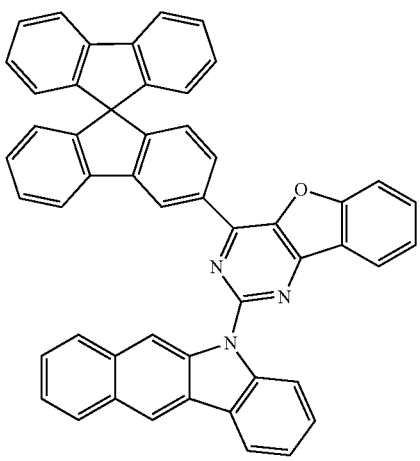
434
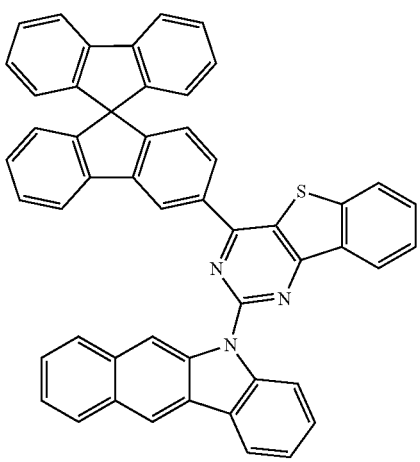
436
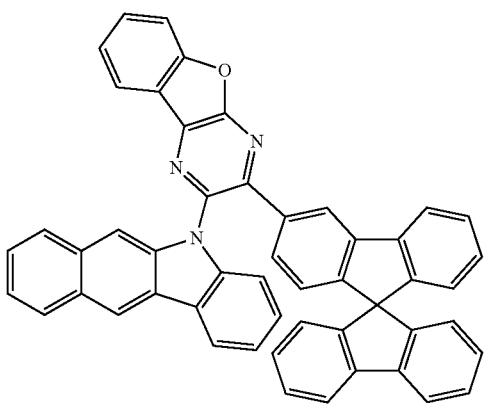

583
-continued
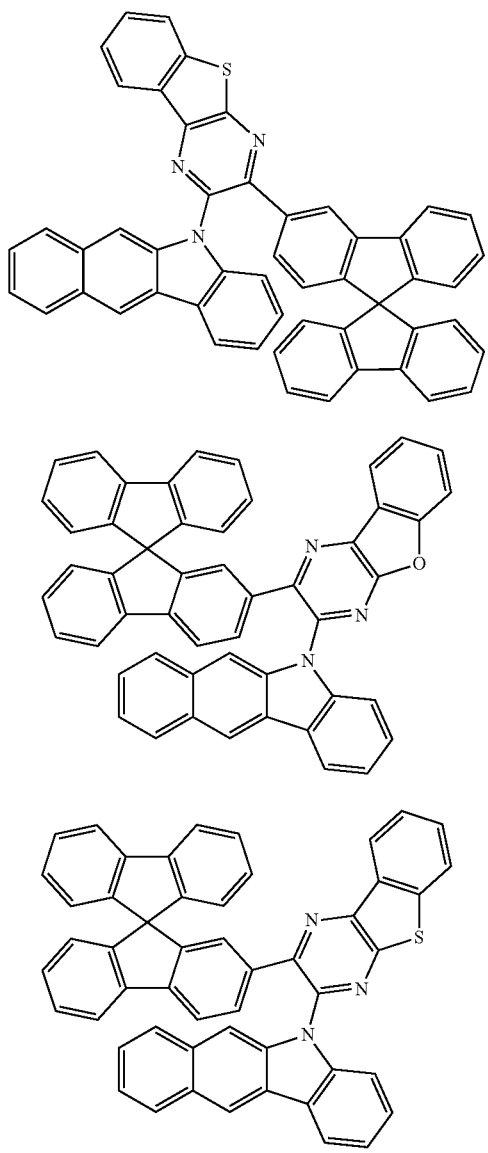
584
-continued
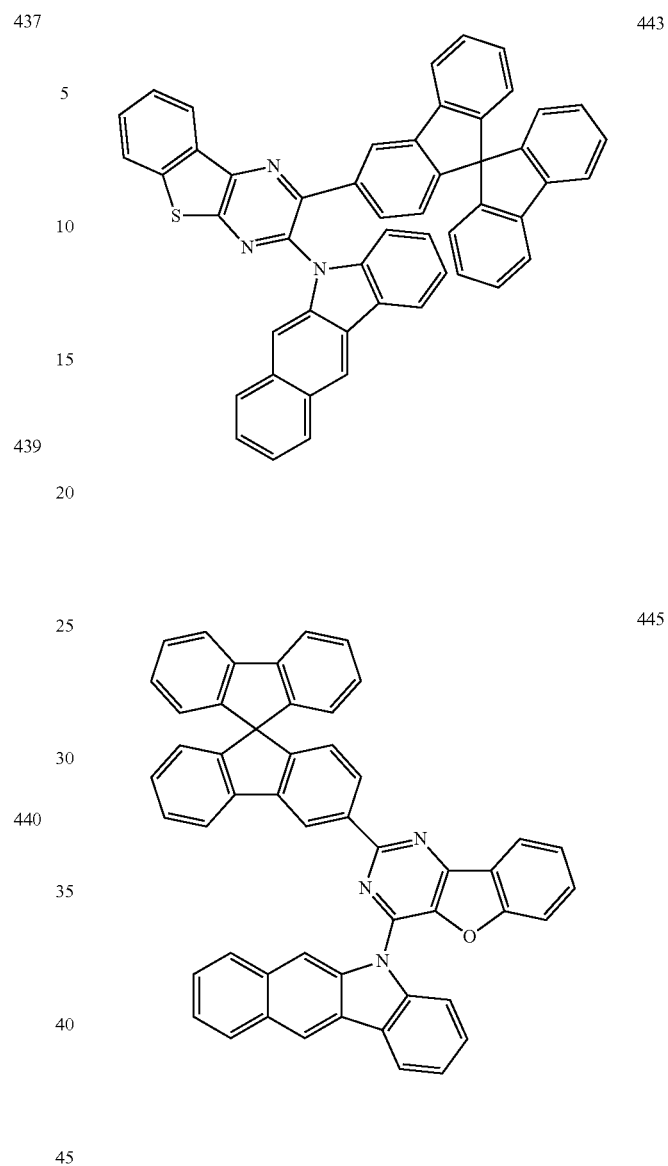
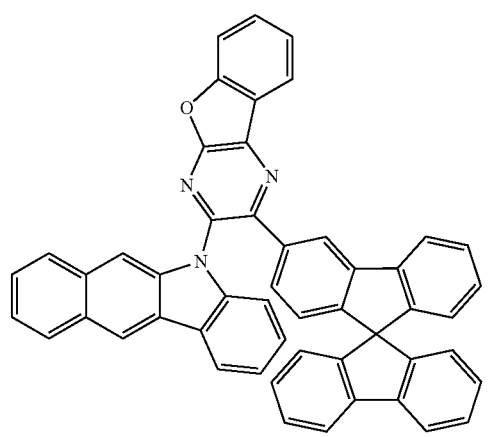
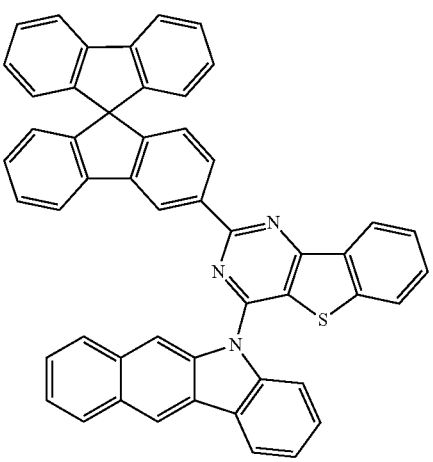

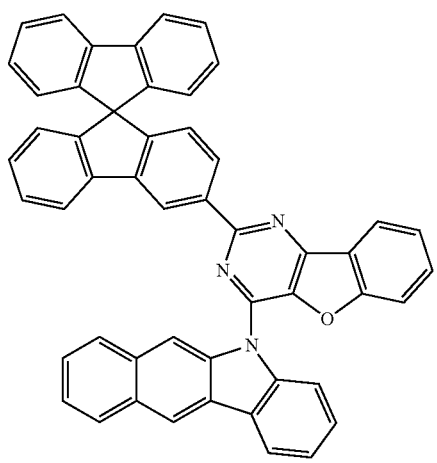
448
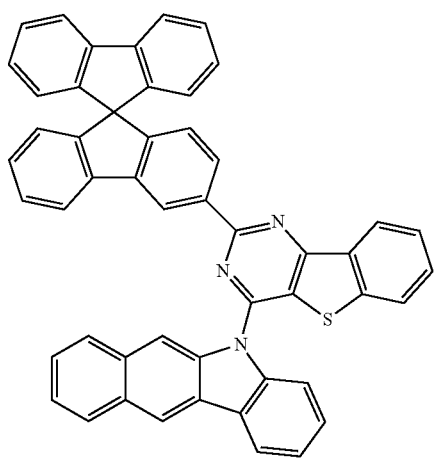
449
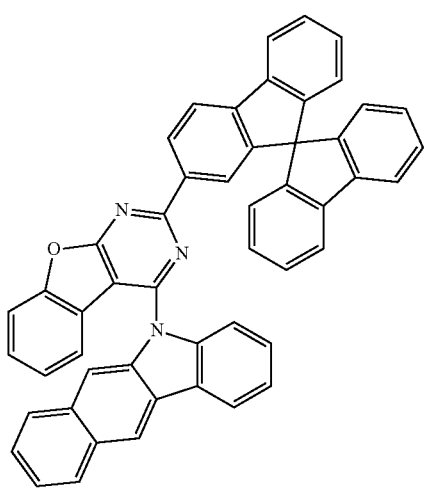
451
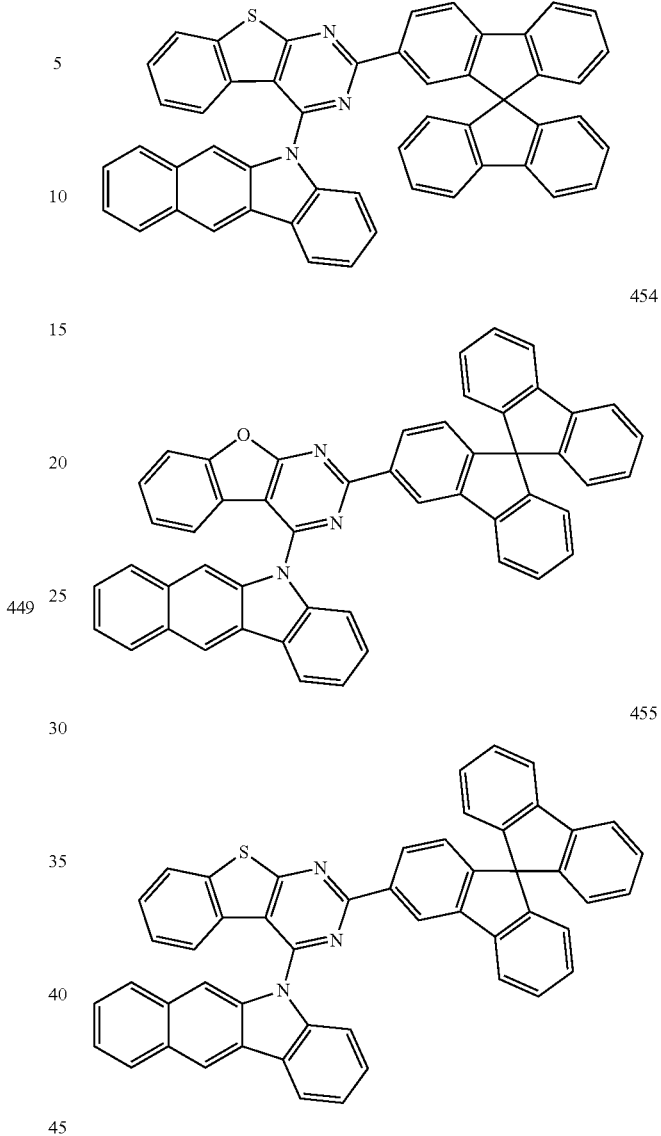

587
-continued
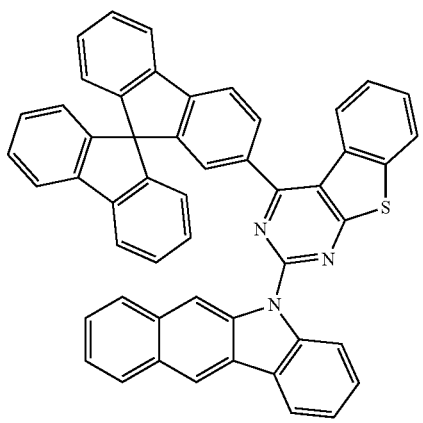
458
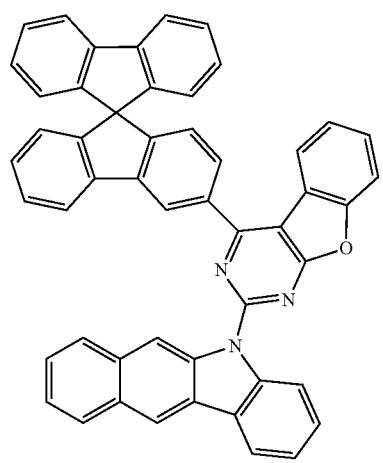
460
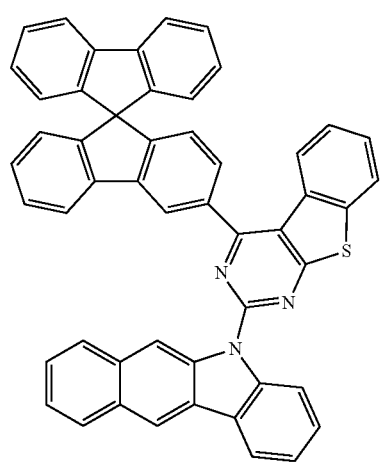
461
588
-continued
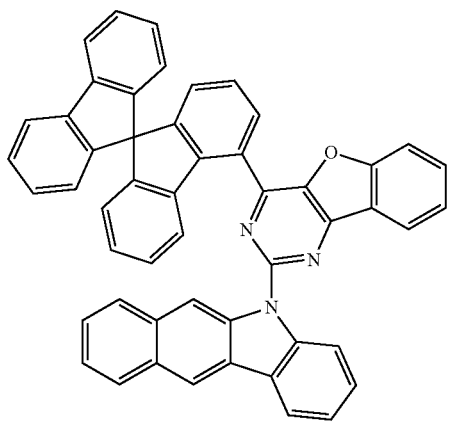
463
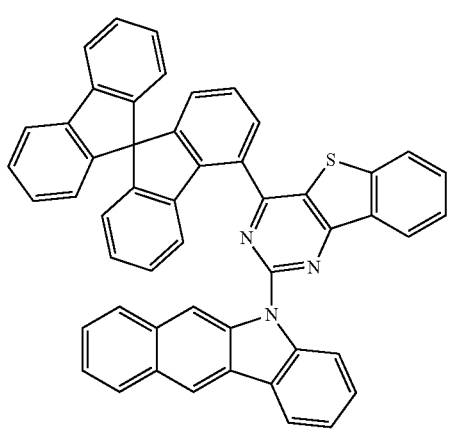
464
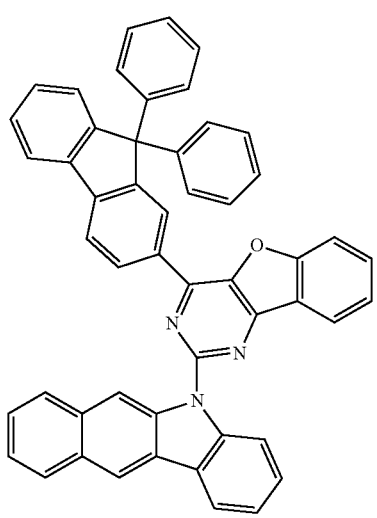
466

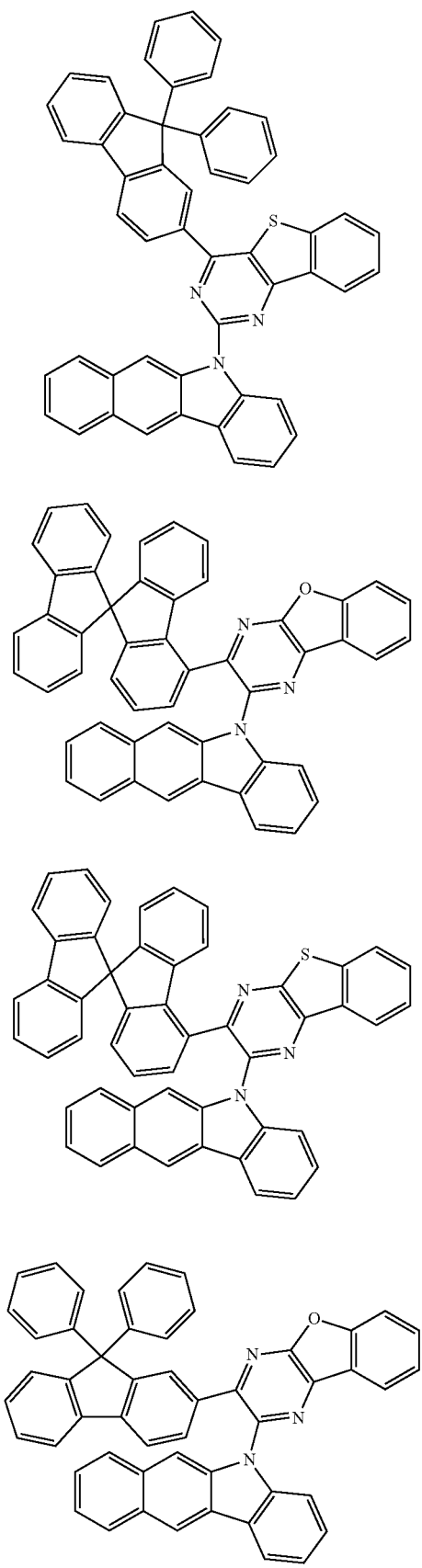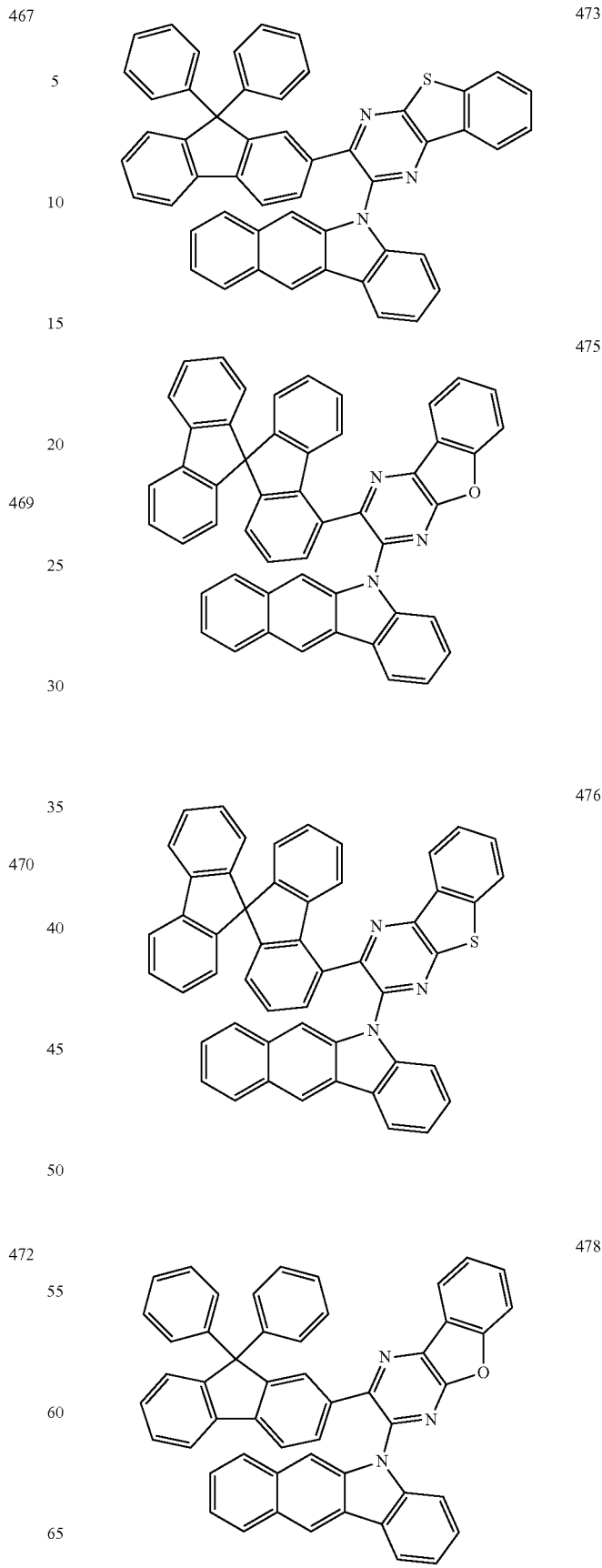

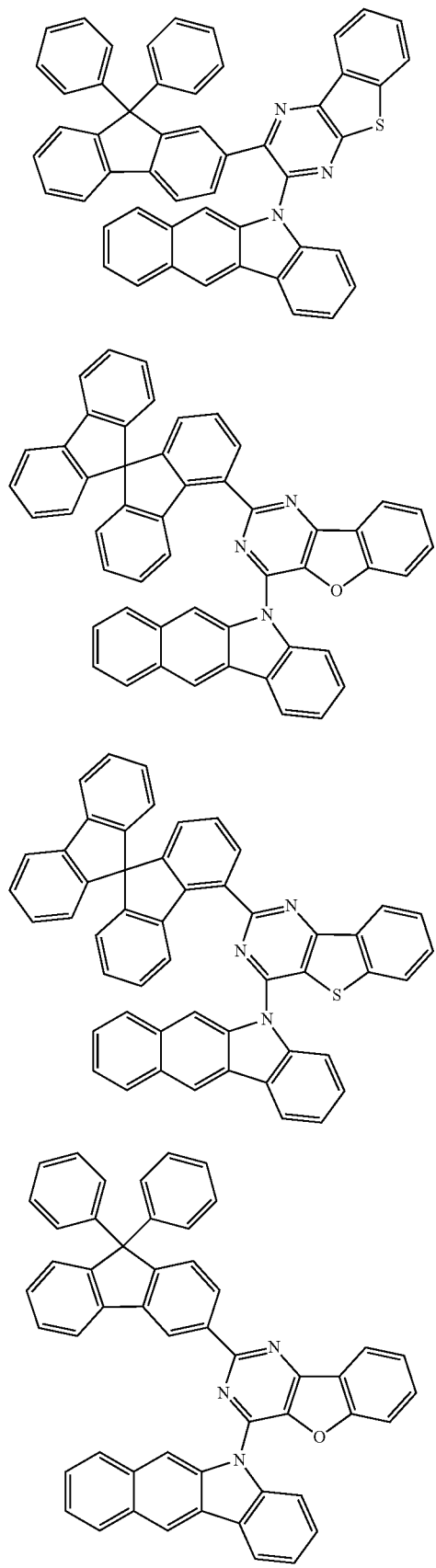
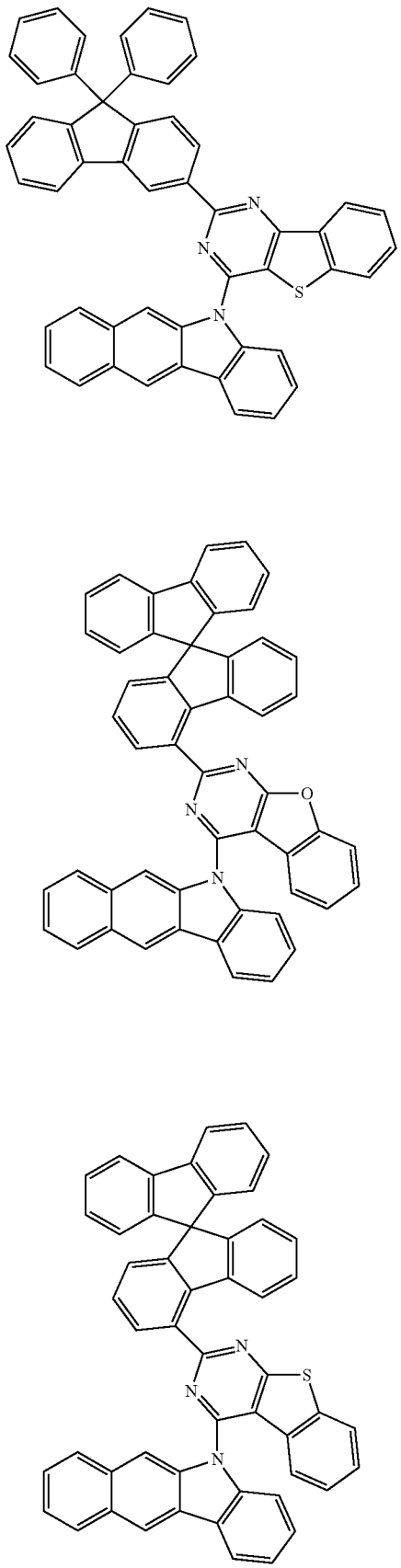

593
-continued
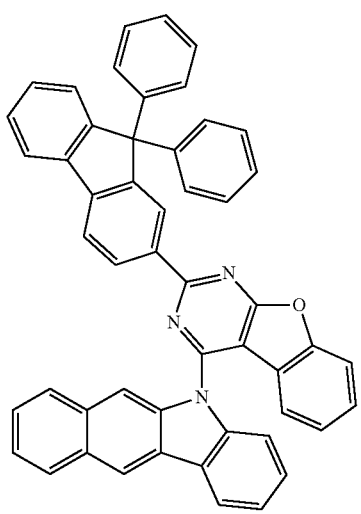
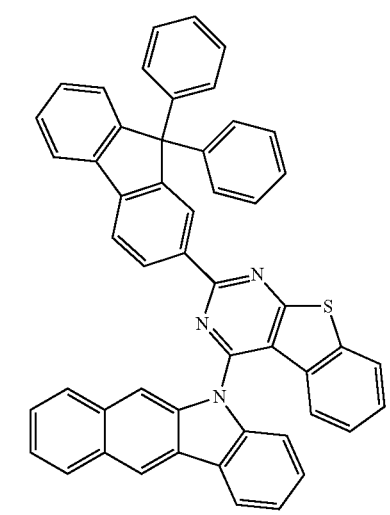
594
-continued
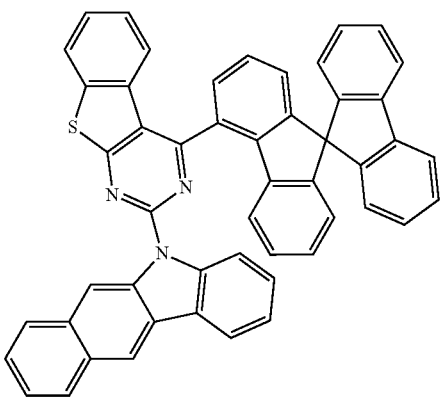
490
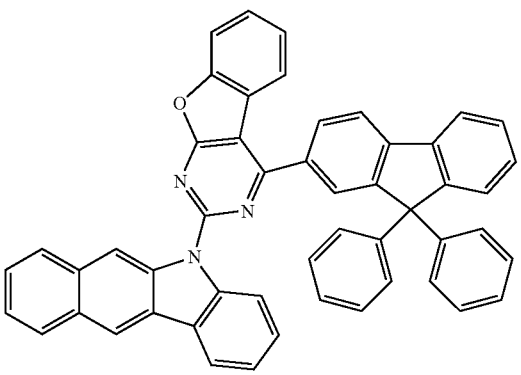
496
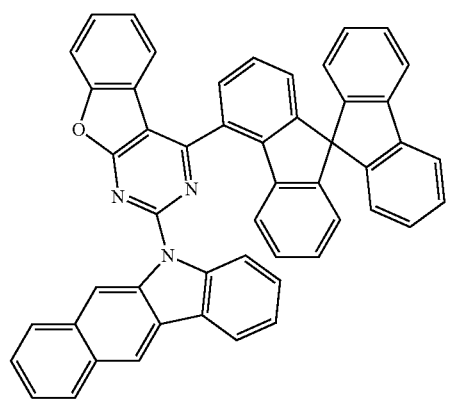
493
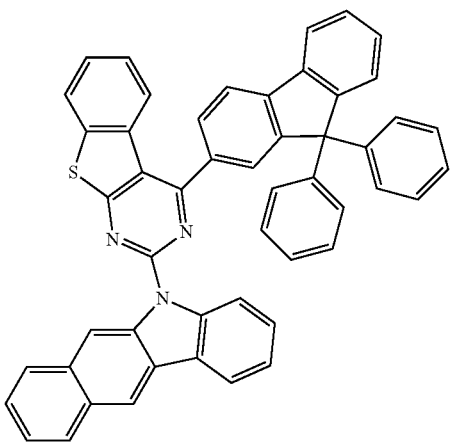
497

499 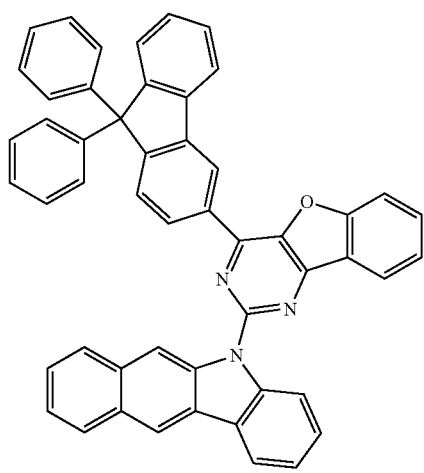
500 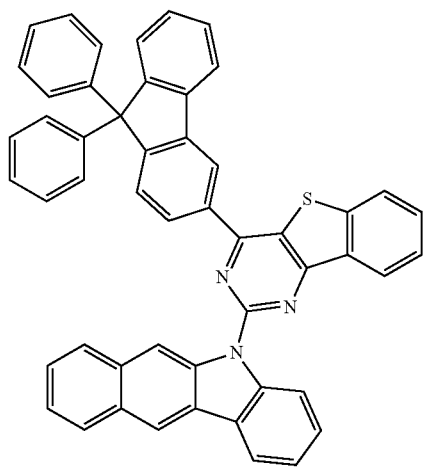
502 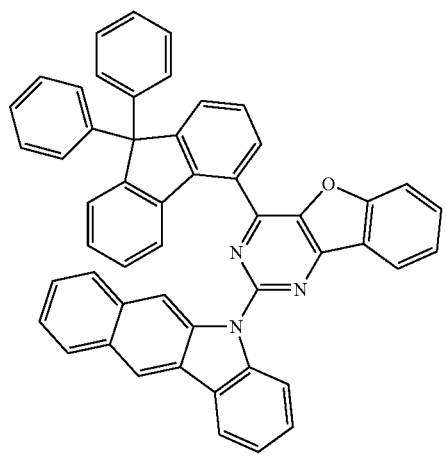
503 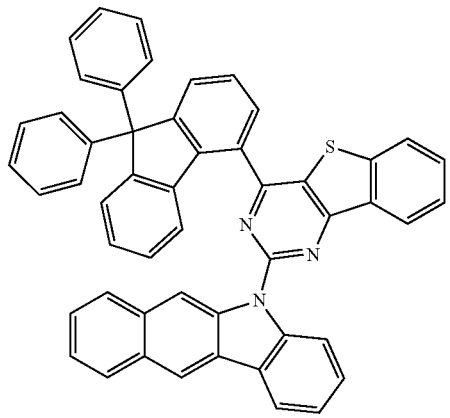
505 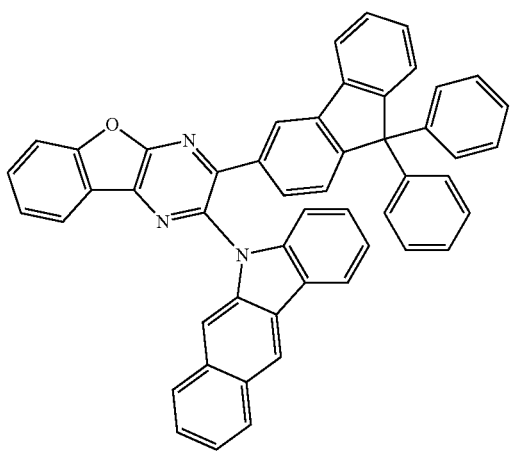
506 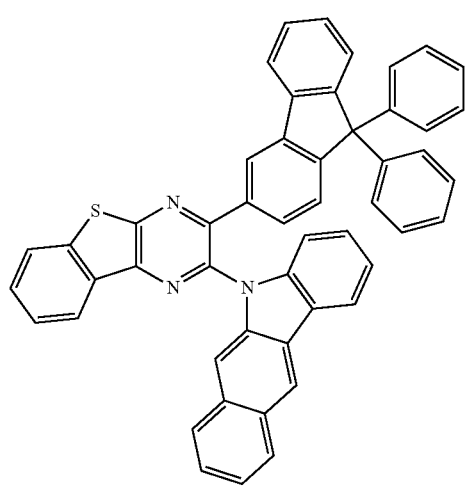

508
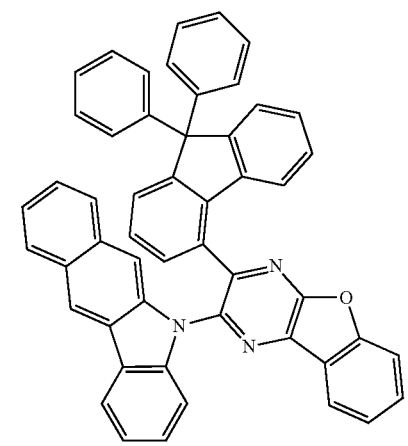
509
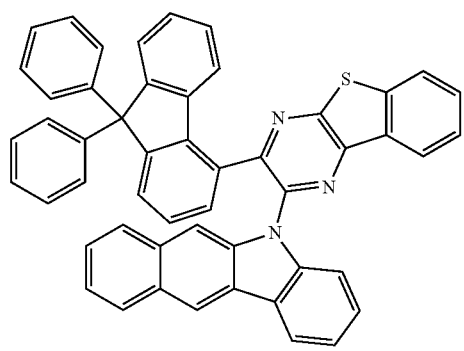
511
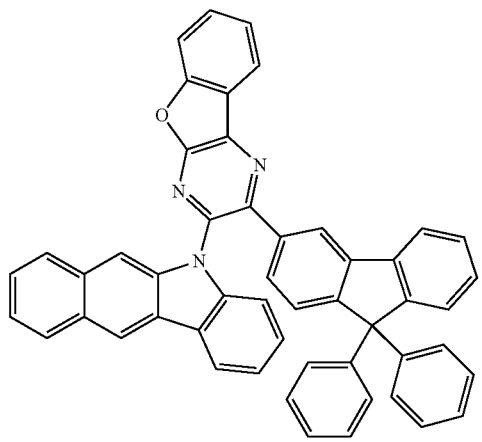
512
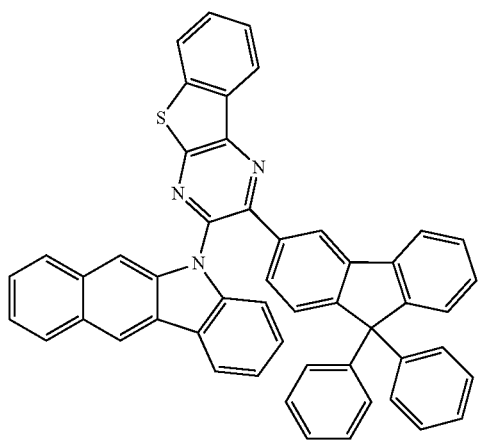
514
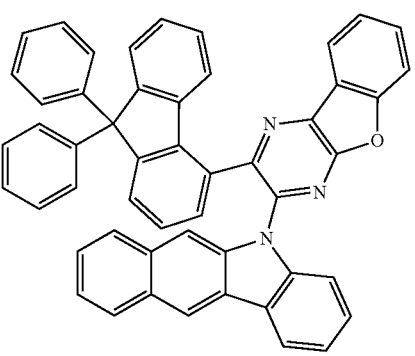
515
517
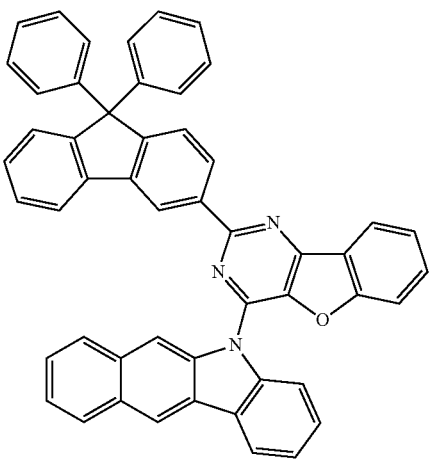

599
-continued
518
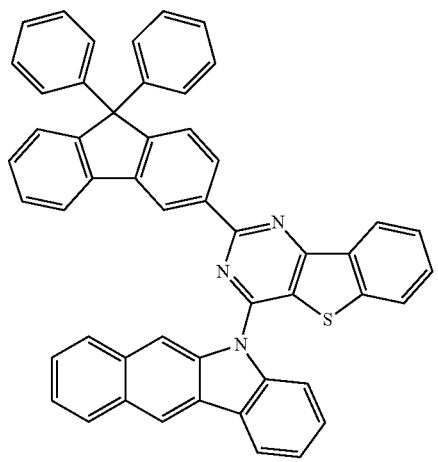
520
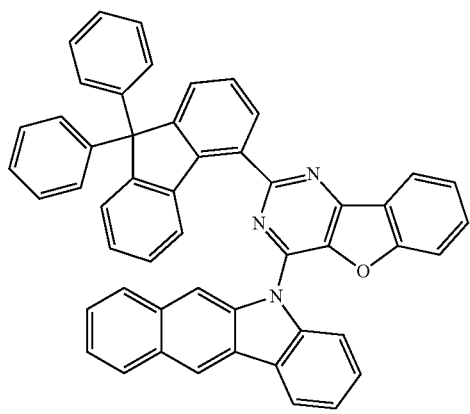
521
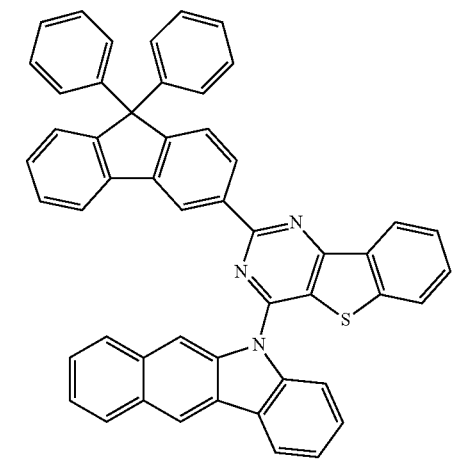
600
-continued
523
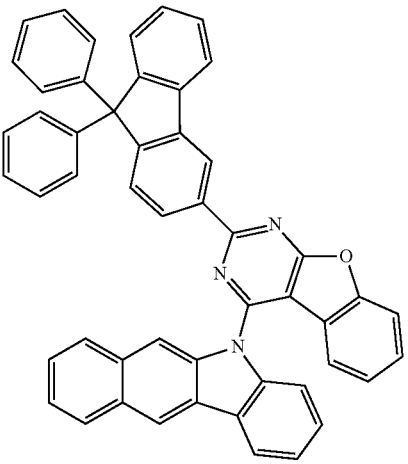
524
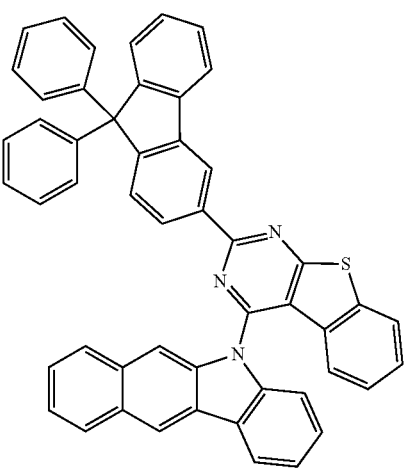
526
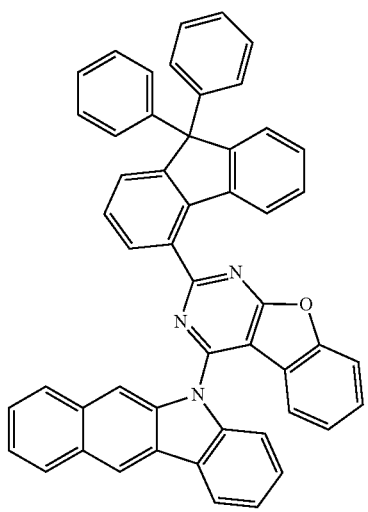

527
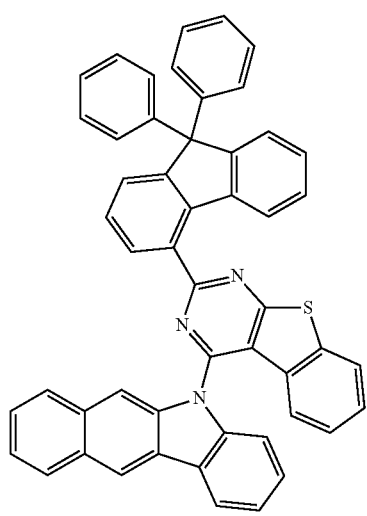
529
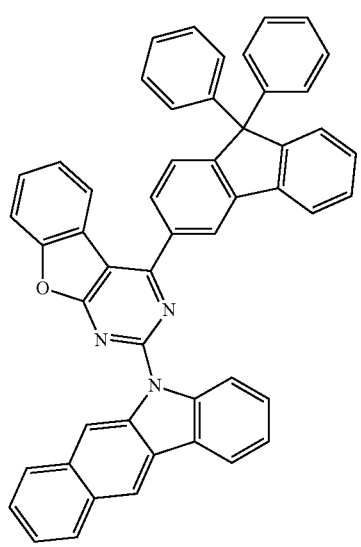
530
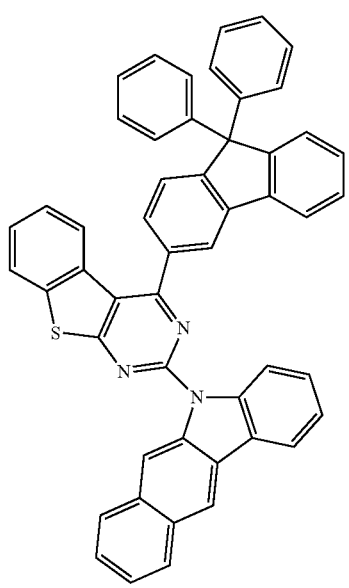
532
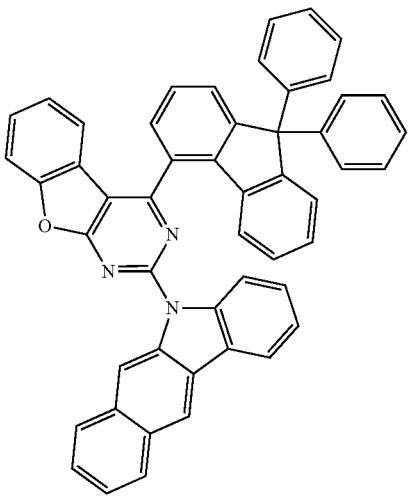
533
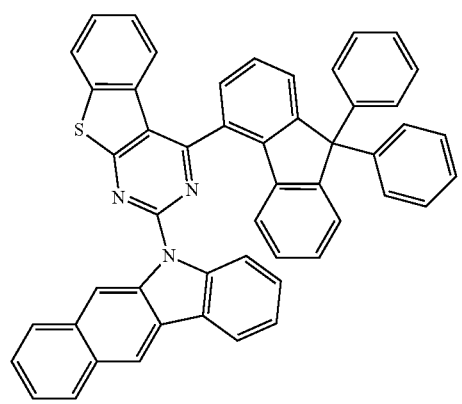
535
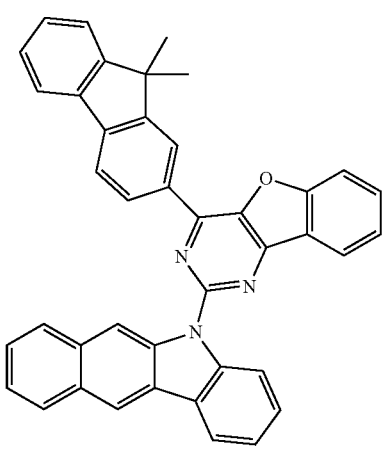

536
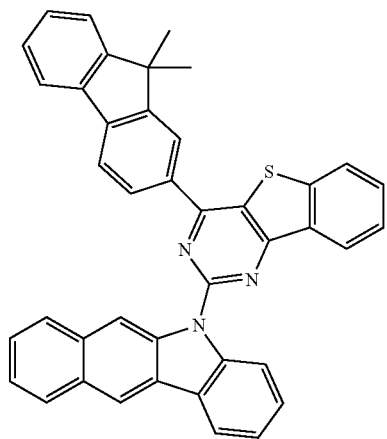
538
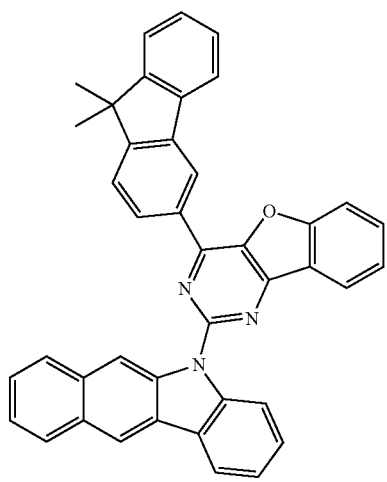
539
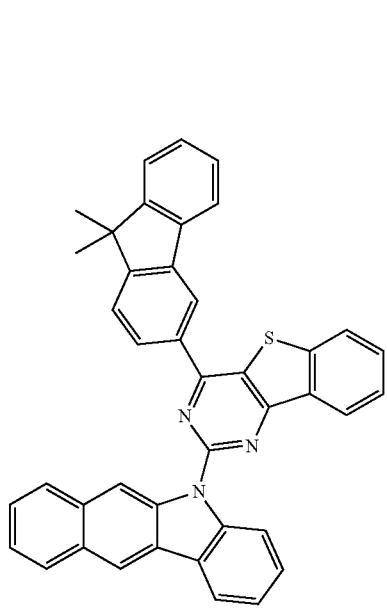
541
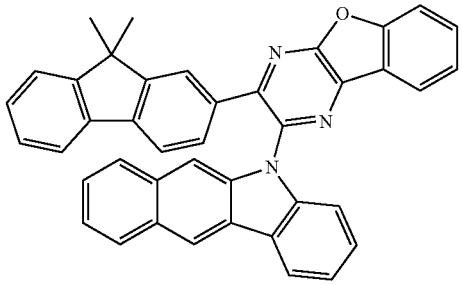
542
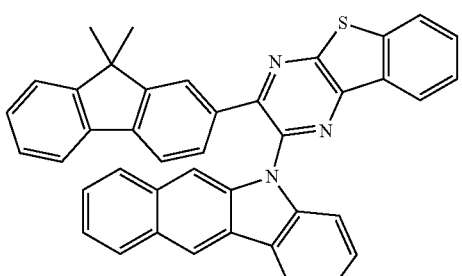
544
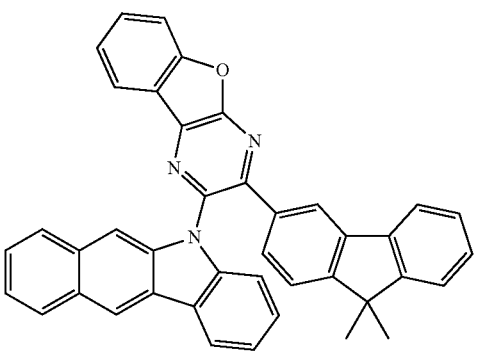
545
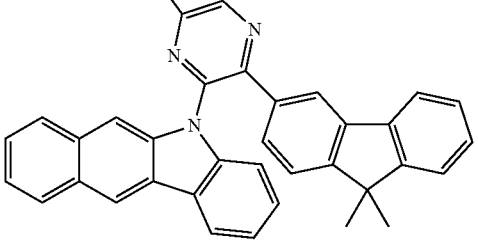
547
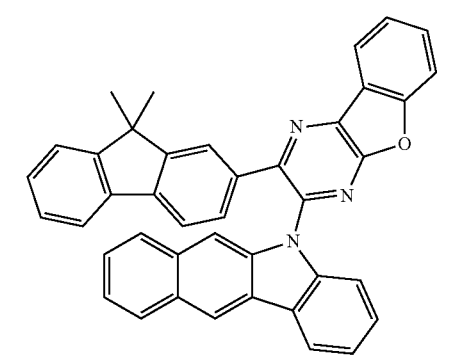

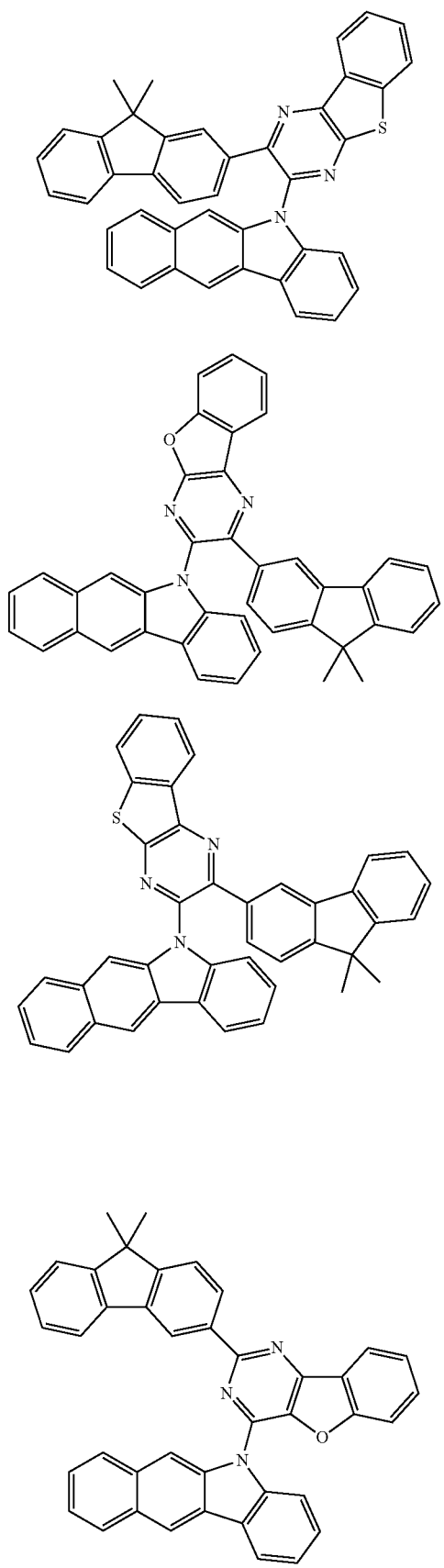
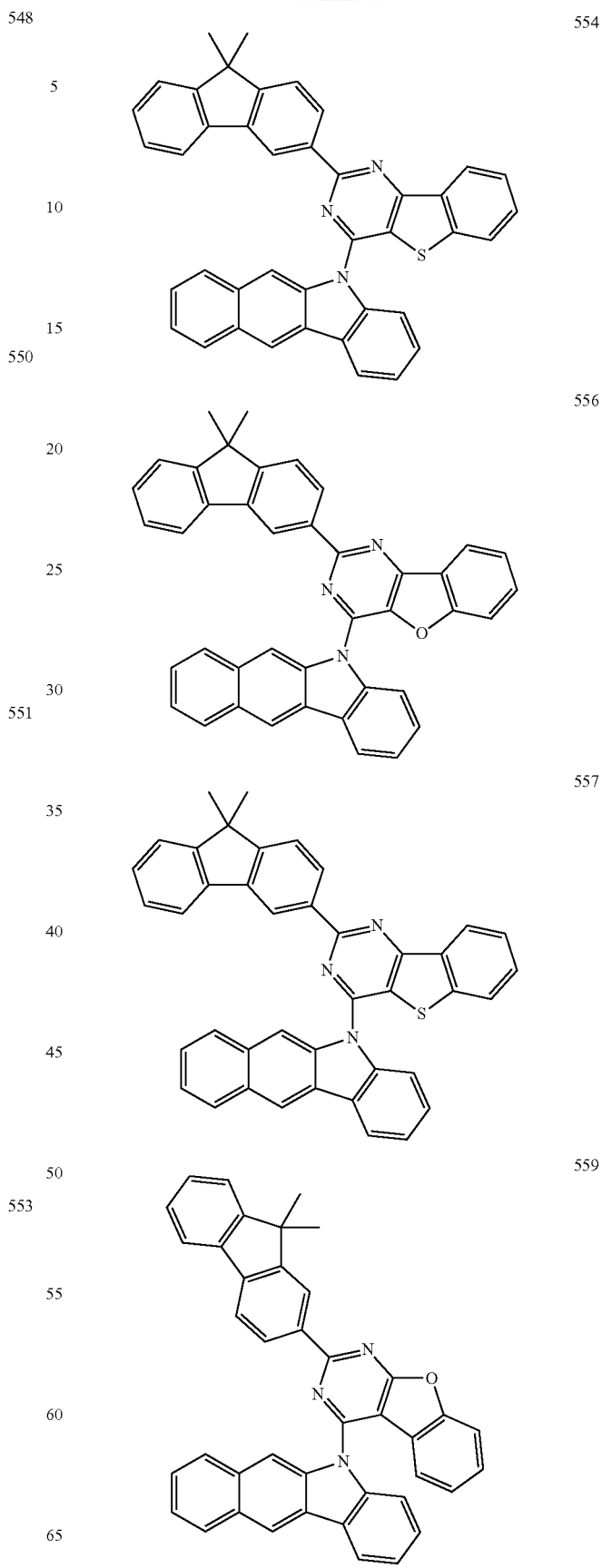

607
-continued
560
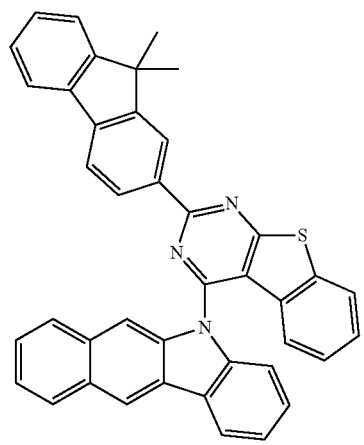
562
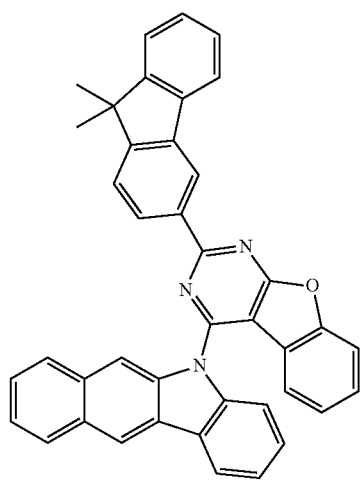
563
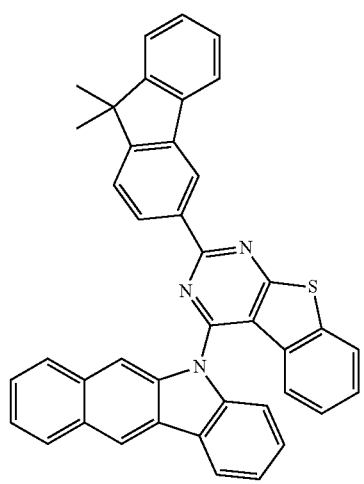
608
-continued
565
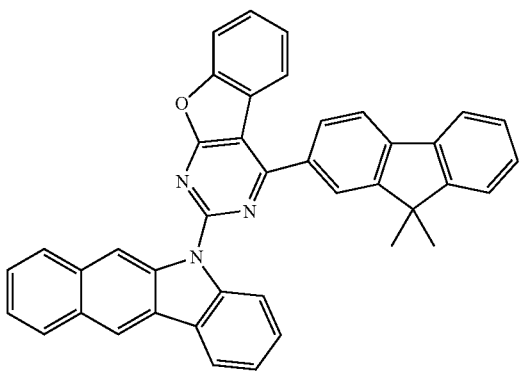
566
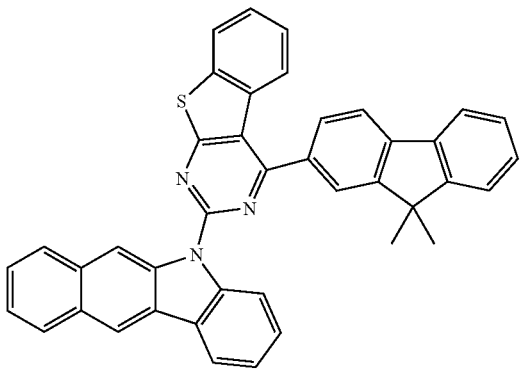
568
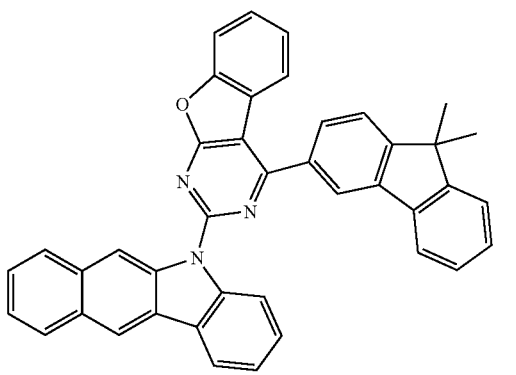
569
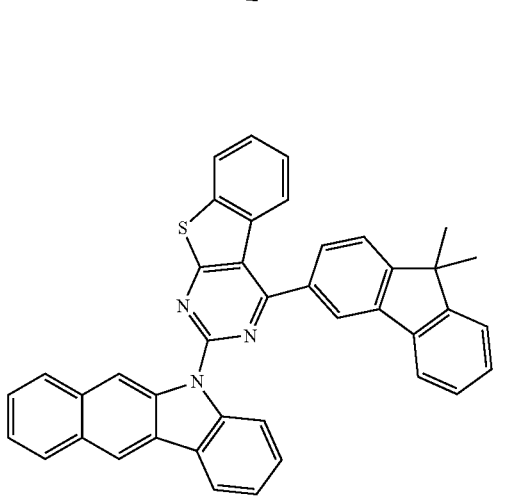

609
-continued
571
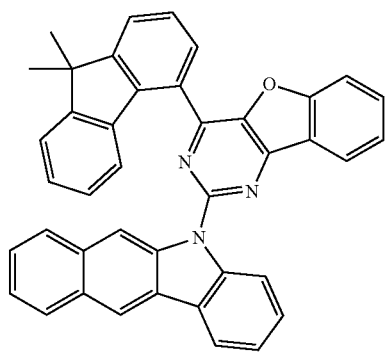
572
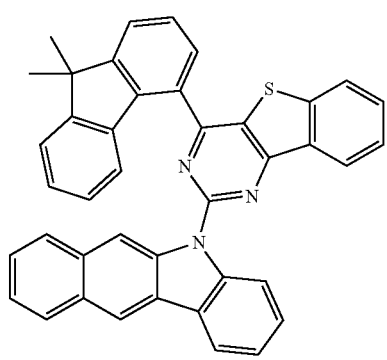
574
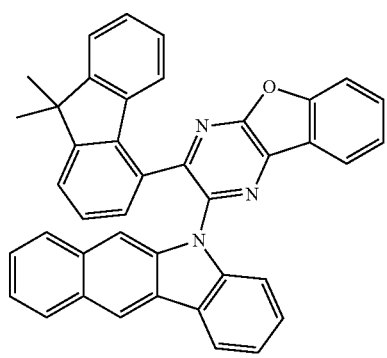
575
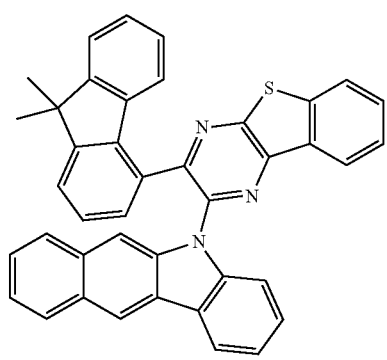
610
-continued
577
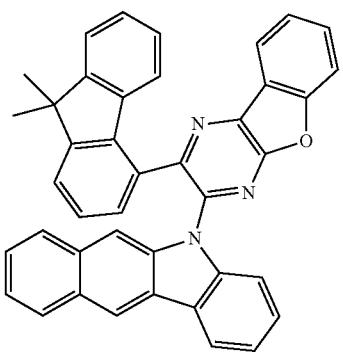
578
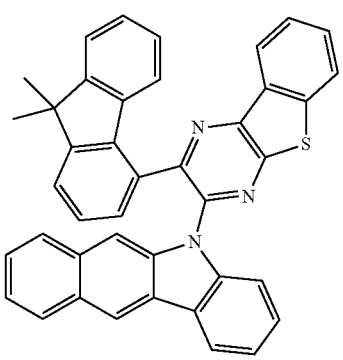
580
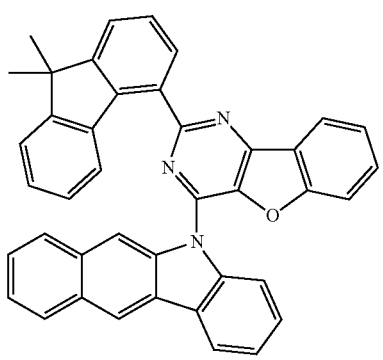
581
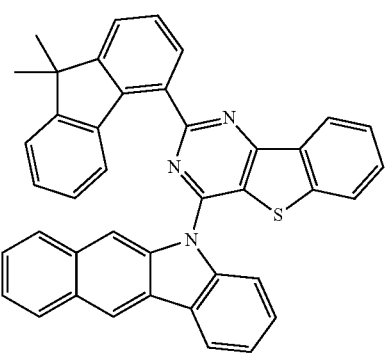

611
-continued
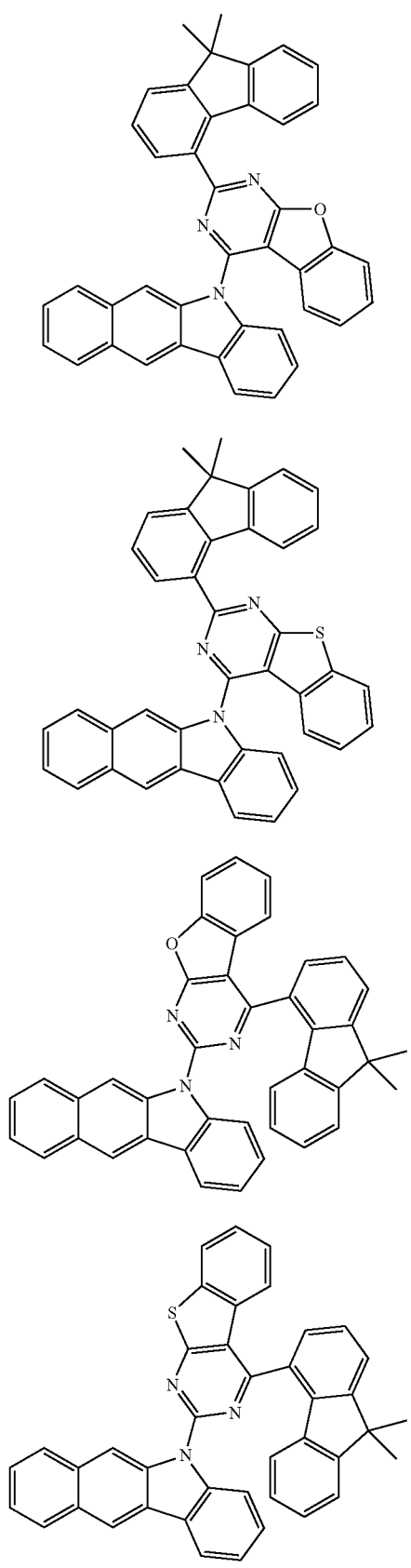
583
584
586
587
612
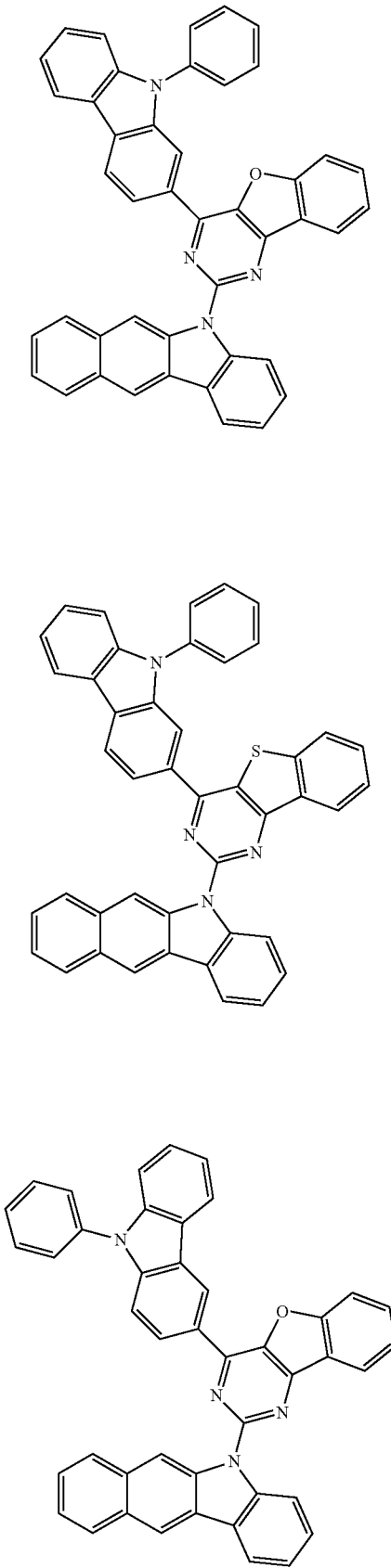
589
590
592

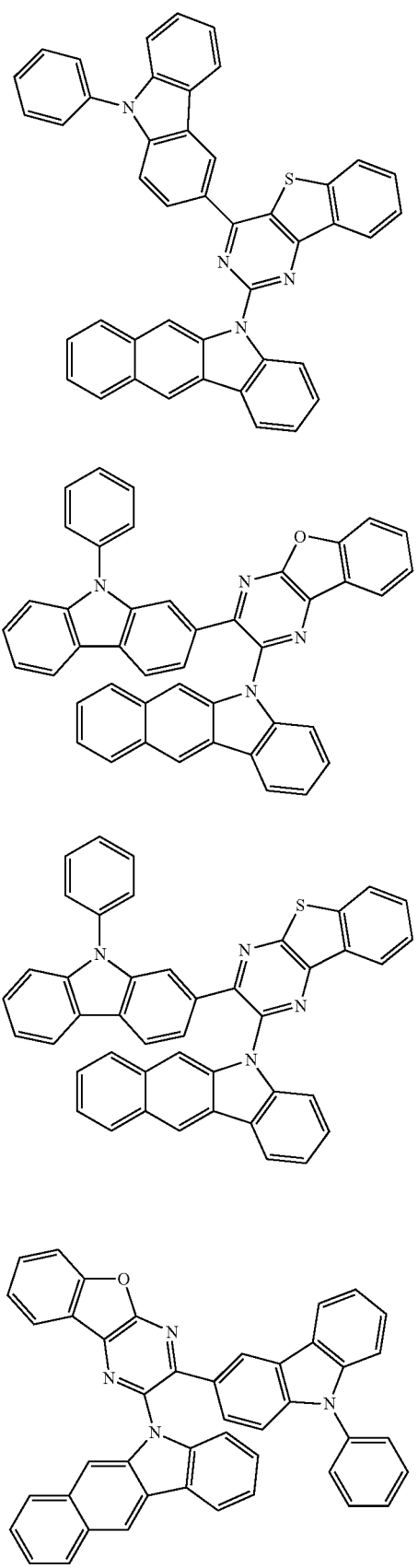
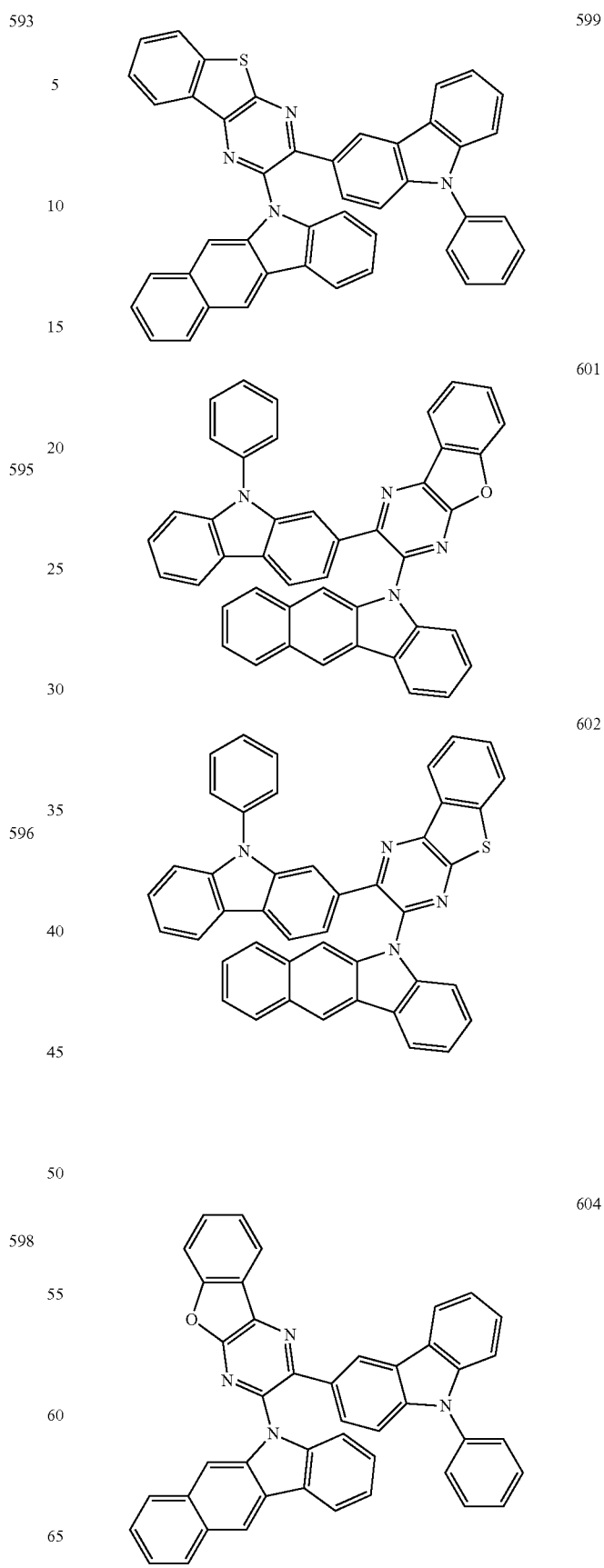

615
-continued
605
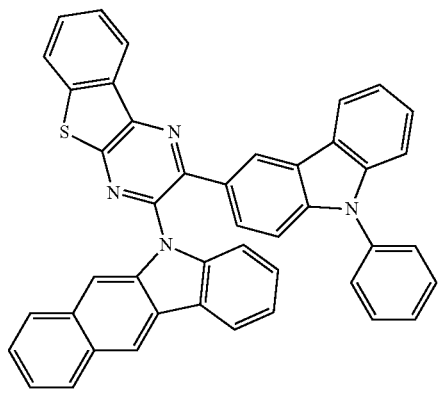
607
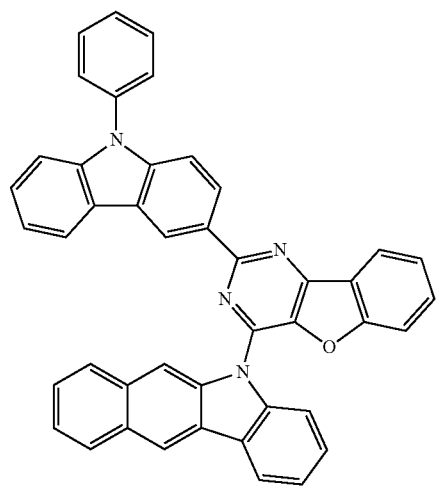
608
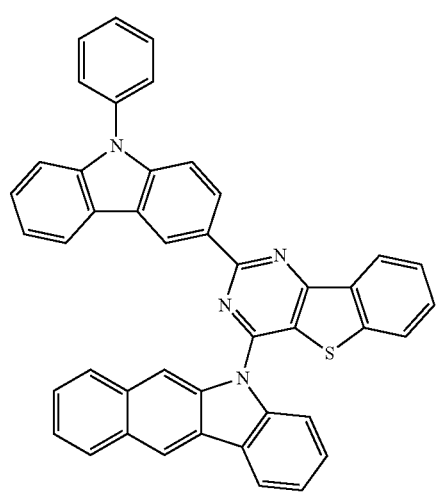
616
-continued
610
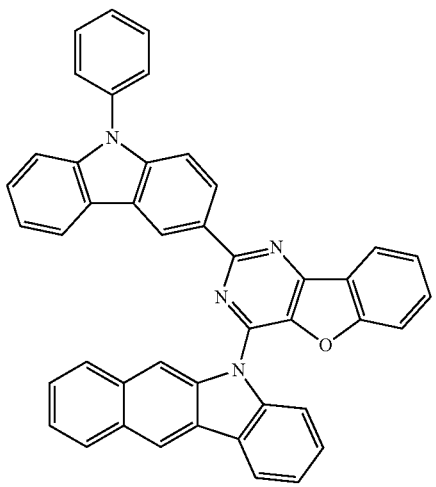
611
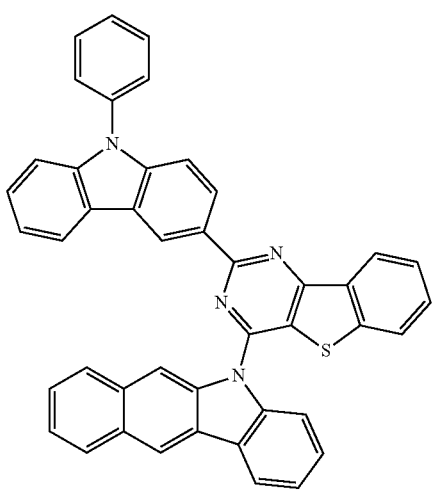
613
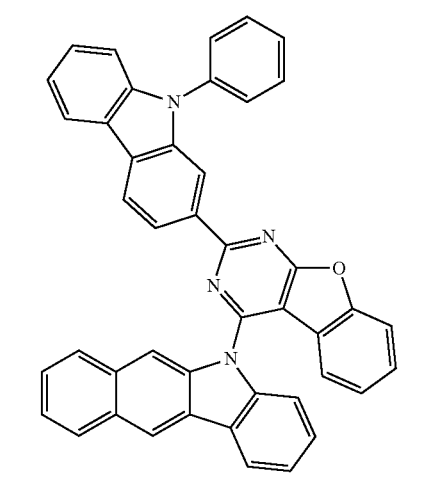

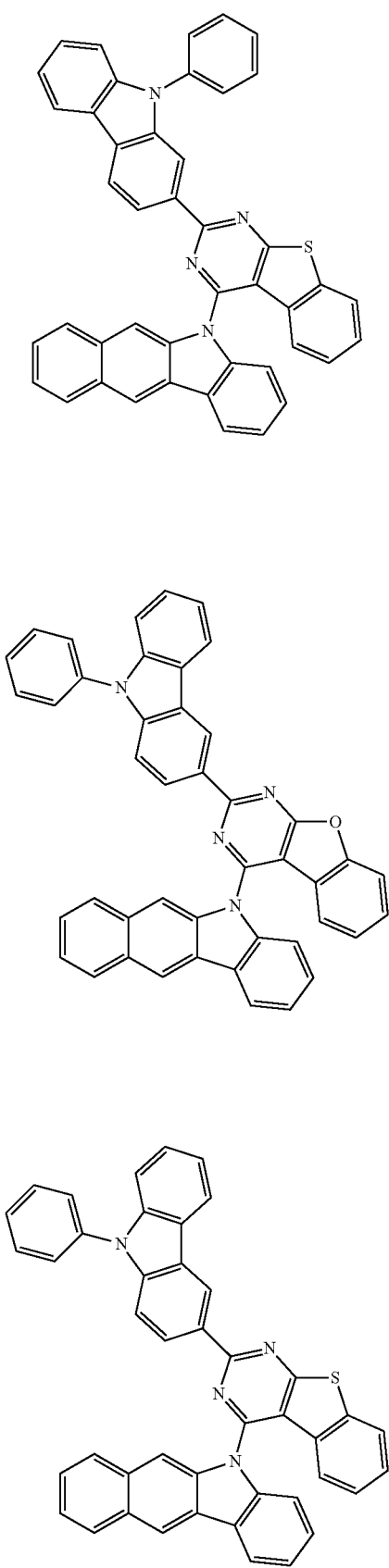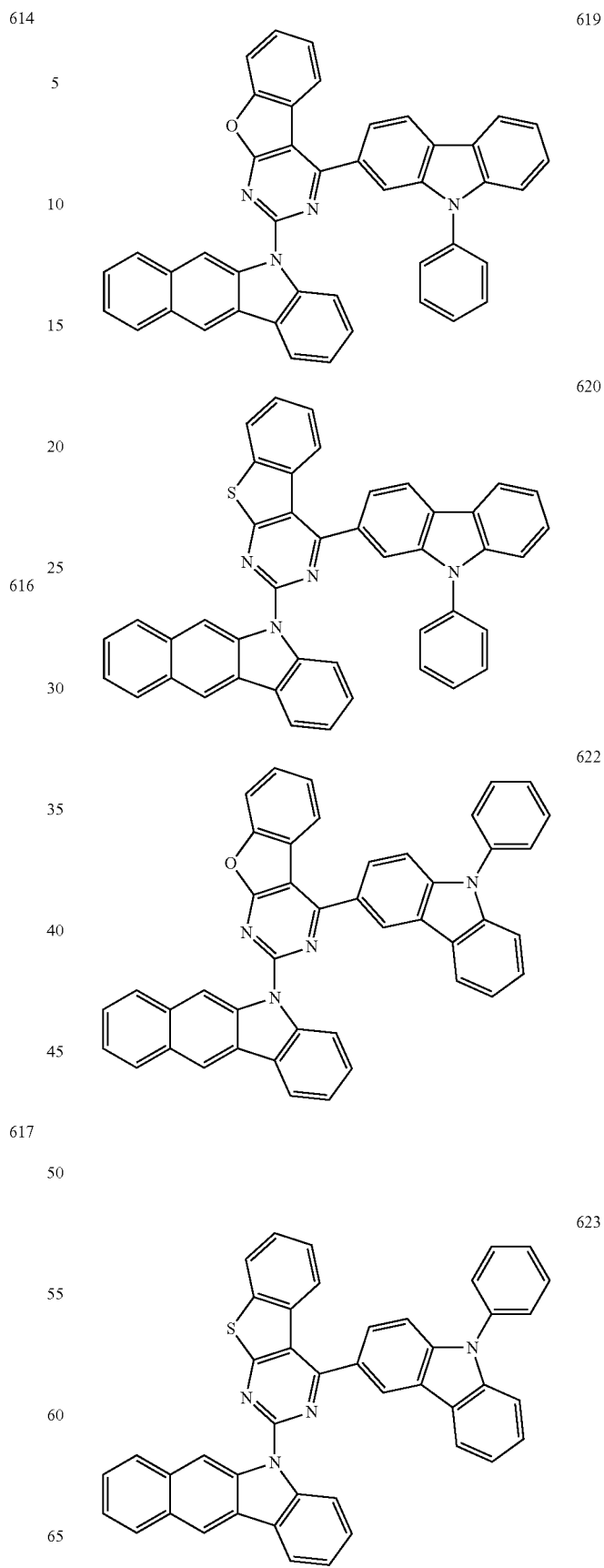

625 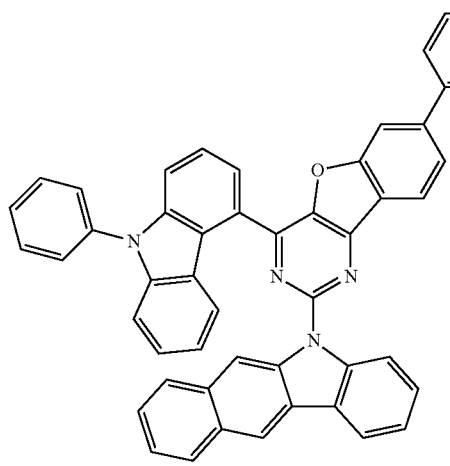
626 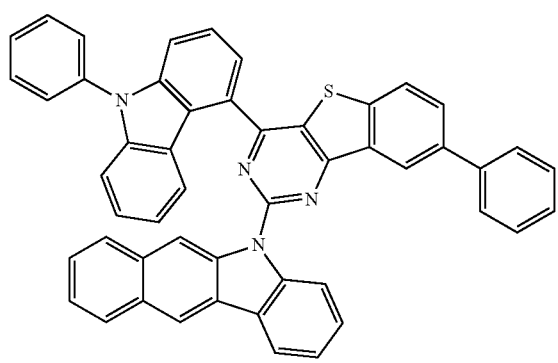
628 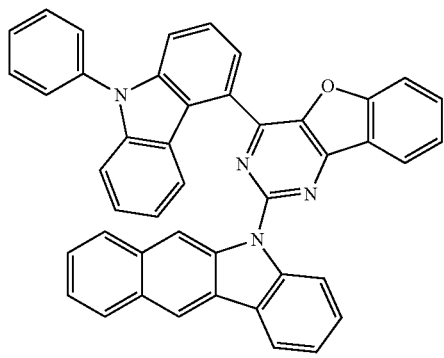
629 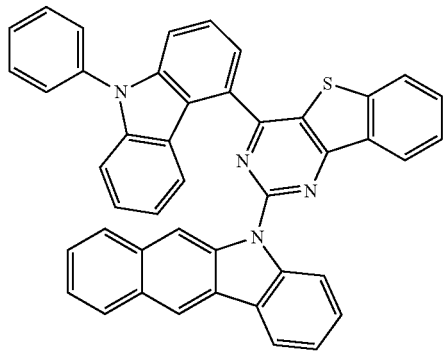
631 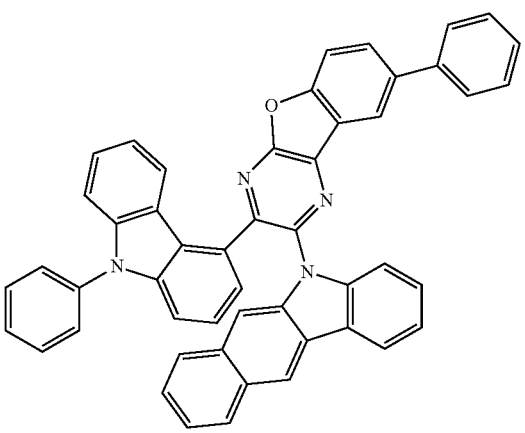
632 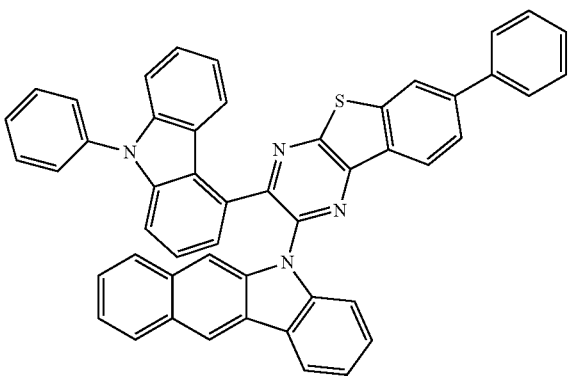
634 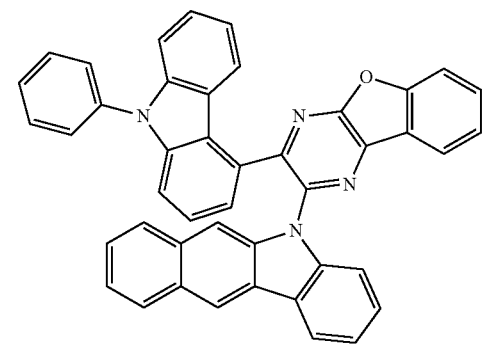
635 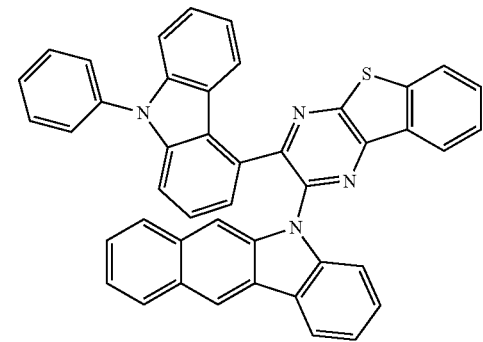

637
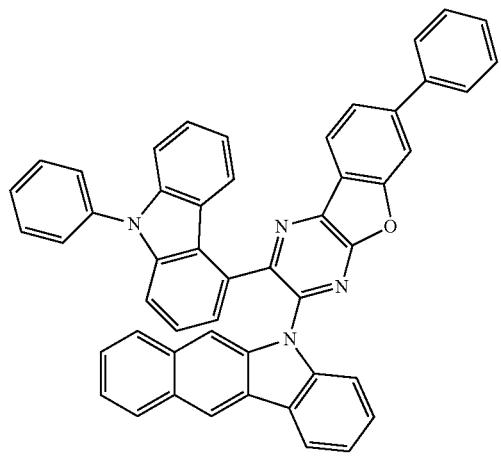
638
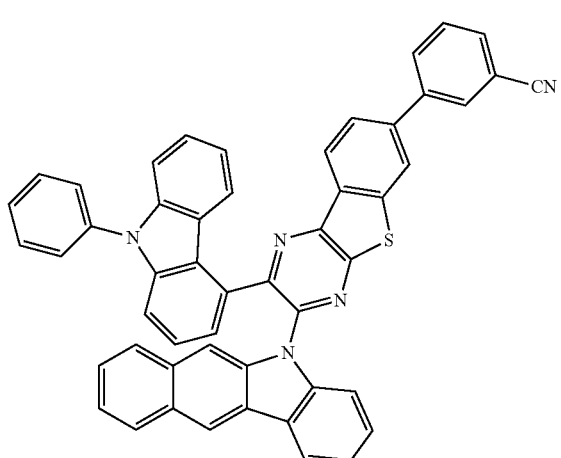
640
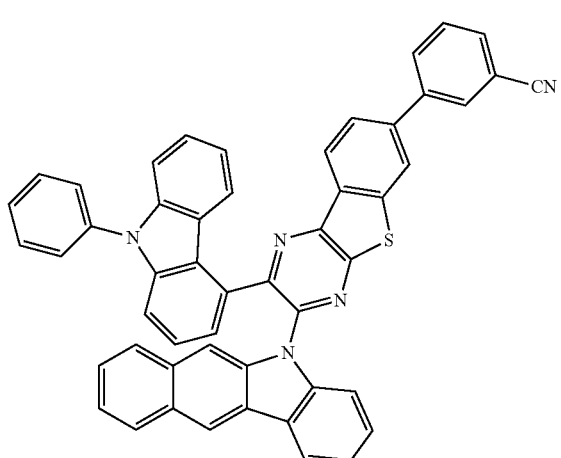
641
643
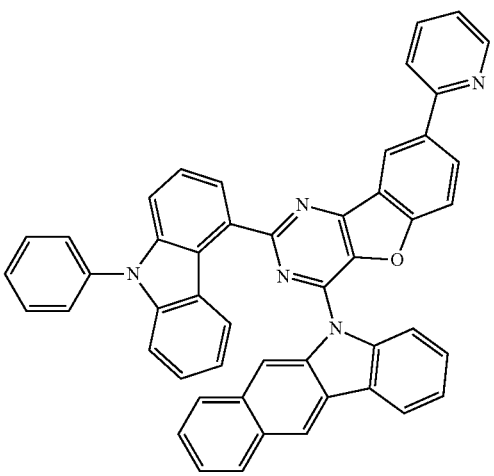
644
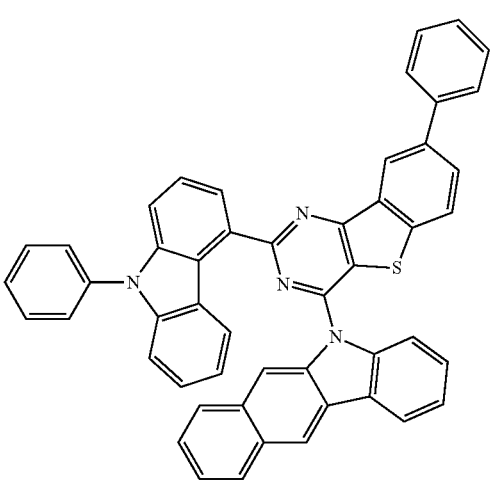
646
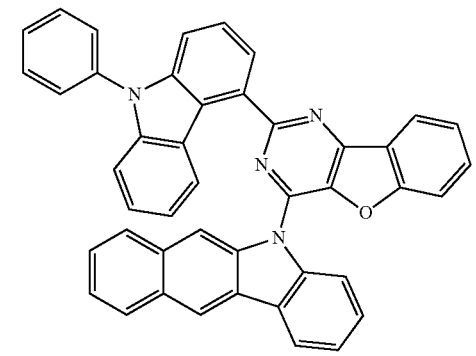
647
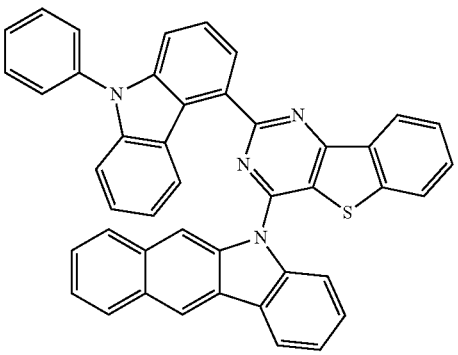

-continued
649
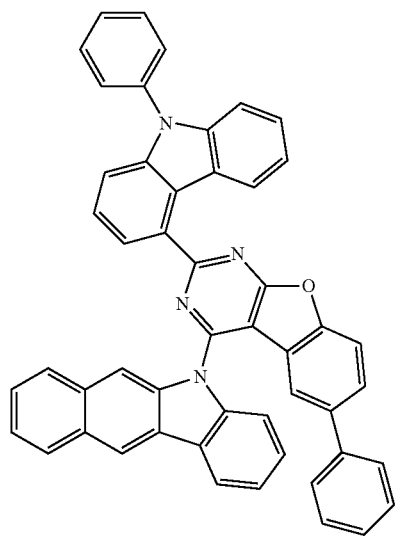
650
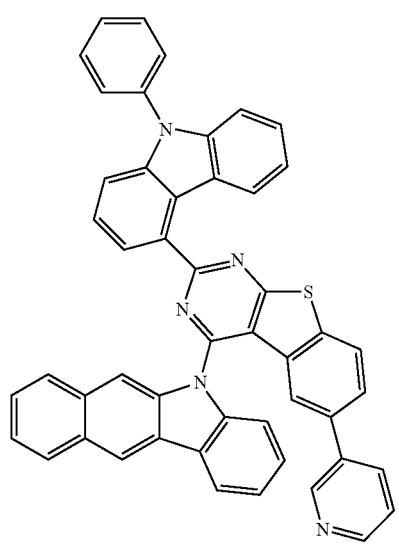
652
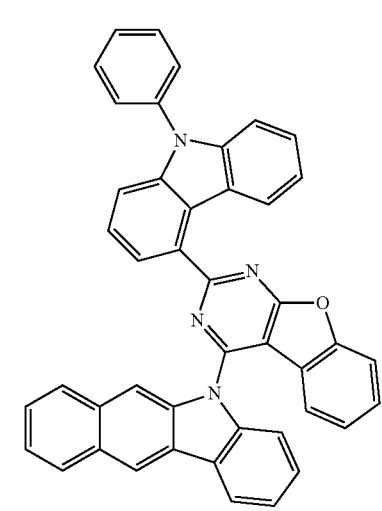
-continued
653
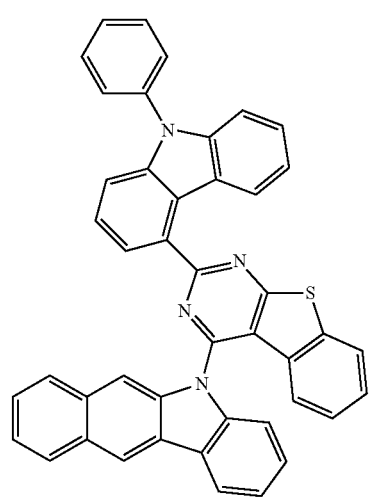
655
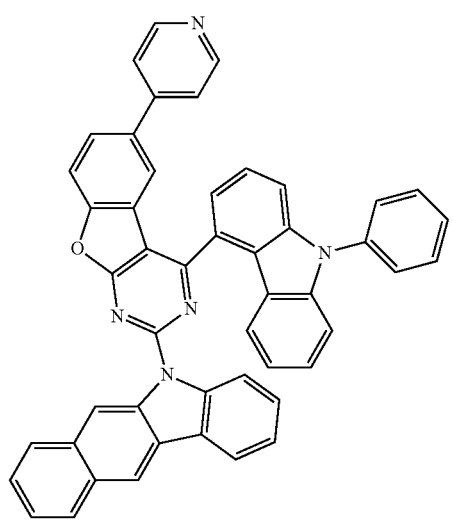
656
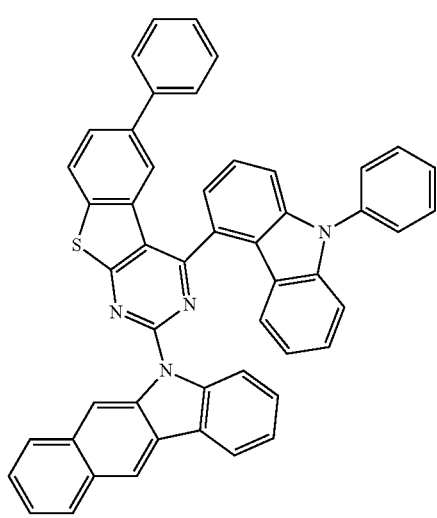

-continued
658
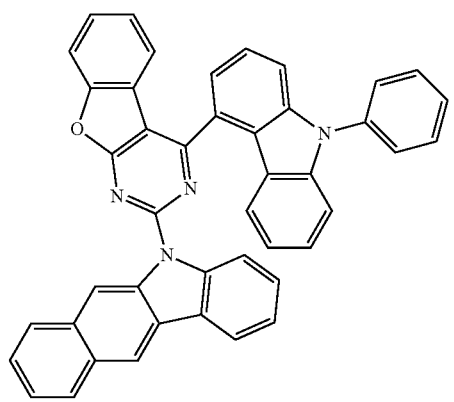
659
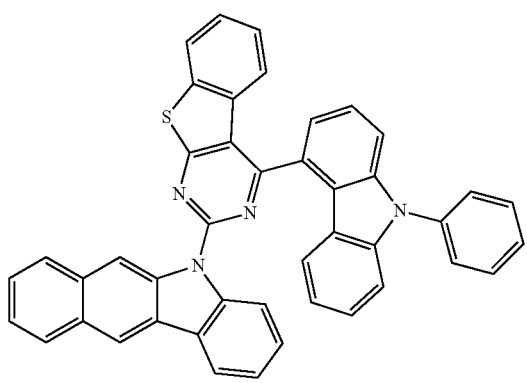
661
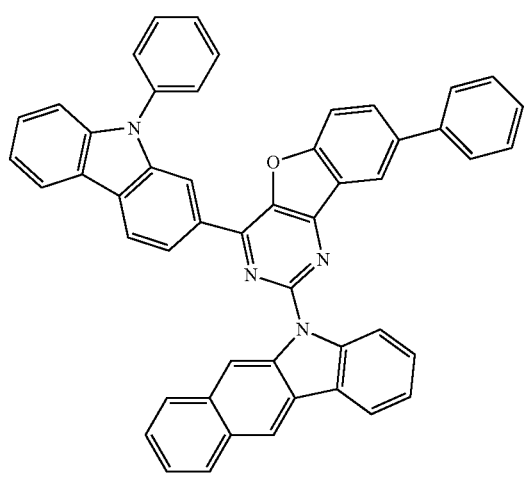
-continued
662
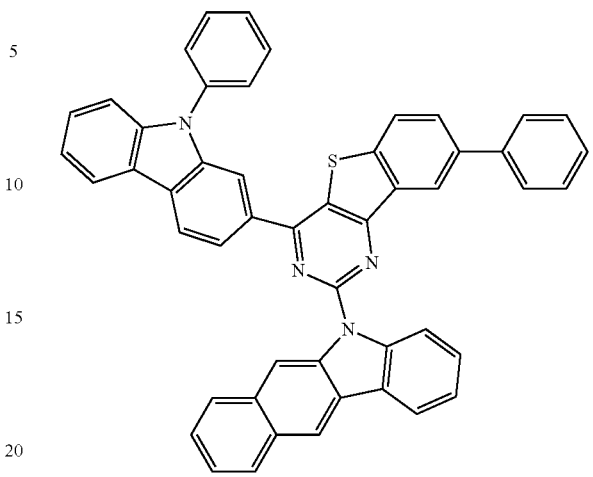
664
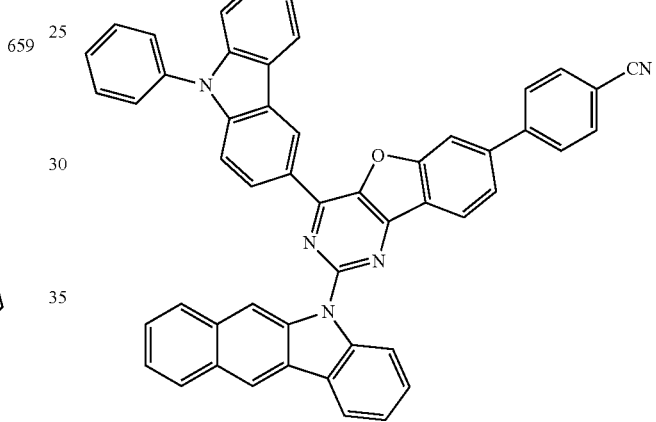
665
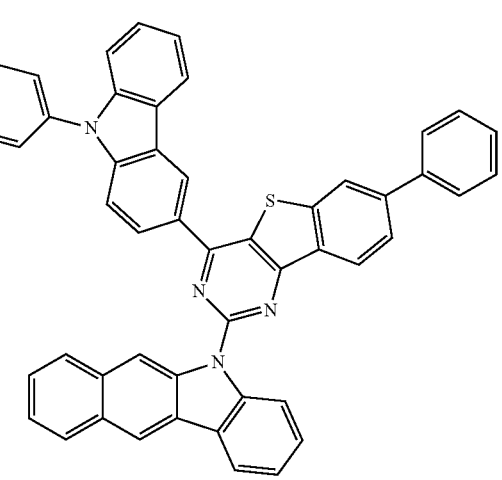

-continued
667
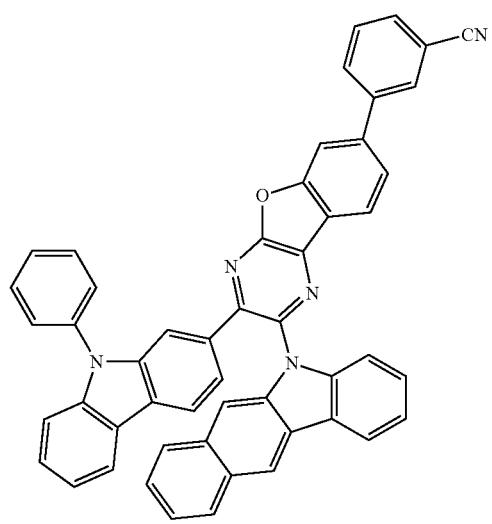
668
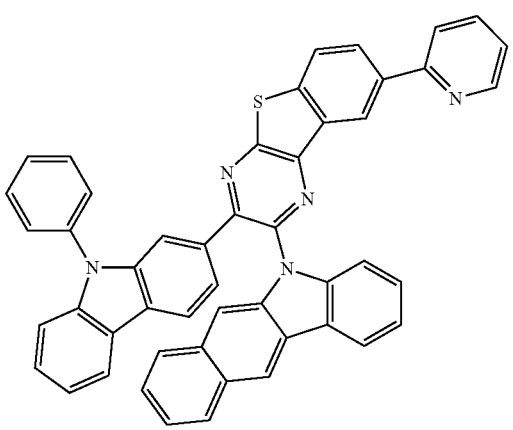
670
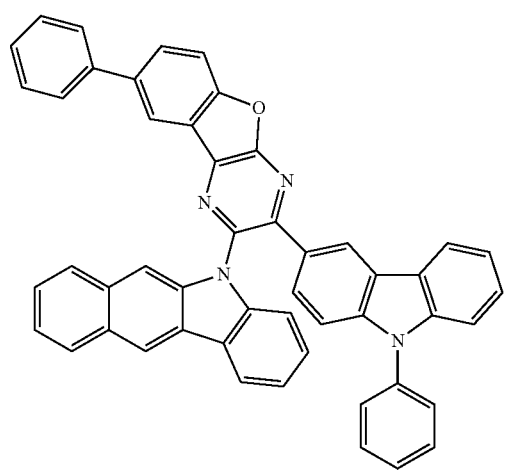
-continued
671
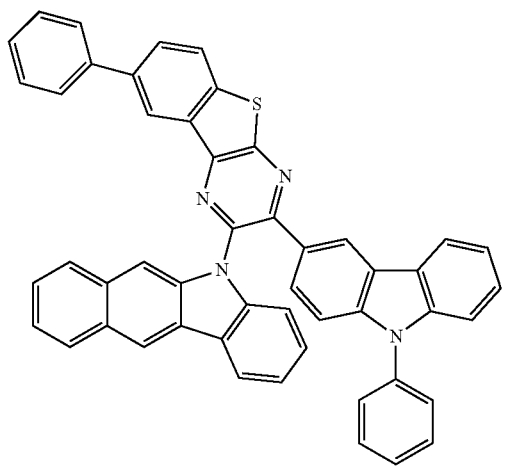
673
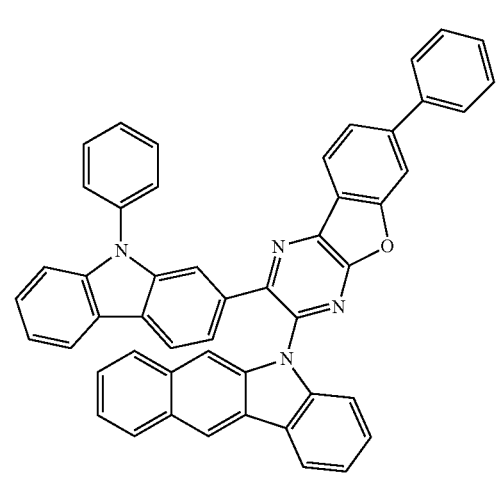
674
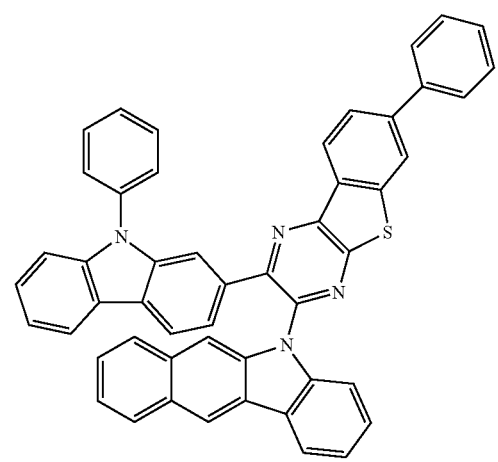

629
-continued
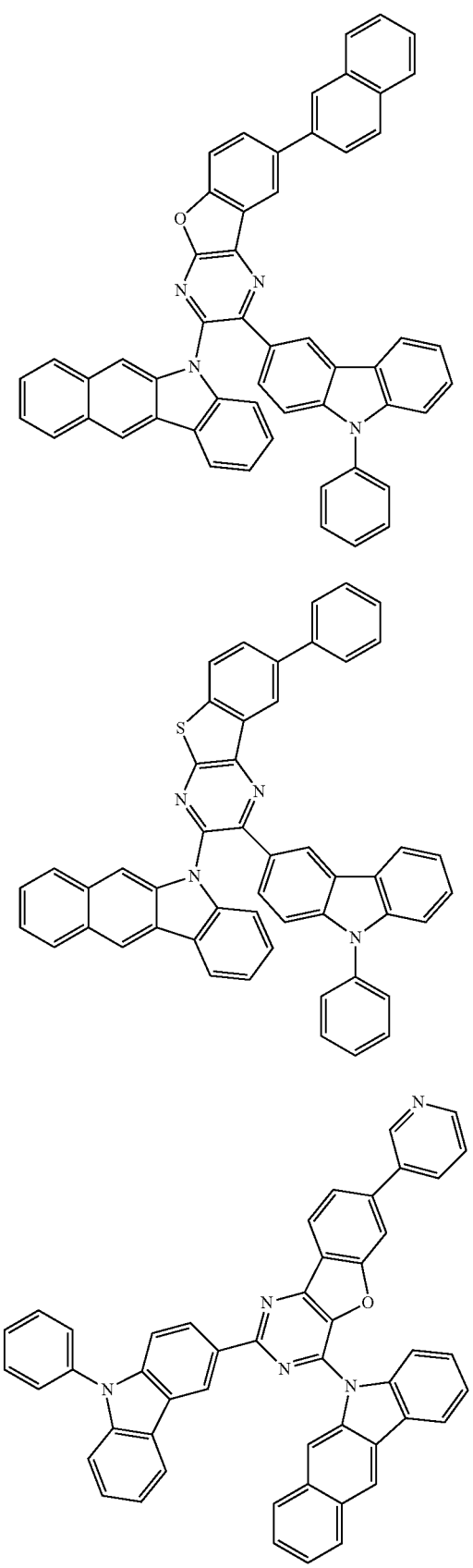
630
-continued
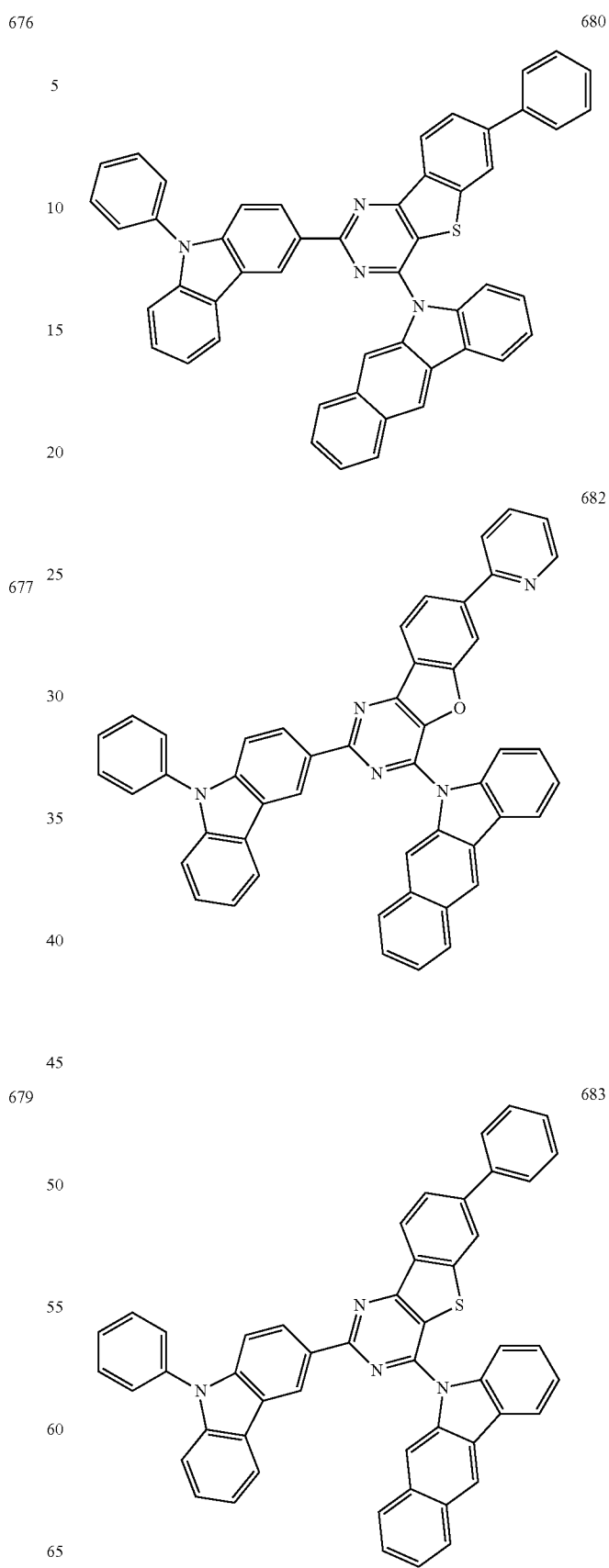

631
-continued
685
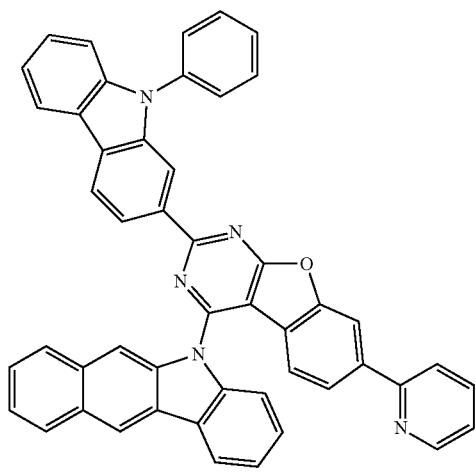
686
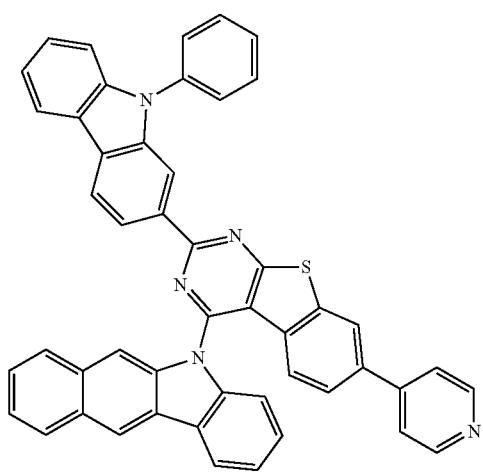
688
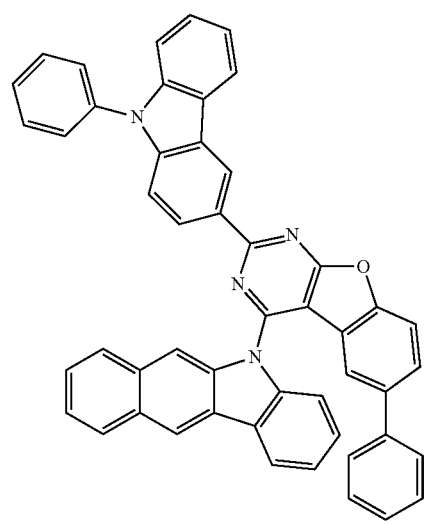
632
-continued
689
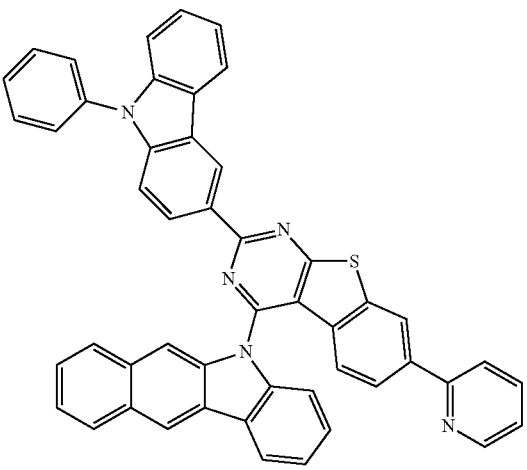
691
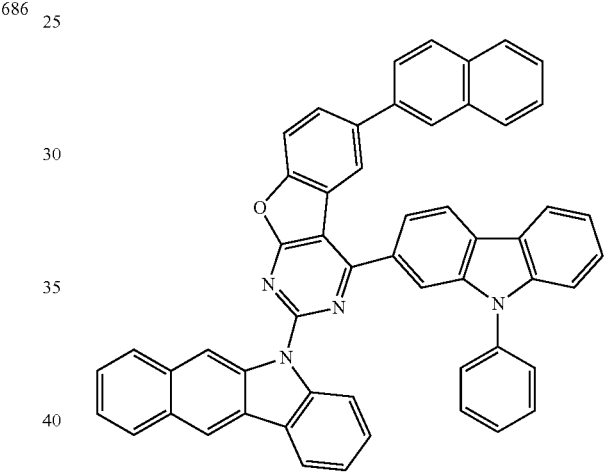
692
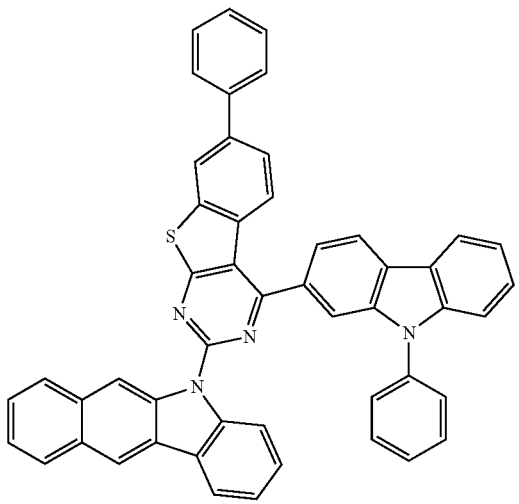

694
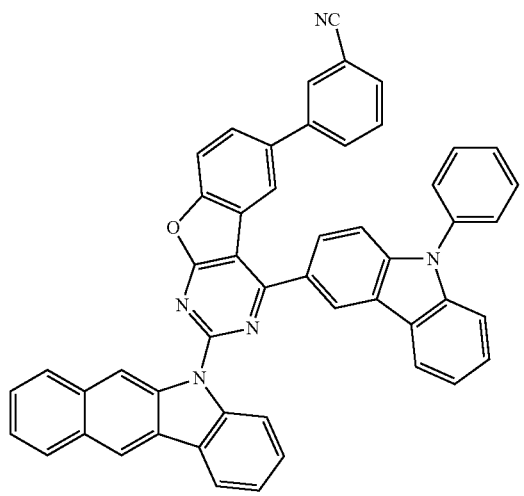
695
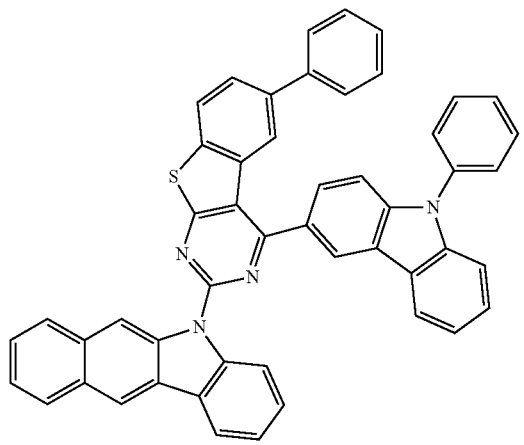
697
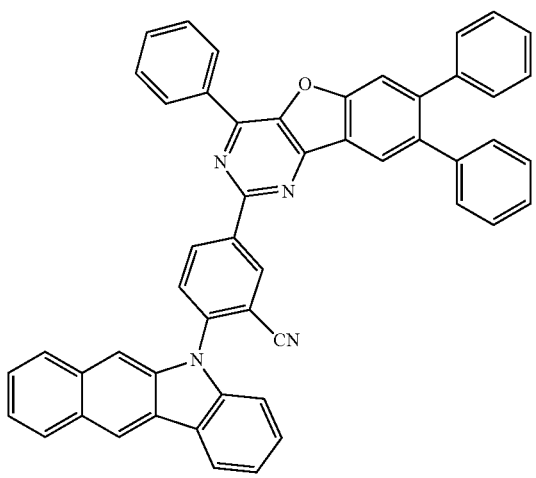
698
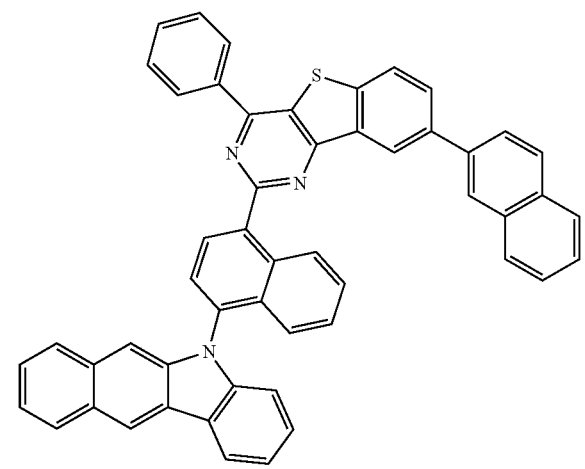
700
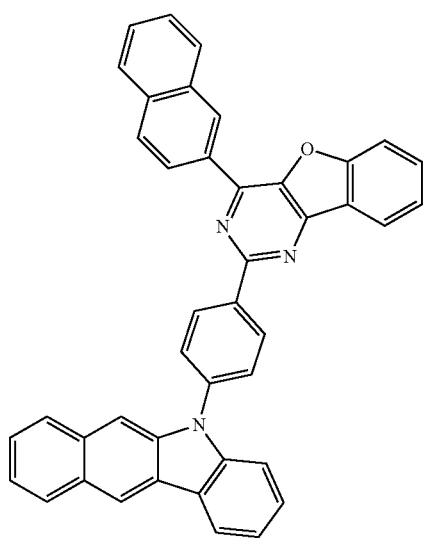
701
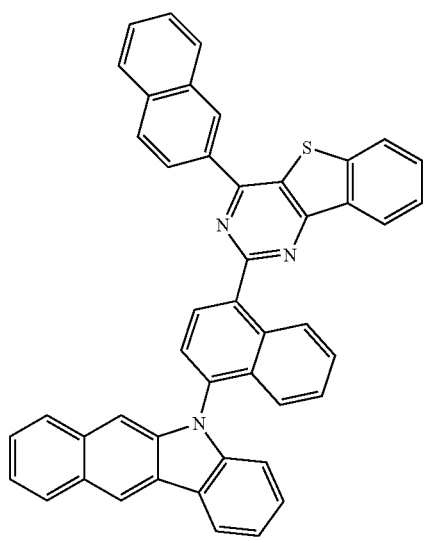

635
-continued
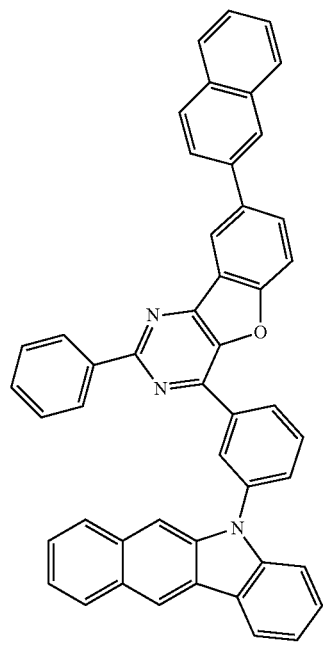
636
-continued
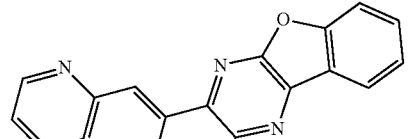
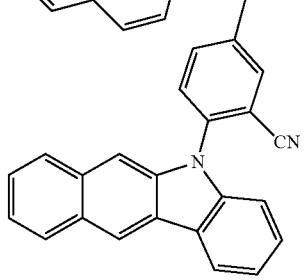
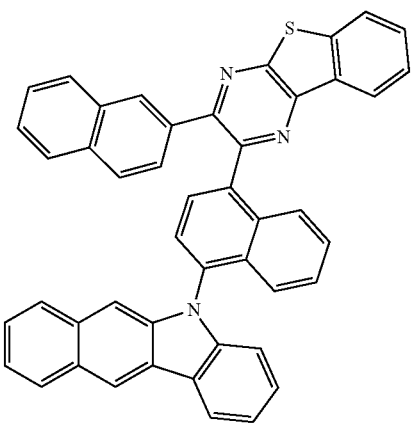
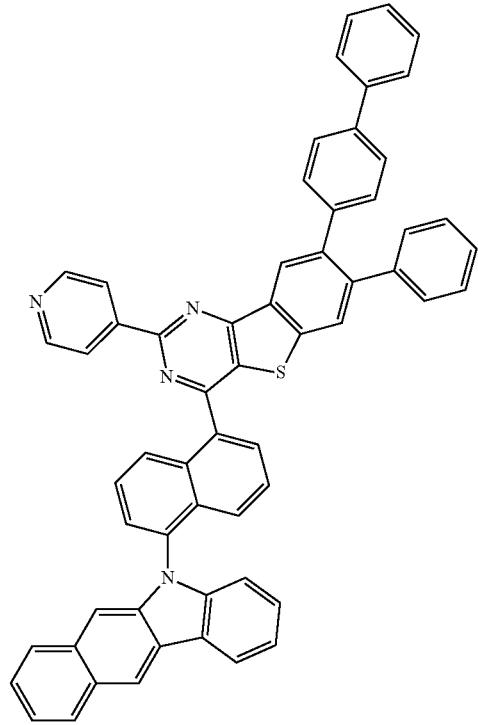
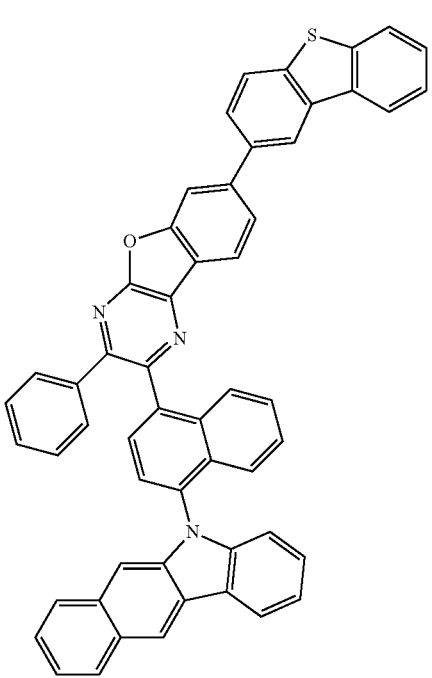

637
-continued
710
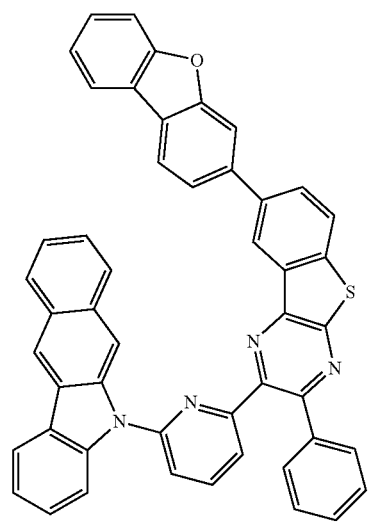
712
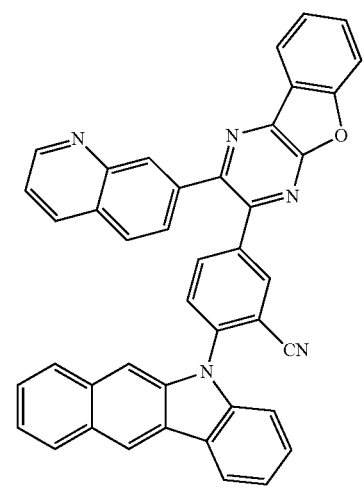
713
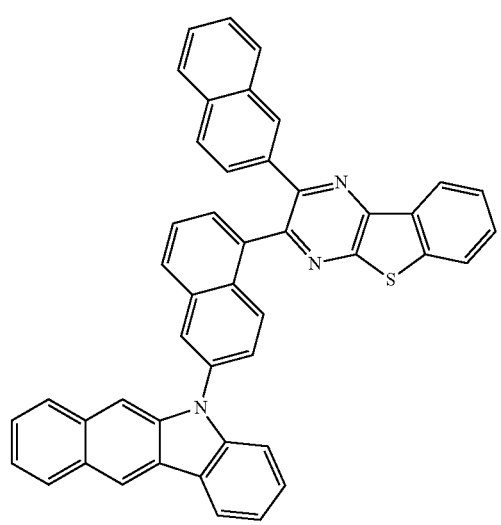
638
-continued
715
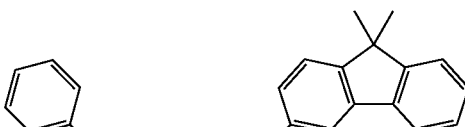
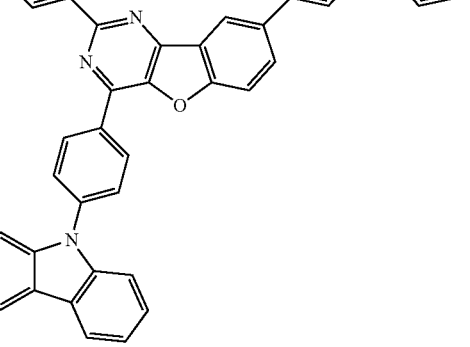
716
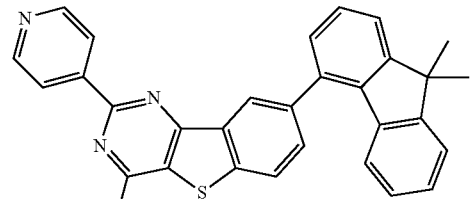
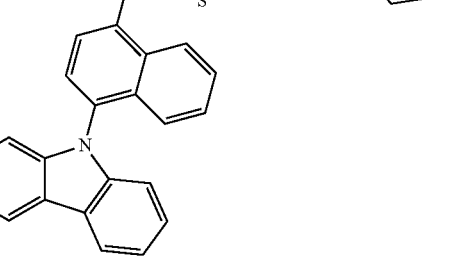
718
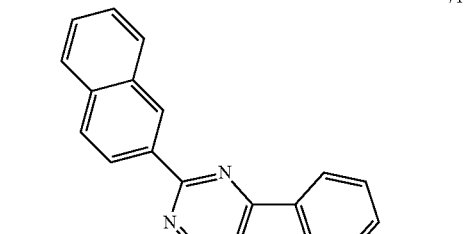
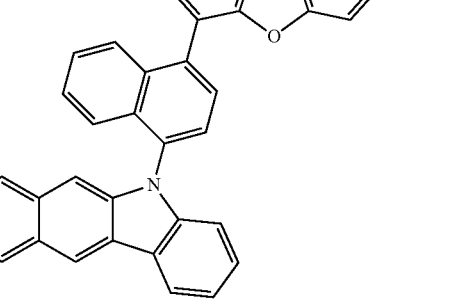

639
-continued
719
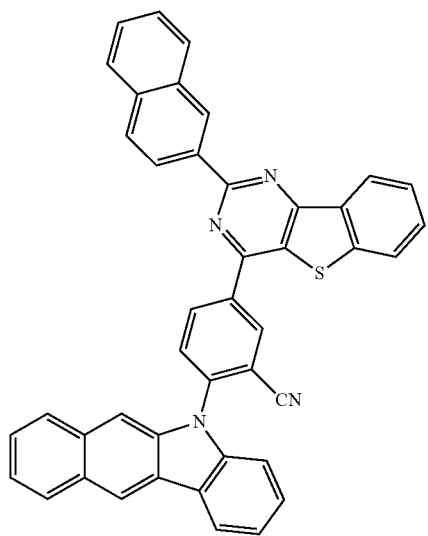
721
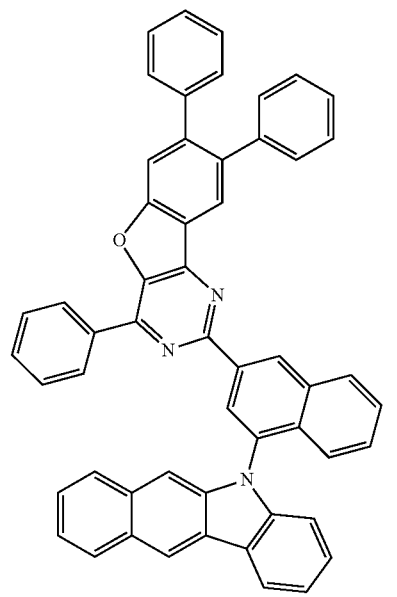
722
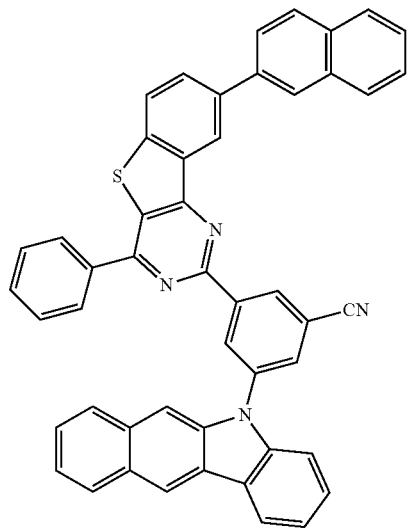
640
-continued
724
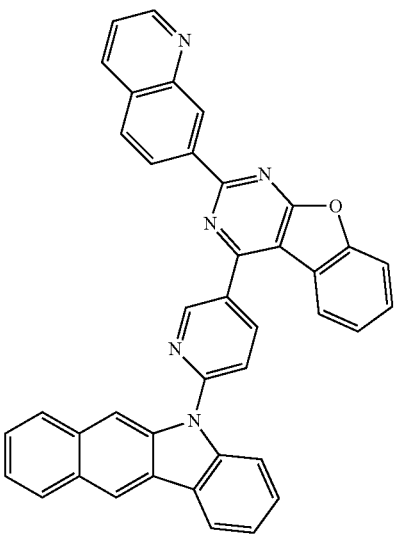
725
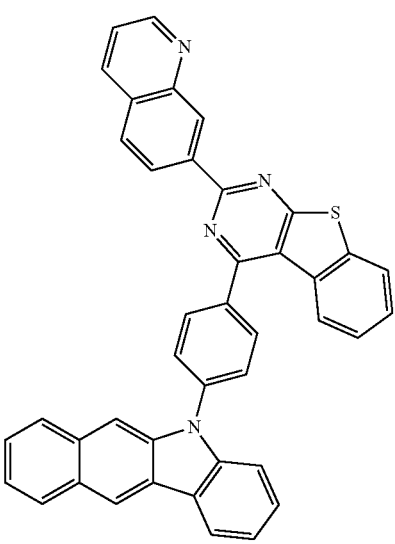
727
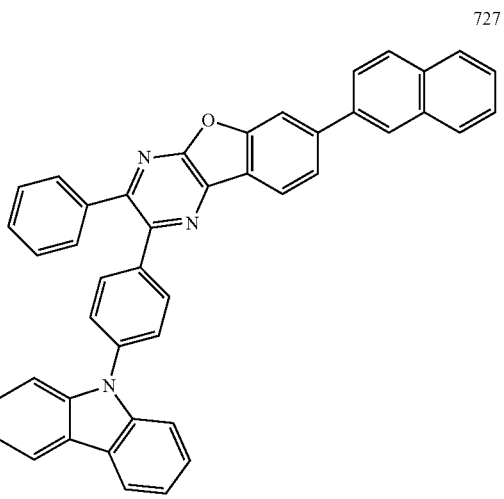

-continued
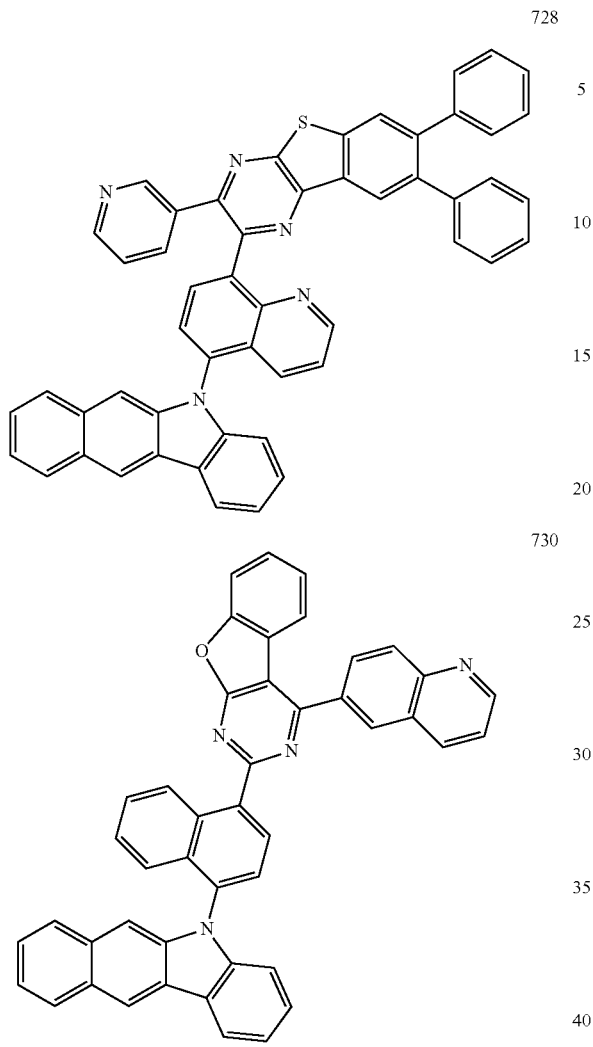
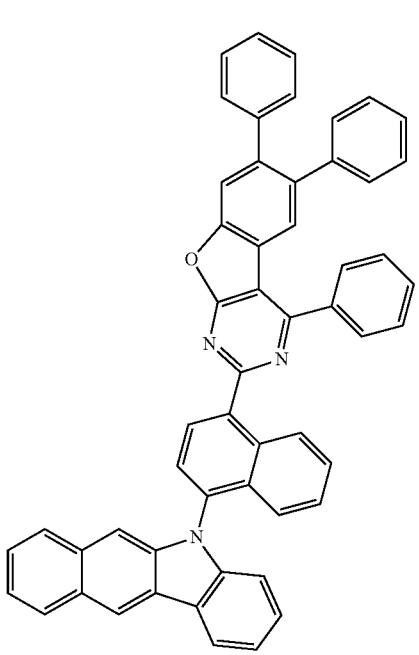
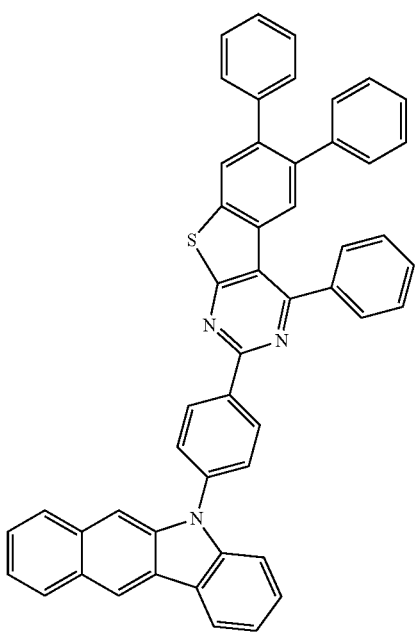

-continued
736
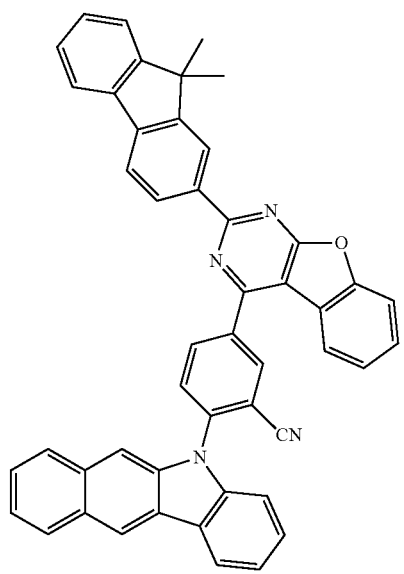
737
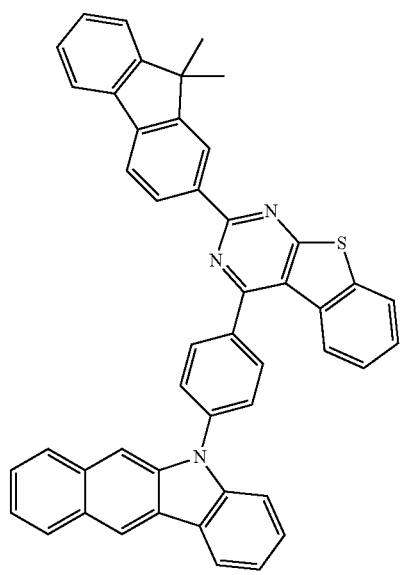
-continued
739
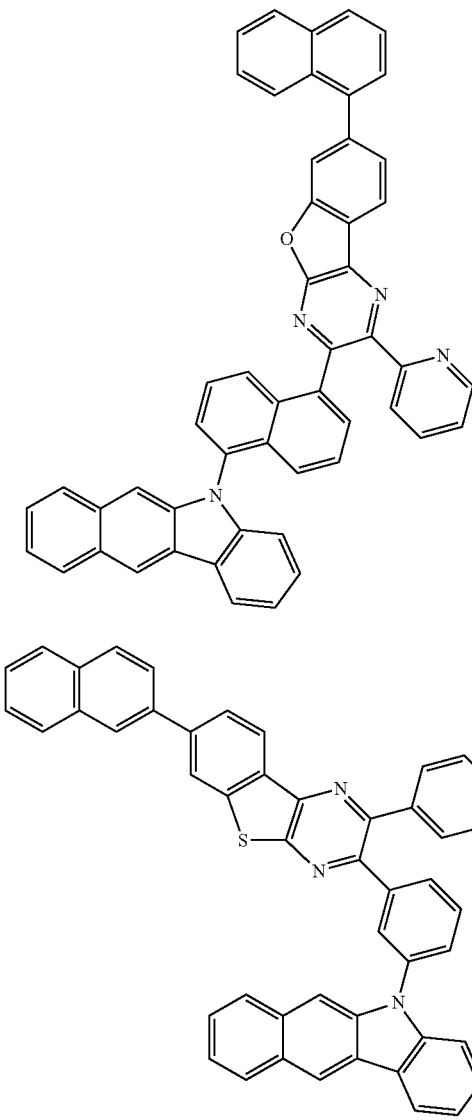
740
742

-continued
743
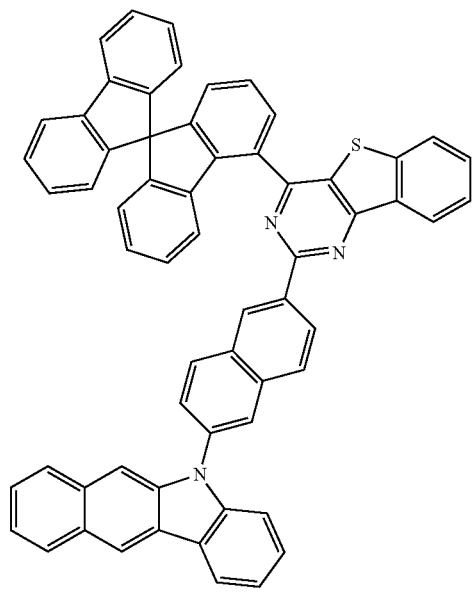
745
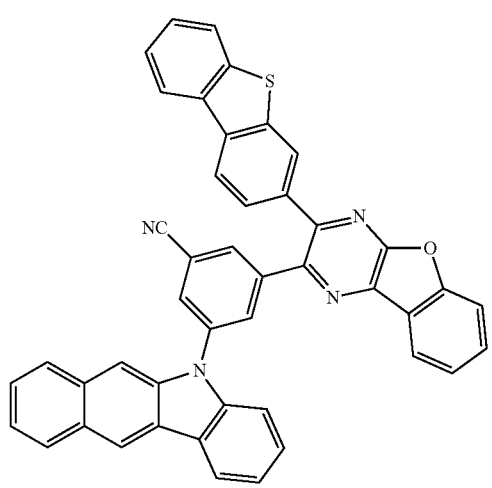
746
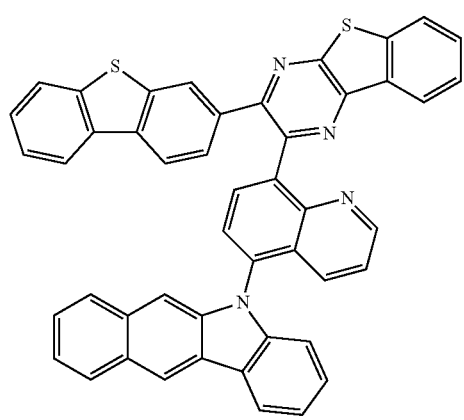
-continued
748
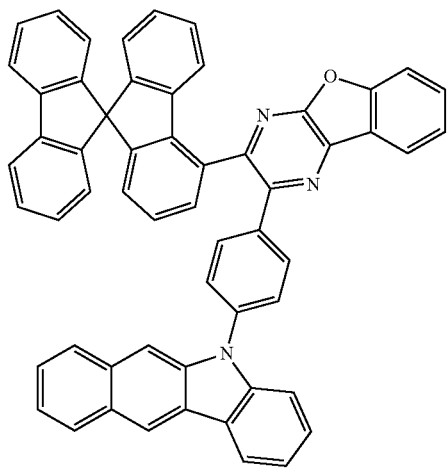
749
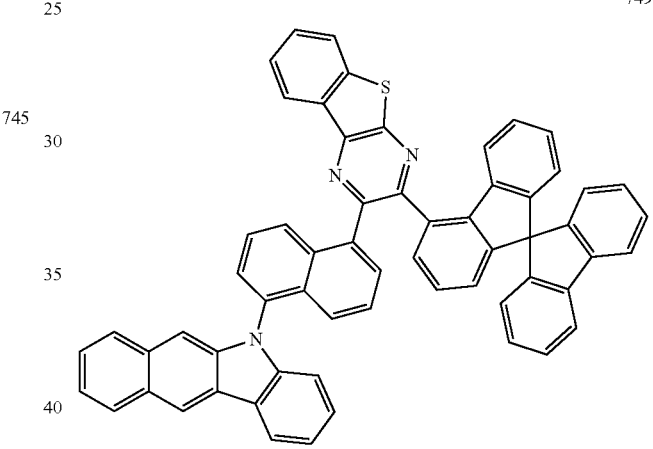
751
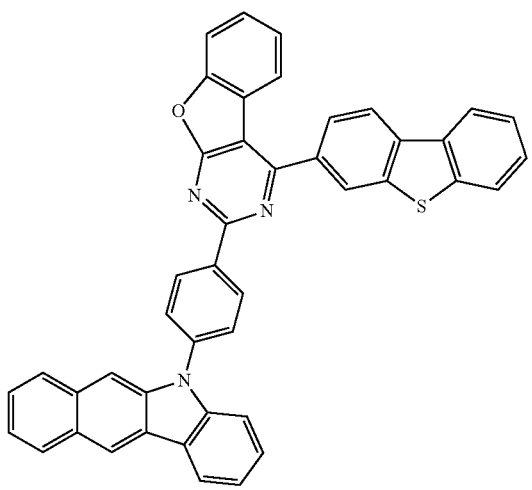

647
-continued
752
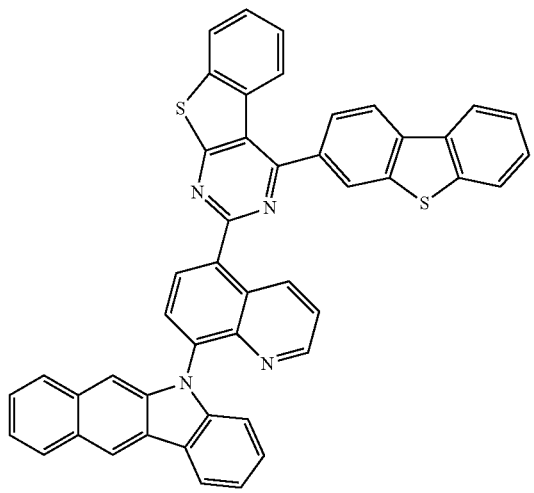
754
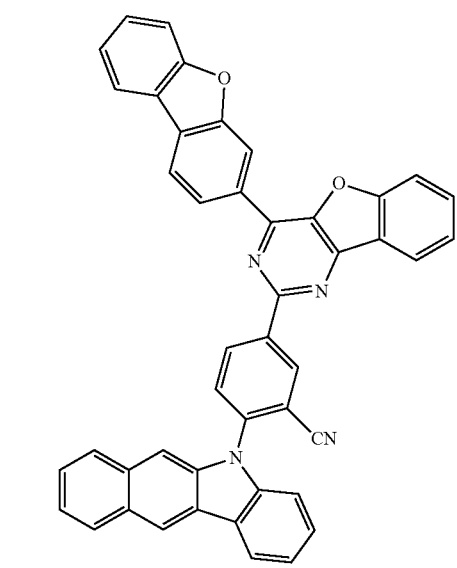
755
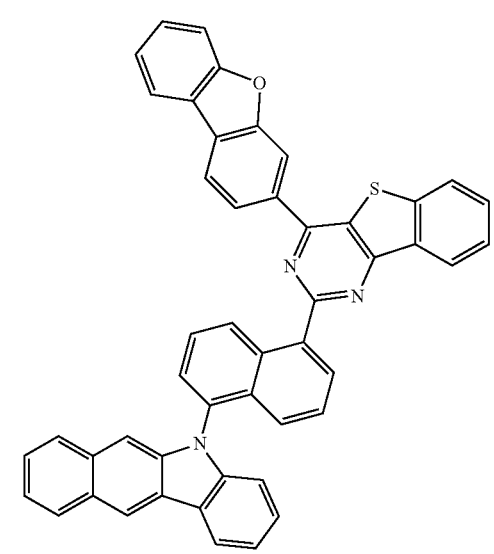
648
-continued
757
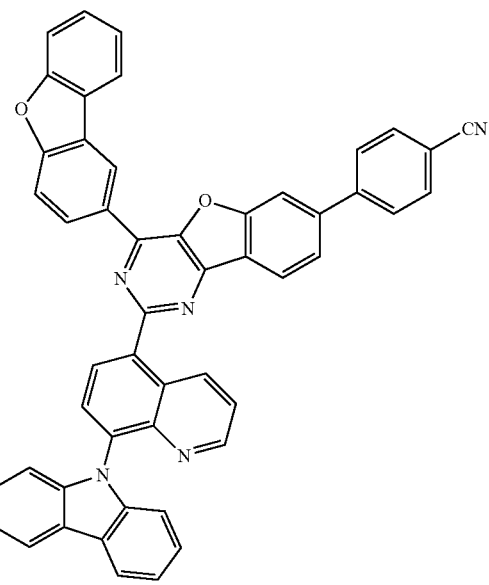
758
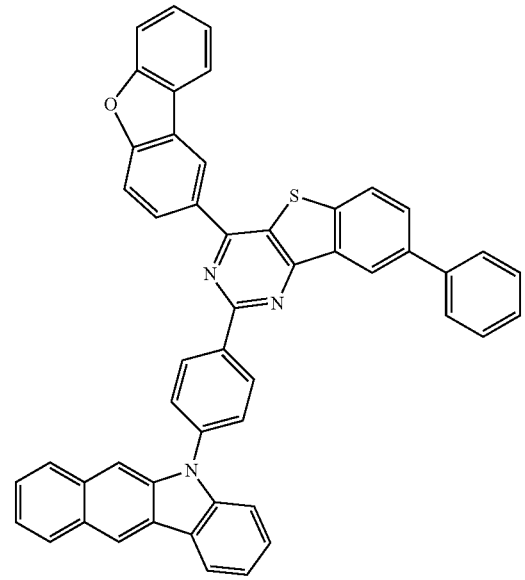

-continued
760
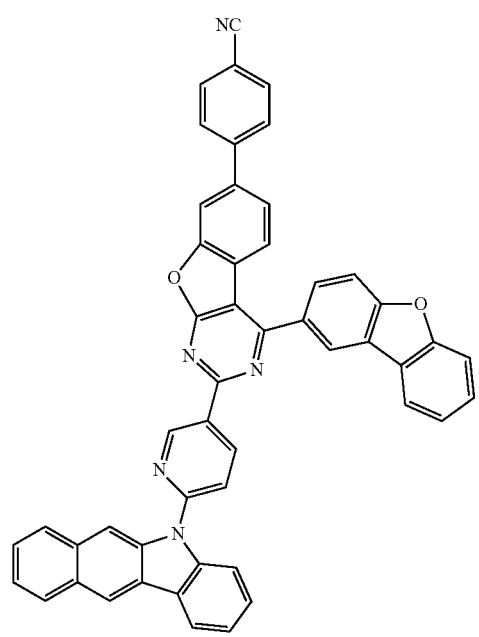
761
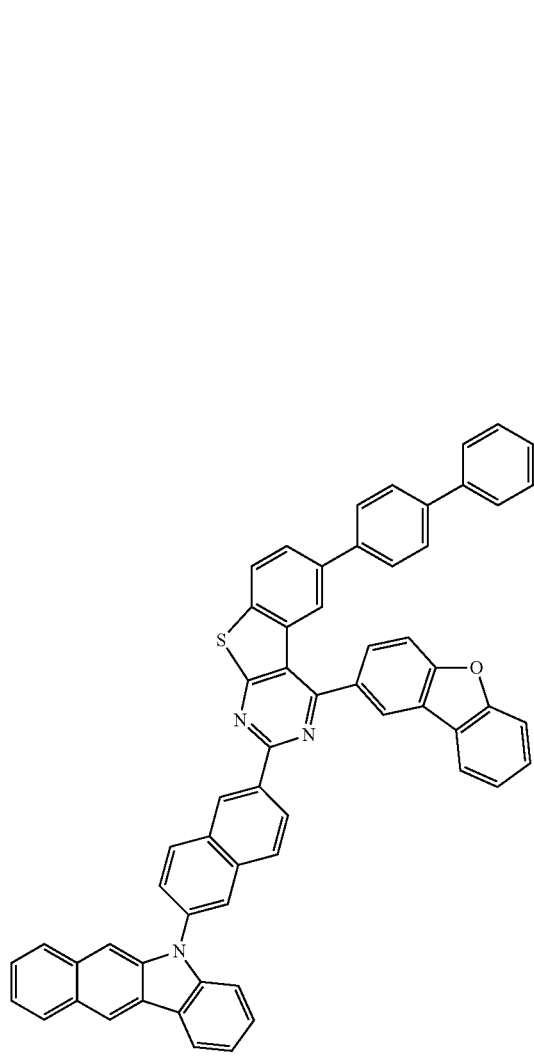
763
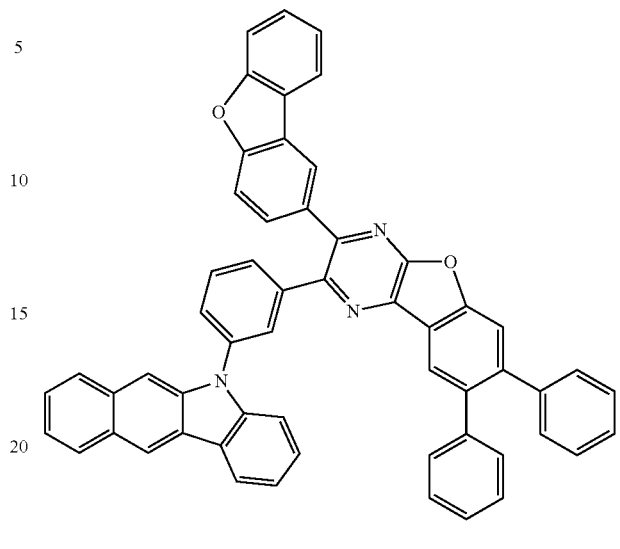
764
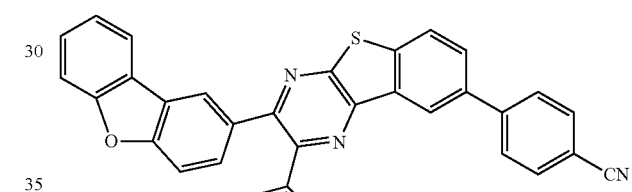
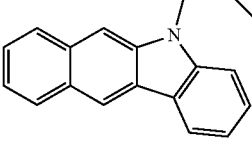
766
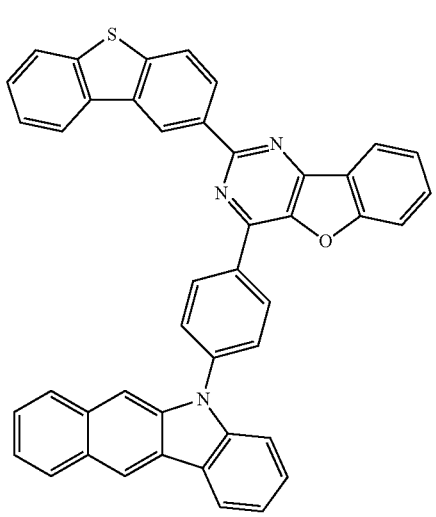

651
-continued
767
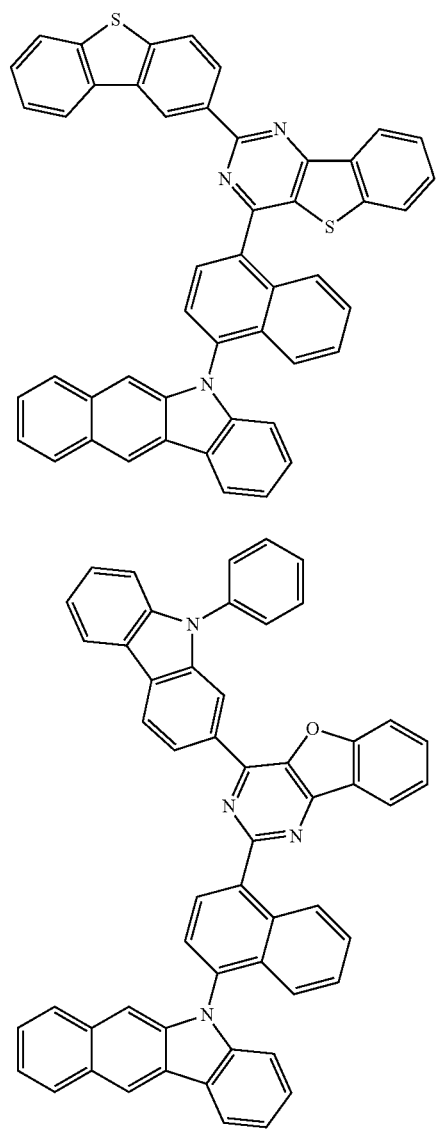
769
770
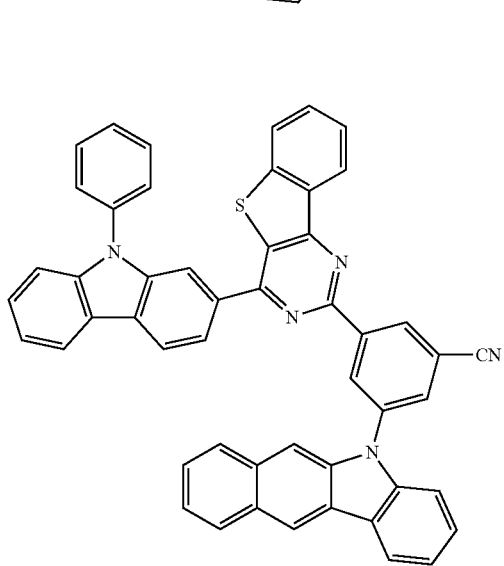
652
-continued
772
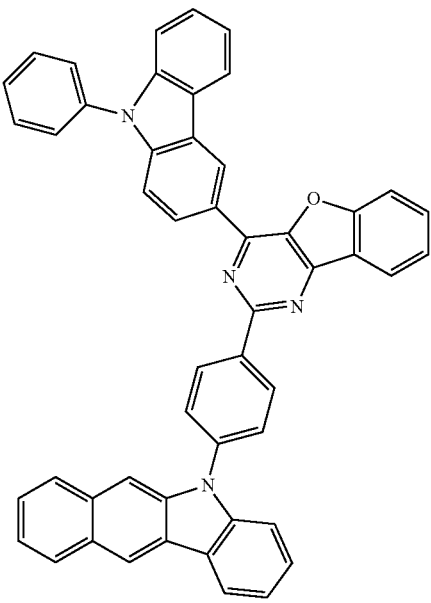
773
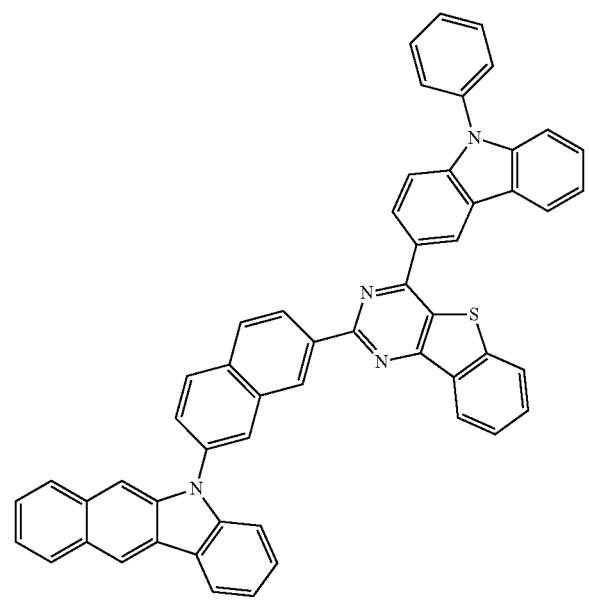

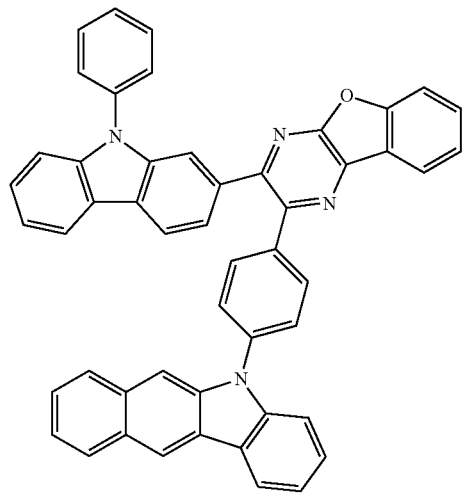
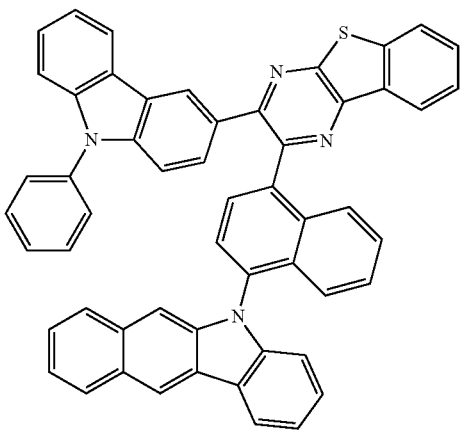
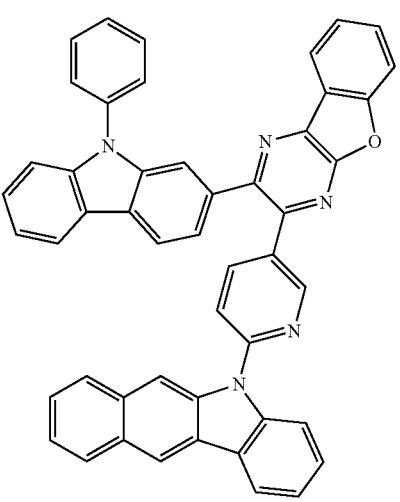
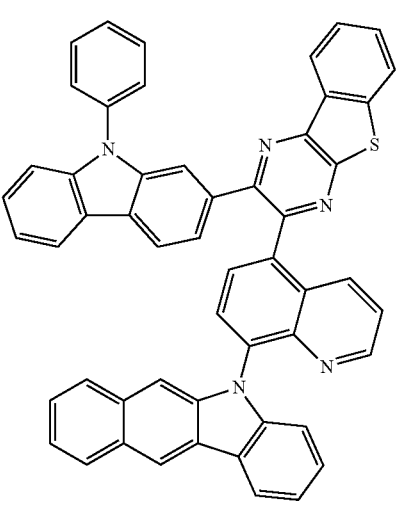

655
-continued
784
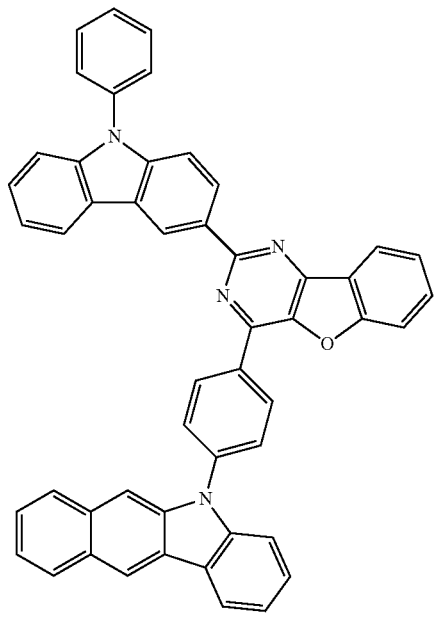
785
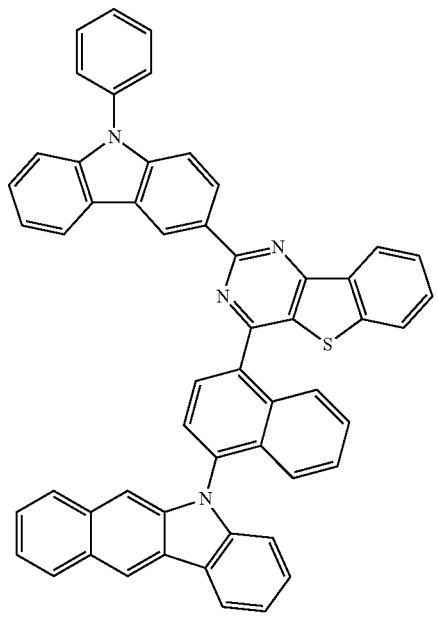
656
-continued
787
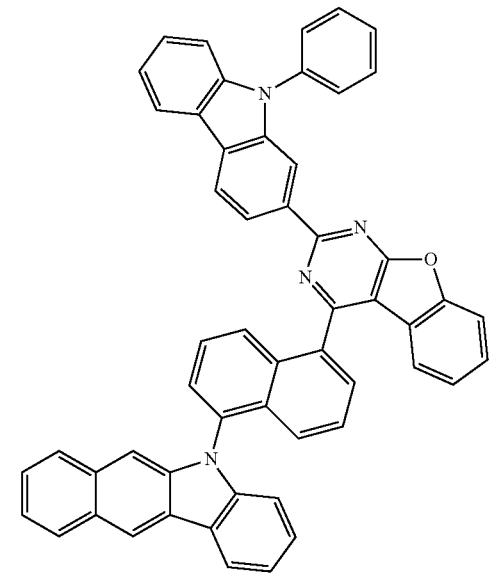
788
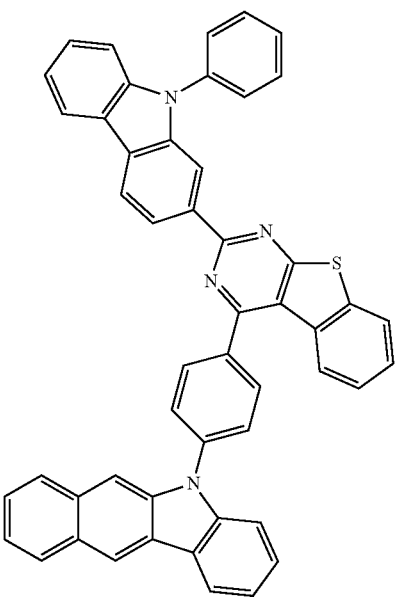

657
-continued
790
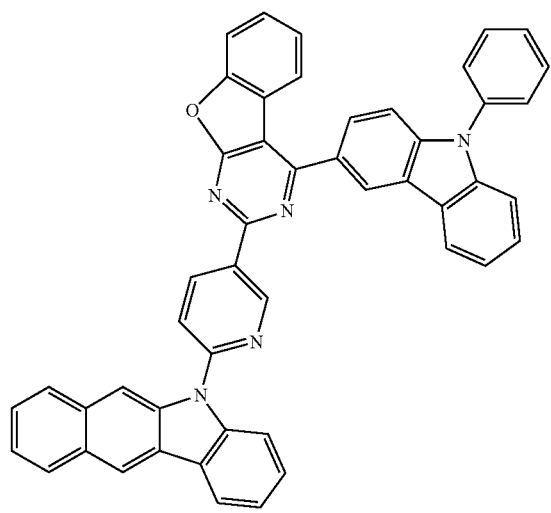
791
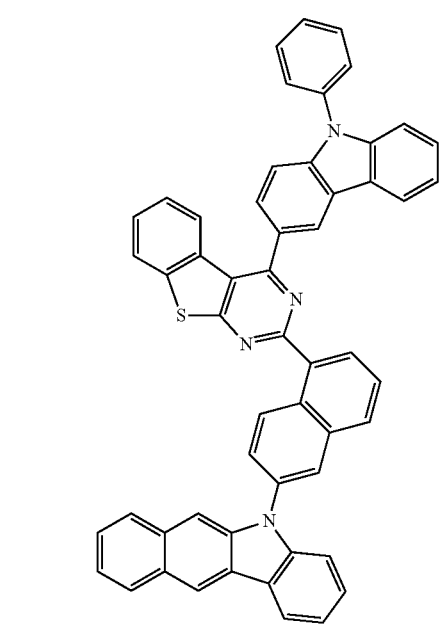
793
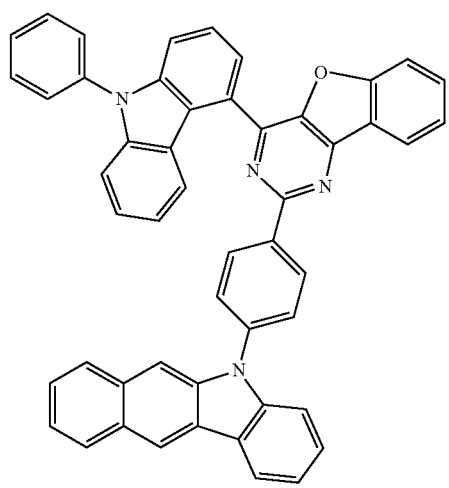
658
-continued
794
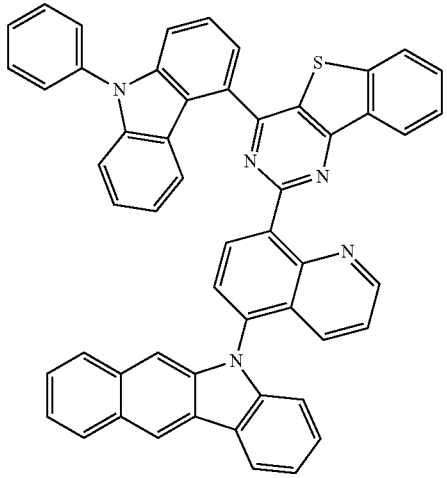
796
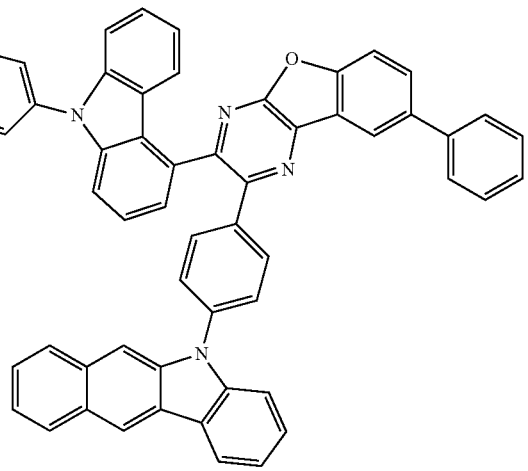
797
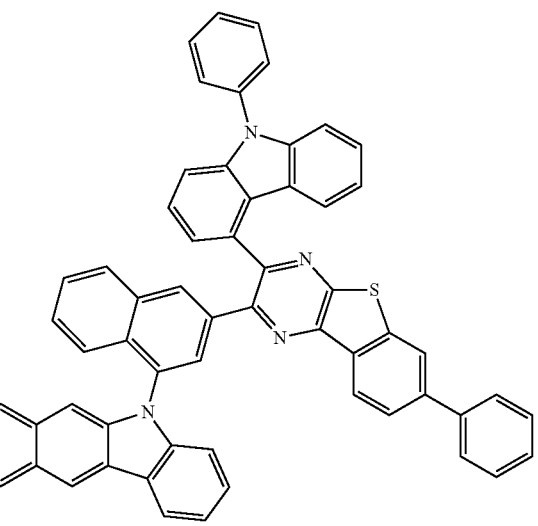

-continued
799
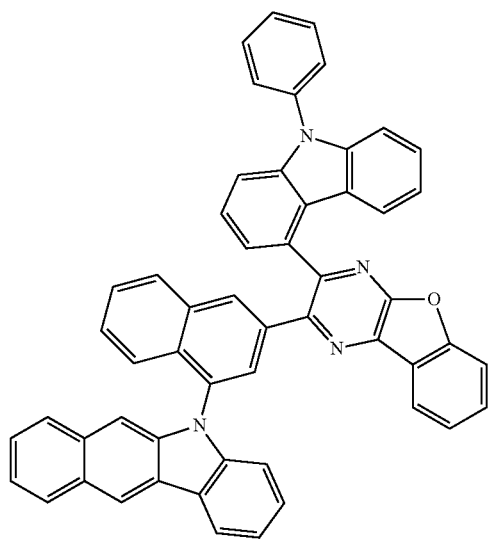
800
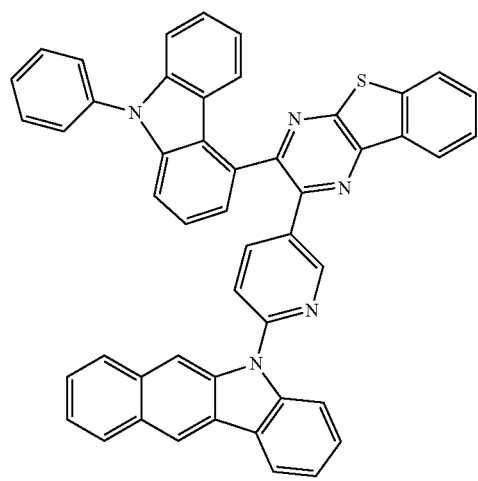
802
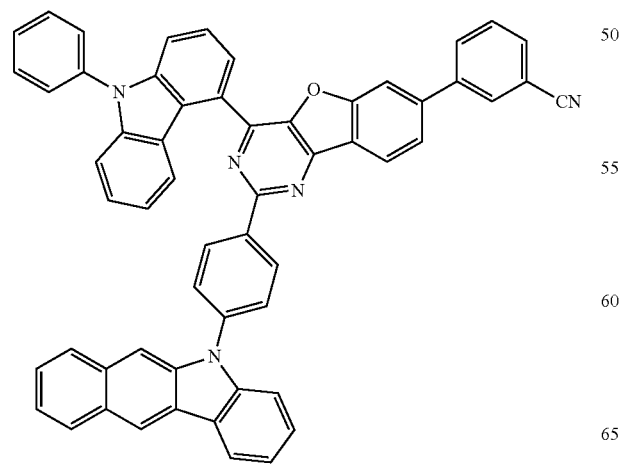
-continued
803
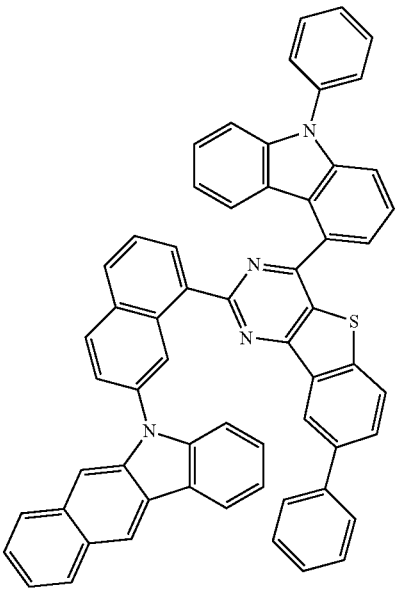
805
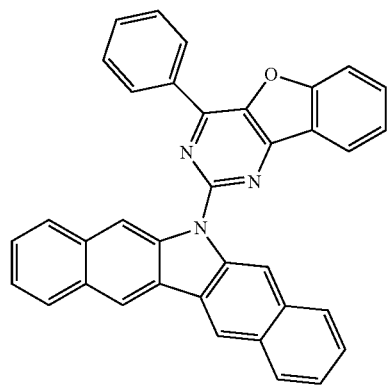
806
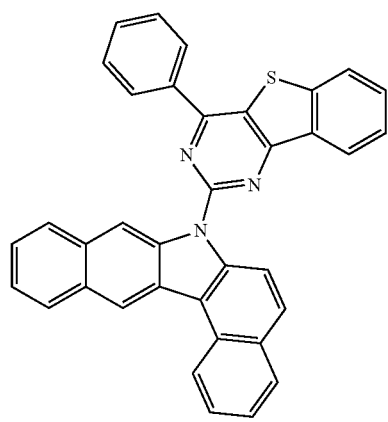

808
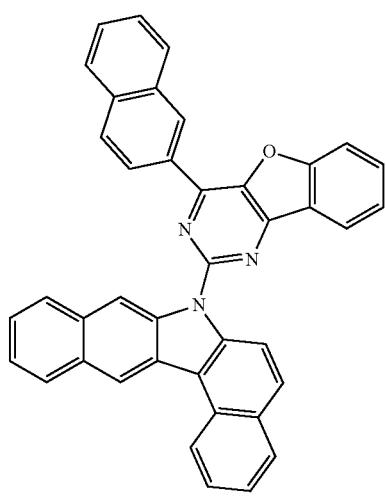
809
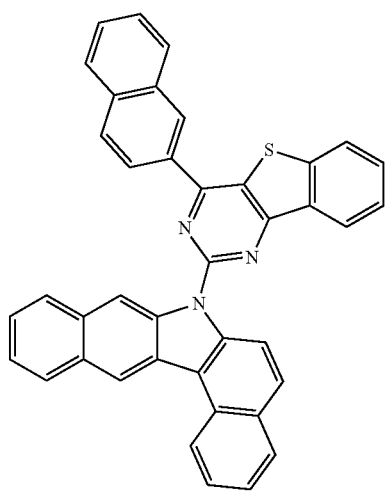
811
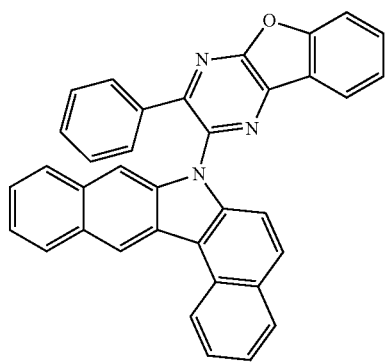
812
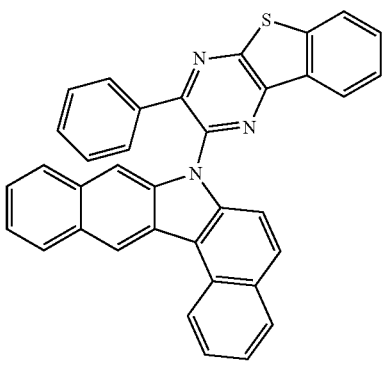
814
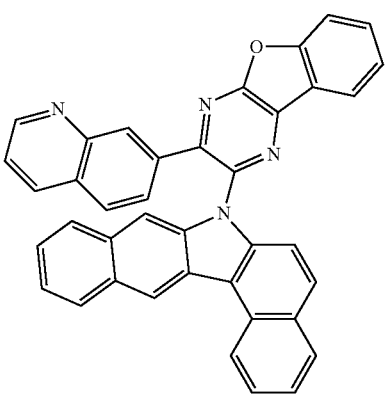
815
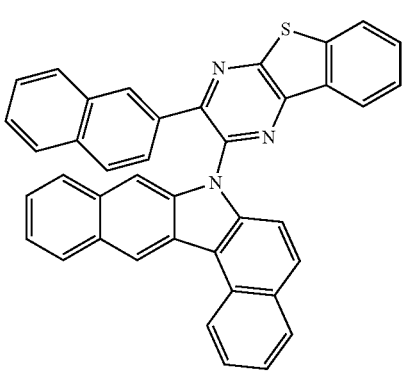
817
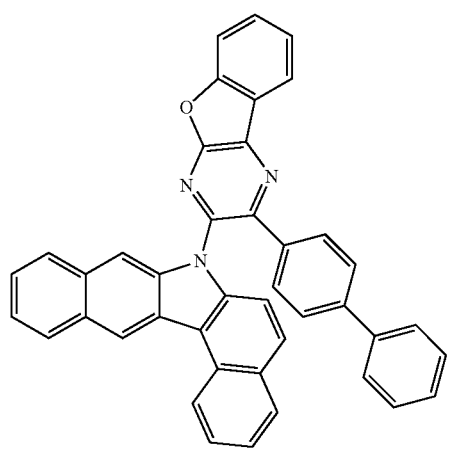

818
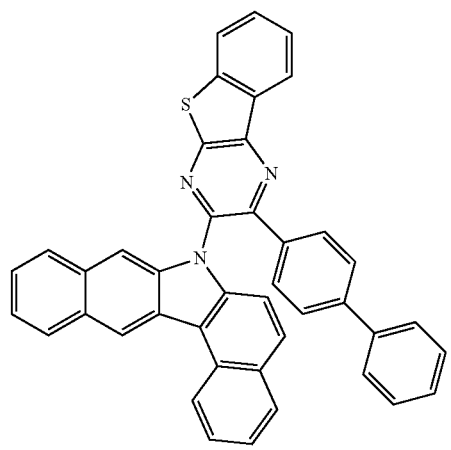
823
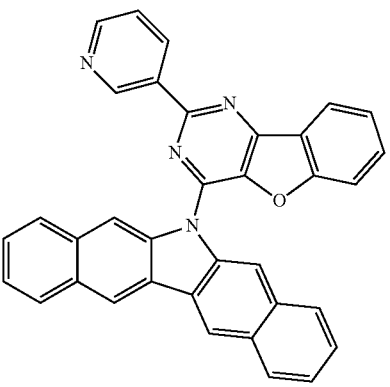
820
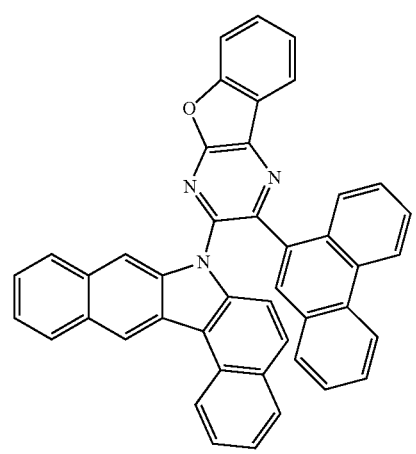
824
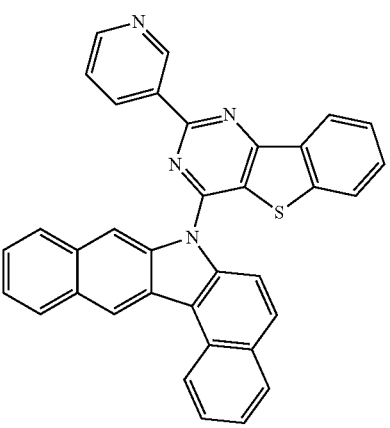
821
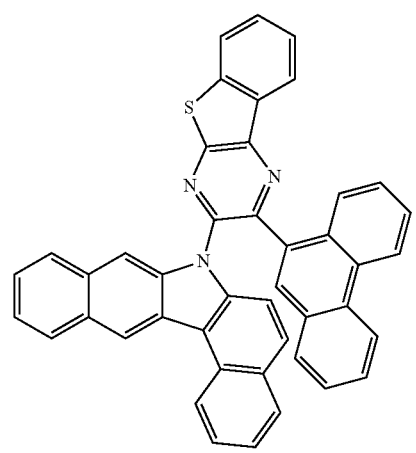
826
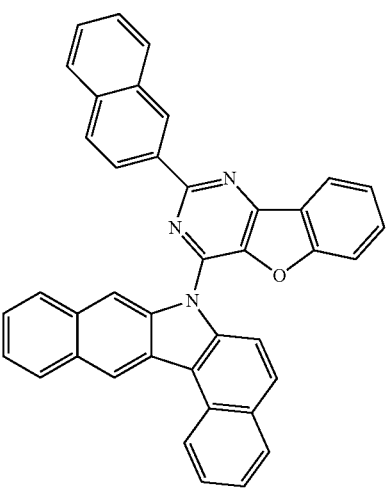

827
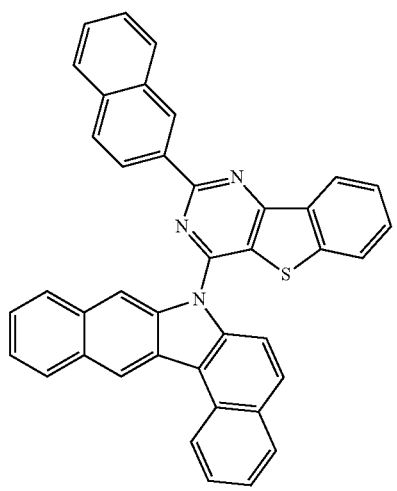
829
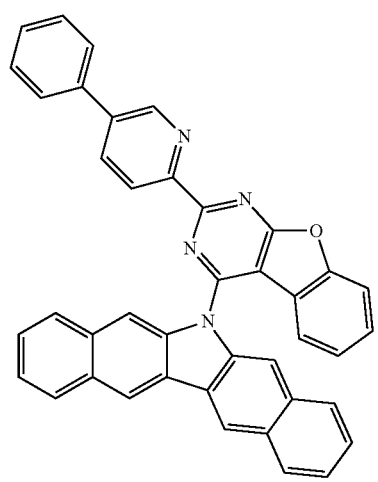
830
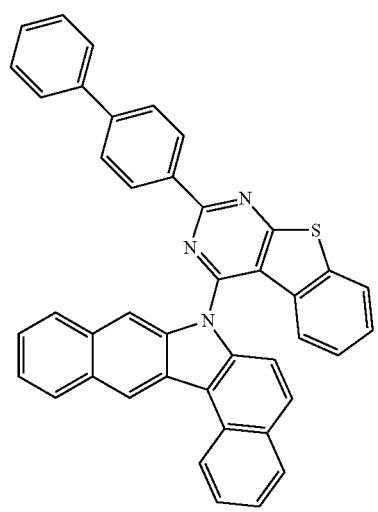
832
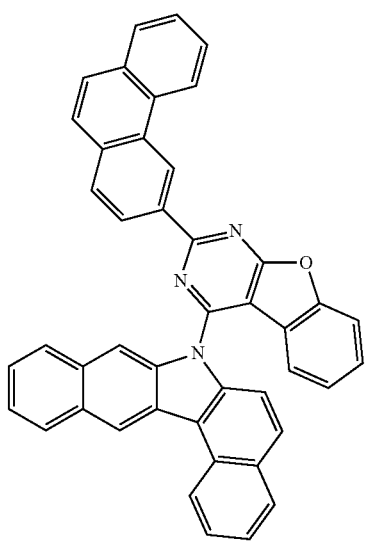
833
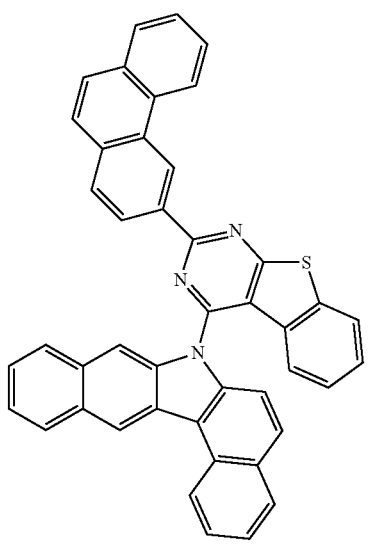
835
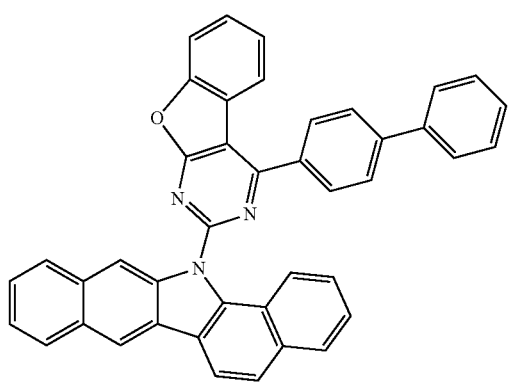

836
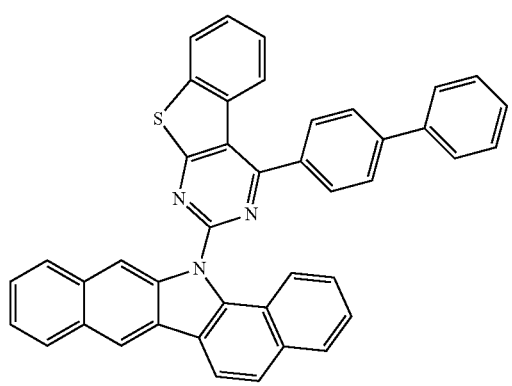
838
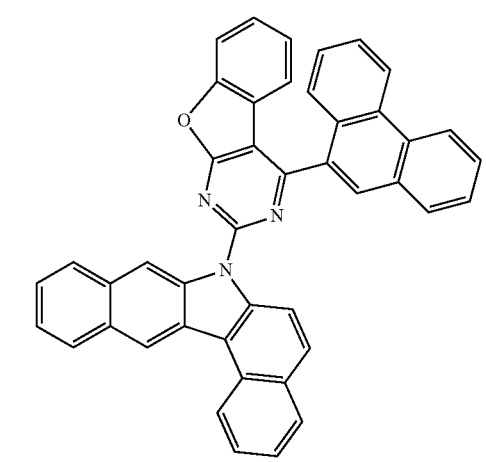
839
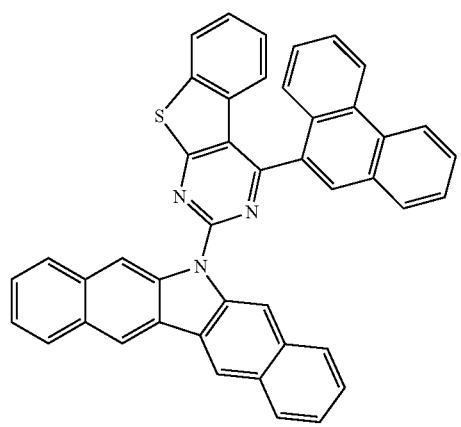
841
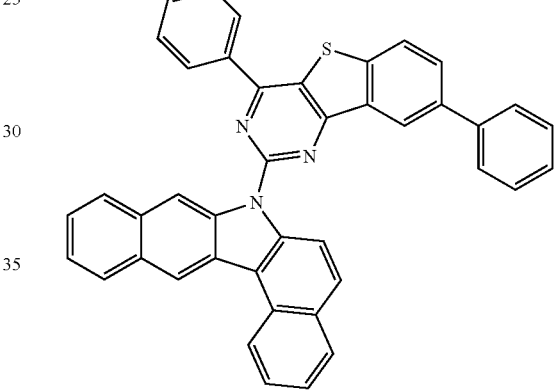
842
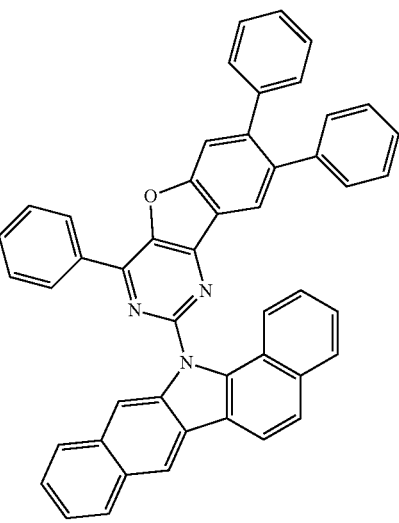
844
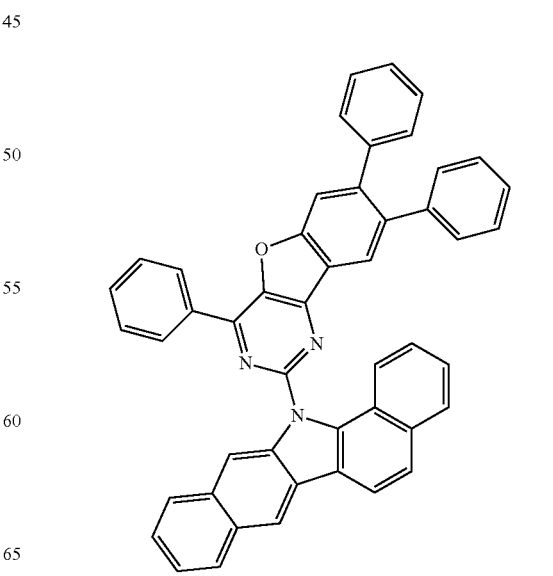

-continued
845
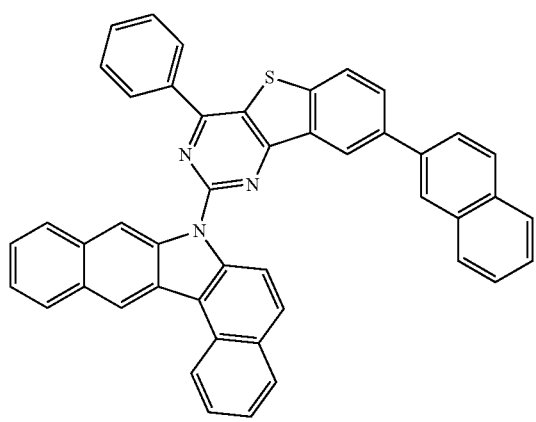
847
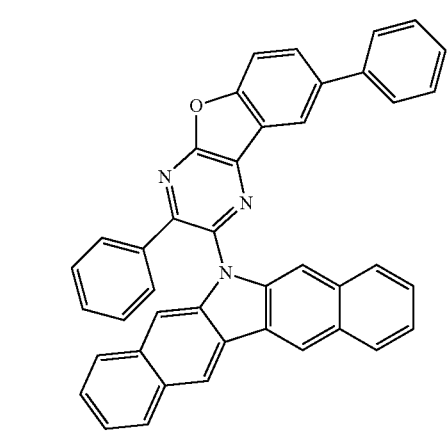
848
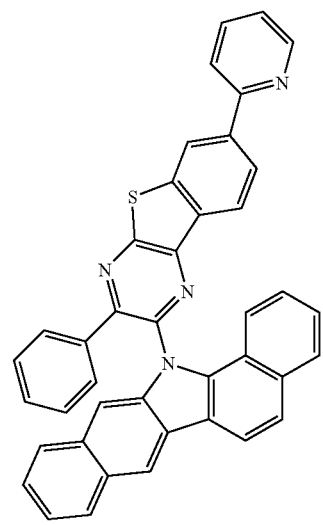
-continued
850
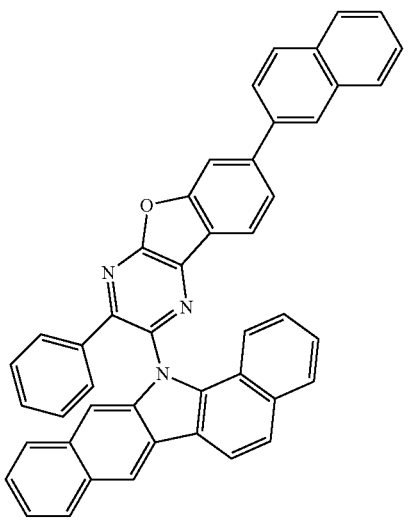
851
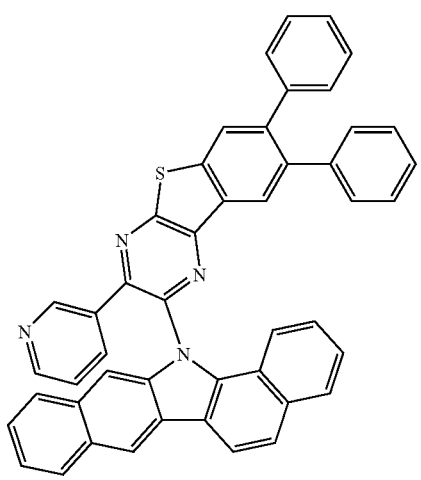
853
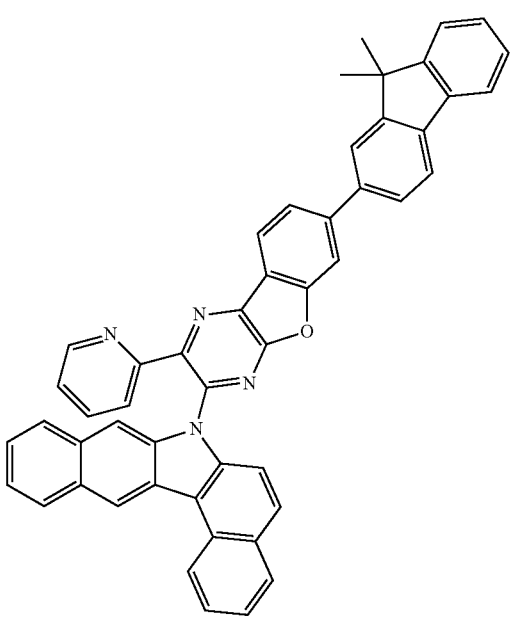

-continued
854
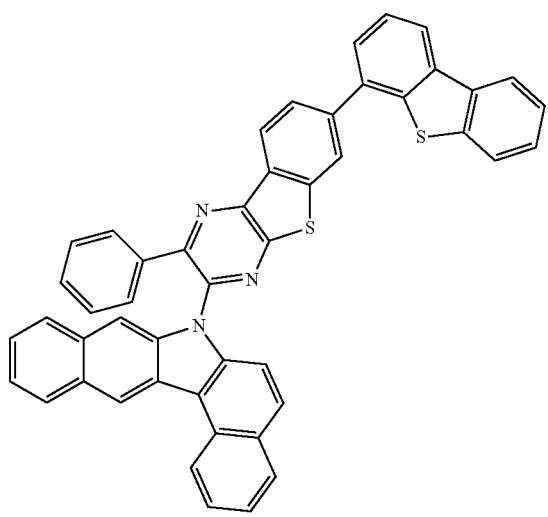
856
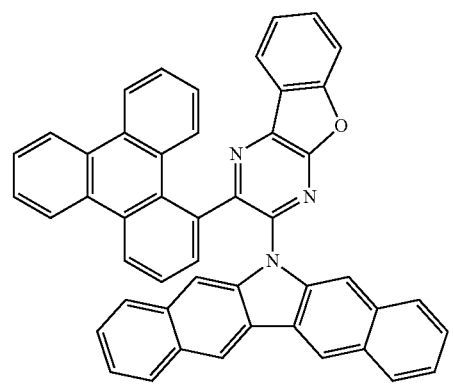
857
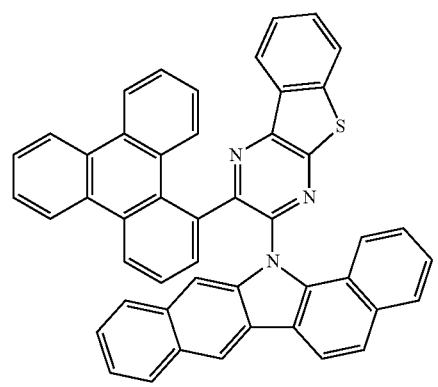
-continued
859
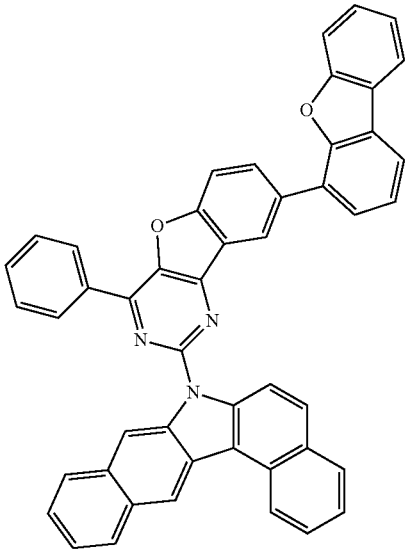
860
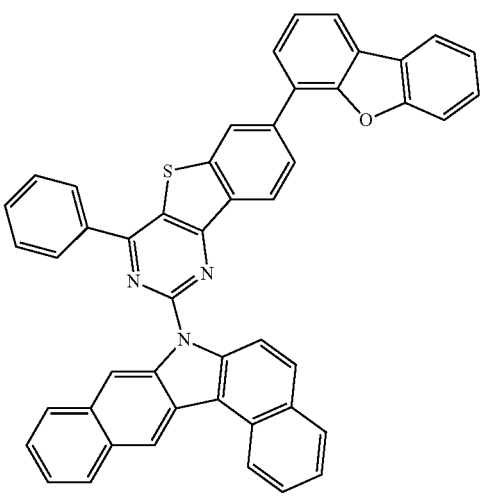
862
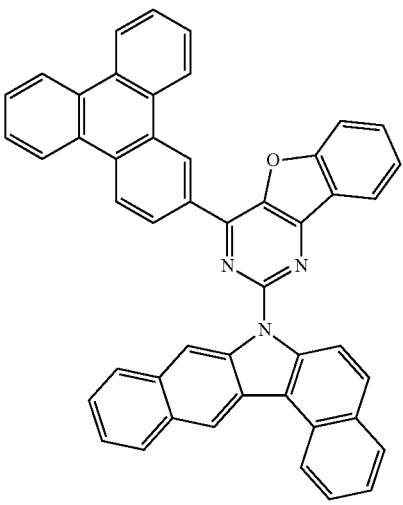

863
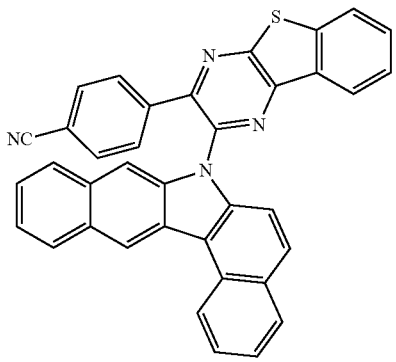
868
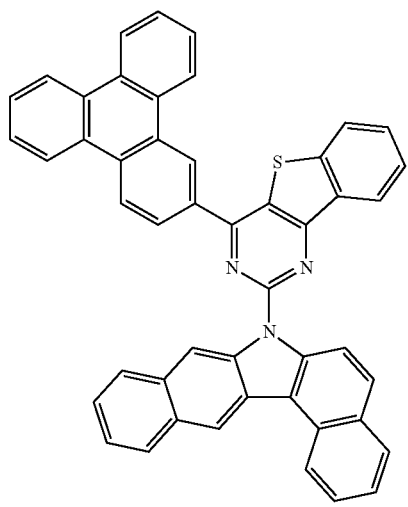
865
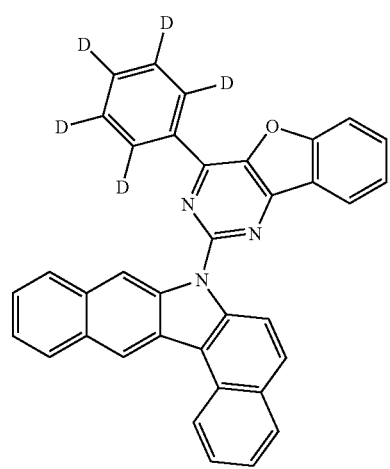
869
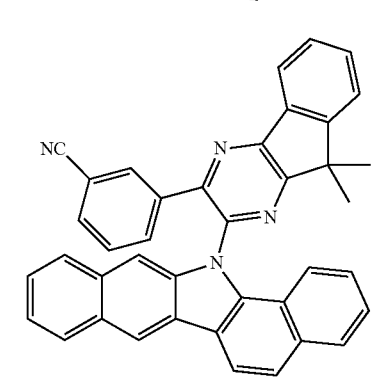
871
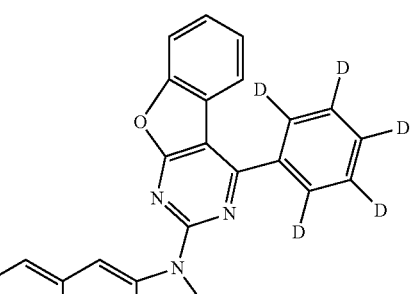
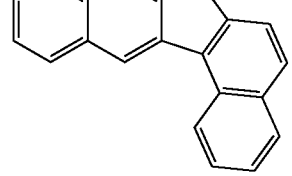
866
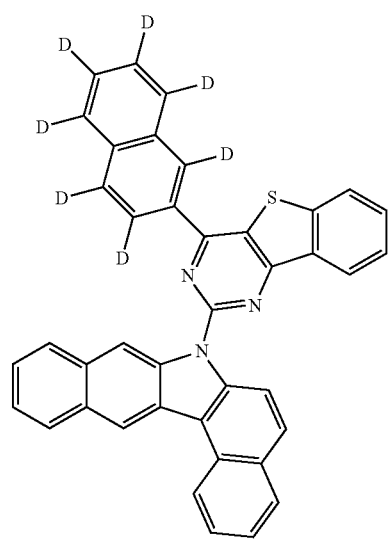
872
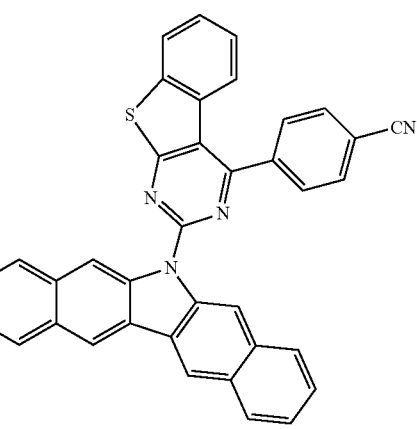

675
874
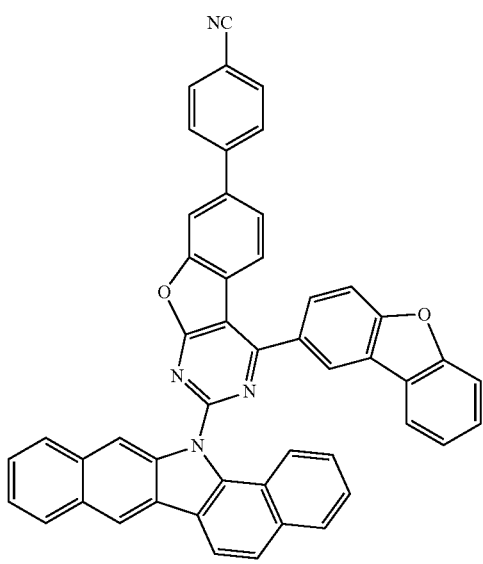
875
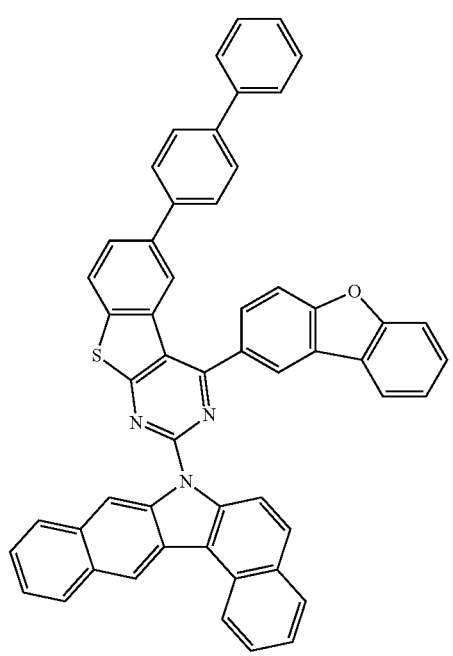
676
877
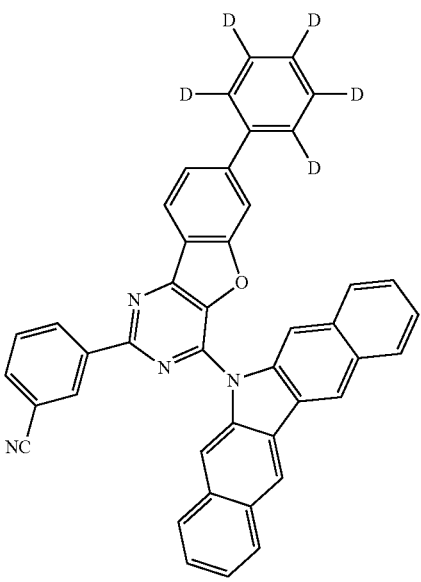
878
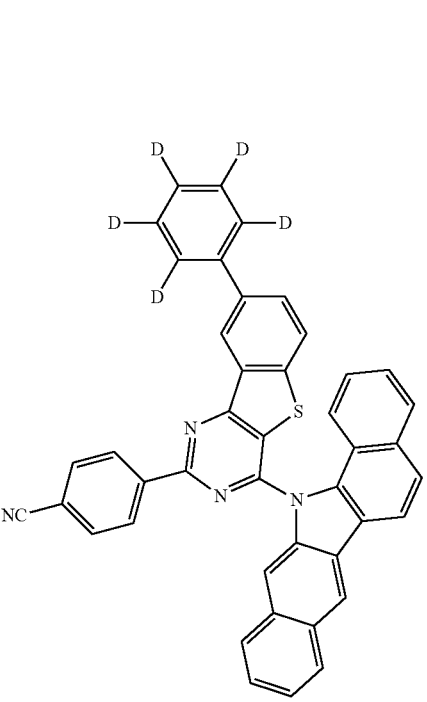

677
-continued
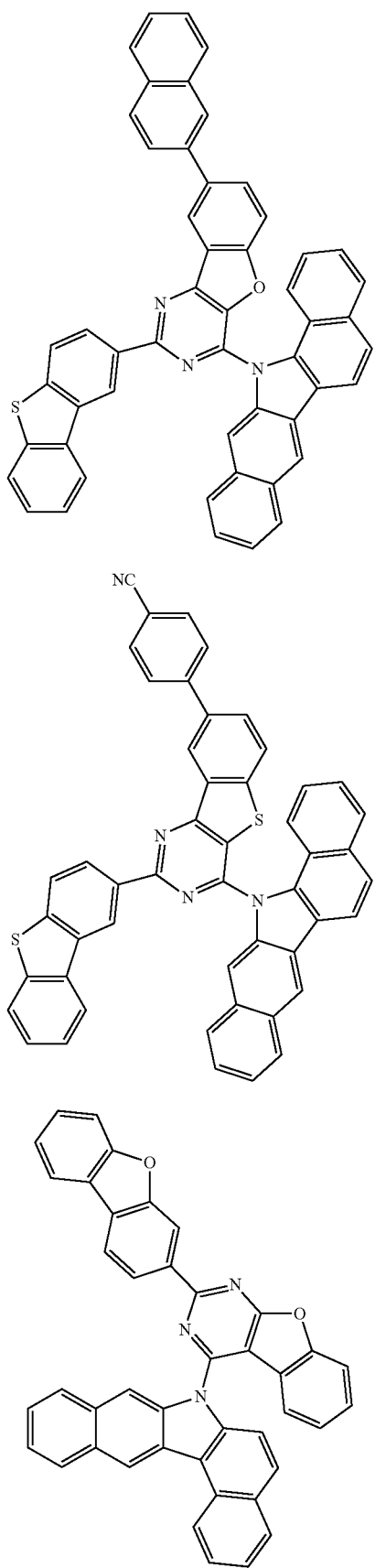
880
881
883
678
-continued
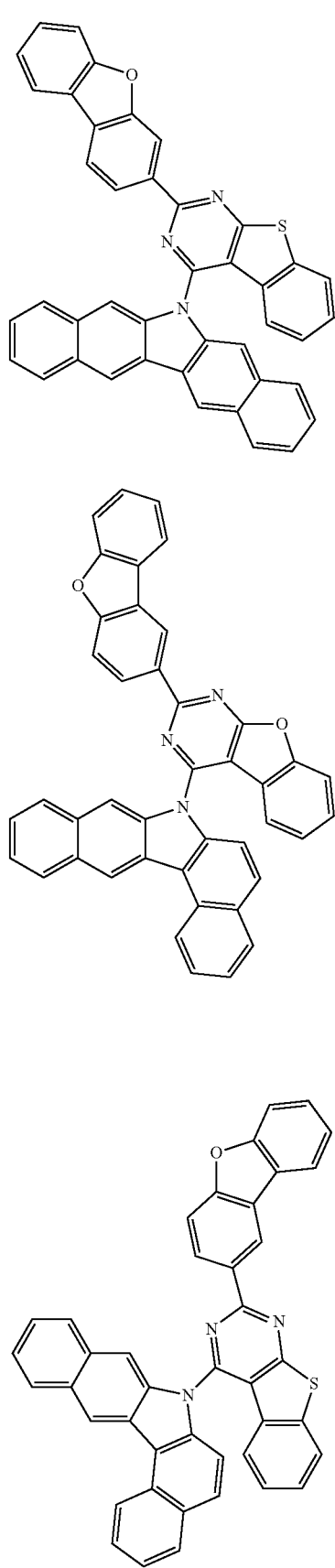
884
886
887

-continued
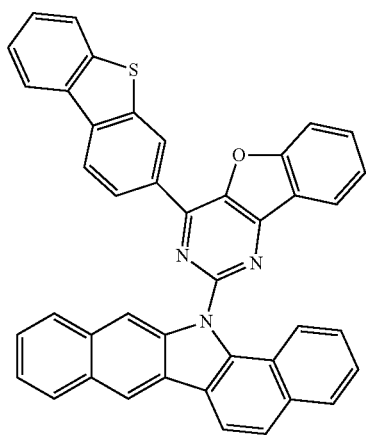
889
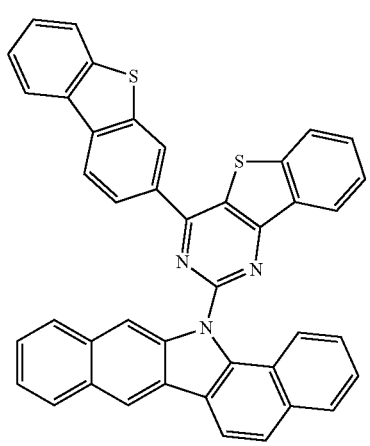
890
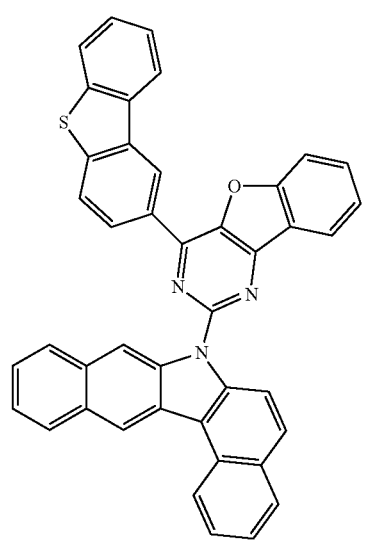
892
-continued
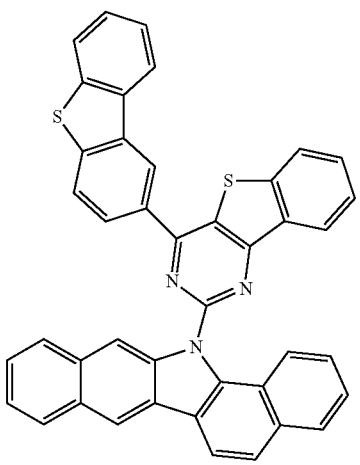
893
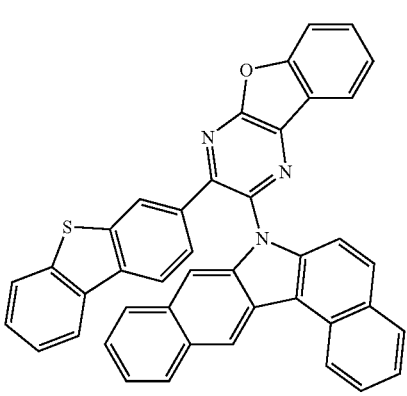
895
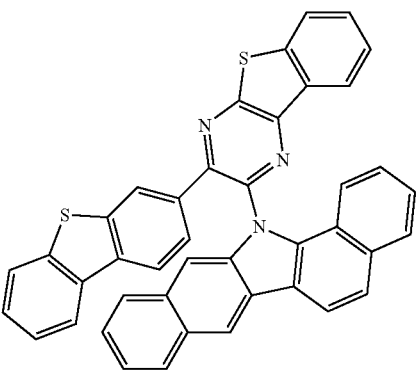
896
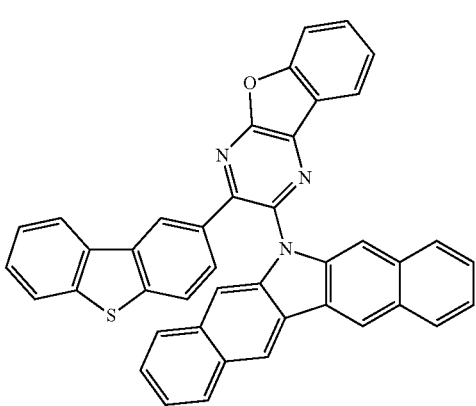
898

681
-continued
899
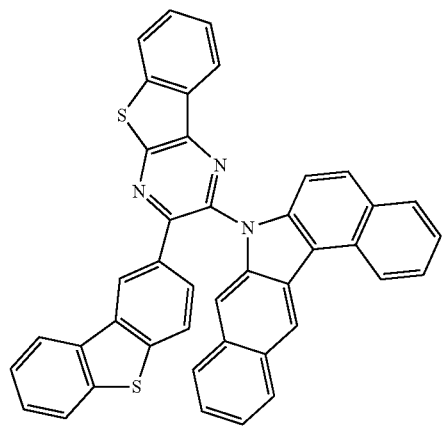
901
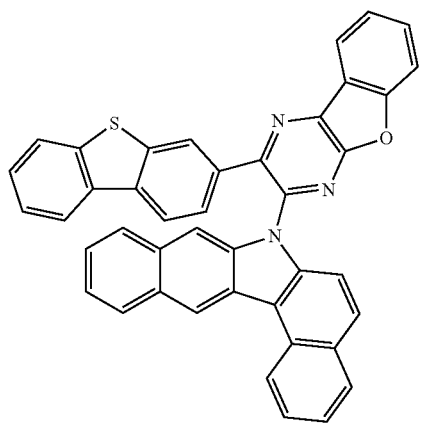
902
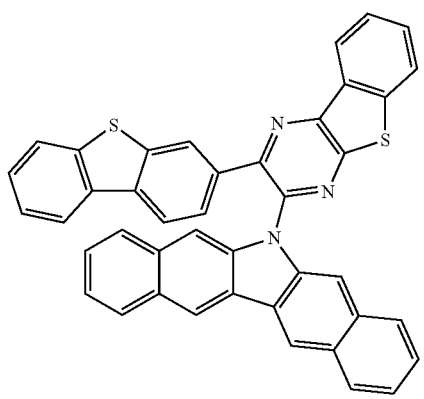
682
-continued
904
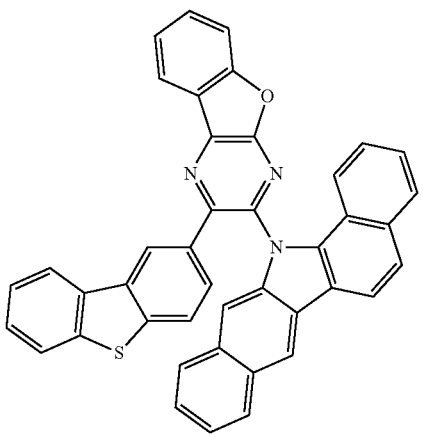
905
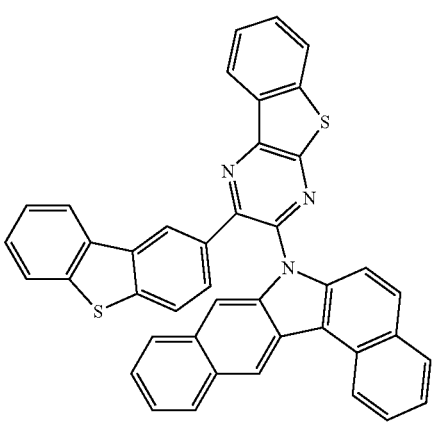
907
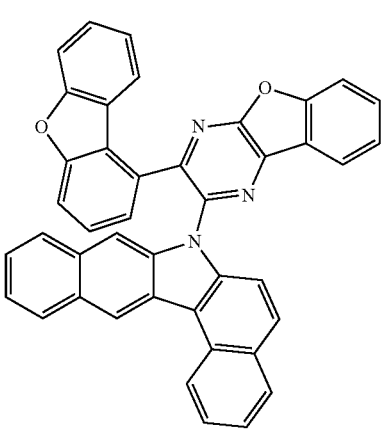

| 683 -continued | 684 -continued |
|---|---|
| 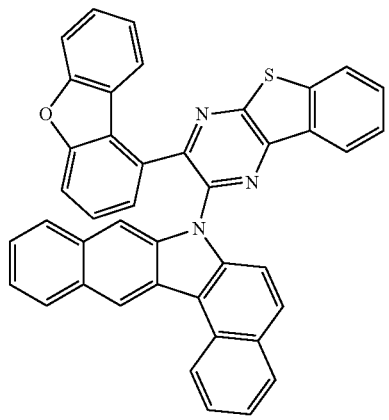 908 | 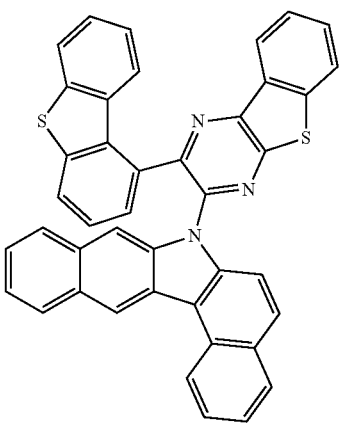 914 |
| 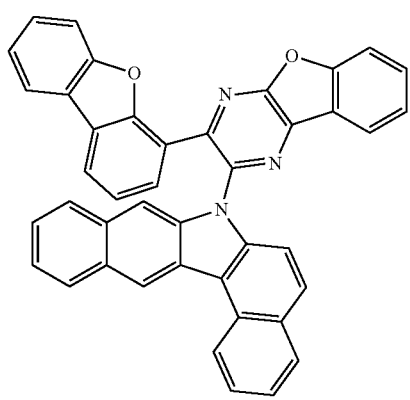 910 | 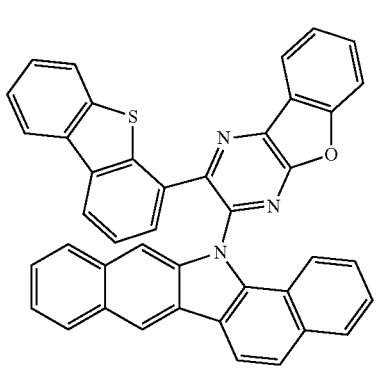 916 |
| 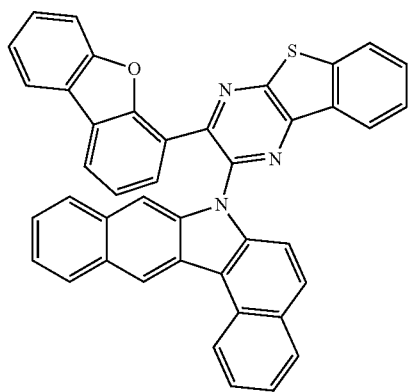 911 | 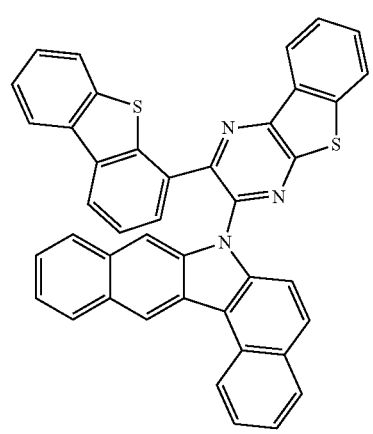 917 |
| 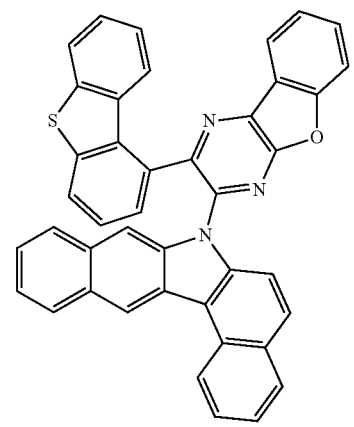 913 | 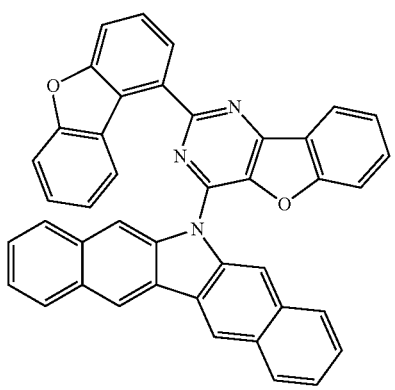 919 |

685
-continued
920
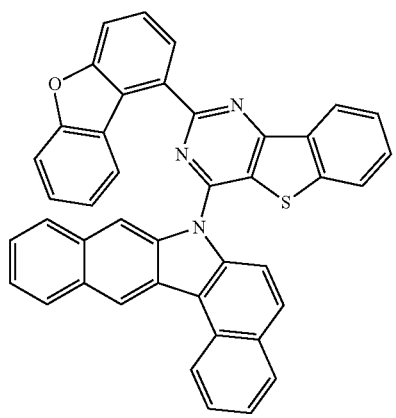
922
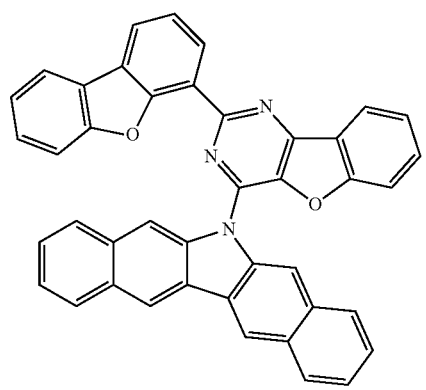
923
686
-continued
925
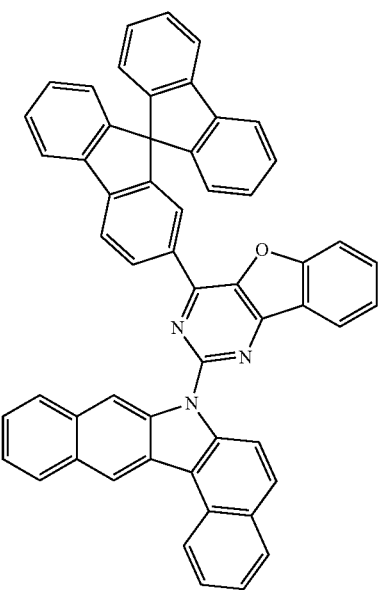
926
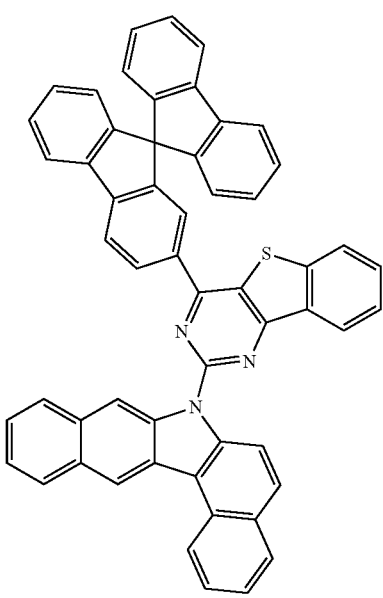

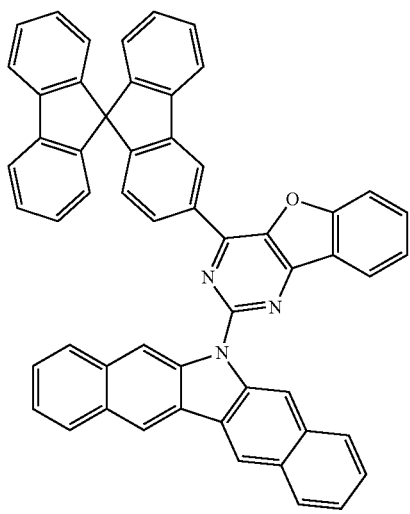
928
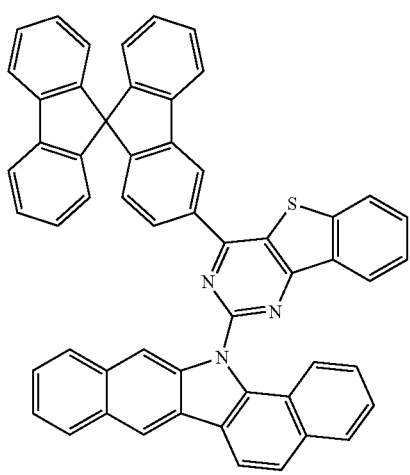
929
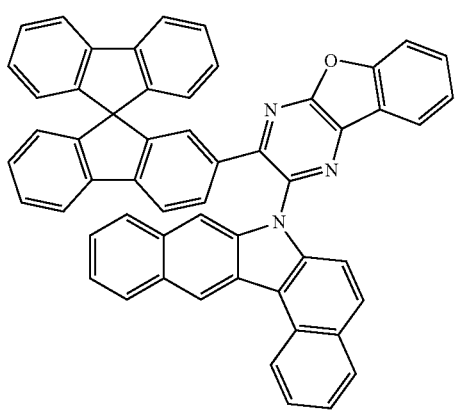
931
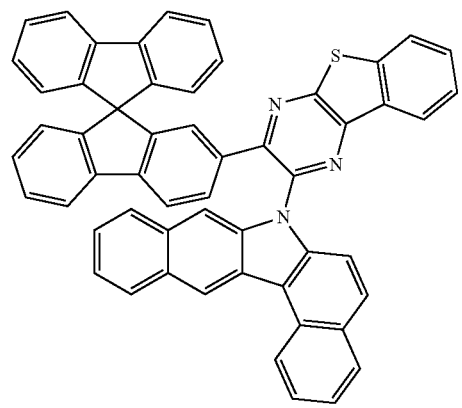
932
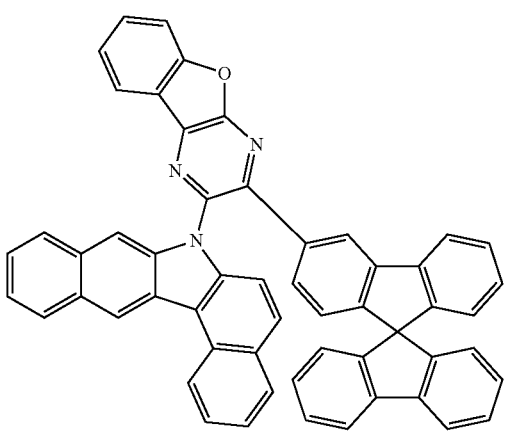
934
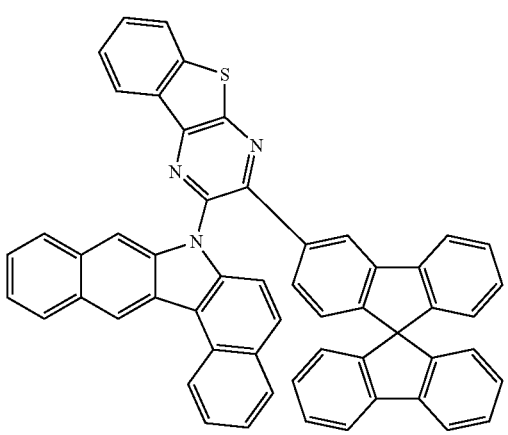
935

689
-continued
937
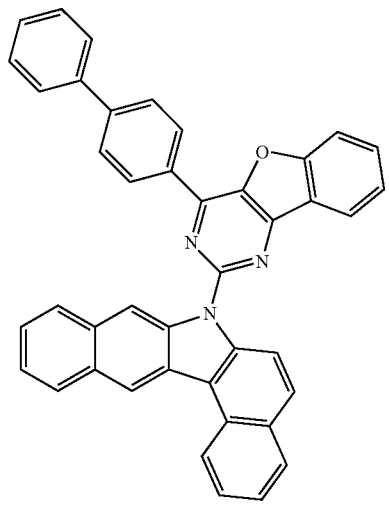
938
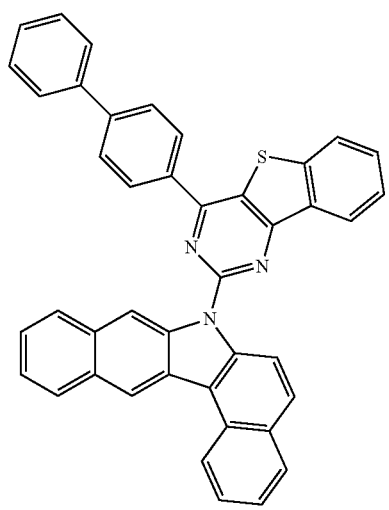
940
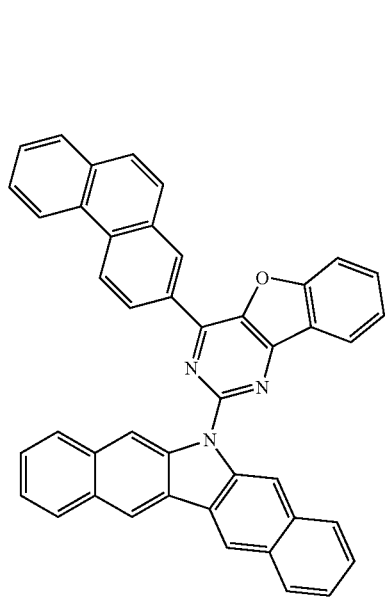
690
-continued
941
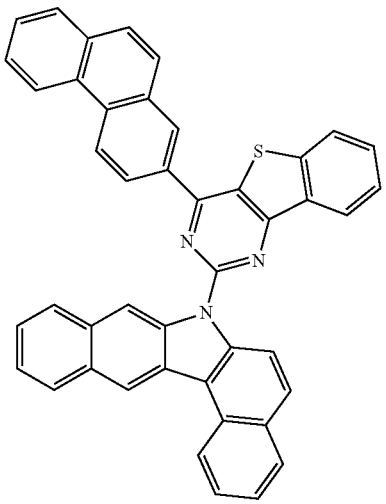
943
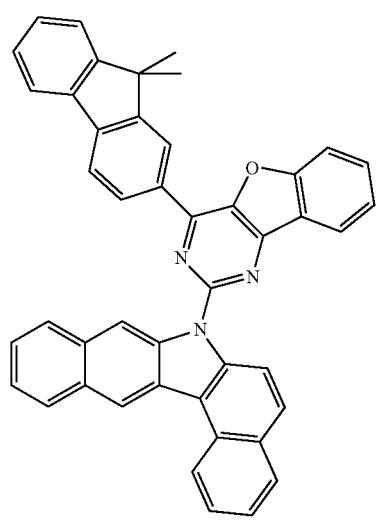
944
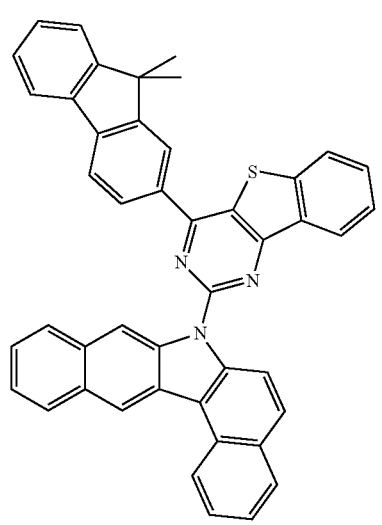

691
-continued
946
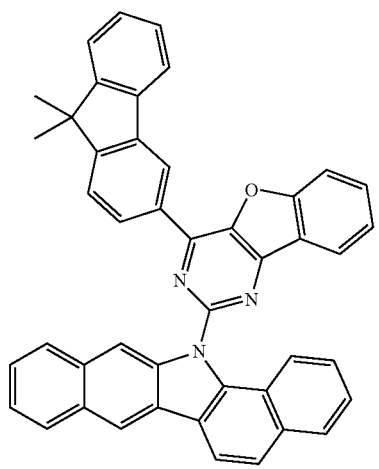
947
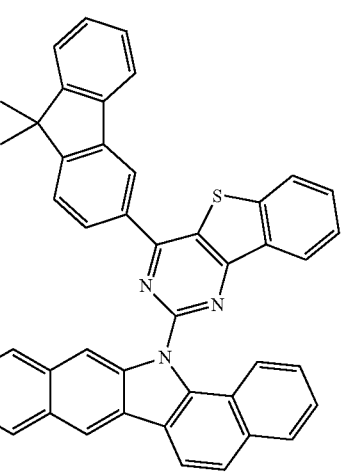
949
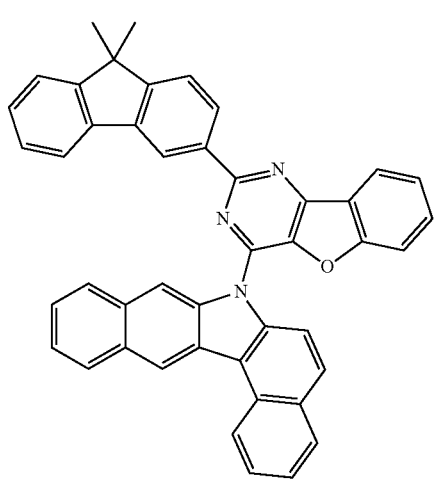
692
-continued
950
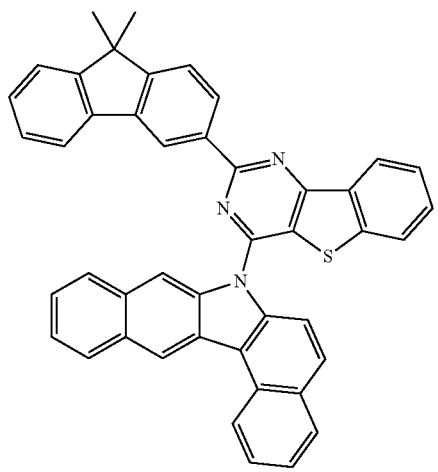
952
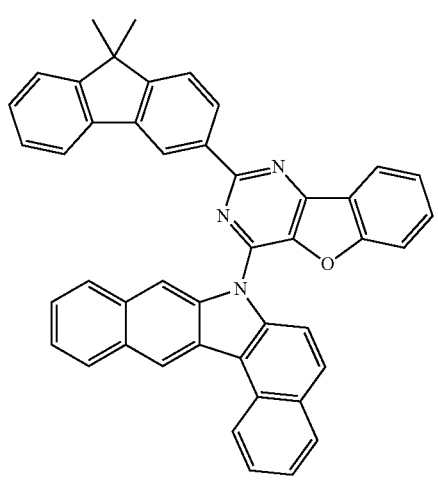
953
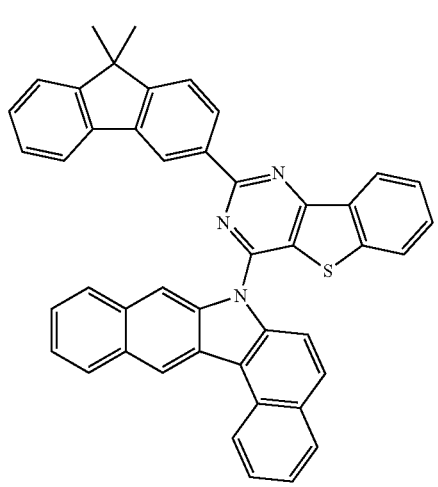

693
-continued
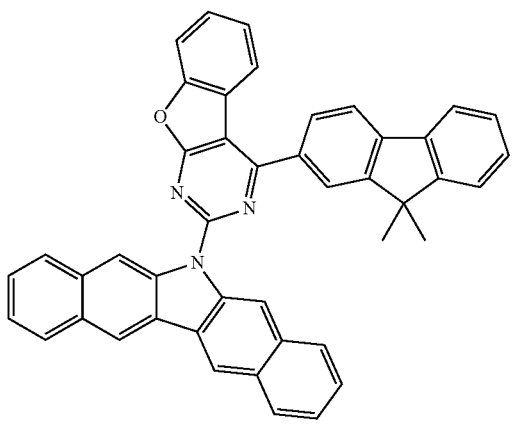
694
-continued
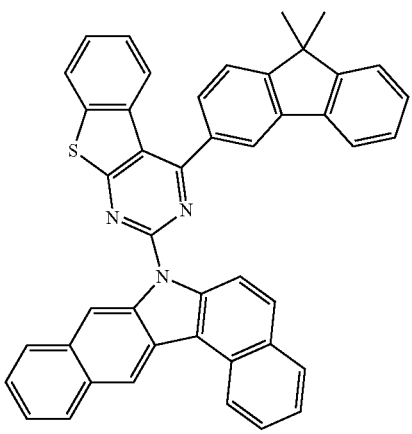
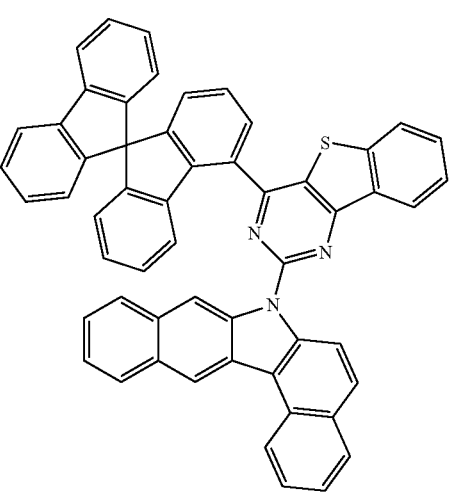

695
-continued
964
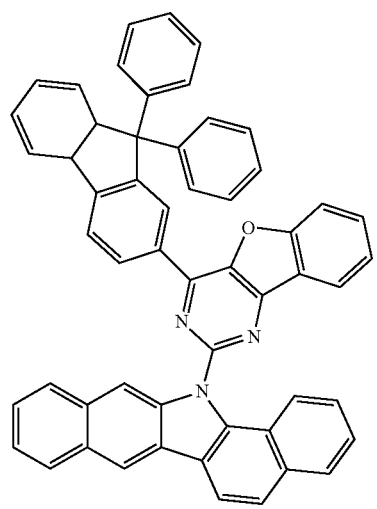
965
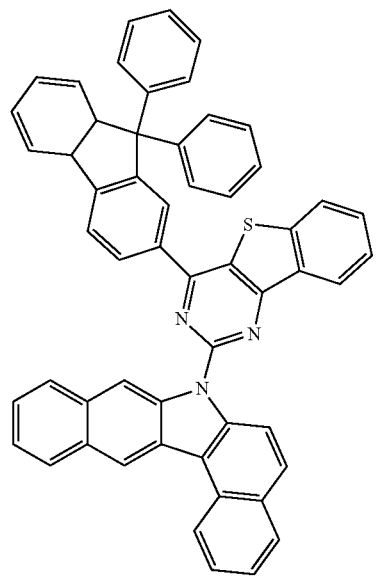
967
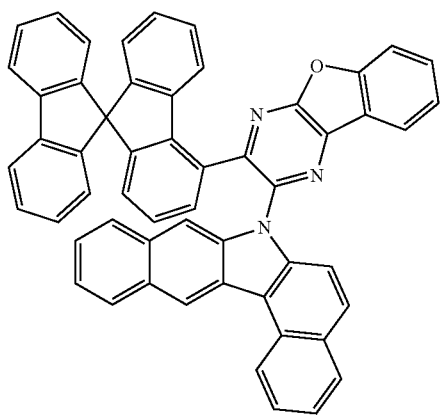
696
-continued
968
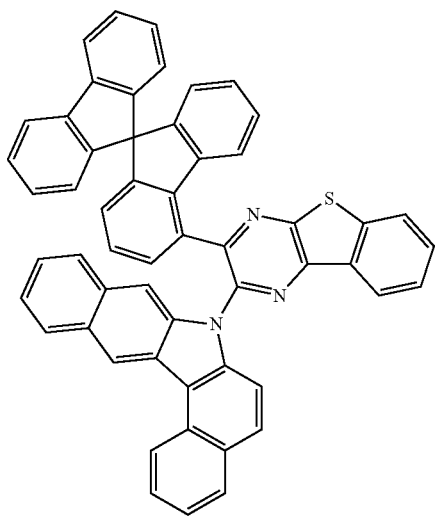
970
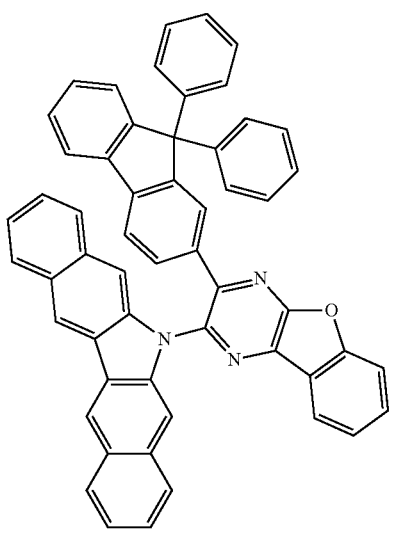
971
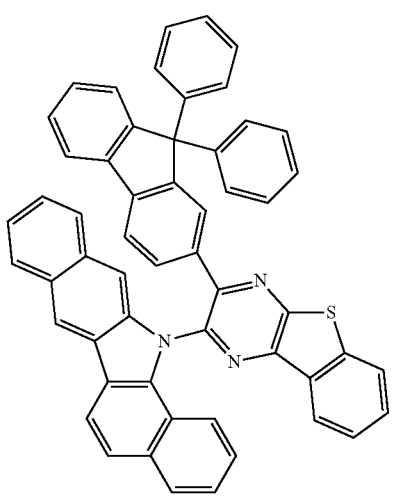

697
-continued
973
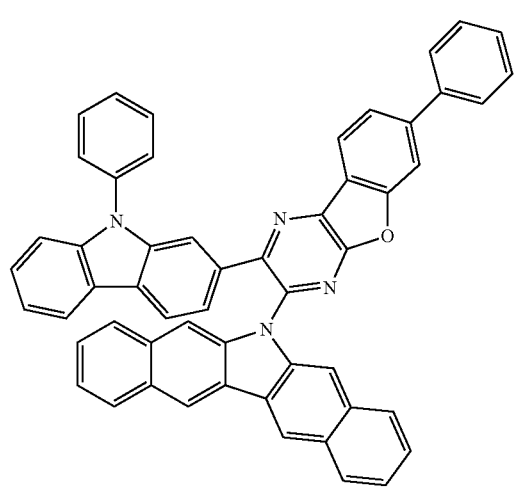
974
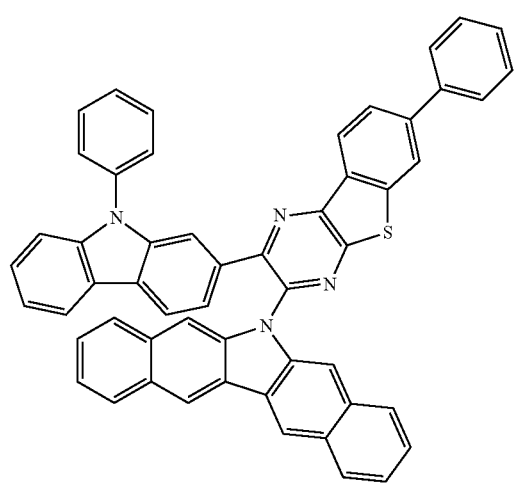
976
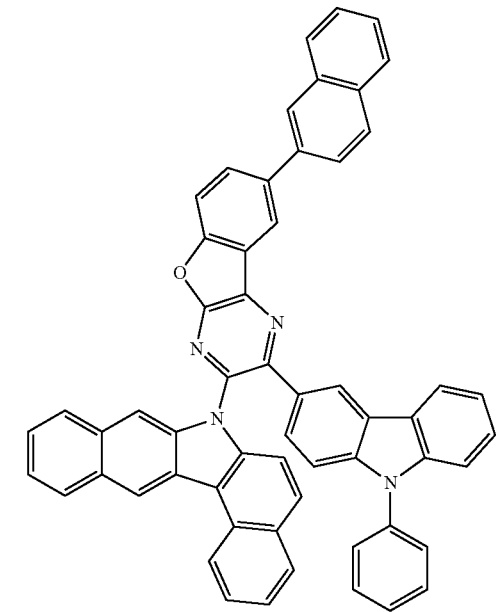
698
-continued
977
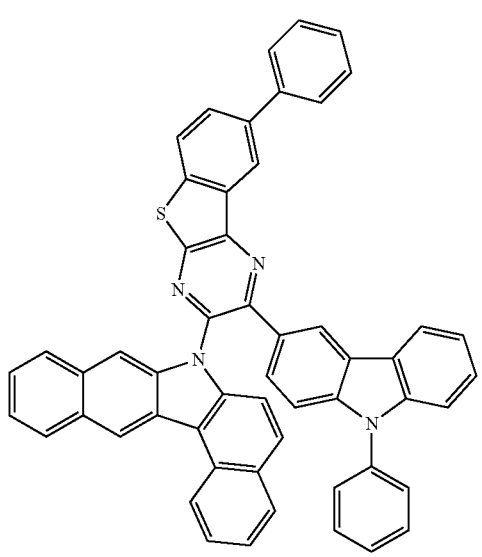
979
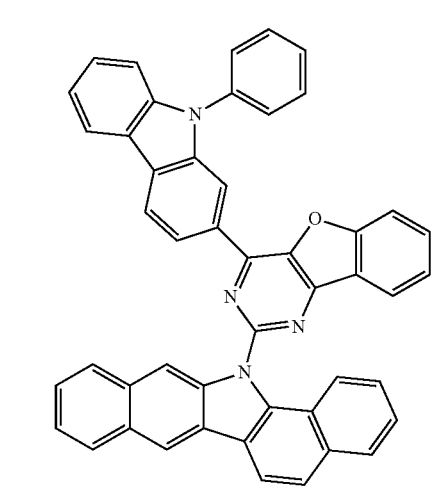
980
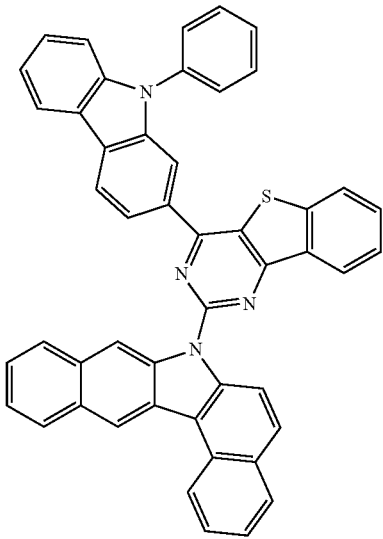

699
-continued
982
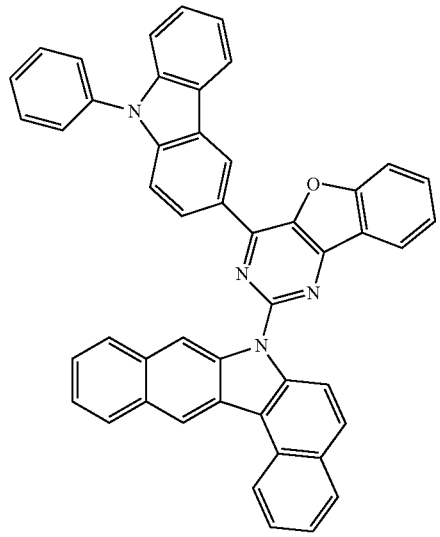
983
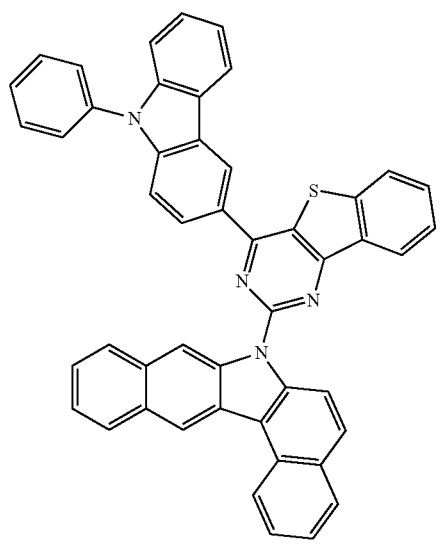
985
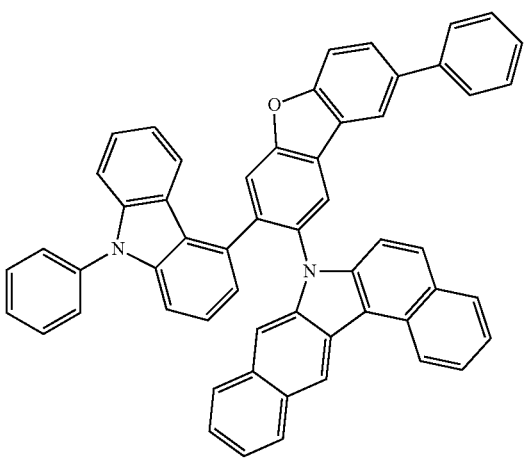
700
-continued
986
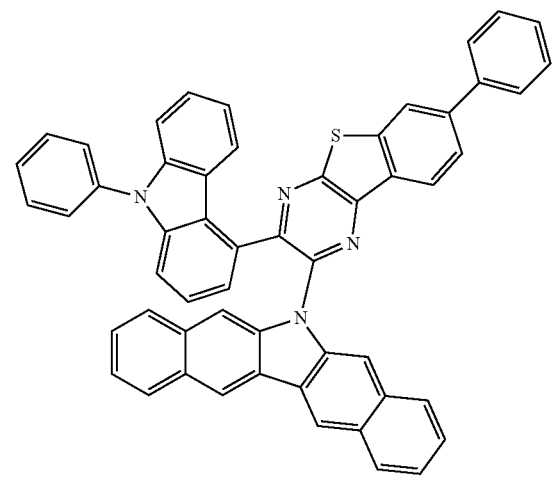
988
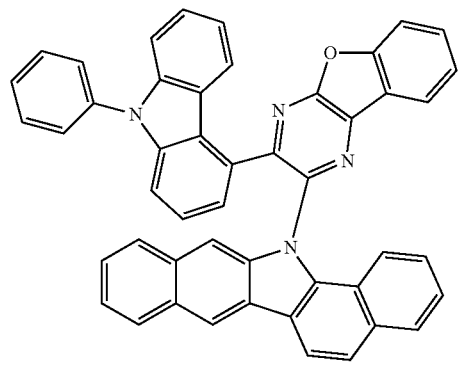
989
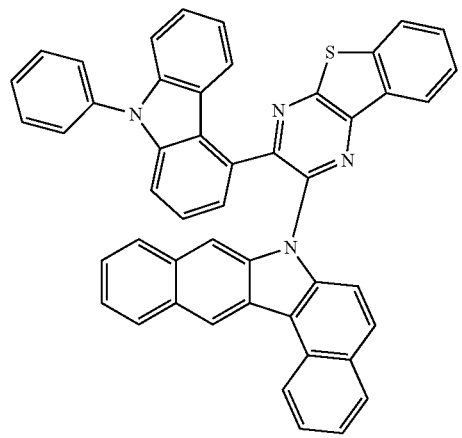

701
-continued
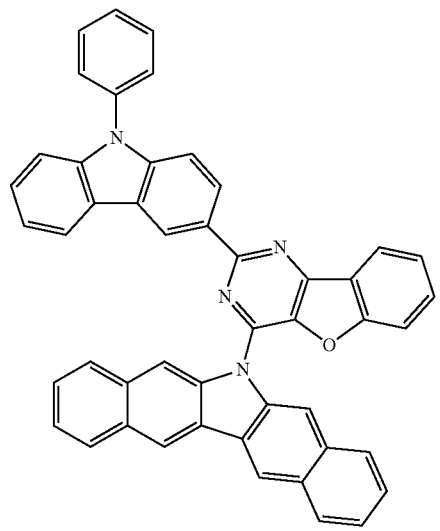
991
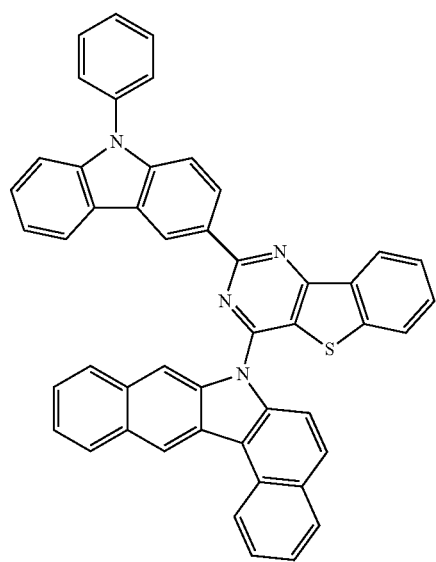
992
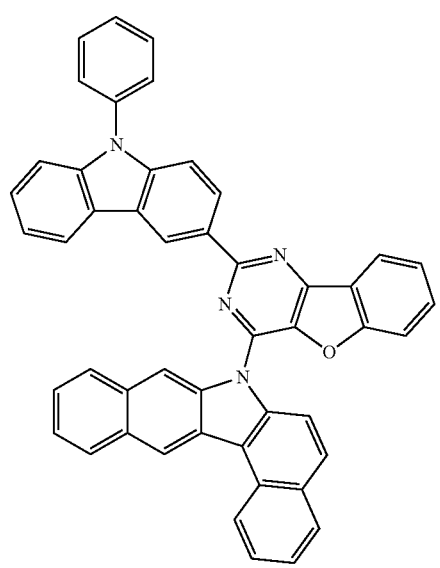
994
702
-continued
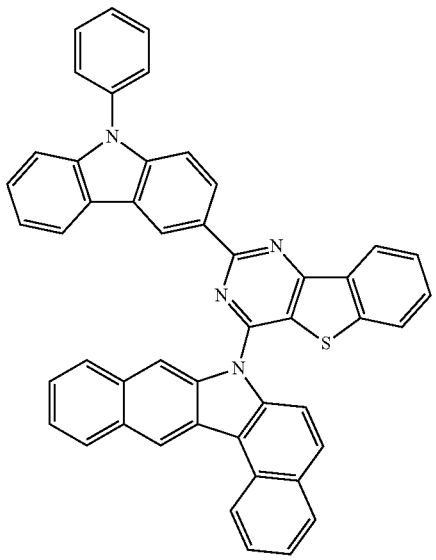
995
997
998
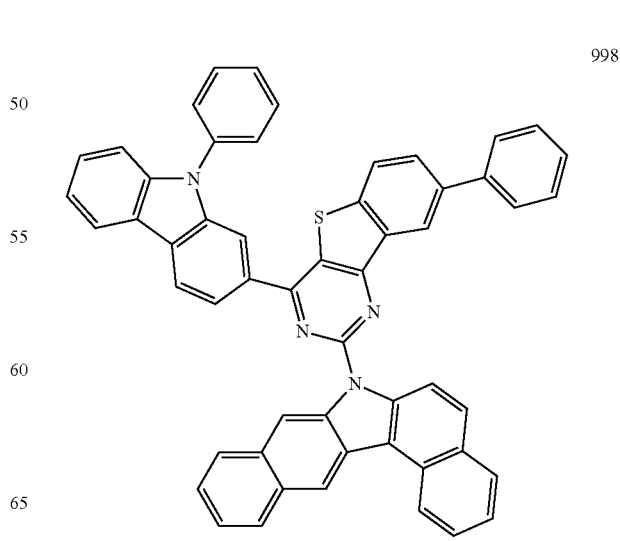

703
-continued
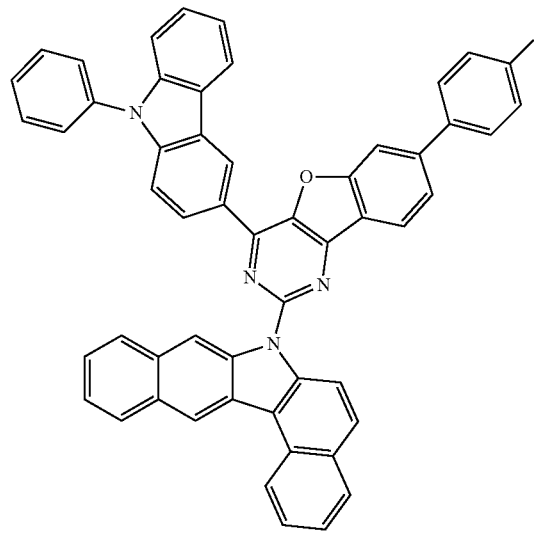
1000
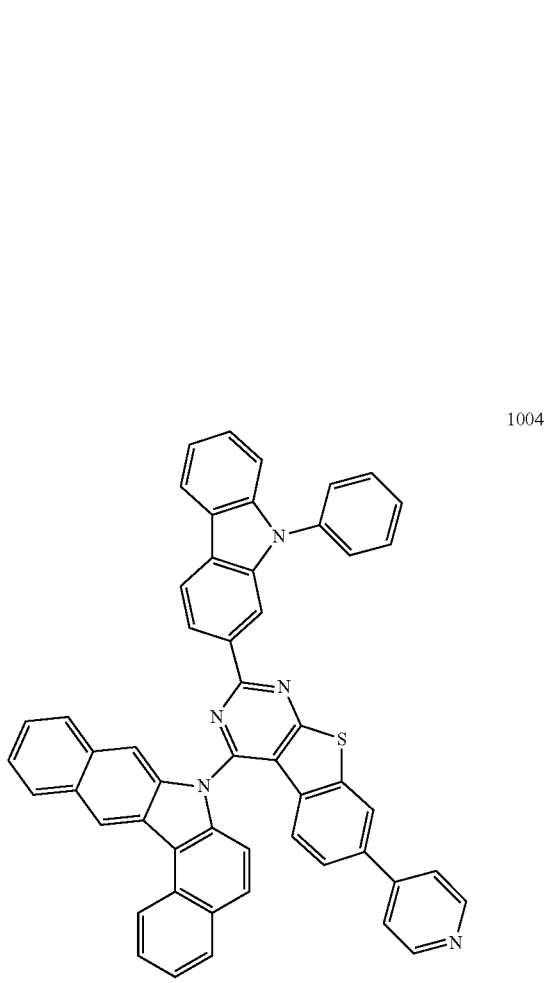
1001
704
-continued
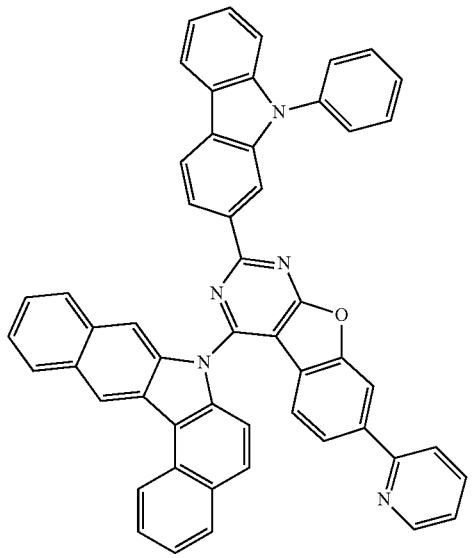
1003
1004

-continued
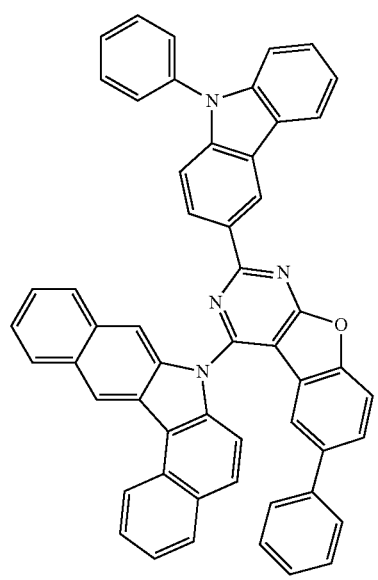
1006
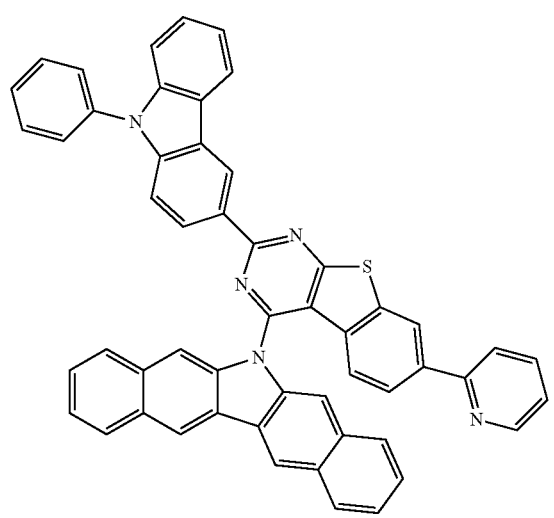
1007
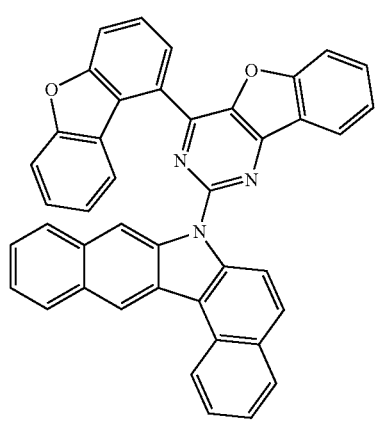
1009
-continued
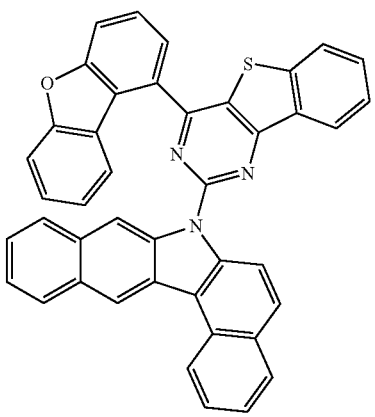
1010
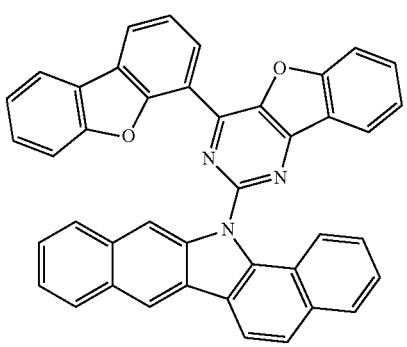
1012
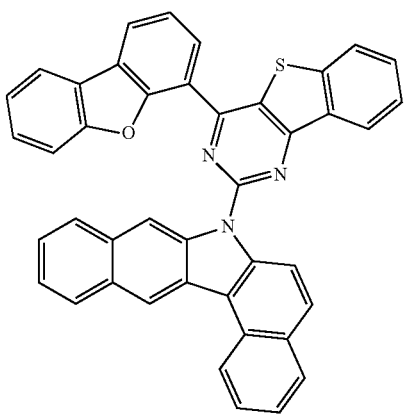
1013

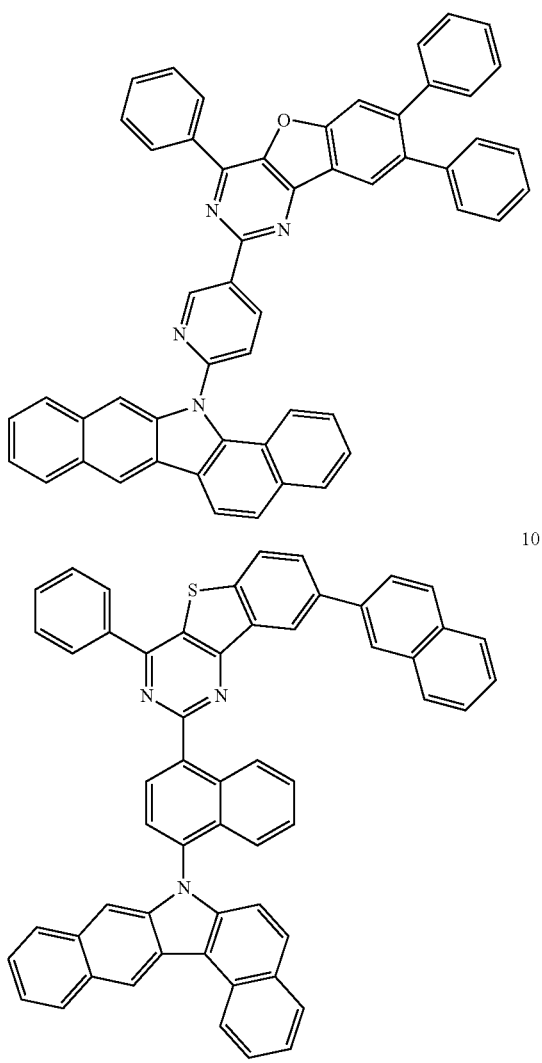
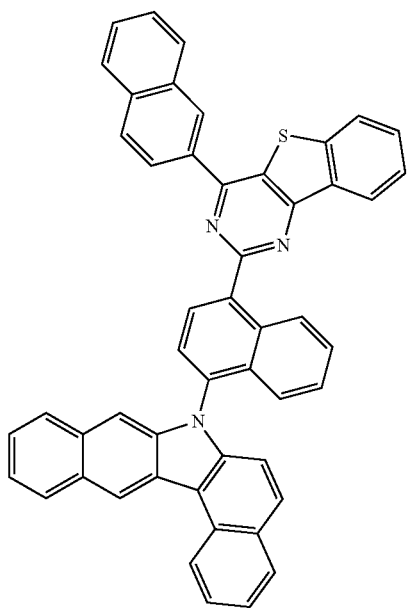
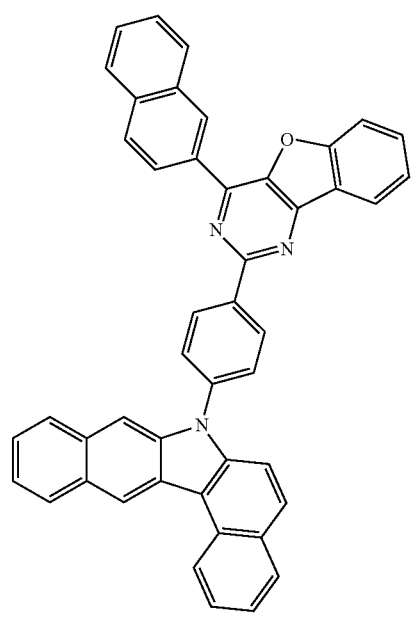
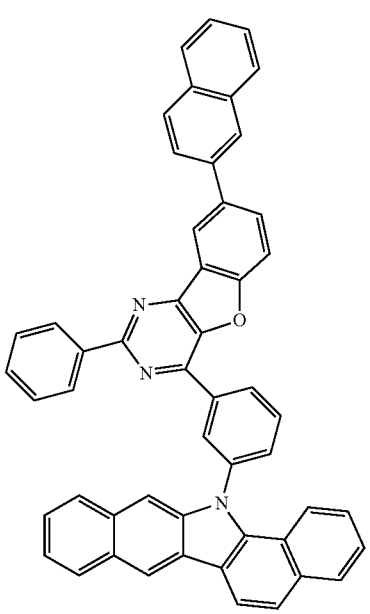

709
-continued
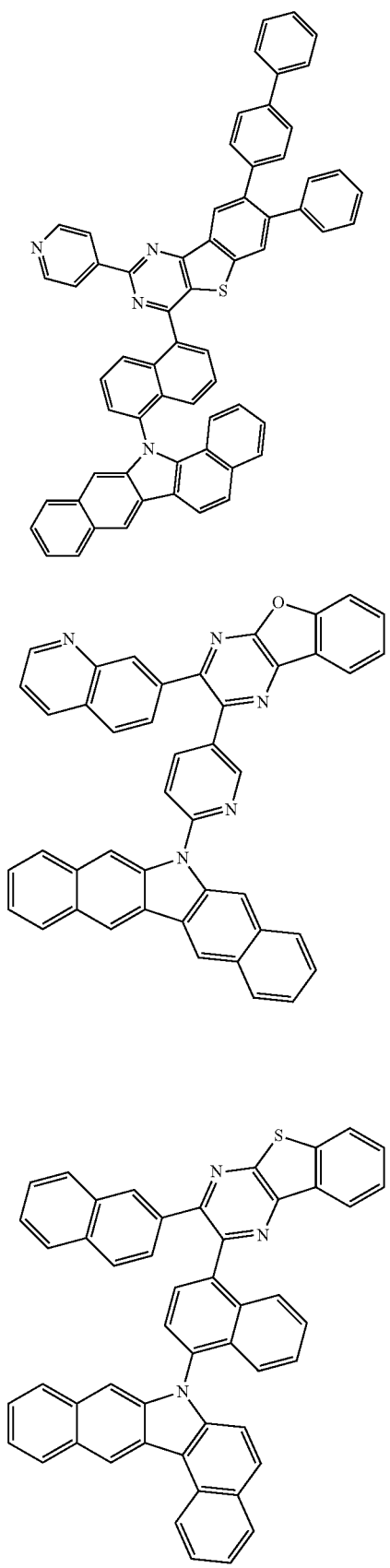
1022
1024
1025
710
-continued
1027
1028

711
-continued
1030
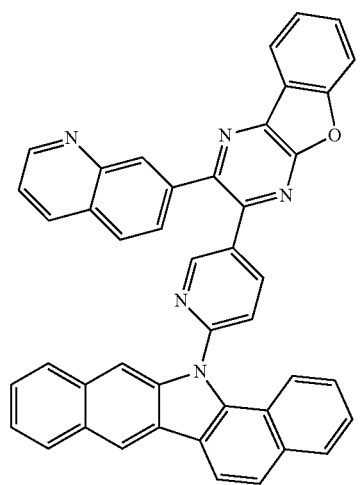
712
1033
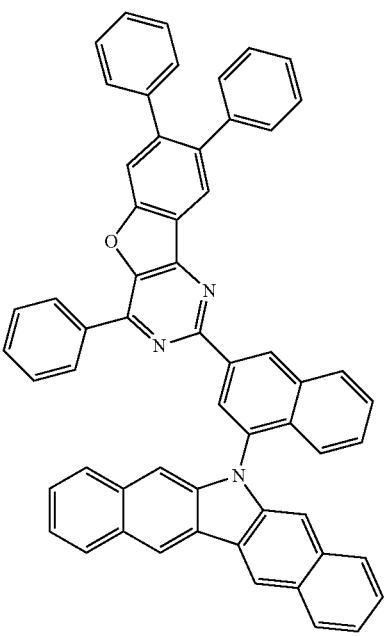
1031
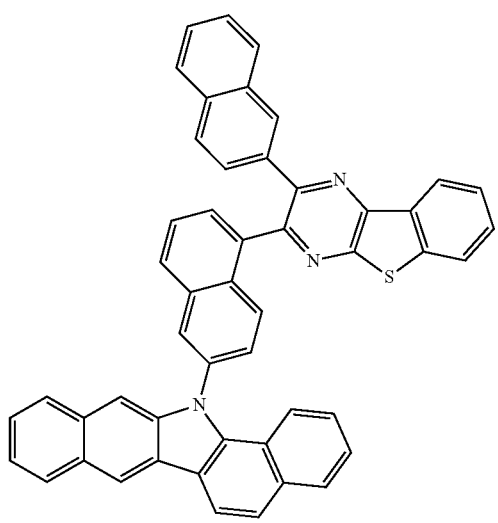
1034
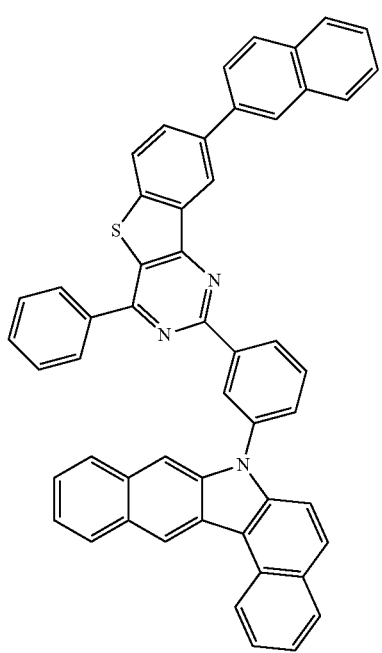

713
-continued
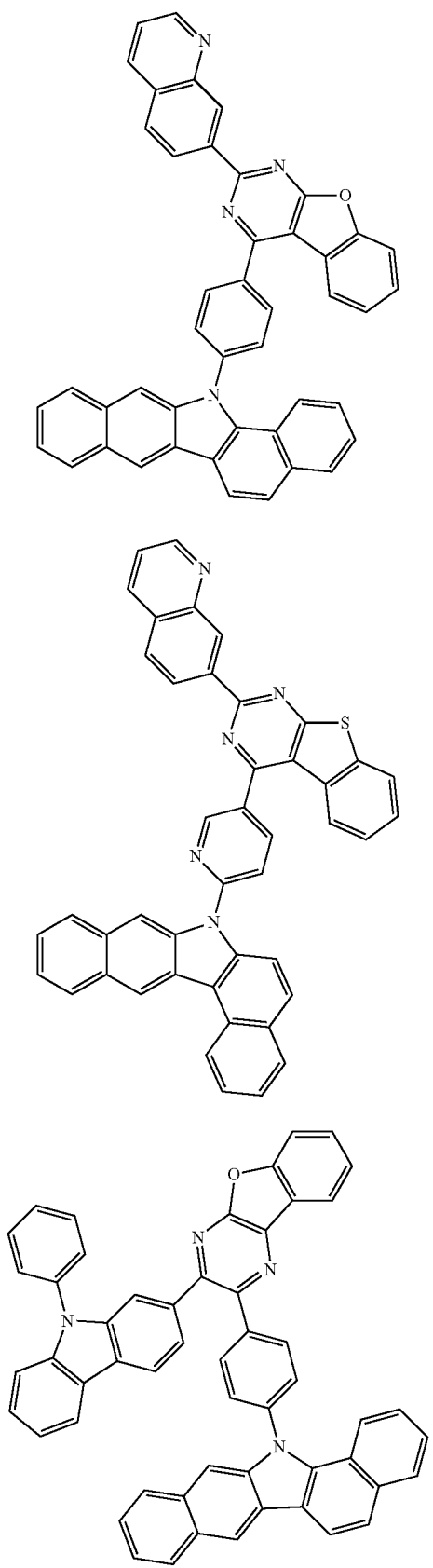
714
-continued
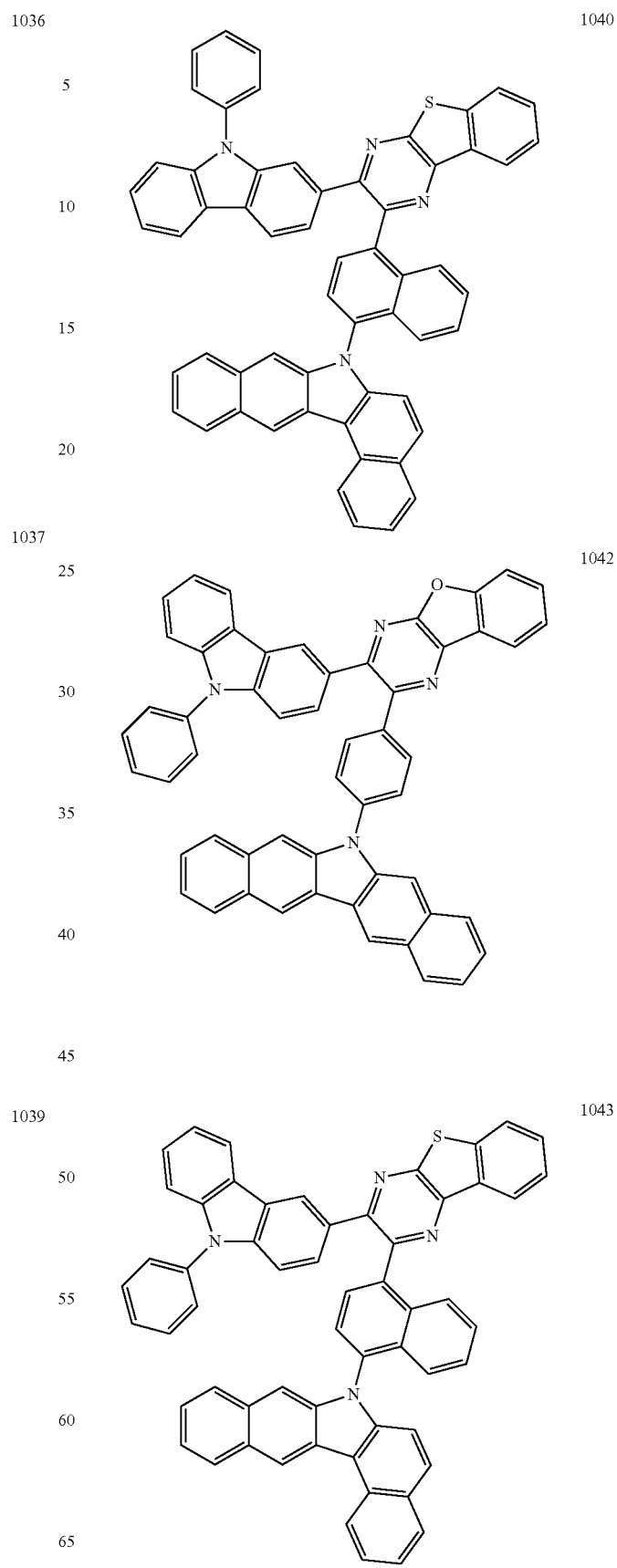

1045
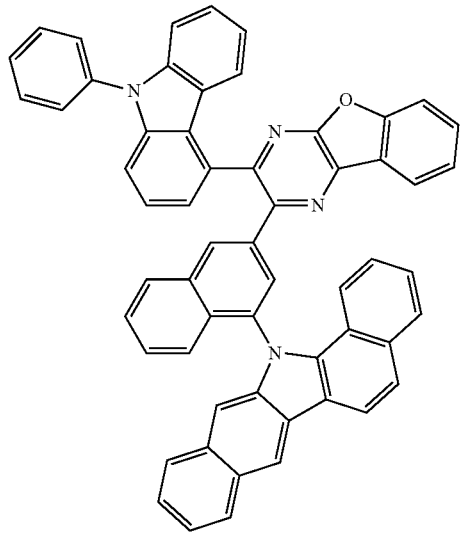
1046
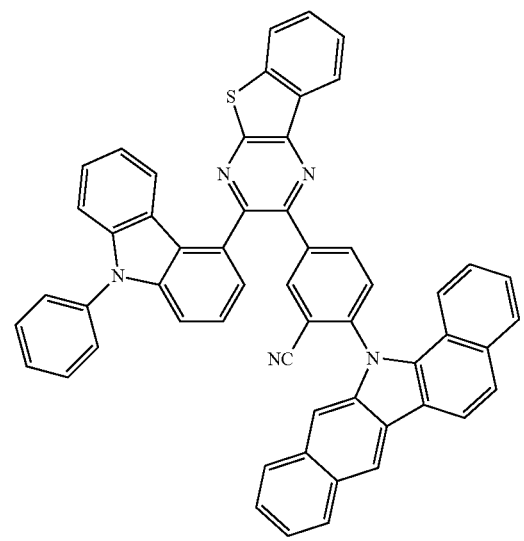
1048
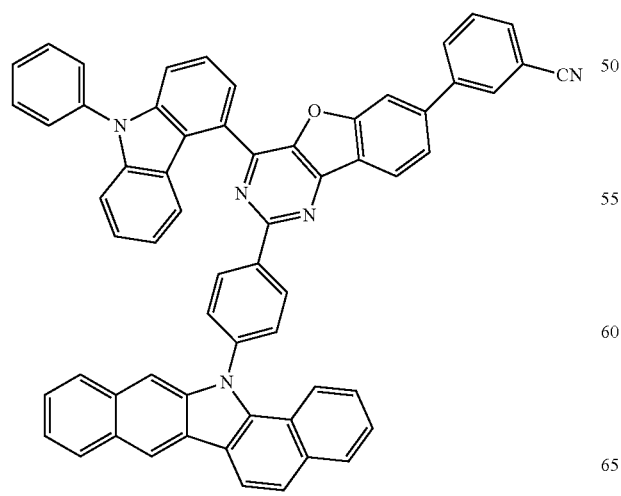
1049
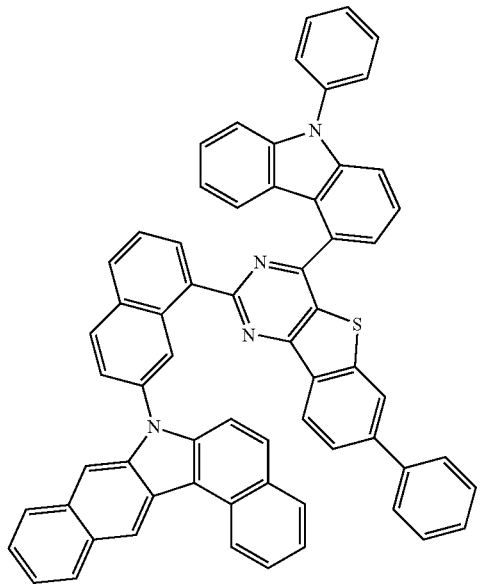
1051
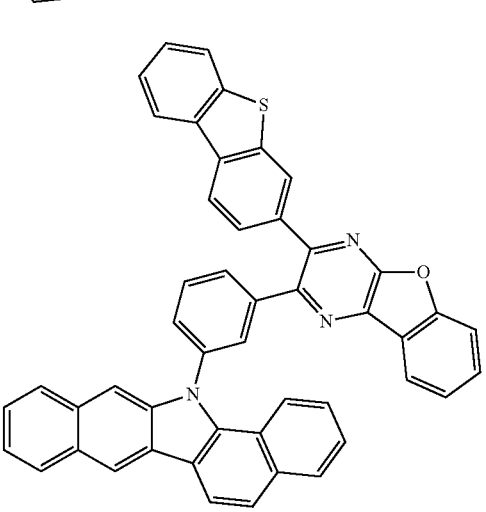
1052
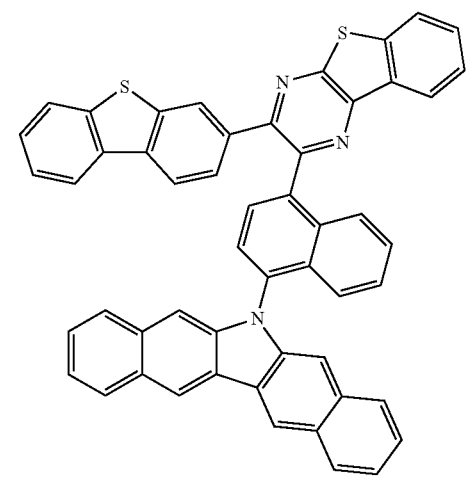

717
-continued
718
-continued
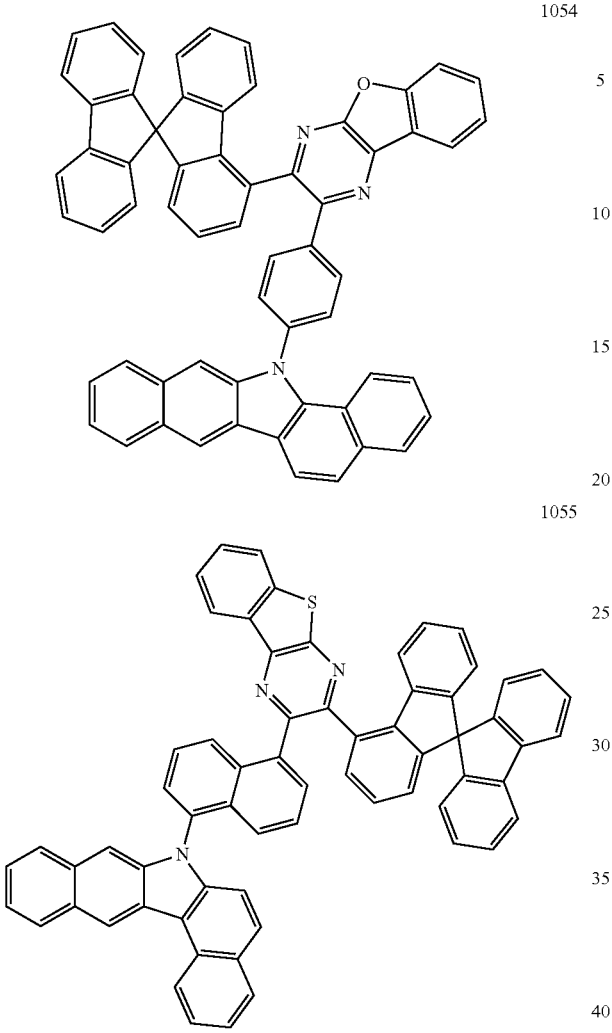
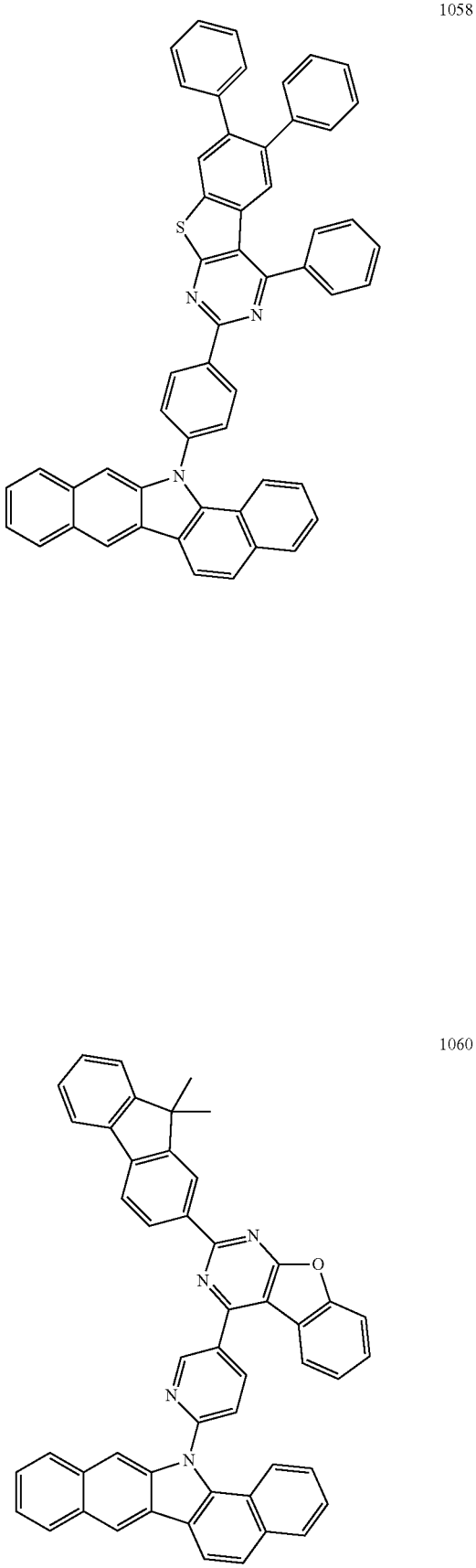

1061

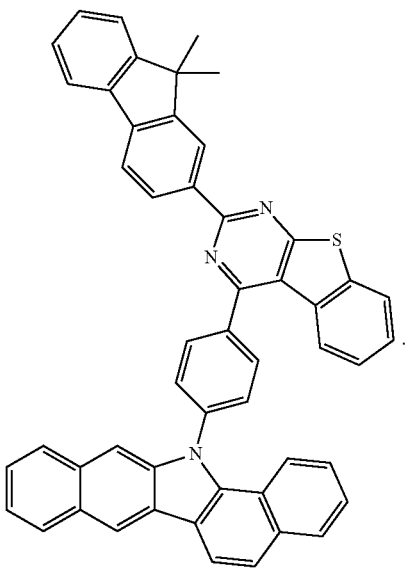

6. An organic light emitting device comprising:
a first electrode,
a second electrode provided to face the first electrode; and
one or more organic material layers provided between the first electrode and the second electrode,
wherein one or more layers of the one or more organic material layers include the compound of claim 1.

7. The organic light emitting device of claim 6, wherein the one or more organic material layers include a hole injection layer or a hole transfer layer, and the hole injection layer or the hole transfer layer includes the compound.

8. The organic light emitting device of claim 6, wherein the one or more organic material layers include a light emitting layer, and the light emitting layer includes the compound.

9. The organic light emitting device of claim 6, wherein the one or more organic material layers include an electron transfer layer or an electron injection layer, and the electron transfer layer or the electron injection layer includes the compound.

10. The organic light emitting device of claim 6, further comprising one, two or more layers selected from the group consisting of a hole injection layer, a hole transfer layer, an electron transfer layer, an electron injection layer, an electron blocking layer and a hole blocking layer.

* * * * *